US010442804B2

(12) United States Patent
Aktoudianakis et al.

(10) Patent No.: US 10,442,804 B2
(45) Date of Patent: Oct. 15, 2019

(54) COMPOUNDS FOR THE TREATMENT OF HEPATITIS B VIRUS INFECTION

(71) Applicant: Gilead Sciences, Inc., Foster City, CA (US)

(72) Inventors: Evangelos Aktoudianakis, Redwood City, CA (US); Eda Canales, San Mateo, CA (US); Kevin S. Currie, North Bend, WA (US); Darryl Kato, San Francisco, CA (US); Jiayao Li, Foster City, CA (US); John O. Link, San Francisco, CA (US); Samuel E. Metobo, Newark, CA (US); Roland D. Saito, San Mateo, CA (US); Scott D. Schroeder, Union City, CA (US); Nathan Shapiro, Belmont, CA (US); Winston C. Tse, Redwood City, CA (US); Qiaoyin Wu, Foster City, CA (US); Yunfeng Eric Hu, Hillsborough, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 0 days.

(21) Appl. No.: 15/885,390

(22) Filed: Jan. 31, 2018

(65) Prior Publication Data
US 2018/0251460 A1 Sep. 6, 2018

Related U.S. Application Data

(60) Provisional application No. 62/453,982, filed on Feb. 2, 2017, provisional application No. 62/506,921, filed on May 16, 2017, provisional application No. 62/536,777, filed on Jul. 25, 2017.

(51) Int. Cl.
C07D 471/14 (2006.01)
C07D 491/22 (2006.01)
C07D 498/14 (2006.01)
C07D 519/00 (2006.01)
A61P 31/20 (2006.01)
C07B 59/00 (2006.01)

(52) U.S. Cl.
CPC ............ *C07D 471/14* (2013.01); *A61P 31/20* (2018.01); *C07B 59/002* (2013.01); *C07D 491/22* (2013.01); *C07D 498/14* (2013.01); *C07D 519/00* (2013.01); *C07B 2200/05* (2013.01)

(58) Field of Classification Search
CPC ... C07D 491/22; C07D 471/14; C07D 498/14
See application file for complete search history.

(56) References Cited

U.S. PATENT DOCUMENTS

| 8,513,184 B2 | 8/2013 | Appleby et al. |
| 8,722,054 B2 | 5/2014 | Apelian et al. |
| 9,845,325 B2 | 12/2017 | Fu et al. |
| 2008/0234251 A1 | 9/2008 | Doherty et al. |
| 2008/0306050 A1 | 12/2008 | Doherty et al. |
| 2009/0047249 A1 | 2/2009 | Graupe et al. |
| 2010/0015178 A1 | 1/2010 | Combs et al. |
| 2010/0029585 A1 | 2/2010 | Howbert et al. |
| 2010/0143301 A1 | 6/2010 | Desai et al. |
| 2011/0092485 A1 | 4/2011 | Howbert et al. |
| 2011/0098248 A1 | 4/2011 | Halcomb et al. |
| 2011/0118235 A1 | 5/2011 | Howbert et al. |
| 2012/0082658 A1 | 4/2012 | Hershberg et al. |
| 2012/0219615 A1 | 8/2012 | Hershberg et al. |
| 2013/0079327 A1 | 3/2013 | Yamamoto et al. |
| 2013/0217880 A1 | 8/2013 | Yamamoto et al. |
| 2013/0251673 A1 | 9/2013 | Hartman et al. |
| 2013/0267517 A1 | 10/2013 | Guo et al. |
| 2013/0344029 A1 | 12/2013 | Aciro et al. |
| 2013/0344030 A1 | 12/2013 | Steadman et al. |
| 2014/0030221 A1 | 1/2014 | Aciro et al. |
| 2014/0045849 A1 | 2/2014 | Mcgowan et al. |
| 2014/0066432 A1 | 3/2014 | Howbert et al. |
| 2014/0073642 A1 | 3/2014 | Mcgowan et al. |
| 2014/0088085 A1 | 3/2014 | Burgess et al. |
| 2014/0171432 A1 | 6/2014 | Kanouni et al. |
| 2014/0194469 A1 | 7/2014 | Nie et al. |
| 2014/0213591 A1 | 7/2014 | Chen et al. |
| 2014/0275084 A1 | 9/2014 | Kanouni et al. |
| 2014/0275092 A1 | 9/2014 | Albrecht et al. |
| 2014/0275167 A1 | 9/2014 | Hartman et al. |
| 2014/0330015 A1 | 11/2014 | Yamamoto et al. |
| 2014/0343032 A1 | 11/2014 | Guo et al. |
| 2014/0350031 A1 | 11/2014 | Mcgowan et al. |

(Continued)

FOREIGN PATENT DOCUMENTS

| WO | WO-2014/0023813 A1 | 2/2014 |
| WO | WO-2014/0033167 A1 | 3/2014 |

(Continued)

OTHER PUBLICATIONS

Fecik, et al., Chiral DNA chirase inhibitors.3. Probing the chiral preference of the active site of DNA Gyrase. Synthesis of 10-fluoro-6methyl-6,7-dihydro-9-piperazinyl-2H-benzo[a]quinoliin-20-one-3-carboxylic acid analogues, Journal of Medicinal Chemistry, 2005, pp. 1229-1236, vol. 48, No. 4.

European Patent Office, International Search Report and Written Opinion for PCT Application No. PCT/US2018/016243, dated Apr. 17, 2018, 13 pages.

Geng, et al., Small-Molecule Inhibitors for the Treatment of Hepatitis B Virus Documented in Patents, Mini-Reviews in Medicinal Chemistry, 2013, pp. 749-776, vol. 13, No. 5.

(Continued)

*Primary Examiner* — Shawquia Jackson
(74) *Attorney, Agent, or Firm* — Mintz, Levin, Cohn, Ferris, Glovsky and Popeo, P.C.

(57) ABSTRACT

The present disclosure generally relates to compounds and pharmaceutical compositions which may be used in methods of treating a hepatitis B virus infection.

20 Claims, 2 Drawing Sheets

(56) References Cited

U.S. PATENT DOCUMENTS

| | | |
|---|---|---|
| 2014/0371195 A1 | 12/2014 | Labelle et al. |
| 2014/0371214 A1 | 12/2014 | Labelle et al. |
| 2015/0210682 A1 | 7/2015 | Han et al. |
| 2016/0039808 A1 | 2/2016 | Kanouni et al. |
| 2016/0102096 A1 | 4/2016 | Boesen et al. |
| 2016/0122344 A1 | 5/2016 | Han et al. |
| 2016/0176899 A1 | 6/2016 | Schwitter et al. |
| 2016/0207914 A9 | 7/2016 | Han et al. |
| 2017/0157133 A1 | 6/2017 | Yang et al. |
| 2017/0342068 A1 | 11/2017 | Aktoudianakis et al. |
| 2017/0342069 A1 | 11/2017 | Han et al. |

FOREIGN PATENT DOCUMENTS

| | | |
|---|---|---|
| WO | WO-2014/0033170 A1 | 3/2014 |
| WO | WO-2014/0033176 A1 | 3/2014 |
| WO | WO-2014/0037480 A1 | 3/2014 |
| WO | WO-2014/056953 A1 | 4/2014 |
| WO | WO-2014/0076221 A1 | 5/2014 |
| WO | WO-2014/0128189 A1 | 8/2014 |
| WO | WO-2014/0131847 A1 | 9/2014 |
| WO | WO-2014/0164708 A1 | 10/2014 |
| WO | WO-2015/0113990 A1 | 8/2015 |
| WO | WO-2015/0173164 A1 | 11/2015 |
| WO | WO-2016/012470 A1 | 1/2016 |
| WO | WO-2016/023877 A1 | 2/2016 |
| WO | WO-2016/0057924 A1 | 4/2016 |
| WO | WO-2016/071215 A1 | 5/2016 |
| WO | WO-2016/102438 A1 | 6/2016 |
| WO | WO-2016/107832 A1 | 7/2016 |
| WO | WO-2016/107833 A1 | 7/2016 |
| WO | WO-2016/113273 A1 | 7/2016 |
| WO | WO-2016/128335 A1 | 8/2016 |
| WO | WO-2016/146598 A1 | 9/2016 |
| WO | WO-2016/177655 A1 | 11/2016 |
| WO | WO-2016/202721 A1 | 12/2016 |
| WO | WO-2017/013046 A1 | 1/2017 |
| WO | WO-2017/016921 A1 | 2/2017 |
| WO | WO-2017/016960 A1 | 2/2017 |
| WO | WO-2017/017042 A1 | 2/2017 |
| WO | WO-2017/017043 A1 | 2/2017 |
| WO | WO-2017/064156 A1 | 4/2017 |
| WO | WO-2017/076791 A1 | 5/2017 |
| WO | WO-2017/102648 A1 | 6/2017 |
| WO | WO-2017/108630 A1 | 6/2017 |
| WO | WO-2017/114812 A1 | 7/2017 |
| WO | WO-2017/140821 A1 | 8/2017 |
| WO | WO-2017/205115 A1 | 11/2017 |
| WO | WO-2017/216685 A1 | 12/2017 |
| WO | WO-2017/216686 A1 | 12/2017 |
| WO | WO-2018/019297 A1 | 2/2018 |
| WO | WO-2018/022282 A1 | 2/2018 |

OTHER PUBLICATIONS

Op Den Brouw, et al., Hepatitis B virus Surface Antigen Impairs Myeloid Dendritic Cell Function: A Possible Immune Escape Mechanism of Hepatitis B Virus, British Society for Immunology, The Journal of cells, molecules, systems and technologies, 2008, pp. 280-289, vol. 126.

Wieland, et al., Stealth and Cunning: Hepatitis B and Hepatitis C Viruses, Journal of Virology, Aug. 2005, pp. 9369-9380, vol. 79, No. 15.

Woltman, et al., Hepatitis B Virus Lacks Immune Activating Capacity, but Actively Inhibits Plasmacytoid Dendritic Cell Function, Plos One, Jan. 2011, 14 pages, vol. 6.

Xu, et al., A facile synthesis of novel tricyclic 4-pyridones, Tetrahedron Letters, 2014, pp. 7194-7197, vol. 55, No. 52.

COMPOUNDS FOR THE TREATMENT OF HEPATITIS B VIRUS INFECTION

CROSS-REFERENCE TO RELATED APPLICATIONS

This application claims priority benefit to U.S. Provisional Application Ser. No 62/453,982, filed on Feb. 2, 2017, U.S. Provisional Application Ser. No. 62/506,921, filed on May 16, 2017, and U.S. Provisional Application Ser. No. 62/536,777, filed on Jul. 25, 2017, the disclosures of which are incorporated by reference in their entirety.

FIELD

The present invention relates to novel small molecule and related pharmaceutical compositions useful in the treatment of hepatitis B virus (HBV) infection.

BACKGROUND

The hepatitis B virus (HBV) is an enveloped, partially double-stranded DNA virus HBV is an infectious disease that affects the liver. Initial symptoms of infection may include vomiting, jaundice, lethargy, dark urine, and abdominal pain. Chronic HBV infection can result in cirrhosis and liver cancer. Currently available therapies can inhibit replication of the virus and minimize liver damage; however, there are no currently available therapies that can clear an HBV infection.

HBV surface antigen (HBsAg) is a protein located in the HBV envelope. It allows HBV virion entry into host cells by binding to the hepatocyte sodium-taurocholate cotransporting polypeptide (NTCP) receptor. HBsAg may also function as a tolerogen, suppressing immune elimination of infected cells. Total HBsAg loss and seroconversion are rarely achieved in chronically infected patients. Inhibiting HBsAg secretion and/or production is thus believed to be a strategy for the treatment of HBV infection, including chronic HBV infection. (Wieland, S. F. & F. V. Chisari, *J. Virol.* (2005), 79, 9369-80; Woltman et al. *PLoS One* (2011), 6, e15324; Op den Brouw et al. *Immunology* (2009b), 126, 280-89).

BRIEF SUMMARY

The present disclosure provides compounds of Formula (I)

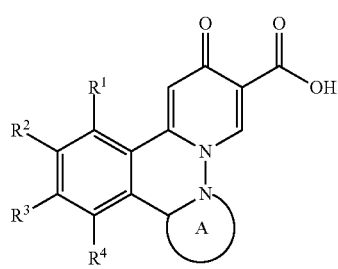

wherein:

A is a 4-7 membered cycloalkyl or heterocyclyl ring substituted with 0-8 $R^5$ groups;

$R^1$ is H or halogen;

$R^2$ is selected from the group consisting of halogen, $R^{2a}O$—, $C_{1-6}$ alkyl, $C_{3-10}$ cycloalkyl, 3-7 membered heterocyclyl, —$NR^aR^b$, —$S(O)_{0-2}R^a$, or —CN, wherein each $C_{1-6}$alkyl, $C_{3-10}$ cycloalkyl or 3-7 membered heterocyclyl is optionally substituted with 1-5 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-5 $R^{20}$ groups;

$R^3$ is selected from the group consisting of $R^{3a}O$—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —$NR^aR^b$, and —$S(O)_{0-2}R^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;

$R^{3a}$ is selected from the group consisting of H, $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

$R^4$ is H or halogen;

each $R^5$ is independently selected from the group consisting of $C_{1-6}$ alkyl, $C_{1-6}$ alkoxy, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$OR^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein any two $R^5$ groups on the same carbon atom can optionally form a =O; and any two $R^5$ groups can optionally join together to form a $C_{3-6}$ cycloalkyl or 3-6 membered heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen.

Another embodiment provides a compound of Formula (II):

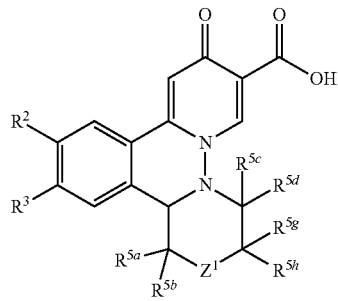

II wherein:

$Z^1$ is a bond, O, $NR^a$ or $CR^{5e}R^{5f}$;

$R^2$ is selected from the group consisting of halogen, $R^{2a}O$—, $C_{1-6}$ alkyl, or —CN, wherein $C_{1-6}$alkyl is optionally substituted with 1-3 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-3 $R^{20}$ groups;

$R^3$ is selected from $C_{1-6}$ alkoxy, $C_{1-6}$alkoxy$C_{1-6}$alkoxy, and $C_{3-8}$cycloalkoxy$C_{1-6}$alkoxy, wherein each $C_{1-6}$ alkoxy, $C_{1-6}$alkoxy$C_{1-6}$alkoxy, and $C_{3-8}$cycloalkoxy$C_{1-6}$alkoxy is optionally substituted with halo;

each of $R^{5a}$, $R^{5b}$, $R^{5c}$, $R^{5d}$, $R^{5e}$, $R^{5f}R^{5g}$ and $R^{5h}$ are independently selected from the group consisting of H, $C_{1-6}$ alkyl, $C_{1-6}$ alkoxy, $C_{2-6}$ alkenyl, $C_{2-6}$ alkynyl, —$NR^aR^b$, halogen, $C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein up to two of $R^{5a}$ and $R^{5b}$, $R^{5c}$ and $R^{5d}$, $R^{5e}$ and $R^{5f}$, or $R^{5g}$ and $R^{5h}$ can optionally form a =O; and wherein any two of $R^{5a}$, $R^{5b}$, $R^{5c}$, $R^{5d}$, $R^{5e}$, $R^{5f}R^{5g}$ and $R^{5h}$ can optionally join together to form a cycloalkyl or heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$; —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

In some embodiments provided herein is a pharmaceutical composition comprising a compound of Formula (I) or (II), or Formula (Ia), (Ib) or (IIa) or a pharmaceutically acceptable salt thereof, and a pharmaceutically acceptable excipient. In some embodiments, the pharmaceutical composition further comprises one or more additional therapeutic agents.

In some embodiments provided herein is a method of inhibiting the production and/or secretion of HBsAg in an individual (e.g. a human) infected with HBV comprising administering a therapeutically effective amount of a compound of Formula (I) or (II), or Formula (Ia), (Ib) or (IIa), or a pharmaceutically acceptable salt thereof, to the individual. In some embodiments, the human is chronically infected with HBV.

In some embodiments provided herein is a method of treating or preventing a HBV infection comprising administering to an individual (e.g. a human) in need thereof a therapeutically effective amount of a compound of Formula (I) or (II), or Formula (Ia), (Ib) or (IIa), or a pharmaceutically acceptable salt thereof. In some embodiments, the individual is chronically infected with HBV. In some embodiments, the methods further comprise administering one or more additional therapeutic agents.

In certain embodiments, a compound of Formula (I) or (II), or Formula (Ia), (Ib) or (IIa), or a pharmaceutically acceptable salt thereof, for use in medical therapy is provided.

In certain embodiments, a compound of Formula (I) or (II), or Formula (Ia), (Ib) or (IIa), or a pharmaceutically acceptable salt thereof, for use in treating or preventing HBV infection is provided In certain embodiments, the use of a compound of Formula (I) or (II), or Formula (Ia), (Ib) or (IIa), or a pharmaceutically acceptable salt thereof, for the manufacture of a medicament for treating or preventing HBV infection is provided.

Kits comprising a compound of Formula (I) or (II), or Formula (Ia), (Ib) or (IIa), or pharmaceutically acceptable salts thereof, or pharmaceutical compositions of the foregoing are also provided. Articles of manufacture comprising a unit dose of the compounds, or pharmaceutically acceptable salts thereof, of the foregoing are also provided. Methods of preparing compounds of the present disclosure are also provided.

DETAILED DESCRIPTION

Figure 1:
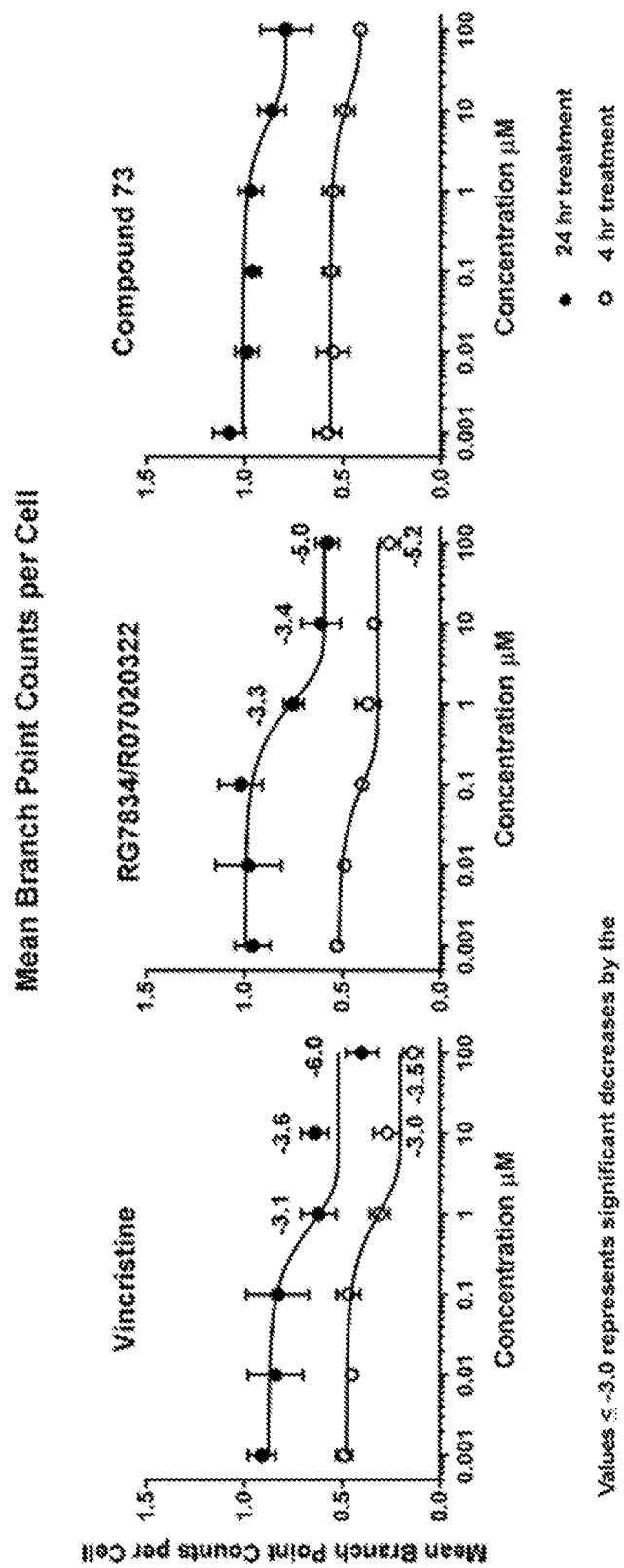
FIG. 1 is a series of graphs plotting mean branch point count per cell as a function of concentration of compound, where the compound is Vincristine, RG783/R07020332, and compound 73.

The description below is made with the understanding that the present disclosure is to be considered as an exemplification of the claimed subject matter, and is not intended to limit the appended claims to the specific embodiments illustrated. The resent disclosure provides reference to various embodiments and techniques. However, it should be understood that many variations and modifications may be made while remaining within the spirit and scope of the present disclosure. The headings used throughout this disclosure are provided for convenience and are not to be construed to limit the claims in any way. Embodiments illustrated under any heading may be combined with embodiments illustrated under any other heading.

Unless defined otherwise, all technical and scientific terms used herein have the same meaning as commonly understood by one of ordinary skill in the art. A dash at the front or end of a chemical group is a matter of convenience to indicate the point of attachment to a parent moiety; chemical groups may be depicted with or without one or more dashes without losing their ordinary meaning. A prefix such as "$C_{u-v}$" or ($C_u$-$C_v$) indicates that the following group has from u to v carbon atoms, where u and v are integers. For example, "$C_{1-6}$alkyl" indicates that the alkyl group has from 1 to 6 carbon atoms.

Unless the context requires otherwise, throughout the present specification and claims, the word "comprise" and variations thereof, such as, "comprises" and "comprising" are to be construed in an open, inclusive sense, that is as "including, but not limited to".

As used herein, "alkyl" is a linear or branched saturated monovalent hydrocarbon. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), and 2,3-dimethyl-2-butyl (—C(CH$_3$)$_2$CH(CH$_3$)$_2$), 3,3-dimethyl-2-butyl (—CH(CH$_3$)C(CH$_3$)$_3$).

"Amino" refers to —NH$_2$. Amino groups may also be substituted as described herein, such as with alkyl, carbonyl or other amino groups. The term "alkylamino" refers to an amino group substituted with one or two alkyl substituents (e.g. dimethylamino or propylamino).

The term "halo" or "halogen" as used herein refers to fluoro (—F), chloro (—Cl), bromo (—Br) and iodo (—I).

The term "haloalkyl" as used herein refers to an alkyl as defined herein, wherein one or more hydrogen atoms of the alkyl are independently replaced by a halogen substituent, which may be the same or different. For example, $C_{1-6}$haloalkyl is a $C_{1-6}$alkyl wherein one or more of the hydrogen atoms of the $C_{1-6}$alkyl have been replaced by a halo substituent. Examples of haloalkyl groups include, but are not limited to, fluoromethyl, fluorochloromethyl, difluoromethyl, difluorochloromethyl, trifluoromethyl, 1,1,1-trifluoroethyl, and pentafluoroethyl.

The term "alkoxy" as used herein refers to a radical of the formula —OR$_x$ where R$_x$ is an alkyl radical as defined above. Non-limiting examples of alkoxy include methoxy, ethoxy, propoxy, and butoxy.

The term "haloalkoxy" as used herein refers to a radical of the formula —OR$_x$ wherein R$_x$ is an alkyl radical as defined above, and wherein one or more hydrogens on the alkyl radical are replaced with halogen.

The terms "alkoxyalkoxy" and "haloalkoxyalkoxy," refer to an alkoxy radical that is substituted with alkoxy or haloalkoxy, respectively. For illustrative purposes only, a non-limiting example of "alkoxyalkoxy" is

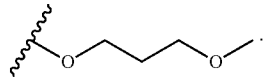 [SMILES: *OCCCOC]

"Alkenyl" refers to any group derived from a straight or branched hydrocarbon with at least one carbon-carbon double bond. Alkenyl groups include, but are not limited to, ethenyl (vinyl), propenyl (allyl), 1-butenyl, 1,3-butadienyl, and the like. Unless otherwise specified, an alkenyl group has from 2 to 10 carbon atoms, for example from 2 to 6 carbon atoms, for example from 2 to 4 carbon atoms.

"Alkynyl" refers to any group derived from a straight or branched hydrocarbon with at least one carbon-carbon triple bond and includes those groups having one triple bond and one double bond. Examples of alkynyl groups include, but are not limited to, ethynyl (—C≡CH), propargyl (—CH$_2$C≡CH), (E)-pent-3-en-1-ynyl, and the like. Unless otherwise specified, an alkynyl group has from 2 to 10 carbon atoms, for example from 2 to 6 carbon atoms, for example from 2 to 4 carbon atoms.

"Aryl" refers to any group derived from one or more aromatic rings, that is, a single aromatic ring, a bicyclic or a multicyclic ring system. Aryl groups include, but are not limited to, those groups derived from acenaphthylene, anthracene, azulene, benzene, chrysene, a cyclopentadienyl anion, naphthalene, fluoranthene, fluorene, indane, perylene, phenalene, phenanthrene, pyrene and the like. Unless otherwise specified, an aryl group has from 5 to 20 carbon atoms.

"Arylalkyl" (also "aralkyl") refers to any combination aryl group and an alkyl group. Arylalkyl groups include, but are not limited to, those groups derived from benzyl, tolyl, dimethylphenyl, 2-phenylethan-1-yl, 2-naphthylmethyl, and the like. An arylalkyl group comprises from 6 to 30 carbon atoms, for example the alkyl group can comprise from 1 to 10 carbon atoms and the aryl group can comprise from 5 to 20 carbon atoms.

"Bridged" refers to a ring fusion wherein non-adjacent atoms on a ring are joined by a divalent substituent, such as an alkylenyl or heteroalkylenyl group or a single heteroatom. Quinuclidinyl and admantanyl are examples of bridged ring systems.

The term "cycloalkyl" or "carbocycle" as used herein refers to a saturated or partially saturated all carbon ring radical. A cycloalkyl group can have one or more cyclic rings and includes fused and bridged groups that are fully saturated or partially unsaturated. Examples include, but are not limited to, cyclopropyl, cyclobutyl, cyclopentyl, cyclohexyl, adamantyl, methylcycloproyl (cyclopropylmethyl), ethylcyclopropyl, cyclohexenyl and the like. Another example includes $C_{5-7}$ cycloakenyl.

The term "cycloalkoxy" as used herein refers to a cycloalkyl group as defined herein appended directly to an —O— or to an alkoxy group as defined herein. Examples of cycloalkoxy groups include cyclopropyloxy, cyclobutylmethoxy, and cyclopentyloxyethyl.

"Heteroaryl" refers to mono or multicyclic aryl group in which one or more of the aromatic carbon atoms (and any associated hydrogen atoms) are independently replaced with the same or different heteroatom or heteroatomic group, as defined above. Multicyclic ring systems are included in heteroaryl and may be attached at the ring with the heteroatom or the aryl ring. Heteroaryl groups include, but are not limited to, groups derived from acridine, benzoimidazole, benzothiophene, benzofuran, benzoxazole, benzothiazole, carbazole, carboline, cinnoline, furan, imidazole, imidazopyridine, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyridone, pyrimidine, pyrrole, pyrrolizine, quinazoline, quinoline, quinolizine, quinoxaline, tetrazole, thiadiazole, thiazole, thiophene, triazole, xanthene, and the like. Heteroaryl groups may have 5-14 members, 5-10 members, or 5-6 members.

"Heterocycle," "heterocyclic," and "heterocyclyl" refer to a saturated or partially unsaturated non-aromatic ring or a partially non-aromatic multiple-ring system with at least one heteroatom or heteroatomic group, as defined above. Heterocycles include, but are not limited to, groups derived from azetidine, aziridine, imidazolidine, morpholine, oxirane (epoxide), oxetane, piperazine, piperidine, pyrazolidine, piperidine, pyrrolidine, pyrrolidinone, tetrahydrofuran, tetrahydrothiophene, dihydropyridine, tetrahydropyridine, tetrahydro-2H-thiopyran 1,1-dioxide, quinuclidine, N-bromopyrrolidine, N-chloropiperidine, and the like. Heterocyclyl groups also include partially unsaturated ring systems containing one or more double bonds, including fused ring systems with one aromatic ring and one non-aromatic ring, but not fully aromatic ring systems. Examples include dihydroquinolines, e.g. 3,4-dihydroquinoline, dihydroisoquinolines, e.g. 1,2-dihydroisoquinoline, dihydroimidazole, tetrahydroimidazole, etc., indoline, isoindoline, isoindolones (e.g. isoindolin-1-one), isatin, dihydrophthalazine, quinolinone, spiro[cyclopropane-1,1'-isoindolin]-3'-one, and the like. Heterocycle groups may have 3-12 members, or 3-10 members, or 3-7 members, or 5-6 members.

"Hydroxyl" and "hydroxy" are used interchangeably and refer to —OH. "Oxo" refers to =O. Where tautomeric forms of the compound exist, hydroxyl and oxo groups are interchangeable.

It is understood that combinations of chemical groups may be used and will be recognized by persons of ordinary skill in the art. For instance, the group "hydroxyalkyl" would refer to a hydroxyl group attached to an alkyl group. A great number of such combinations may be readily envisaged. Additional examples of substituent combinations used herein include: $C_{1-6}$ alkylamiocarbonyl (e.g. $CH_3CH_2NHC(O)$—) $C_{1-6}$ alkoxycarbonyl (e.g. $CH_3O$—C(O)—), 5-7 membered heterocyclyl-$C_{1-6}$ alkyl (e.g. piperazinyl-$CH_2$—), $C_{1-6}$ alkylsulfonyl-5-7 membered heterocyclyl (e.g. $CH_3S(O)_2$-morpholinyl-), 5-7 membered heterocyclyl $C_{1-6}$ alkoxy (e.g. pyrrolidinyl-O—), 5-7 membered heterocyclyloxy, (4-7 membered heterocyclyl)-4-7 membered heterocyclyl (e.g. oxetanyl-pyrrolidinyl-), $C_{3-6}$ cycloalkylaminocarbonyl (e.g. cyclopropyl-NH—C(O)—), 5-7 membered heterocyclyl-$C_{2-6}$ alkynyl (e.g. N-piperazinyl-$CH_2C{\equiv}CCH_2$—), and $C_{6-10}$ arylaminocarbonyl (e.g. phenyl-NH—C(O)—).

As used herein, "appended to the same group" indicates that multiple substituents or R-groups are bound to the same base group and cannot be bound or fused with other groups from different parts of the molecule. For example, "two $R^{20}$ groups appended to the same group join together to form a fused, spiro or bridged $C_{3-10}$ cylcloalkyl or 3-12 membered heterocyclyl ring," indicates that the $R^{20}$ groups capable of being fused, spiroed or bridged are bound together only with atoms from the group with which they were derived (e.g. $R^2$ exclusively) and not $R^{20}$ groups on different substituents (i.e. not $R^2$ and $R^3$).

Reference to the rings "A" and "B" are made by the letter designation. It is understood that "A" can be replaced with "ring A" or "B" can be replaced with "ring B".

"Spiro" refers to a ring substituent which is joined by two bonds at the same carbon atom. Examples of spiro groups include 1,1-diethylcyclopentane, dimethyl-dioxolane, and 4-benzyl-4-methylpiperidine, wherein the cyclopentane and piperidine, respectively, are the spiro substituents. When substituents (R-groups) are taken together (e.g. when $R^7$ and $R^8$ are taken together) they may be taken from the same point of attachment to form a spiro ring. "Fused" refers to a ring substituent which is joined by two bonds at adjacent carbon atoms, such as decahydronaphthalene. "Bridged" refers to a ring substituent which is joined by two bonds at the non-adjacent carbon atoms, such as a quinuclidine.

The nomenclature used herein to name the subject compounds is illustrated in the Examples and elsewhere herein.

As used herein, "treatment" or "treating" is an approach for obtaining beneficial or desired results. For purposes of the present disclosure, beneficial or desired results include, but are not limited to, alleviation of a symptom and/or diminishment of the extent of a symptom associated with a disease or condition. In one embodiment, "treatment" or "treating" includes one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

As used herein, "prevention" or "preventing" refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing HBV infection" refers to administering to a subject who does not have a detectable HBV infection an anti-HBV therapeutic substance. It is understood that the subject for anti-HBV preventative therapy may be an individual at risk of contracting the HBV virus.

As used herein, the term "therapeutically effective amount" or "effective amount" refers to an amount that is effective to elicit the desired biological or medical response, including the amount of a compound that, when administered to a subject for treating a disease, is sufficient to effect such treatment for the disease. The effective amount will vary depending on the particular compound, and characteristics of the subject to be treated, such as age, weight, etc. The effective amount can include a range of amounts. As is understood in the art, an effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds.

As used herein, "co-administration" includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Also provided herein are pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are suitable for veterinary or human pharmaceutical use.

Compounds described herein may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids or bases. For example, a compound that contains a basic nitrogen may be prepared as a pharmaceutically acceptable salt by contacting the compound with an inorganic or organic acid. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington: The Science and Practice of Pharmacy, 21$^{st}$ Edition, Lippincott Wiliams and Wilkins, Philadelphia, Pa., 2006.

Non-limiting examples of "pharmaceutically acceptable salts" of the compounds disclosed herein also include salts derived from an appropriate base, such as an alkali metal (for example, sodium, potassium), an alkaline earth metal (for example, magnesium), ammonium and $NX_4^+$ (wherein X is $C_1$-$C_4$ alkyl). Also included are base addition salts, such as sodium or potassium salts.

A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are non-superimposable mirror images of one another.

Compounds described herein may have chiral centers and/or geometric isomeric centers (E- and Z-isomers), and it is to be understood that the invention encompasses all such optical, enantiomeric, diastereoisomeric and geometric isomers. Where compounds are represented in their chiral form, it is understood that the embodiment encompasses, but is not limited to, the specific diastereomerically or enantiomerically enriched form. Where chirality is not specified but is present, it is understood that the embodiment is directed to either the specific diastereomerically or enantiomerically enriched form; or a racemic or scalemic mixture of such compound(s). As used herein, "scalemic mixture" is a mixture of stereoisomers at a ratio other than 1:1.

A "tautomer" refers to a proton shift from one atom of a molecule to another atom of the same molecule. The present disclosure includes tautomers of any said compounds.

A "solvate" is formed by the interaction of a solvent and a compound. Solvates of salts of the compounds described herein are also provided. Hydrates of the compounds described herein are also provided.

The term "prodrug" as used herein is a biologically inactive derivative of a drug that upon administration to the human body is converted to the biologically active parent drug according to some chemical or enzymatic pathway.

Compounds

The present disclosure provides compounds of Formula (I):

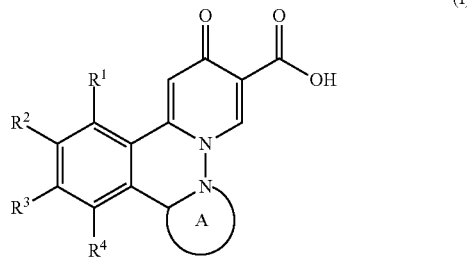

wherein:

A is a 4-7 membered cycloalkyl or heterocyclyl ring substituted with 0-8 $R^5$ groups;

$R^1$ is H or halogen;

$R^2$ is selected from the group consisting of halogen, $R^{2a}O$—, $C_{1-6}$ alkyl, $C_{3-10}$ cycloalkyl, 3-7 membered heterocyclyl, —$NR^aR^b$, —$S(O)_{0-2}R^a$, or —CN, wherein each $C_{1-6}$alkyl, $C_{3-10}$ cycloalkyl or 3-7 membered heterocyclyl is optionally substituted with 1-5 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-5 $R^{20}$ groups;

$R^3$ is selected from the group consisting of $R^{3a}O$—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —$NR^aR^b$, and —$S(O)_{0-2}R^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;

$R^{3a}$ is selected from the group consisting of H, $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

$R^4$ is H or halogen;

each $R^5$ is independently selected from the group consisting of $C_{1-6}$alkyl, $C_{1-6}$ alkoxy, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$OR^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein any two $R^5$ groups on the same carbon atom can optionally form a =O; and any two $R^5$ groups can optionally join together to form a $C_{3-6}$ cycloalkyl or 3-6 membered heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$; —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen.

The present disclosure provides compounds of Formula (Ia):

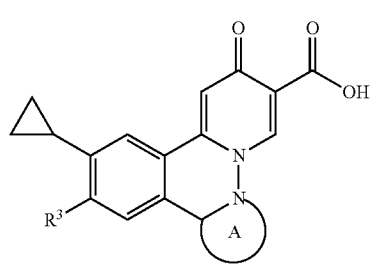

wherein:

A is a 4-7 membered cycloalkyl or heterocyclyl ring substituted with 0-8 $R^5$ groups;

$R^3$ is selected from the group consisting of $R^{3a}O$—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —$NR^aR^b$, and —$S(O)_{0-2}R^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;

$R^{3a}$ is selected from the group consisting of H, $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two R$^{20}$ groups appended to the same group can join together to form a fused, spiro or bridged C$_{3-10}$ cylcloalkyl or 3-12 membered heterocyclyl ring, wherein each C$_{1-6}$ alkyl, C$_{3-10}$ cycloalkyl, C$_{1-6}$ alkoxy, 3-12 membered heterocyclyl, C$_{6-10}$ aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$; —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$; and each R$^{21}$ is independently selected from the group consisting C$_{1-6}$ alkyl, C$_{1-6}$haloalkyl, C$_{3-10}$ cycloalkyl, C$_{1-6}$ alkoxy, 3-12 membered heterocyclyl, C$_{6-10}$ aryl, 5-10 membered heteroaryl, hydroxyl, amino, C$_{1-6}$ alkylamino, —CN or halogen;

or a pharmaceutically acceptable salt thereof.

In another embodiment, each R$^{21}$ is independently selected from the group consisting C$_{1-6}$ alkyl, C$_{3-10}$ cycloalkyl, C$_{1-6}$ alkoxy, 3-12 membered heterocyclyl, C$_{6-10}$ aryl, 5-10 membered heteroaryl, hydroxyl, amino, C$_{1-6}$ alkylamino, —CN or halogen.

The present disclosure provides compounds of Formula (Ib):

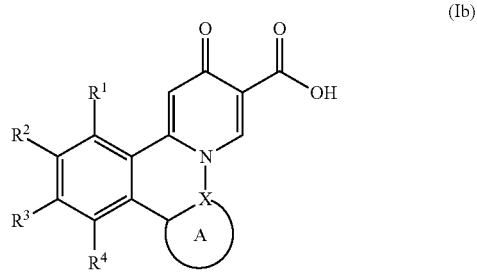

(Ib)

wherein:

A is a 4-7 membered cycloalkyl or heterocyclyl ring substituted with 0-8 R$^5$ groups;

X is CH or N;

R$^1$ is H or halogen;

R$^2$ is selected from the group consisting of halogen, R$^{2a}$O—, C$_{1-6}$ alkyl, C$_{3-10}$ cycloalkyl, 3-7 membered heterocyclyl, —NR$^a$R$^b$, —S(O)$_{0-2}$R$^a$, or —CN, wherein each C$_{1-6}$alkyl, C$_{3-10}$ cycloalkyl or 3-7 membered heterocyclyl is optionally substituted with 1-5 R$^{20}$ groups;

R$^{2a}$ is selected from the group consisting of H, C$_{3-6}$ cycloalkyl or C$_{1-6}$ alkyl, wherein each C$_{3-6}$ cycloalkyl or C$_{1-6}$ alkyl is optionally substituted with 1-5 R$^{20}$ groups;

R$^3$ is selected from the group consisting of R$^{3a}$O—, C$_{1-6}$ alkyl, 5-10 membered heteroaryl, 3-12 membered heterocyclyl, C$_{2-6}$ alkenyl, C$_{2-6}$ alkynyl, C$_{6-10}$ aryl, C$_{3-10}$ cycloalkyl, —NR$^a$R$^b$, and —S(O)$_{0-2}$R$^a$, wherein each C$_{1-6}$ alkyl, 5-10 membered heteroaryl, 3-12 membered heterocyclyl, C$_{2-6}$ alkenyl, C$_{2-6}$ alkynyl, C$_{6-10}$ aryl, or C$_{3-10}$ cycloalkyl is optionally substituted with 1-5 R$^{20}$ groups;

R$^{3a}$ is selected from the group consisting of H, C$_{1-6}$ alkyl, C$_{1-6}$ alkoxyC$_{1-6}$alkyl, 5-10 membered heteroaryl, 3-12 membered heterocyclyl, C$_{6-10}$ aryl and C$_{3-10}$ cycloalkyl, wherein each C$_{1-6}$ alkyl, C$_{1-6}$ alkoxyC$_{1-6}$alkyl, 5-10 membered heteroaryl, 3-12 membered heterocyclyl, C$_{6-10}$ aryl and C$_{3-10}$ cycloalkyl is optionally substituted with 1-5 R$^{20}$ groups;

R$^4$ is H or halogen;

each R$^5$ is independently selected from the group consisting of C$_{1-6}$ alkyl, C$_{1-6}$ alkoxy, C$_{2-6}$ alkenyl, C$_{2-6}$ alkynyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —OR$^a$, C$_{6-10}$ aryl, C$_{3-10}$ cycloalkyl, 5-10 membered heteroaryl and 3-12 membered heterocyclyl, wherein each C$_{1-6}$ alkyl, C$_{1-6}$ alkoxy, C$_{2-6}$ alkenyl, C$_{2-6}$ alkynyl, C$_{6-10}$ aryl, C$_{3-10}$ cycloalkyl, 5-10 membered heteroaryl and 3-12 membered heterocyclyl is optionally substituted with 1-5 R$^{20}$ groups;

wherein any two R$^5$ groups on the same carbon atom can optionally form a =O; and any two R$^5$ groups can optionally join together to form a C$_{3-6}$ cycloalkyl or 3-6 membered heterocyclyl ring optionally substituted with 1-3 R$^{21}$ groups;

each R$^a$ and R$^b$ is independently selected from the group consisting H; or C$_{1-6}$ alkyl, C$_{3-10}$ cycloalkyl, 3-12 membered heterocyclyl, C$_{6-10}$ aryl, 5-10 membered heteroaryl, each of which is optionally substituted with from one to five R$^{21}$ groups; or R$^a$ and R$^b$ together with the atoms to which they are attached form a 3-12 membered heterocyclyl optionally substituted with one to five R$^{21}$ groups;

each R$^{20}$ is independently selected from the group consisting C$_{1-6}$ alkyl, C$_{3-10}$ cycloalkyl, C$_{1-6}$ alkoxy, 3-12 membered heterocyclyl, C$_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two R$^{20}$ groups appended to the same group can join together to form a fused, spiro or bridged C$_{3-10}$ cylcloalkyl or 3-12 membered heterocyclyl ring, wherein each C$_{1-6}$ alkyl, C$_{3-10}$ cycloalkyl, C$_{1-6}$ alkoxy, 3-12 membered heterocyclyl, C$_{6-10}$ aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$; and each R$^{21}$ is independently selected from the group consisting C$_{1-6}$ alkyl, C$_{1-6}$haloalkyl, C$_{3-10}$ cycloalkyl, C$_{1-6}$ alkoxy, 3-12 membered heterocyclyl, C$_{6-10}$ aryl, 5-10 membered heteroaryl, hydroxyl, amino, C$_{1-6}$ alkylamino, —CN or halogen;

or a pharmaceutically acceptable salt thereof.

In another embodiment, each R$^{21}$ is independently selected from the group consisting C$_{1-6}$ alkyl, C$_{3-10}$ cycloalkyl, C$_{1-6}$ alkoxy, 3-12 membered heterocyclyl, C$_{6-10}$ aryl, 5-10 membered heteroaryl, hydroxyl, amino, C$_{1-6}$ alkylamino, —CN or halogen.

The present disclosure provides compounds of Formula (Ic):

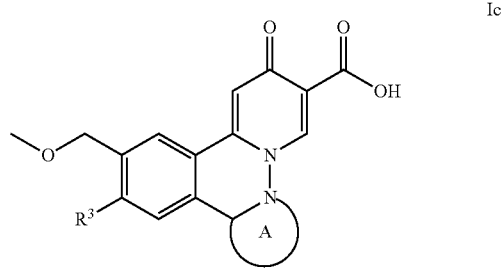

Ic wherein:

A is a 4-7 membered cycloalkyl or heterocylyl ring substituted with 0-8 $R^5$ groups;

$R^1$ is H or halogen;

$R^3$ is selected from the group consisting of $R^{3a}O$—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —$NR^aR^b$, and —$S(O)_{0-2}R^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;

$R^{3a}$ is selected from the group consisting of H, $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

$R^4$ is H or halogen;

each $R^5$ is independently selected from the group consisting of $C_{1-6}$ alkyl, $C_{1-6}$ alkoxy, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$OR^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein any two $R^5$ groups on the same carbon atom can optionally form a =O; and any two $R^5$ groups can optionally join together to form a $C_{3-6}$ cycloalkyl or 3-6 membered heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —$CN$, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$; —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —$CN$, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —$CN$ or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —$CN$ or halogen;

In another embodiment, X is N. In another embodiment, X is CH.

The following embodiments are inclusive of definitions for Formula (I), Formula (Ia), Formula (Ib), Formula (II) and/or Formula (IIa).

In one embodiment, $R^2$ is selected from the group consisting of halogen, $C_{3-10}$ cycloalkyl, $C_{3-10}$ cycloalkoxy, $C_{1-6}$ alkyl, $C_{1-6}$alkoxy, or —$CN$, wherein each $C_{3-10}$ cycloalkyl, $C_{4-10}$ cycloalkoxy, $C_{1-6}$ alkyl, $C_{1-6}$alkoxy is optionally substituted with halo. In another embodiment, $R^2$ is selected from the group consisting of chloro, methoxy, ethoxy, —$OCH(CH_3)_2$, $OC(CH_3)_3$, cyclopropyl, —$OCHF_2$ and

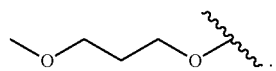 [SMILES: *OCCCOC]

In another embodiment, $R^2$ is halogen. In another embodiment, $R^2$ is chloro. In another embodiment, $R^2$ is methoxy. In another embodiment, $R^2$ is $C_{3-6}$cycloalkyl. In another embodiment, $R^2$ is cyclopropyl, or a pharmaceutically acceptable salt thereof. In another embodiment, $R^2$ is 3-7 membered heterocyclyl. In another embodiment, $R^2$ is oxetanyl. In another embodiment, $R^2$ is oxetan-3-yl.

In another embodiment, $R^2$ is $R^{2a}O$—. In another embodiment, $R^{2a}$ is $C_{3-6}$ cycloalkyl optionally substituted with 1-2 $R^{20}$ groups. In another embodiment, $R^{2a}$ is cyclopropyl. In another embodiment, $R^{2a}$ is $C_{1-6}$ alkyl. In another embodiment, $R^{2a}$ is $C_{3-6}$ cycloalkyl$C_{1-6}$alkyl. In another embodiment, $R^{2a}$ is $C_{6-10}$ aryl$C_{1-6}$alkyl. In another embodiment, $R^{2a}$ is 3-7 membered heterocyclyl$C_{1-6}$alkyl. In another embodiment, $R^{2a}$ is 5-7 membered heteroaryl$C_{1-6}$alkyl. In another embodiment, $R^{2a}$ is $C_{1-6}$ haloalkyl. In another embodiment, $R^{2a}$ is —$CF_3$.

In another embodiment, $R^2$ is —$CH_2OCH_3$ (methoxymethyl). In another embodiment, $R^2$ is $C_{1-3}$ alkoxymethyl.

In another embodiment, $R^2$ is $C_{3-6}$ cycloalkyl substituted with 1-3 fluoro groups. More particularly, 2 fluoro groups. More particularly, 2 fluoro groups on the same carbon.

In another embodiment, $R^3$ is selected from $C_{1-6}$ alkoxy, $C_{1-6}$alkoxy$C_{1-6}$alkoxy, and $C_{3-8}$cycloalkoxy$C_{1-6}$alkoxy, halo$C_{1-3}$ alkyl$C_{3-6}$cycloalkylaminocarbonyloxy$C_{2-6}$alkoxy, wherein each $C_{1-6}$ alkoxy, $C_{1-6}$alkoxy$C_{1-6}$alkoxy, and $C_{3-8}$cycloalkoxy$C_{1-6}$alkoxy is optionally substituted with halo. In another embodiment, $R^3$ is $C_{1-6}$alkoxy$C_{1-6}$alkoxy or $C_{1-6}$haloalkoxy$C_{1-6}$alkoxy.

In another embodiment, $R^3$ is $C_{3-6}$halocycloalkyloxy$C_{3-6}$alkyoxy. In another embodiment, $R^3$ is halo$C_{1-3}$alkyl$C_{3-6}$cycloalkylaminocarbonyloxy$C_{2-6}$alkoxy.

In another embodiment, $R^3$ is selected from the group consisting of $C_{2-6}$ alkenyl, $C_{6-10}$ aryl, 3-7 membered heterocyclyl, $C_{3-6}$ cycloalkyl, $C_{1-6}$ alkoxy$C_{1-6}$alkyl, $C_{3-6}$ cycloalkyl$C_{1-6}$alkyl, 5-10 membered heteroaryl, $C_{2-6}$ alkynyl, each optionally substituted with 1-3 $R^{20}$ groups. In another embodiment, $R^3$ is $C_{3-6}$ cycloalkyl. In another embodiment, $R^3$ is $C_{3-6}$ cycloalkoxy.

In another embodiment, $R^3$ is $C_{1-6}$ alkoxy$C_{1-6}$alkyl. In another embodiment, $R^3$ is $C_{3-6}$ cycloalkyl$C_{1-6}$alkyl.

In another embodiment, $R^3$ is $C_{2-6}$ alkynyl optionally substituted with 1-3 $R^{20}$ groups. More particularly, the $C_{2-6}$ alkynyl group is substituted with heteroaryl or $C_{1-6}$alkoxy$C_{1-6}$alkyl, each optionally substituted with 1-3 methyl groups.

In another embodiment $R^3$ is $R^{3a}O$—, wherein $R^{3a}$ is optionally substituted with 1-3 $R^{20}$ groups. In another embodiment, $R^{3a}$ is $C_{3-6}$ cycloalkyl. In another embodiment, $R^{3a}$ is $C_{3-6}$ cycloalkyl$C_{1-6}$ alkyl, wherein the $C_{3-6}$ cycloalkyl is optionally substituted with oxo or 1-3 fluoro groups. In another embodiment, $R^{3a}$ is 5-10 membered heteroaryl. In another embodiment, $R^{3a}$ is 3-7 membered heterocyclyl$C_{1-6}$alkyl. In another embodiment, $R^{3a}$ is $C_{1-6}$haloalkoxy$C_{1-6}$alkyl. In another embodiment, $R^{3a}$ is $C_{1-6}$ alkyl substituted with $R^{20}$ selected from $C_{3-6}$ cycloalkyl, $C_{6-10}$ aryl, 3-7 membered heterocyclyl, 5-7 membered heteroaryl. In another embodiment $R^{3a}$ is 5-10 membered heteroaryl, 3-12 membered heterocyclyl or $C_{6-10}$ aryl.

In another embodiment, $R^3$ is selected from the group consisting of:

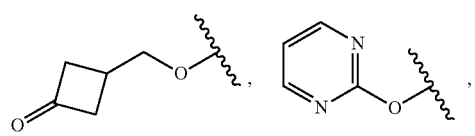

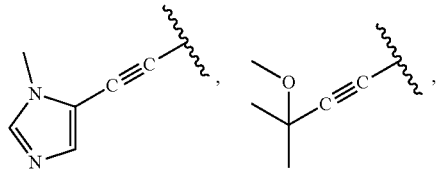

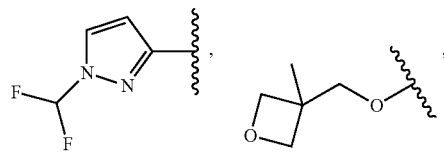

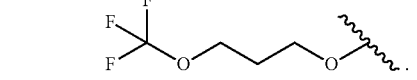

and

In another embodiment, $R^3$ is

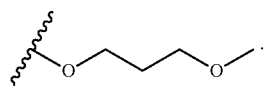 [SMILES: *OCCCOC]

In another embodiment, $R^3$ is not

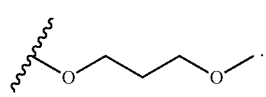

In another embodiment, $R^3$ is selected from the group consisting of:

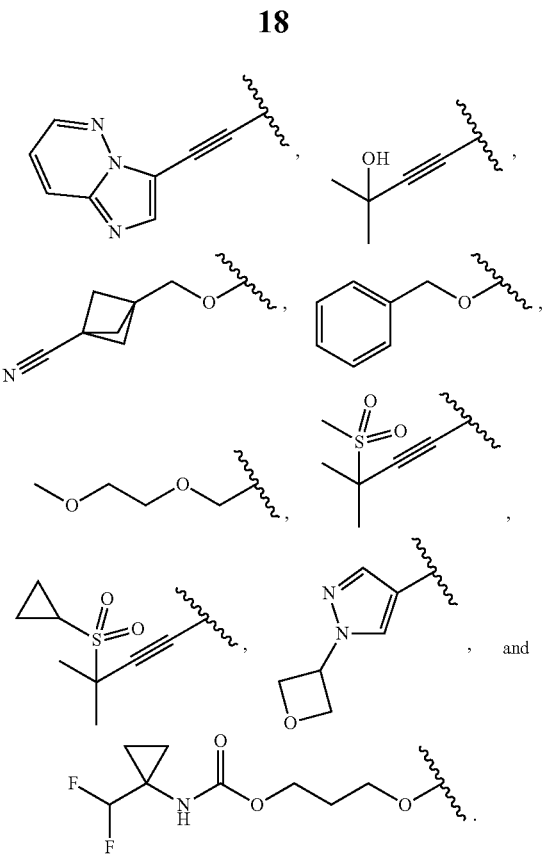

In another embodiment, $R^3$ is

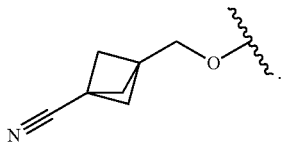 [SMILES: *OCC12CC(C#N)(C1)C2]

In another embodiment, $R^3$ is selected from a group consisting of:

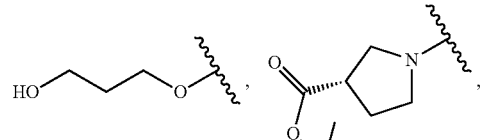

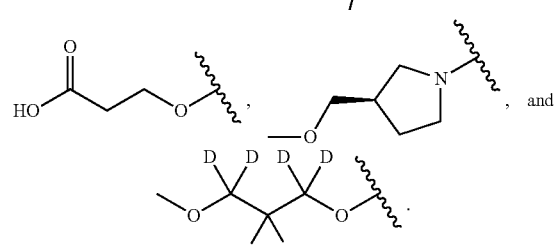

In another embodiment, $R^1$ and $R^4$ are both H. In another embodiment, $R^4$ is bromo. In another embodiment, $R^1$ is bromo. In another embodiment, R¹ is H. In another embodiment, R⁴ is H. In another embodiment, one of R¹ or R⁴ is halo.

In another embodiment, at least one of R⁵ is $C_{1-3}$ alkyl optionally substituted with halo. In another embodiment, at least two R⁵ groups are $C_{1-3}$ alkyl. In another embodiment, at least two R⁵ groups are methyl, or a pharmaceutically acceptable salt thereof. In another embodiment, at least two R⁵ groups are methyl bound at the same carbon atom, or a pharmaceutically acceptable salt thereof. In another embodiment, two R⁵ groups join together at the same carbon atom to form a cyclopropyl, or a pharmaceutically acceptable salt thereof. In another embodiment, the compound of Formula (I) or (II), or Formula (Ia), (Ib) or (IIa), is/are substituted with 0-7, 0-6, 0-5, 0-4, 0-3 or 0-2R⁵ groups.

In another embodiment, R¹ and R⁴ are both H. In another embodiment, R¹ and R⁴ are both H and R² is cyclopropyl.

In another embodiment, two R⁵ groups join together at the same carbon atom to form a $C_{3-6}$ cycloalkyl or 3-6 membered heterocyclyl ring, each optionally substituted with 1-3 R²⁰ groups.

In another embodiment, each R²⁰ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$.

In another embodiment, each of R², R$^{2a}$, R³, R$^{3a}$ and R⁵ are substituted with 0-5, 0-4, 0-3, 0-2 or 0-1R²⁰ groups. In another embodiment, each R$^a$ or R$^b$ group is substituted with 0-5, 0-4, 0-3, 0-2 or 0-1R²¹ groups. In another embodiment, In some embodiments, R² is $C_{1-6}$alkoxy$C_{1-6}$alkoxy. In some embodiments, R² is selected from

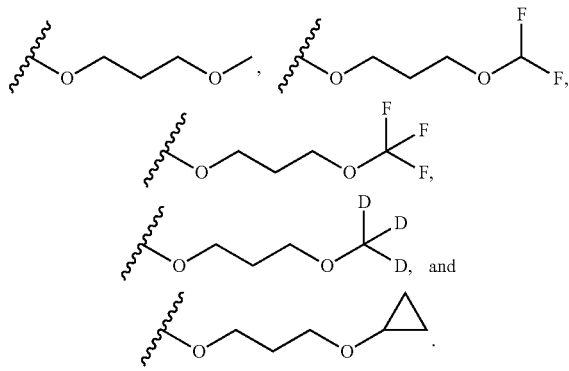

In certain embodiments, ring A is selected from the group consisting of:

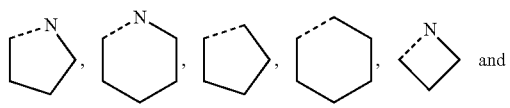

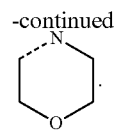

In another embodiment, ring A from Formula (I) or Formula (Ia) or Formula (Ib) is:

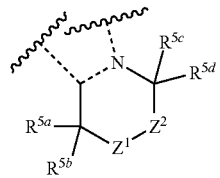

wherein:
Z¹ is a bond, O, NR$^a$ or CR$^{5e}$R$^{5f}$;
Z² is a bond, O, NR$^a$ or CR$^{5g}$R$^{5h}$;
provided only one of Z¹ and Z² is O or NR$^a$;
each of R$^{5a}$, R$^{5b}$, R$^{5c}$, R$^{5d}$, R$^{5e}$, R$^{5f}$R$^{5g}$ and R$^{5h}$ are independently selected from the group consisting of H, $C_{1-6}$ alkyl, $C_{1-6}$ alkoxy, $C_{2-6}$ alkenyl, $C_{2-6}$ alkynyl, —NR$^a$R$^b$, halogen, C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$R$^a$; —S(O)$_2$NR$^a$R$^b$, —NR$^a$S(O)$_2$R$^b$, —N$_3$, —CN, —NO$_2$, —OR$^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 R²⁰ groups;
wherein up to two of R$^{5a}$ and R$^{5b}$, R$^{5c}$ and R$^{5d}$, R$^{5e}$ and R$^{5f}$, or R$^{5g}$ and R$^{5h}$ can form a =O;
wherein any two of R$^{5a}$, R$^{5b}$, R$^{5c}$, R$^{5d}$, R$^{5e}$, R$^{5f}$, R$^{5g}$ and R$^{5h}$ can join together to form a cycloalkyl or heterocyclyl ring optionally substituted with 1-3 R²¹ groups;
each R$^a$ and R$^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five R²¹ groups; or R$^a$ and R$^b$ together with the atoms to which they are attached form a 3-12 membered heterocyclyl optionally substituted with one to five R²¹ groups;
each R²⁰ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two R²⁰ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$; —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$; and
each R²¹ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;
or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen.

In another embodiment, $Z^2$ is $CR^{5g}R^{5h}$. In another embodiment, $R^{5g}$ and $R^{5h}$ are H or $CH_3$.

Another embodiment of the present invention provides a compound of Formula (II):

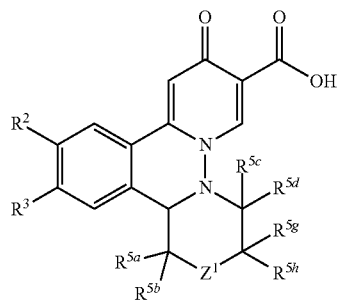

II wherein:

$Z^1$ is a bond, O, $NR^a$ or $CR^{5e}R^{5f}$;

$R^2$ is selected from the group consisting of halogen, $R^{2a}O—$, $C_{1-6}$ alkyl, or —CN, wherein $C_{1-6}$alkyl is optionally substituted with 1-3 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-3 $R^{20}$ groups;

$R^3$ is selected from $C_{1-6}$ alkoxy, $C_{1-6}$alkoxy$C_{1-6}$alkoxy, and $C_{3-8}$cycloalkoxy$C_{1-6}$alkoxy, wherein each $C_{1-6}$ alkoxy, $C_{1-6}$alkoxy$C_{1-6}$alkoxy, and $C_{3-8}$cycloalkoxy$C_{1-6}$alkoxy is optionally substituted with halo;

each of $R^{5a}$, $R^{5b}$, $R^{5c}$, $R^{5d}$, $R^{5e}$, $R^{5f}$, $R^{5g}$ and $R^{5h}$ are independently selected from the group consisting of H, $C_{1-6}$ alkyl, $C_{1-6}$ alkoxy, $C_{2-6}$ alkenyl, $C_{2-6}$ alkynyl, —$NR^aR^b$, halogen, $C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein up to two of $R^{5a}$ and $R^{5b}$, $R^{5c}$ and $R^{5d}$, $R^{5e}$ and $R^{5f}$, or $R^{5g}$ and $R^{5h}$ can optionally form a =O; and wherein any two of $R^{5a}$, $R^{5b}$, $R^{5c}$, $R^{5d}$, $R^{5e}$, $R^{5f}/R^{5g}$ and $R^{5h}$ can optionally join together to form a cycloalkyl or heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS$ $(O)_2R^b$, —$N_3$, —CN, or —$NO_2$, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$; —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$ haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen.

In another embodiment, $Z^1$ is O.

Another embodiment provides a compound of Formula (IIa):

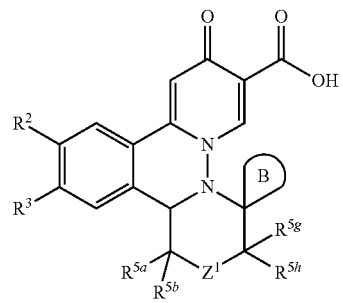

IIa wherein:

B is a 3-6 membered cycloalkyl or 3-6 membered heterocyclyl ring each substituted with 0-2 $R^{21}$ groups;

$Z^1$ is a bond, O, $NR^a$ or $CR^{5e}R^{5f}$;

$R^2$ is selected from the group consisting of halogen, $R^{2a}O—$, $C_{1-6}$ alkyl, or —CN, wherein $C_{1-6}$alkyl is optionally substituted with 1-3 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-3 $R^{20}$ groups;

$R^3$ is selected from $C_{1-6}$ alkoxy, $C_{1-6}$alkoxy$C_{1-6}$alkoxy, and $C_{3-8}$cycloalkoxy$C_{1-6}$alkoxy, wherein each $C_{1-6}$ alkoxy, $C_{1-6}$alkoxy$C_{1-6}$alkoxy, and $C_{3-8}$cycloalkoxy$C_{1-6}$alkoxy is optionally substituted with halo;

each of $R^{5a}$, $R^{5b}R^{5e}$, $R^{5f}R^{5g}$ and $R^{5h}$ are independently selected from the group consisting of H, $C_{1-6}$ alkyl, $C_{1-6}$ alkoxy, $C_{2-6}$ alkenyl, $C_{2-6}$ alkynyl, —$NR^aR^b$, halogen, $C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein up to two of $R^{5a}$ and $R^{5b}$, $R^{5e}$ and $R^{5f}$, or $R^{5g}$ and $R^{5h}$ can optionally form a =O; and wherein any two of $R^{5a}$, $R^{5b}$, $R^{5e}$, $R^{5f}/R^{5g}$ and $R^{5h}$ can optionally join together to form a cycloalkyl or heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$; —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$ haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

In another embodiment, each $R^{21}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen.

In another embodiment, B is selected from the group consisting of oxetanyl, 2,2-dimethyl-1,3-dioxanyl, or cyclopropyl.

In another embodiment, $Z^1$ is O.

The following embodiments are inclusive of definitions for Formula (I), (Ia), (Ib), and/or (II) or (IIa).

In another embodiment, $Z^1$ is a bond. In another embodiment, $Z^1$ is $CR^eR^{5f}$. In another embodiment, $Z^1$ is O.

In another embodiment, $R^{5e}$ and $R^{5f}$ are H, halo, or $C_{1-3}$ alkyl. In another embodiment, $R^{5c}$ and $R^{5d}$ are H. In another embodiment, $R^{5c}$ and $R^{5d}$ are $C_{1-3}$ alkyl. In another embodiment, $R^{5c}$ and $R^{5d}$ are $CH_3$. In another embodiment, $R^{5c}$ is H and $R^{5d}$ is $CH_3$. In another embodiment, $R^{5c}$ and $R^{5d}$ are taken together to form cyclopropyl. In another embodiment, $R^{5a}$ and $R^{5b}$ are H. In another embodiment, $R^{5a}$ and $R^{5b}$ are $CH_3$. In another embodiment, $R^{5g}$ and $R^{5h}$ are H. In another embodiment, $R^{5g}$ and $R^{5h}$ are $CH_3$, or a pharmaceutically acceptable salt thereof.

In another embodiment, $R^{5c}$ and $R^{5d}$ are taken together to form a $C_{3-6}$ cycloalkyl or 3-6 membered heterocyclyl ring. In another embodiment, $R^{5c}$ and $R^{5d}$ are taken together to form a $C_{3-6}$ cycloalkyl. In another embodiment, $R^{5c}$ and $R^{5d}$ are taken together to form cyclopropyl or cyclobutyl.

In another embodiment, $R^{5a}$ and $R^{5b}$ are taken together to form a ring selected from the group consisting of oxetanyl, 2,2-dimethyl-1,3-dioxanyl, or cyclopropyl.

In another embodiment, $R^{5a}$ and $R^{5b}$ are both methoxymethyl.

In one embodiment, the compounds are selected from the group consisting of:

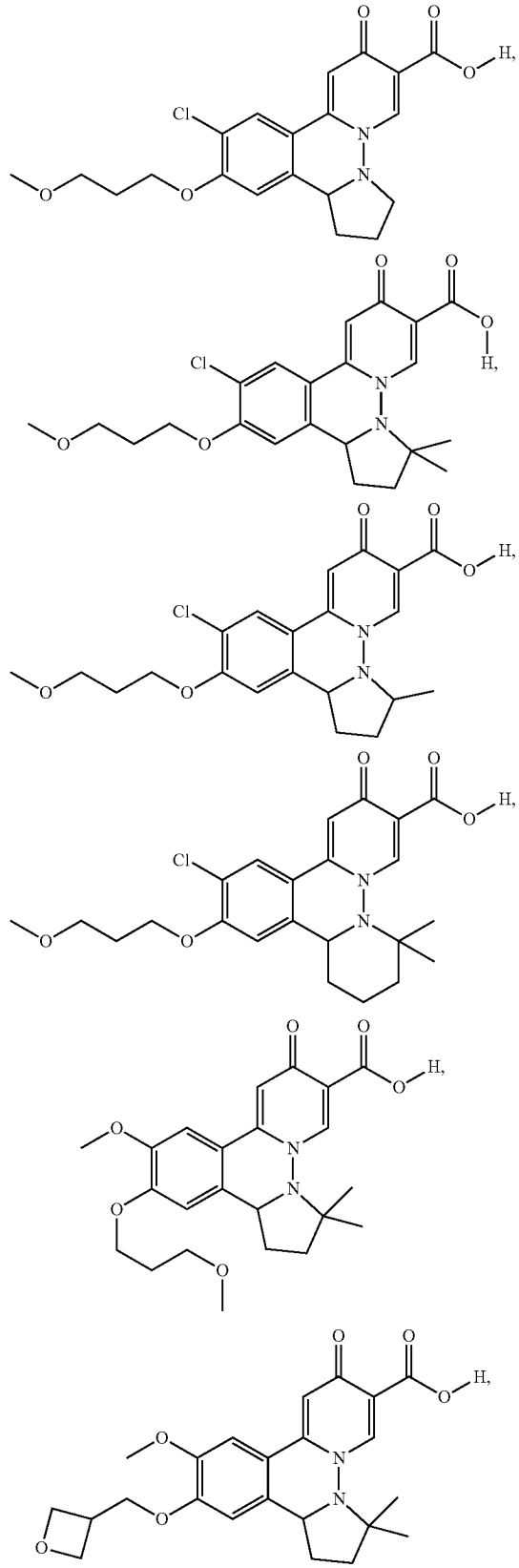

25
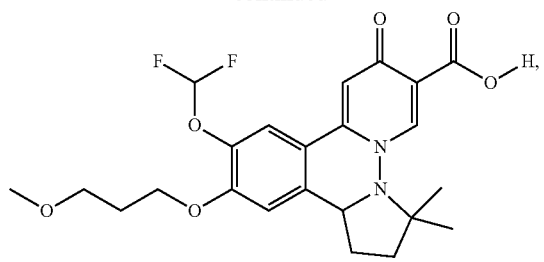
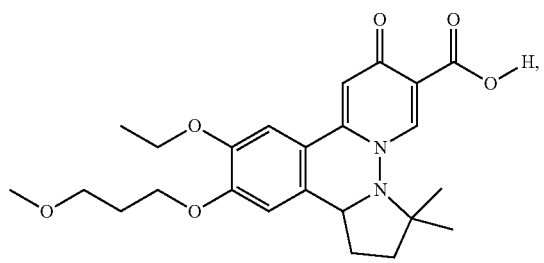
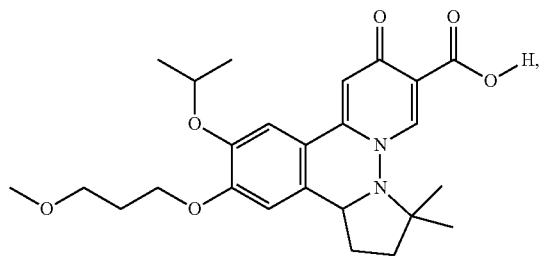
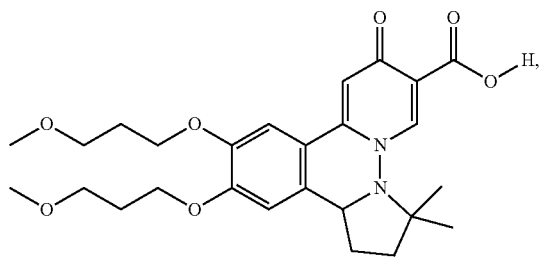
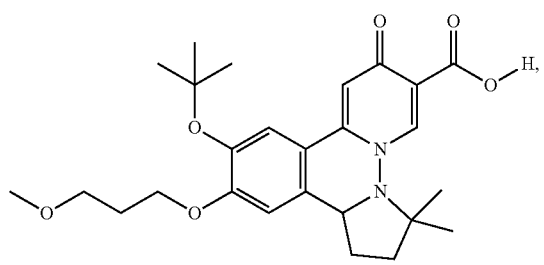
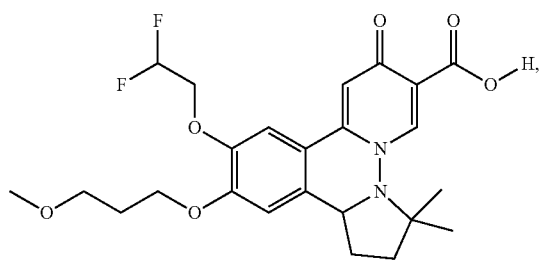
26
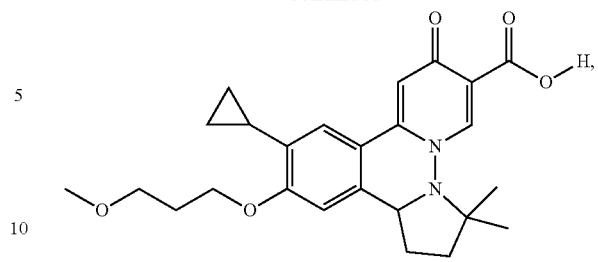
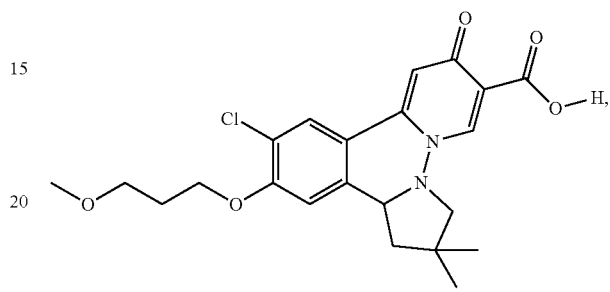
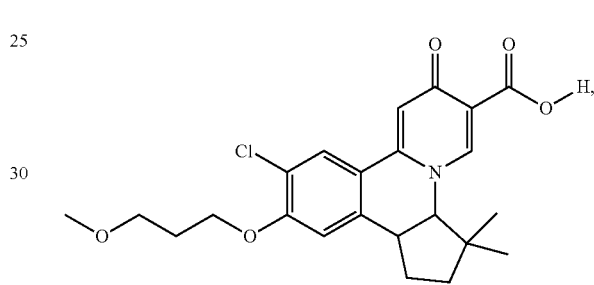
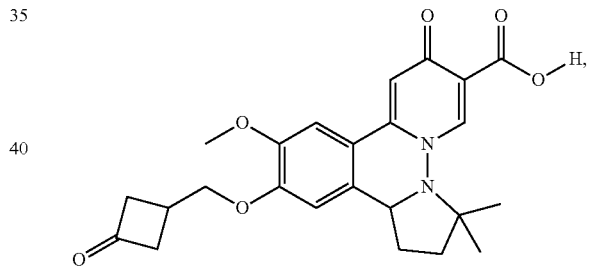
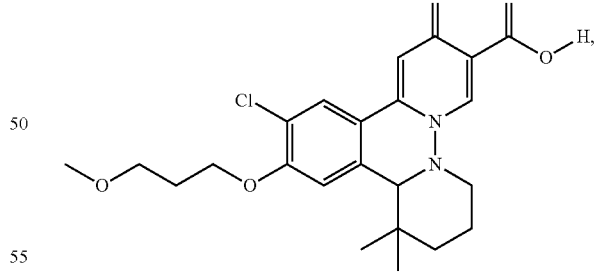
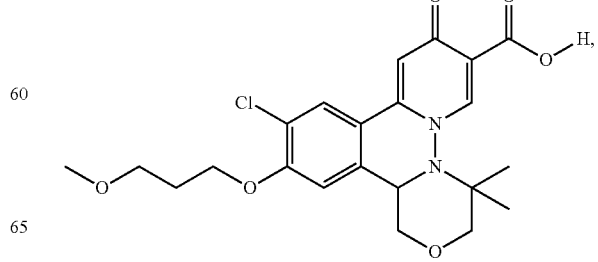

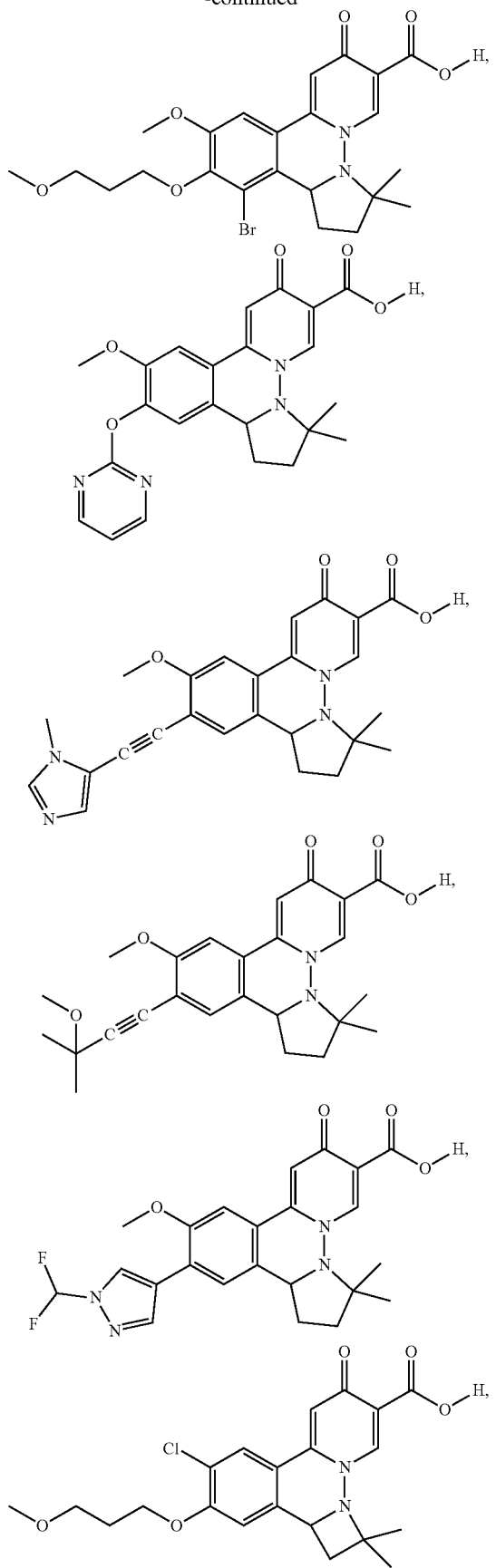
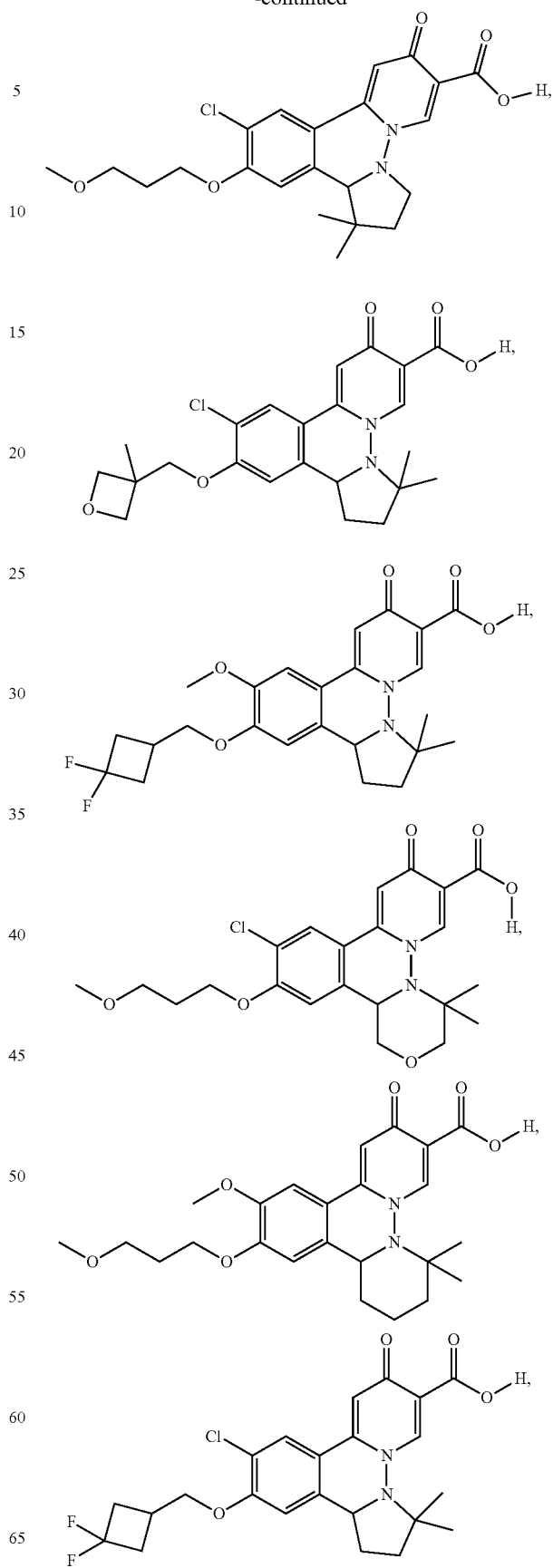

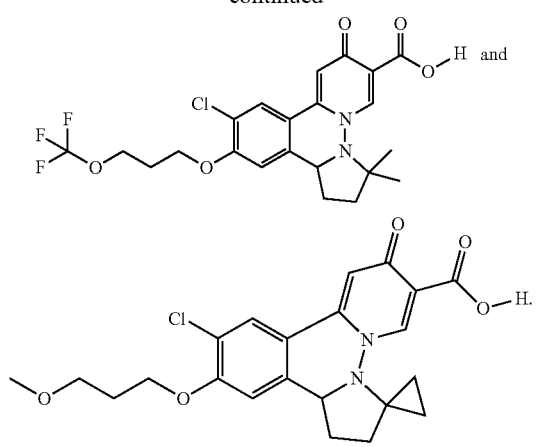
It is understood that the compounds depicted without stereochemistry encompass all such optical, enantiomeric, diastereoisomeric and geometric isomers as well as scalemic and racemic mixtures thereof.
In another embodiment, the compounds are selected from the group consisting of:
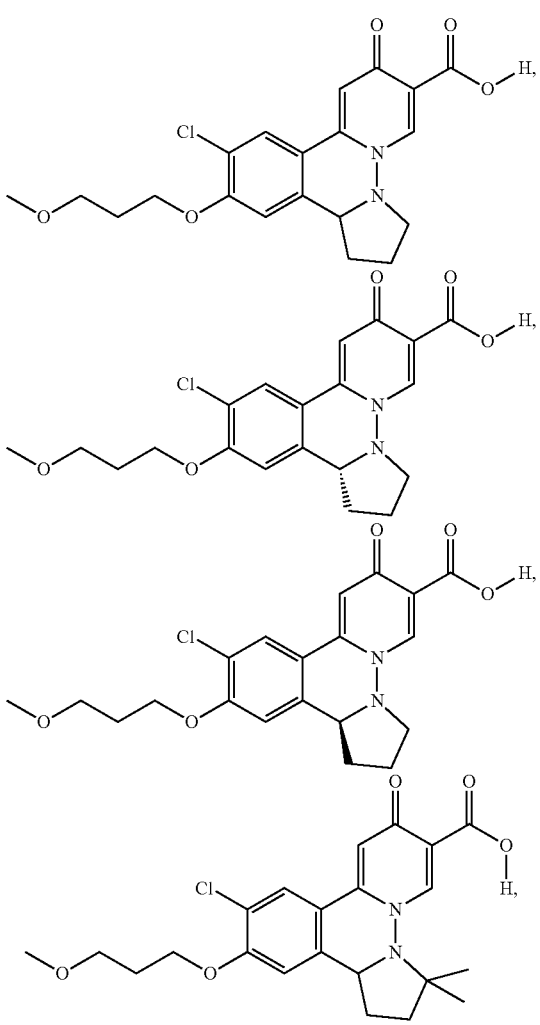
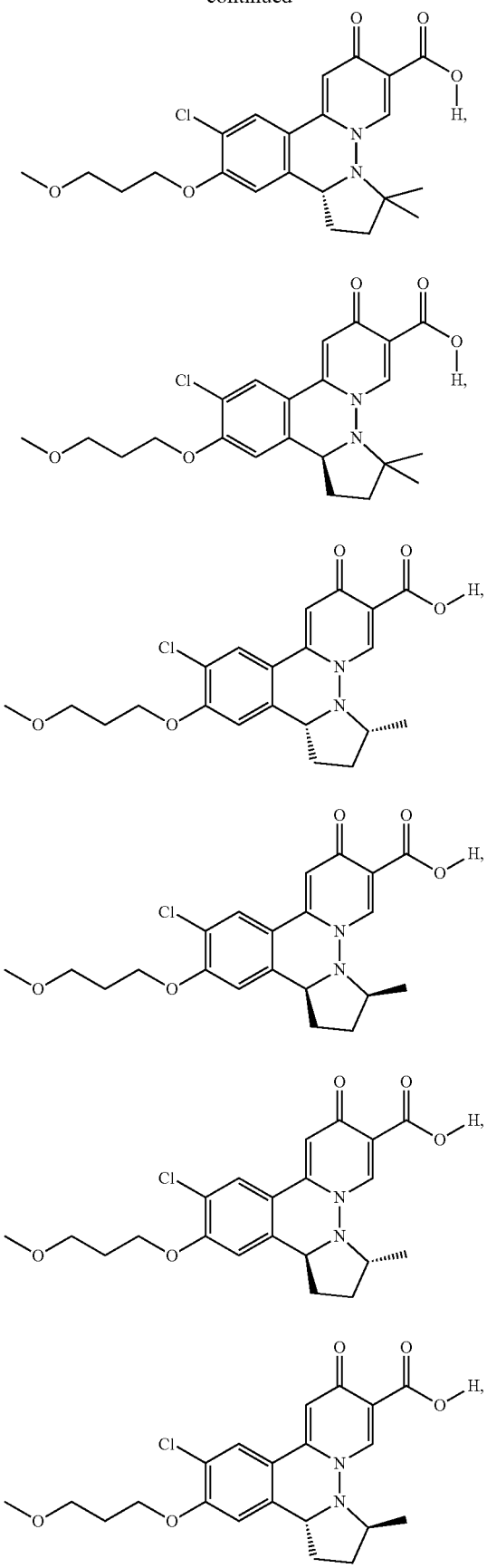

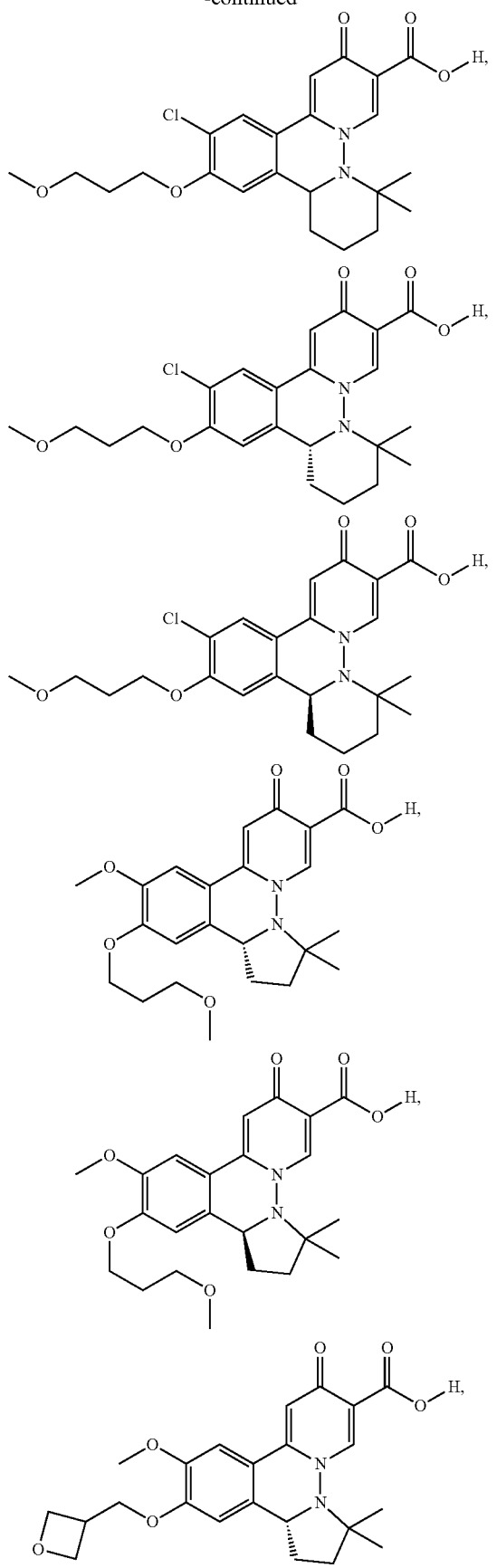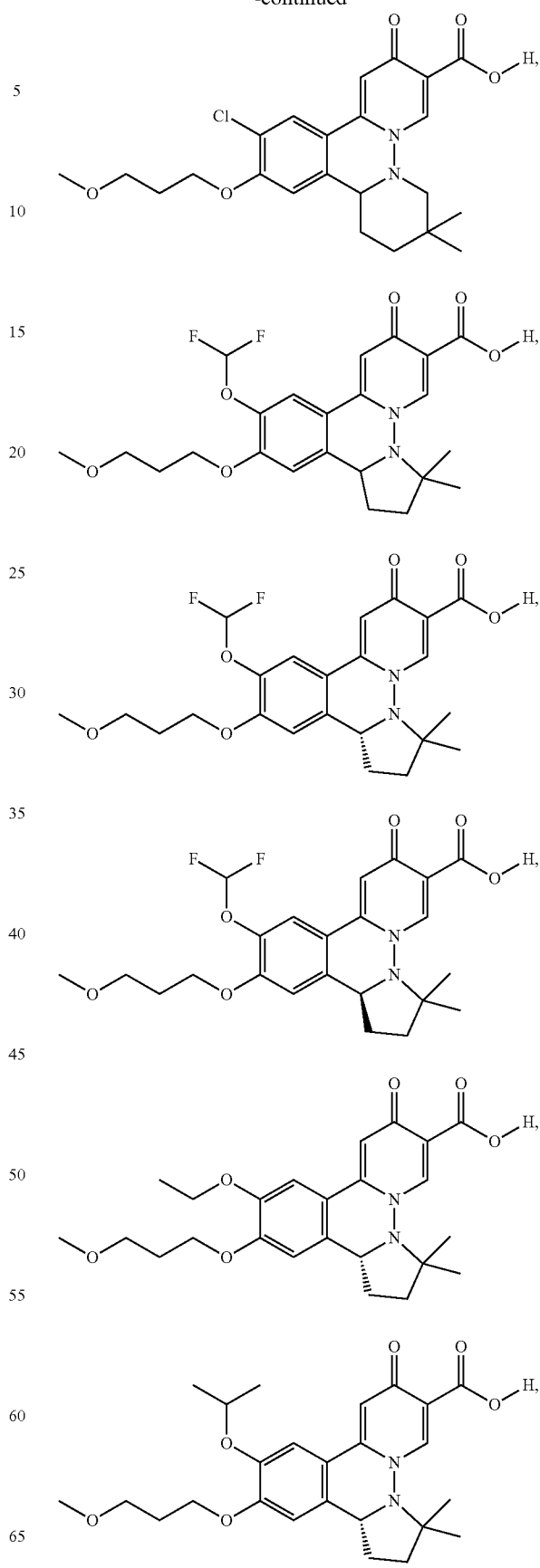

33
-continued
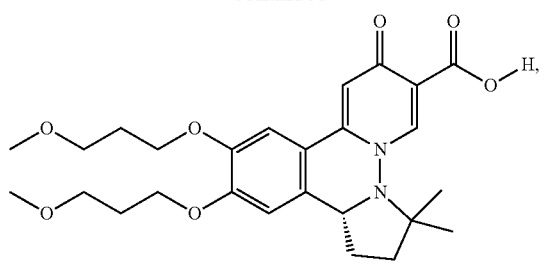
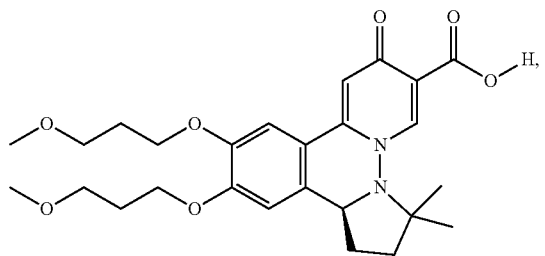
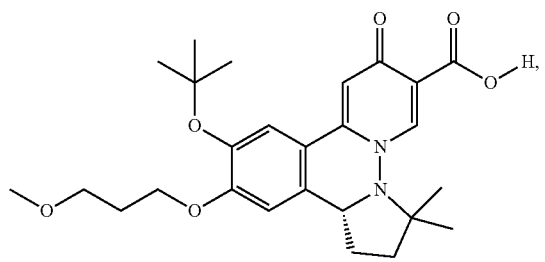
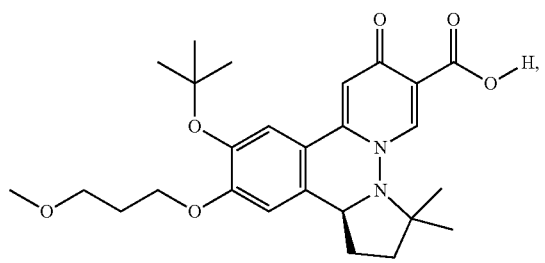
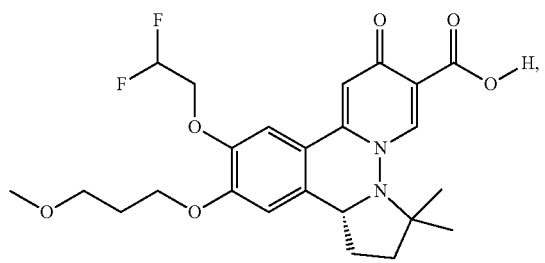
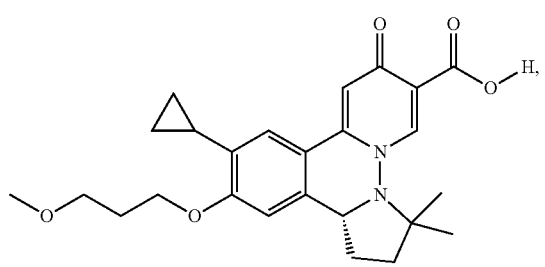
34
-continued
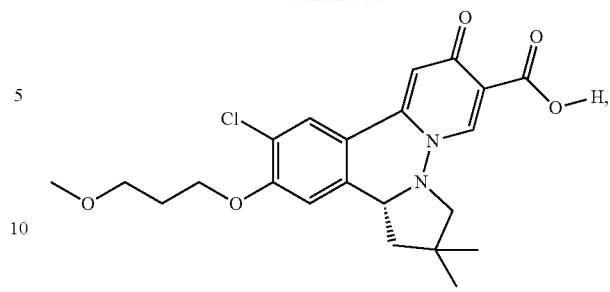
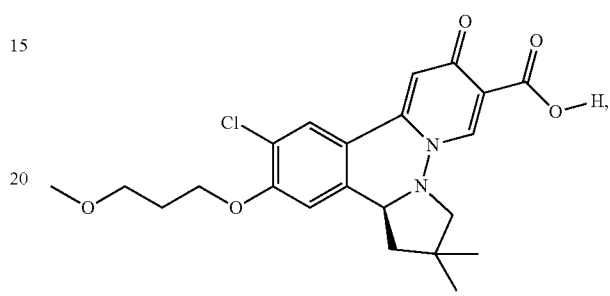
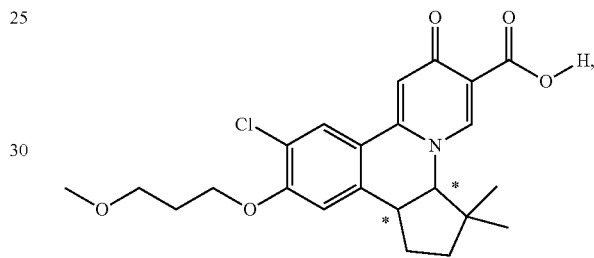
*cis isomer
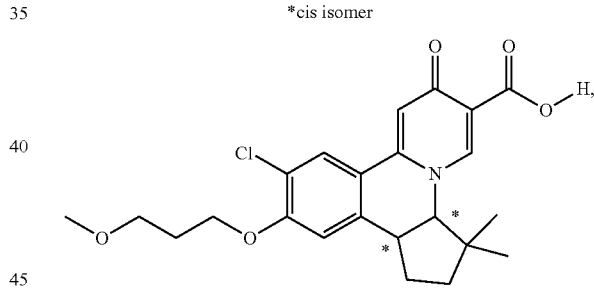
*trans isomer
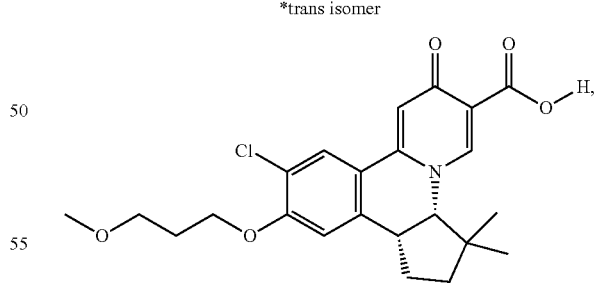
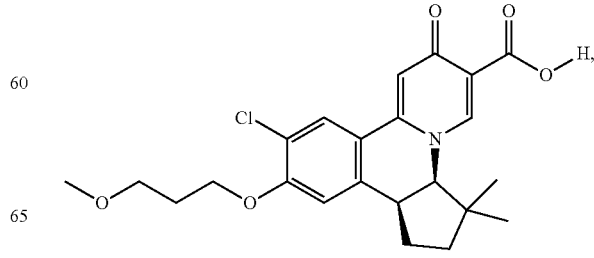

35
-continued
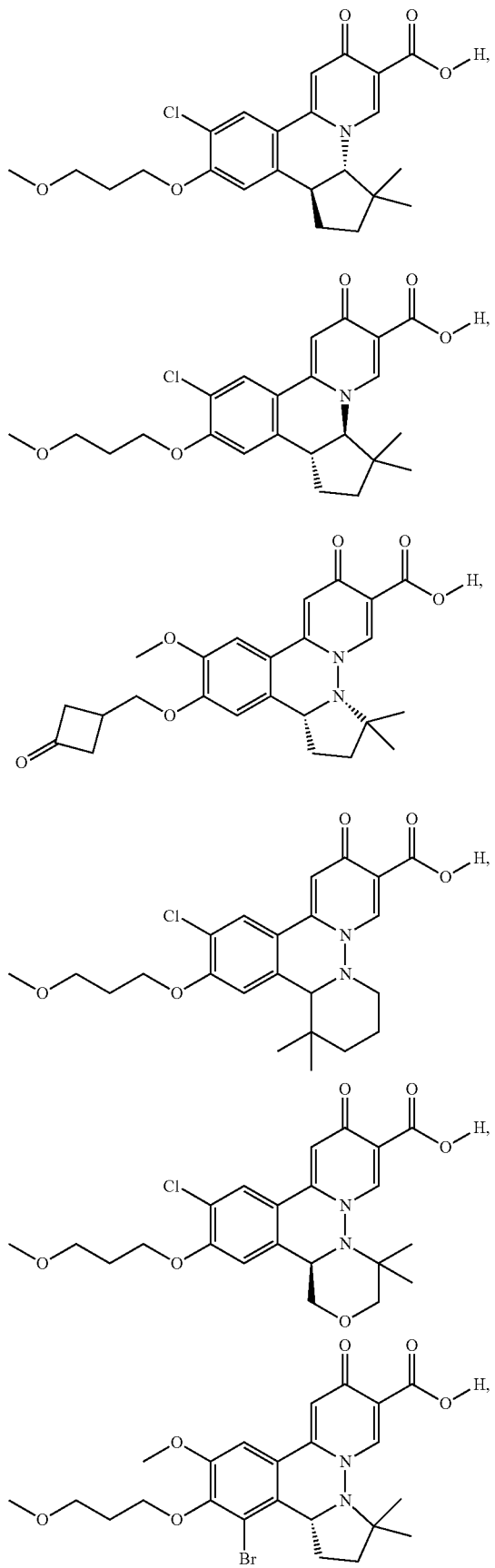
36
-continued
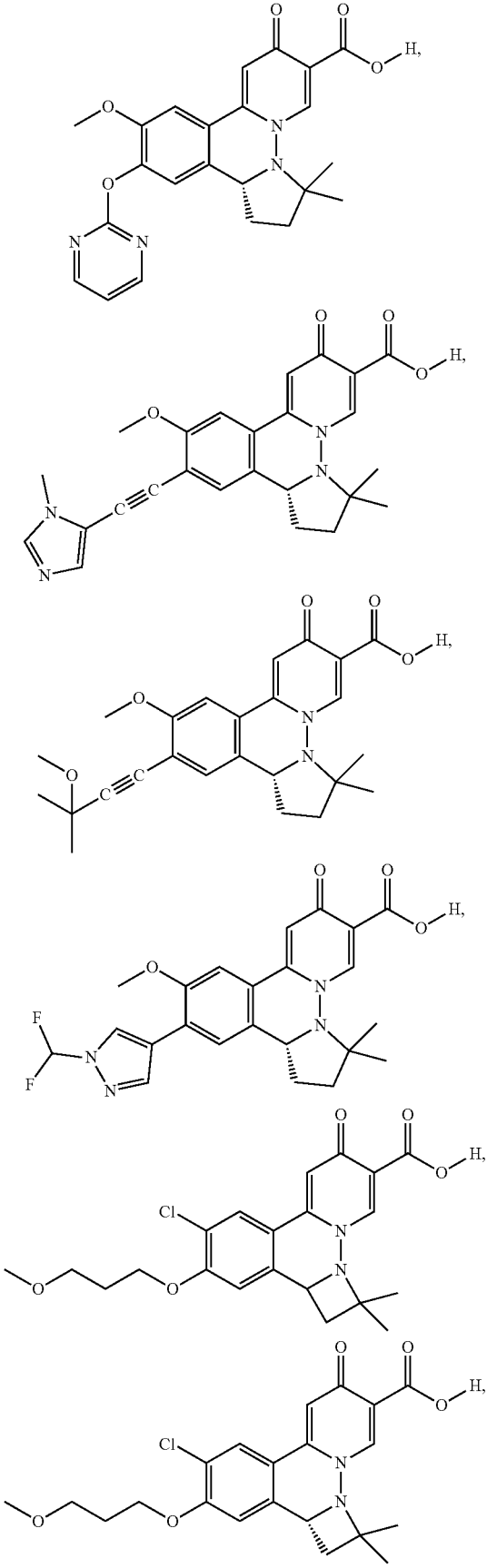

37
-continued
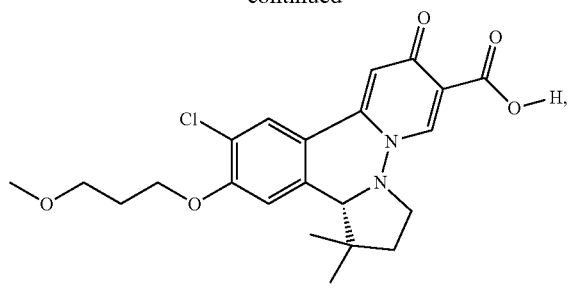
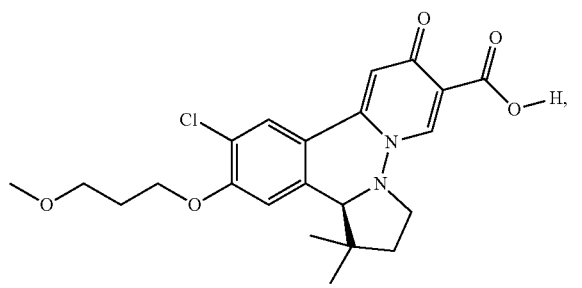
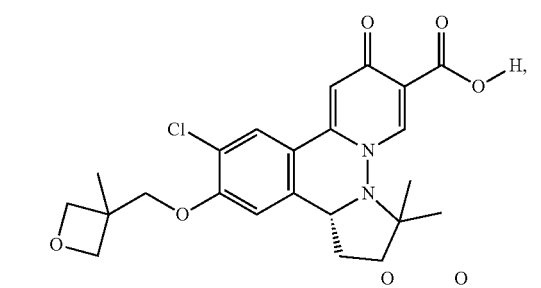
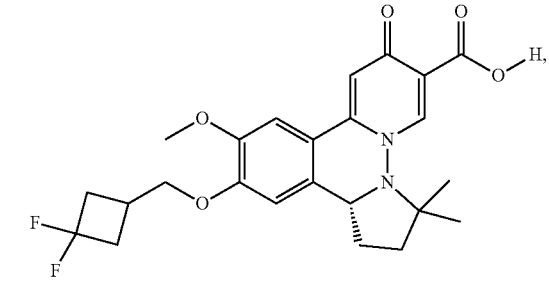
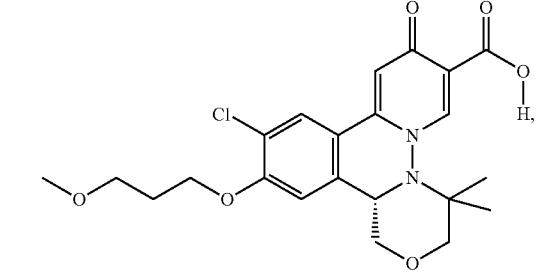
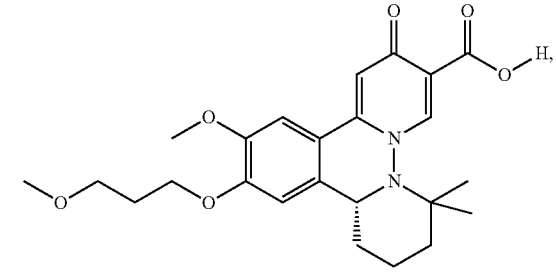
38
-continued
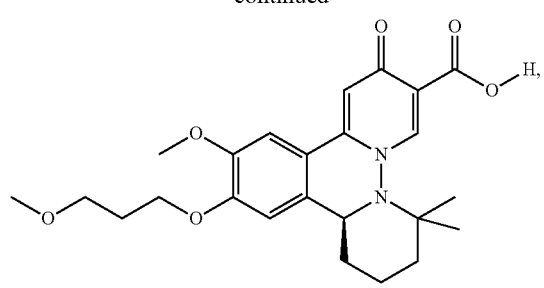
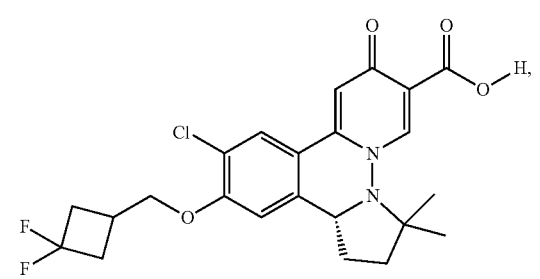
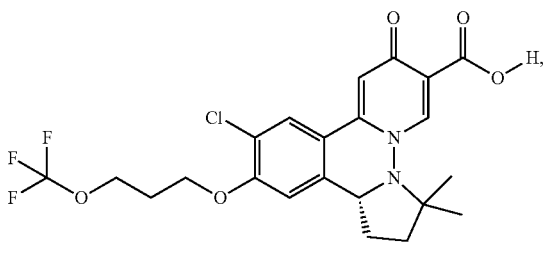
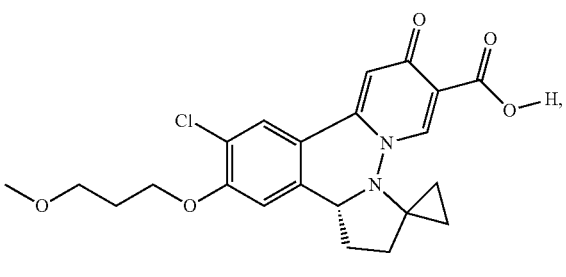
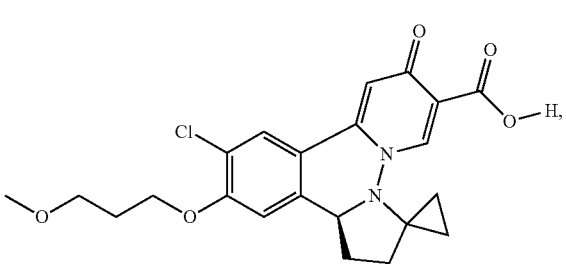
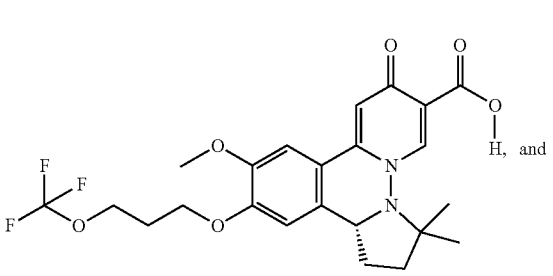

-continued
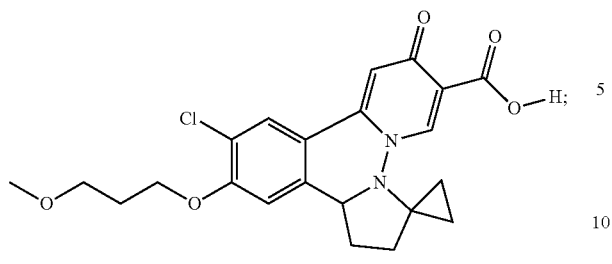
or a pharmaceutically acceptable salt thereof.
In another embodiment, the compounds are selected from the group consisting of:
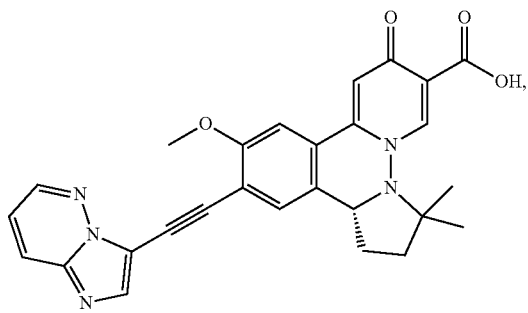
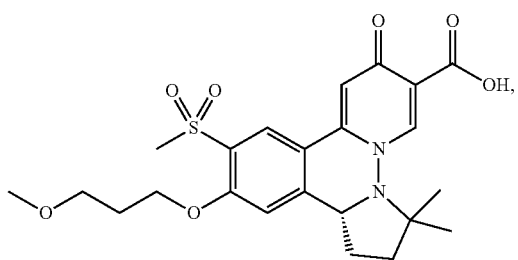
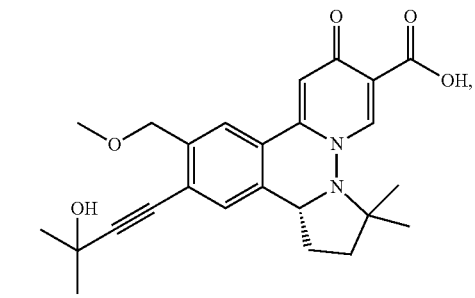
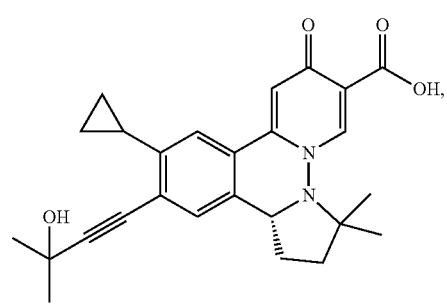
-continued
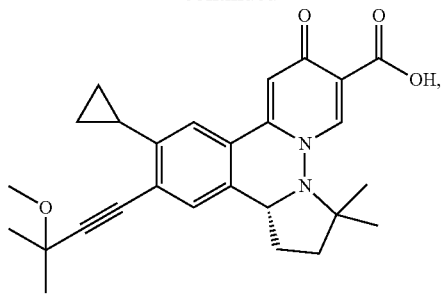
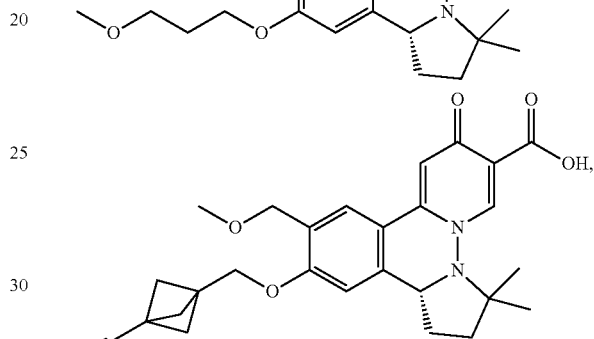
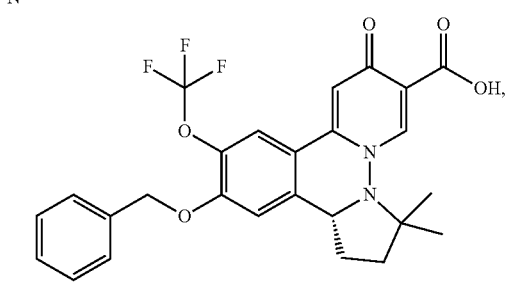
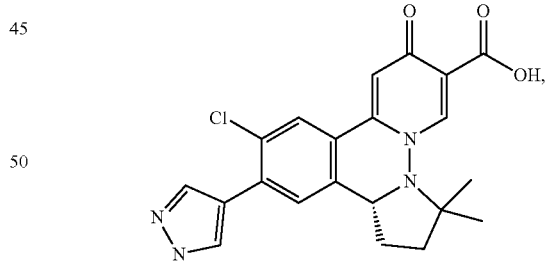
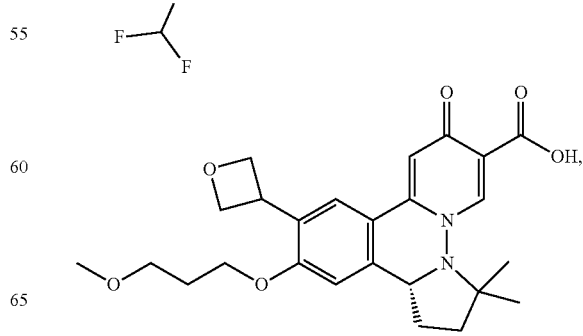

41
-continued
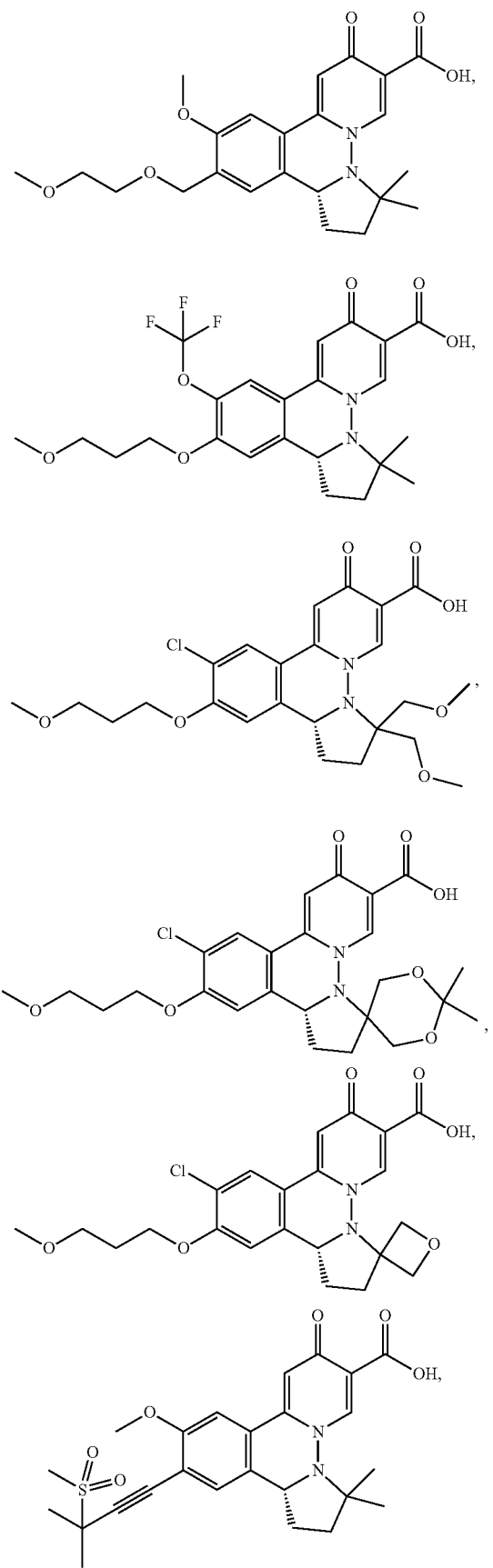
42
-continued
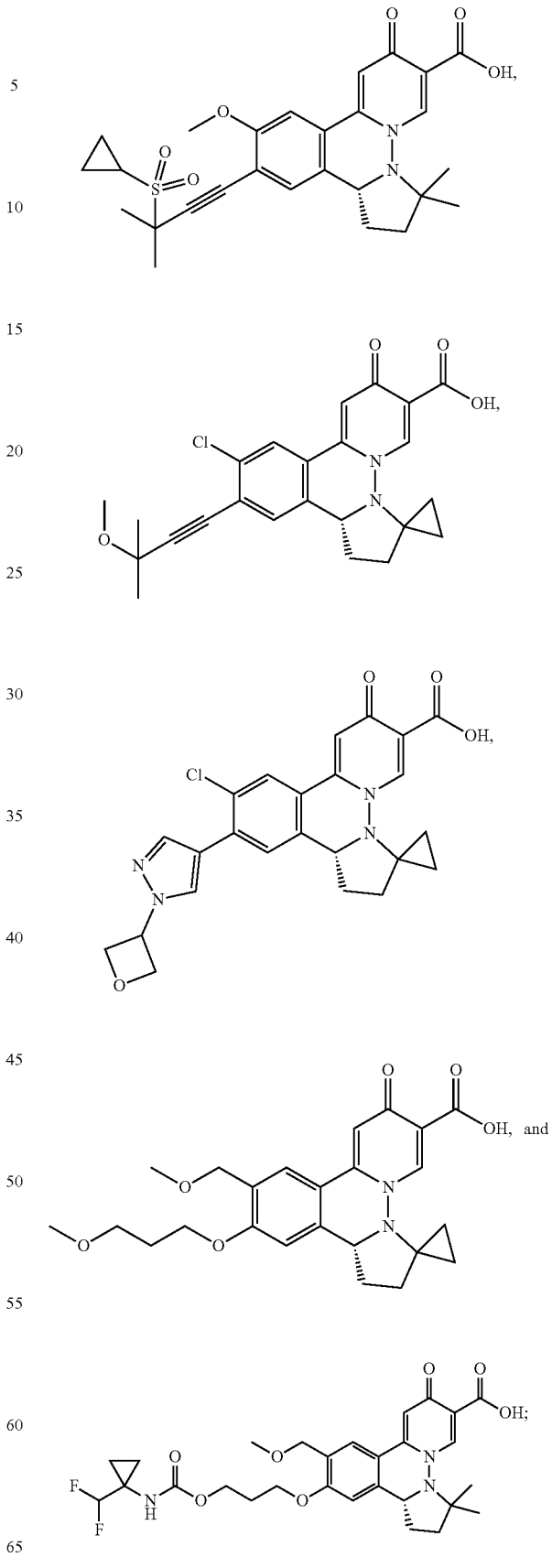
or a pharmaceutically acceptable salt thereof.

In another embodiment, the compound is selected from:
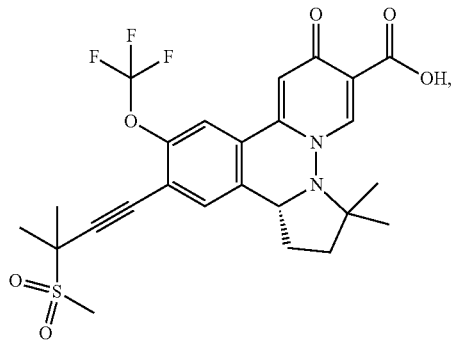
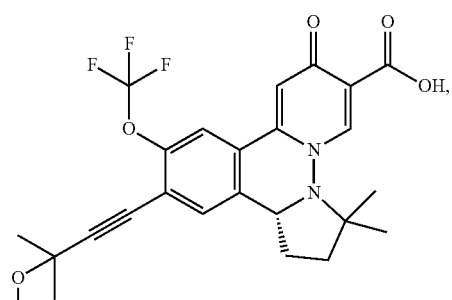
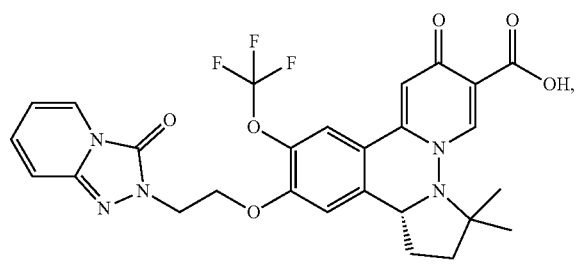
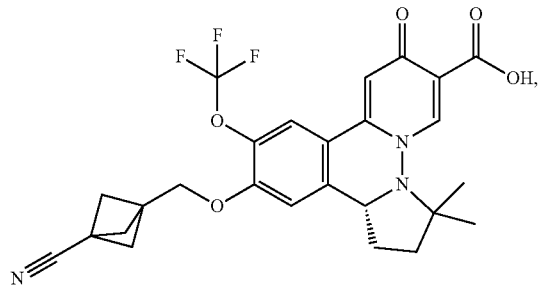
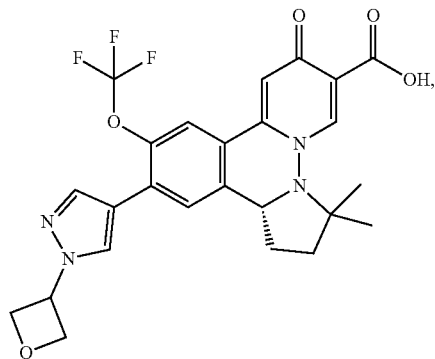
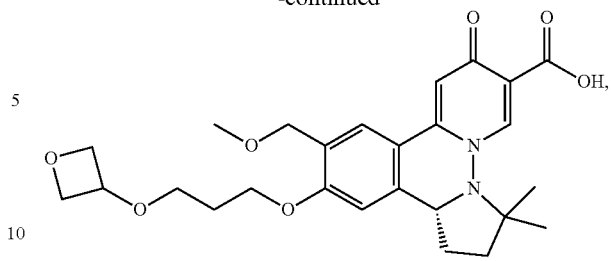
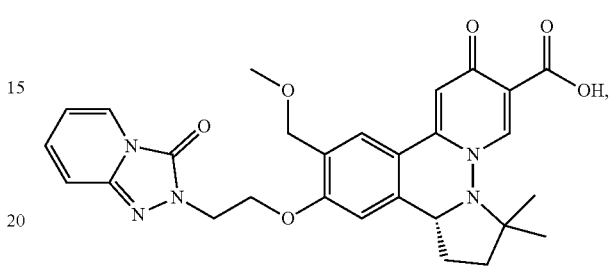
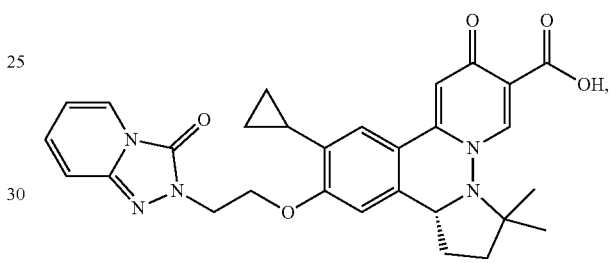
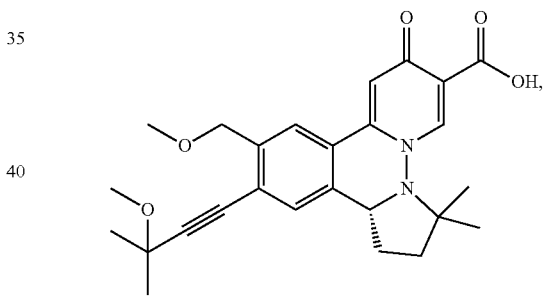
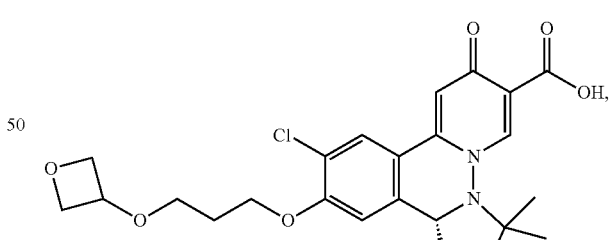
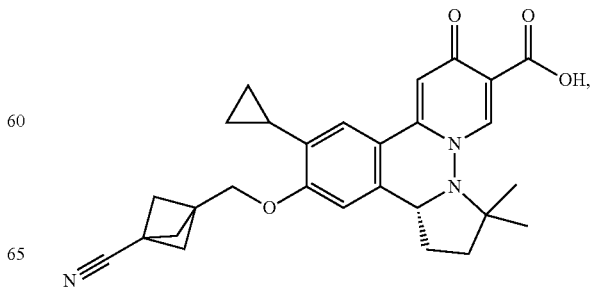

45
-continued
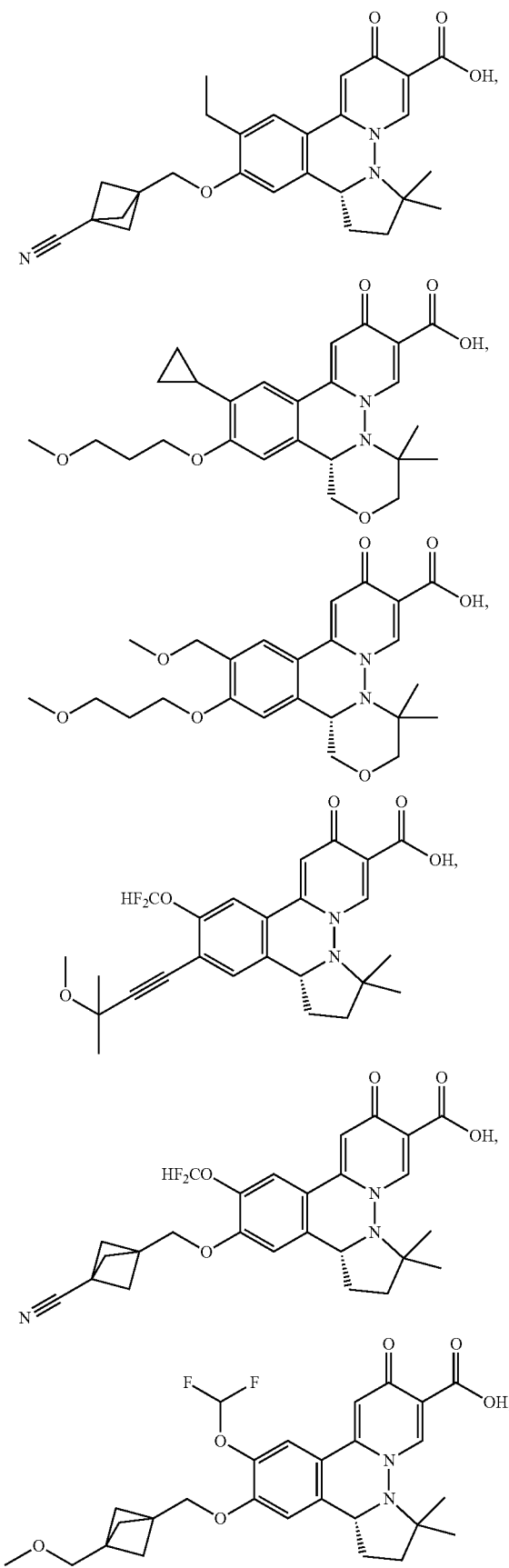
46
-continued
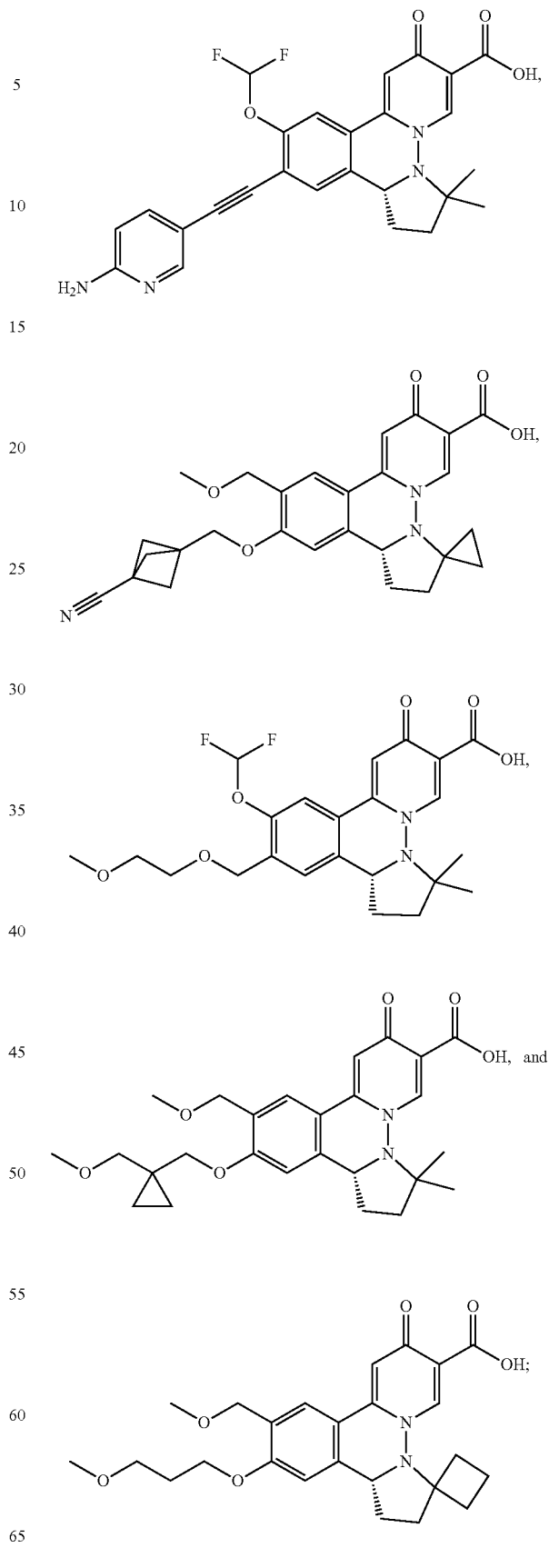
or a pharmaceutically acceptable salt thereof.

Another embodiment provides a compound of the formula:

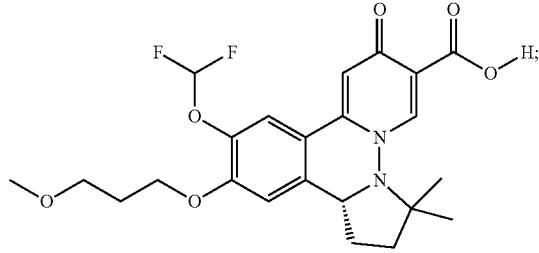

or a pharmaceutically acceptable salt thereof.

Another embodiment provides a compound of the formula:

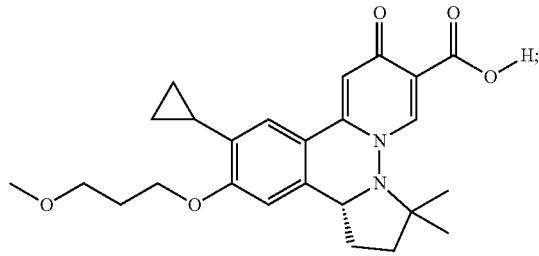

or a pharmaceutically acceptable salt thereof.

Another embodiment provides a compound of the formula:

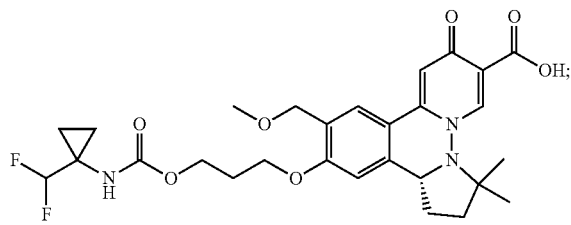 [SMILES: COCc1cc2c(cc1OCCCOC(=O)NC1(C(F)F)CC1)[C@H]1CCC(C)(C)N1n1cc(C(=O)O)c(=O)cc1-2]

or a pharmaceutically acceptable salt thereof.

In another embodiment, the compound is selected from a group consisting of:

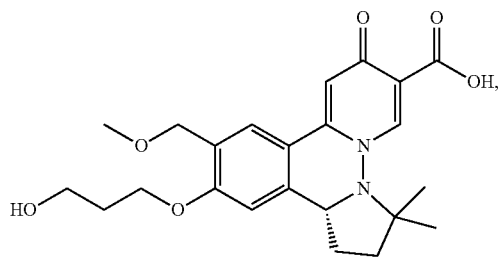

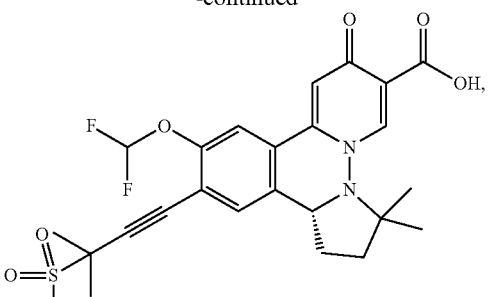

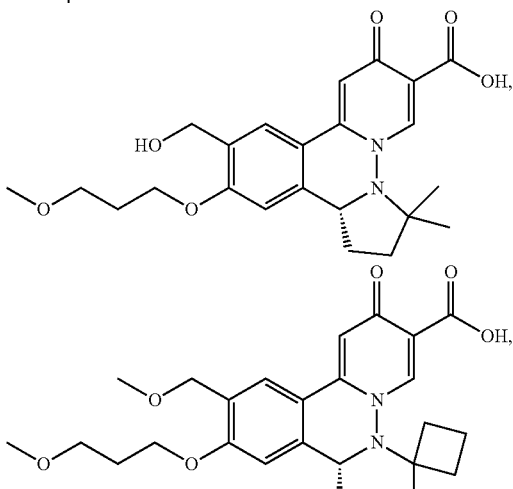

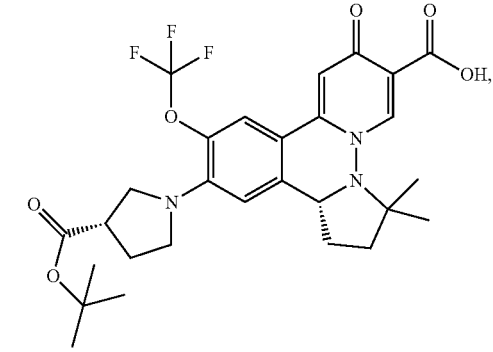

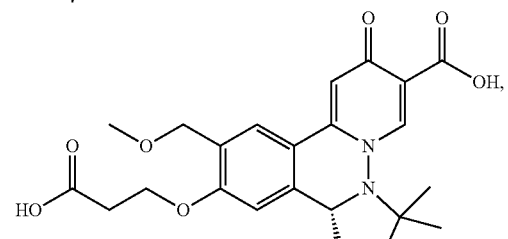

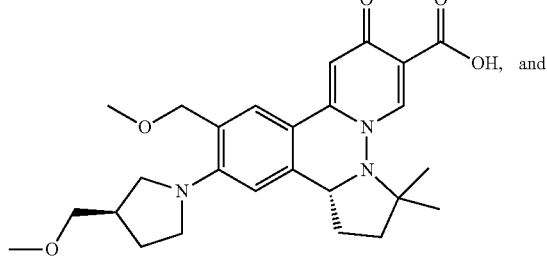

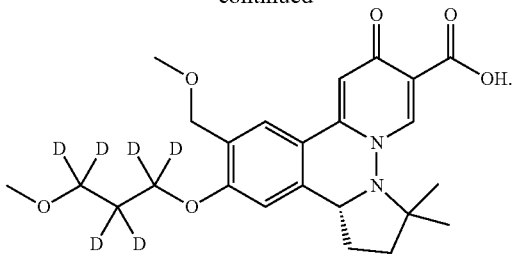

Another embodiment provides a pharmaceutical composition comprising a compound or pharmaceutically acceptable salt as described herein, and a pharmaceutically acceptable excipient.

Another embodiment further comprises one or more additional therapeutic agents. More particularly, the one or more additional therapeutic agents are selected from the group consisting of HBV DNA polymerase inhibitors, toll-like receptor 7 modulators, toll-like receptor 8 modulators, toll-like receptor 7 and 8 modulators, toll-like receptor 3 modulators, interferon alpha ligands, HBsAg inhibitors, compounds targeting HBcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), HBeAg inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, recombinant thymosin alpha-1 and hepatitis B virus replication inhibitors, hepatitis B surface antigen (HBsAg) secretion or assembly inhibitors, IDO inhibitors, KDM5 inhibitors, and combinations thereof.

In another embodiment, the one or more additional therapeutic agents are selected from the group consisting of adefovir (Hepsera®), tenofovir disoproxil fumarate+emtricitabine (Truvada®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine®, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (Axxo), Alfaferone, interferon alfa-2b (BioGeneric Pharma), Feron, interferon-alpha 2 (CJ), Bevac, Laferonum, Vipeg, Blauferon-B, Blauferon-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2), recombinant human interleukin-2, Layfferon, Ka Shu Ning, Shang Sheng Lei Tai, Intefen, Sinogen, Fukangtai, Alloferon, and celmoleukin, and combinations thereof. In another embodiment, the one or more additional therapeutic agents are selected from the group consisting of entecavir, adefovir, tenofovir disoproxil fumarate, tenofovir alafenamide, tenofovir, tenofovir disoproxil, tenofovir alafenamide fumarate, tenofovir alafenamide hemifumarate, telbivudine and lamivudine.

Another embodiment provides a method of inhibiting the production and/or secretion of HBsAg in an individual infected with HBV comprising administering a therapeutically effective amount of a compound as described herein to the individual.

Another embodiment provides a method of treating or preventing an HBV infection comprising administering to an individual in need thereof a therapeutically effective amount of a compound as described herein to the individual. In another embodiment, the individual is chronically infected with HBV.

Another embodiment provides an article of manufacture comprising a unit dosage of a compound as described herein.

Another embodiment provides a compound as described herein for use in medical therapy.

Another embodiment provides a compound as described herein for use in treating or preventing an HBV infection in an individual.

Another embodiment provides use of a compound as described herein for the manufacture of a medicament for use in medical therapy.

Another embodiment provides a compound as described herein for use in inhibiting the production or secretion of HBsAg in vitro.

Any of the compounds described herein is optionally comprises a pharmaceutically acceptable salt.

Also provided herein are compounds of Formula (I) or (II), or Formula (Ia), (Ib) or (IIa) in which from 1 to n hydrogen atoms attached to a carbon atom may be replaced by a deuterium atom or D, in which n is the number of hydrogen atoms in the molecule. As known in the art, the deuterium atom is a non-radioactive isotope of the hydrogen atom. Such compounds may increase resistance to metabolism, and thus may be useful for increasing the half-life of the compounds described herein or pharmaceutically acceptable salts, isomers, or mixtures thereof when administered to a mammal. See, e.g., Foster, "Deuterium Isotope Effects in Studies of Drug Metabolism", Trends Pharmacol. Sci., 5(12):524-527 (1984). Such compounds are synthesized by means known in the art, for example by employing starting materials in which one or more hydrogen atoms have been replaced by deuterium.

Examples of isotopes that can be incorporated into the disclosed compounds also include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$ S, $^{18}F$, $^{36}Cl$, $^{123}I$, and $^{125}I$, respectively. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of Formula (I) or (II), or Formula (Ia), (Ib) or (IIa), can generally be prepared by conventional techniques known to those skilled in the art or by processes analogous to those described in the Examples as set out below using an appropriate isotopically-labeled reagent in place of the non-labeled reagent previously employed.

Additionally, in one embodiment, the compounds described herein are pegylated at a substituent or functional group (i.e. a polyethylene glycol moiety is appended thereto).

The compounds disclosed herein may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present disclosure is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). Likewise, all tautomeric forms are also intended to be included.

In certain embodiments, the present disclosure provides a pharmaceutical composition comprising a compound of the present disclosure, or a pharmaceutically acceptable salt thereof, and a pharmaceutically acceptable excipient. In certain embodiments, the pharmaceutical composition comprises one or more additional therapeutic agents, as described in more detail below.

Pharmaceutical compositions comprising the compounds disclosed herein, or pharmaceutically acceptable salts thereof, may be prepared with one or more pharmaceutically acceptable excipients which may be selected in accord with ordinary practice. "Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

In certain embodiments, pharmaceutical compositions are provided as a solid dosage form, including a solid oral dosage form, such as a tablet. Tablets may contain excipients including glidants, fillers, binders and the like. Aqueous compositions may be prepared in sterile form, and when intended for delivery by other than oral administration generally may be isotonic. All compositions may optionally contain excipients such as those set forth in the Rowe et al, Handbook of Pharmaceutical Excipients, 6$^{th}$ edition, American Pharmacists Association, 2009. Excipients can include ascorbic acid and other antioxidants, chelating agents such as EDTA, carbohydrates such as dextrin, hydroxyalkylcellulose, hydroxyalkylmethylcellulose, stearic acid and the like.

Pharmaceutical compositions disclosed herein include those suitable for various administration routes, including oral administration. The compositions may be presented in unit dosage form and may be prepared by any of the methods well known in the art of pharmacy. Such methods include the step of bringing into association the active ingredient (e.g., a compound of the present disclosure or a pharmaceutical salt thereof) with one or more pharmaceutically acceptable excipients. The compositions may be prepared by uniformly and intimately bringing into association the active ingredient with liquid excipients or finely divided solid excipients or both, and then, if necessary, shaping the product. Techniques and formulations generally are found in Remington: The Science and Practice of Pharmacy, 21$^{st}$ Edition, Lippincott Wiliams and Wilkins, Philadelphia, Pa., 2006.

Compositions described herein that are suitable for oral administration may be presented as discrete units (a unit dosage form) including but not limited to capsules, cachets or tablets each containing a predetermined amount of the active ingredient. In one embodiment, the pharmaceutical composition is a tablet.

Pharmaceutical compositions disclosed herein comprise one or more compounds disclosed herein, or a pharmaceutically acceptable salt thereof, together with a pharmaceutically acceptable excipient and optionally other therapeutic agents. Pharmaceutical compositions containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more excipients including sweetening agents, flavoring agents, coloring agents and preserving agents, in order to provide a palatable preparation. Tablets containing the active ingredient in admixture with non-toxic pharmaceutically acceptable excipients which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that may be combined with the inactive ingredients to produce a dosage form may vary depending upon the intended treatment subject and the particular mode of administration. For example, in some embodiments, a dosage form for oral administration to humans may contain approximately 1 to 1000 mg of active material formulated with an appropriate and convenient amount of a pharmaceutically acceptable excipient. In certain embodiments, the pharmaceutically acceptable excipient varies from about 5 to about 95% of the total compositions (weight:weight).

Methods

In certain embodiments, the present disclosure provides methods of treating or preventing an HBV infection. In certain embodiments, a method of treating or preventing an HBV infection comprises administering to an individual (e.g. a human) a therapeutically effective amount a compound disclosed herein, or a pharmaceutically acceptable salt thereof. In certain embodiments, the present disclosure also provides methods for treating an HBV infection comprising administering to an individual (e.g. a human) infected with HBV a therapeutically effective amount a compound disclosed herein or a pharmaceutically acceptable salt thereof. In some embodiments, the individual is chronically infected with HBV. In some embodiments, the individual is acutely infected with HBV. In some embodiments, a method of treating an individual (e.g. a human) infected with HBV comprises inhibiting HBsAg secretion and/or production.

In certain embodiments, a compound disclosed herein or a pharmaceutically acceptable salt thereof for use in medical therapy is provided. In certain embodiments, the disease or condition is an HBV infection. In certain embodiments, a compound disclosed herein for use in treating or preventing an HBV infection is provided.

In certain embodiments, the use of a compound of the present disclosure, or a pharmaceutically acceptable salt thereof, for the manufacture of a medicament for treating or preventing HBV infection is provided. In certain embodiments, a compound of the present disclosure, or a pharmaceutically acceptable salt thereof, for the manufacture of a medicament for treating or preventing an HBV infection is provided.

As described more fully herein, compounds of the present disclosure can be administered with one or more additional therapeutic agent(s) to an individual (e.g. a human) infected with HBV. The additional therapeutic agent(s) can be administered to the infected individual (e.g. a human) at the same time as a compound disclosed herein or before or after administration of a compound disclosed herein. For example, in certain embodiments, when used to treat or prevent a HBV infection, a compound disclosed herein is administered with one or more additional therapeutic agent(s) selected from the group consisting of HBV DNA polymerase inhibitors, toll-like receptor 7 modulators, toll-like receptor 8 modulators, Toll-like receptor 7 and 8 modulators, Toll-like receptor 3 modulators, interferon alpha ligands, HBsAg inhibitors, compounds targeting HBcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, recombinant thymosin alpha-1 and hepatitis B virus replication inhibitors, and combinations thereof. Specific examples are more fully described below.

In certain embodiments, the present disclosure provides a method for ameliorating a symptom associated with an HBV infection, wherein the method comprises administering to an individual (e.g. a human) infected with hepatitis B virus a therapeutically effective amount of a compound of the present disclosure, or a pharmaceutically acceptable salt thereof, wherein the therapeutically effective amount is sufficient to ameliorate a symptom associated with the HBV infection. Such symptoms include the presence of HBV virus particles in the blood, liver inflammation, jaundice, muscle aches, weakness and tiredness.

In certain embodiments, the present disclosure provides a method for reducing the rate of progression of a hepatitis B viral infection in an individual (e.g. a human), wherein the method comprises administering to an individual (e.g. a human) infected with hepatitis B virus a therapeutically effective amount of a compound disclosed herein, or a pharmaceutically acceptable salt thereof, wherein the therapeutically effective amount is sufficient to reduce the rate of progression of the hepatitis B viral infection. The rate of progression of the infection can be followed by measuring the amount of HBV virus particles in the blood.

In certain embodiments, the present disclosure provides a method for reducing the viral load associated with HBV infection, wherein the method comprises administering to an individual (e.g. a human) infected with HBV a therapeutically effective amount of a compound of the present disclosure, or a pharmaceutically acceptable salt thereof, wherein the therapeutically effective amount is sufficient to reduce the HBV viral load in the individual. In some embodiments, a method of treating an individual (e.g. a human) infected with hepatitis B virus comprises reducing the viral load associated with HBV infection as measured by PCR testing.

Compounds disclosed herein can be administered by any route appropriate for use in a method described herein. Suitable routes include oral, rectal, nasal, topical (including buccal and sublingual), transdermal, vaginal and parenteral (including subcutaneous, intramuscular, intravenous, intradermal, intrathecal and epidural), and the like.

Compounds disclosed herein may be administered to an individual in accordance with an effective dosing regimen for a desired period of time or duration, such as at least one week, at least about one month, at least about 2 months, at least about 3 months, at least about 6 months, or at least about 12 months or longer. In one variation, the compound is administered on a daily or intermittent schedule for the duration of the individual's life.

The dosage or dosing frequency of a compound of the present disclosure may be adjusted over the course of the treatment, based on the judgment of the administering physician.

Therapeutically effective amounts of compounds disclosed herein are from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day, or such as from about 0.3 µg to about 30 mg per day, or such as from about 30 µg to about 300 µg per day.

A compound of the present disclosure (e.g., any compound of Formula (I) or (II), or Formula (Ia), (Ib) or (IIa)) may be combined with one or more additional therapeutic agents in any dosage amount of the compound of the present disclosure (e.g., from 1 mg to 1000 mg of compound). Therapeutically effective amounts of the compound of Formula (I) or (II), or Formula (Ia), (Ib) or (IIa) can range from about 0.01 mg per dose to about 1000 mg per dose, such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose. Other therapeutically effective amounts of the compound of Formula (I) or (II), or Formula (Ia), (Ib) or (IIa) are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of Formula (I) or (II), or Formula (Ia), (Ib) or (IIa) are about 100 mg per dose, or about 125, 150, 175, 200, 225, 250, 275, 300, 350, 400, 450, or about 500 mg per dose.

A single dose can be administered hourly, daily, or weekly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein.

The frequency of dosage of a compound disclosed herein will be determined by the needs of the individual patient and can be, for example, once per day or twice, or more times, per day. Administration of a compound continues for as long as necessary to treat an HBV infection. For example, a compound disclosed herein can be administered to a human being infected with HBV for a period of from 20 days to 180 days or, for example, for a period of from 20 days to 90 days or, for example, for a period of from 30 days to 60 days.

Administration can be intermittent, with a period of several or more days during which a patient receives a daily dose of a compound disclosed herein, followed by a period of several or more days during which a patient does not receive a daily dose of the compound. For example, a patient can receive a dose of a compound every other day, or three times per week. Again by way of non-limiting example, a patient can receive a dose of a compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

In one embodiment, pharmaceutical compositions comprising a compound of the present disclosure, or a pharmaceutically acceptable salt thereof, in combination with one or more (e.g., one, two, three, four, one or two, one to three, or one to four) additional therapeutic agents, and a pharmaceutically acceptable excipient are provided.

In one embodiment, kits comprising a compound of the present disclosure, or a pharmaceutically acceptable salt thereof, in combination with one or more (e.g., one, two, three, four, one or two, one to three, or one to four) additional therapeutic agents are provided.

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with one additional therapeutic agent. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In certain embodiments, when a compound of the present disclosure is combined with one or more additional therapeutic agents as described herein, the components of the composition are administered as a simultaneous or sequential regimen. When administered sequentially, the combination may be administered in two or more administrations.

In certain embodiments, a compound of the present disclosure is combined with one or more additional therapeutic agents in a unitary dosage form for simultaneous administration to a patient, for example as a solid dosage form for oral administration.

In certain embodiments, a compound of the present disclosure is administered with one or more additional therapeutic agents. Co-administration of a compound of the present disclosure with one or more additional therapeutic agents generally refers to simultaneous or sequential administration of a compound of the present disclosure and one or more additional therapeutic agents, such that therapeutically effective amounts of the compound disclosed herein and one or more additional therapeutic agents are both present in the body of the patient.

Co-administration includes administration of unit dosages of the compounds disclosed herein before or after administration of unit dosages of one or more additional therapeutic agents, for example, administration of the compound disclosed herein within seconds, minutes, or hours of the administration of one or more additional therapeutic agents. For example, in some embodiments, a unit dose of a compound of the present disclosure is administered first, followed within seconds or minutes by administration of a unit dose of one or more additional therapeutic agents. Alternatively, in other embodiments, a unit dose of one or more additional therapeutic agents is administered first, followed by administration of a unit dose of a compound of the present disclosure within seconds or minutes. In some embodiments, a unit dose of a compound of the present disclosure is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of a compound of the present disclosure.

Combination Therapy

In certain embodiments, a method for treating or preventing an HBV infection in an individual (e.g. a human) having or at risk of having the infection is provided, comprising administering to the individual a therapeutically effective amount of a compound of the present disclosure, or a pharmaceutically acceptable salt thereof, in combination with a therapeutically effective amount of one or more (e.g., one, two, three, four, one or two, one to three or one to four) additional therapeutic agents. In one embodiment, a method for treating an HBV infection in an individual (e.g. a human) having or at risk of having the infection is provided, comprising administering to the individual a therapeutically effective amount of a compound of the present disclosure, or a pharmaceutically acceptable salt thereof, in combination with a therapeutically effective amount of one or more (e.g., one, two, three, four, one or two, one to three or one to four) additional therapeutic agents. In some embodiments, a therapeutically effective amount of a compound of the present disclosure, or a pharmaceutically acceptable salt thereof, and one or more additional therapeutic agents are administered in a "fixed dose combination," also termed a "combined dosage form," wherein the active agents are combined in a solid (e.g. tablet or capsule), liquid (e.g. IV), or vaporized formulation.

In certain embodiments, the present disclosure provides a method for treating an HBV infection, comprising administering to a patient in need thereof a therapeutically effective amount of a compound of the present disclosure, or a pharmaceutically acceptable salt thereof, in combination with a therapeutically effective amount of one or more (e.g., one, two, three, four, one or two, one to three or one to four) additional therapeutic agents which are suitable for treating an HBV infection. In certain embodiments, one or more additional therapeutic agents includes, for example, one, two, three, four, one or two, one to three or one to four additional therapeutic agents.

In the above embodiments, the additional therapeutic agent may be an anti-HBV agent. For example, in some embodiments, the additional therapeutic agent is selected from the group consisting of HBV combination drugs, HBV DNA polymerase inhibitors, immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, hepatitis B surface antigen (HBsAg) inhibitors, compounds targeting hepatitis B core antigen (HBcAg), cyclophilin inhibitors, HBV therapeutic vaccines, HBV prophylactic vaccines, HBV viral entry inhibitors, NTCP (Na+-taurocholate cotransporting polypeptide) inhibitors, antisense oligonucleotide targeting viral mRNA, short interfering RNAs (siRNA), miRNA gene therapy agents, endonuclease modulators, inhibitors of ribonucleotide reductase, hepatitis B virus E antigen inhibitors, recombinant scavenger receptor A (SRA) proteins, Src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), Hepatitis B virus replication inhibitors, compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), and other drugs for treating HBV, and combinations thereof. In some embodiments, the additional therapeutic agent is further selected from hepatitis B surface antigen (HBsAg) secretion or assembly inhibitors, TCR-like antibodies, IDO inhibitors, cccDNA epigenetic modifiers, IAPs inhibitors, SMAC mimetics, and compounds such as those disclosed in US20100015178 (Incyte), In the above embodiments, the additional therapeutic agent may be an anti-HBV agent.

For example, the additional therapeutic agent may be selected from the group consisting of HBV combination drugs, other drugs for treating HBV, 3-dioxygenase (IDO) inhibitors, antisense oligonucleotide targeting viral mRNA, Apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting HBcAg, compounds targeting hepatitis B core antigen (HBcAg), covalently closed circular DNA (cccDNA) inhibitors, cyclophilin inhibitors, cytokines, cytotoxic T-lymphocyte-associated protein 4 (ipi4) inhibitors, DNA polymerase inhibitor, Endonuclease modulator, epigenetic modifiers, Farnesoid X receptor agonist, gene modifiers or editors, HBsAg inhibitors, HBsAg secretion or assembly inhibitors, HBV antibodies, HBV DNA polymerase inhibitors, HBV replication inhibitors, HBV RNAse inhibitors, HBV vaccines, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, IAPs inhibitors, IL-2 agonist, IL-7 agonist, Immunoglobulin agonist, Immunoglobulin G modulator, immunomodulators, indoleamine-2, inhibitors of ribonucleotide reductase, Interferon agonist, Interferon alpha 1 ligand, Interferon alpha 2 ligand, Interferon alpha 5 ligand modulator, Interferon alpha ligand, Interferon alpha ligand modulator, interferon alpha receptor ligands, Interferon beta ligand, Interferon ligand, Interferon receptor modulator, Interleukin-2 ligand, ipi4 inhibitors, lysine demethylase inhibitors, histone demethylase inhibitors, KDM5 inhibitors, KDM1 inhibitors, killer cell lectin-like receptor subfamily G member 1 inhibitors, lymphocyte-activation gene 3 inhibitors, lymphotoxin beta receptor activators, microRNA (miRNA) gene therapy agents, modulators of Axl, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, PD-1 inhibitors, PD-L1 inhibitors, PEG-Interferon Lambda, Peptidylprolyl isomerase inhibitor, phosphatidylinositol-3 kinase (PI3K) inhibitors, recombinant scavenger receptor A (SRA) proteins, recombinant thymosin alpha-1, Retinoic acid-inducible gene 1 stimulator, Reverse transcriptase inhibitor, Ribonuclease inhibitor, RNA DNA polymerase inhibitor, short interfering RNAs (siRNA), short synthetic hairpin RNAs (sshRNAs), SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonist, TLR-7 agonist, TLR-9 agonist, TLR9 gene stimulator, toll-like receptor (TLR) modulators, Viral ribonucleotide reductase inhibitor, zinc finger nucleases or synthetic nucleases (TALENs), and combinations thereof.

In certain embodiments, the additional therapeutic agent is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HBcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen (HBeAg) inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof. In certain embodiments, the additional therapeutic is selected from hepatitis B surface antigen (HBsAg) secretion or assembly inhibitors, IDO inhibitors, and combinations thereof.

In certain embodiments, the additional therapeutic agent is selected from the group consisting of HBV combination drugs, HBV DNA polymerase inhibitors, toll-like receptor 7 modulators, toll-like receptor 8 modulators, Toll-like receptor 7 and 8 modulators, Toll-like receptor 3 modulators, interferon alpha receptor ligands, HBsAg inhibitors, compounds targeting HBcAg, cyclophilin inhibitors, HBV therapeutic vaccines, HBV prophylactic vaccines, HBV viral entry inhibitors, NTCP inhibitors, antisense oligonucleotide targeting viral mRNA, short interfering RNAs (siRNA), hepatitis B virus E antigen (HBeAg) inhibitors, HBx inhibitors, cccDNA inhibitors, HBV antibodies including HBV antibodies targeting the surface antigens of the hepatitis B virus, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, BTK inhibitors, and hepatitis B virus replication inhibitors, and combinations thereof. In certain embodiments, the additional therapeutic is selected from hepatitis B surface antigen (HBsAg) secretion or assembly inhibitors, IDO inhibitors, KDM5 inhibitors, and combinations thereof.

In certain embodiments a compound of the present disclosure is formulated as a tablet, which may optionally contain one or more other compounds useful for treating HBV. In certain embodiments, the tablet can contain another active ingredient for treating HBV, such as HBV DNA polymerase inhibitors, immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), modulators of tlr7, modulators of tlr8, modulators of tlr7 and tlr8, interferon alpha receptor ligands, hyaluronidase inhibitors, hepatitis B surface antigen (HBsAg) inhibitors, compounds targeting hepatitis B core antigen (HBcAg), cyclophilin inhibitors, HBV viral entry inhibitors, NTCP (Na+-taurocholate cotransporting polypeptide) inhibitors, endonuclease modulators, inhibitors of ribonucleotide reductase, hepatitis B virus E antigen inhibitors, Src kinase inhibitors, HBx inhibitors, cccDNA inhibitors, CCR2 chemokine antagonists, thymosin agonists, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, BTK inhibitors, modulators of TIGIT, modulators of CD47, modulators of SIRP alpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, and Hepatitis B virus replication inhibitors, and combinations thereof. In certain embodiments, the tablet can contain another active ingredient for treating HBV, such as hepatitis B surface antigen (HBsAg) secretion or assembly inhibitors, cccDNA epigenetic modifiers, IAPs inhibitors, SMAC mimetics, and IDO inhibitors.

In certain embodiments, such tablets are suitable for once daily dosing.

In certain embodiments, the additional therapeutic agent is selected from one or more of:

(1) Combination drugs selected from the group consisting of tenofovir disoproxil fumarate+emtricitabine (TRUVADA®); adefovir+clevudine and GBV-015, as well as combination drugs selected from ABX-203+lamivudine+PEG-IFNalpha, ABX-203+adefovir+PEG-IFNalpha, and INO-9112+RG7944 (INO-1800);

(2) HBV DNA polymerase inhibitors selected from the group consisting of besifovir, entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, telbivudine (Tyzeka®), pradefovir, Clevudine, emtricitabine (Emtriva®), ribavirin, lamivudine (Epivir-HBV®), phosphazide, famciclovir, SNC-019754, FMCA, fusolin, AGX-1009 and metacavir, as well as HBV DNA polymerase inhibitors selected from AR-II-04-26 and HS-10234;

(3) Immunomodulators selected from the group consisting of rintatolimod, imidol hydrochloride, ingaron, dermaVir, plaquenil (hydroxychloroquine), proleukin, hydroxyurea, mycophenolate mofetil (MPA) and its ester derivative mycophenolate mofetil (MMF), WF-10, ribavirin, IL-12, polymer polyethyleneimine (PEI), Gepon, VGV-1, MOR-22, BMS-936559 and IR-103, as well as immunomodulators selected from INO-9112, polymer polyethyleneimine (PEI), Gepon, VGV-1, MOR-22, BMS-936559, RO-7011785, RO-6871765 and IR-103;

(4) Toll-like receptor 7 modulators selected from the group consisting of GS-9620, GSK-2245035, imiquimod, resiquimod, DSR-6434, DSP-3025, IMO-4200, MCT-465, 3M-051, SB-9922, 3M-052, Limtop, TMX-30X, TMX-202 RG-7863 and RG-7795;

(5) Toll-like receptor 8 modulators selected from the group consisting of motolimod, resiquimod, 3M-051, 3M-052, MCT-465, IMO-4200, VTX-763, VTX-1463;

(6) Toll-like receptor 3 modulators selected from the group consisting of rintatolimod, poly-ICLC, MCT-465, MCT-475, Riboxxon, Riboxxim and ND-1.1;

(7) Interferon alpha receptor ligands selected from the group consisting of interferon alpha-2b (Intron A®), pegylated interferon alpha-2a (Pegasys®), interferon alpha 1b (Hapgen®), Veldona, Infradure, Roferon-A, YPEG-interferon alfa-2a (YPEG-rhIFNalpha-2a), P-1101, Algeron, Alfarona, Ingaron (interferon gamma), rSIFN-co (recombinant super compound interferon), Ypeginterferon alfa-2b (YPEG-rhIFNalpha-2b), MOR-22, peginterferon alfa-2b (PEG-Intron®), Bioferon, Novaferon, Inmutag (Inferon), Multiferon®, interferon alfa-n1(Humoferon®), interferon beta-1a (Avonex®), Shaferon, interferon alfa-2b (AXXO), Alfaferone, interferon alfa-2b (BioGeneric Pharma), interferon-alpha 2 (CJ), Laferonum, VIPEG, BLAUFERON-B, BLAUFERON-A, Intermax Alpha, Realdiron, Lanstion, Pegaferon, PDferon-B PDferon-B, interferon alfa-2b (IFN, Laboratorios Bioprofarma), alfainterferona 2b, Kalferon, Pegnano, Feronsure, Pegi-Hep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, Layfferon, Shang Sheng Lei Tai, INTEFEN, SINOGEN, Fukangtai, Pegstat, rHSA-IFN alpha-2b and Interapo (Interapa);

(8) Hyaluronidase inhibitors selected from the group consisting of astodrimer;

(9) Modulators of IL-10;

(10) HBsAg inhibitors selected from the group consisting of HBF-0259, PBHBV-001, PBHBV-2-15, PBHBV-2-1, REP 9AC, REP-9C and REP 9AC', as well as HBsAg inhibitors selected from REP-9, REP-2139, REP-2139-Ca, REP-2165, REP-2055, REP-2163, REP-2165, REP-2053, REP-2031 and REP-006 and REP-9AC'

(11) Toll like receptor 9 modulators selected from CYT003, as well as Toll like receptor 9 modulators selected from CYT-003, IMO-2055, IMO-2125, IMO-3100, IMO-8400, IMO-9200, agatolimod, DIMS-9054, DV-1179, AZD-1419, MGN-1703, and CYT-003-QbG10;

(12) Cyclophilin inhibitors selected from the group consisting of OCB-030, SCY-635 and NVP-018;

(13) HBV Prophylactic vaccines selected from the group consisting of Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, Engerix B®, recombinant hepatitis B vaccine (intramuscular, Kangtai Biological Products), recombinant hepatitis B vaccine (*Hansenual polymorpha* yeast, intramuscular, Hualan Biological Engineering), Bimmugen, Euforavac, Eutravac, anrix-DTaP-IPV-Hep B, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan6, rhHBsAG vaccine, and DTaP-rHB-Hib vaccine;

(14) HBV Therapeutic vaccines selected from the group consisting of HBsAG-HBIG complex, Bio-Hep-B, NAS-VAC, abi-HB (intravenous), ABX-203, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, TG-1050, NU-500, HBVax, im/TriGrid/antigen vaccine, Mega-CD40L-adjuvanted vaccine, HepB-v, NO-1800, recombinant VLP-based therapeutic vaccine (HBV infection, VLP Biotech), AdTG-17909, AdTG-17910 AdTG-18202, ChronVac-B, and Lm HBV, as well as HBV Therapeutic vaccines selected from FP-02.2 and RG7944 (INO-1800);

(15) HBV viral entry inhibitor selected from the group consisting of Myrcludex B;

(16) Antisense oligonucleotide targeting viral mRNA selected from the group consisting of ISIS-HBVRx;

(17) short interfering RNAs (siRNA) selected from the group consisting of TKM-HBV (TKM-HepB), ALN-HBV, SR-008, ddRNAi and ARC-520;

(18) Endonuclease modulators selected from the group consisting of PGN-514;

(19) Inhibitors of ribonucleotide reductase selected from the group consisting of Trimidox;

(20) Hepatitis B virus E antigen inhibitors selected from the group consisting of wogonin;

(21) HBV antibodies targeting the surface antigens of the hepatitis B virus selected from the group consisting of GC-1102, XTL-17, XTL-19, XTL-001, KN-003 and fully human monoclonal antibody therapy (hepatitis B virus infection, Humabs BioMed), as well as HBV antibodies targeting the surface antigens of the hepatitis B virus selected from IV Hepabulin SN;

(22) HBV antibodies including monoclonal antibodies and polyclonal antibodies selected from the group consisting of Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, hepatitis B immunoglobulin (intravenous, pH4, HBV infection, Shanghai RAAS Blood Products) and Fovepta (BT-088);

(23) CCR2 chemokine antagonists selected from the group consisting of propagermanium;

(24) Thymosin agonists selected from the group consisting of Thymalfasin;

(25) Cytokines selected from the group consisting of recombinant IL-7, CYT-107, interleukin-2 (IL-2, Immunex); recombinant human interleukin-2 (Shenzhen Neptunus) and celmoleukin, as well as cytokines selected from IL-15, IL-21, IL-24;

(26) Nucleoprotein inhibitors (HBV core or capsid protein inhibitors) selected from the group consisting of NVR-1221, NVR-3778, BAY 41-4109, morphothiadine mesilate and DVR-23;

(27) Stimulators of retinoic acid-inducible gene 1 selected from the group consisting of SB-9200, SB-40, SB-44, ORI-7246, ORI-9350, ORI-7537, ORI-9020, ORI-9198 and ORI-7170;

(28) Stimulators of NOD2 selected from the group consisting of SB-9200;

(29) Recombinant thymosin alpha-1 selected from the group consisting of NL-004 and PEGylated thymosin alpha 1;

(30) Hepatitis B virus replication inhibitors selected from the group consisting of isothiafludine, IQP-HBV, RM-5038 and Xingantie;

(31) PI3K inhibitors selected from the group consisting of idelalisib, AZD-8186, buparlisib, CLR-457, pictilisib, neratinib, rigosertib, rigosertib sodium, EN-3342, TGR-1202, alpelisib, duvelisib, UCB-5857, taselisib, XL-765, gedatolisib, VS-5584, copanlisib, CAI orotate, perifosine, RG-7666, GSK-2636771, DS-7423, panulisib, GSK-2269557, GSK-2126458, CUDC-907, PQR-309, INCB-040093, pilaralisib, BAY-1082439, puquitinib mesylate, SAR-245409, AMG-319, RP-6530, ZSTK-474, MLN-1117, SF-1126, RV-1729, sonolisib, LY-3023414, SAR-260301 and CLR-1401;

(32) cccDNA inhibitors selected from the group consisting of BSBI-25;

(33) PD-L1 inhibitors selected from the group consisting of MEDI-0680, RG-7446, durvalumab, KY-1003, KD-033, MSB-0010718C, TSR-042, ALN-PDL, STI-A1014 and BMS-936559;

(34) PD-1 inhibitors selected from the group consisting of nivolumab, pembrolizumab, pidilizumab, BGB-108 and mDX-400;

(35) BTK inhibitors selected from the group consisting of ACP-196, dasatinib, ibrutinib, PRN-1008, SNS-062, ONO-4059, BGB-3111, MSC-2364447, X-022, spebrutinib, TP-4207, HM-71224, KBP-7536, AC-0025;

(36) Other drugs for treating HBV selected from the group consisting of gentiopicrin (gentiopicroside), nitazoxanide, birinapant, NOV-205 (Molixan; BAM-205), Oligotide, Mivotilate, Feron, levamisole, Ka ShuNing, Alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-006IA, Hepuyinfen, DasKloster 0014-01, Jiangantai (Ganxikang), picroside, GA5 NM-HBV, DasKloster-0039, hepulantai, IMB-2613, TCM-800B and ZH-2N, as well as other drugs for treating HBV selected from reduced glutathione, and RO-6864018; and

(37) The compounds disclosed in US20100143301 (Gilead Sciences), US20110098248 (Gilead Sciences), US20090047249 (Gilead Sciences), U.S. Pat. No. 8,722,054 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (VentirxPharma), US20140275167 (Novira therapeutics), US20130251673 (Novira therapeutics), U.S. Pat. No. 8,513,184 (Gilead Sciences), US20140030221 (Gilead Sciences), US20130344030 (Gilead Sciences), US20130344029 (Gilead Sciences), US20140343032 (Roche), WO2014037480 (Roche), US20130267517 (Roche), WO2014131847 (Janssen), WO2014033176 (Janssen), WO2014033170 (Janssen), WO2014033167 (Janssen), US20140330015 (Ono pharmaceutical), US20130079327 (Ono pharmaceutical), and US20130217880 (Ono pharmaceutical), and the compounds disclosed in US20100015178 (Incyte);

(38) IDO inhibitors selected from the group consisting of epacadostat (INCB24360), F-001287, resminostat (4SC-201), SN-35837, NLG-919, GDC-0919, and indoximod;

(39) Arginase inhibitors selected from CB-1158, C-201, and resminostat;

(40) Cytotoxic T-lymphocyte-associated protein 4 (ipi4) inhibitors selected from ipilumimab, belatacept, PSI-001, PRS-010, tremelimumab, and JHL-1155; and

(41) KDM5 inhibitors include the compounds disclosed in WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel).

In certain embodiments, a compound of the present disclosure, or a pharmaceutically acceptable salt thereof, is combined with one, two, three, four or more additional therapeutic agents. In certain embodiments, a compound of the present disclosure, or a pharmaceutically acceptable salt thereof, is combined with two additional therapeutic agents. In other embodiments, a compound of the present disclosure, or a pharmaceutically acceptable salt thereof, is combined with three additional therapeutic agents. In further embodiments, a compound of the present disclosure, or a pharmaceutically acceptable salt thereof, is combined with four additional therapeutic agents. The one, two, three, four or more additional therapeutic agents can be different therapeutic agents selected from the same class of therapeutic agents, and/or they can be selected from different classes of therapeutic agents.

In one embodiment, a compound of the present disclosure, or a pharmaceutically acceptable salt thereof, is combined with an HBV DNA polymerase inhibitor. In another embodiment, a compound of the present disclosure, or a pharmaceutically acceptable salt thereof, is combined with an HBV DNA polymerase inhibitor and at least one additional therapeutic agent selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, HBsAg inhibitors, compounds targeting HBcAg, cyclophilin inhibitors, HBV therapeutic vaccines, HBV prophylactic vaccines HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambda, recombinant thymosin alpha-1, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), and Hepatitis B virus replication inhibitors. In certain embodiments the at least one additional therapeutic agent is further selected from hepatitis B surface antigen (HBsAg) secretion or assembly inhibitors, TCR-like antibodies, cccDNA epigenetic modifiers, IAPs inhibitors, SMAC mimetics, and IDO inhibitors.

In another embodiment, a compound of the present disclosure, or a pharmaceutically acceptable salt thereof, is combined with an HBV DNA polymerase inhibitor and at least one additional therapeutic agent selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In another embodiment, a compound of the present disclosure, or a pharmaceutically acceptable salt thereof, is combined with an HBV DNA polymerase inhibitor, one or two additional therapeutic agents selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors). In certain embodiments one or two additional therapeutic agents is further selected from hepatitis B surface antigen (HBsAg) secretion or assembly inhibitors, TCR-like antibodies, and IDO inhibitors.

In a particular embodiment, a compound of the present disclosure, or a pharmaceutically acceptable salt thereof, is combined with one, two, three, four or more additional therapeutic agents selected from adefovir (Hepsera®), tenofovir disoproxil fumarate+emtricitabine (TRUVADA®), tenofovir disoproxil fumarate (Viread®), entecavir (Baraclude®), lamivudine (Epivir-HBV®), tenofovir alafenamide, tenofovir, tenofovir disoproxil, tenofovir alafenamide fumarate, tenofovir alafenamide hemifumarate, telbivudine (Tyzeka®), Clevudine, emtricitabine (Emtriva®), peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin In a particular embodiment, a compound of the present disclosure, or a pharmaceutically acceptable salt thereof, is combined with entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) In a particular embodiment, a compound of the present disclosure, or a pharmaceutically acceptable salt thereof, is combined with entecavir (Baraclude®), adefovir (Hepsera®), tenofovir disoproxil fumarate (Viread®), tenofovir alafenamide hemifumarate, telbivudine (Tyzeka®) or lamivudine (Epivir-HBV®).

In a particular embodiment, a compound of the present disclosure, or a pharmaceutically acceptable salt thereof is combined with a PD-1 inhibitor. In a particular embodiment, a compound of the present disclosure, or a pharmaceutically acceptable salt thereof is combined with a PD-L1 inhibitor. In a particular embodiment, a compound of the present disclosure, or a pharmaceutically acceptable salt thereof is combined with an IDO inhibitor. In a particular embodiment, a compound of the present disclosure, or a pharmaceutically acceptable salt thereof is combined with an IDO inhibitor and a PD-1 inhibitor. In a particular embodiment, a compound of the present disclosure, or a pharmaceutically acceptable salt thereof, is combined with an IDO inhibitor and a PD-L1 inhibitor. In a particular embodiment, a compound of the present disclosure, or a pharmaceutically acceptable salt thereof, is combined with a TLR7 modulator, such as GS-9620. As used herein, GS-9620 (4-amino-2-butoxy-8-({3-[(pyrrolidin-1-yl)methyl]phenyl}methyl)-7,8-dihydropteridin-6(5H)-one), includes pharmaceutically acceptable salts thereof.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least one additional therapeutic agent selected from the group consisting of immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), interferon alpha receptor ligands, hyaluronidase inhibitors, recombinant IL-7, HBsAg inhibitors, compounds targeting HBcAg, cyclophilin inhibitors, HBV Therapeutic vaccines, HBV prophylactic vaccines, HBV viral entry inhibitors, NTCP inhibitors, antisense oligonucleotide targeting viral mRNA, short interfering RNAs (siRNA), miRNA gene therapy agents, endonuclease modulators, inhibitors of ribonucleotide reductase, Hepatitis B virus E antigen inhibitors, recombinant scavenger receptor A (SRA) proteins, src kinase inhibitors, HBx inhibitors, cccDNA inhibitors, short synthetic hairpin RNAs (sshRNAs), HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), CCR2 chemokine antagonists, thymosin agonists, cytokines, nucleoprotein inhibitors (HBV core or capsid protein inhibitors), stimulators of retinoic acid-inducible gene 1, stimulators of NOD2, stimulators of NOD1, recombinant thymosin alpha-1, Arginase-1 inhibitors, STING agonists, PI3K inhibitors, lymphotoxin beta receptor activators, Natural Killer Cell Receptor 2B4 inhibitors, Lymphocyte-activation gene 3 inhibitors, CD160 inhibitors, cytotoxic T-lymphocyte-associated protein 4 inhibitors, CD137 inhibitors, Killer cell lectin-like receptor subfamily G member 1 inhibitors, TIM-3 inhibitors, B- and T-lymphocyte attenuator inhibitors, CD305 inhibitors, PD-1 inhibitors, PD-L1 inhibitors, PEG-Interferon Lambd, BTK inhibitors, modulators of TIGIT, modulators of CD47, modulators of SIRPalpha, modulators of ICOS, modulators of CD27, modulators of CD70, modulators of OX40, modulators of NKG2D, modulators of Tim-4, modulators of B7-H4, modulators of B7-H3, modulators of NKG2A, modulators of GITR, modulators of CD160, modulators of HEVEM, modulators of CD161, modulators of Axl, modulators of Mer, modulators of Tyro, gene modifiers or editors such as CRISPR (including CRISPR Cas9), zinc finger nucleases or synthetic nucleases (TALENs), a and Hepatitis B virus replication inhibitors. In certain embodiments, the at least one additional therapeutic agent is further selected from hepatitis B surface antigen (HBsAg) secretion or assembly inhibitors, TCR-like antibodies, IDO inhibitors, cccDNA epigenetic modifiers, IAPs inhibitors, and SMAC mimetics.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least a one additional therapeutic agent selected from the group consisting of peginterferon alfa-2b (PEG-Intron®), Multiferon®, interferon alpha 1b (Hapgen®), interferon alpha-2b (Intron A®), pegylated interferon alpha-2a (Pegasys®), interferon alfa-n1(Humoferon®), ribavirin, interferon beta-1a (Avonex®), Bioferon, Ingaron, Inmutag (Inferon), Algeron, Roferon-A, Oligotide, Zutectra, Shaferon, interferon alfa-2b (AXXO), Alfaferone, interferon alfa-2b (BioGeneric Pharma), Feron, interferon-alpha 2 (CJ), BEVAC, Laferonum, VIPEG, BLAUFERON-B, BLAUFERON-A, Intermax Alpha, Realdiron, Lanstion, Pegaferon, PDferon-B, interferon alfa-2b (IFN, Laboratorios Bioprofarma), alfainterferona 2b, Kalferon, Pegnano, Feronsure, PegiHep, interferon alfa 2b (Zydus-Cadila), Optipeg A, Realfa 2B, Reliferon, interferon alfa-2b (Amega), interferon alfa-2b (Virchow), peginterferon alfa-2b (Amega), Reaferon-EC, Proquiferon, Uniferon, Urifron, interferon alfa-2b (Changchun Institute of Biological Products), Anterferon, Shanferon, MOR-22, interleukin-2 (IL-2, Immunex), recombinant human interleukin-2 (Shenzhen Neptunus), Layfferon, Ka Shu Ning, Shang Sheng Lei Tai, INTEFEN, SINOGEN, Fukangtai, Alloferon and celmoleukin.

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®) and at least one additional therapeutic agent selected from the group consisting of HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors).

In a particular embodiment, a compound of the present disclosure, or a pharmaceutically acceptable salt thereof, is combined with a first additional therapeutic agent selected from the group consisting of: entecavir (Baraclude®), adefovir (Hepsera®), tenofovir disoproxil fumarate (Viread®), tenofovir alafenamide, tenofovir, tenofovir disoproxil, tenofovir alafenamide fumarate, tenofovir alafenamide hemifumarate, telbivudine (Tyzeka®) or lamivudine (Epivir-HBV®), one or two additional therapeutic agents selected from the group consisting of: immunomodulators, toll-like receptor modulators (modulators of TLR-1, TLR-2, TLR-3, TLR-4, TLR-5, TLR-6, TLR-7, TLR-8, TLR-9, TLR-10, TLR-11, TLR-12 and TLR-13), HBsAg inhibitors, HBV therapeutic vaccines, HBV antibodies including HBV antibodies targeting the surface antigens of the hepatitis B virus and bispecific antibodies and "antibody-like" therapeutic proteins (such as DARTs®, Duobodies®, Bites®, XmAbs®, TandAbs®, Fab derivatives), cyclophilin inhibitors, stimulators of retinoic acid-inducible gene 1, PD-1 inhibitors, PD-L1 inhibitors, Arginase-1 inhibitors, PI3K inhibitors and stimulators of NOD2, and one or two additional therapeutic agents selected from the group consisting of: HBV viral entry inhibitors, NTCP inhibitors, HBx inhibitors, cccDNA inhibitors, HBV antibodies targeting the surface antigens of the hepatitis B virus, short interfering RNAs (siRNA), miRNA gene therapy agents, short synthetic hairpin RNAs (sshRNAs), and nucleoprotein inhibitors (HBV core or capsid protein inhibitors). In certain embodiments, the one or two additional therapeutic agents is further selected from hepatitis B surface antigen (HBsAg) secretion or assembly inhibitors, TCR-like antibodies, and IDO inhibitors.

In a particular embodiment, a compound of the present disclosure, or a pharmaceutically acceptable salt thereof, is combined with a first additional therapeutic agent selected from the group consisting of: tenofovir disoproxil fumarate (Viread®), tenofovir alafenamide, tenofovir, tenofovir disoproxil, tenofovir alafenamide fumarate, and tenofovir alafenamide hemifumarate; and a second therapeutic agent selected from the group consisting of: modulators of TLR-7 and modulators of TLR-8.

In certain embodiments, a compound of the present disclosure, or a pharmaceutically acceptable salt thereof, is combined with 5-30 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 5-10; 5-15; 5-20; 5-25; 25-30; 20-30; 15-30; or 10-30 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 10 mg tenofovir alafenamide fumarate, tenofovir alafenamide hemifumarate, or tenofovir alafenamide. In certain embodiments, a compound of the present disclosure, or a pharmaceutically acceptable salt thereof, is combined with 25 mg tenofovir alafenamide fumarate, tenofovir alafenamide hemifumarate, or tenofovir alafenamide. A compound of the present disclosure (e.g., a compound of Formula (I) or (II), or Formula (Ia), (Ib) or (IIa)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I) or (II), or Formula (Ia), (Ib) or (IIa)) may be combined with the agents provided herein in any dosage amount of the compound (e.g. from about 1 mg to about 150 mg of compound) the same as if each combination of dosages were specifically and individually listed.

In certain embodiments, a compound of the present disclosure, or a pharmaceutically acceptable salt thereof, is combined with 100-400 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 300 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 250 mg tenofovir disoproxil fumarate, tenofovir disoproxil hemifumarate, or tenofovir disoproxil. In certain embodiments, a compound of the present disclosure, or a pharmaceutically acceptable salt thereof, is combined with 150 mg tenofovir disoproxil fumarate, tenofovir disoproxil hemifumarate, or tenofovir disoproxil. A compound of the present disclosure (e.g., a compound of Formula (I) or (II), or Formula (Ia), (Ib) or (IIa)) may be combined with the agents provided herein in any dosage amount of the compound (e.g., from 50 mg to 500 mg of compound) the same as if each combination of dosages were specifically and individually listed. A compound of the present disclosure (e.g., a compound of Formula (I) or (II), or Formula (Ia), (Ib) or (IIa)) may be combined with the agents provided herein in any dosage amount of the compound (e.g., from about 1 mg to about 150 mg of compound) the same as if each combination of dosages were specifically and individually listed.

Also provided herein is a compound of the present disclosure (e.g., a compound of Formula (I) or (II), or Formula (Ia), (Ib) or (IIa)), or a pharmaceutically acceptable salt thereof, and one or more additional active ingredients for treating HBV, for use in a method of treating or preventing HBV.

Also provided herein is a compound of the present disclosure (e.g., a compound of Formula (I) or (II), or Formula (Ia), (Ib) or (IIa)), or a pharmaceutically acceptable salt thereof, for use in a method of treating or preventing HBV, wherein the compound, or a pharmaceutically acceptable salt thereof is administered simultaneously, separately or sequentially with one or more additional therapeutic agents fort for treating HBV.

Kits

The present disclosure provides a kit comprising a compound of the present disclosure or a pharmaceutically acceptable salt thereof. The kit may further comprise instructions for use in treating an HBV infection. The instructions may be written instructions or electronic storage media (e.g., magnetic diskette or optical disk) containing instructions.

The present disclosure also provides a pharmaceutical kit comprising one or more containers comprising a compound of the present disclosure or a pharmaceutically acceptable salt thereof. Optionally associated with such container(s) can be a notice in the form prescribed by a governmental agency regulating the manufacture, use or sale of pharmaceuticals, which notice reflects approval by the agency for the manufacture, use or sale for human administration. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. Kits may also include multiple unit doses of the compounds and instructions for use and be packaged in quantities sufficient for storage and use in pharmacies (e.g., hospital pharmacies and compounding pharmacies).

Compound Preparation

Also provided are articles of manufacture comprising a unit dosage of a compound of the present disclosure or a pharmaceutically acceptable salt thereof, in suitable packaging for use in the methods described herein. Suitable packaging is known in the art and includes, for example, vials, vessels, ampules, bottles, jars, flexible packaging and the like. An article of manufacture may further be sterilized and/or sealed.

Some embodiments of the instant disclosure are directed to processes and intermediates useful for preparing the subject compounds or pharmaceutically acceptable salts thereof.

Many general references providing commonly known chemical synthetic schemes and conditions useful for synthesizing the disclosed compounds are available (see, e.g., Smith, March's Advanced Organic Chemistry: Reactions, Mechanisms, and Structure, $7^{th}$ edition, Wiley-Interscience, 2013.) Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4th ed., Wiley, New York 2006. The protecting groups may be removed at a convenient subsequent stage using methods known from the art.

EXAMPLES

Exemplary chemical entities of the present disclosure are provided in the specific examples that follow. Those skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

In the following description of the Examples, specific embodiments are described. These embodiments are described in sufficient detail to enable those skilled in the art to practice certain embodiments of the present disclosure. Other embodiments may be utilized and logical and other changes may be made without departing from the scope of the disclosure. The following description is, therefore, not intended to limit the scope of the present disclosure.

Example 1: 11-chloro-12-(3-methoxypropoxy)-8-oxo-2,3,8,13b-tetrahydro-1H-pyrido[2,1-a]pyrrolo[1,2-c]phthalazine-7-carboxylic acid

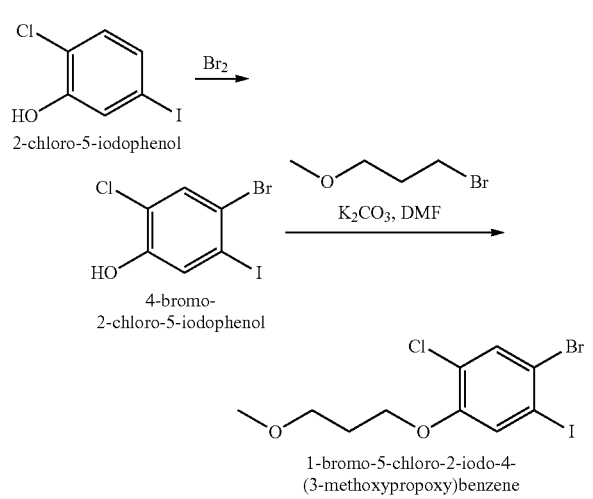

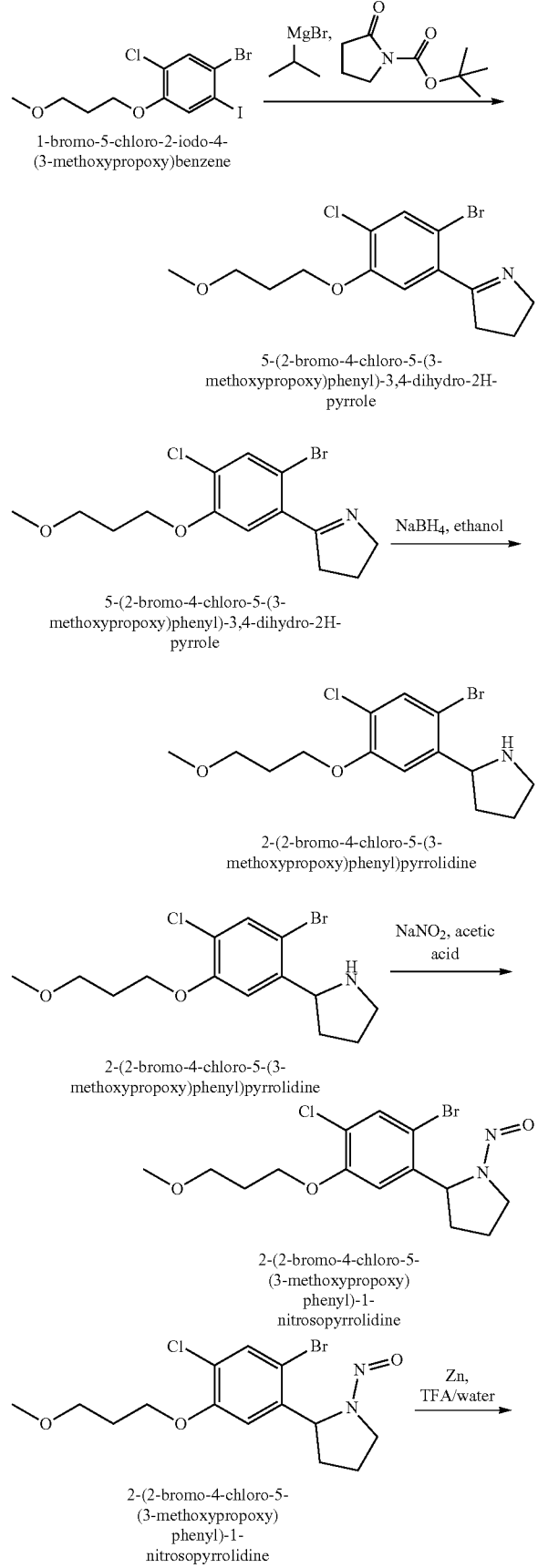

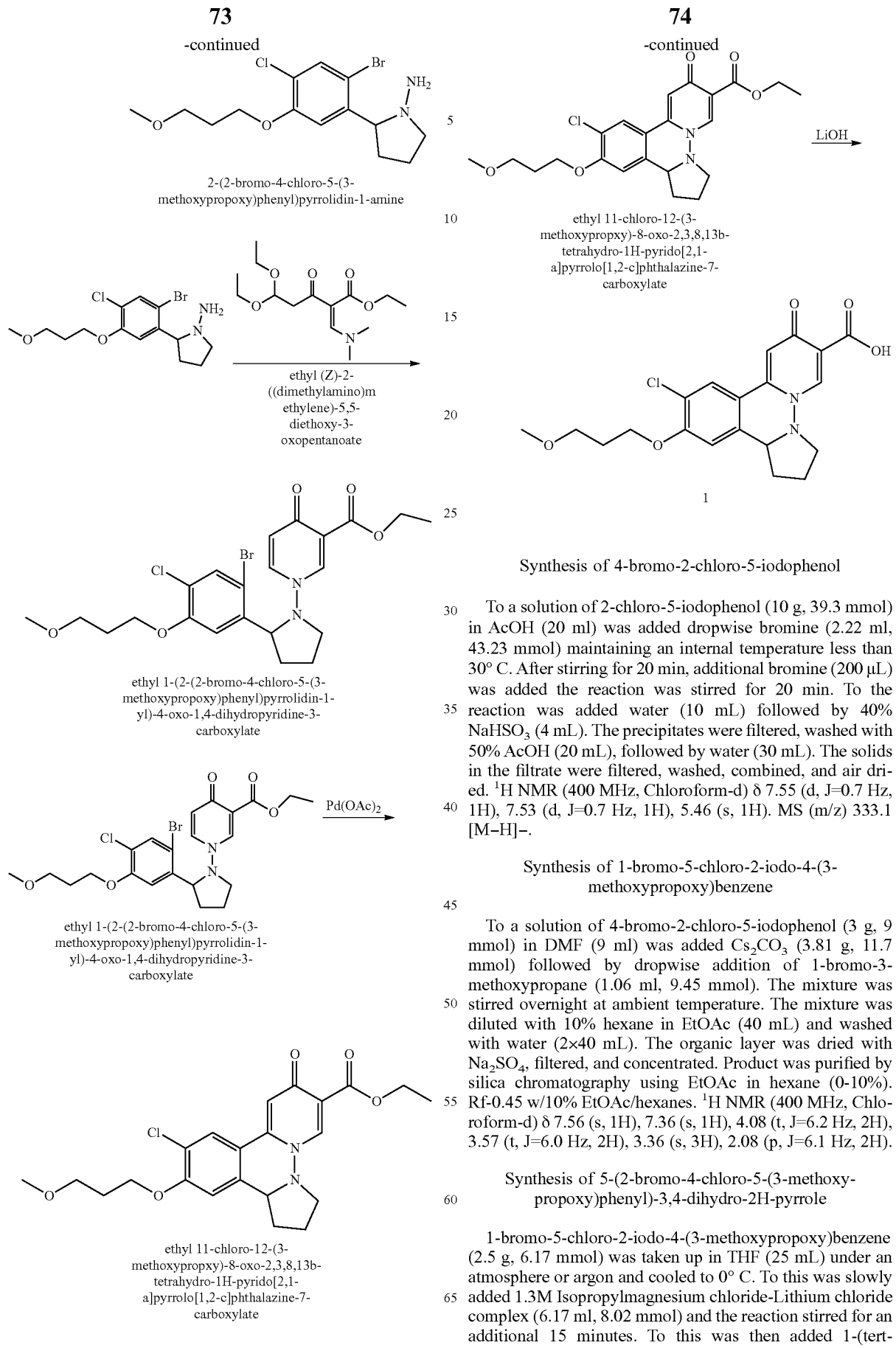

Synthesis of 4-bromo-2-chloro-5-iodophenol

To a solution of 2-chloro-5-iodophenol (10 g, 39.3 mmol) in AcOH (20 ml) was added dropwise bromine (2.22 ml, 43.23 mmol) maintaining an internal temperature less than 30° C. After stirring for 20 min, additional bromine (200 µL) was added the reaction was stirred for 20 min. To the reaction was added water (10 mL) followed by 40% $NaHSO_3$ (4 mL). The precipitates were filtered, washed with 50% AcOH (20 mL), followed by water (30 mL). The solids in the filtrate were filtered, washed, combined, and air dried. $^1$H NMR (400 MHz, Chloroform-d) δ 7.55 (d, J=0.7 Hz, 1H), 7.53 (d, J=0.7 Hz, 1H), 5.46 (s, 1H). MS (m/z) 333.1 [M−H]−.

Synthesis of 1-bromo-5-chloro-2-iodo-4-(3-methoxypropoxy)benzene

To a solution of 4-bromo-2-chloro-5-iodophenol (3 g, 9 mmol) in DMF (9 ml) was added $Cs_2CO_3$ (3.81 g, 11.7 mmol) followed by dropwise addition of 1-bromo-3-methoxypropane (1.06 ml, 9.45 mmol). The mixture was stirred overnight at ambient temperature. The mixture was diluted with 10% hexane in EtOAc (40 mL) and washed with water (2×40 mL). The organic layer was dried with $Na_2SO_4$, filtered, and concentrated. Product was purified by silica chromatography using EtOAc in hexane (0-10%). Rf-0.45 w/10% EtOAc/hexanes. $^1$H NMR (400 MHz, Chloroform-d) δ 7.56 (s, 1H), 7.36 (s, 1H), 4.08 (t, J=6.2 Hz, 2H), 3.57 (t, J=6.0 Hz, 2H), 3.36 (s, 3H), 2.08 (p, J=6.1 Hz, 2H).

Synthesis of 5-(2-bromo-4-chloro-5-(3-methoxypropoxy)phenyl)-3,4-dihydro-2H-pyrrole 1-bromo-5-chloro-2-iodo-4-(3-methoxypropoxy)benzene (2.5 g, 6.17 mmol) was taken up in THF (25 mL) under an atmosphere or argon and cooled to 0° C. To this was slowly added 1.3M Isopropylmagnesium chloride-Lithium chloride complex (6.17 ml, 8.02 mmol) and the reaction stirred for an additional 15 minutes. To this was then added 1-(tert- Butoxycarbonyl)-2-pyrrolidinone 97% (1.05 ml, 6.17 mmol) and the reaction stirred for 15 minutes. Reaction was diluted in EtOAc/aq. ammonium chloride and extracted with EtOAc (3×). Organics were then washed with aq. ammonium chloride (1×), water (1×), brine, then dried over sodium sulfate before filtering and evaporating organics under reduced pressure to afford crude residue. Crude residue was taken up in DCM (10 mL) and to this was added TFA (10 mL) and stirred at room temperature for 1 hour. At this point reaction was complete and solvents were removed under reduced pressure to afford crude residue. Crude residue was diluted in EtOAc then washed with dilute aq. sodium bicarbonate (3×), water (1×), brine, then dried over sodium sulfate before filtering and evaporating organics under reduced pressure to afford crude residue. MS (m/z) 348.2 [M+H]+.

Synthesis of 2-(2-bromo-4-chloro-5-(3-methoxypropoxy)phenyl)pyrrolidine

Crude residue was then taken up in 20 mL EtOH and cooled to 0° C. under an argon atmosphere. To this was then added in portions sodium borohydride (0.65 g, 20 mmol) and reaction allowed to stir for 15 minutes. Reaction was quenched with slow addition of aq. ammonium chloride, then reaction was diluted in EtOAc/H₂O and EtOAc (3×). Organics were then washed with 1N aq HCl (3×). Acid aqueous extracts were then basified with aqueous sodium hydroxide and extracted EtOAc (3×). Organics were washed with water and brine then dried over sodium sulfate, filtered and evaporated to dryness to afford the desired product as a light colored oil. MS (m/z) 350.2 [M+H]+.

Synthesis of 2-(2-bromo-4-chloro-5-(3-methoxypropoxy)phenyl)-1-nitrosopyrrolidine To 2-(2-bromo-4-chloro-5-(3-methoxypropoxy)phenyl)pyrrolidine (930 mg, 2.67 mmol) in 16 mL 3:1 THF:water was added Sodium nitrite (544.09 mg, 7.9 mmol), followed by acetic acid (0.38 ml, 6.67 mmol) and the reaction stirred at 50° C. for 1 hour. Reaction was diluted in EtOAc/H₂O and extracted with EtOAc (3×). Organics were then washed with water (2×), brine, then dried over sodium sulfate before filtering and evaporating organics under reduced pressure to afford crude residue. MS (m/z) 379.0 [M+H]+.

Synthesis of 2-(2-bromo-4-chloro-5-(3-methoxypropoxy)phenyl)pyrrolidin-1-amine

Crude 2-(2-bromo-4-chloro-5-(3-methoxypropoxy)phenyl)-1-nitrosopyrrolidine was taken up in 16 mL of a 3:1 TFA:water mixture and to this was added zinc powder (780 mg, 12 mmol) and the suspension sonicated for 30 minutes. At this point reaction is complete and was filtered rinsed with EtOAc then the filtrate was diluted in EtOAc/H₂O and extracted with EtOAc (3×). Organics were then washed with water (2×), brine, then dried over sodium sulfate before filtering and evaporating organics under reduced pressure to afford crude residue. MS (m/z) 365.1 [M+H]+.

Synthesis of ethyl (Z)-2-((dimethylamino)methylene)-5,5-diethoxy-3-oxopentanoate

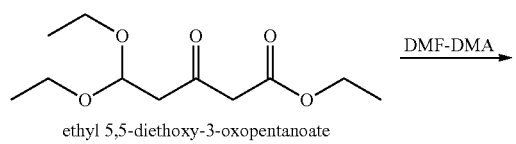

ethyl 5,5-diethoxy-3-oxopentanoate

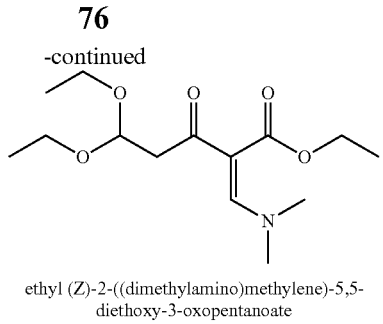

ethyl (Z)-2-((dimethylamino)methylene)-5,5-diethoxy-3-oxopentanoate

Ethyl 5,5-diethoxy-3-oxopentanoate (2.34 g, 10 mmol) and N,N-dimethylformamide dimethylacetal (2.24 mL, 15 mmol) were combined. The mixture was stirred at RT, then concentrated under reduced pressure. The crude material was purified by silica column chromatography (0% to 20% EtOAc/Hex) to afford ethyl (Z)-2-((dimethylamino)methylene)-5,5-diethoxy-3-oxopentanoate (2.90 g, 86%). %). ¹H NMR (400 MHz, Chloroform-d) δ 7.66 (s, 1H), 5.00 (t, J=5.8 Hz, 1H), 4.20 (q, J=7.1 Hz, 2H), 3.64 (dq, J=9.3, 7.0 Hz, 2H), 3.52 (dq, J=9.4, 7.1 Hz, 2H), 3.08 (d, J=5.8 Hz, 2H), 1.30 (t, J=7.1 Hz, 4H), 1.16 (t, J=7.1 Hz, 6H). MS (m/z) 242.0 [M-EtO]+.

Synthesis of ethyl 1-(2-(2-bromo-4-chloro-5-(3-methoxypropoxy)phenyl)pyrrolidin-1-yl)-4-oxo-1,4-dihydropyridine-3-carboxylate Crude 2-(2-bromo-4-chloro-5-(3-methoxypropoxy)phenyl)pyrrolidin-1-amine was dissolved in 5 mL EtOH and to this was added ethyl (Z)-2-((dimethylamino)methylene)-5,5-diethoxy-3-oxopentanoate (839.52 mg, 2.92 mmol)). Reaction was then heated to 70° C. for 1 hour at which point reaction was diluted in EtOAc/H₂O and extracted with EtAc (3×). Organics were then washed with water (2×), brine, then dried over sodium sulfate before filtering and evaporating organics under reduced pressure to afford crude residue. Crude material was purified by silica gel chromatography using EtOAc/MeOH (0 to 25% methanol) to afford 720 mg (60%) of the title compound as a yellow solid. MS (m/z) 515.3 [M+H]+. ¹H NMR (400 MHz, Chloroform-d) δ 8.32 (d, J=2.8 Hz, 1H), 7.46 (s, 1H), 7.42 (dd, J=8.0, 2.8 Hz, 1H), 7.16 (s, 1H), 6.39 (d, J=8.0 Hz, 1H), 4.65 (t, J=8.2 Hz, 1H), 4.32 (qd, J=7.1, 1.5 Hz, 2H), 4.14 (ddt, J=32.9, 9.2, 6.2 Hz, 2H), 3.71-3.53 (m, 3H), 3.37 (s, 3H), 3.24 (q, J=8.8 Hz, 1H), 2.50 (dq, J=13.0, 7.7 Hz, 1H), 2.19-2.04 (m, 4H), 1.75 (dq, J=13.0, 8.4 Hz, 1H), 1.34 (t, J=7.1 Hz, 3H).

Synthesis of ethyl 11-chloro-12-(3-methoxypropoxy)-8-oxo-2,3,8,13b-tetrahydro-1H-pyrido[2,1-a]pyrrolo[1,2-c]phthalazine-7-carboxylate Ethyl 1-(2-(2-bromo-4-chloro-5-(3-methoxypropoxy)phenyl)pyrrolidin-1-yl)-4-oxo-1,4-dihydropyridine-3-carboxylate (215 mg, 0.42 mmol), palladium(II) acetate (9.39 mg, 0.04 mmol), Bis[(2-diphenylphosphino)phenyl]ether, DPEPhos (22.54 mg, 0.04 mmol) and potassium carbonate (144.51 mg, 1.05 mmol) were suspended in DMA (5 mL) in a sealed tube and heated to 110° C. for 1 hour. At this point reaction was cooled then filtered and rinsed with 1-2 mL of THF. MS (m/z) 433.3 [M+H]+.

Synthesis of 11-chloro-12-(3-methoxypropoxy)-8-oxo-2,3,8,13b-tetrahydro-1H-pyrido[2,1-a]pyrrolo[1,2-c]phthalazine-7-carboxylic acid (1)

To the THF solution was added 1 mL of 2N LiOH and the reaction heated at 60° C. for 2 hours. Reaction was then cooled and to the solution was added 2 drops of TFA and the material was purified by reverse phase HPLC using ACN/H2O with 0.1% TFA as the eluent on a Gemini C18 column to afford the title compound 11-chloro-12-(3-methoxypropoxy)-8-oxo-2,3,8,13b-tetrahydro-1H-pyrido[2,1-a]pyrrolo[1,2-c]phthalazine-7-carboxylic acid. MS (m/z) 405.3 [M+H]+. ¹H NMR (400 MHz, DMSO-d6) δ 8.57 (s, 1H), 8.31 (s, 1H), 7.50 (s, 1H), 7.23 (d, J=1.0 Hz, 1H), 4.78 (d, J=6.3 Hz, 1H), 4.26 (ddt, J=29.1, 9.9, 6.3 Hz, 2H), 3.54-3.45 (m, 3H), 3.24 (s, 3H), 2.78-2.60 (m, 2H), 2.33-2.21 (m, 1H), 1.99 (p, J=6.2 Hz, 2H), 1.95-1.81 (m, 1H), 1.69-1.56 (m, 1H).

Example 2: (R)-11-chloro-12-(3-methoxypropoxy)-8-oxo-2,3,8,13b-tetrahydro-1H-pyrido[2,1-a]pyrrolo[1,2-c]phthalazine-7-carboxylic acid and (S)-11-chloro-12-(3-methoxypropoxy)-8-oxo-2,3,8,13b-tetrahydro-1H-pyrido[2,1-a]pyrrolo[1,2-c]phthalazine-7-carboxylic acid

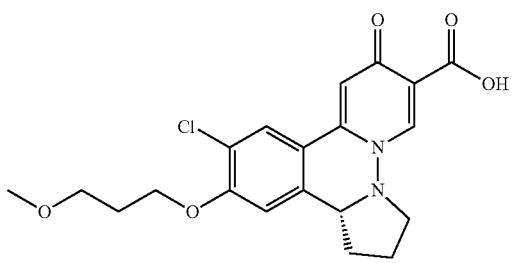

11-chloro-12-(3-methoxypropoxy)-8-oxo-2,3,8,13b-tetrahydro-1H-pyrido[2,1-a]pyrrolo[1,2-c]phthalazine-7-carboxylic acid (1) was separated into its enantiomers by chiral SFC chromatography using OD-H 4.6×100 mm columns with 30% methanol as the co-solvent. Example 2 is the slower eluting peak retention time of 5.75 min. ¹H NMR (400 MHz, DMSO-d6) δ 8.57 (s, 1H), 8.31 (s, 1H), 7.50 (s, 1H), 7.23 (d, J=1.0 Hz, 1H), 4.78 (d, J=6.3 Hz, 1H), 4.26 (ddt, J=29.1, 9.9, 6.3 Hz, 2H), 3.54-3.45 (m, 3H), 3.24 (s, 3H), 2.78-2.60 (m, 2H), 2.33-2.21 (m, 1H), 1.99 (p, J=6.2 Hz, 2H), 1.95-1.81 (m, 1H), 1.69-1.56 (m, 1H).

Example 3: (S)-11-chloro-12-(3-methoxypropoxy)-8-oxo-2,3,8,13b-tetrahydro-1H-pyrido[2,1-a]pyrrolo[1,2-c]phthalazine-7-carboxylic acid

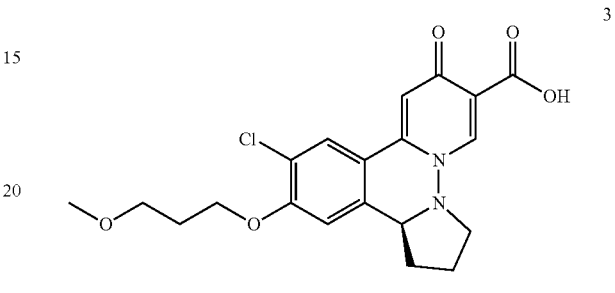

11-chloro-12-(3-methoxypropoxy)-8-oxo-2,3,8,13b-tetrahydro-1H-pyrido[2,1-a]pyrrolo[1,2-c]phthalazine-7-carboxylic acid (1) was separated into its enantiomers by chiral SFC chromatography using OD-H 4.6×100 mm columns with 30% methanol as the co-solvent. Example 3 is the faster eluting peak retention time of 4.4 min. ¹H NMR (400 MHz, DMSO-d6) δ 8.57 (s, 1H), 8.31 (s, 1H), 7.50 (s, 1H), 7.23 (d, J=1.0 Hz, 1H), 4.78 (d, J=6.3 Hz, 1H), 4.26 (ddt, J=29.1, 9.9, 6.3 Hz, 2H), 3.54-3.45 (m, 3H), 3.24 (s, 3H), 2.78-2.60 (m, 2H), 2.33-2.21 (m, 1H), 1.99 (p, J=6.2 Hz, 2H), 1.95-1.81 (m, 1H), 1.69-1.56 (m, 1H).

Example 4: 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

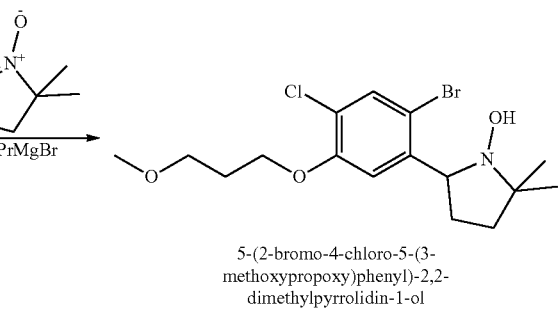

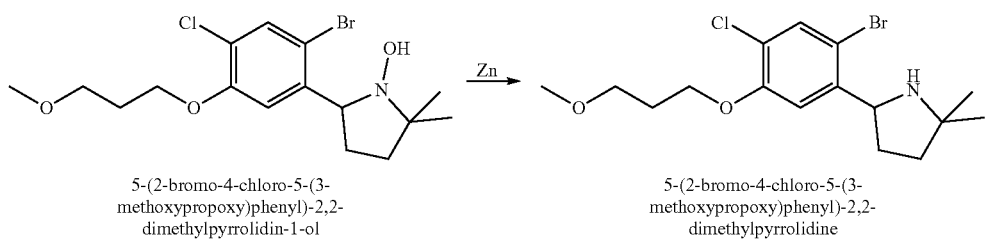

-continued

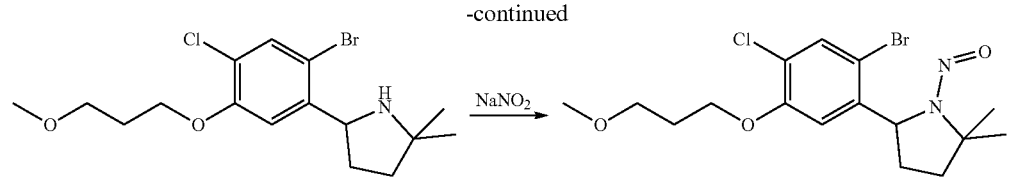

5-(2-bromo-4-chloro-5-(3-methoxypropoxy)phenyl)-2,2-dimethylpyrrolidine 5-(2-bromo-4-chloro-5-(3-methoxypropoxy)phenyl)-2,2-dimethyl-1-nitrosopyrrolidine

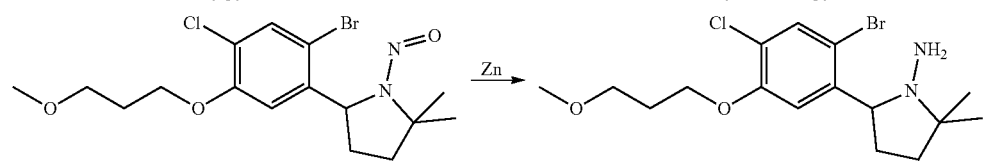

5-(2-bromo-4-chloro-5-(3-methoxypropoxy)phenyl)-2,2-dimethyl-1-nitrosopyrrolidine 5-(2-bromo-4-chloro-5-(3-methoxypropoxy)phenyl)-2,2-dimethylpyrrolidin-1-amine

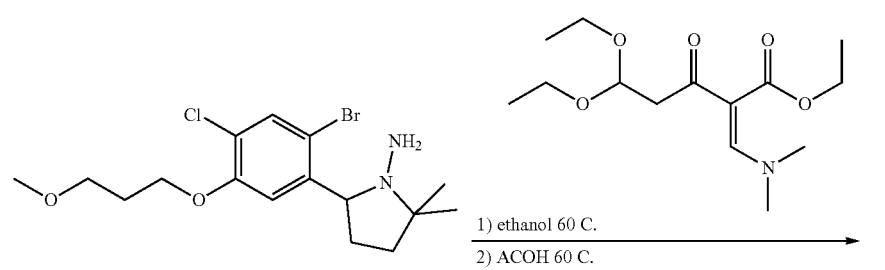
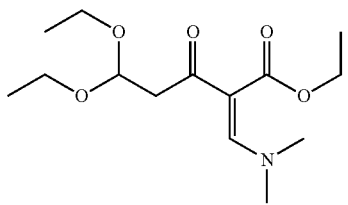

5-(2-bromo-4-chloro-5-(3-methoxypropoxy)phenyl)-2,2-dimethylpyrrolidin-1-amine

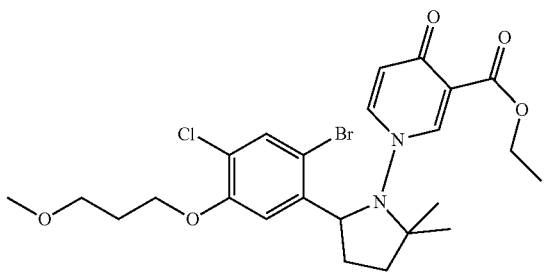

ethyl 1-(5-(2-bromo-4-chloro-5-(3-methoxypropoxy)phenyl)-2,2-dimethylpyrrolidin-1-yl)-4-oxo-1,4-dihydropyridine-3-carboxylate

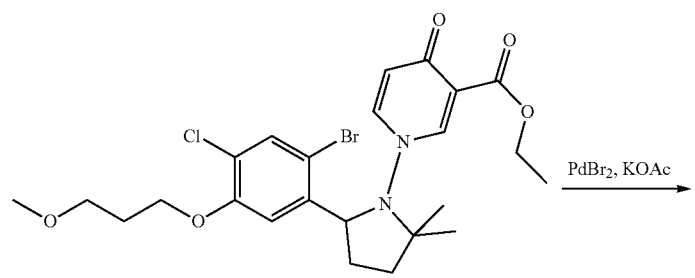

ethyl 1-(5-(2-bromo-4-chloro-5-(3-methoxypropoxy)phenyl)-2,2-dimethylpyrrolidin-1-yl)-4-oxo-1,4-dihydropyridine-3-carboxylate

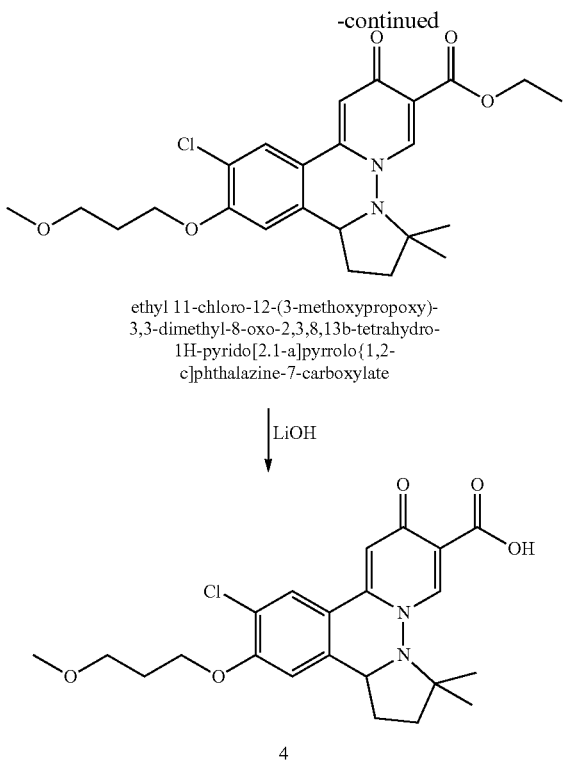

ethyl 11-chloro-12-(3-methoxypropoxy)-
3,3-dimethyl-8-oxo-2,3,8,13b-tetrahydro-
1H-pyrido[2.1-a]pyrrolo{1,2-
c]phthalazine-7-carboxylate

4

Synthesis of 5-(2-bromo-4-chloro-5-(3-methoxypropoxy)phenyl)-2,2-dimethylpyrrolidin-1-ol To a solution of 1-bromo-5-chloro-2-iodo-4-(3-methoxypropoxy)benzene (2.0 g, 4.9 mmol) in MeTHF (20 ml) at 0° C., was slowly added 2.9M isopropylmagnesium Bromide (3.4 ml, 9.9 mmol). The mixture was stirred for 10 minutes, then 2,2-dimethyl-3,4-dihydro-2H-pyrrole 1-oxide (1.1 g, 9.9 mmol) was added and the mixture was stirred for 10 minutes. The reaction was quenched with saturated NH$_4$Cl and extracted 2× with EtOAc. The combined organics were dried over sodium sulfate, concentrated and purified by flash column chromatography. MS (m/z) 394.14 [M+H]+.

Synthesis of 5-(2-bromo-4-chloro-5-(3-methoxypropoxy)phenyl)-2,2-dimethylpyrrolidine To a solution of 5-(2-bromo-4-chloro-5-(3-methoxypropoxy)phenyl)-2,2-dimethylpyrrolidin-1-ol (0.74 g, 1.9 mmol) in TFA (11.3 ml) and water (4.5 ml) was added zinc powder (0.6 g, 9.4 mmol). The mixture was heated to 50° C. until done about 30 minutes. The solution was concentrated under vacuum. The crude mixture was quenched with saturated sodium bicarbonate until fizzing stops. The product was extracted with DCM. The organic layer was washed with water, dried under Na$_2$SO$_4$, filtered, and concentrated. The product was used crude in the next reaction. MS (m/z) 378.1 [M+H]+.

Synthesis of 5-(2-bromo-4-chloro-5-(3-methoxypropoxy)phenyl)-2,2-dimethyl-1-nitrosopyrrolidine To a solution of 5-(2-bromo-4-chloro-5-(3-methoxypropoxy)phenyl)-2,2-dimethylpyrrolidine (0.7 g, 1.9 mmol) in THF (5.0 mL) was added an aqueous solution of NaNO$_2$ (307.7 mg, 4.5 mmol in 2.5 mL of water) followed by acetic acid (0.3 mL, 4.6 mmol). The mixture was stirred at 50° C. until done (about 1 hour). The reaction mixture was then diluted with EtOAc, washed with brine, dried with Na$_2$SO$_4$, filtered, and concentrated. MS (m/z) 407.6 [M+H]+.

Synthesis of 5-(2-bromo-4-chloro-5-(3-methoxypropoxy)phenyl)-2,2-dimethylpyrrolidin-1-amine To a solution of 5-(2-bromo-4-chloro-5-(3-methoxypropoxy)phenyl)-2,2-dimethyl-1-nitrosopyrrolidine (0.75 g, 1.9 mmol) in TFA (11.1 ml) and water (4.5 ml) was added zinc powder (0.6 g, 9.4 mmol). The mixture was heated to 50° C. until done about 30 minutes. The solution was concentrated under vacuum. The crude mixture was quenched with saturated sodium bicarbonate until fizzing stops. The product was extracted with DCM. The organic layer was washed with water, dried under Na$_2$SO$_4$, filtered, and concentrated. The product was used crude in the next reaction. MS (m/z) 391.9 [M+H]+.

Synthesis of ethyl 1-(5-(2-bromo-4-chloro-5-(3-methoxypropoxy)phenyl)-2,2-dimethylpyrrolidin-1-yl)-4-oxo-1,4-dihydropyridine-3-carboxylate To a solution of 5-(2-bromo-4-chloro-5-(3-methoxypropoxy)phenyl)-2,2-dimethylpyrrolidin-1-amine (0.72 g, 1.8 mmol) in EtOH (4.5 ml) was added ethyl (Z)-2-((dimethylamino)methylene)-5,5-diethoxy-3-oxopentanoate (0.79 g, 2.7 mmol). The mixture was heated to 60° C. for 90 minutes after which acetic acid (4.5 ml) was added. The reaction was stirred overnight and checked for completion. The crude mixture was diluted with saturated K$_2$HPO$_4$ and EtOAc, the organic layer was then washed with brine and dried under Na$_2$SO$_4$, filtered, and concentrated. The product was purified by flash column chromatography. MS (m/z) 543.3 [M+H]+.

Synthesis of ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate A solution of ethyl 1-(5-(2-bromo-4-chloro-5-(3-methoxypropoxy)phenyl)-2,2-dimethylpyrrolidin-1-yl)-4-oxo-1,4-dihydropyridine-3-carboxylate (460 mg, 0.85 mmol), PdBr$_2$ (34 mg, 0.13 mmol), and potassium acetate (207 mg, 2.1 mmol) in N,N-dimethylacetamide (5 ml) was purged with argon for 2 min. The reaction vessel was sealed and the mixture was stirred overnight at 90° C., reaction was not complete, added more. PdBr$_2$ (34 mg, 0.13 mmol). The mixture was cooled, diluted with EtOAc and water, extract 2×EtOAc and washed organic with brine. The organic layer was dried with Na$_2$SO$_4$, filtered, and concentrated. Product was purified by flash column chromatography. MS (m/z) 461.6 [M+H]+.

Synthesis of 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (4)

A solution of ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate (25 mg, 0.05 mmol) in EtOH (1 ml) and 2M LiOH (0.3 ml) was stirred at room temperature until complete. The mixture was quenched with TFA (0.5 ml) and water (0.5 ml), filtered and purified by HPLC. $^1$H NMR (400 MHz, Chloroform-d) δ 8.56 (s, 1H), 7.79 (s, 1H), 7.09 (s, 1H), 6.87 (s, 1H), 4.79 (d, 1H), 4.31-4.14 (m, 2H), 3.61 (q, 2H), 3.37 (s, 3H), 2.55-2.43 (m, 1H), 2.44-2.34 (m, 1H), 2.20-2.09 (m, 2H), 1.97-1.86 (m, 1H), 1.70-1.57 (m, 1H), 1.38 (s, 3H), 0.68 (s, 3H). MS (m/z) 433.3 [M+H]+.

Example 5: (R)-11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

5

Ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using AD-H 4.6×100 mm columns with 30% methanol as the co-solvent. The faster eluting peak with a retention time of 2.1 min was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. 1H NMR (400 MHz, Chloroform-d) δ 8.54 (s, 1H), 7.78 (s, 1H), 7.06 (s, 1H), 6.87 (s, 1H), 4.79 (d, 1H), 4.28-4.14 (m, 2H), 3.68-3.54 (m, 2H), 3.37 (s, 3H), 2.56-2.43 (m, 1H), 2.44-2.34 (m, 1H), 2.20-2.10 (m, 2H), 1.95-1.86 (m, 1H), 1.69-1.56 (m, 1H), 1.38 (s, 3H), 0.68 (s, 3H). MS (m/z) 433.3 [M+H]+.

Example 6: (S)-11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

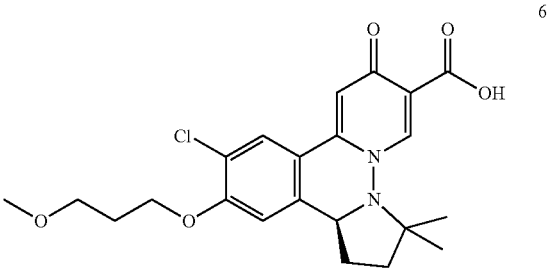 [SMILES: COCCCOc1cc2c(cc1Cl)-c1cc(=O)c(C(=O)O)cn1N1[C@H]2CCC1(C)C]

6

Ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using AD-H 4.6×100 mm columns with 30% methanol as the co-solvent. The slower eluting peak with a retention time of 3.45 min was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.54 (s, 1H), 7.78 (s, 1H), 7.06 (s, 1H), 6.87 (s, 1H), 4.79 (d, 1H), 4.28-4.14 (m, 2H), 3.68-3.54 (m, 2H), 3.37 (s, 3H), 2.56-2.43 (m, 1H), 2.44-2.34 (m, 1H), 2.20-2.10 (m, 2H), 1.95-1.86 (m, 1H), 1.69-1.56 (m, 1H), 1.38 (s, 3H), 0.68 (s, 3H). MS (m/z) 433.3 [M+H]+.

Example 7: (3S,13bS)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid

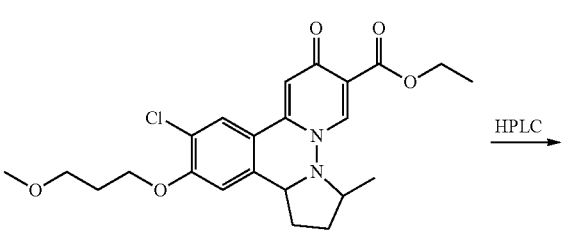

ethyl 11-chloro-12-(3-methoxypropoxy)-3-methyl-8-oxo-2,3,8,13b-tetrahydro-1H-pyrido[2,1-a]pyrrolo[1,2-c]phthalazine-7-carboxylate

HPLC →

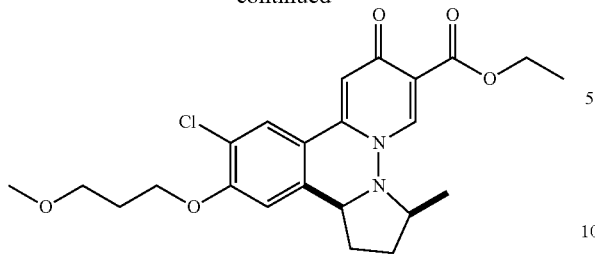

ethyl cis-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate

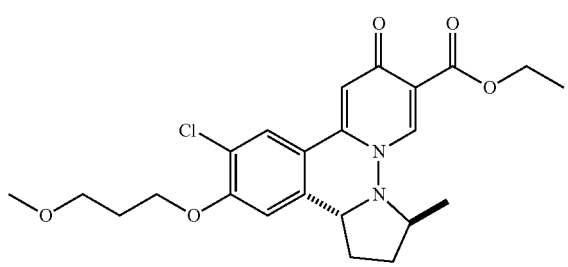

ethyl trans-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate Synthesis of ethyl-1-chloro-12-(3-methoxypropoxy)-3-methyl-8-oxo-2,3,8,13b-tetrahydro-1H-pyrido[2,1-a]pyrrolo[1,2-c]phthalazine-7-carboxylate Ethyl-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate was prepared similarly to example 1 using tert-butyl (R,S)-2-methyl-5-oxopyrrolidine-1-carboxylate in place of 1-(tert-butoxycarbonyl)-2-pyrrolidinone. The cis/trans mixture was separated by reverse phase HPLC using ACN/H2O with 0.1% TFA as the eluent on a Gemini C18 column. The cis isomer was assigned to be the faster eluting peak and the trans the slower.

Ethyl cis-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate $^1$H NMR (400 MHz, Chloroform-d) δ 8.61 (s, 1H), 7.91 (s, 1H), 7.76 (s, 1H), 6.86 (s, 1H), 4.77 (d, J=6.3 Hz, 1H), 4.43 (qd, J=7.1, 3.4 Hz, 2H), 4.23 (tdd, J=9.2, 6.3, 3.0 Hz, 2H), 4.03 (q, J=6.7 Hz, 1H), 3.71-3.53 (m, 2H), 3.38 (s, 3H), 2.61-2.40 (m, 2H), 2.32 (dtd, J=11.8, 7.9, 3.5 Hz, 1H), 2.15 (p, J=6.0 Hz, 2H), 1.49 (ddd, J=13.7, 8.9, 5.5 Hz, 1H), 1.41 (t, J=7.1 Hz, 3H), 0.69 (d, J=6.6 Hz, 3H). MS (m/z) 447.3 [M+H]+.

(3R,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid (7)

Ethyl cis-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate intermediate was separated into its single enantiomers by chiral SFC chromatography using a IA 4.6×100 mm column with 30% methanol as the co-solvent. The faster eluting peak with a retention time of 5.56 min was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.58 (s, 1H), 7.78 (s, 1H), 7.04 (s, 1H), 6.87 (s, 1H), 4.71 (d, J=6.1 Hz, 1H), 4.33-4.09 (m, 2H), 3.94 (q, J=6.8 Hz, 1H), 3.68-3.54 (m, 2H), 3.37 (s, 3H), 2.49 (dd, J=16.7, 8.0 Hz, 2H), 2.40-2.22 (m, 1H), 2.15 (p, J=6.1 Hz, 2H), 1.48-1.35 (m, 1), 0.66 (d, J=6.7 Hz, 3H). MS (m/z) 419.4 [M+H]+.

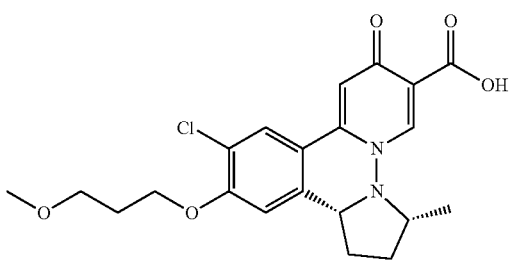

7

Example 8: (3S,13bS)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid

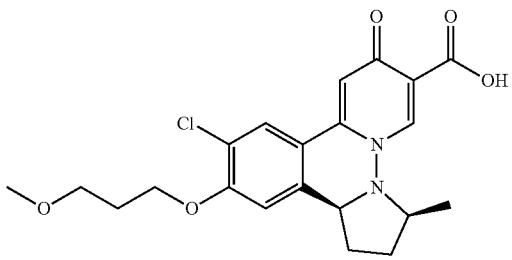

8

Ethyl cis-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate intermediate was separated into its single enantiomers by chiral SFC chromatography using a IA 4.6×100 mm column with 30% methanol as the co-solvent. The slower eluting peak with a retention time of 6.11 min was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. ¹H NMR (400 MHz, Chloroform-d) δ 8.58 (s, 1H), 7.78 (s, 1H), 7.04 (s, 1H), 6.87 (s, 1H), 4.71 (d, J=6.1 Hz, 1H), 4.33-4.09 (m, 2H), 3.94 (q, J=6.8 Hz, 1H), 3.68-3.54 (m, 2H), 3.37 (s, 3H), 2.49 (dd, J=16.7, 8.0 Hz, 2H), 2.40-2.22 (m, 1H), 2.15 (p, J=6.1 Hz, 2H), 1.48-1.35 (m, 1), 0.66 (d, J=6.7 Hz, 3H). MS (m/z) 419.4 [M+H]+.

Example 9: (3R,13bS)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid

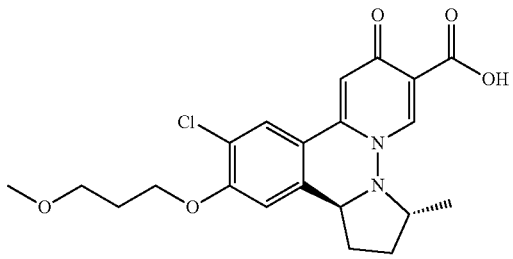

Ethyl trans-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate ¹H NMR (400 MHz, Chloroform-d) δ 8.54 (s, 1H), 7.89 (s, 1H), 7.63 (s, 1H), 6.92-6.89 (m, 1H), 4.81 (d, J=6.3 Hz, 1H), 4.40 (tq, J=7.1, 3.4 Hz, 2H), 4.23 (tdd, J=9.2, 6.2, 3.0 Hz, 2H), 3.74-3.50 (m, 2H), 3.12-3.02 (m, 1H), 2.58-2.37 (m, 2H), 2.14 (p, J=6.1 Hz, 2H), 1.99-1.86 (m, 1H), 1.74-1.55 (m, 1H), 1.39 (t, J=7.1 Hz, 3H), 1.19 (d, J=6.1 Hz, 3H). MS (m/z) 447.3 [M+H]+.

Ethyl trans-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate intermediate was separated into its single enantiomers by chiral SFC chromatography using a IA 4.6×100 mm column with 30% methanol as the co-solvent. The faster eluting peak with a retention time of 5.11 min was taken up in in EtOH (1 ml) and 2M LiOH (0.3 ml) then stirred at room temperature until hydrolysis was complete. ¹H NMR (400 MHz, Chloroform-d) δ 8.57 (s, 1H), 7.80 (s, 1H), 7.04 (s, 1H), 6.89 (s, 1H), 4.74 (d, J=6.4 Hz, 1H), 4.33-4.13 (m, 2H), 3.61 (q, J=5.8 Hz, 2H), 3.37 (s, 3H), 3.03 (q, J=7.2 Hz, 1H), 2.56-2.26 (m, 2H), 2.14 (p, J=6.1 Hz, 2H), 1.91 (dq, J=13.0, 9.0 Hz, 1H), 1.62 (ddt, J=13.3, 7.3, 3.3 Hz, 1H), 1.18 (d, J=6.1 Hz, 4H). MS (m/z) 419.3 [M+H]+.

Example 10: (3S,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid

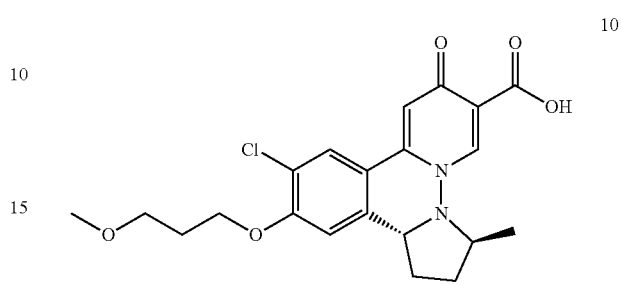

(3S,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid Ethyl trans-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate intermediate was separated into its single enantiomers by chiral SFC chromatography using a IA 4.6×100 mm column with 30% methanol as the co-solvent. The slower eluting peak with a retention time of 6.99 min was taken up in in EtOH (1 ml) and 2M LiOH (0.3 ml) then stirred at room temperature until hydrolysis was complete. ¹H NMR (400 MHz, Chloroform-d) δ 8.57 (s, 1H), 7.80 (s, 1H), 7.04 (s, 1H), 6.89 (s, 1H), 4.74 (d, J=6.4 Hz, 1H), 4.33-4.13 (m, 2H), 3.61 (q, J=5.8 Hz, 2H), 3.37 (s, 3H), 3.03 (q, J=7.2 Hz, 1H), 2.56-2.26 (m, 2H), 2.14 (p, J=6.1 Hz, 2H), 1.91 (dq, J=13.0, 9.0 Hz, 1H), 1.62 (ddt, J=13.3, 7.3, 3.3 Hz, 1H), 1.18 (d, J=6.1 Hz, 4H). MS (m/z) 419.3 [M+H]+.

(3S,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid Ethyl trans-11-chloro-12-(3-methoxypropoxy)-3-methyl-8-oxo-2,3,8,13b-tetrahydro-1H-pyrido[2,1-a]pyrrolo[1,2-c]phthalazine-7-carboxylate intermediate was separated into its single enantiomers by chiral SFC chromatography using a IA 4.6×100 mm column with 30% methanol as the co-solvent. The slower eluting peak with a retention time of 6.99 min was taken up in in EtOH (1 ml) and 2M LiOH (0.3 ml) then stirred at room temperature until hydrolysis was complete. ¹H NMR (400 MHz, Chloroform-d) δ 8.57 (s, 1H), 7.80 (s, 1H), 7.04 (s, 1H), 6.89 (s, 1H), 4.74 (d, J=6.4 Hz, 1H), 4.33-4.13 (m, 2H), 3.61 (q, J=5.8 Hz, 2H), 3.37 (s, 3H), 3.03 (q, J=7.2 Hz, 1H), 2.56-2.26 (m, 2H), 2.14 (p, J=6.1 Hz, 2H), 1.91 (dq, J=13.0, 9.0 Hz, 1H), 1.62 (ddt, J=13.3, 7.3, 3.3 Hz, 1H), 1.18 (d, J=6.1 Hz, 4H). MS (m/z) 419.3 [M+H]+.

Example 11: 13-chloro-12-(3-methoxypropoxy)-7,7-dimethyl-2-oxo-2,7,8,9,10,10a-hexahydrodipyrido[2,1-a:1',2'-c]phthalazine-3-carboxylic acid

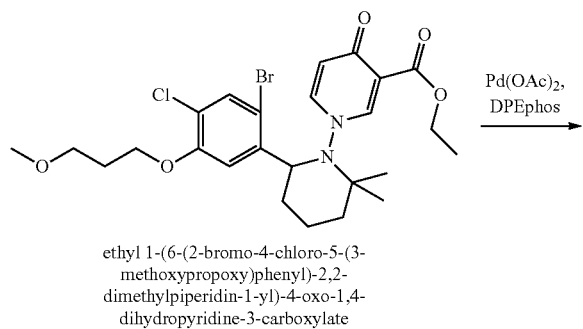

ethyl 1-(6-(2-bromo-4-chloro-5-(3-methoxypropoxy)phenyl)-2,2-dimethylpiperidin-1-yl)-4-oxo-1,4-dihydropyridine-3-carboxylate

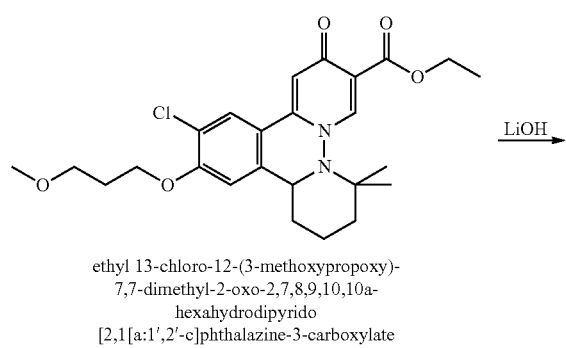

ethyl 13-chloro-12-(3-methoxypropoxy)-7,7-dimethyl-2-oxo-2,7,8,9,10,10a-hexahydrodipyrido[2,1[a:1',2'-c]phthalazine-3-carboxylate

11

Ethyl 1-(6-(2-bromo-4-chloro-5-(3-methoxypropoxy)phenyl)-2,2-dimethylpiperidin-1-yl)-4-oxo-1,4-dihydropyridine-3-carboxylate was prepared similarly to example 4 using 2,2-dimethyl-2,3,4,5-tetrahydropyridine 1-oxide in place of 2,2-dimethyl-3,4-dihydro-2H-pyrrole 1-oxide. MS (m/z) 555.2 [M+H]+.

Synthesis of ethyl 13-chloro-12-(3-methoxypropoxy)-7,7-dimethyl-2-oxo-2,7,8,9,10,10a-hexahydrodipyrido[2,1-a:1',2'-c]phthalazine-3-carboxylate Ethyl 1-(6-(2-bromo-4-chloro-5-(3-methoxypropoxy)phenyl)-2,2-dimethylpiperidin-1-yl)-4-oxo-1,4-dihydropyridine-3-carboxylate (289 mg, 0.5 mmol) was dissolved in DMA (3.9 mL) with potassium propionate (146 mg, 1.3 mmol) under argon. Pd(OAc)$_2$ (12 mg, 0.5 mmol), and (Oxydi-2,1-phenylene)bis(diphenylphosphine) (28 mg, 0.05 mmol) were added and the mixture was flushed with argon. The reaction was heated to 100° C. until done. Once cool dilute with EtOAc and brine, extract with EtOAc 2×, dry the organics over sodium sulfate, concentrate, and purify by flash column chromatography. MS (m/z) 475.4 [M+H]+.

13-chloro-12-(3-methoxypropoxy)-7,7-dimethyl-2-oxo-2,7,8,9,10,10a-hexahydrodipyrido[2,1-a:1',2'-c]phthalazine-3-carboxylic acid To a vial add ethyl 13-chloro-12-(3-methoxypropoxy)-7,7-dimethyl-2-oxo-2,7,8,9,10,10a-hexahydrodipyrido[2,1-a:1',2'-c]phthalazine-3-carboxylate (4 mg, 0.008 mmol), EtOH (1 ml) and 2 M LiOH (0.2 ml), stir reaction until done, dilute with 0.5 ml 1:1 TFA:water and 1 ml DMF, filter, purify by HPLC. $^1$H NMR (400 MHz, Chloroform-d) δ 8.64 (s, 1H), 7.77 (s, 1H), 7.08 (s, 1H), 6.95-6.87 (m, 1H), 4.62-4.54 (m, 1H), 4.30-4.16 (m, 2H), 3.70-3.55 (m, 2H), 3.38 (s, 3H), 2.60-2.50 (m, 1H), 2.26-2.10 (m, 3H), 1.85-1.73 (m, 1H), 1.72-1.53 (m, 3H), 1.16 (s, 3H), 0.43 (s, 3H). MS (m/z) 447.4 [M+H]+.

Synthesis of 2,2-dimethyl-2,3,4,5-tetrahydropyridine 1-oxide

To a RB was added 2,2-dimethylpiperidine (1.3 g, 11.8 mmol), water (4.3 ml) and sodium tungstate dihydrate (366.4 mg, 1.2 mmol). The mixture was cooled to 0° C. then hydrogen peroxide was slowly added (3.6 ml, 35.3 mmol, 30% aq. solution) and stirred for 2 hours allowing to warm to RT. Follow reaction by NMR looking for triplet at 7.04 ppm using CDCl$_3$ as extraction solvent. Once complete, dilute with extract reaction mixture 2× with DCM, dry the organics over sodium sulfate, concentrate and use crude in the next reaction. $^1$H NMR (400 MHz, Chloroform-d) δ 7.04 (t, 1H), 2.42-2.33 (m, 2H), 1.91-1.85 (m, 2H), 1.75-1.67 (m, 2H), 1.45 (s, 6H).

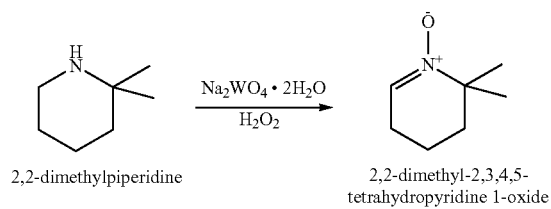

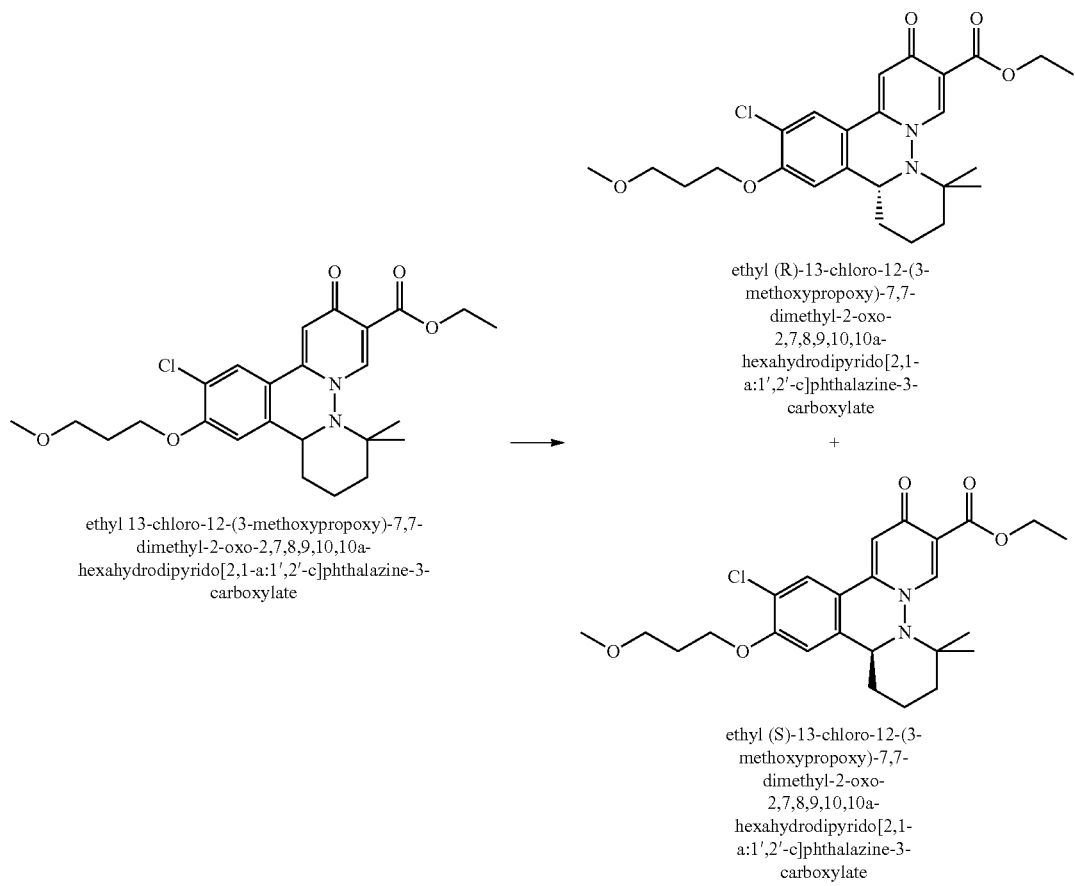

Ethyl (R)-13-chloro-12-(3-methoxypropoxy)-7,7-dimethyl-2-oxo-2,7,8,9,10,10a-hexahydrodipyrido[2,1-a:1',2'-c]phthalazine-3-carboxylate and ethyl (S)-13-chloro-12-(3-methoxypropoxy)-7,7-dimethyl-2-oxo-2,7,8,9,10,10a-hexahydrodipyrido[2,1-a:1',2'-c]phthalazine-3-carboxylate Ethyl 13-chloro-12-(3-methoxypropoxy)-7,7-dimethyl-2-oxo-2,7,8,9,10,10a-hexahydrodipyrido[2,1-a:1',2'-c]phthalazine-3-carboxylate was separated into its enantiomers by chiral SFC chromatography using AD-H 4.6×100 mm columns with 30% methanol as the co-solvent. Peak 1 is the R isomer and has a retention time of 2.55 minutes and peak 2 is the S isomer and has a retention time of 3.72 minutes. Both have a MS (m/z) 475.4 [M+H]+.

Example 12: (R)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid

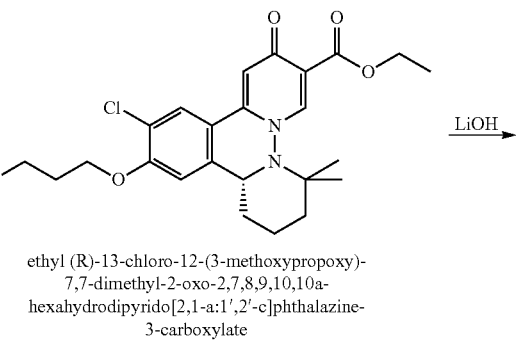

(R)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid

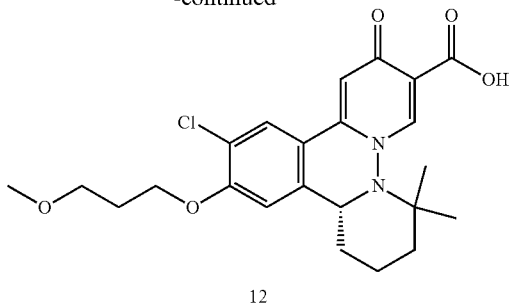

12

Ethyl (R)-13-chloro-12-(3-methoxypropoxy)-7,7-dimethyl-2-oxo-2,7,8,9,10,10a-hexahydrodipyrido[2,1-a: 1',2'-c]phthalazine-3-carboxylate was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.64 (s, 1H), 7.77 (s, 1H), 7.08 (s, 1H), 6.95-6.87 (m, 1H), 4.62-4.54 (m, 1H), 4.30-4.16 (m, 2H), 3.70-3.55 (m, 2H), 3.38 (s, 3H), 2.60-2.50 (m, 1H), 2.26-2.10 (m, 3H), 1.85-1.73 (m, 1H), 1.72-1.53 (m, 3H), 1.16 (s, 3H), 0.43 (s, 3H). MS (m/z) 447.4 [M+H]+.

Example 13: (S)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid

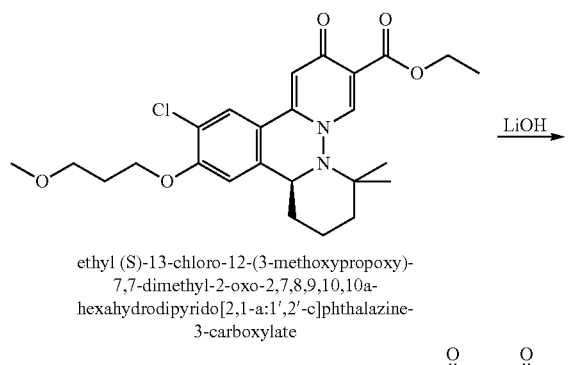

ethyl (S)-13-chloro-12-(3-methoxypropoxy)-7,7-dimethyl-2-oxo-2,7,8,9,10,10a-hexahydrodipyrido[2,1-a:1',2'-c]phthalazine-3-carboxylate LiOH

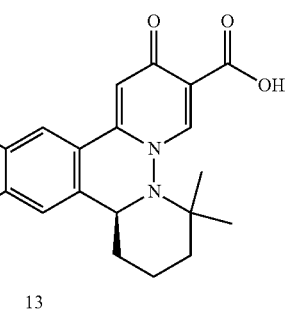

13

(S)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid Ethyl (S)-13-chloro-12-(3-methoxypropoxy)-7,7-dimethyl-2-oxo-2,7,8,9,10,10a-hexahydrodipyrido[2,1-a: 1',2'-c]phthalazine-3-carboxylate was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.64 (s, 1H), 7.77 (s, 1H), 7.08 (s, 1H), 6.95-6.87 (m, 1H), 4.62-4.54 (m, 1H), 4.30-4.16 (m, 2H), 3.70-3.55 (m, 2H), 3.38 (s, 3H), 2.60-2.50 (m, 1H), 2.26-2.10 (m, 3H), 1.85-1.73 (m, 1H), 1.72-1.53 (m, 3H), 1.16 (s, 3H), 0.43 (s, 3H). MS (m/z) 447.4 [M+H]+.

Example 14: (R)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

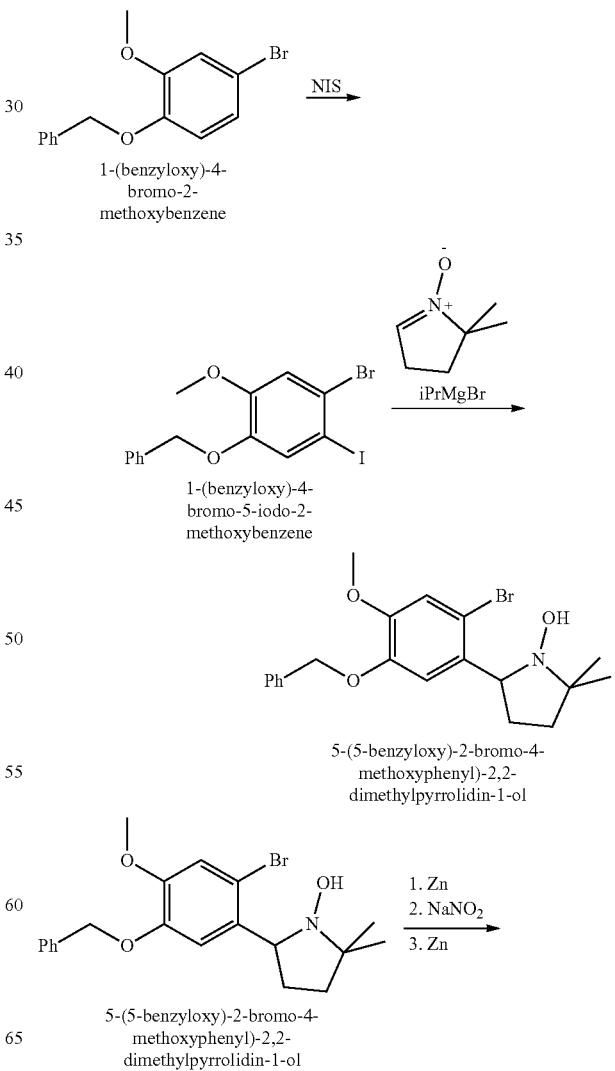

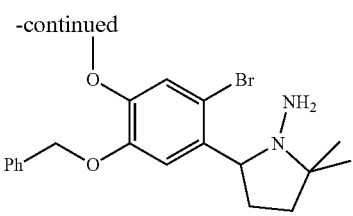

5-(5-benzyloxy)-2-bromo-4-methoxyphenyl)-2,2-dimethylpyrrolidin-1-amine

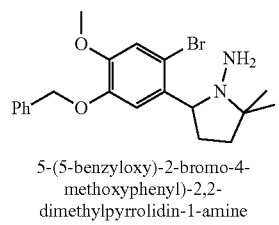

5-(5-benzyloxy)-2-bromo-4-methoxyphenyl)-2,2-dimethylpyrrolidin-1-amine

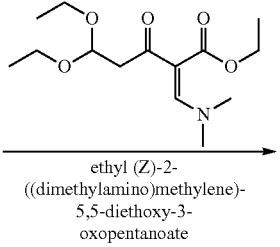

ethyl (Z)-2-((dimethylamino)methylene)-5,5-diethoxy-3-oxopentanoate

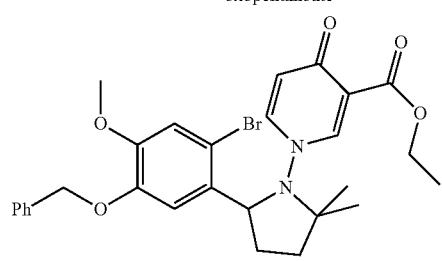

ethyl 1-(5-(5-benzyloxy)-2-bromo-4-methoxyphenyl)-2,2-dimethylpyrrolidin-1-yl)-4-oxo-1,4-dihydropyridine-3-carboxylate

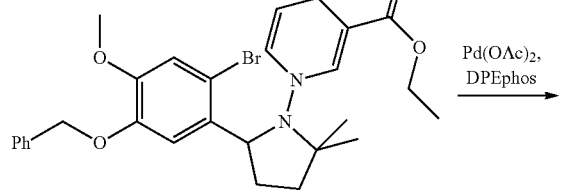

ethyl 1-(5-(5-benzyloxy)-2-bromo-4-methoxyphenyl)-2,2-dimethylpyrrolidin-1-yl)-4-oxo-1,4-dihydropyridine-3-carboxylate Pd(OAc)$_2$, DPEphos

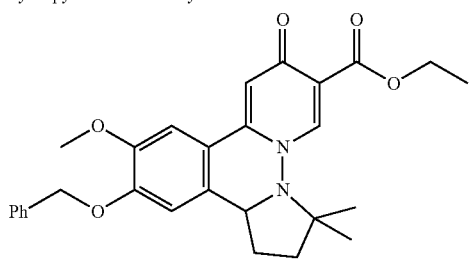

ethyl 12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate 1-(benzyloxy)-4-bromo-5-iodo-2-methoxybenzene 1-(benzyloxy)-4-bromo-2-methoxybenzene (18.2 g, 62 mmol) was suspended in 162 mL methanol and 18 mL water. N-Iodosuccinimide (18.1 g, 81 mmol) and trifluoroacetic acid (3.8 mL, 50 mmol) were added sequentially. The mixture was warmed to 35° C. and stirred for 7 hours in the dark. Water (54 mL) was added dropwise over 15 minutes, then the mixture was allowed to cool slowly to room temperature while stirring overnight. The crystalline product was filtered, and rinsed with a 6:4 mixture of methanol:water (2×20 mL). The solids were dried in vacuo at 50° C. to provide 1-(benzyloxy)-4-bromo-5-iodo-2-methoxybenzene. 1H NMR (400 MHz, Chloroform-d) δ 7.45-7.32 (m, 5H), 7.29 (s, 1H), 7.10 (s, 1H), 5.07 (s, 2H), 3.84 (s, 3H). MS (m/z) 419.8 [M+H]+.

5-(5-(benzyloxy)-2-bromo-4-methoxyphenyl)-2,2-dimethylpyrrolidin-1-ol 1-(benzyloxy)-4-bromo-5-iodo-2-methoxybenzene (8.8 g, 21 mmol) was suspended in 2-MeTHF (24 mL) at 5° C. under argon. iPrMgBr (2.9 M in 2-MeTHF, 7.2 mL, 21 mmol) was added dropwise over 10 minutes with stirring. After 5 minutes, 2,2-dimethyl-3,4-dihydro-2H-pyrrole 1-oxide (2.6 g, 23 mmol) was added in a single portion. The mixture was stirred at the same temperature for 45 minutes followed by the addition of aqueous saturated ammonium chloride (4 mL) and water (20 mL). The aqueous layer was removed and the organic layer was dried over sodium sulfate, filtered, and concentrated in vacuo. The crude solid was recrystallized from ethyl acetate/hexanes (1:2) to yield 5-(5-(benzyloxy)-2-bromo-4-methoxyphenyl)-2,2-dimethylpyrrolidin-1-ol. 1H NMR (400 MHz, Chloroform-d) δ 7.46 (d, J=7.4 Hz, 2H), 7.39-7.33 (m, 2H), 7.33-7.27 (m, 1H), 7.18 (s, 1H), 6.99 (s, 1H), 5.28 (d, J=12.6 Hz, 1H), 5.18 (d, J=12.7 Hz, 1H), 3.87 (s, 3H), 3.65 (s, 1H), 2.37-2.18 (m, 1H), 1.76-1.52 (m, 4H), 1.27 (s, 3H), 1.15 (s, 3H). MS (m/z) 406.4 [M+H]+.

5-(5-(benzyloxy)-2-bromo-4-methoxyphenyl)-2,2-dimethylpyrrolidin-1-amine 5-(5-(benzyloxy)-2-bromo-4-methoxyphenyl)-2,2-dimethylpyrrolidin-1-ol (5.65 g, 13.9 mmol) was suspended in trifluoroacetic acid (6.3 mL) and water (3 mL). Zinc powder (2.6 g, 40 mmol) was added and the mixture was stirred at 40° C. for 15 minutes. LCMS analysis showed complete conversion to 5-(5-(benzyloxy)-2-bromo-4-methoxyphenyl)-2,2-dimethylpyrrolidine (MS (m/z) 392.0 [M+H]+). The crude mixture was concentrated to dryness, redissolved in DCM (20 mL) and slowly quenched with saturated aqueous sodium bicarbonate. The aqueous layer was extracted with DCM (3×20 mL). The combined organic layers were dried over sodium sulfate, filtered, and concentrated in vacuo. The crude 5-(5-(benzyloxy)-2-bromo-4-methoxyphenyl)-2,2-dimethylpyrrolidine was resuspended in THF (30 mL), acetic acid (2 mL, 35 mmol), and water (2 mL). A solution of sodium nitrite (2.3 g, 33 mmol) in water (15 mL) was added dropwise over 10 minutes. The reaction was warmed to 40° C. and stirred for 35 minutes after which time LCMS analysis showed complete conversion to 5-(5-(benzyloxy)-2-bromo-4-methoxyphenyl)-2,2-dimethyl-1-nitrosopyrrolidine (MS (m/z) 421.0 [M+H]+). The reaction mixture was cooled to room temperature, diluted with ethyl acetate, rinsed with aqueous sodium bicarbonate and brine, dried over sodium sulfated, filtered, and concentrated in vacuo. The resulting crude 5-(5-(benzyloxy)-2-bromo-4-methoxyphenyl)-2,2-dimethyl-1-nitrosopyrrolidine was dissolved in trifluoroacetic acid (6.3 mL) and water (3 mL). Zinc powder (2.6 g, 40 mmol) was added. A rapid exotherm to boiling was observed, and the reaction was cooled on ice. After cooling, the reaction was warmed to 40° C. After 2 hours, the reaction was cooled to room temperature, concentrated in vacuo and quenched with aqueous sodium bicarbonate/sodium carbonate. The crude mixture was extracted with DCM (2×20 mL), dried over sodium sulfate and concentrated to provide crude 5-(5-(benzyloxy)-2-bromo-4-methoxyphenyl)-2,2-dimethylpyrrolidin-1-amine. MS (m/z) 405.4 [M+H]+.

Ethyl 1-(5-(5-(benzyloxy)-2-bromo-4-methoxyphenyl)-2,2-dimethylpyrrolidin-1-yl)-4-oxo-1,4-dihydropyridine-3-carboxylate Crude 5-(5-(benzyloxy)-2-bromo-4-methoxyphenyl)-2,2-dimethylpyrrolidin-1-amine (5.64 g, 13.9 mmol, ~75% purity), was dissolved in ethanol (5 mL) with trifluoroacetic acid (0.2 mL). The solution was concentrated to dryness. The mixture was redissolved in ethanol (22 mL) with ethyl (Z)-2-((dimethylamino)methylene)-5,5-diethoxy-3-oxopentanoate (5.6 g, 19.5 mmol). The mixture was stirred at 60° C. for 90 minutes. Acetic acid (1 mL) and water (2 mL) were added and the mixture was stirred at 50° C. overnight. The next day additional acetic acid (1 mL) was added and the reaction temperature was increased to 65° C. After an additional 5 hours, trifluoroacetic acid (0.3 mL) was added and the reaction temperature was increased to 75° C. After 1 hour, the reaction was cooled to room temperature, diluted with ethyl acetate and sodium bicarbonate. The organic layer was separated, dried over sodium sulfate, filtered, and concentrated. The mixture was purified by flash column chromatography (hexanes/ethyl acetate/ethanol) to provide ethyl 1-(5-(5-(benzyloxy)-2-bromo-4-methoxyphenyl)-2,2-dimethylpyrrolidin-1-yl)-4-oxo-1,4-dihydropyridine-3-carboxylate. 1H NMR (400 MHz, Chloroform-d) δ 8.21 (s, 1H), 7.46-7.32 (m, 5H), 6.95-6.83 (m, 2H), 5.28 (s, 1H), 5.12 (d, J=13.2 Hz, 1H), 4.87 (t, J=7.8 Hz, 1H), 4.32 (qd, J=7.1, 4.3 Hz, 2H), 3.86 (s, 3H), 2.39-2.25 (m, 1H), 1.89 (t, J=7.7 Hz, 2H), 1.74-1.51 (m, 2H), 1.33 (t, J=7.1 Hz, 3H), 1.19 (s, 3H), 1.14 (s, 3H). MS (m/z) 557.2 [M+H]+.

Ethyl 12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate Ethyl 1-(5-(5-(benzyloxy)-2-bromo-4-methoxyphenyl)-2,2-dimethylpyrrolidin-1-yl)-4-oxo-1,4-dihydropyridine-3-carboxylate (3.67 g, 6.6 mmol) was dissolved in DMA (20 mL) with potassium propionate (1.9 g, 17 mmol) under argon. Pd(OAc)₂ (180 mg, 0.8 mmol), and (Oxydi-2,1-phenylene)bis(diphenylphosphine) (430 mg, 0.8 mmol) were added and the mixture was flushed with argon. The reaction was heated to 100° C. for 1 hour. The mixture was cooled to room temperature while water (40 mL) was added dropwise over 1 hour. The supernatant was poured off and the remaining gummy solid was redissolved in DCM, dried over sodium sulfate and concentrated in vacuo. The mixture was purified by flash column chromatography (hexanes/ ethyl acetate/ethanol) to provide ethyl 12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate. 1H NMR (400 MHz, Chloroform-d) δ 8.30 (s, 1H), 7.45-7.30 (m, 6H), 7.20 (s, 1H), 6.72 (s, 1H), 5.25 (d, J=12.4 Hz, 1H), 5.20 (d, J=12.4 Hz, 1H), 4.69 (d, J=6.3 Hz, 1H), 4.39 (q, J=7.1 Hz, 2H), 3.94 (s, 3H), 2.38-2.26 (m, 1H), 2.21-2.11 (m, 1H), 1.83-1.71 (m, 1H), 1.50-1.42 (m, 1H), 1.39 (t, J=7.1 Hz, 3H), 1.32 (s, 3H), 0.66 (s, 3H). MS (m/z) 475.4 [M+H]+.

Ethyl (R)-12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate was separated into its enantiomers by SFC using an OJ-H column with methanol as the co-solvent. Retention time of 1.1 min. ¹H NMR (400 MHz, Chloroform-d) δ 8.30 (s, 1H), 7.45-7.30 (m, 6H), 7.20 (s, 1H), 6.72 (s, 1H), 5.25 (d, J=12.4 Hz, 1H), 5.20 (d, J=12.4 Hz, 1H), 4.69 (d, J=6.3 Hz, 1H), 4.39 (q, J=7.1 Hz, 2H), 3.94 (s, 3H), 2.38-2.26 (m, 1H), 2.21-2.11 (m, 1H), 1.83-1.71 (m, 1H), 1.50-1.42 (m, 1H), 1.39 (t, J=7.1 Hz, 3H), 1.32 (s, 3H), 0.66 (s, 3H). MS (m/z) 475.4 [M+H]+.

Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate

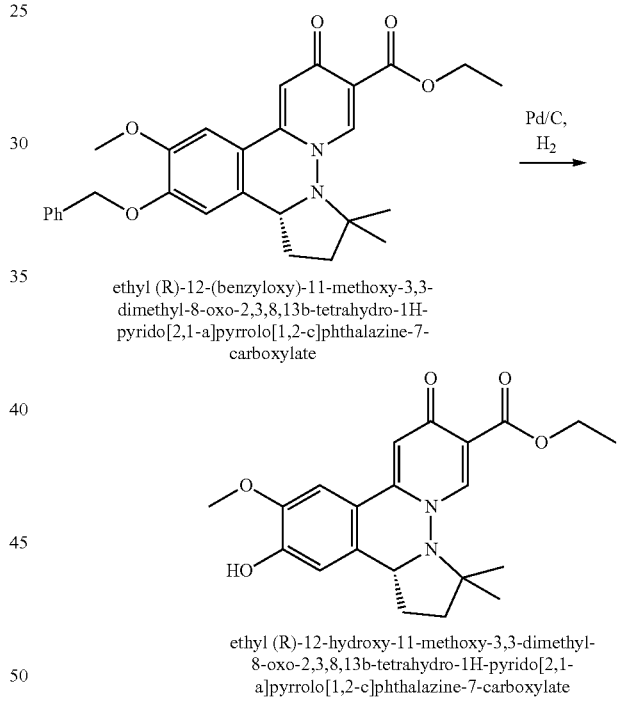

ethyl (R)-12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate Ethyl (R)-12-(benzyloxy)-11-methoxy-3,3-dimethyl-8-oxo-2,3,8,13b-tetrahydro-1H-pyrido[2,1-a]pyrrolo[1,2-c] phthalazine-7-carboxylate (593 mg, 1.3 mmol) was dissolved in ethanol (10 mL) and the solution was purged with argon. Palladium on carbon (10 wt %, wet, E101 NE/W, 160 mg) was added. The reaction was purged with argon, evacuated and refilled with hydrogen gas. The mixture was stirred vigorously under an atmosphere of hydrogen for 40 minutes after which time LCMS analysis showed complete consumption of starting material. The reaction was purged with argon, diluted with ethyl acetate (10 mL) and filtered through celite. The solution was concentrated to provide ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate. MS (m/z) 385.3 [M+H]+.

(R)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

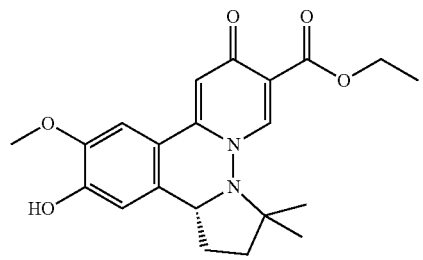

ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate

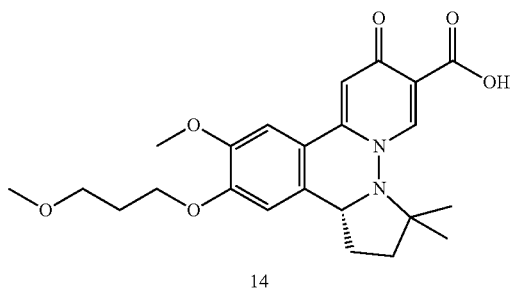

14

Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (100 mg, 0.26 mmol) was combined in DMF (0.4 mL) with potassium carbonate (72 mg, 0.52 mmol) and 1-bromo-3-methoxypropane (58 µL, 0.52 mmol). The reaction mixture was stirred at 65° C. for 40 minutes, followed by stirring at 70° C. for 1 hour. The mixture was cooled to room temperature. Aqueous lithium hydroxide (1 M, 0.39 mL, 0.39 mmol) and ethanol (0.5 mL) were added and the mixture was stirred at 40° C. After 45 minutes, the mixture was diluted with trifluoroacetic acid and purified by preparative HPLC to provide (R)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid as a trifluoroacetic acid salt. $^1$H NMR (400 MHz, Acetonitrile-d3) δ 8.44 (s, 1H), 7.38 (s, 1H), 7.25 (s, 1H), 6.95 (s, 1H), 4.84 (d, J=6.2 Hz, 1H), 4.28-4.09 (m, 2H), 3.92 (s, 3H), 3.54 (t, J=6.2 Hz, 2H), 3.32 (s, 3H), 2.57-2.35 (m, 2H), 2.05 (p, J=6.4 Hz, 2H), 1.88 (ddd, J=12.6, 7.9, 2.7 Hz, 1H), 1.67-1.56 (m, 1H), 1.36 (s, 3H), 0.67 (s, 3H). 19F NMR (377 MHz, Acetonitrile-d3) δ−77.32. MS (m/z) 429.3 [M+H]+.

Example 15: (S)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

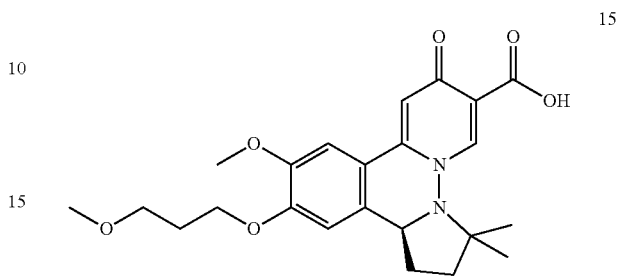

15

(S)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid was prepared similarly to example 14 utilizing the slower eluting isomer from the resolution of racemic ethyl 12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate. Retention time of 1.37 min. 1H NMR (400 MHz, Acetonitrile-d3) δ 8.44 (s, 1H), 7.38 (s, 1H), 7.25 (s, 1H), 6.95 (s, 1H), 4.84 (d, J=6.2 Hz, 1H), 4.28-4.09 (m, 2H), 3.92 (s, 3H), 3.54 (t, J=6.2 Hz, 2H), 3.32 (s, 3H), 2.57-2.35 (m, 2H), 2.05 (p, J=6.4 Hz, 2H), 1.88 (ddd, J=12.6, 7.9, 2.7 Hz, 1H), 1.67-1.56 (m, 1H), 1.36 (s, 3H), 0.67 (s, 3H). $^{19}$F NMR (377 MHz, Acetonitrile-d3) δ−77.32. MS (m/z) 429.3 [M+H]+.

Example 16: (R)-11-methoxy-3,3-dimethyl-12-(oxetan-3-ylmethoxy)-8-oxo-2,3,8,13b-tetrahydro-1H-pyrido[2,1-a]pyrrolo[1,2-c]phthalazine-7-carboxylic acid

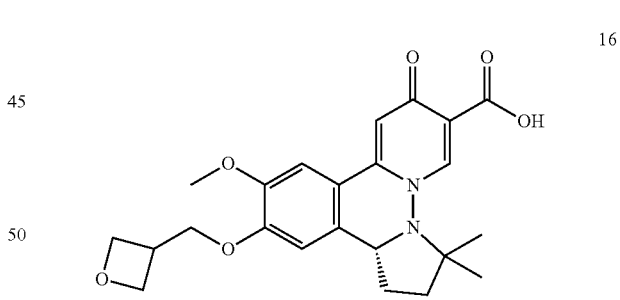

16

(R)-11-methoxy-3,3-dimethyl-12-(oxetan-3-ylmethoxy)-8-oxo-2,3,8,13b-tetrahydro-1H-pyrido[2,1-a]pyrrolo[1,2-c]phthalazine-7-carboxylic acid was prepared according to the procedure for (R)-11-methoxy-12-(3-methoxypropoxy)-3,3-dimethyl-8-oxo-2,3,8,13b-tetrahydro-1H-pyrrolo[1,2-c]phthalazine-7-carboxylic acid using 3-(bromomethyl)oxetane in place of 1-bromo-3-methoxypropane. 1H NMR (400 MHz, Acetonitrile-d3) δ 8.44 (d, J=1.9 Hz, 1H), 7.39 (s, 1H), 7.23 (d, J=1.9 Hz, 1H), 6.99 (s, 1H), 4.96-4.70 (m, 3H), 4.49 (t, J=6.2 Hz, 2H), 4.36 (dt, J=29.9, 9.1 Hz, 2H), 3.92 (d, J=1.9 Hz, 2H), 3.52-3.41 (m, 1H), 2.60-2.37 (m, 2H), 1.63 (q, J=10.5 Hz, 1H), 1.37 (s, 3H), 1.29 (s, 2H), 0.67 (s, 3H). MS (m/z) 427.2 [M+H]+.

Example 17: 13-chloro-12-(3-methoxypropoxy)-8,8-dimethyl-2-oxo-2,7,8,9,10,10a-hexahydrodipyrido[2,1-a:1',2'-c]phthalazine-3-carboxylic acid

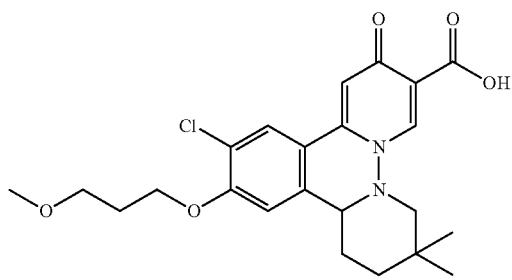

13-Chloro-12-(3-methoxypropoxy)-8,8-dimethyl-2-oxo-2,7,8,9,10,10a-hexahydrodipyrido[2,1-a: 1',2'-c]phthalazine-3-carboxylic acid prepared similarly to example 11 using 3,3-dimethylpiperidine in place of 2,2-dimethylpiperidine. $^1$H NMR (400 MHz, Chloroform-d) δ 8.64 (s, 1H), 7.82 (s, 1H), 7.06 (s, 1H), 6.92 (s, 1H), 4.57 (s, 1H), 4.31-4.15 (m, 2H), 3.71-3.56 (m, 2H), 3.38 (s, 3H), 3.02 (d, 1H), 2.61-2.46 (m, 2H), 2.44-2.35 (m, 2H), 2.22-2.09 (m, 2H), 1.36 (d, 1H), 1.32-1.15 (m, 1H), 1.24 (s, 3H), 0.80 (s, 3H). (m/z) 447.4 [M+H]+.

Example 18: 11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

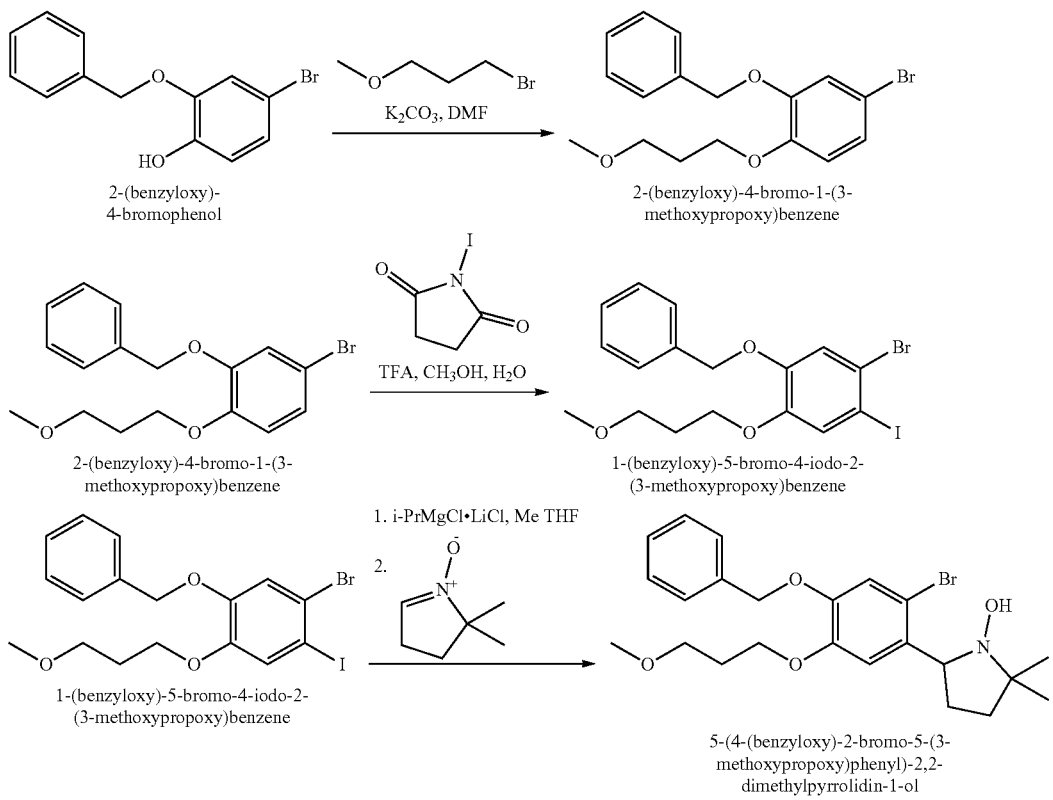

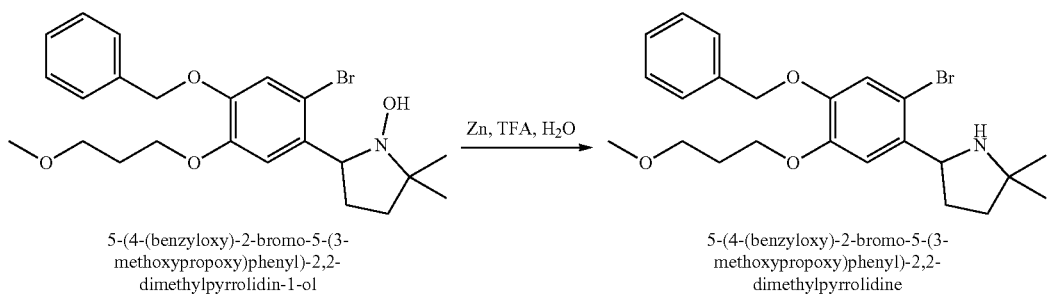

-continued

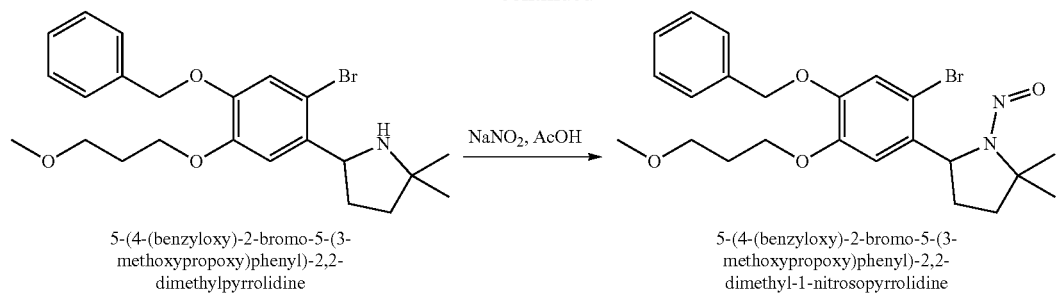

5-(4-(benzyloxy)-2-bromo-5-(3-methoxypropoxy)phenyl)-2,2-dimethylpyrrolidine → 5-(4-(benzyloxy)-2-bromo-5-(3-methoxypropoxy)phenyl)-2,2-dimethyl-1-nitrosopyrrolidine NaNO$_2$, AcOH

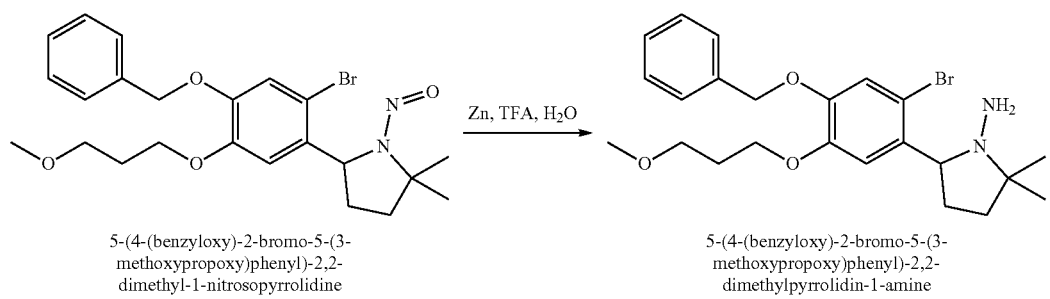

5-(4-(benzyloxy)-2-bromo-5-(3-methoxypropoxy)phenyl)-2,2-dimethyl-1-nitrosopyrrolidine → 5-(4-(benzyloxy)-2-bromo-5-(3-methoxypropoxy)phenyl)-2,2-dimethylpyrrolidin-1-amine Zn, TFA, H$_2$O

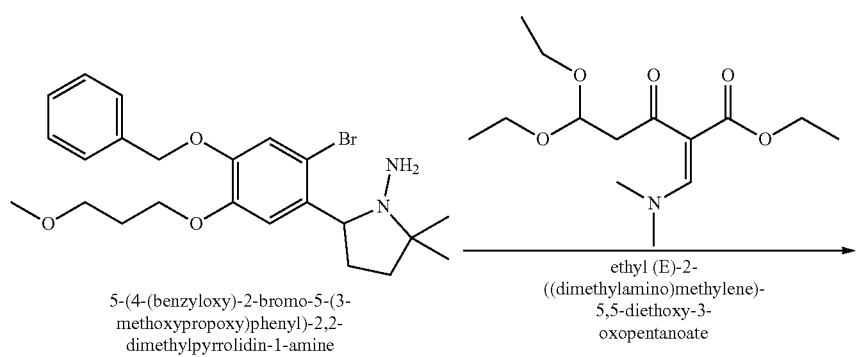

5-(4-(benzyloxy)-2-bromo-5-(3-methoxypropoxy)phenyl)-2,2-dimethylpyrrolidin-1-amine ethyl (E)-2-((dimethylamino)methylene)-5,5-diethoxy-3-oxopentanoate

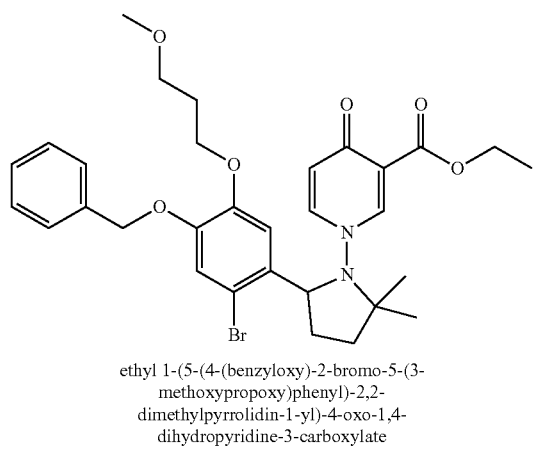

ethyl 1-(5-(4-(benzyloxy)-2-bromo-5-(3-methoxypropoxy)phenyl)-2,2-dimethylpyrrolidin-1-yl)-4-oxo-1,4-dihydropyridine-3-carboxylate

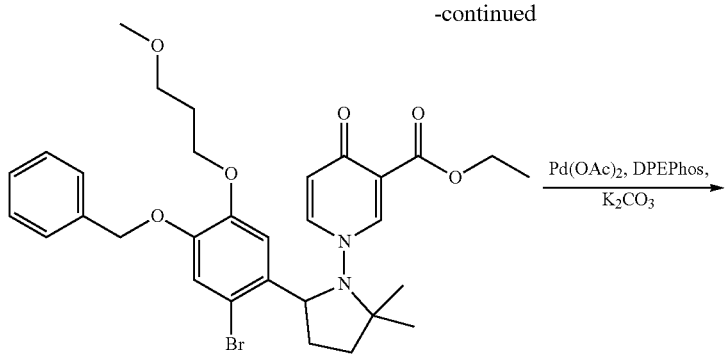

ethyl 1-(5-(4-(benzyloxy)-2-bromo-5-(3-methoxypropoxy)phenyl)-2,2-dimethylpyrrolidin-1-yl)-4-oxo-1,4-dihydropyridine-3-carboxylate

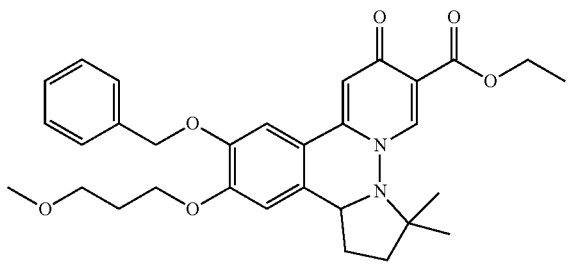

ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate Synthesis of 2-(benzyloxy)-4-bromo-1-(3-methoxypropoxy)benzene To a stirring solution of 2-(benzyloxy)-4-bromophenol (34.85 g, 0.12 mol) in DMF (35 ml) was added cesium carbonate (44.77 g, 0.14 mol) followed by 1-bromo-3-methoxypropane (16.67 ml, 0.14 mol). The reaction was heated at 60° C. for 1 h. The mixture was cooled, diluted with water (400 ml) and extracted with EtOAc (2×300 ml). The organic layers were combined, washed with 5% LiCl (aq, 500 ml), followed by water (500 ml). The organic layer was dried with $Na_2SO_4$, filtered, and concentrated. Product was purified by silica chromatography using EtOAc in hexane (0-20%). 23.1 g $^1$H NMR (400 MHz, Chloroform-d) δ 7.48-7.28 (m, 5H), 7.07-6.93 (m, 2H), 6.79 (d, J=8.3 Hz, 1H), 5.09 (s, 2H), 4.08 (t, J=6.3 Hz, 2H), 3.55 (t, J=6.2 Hz, 2H), 3.33 (s, 3H), 2.07 (t, J=6.3 Hz, 2H).

Synthesis of 1-(benzyloxy)-5-bromo-4-iodo-2-(3-methoxypropoxy)benzene

To a solution of 2-(benzyloxy)-4-bromo-1-(3-methoxypropoxy)benzene (23.1 g, 65.77 mmol) in methanol/water (9:1) (230 ml) was added N-iodosuccinimide (17.02 g, 75.63 mmol) followed by trifluoroacetic acid (1.26 ml, 16.44 mmol). After heating at 35° C. for 15 h, the mixture was heated to reflux for 1 h. Additional N-iodosuccinimide (1.7 g, 7.56 mmol) was added and the mixture was refluxed for 2.5 h. The reaction was cooled to ambient temperature and water (90 ml) was added. The solids were filtered, washed with water, and the resulting solids were taken up into ethyl acetate (150 ml). The organic solution was washed with 5% $NaHSO_3$ (100 ml) followed by water (100 ml) and brine (100 ml). The organic layer was dried with $Na_2SO_4$, filtered, and concentrated. The product was precipitated from 8:1 heptane:i-PrOAc (100 ml) by vigorously stirring for 30 minutes. The solids were filtered, washed with hexane, and dried under vacuum. 27.5 g. $^1$H NMR (400 MHz, Chloroform-d) δ 7.44-7.31 (m, 5H), 7.30 (s, 1H), 7.13 (s, 1H), 5.07 (s, 2H), 4.06 (t, J=6.3 Hz, 2H), 3.54 (t, J=6.1 Hz, 2H), 3.34 (s, 3H), 2.06 (p, J=6.2 Hz, 2H).

5-(4-(benzyloxy)-2-bromo-5-(3-methoxypropoxy) phenyl)-2,2-dimethylpyrrolidin-1-ol To a solution of 1-(benzyloxy)-5-bromo-4-iodo-2-(3-methoxypropoxy)benzene (12.65 g, 26.51 mmol) in 2-MeTHF (36 ml) was added isopropylmagnesium chloride (1.3M in 2-MeTHF) (22.4 ml) over 5 minutes maintaining an internal temperature below 0° C. The reaction was stirred for an additional 5 minutes after the addition was complete. To the cooled solution was added dropwise 2,2-dimethyl-3,4-dihydro-2H-pyrrole 1-oxide (3.6 g, 31.81 mmol) in 2-MeTHF (10 ml) maintaining an internal temperature below 5° C. The mixture was stirred for 20 minutes, 1M $NH_4Cl$ (75 ml) was added, and the layers were separated. The organic layer was washed with 1.0M NaCl (75 ml). The organic layer was dried with $Na_2SO_4$, filtered, and concentrated. The product was purified by silica chromatography using EtOAc in hexane (5-25%). 10.1 g $^1$H NMR (400 MHz, Chloroform-d) δ 7.46-7.28 (m, 5H), 7.09 (s, 1H), 6.22 (s, 1H), 5.40 (dd, J=8.7, 4.0 Hz, 1H), 5.05 (s, 2H), 3.96 (t, J=6.2 Hz, 2H), 3.58-3.41 (m, 2H), 3.30 (s, 3H), 2.57-2.39 (m, 1H), 2.08-1.91 (m, 4H), 1.86 (s, 4H), 1.69 (s, 3H). MS (m/z) 464.6 [M+H]+.

Synthesis of 5-(4-(benzyloxy)-2-bromo-5-(3-methoxypropoxy)phenyl)-2,2-dimethylpyrrolidine 5-(4-(benzyloxy)-2-bromo-5-(3-methoxypropoxy)phenyl)-2,2-dimethylpyrrolidine was prepared analogously to 5-(2-bromo-4-chloro-5-(3-methoxypropoxy)phenyl)-2,2-dimethylpyrrolidine in Example 4. MS (m/z) 448.8 [M+H]+.

Synthesis of 5-(4-(benzyloxy)-2-bromo-5-(3-methoxypropoxy)phenyl)-2,2-dimethyl-1-nitrosopyrrolidine 5-(4-(benzyloxy)-2-bromo-5-(3-methoxypropoxy)phenyl)-2,2-dimethyl-1-nitrosopyrrolidine was prepared analogously to 5-(2-bromo-4-chloro-5-(3-methoxypropoxy)phenyl)-2,2-dimethyl-1-nitrosopyrrolidine in Example 4. $^1$H NMR (400 MHz, Chloroform-d) δ7.46-7.28 (m, 5H), 7.09 (s, 1H), 6.22 (s, 1H), 5.40 (dd, J=8.7, 4.0 Hz, 1H), 5.05 (s, 2H), 3.96 (t, J=6.2 Hz, 2H), 3.58-3.41 (m, 2H), 3.30 (s, 3H), 2.57-2.39 (m, 1H), 2.08-1.91 (m, 4H), 1.86 (s, 4H), 1.69 (s, 3H). MS (m/z) 477.7 [M+H]+.

Synthesis of 5-(4-(benzyloxy)-2-bromo-5-(3-methoxypropoxy)phenyl)-2,2-dimethyl pyrrolidin-1-amine 5-(4-(benzyloxy)-2-bromo-5-(3-methoxypropoxy)phenyl)-2,2-dimethyl pyrrolidin-1-amine was prepared analogously to 5-(2-bromo-4-chloro-5-(3-methoxypropoxy)phenyl)-2,2-dimethylpyrrolidin-1-amine in example 4. MS (m/z) 463.7 [M+H]+.

Synthesis of ethyl 1-(5-(4-(benzyloxy)-2-bromo-5-(3-methoxypropoxy)phenyl)-2,2-dimethylpyrrolidin-1-yl)-4-oxo-1,4-dihydropyridine-3-carboxylate Ethyl 1-(5-(4-(benzyloxy)-2-bromo-5-(3-methoxypropoxy)phenyl)-2,2-dimethylpyrrolidin-1-yl)-4-oxo-1,4-dihydropyridine-3-carboxylate was prepared analogously to ethyl 1-(5-(2-bromo-4-chloro-5-(3-methoxypropoxy)phenyl)-2,2-dimethylpyrrolidin-1-yl)-4-oxo-1,4-dihydropyridine-3-carboxylate in example 4. $^1$H NMR (400 MHz, Chloroform-d) δ 8.24 (s, 1H), 7.44-7.27 (m, 6H), 7.04 (s, 1H), 6.96 (s, 1H), 6.32 (d, J=7.8 Hz, 1H), 5.11-5.00 (s, 2H), 4.93 (t, J=7.9 Hz, 1H), 4.37-4.27 (m, 2H), 4.17-4.09 (m, 1H), 4.07-4.00 (m, 1H), 3.59-3.49 (m, 2H), 3.33 (s, 3H), 2.46-2.26 (m, 1H), 2.08-1.99 (m, 3H), 1.99-1.87 (m, 1H), 1.78-1.65 (m, 1H), 1.40-1.32 (m, 6H), 1.20 (s, 3H). MS (m/z) δ14.0 [M+H]+.

Synthesis of ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate Argon was bubbled through a mixture of ethyl 1-(5-(4-(benzyloxy)-2-bromo-5-(3-methoxypropoxy)phenyl)-2,2-dimethylpyrrolidin-1-yl)-4-oxo-1,4-dihydropyridine-3-carboxylate (6.5 g, 10.59 mmol), Pd(OAc)$_2$ (0.24 g, 1.06 mmol), DPEphos (0.57 g, 1.06 mmol), and potassium carbonate (3.66 g, 26.51 mmol) in N,N-dimethylacetamide (40 ml). The mixture was heated at 110° C. for 3 h. After cooling to ambient temperature, the mixture was filtered through celite. The mixture was diluted with water (200 ml) and product extracted with ethyl acetate (200 ml). The extractive mixture was filtered. The organic layer was washed with 5% LiCl (aq, 2×200 ml). The organic layer was dried with Na$_2$SO$_4$, filtered, and concentrated. Product was purified by silica chromatography using EtOH in dichloromethane. The partially purified product was precipitated from 3:1 MTBE:hexane (30 ml), filtered, and dried under vacuum. The filtrate was concentrated and additional product was isolated from 3:1 MTBE/EtOAc. 3.58 g $^1$H NMR (400 MHz, Chloroform-d) δ 8.27 (s, 1H), 7.48-7.41 (m, 2H), 7.41-7.34 (m, 2H), 7.34-7.28 (m, 1H), 7.23 (s, 1H), 6.81 (s, 1H), 6.78 (s, 1H), 5.13 (s, 2H), 4.72 (d, J=5.9 Hz, 1H), 4.43-4.31 (m, 2H), 4.16 (qt, J=9.3, 6.3 Hz, 2H), 3.64-3.51 (m, 2H), 3.34 (s, 3H), 2.45-2.27 (m, 2H), 2.11 (p, J=6.2 Hz, 2H), 1.82 (ddd, J=12.5, 7.6, 2.8 Hz, 1H), 1.60 (ddd, J=12.5, 10.8, 7.8 Hz, 1H), 1.38 (t, J=7.1 Hz, 3H), 1.32 (s, 3H), 0.68 (s, 3H). MS (m/z) 533.6 [M+H]+.

Synthesis of ethyl 11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate

ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate ethyl 11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate A solution of ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate (400 mg g, 0.75 mmol) in EtOH (3 ml) and dichloromethane (3 ml) was added to 10% palladium on carbon (40 mg, 0.04 mmol). The reaction was stirred under a hydrogen balloon for 1.5 h. The reaction vessel was purged with nitrogen and solids filtered through celite. The filtrate was concentrated under vacuum. The product was taken to next step without further purification. 330 mg. $^1$H NMR (400 MHz, Chloroform-d) δ 8.29 (s, 1H), 7.41 (s, 1H), 6.94 (s, 1H), 6.78-6.74 (m, 1H), 4.72 (d, J=6.0 Hz, 1H), 4.38 (qd, J=7.1, 1.7 Hz, 2H), 4.27-4.10 (m, 2H), 3.60 (m, 2H), 3.38 (s, 3H), 2.46-2.25 (m, 1H), 2.10 (p, J=6.0 Hz, 2H), 1.82 (m, 1H), 1.67-1.54 (m, 1H), 1.39 (t, J=7.1 Hz, 3H), 1.32 (s, 3H), 0.69 (s, 3H). MS (m/z) 443.4 [M+H]+.

11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

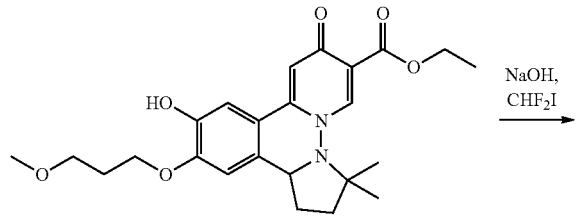

ethyl 11-hydroxy-12-(3-methoxypropoxy)-3,3-dimethyl-8-oxo-2,3,8,13b-tetrahydro-1H-pyrido[2,1-a]pyrrolo]1,2-c]phthalazine-7-carboxylate

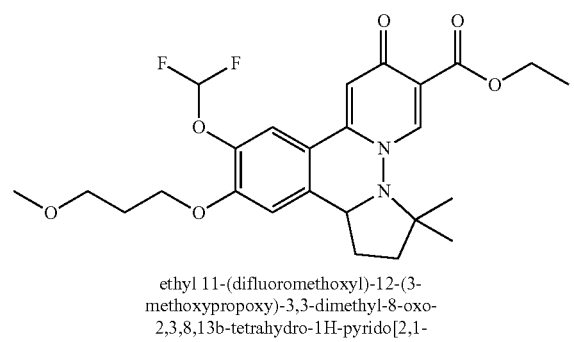

ethyl 11-(difluoromethoxyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylate ↓ LiOH

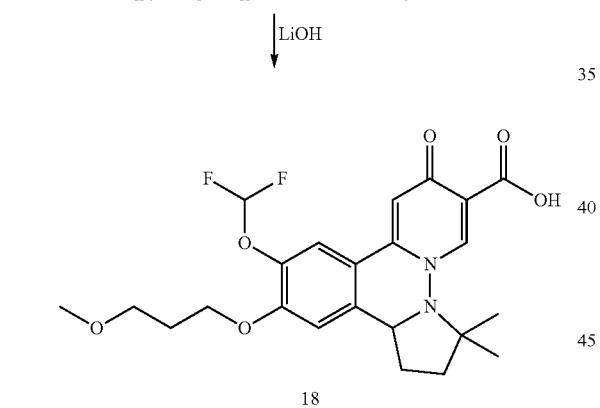

18

To a vigorously stirring solution of ethyl 11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (85 mg, 0.19 mmol) in acetonitrile (0.4 ml) and 8M NaOH (0.2 ml) was added dropwise difluoroiodomethane (10% in THF) (751.87 mg, 0.42 mmol). After stirring for 30 minutes, the mixture was concentrated and the resulting mixture was diluted with ethanol (0.5 ml) and heated at 45° C. for 45 minutes. The mixture was concentrated and acidified with 1.0M HCl (1.5 ml). The product was purified by prep HPLC using ACN in water with 0.1% TFA. 35 mg. $^1$H NMR (400 MHz, Chloroform-d) δ 8.54 (s, 1H), 7.57 (s, 1H), 7.04 (s, 1H), 6.92-6.14 (m, 2H), 4.80 (d, J=6.2 Hz, 1H), 4.20 (qt, J=9.2, 6.3 Hz, 2H), 3.67-3.47 (m, 2H), 3.36 (s, 3H), 2.50 (tdd, J=10.9, 7.9, 6.4 Hz, 1H), 2.44-2.31 (m, 1H), 2.12 (p, J=6.1 Hz, 2H), 1.96-1.86 (m, 1H), 1.70-1.57 (m, 1H), 1.38 (s, 3H), 0.69 (s, 3H). MS (m/z) 465.4 [M+H]+.

Example 19: (R)-11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

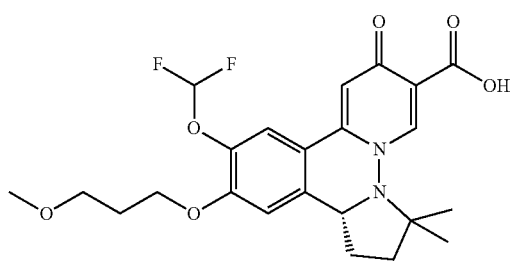

19

11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (18) was separated into its enantiomers by chiral SFC chromatography using AD-H 4.6×100 mm columns with 30% methanol as the co-solvent. Example 18 is the faster eluting peak with a retention time of 1.63 min. $^1$H NMR (400 MHz, Chloroform-d) δ 8.55 (s, 1H), 7.58 (s, 1H), 7.05 (s, 1H), 6.91 (s, 1H), 6.60 (t, J=74.0 Hz, 1H), 4.80 (d, J=6.3 Hz, 1H), 4.36-4.02 (m, 2H), 3.71-3.42 (m, 2H), 3.37 (s, 3H), 2.60-2.45 (m, 1H), 2.45-2.30 (m, 1H), 2.13 (p, J=6.1 Hz, 2H), 1.92 (ddd, J=12.8, 7.9, 2.6 Hz, 1H), 1.64 (ddd, J=12.7, 10.9, 7.7 Hz, 1H), 1.39 (s, 3H), 0.69 (s, 3H). MS (m/z) 465.6 [M+H]+.

Example 20: (S)-11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

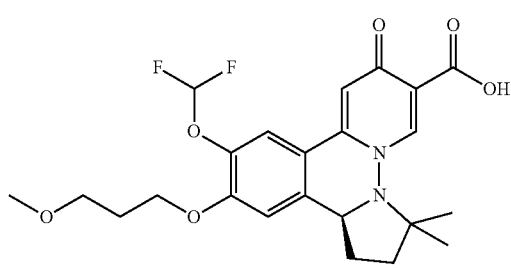

20

11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (18) was separated into its enantiomers by chiral SFC chromatography using AD-H 4.6×100 mm columns with 30% methanol as the co-solvent. Example 20 is the slower eluting peak with a retention time of 2.06 min. $^1$H NMR (400 MHz, Chloroform-d) δ 8.55 (s, 1H), 7.58 (s, 1H), 7.05 (s, 1H), 6.91 (s, 1H), 6.60 (t, J=74.0 Hz, 1H), 4.80 (d, J=6.3 Hz, 1H), 4.36-4.02 (m, 2H), 3.71-3.42 (m, 2H), 3.37 (s, 3H), 2.60-2.45 (m, 1H), 2.45-2.30 (m, 1H), 2.13 (p, J=6.1 Hz, 2H), 1.92 (ddd, J=12.8, 7.9, 2.6 Hz, 1H), 1.64 (ddd, J=12.7, 10.9, 7.7 Hz, 1H), 1.39 (s, 3H), 0.69 (s, 3H). MS (m/z) 465.6 [M+H]+.

Example 21: (R)-11-ethoxy-12-(3-methoxy-propoxy)-3,3-dimethyl-8-oxo-2,3,8,13b-tetrahydro-1H-pyrido[2,1-a]pyrrolo[1,2-c]phthalazine-7-carboxylic

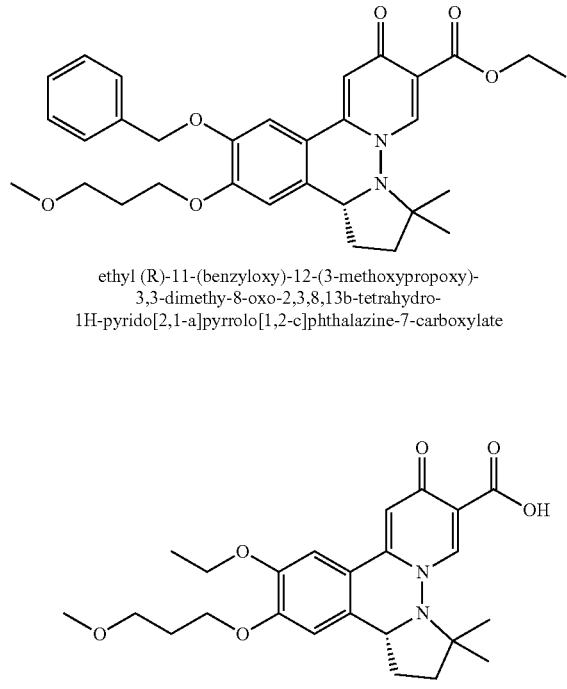

Synthesis of ethyl (R)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate and ethyl (S)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate Racemic ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate (3.2 g) was purified by chiral SFC chromatography using AD-H 4.6×100 mm columns with 30% ethanol as the co-solvent. To give the faster eluting peak as ethyl (S)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate (1.43 g), retention time 1.63 min. $^1$H NMR (400 MHz, Chloroform-d) δ 8.27 (s, 1H), 7.48-7.41 (m, 2H), 7.41-7.34 (m, 2H), 7.34-7.28 (m, 1H), 7.23 (s, 1H), 6.81 (s, 1H), 6.78 (s, 1H), 5.13 (s, 2H), 4.72 (d, J=5.9 Hz, 1H), 4.43-4.31 (m, 2H), 4.16 (qt, J=9.3, 6.3 Hz, 2H), 3.64-3.51 (m, 2H), 3.34 (s, 3H), 2.45-2.27 (m, 2H), 2.11 (p, J=6.2 Hz, 2H), 1.82 (ddd, J=12.5, 7.6, 2.8 Hz, 1H), 1.60 (ddd, J=12.5, 10.8, 7.8 Hz, 1H), 1.38 (t, J=7.1 Hz, 3H), 1.32 (s, 3H), 0.68 (s, 3H). MS (m/z) 533.6 [M+H]+.

And ethyl (R)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate (1.47 g) as the slower eluting peak, retention time 2.06 min. $^1$H NMR (400 MHz, Chloroform-d) δ 8.27 (s, 1H), 7.48-7.41 (m, 2H), 7.41-7.34 (m, 2H), 7.34-7.28 (m, 1H), 7.23 (s, 1H), 6.81 (s, 1H), 6.78 (s, 1H), 5.13 (s, 2H), 4.72 (d, J=5.9 Hz, 1H), 4.43-4.31 (m, 2H), 4.16 (qt, J=9.3, 6.3 Hz, 2H), 3.64-3.51 (m, 2H), 3.34 (s, 3H), 2.45-2.27 (m, 2H), 2.11 (p, J=6.2 Hz, 2H), 1.82 (ddd, J=12.5, 7.6, 2.8 Hz, 1H), 1.60 (ddd, J=12.5, 10.8, 7.8 Hz, 1H), 1.38 (t, J=7.1 Hz, 3H), 1.32 (s, 3H), 0.68 (s, 3H). MS (m/z) 533.6 [M+H]+.

Synthesis of ethyl (S)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl (S)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate was prepared analogously to ethyl 11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate in Example 18. $^1$H NMR (400 MHz, Chloroform-d) δ 8.29 (s, 1H), 7.42 (s, 1H), 6.96 (s, 1H), 6.76 (d, J=1.0 Hz, 1H), 4.72 (d, J=5.9 Hz, 1H), 4.43-4.31 (m, 2H), 4.27-4.11 (m, 2H), 3.60 (td, J=6.0, 1.5 Hz, 2H), 3.38 (s, 3H), 2.41-2.26 (m, 1H), 2.10 (p, J=6.0 Hz, 2H), 1.82 (ddd, J=12.6, 7.8, 2.8 Hz, 1H), 1.65-1.56 (m, 1H), 1.39 (t, J=7.1 Hz, 3H), 1.32 (s, 3H), 0.68 (s, 3H). MS (m/z) 443.3 [M+H]+. The absolute stereochemistry was assigned unambiguously by X-ray crystallography.

Synthesis of ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl (R)-11-hydroxy-12-(3-methoxypropoxy)-3,3-dimethyl-8-oxo-2,3,8,13b-tetrahydro-1H-pyrido[2,1-a]pyrrolo

[1,2-c]phthalazine-7-carboxylate was prepared analogously to ethyl 11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate in Example 18. $^1$H NMR (400 MHz, Chloroform-d) δ 8.29 (s, 1H), 7.42 (s, 1H), 6.96 (s, 1H), 6.76 (d, J=1.0 Hz, 1H), 4.72 (d, J=5.9 Hz, 1H), 4.43-4.31 (m, 2H), 4.27-4.11 (m, 2H), 3.60 (td, J=6.0, 1.5 Hz, 2H), 3.38 (s, 3H), 2.41-2.26 (m, 1H), 2.10 (p, J=6.0 Hz, 2H), 1.82 (ddd, J=12.6, 7.8, 2.8 Hz, 1H), 1.65-1.56 (m, 1H), 1.39 (t, J=7.1 Hz, 3H), 1.32 (s, 3H), 0.68 (s, 3H). MS (m/z) 443.3 [M+H]+.

Synthesis of (R)-11-ethoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid To a solution of ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (30 mg, 0.07 mmol) in DMF (0.2 ml) was added Cs$_2$CO$_3$ (32.95 mg, 0.1 mmol) followed by diethyl sulfate (9.58 μl, 0.07 mmol). The reaction was heated at 70° C. for 2 h. The reaction was cooled to ambient temperature and 2M LiOH (aq) (0.15 ml) was added. The reaction was stirred for 1 h, acidified with 2M HCl (300 uL), and the product was purified by prep HPLC using acetonitrile in water with 0.1% TFA. $^1$H NMR (400 MHz, Chloroform-d) δ 8.54 (s, 1H), 7.18 (s, 1H), 7.12 (s, 1H), 6.80 (s, 1H), 4.77 (d, J=5.8 Hz, 1H), 4.24-4.07 (m, 4H), 3.65-3.51 (m, 2H), 3.36 (s, 3H), 2.52-2.34 (m, 2H), 2.12 (p, J=6.3 Hz, 2H), 1.92-1.82 (m, 1H), 1.67-1.54 (m, 1H), 1.47 (t, J=7.0 Hz, 3H), 1.36 (s, 3H), 0.66 (s, 3H). MS (m/z) 443.3 [M+H]+.

Example 22: (R)-11-isopropoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

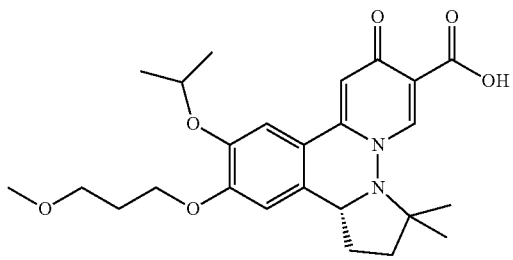

22

(R)-11-isopropoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid was prepared analogously to Example 21 using 2-iodopropane in place of diethyl sulfate. $^1$H NMR (400 MHz, Chloroform-d) δ 8.54 (s, 1H), 7.24 (s, 1H), 7.12 (s, 1H), 6.79 (s, 1H), 4.76 (d, J=5.8 Hz, 1H), 4.53 (hept, J=6.1 Hz, 1H), 4.22-4.08 (m, 2H), 3.64-3.51 (m, 2H), 3.35 (s, 3H), 2.51-2.33 (m, 2H), 2.12 (q, J=6.2 Hz, 2H), 1.93-1.82 (m, 1H), 1.68-1.55 (m, 1H), 1.41-1.33 (m, 9H), 0.66 (s, 3H). MS (m/z) 457.4 [M+H]+.

Example 23: (R)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid

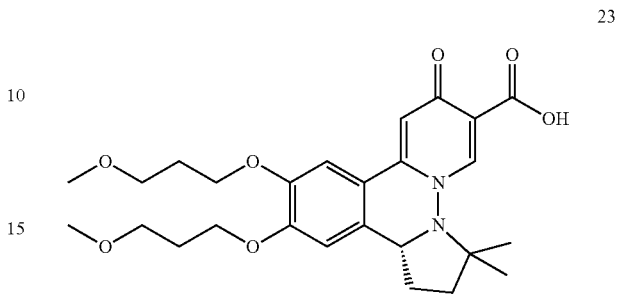

23

(R)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid was prepared analogously to Example 21 using 1-bromo-3-methoxypropane in place of diethyl sulfate. 23 mg. $^1$H NMR (400 MHz, Chloroform-d) δ8.53 (s, 1H), 7.22 (s, 1H), 7.08 (s, 1H), 6.78 (s, 1H), 4.76 (d, J=5.8 Hz, 1H), 4.23-4.08 (m, 4H), 3.64-3.50 (m, 4H), 3.37 (s, 3H), 3.35 (s, 3H), 2.49-2.31 (m, 2H), 2.16-2.05 (m, 4H), 1.92-1.81 (m, 1H), 1.66-1.54 (m, 1H), 1.35 (s, 3H), 0.66 (s, 3H). MS (m/z) 487.4 [M+H]+.

Example 24: (S)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid

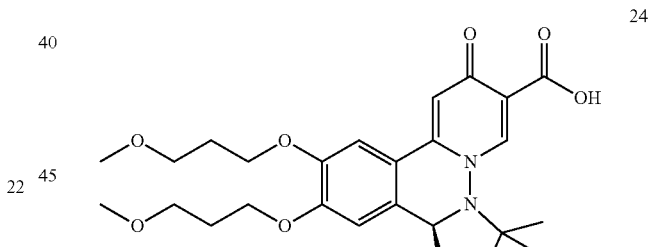

24

(S)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid was prepared analogously to Example 23 using ethyl (S)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate in place of ethyl (R)-11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Chloroform-d) δ 8.53 (s, 1H), 7.22 (s, 1H), 7.08 (s, 1H), 6.78 (s, 1H), 4.76 (d, J=5.8 Hz, 1H), 4.23-4.08 (m, 4H), 3.64-3.50 (m, 4H), 3.37 (s, 3H), 3.35 (s, 3H), 2.49-2.31 (m, 2H), 2.16-2.05 (m, 4H), 1.92-1.81 (m, 1H), 1.66-1.54 (m, 1H), 1.35 (s, 3H), 0.66 (s, 3H). MS (m/z) 487.4 [M+H]+.

Example 25: (R)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

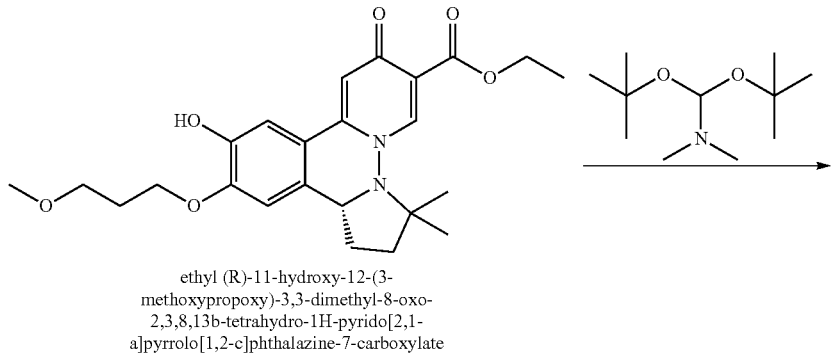

ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate

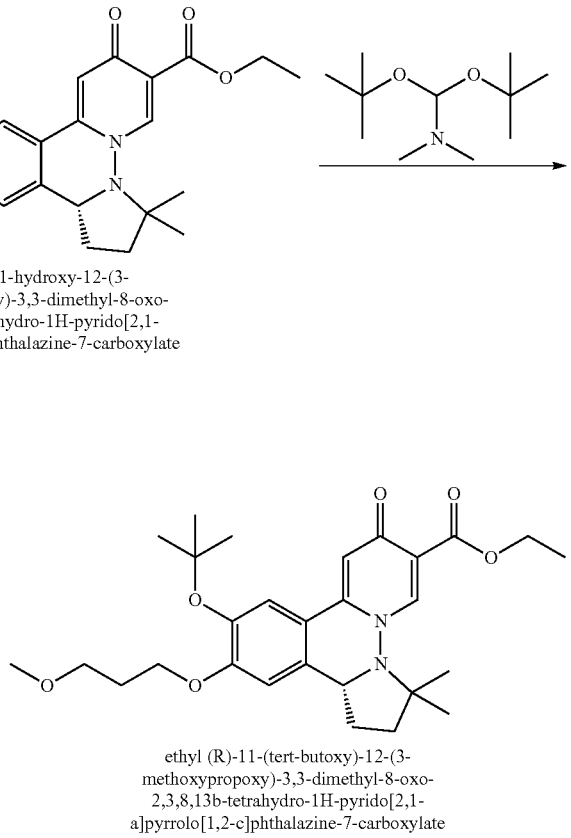

ethyl (R)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate

LiOH

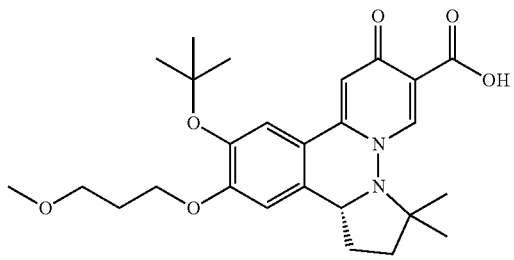

25

To a solution of ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (60 mg, 0.07 mmol) in toluene (5 ml) was added dropwise 1,1-di-tert-butoxy-N,N-dimethylmethanamine (406.38 µl, 1.69 mmol) over 1 h at 80° C. The mixture was heated for 45 minutes, concentrated under vacuum, and the resulting mixture was diluted with ethanol (0.5 ml) and treated with 2M LiOH(aq) (0.15 ml). After stirring for 1 h, the mixture was acidified with 2M HCl (0.2 ml). The product was purified by prep HPLC using acetonitrile in water with 0.1% TFA. 23 mg. 1H NMR (400 MHz, Chloroform-d) δ 8.53 (s, 1H), 7.38 (s, 1H), 7.07 (s, 1H), 6.81 (s, 1H), 4.77 (d, J=5.9 Hz, 1H), 4.19-4.04 (m, 2H), 3.65-3.52 (m, 2H), 3.35 (s, 3H), 2.54-2.34 (m, 2H), 2.11 (p, J=6.2 Hz, 2H), 1.93-1.83 (m, 1H), 1.67-1.55 (m, 1H), 1.36 (s, 9H), 1.35 (s, 3H), 0.64 (s, 3H). MS (m/z) 471.3 [M+H]+.

Example 26: (S)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

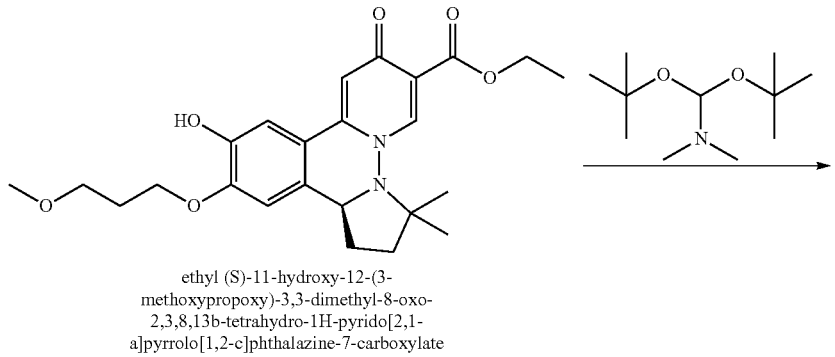

ethyl (S)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate

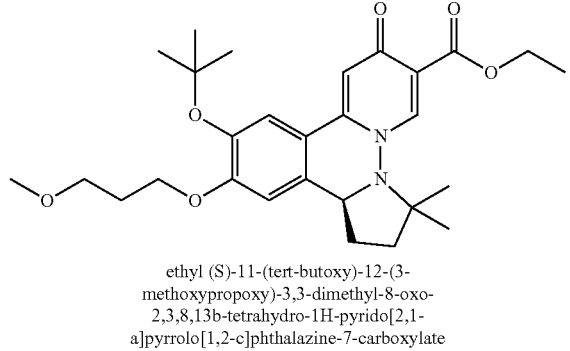

ethyl (S)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate

LiOH

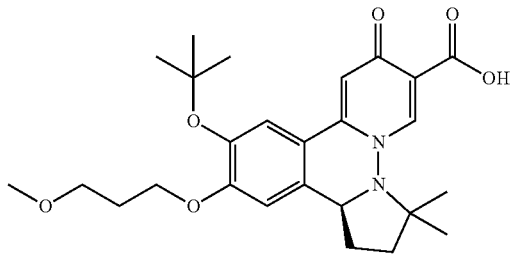

26

To a solution of ethyl (S)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (60 mg, 0.07 mmol) in toluene (5 ml) was added dropwise 1,1-di-tert-butoxy-N,N-dimethylmethanamine (406.38 μl, 1.69 mmol) over 1 h at 80° C. The mixture was heated for 45 minutes, concentrated under vacuum, and the resulting mixture was diluted with ethanol (0.5 ml) and treated with 2M LiOH(aq) (0.15 ml). After stirring for 1 h, the mixture was acidified with 2M HCl (0.2 ml). The product was purified by prep HPLC using acetonitrile in water with 0.1% TFA. $^1$H NMR (400 MHz, Chloroform-d) δ 8.53 (s, 1H), 7.38 (s, 1H), 7.07 (s, 1H), 6.81 (s, 1H), 4.77 (d, J=5.9 Hz, 1H), 4.19-4.04 (m, 2H), 3.65-3.52 (m, 2H), 3.35 (s, 3H), 2.54-2.34 (m, 2H), 2.11 (p, J=6.2 Hz, 2H), 1.93-1.83 (m, 1H), 1.67-1.55 (m, 1H), 1.36 (s, 9H), 1.35 (s, 3H), 0.64 (s, 3H). MS (m/z) 471.3 [M+H]+.

Example 27: (R)-11-(2,2-difluoroethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

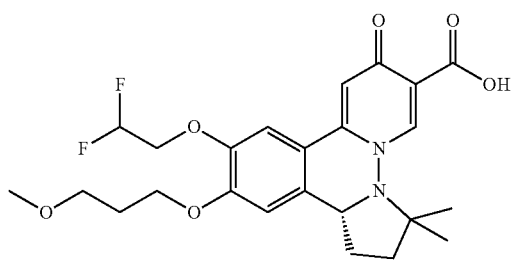

27

A mixture of ethyl (S)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (30 mg, 0.07 mmol), $Cs_2CO_3$ (88.4 mg, 0.27 mmol), and 1,1-difluoro-2-iodoethane (52.05 mg, 0.27 mmol) in was stirred at 50° C. for 2 h. To the reaction was added ethanol (0.5 ml) followed by 2M LiOH (aq) (0.1 ml). The mixture was stirred for 30 min at 50° C. The mixture was acidified with trifluoroacetic acid (10 uL) and the product was purified by prep HPLC using ACN in water with 0.1% TFA (35%-65%). $^1$H NMR (400 MHz, Chloroform-d) δ 8.56 (s, 1H), 7.29 (s, 1H), 7.18 (s, 1H), 6.84 (s, 1H), 6.13 (tt, J=54.9, 4.0 Hz, 1H), 4.79 (d, J=6.1 Hz, 1H), 4.34-4.09 (m, 4H), 3.65-3.50 (m, 2H), 3.37 (s, 3H), 2.55-2.31 (m, 2H), 2.13 (p, J=6.2 Hz, 2H), 1.95-1.85 (m, 1H), 1.69-1.56 (m, 1H), 1.38 (s, 3H), 0.67 (s, 3H). MS (m/z) 479.4 [M+H]+.

Example 28: (R)-11-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

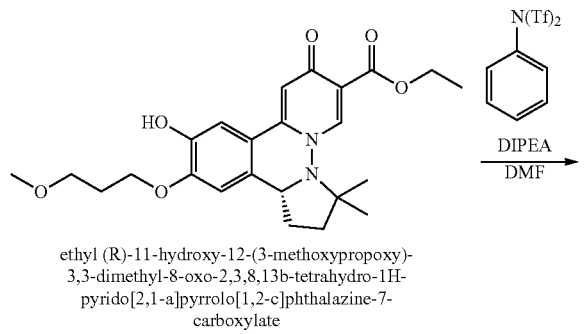

ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate

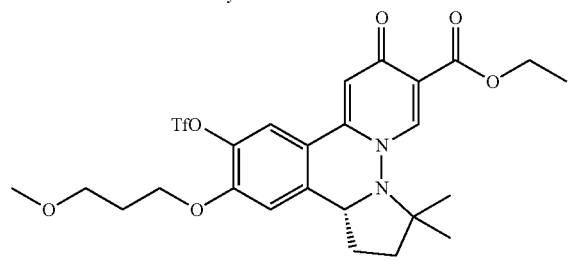

ethyl (R)-12-(3-methoxypropoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalazine-7-carboxylate

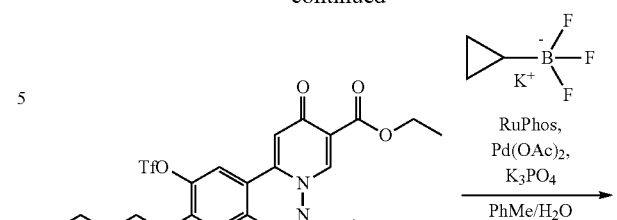

ethyl (R)-12-(3-(λ$^1$-oxidanyl)propoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalazine-7-carboxylate

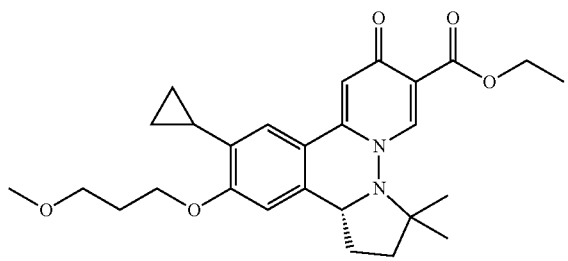

ethyl (R)-11-cyclopropyl-12-(3-methoxypropoxy)-3,3-dimethyl-8-oxo 2,3,8,13b-tetrahydro-1H-pyrido[2,1-a]pyrrolo[1,2-c]phthalazine-7-carboxylate

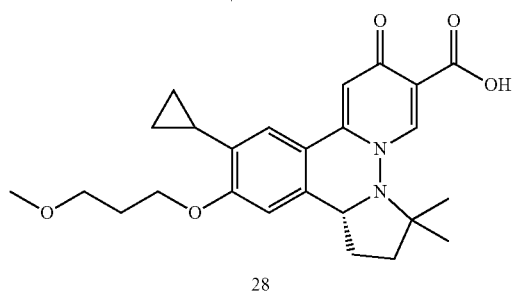

28

Synthesis of ethyl (R)-12-(3-methoxypropoxy)-3,3-dimethyl-8-oxo-11-(((trifluoromethyl)-sulfonyl)oxy)-2,3,8,13b-tetrahydro-1H-pyrido[2,1-a]pyrrolo[1,2-c]phthalazine-7-carboxylate Ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (200 mg, 0.452 mmol) and N-phenyl-bis(trifluoromethanesulfonimide) (242 mg, 0.678 mmol) were suspended in DMF (2.25 mL) and DIPEA (0.40 mL, 2.26 mmol) was added. After stirring o/n at RT, the reaction mixture was diluted with EtOAc and washed with $H_2O$ and brine. The organic layer was dried over $MgSO_4$, filtered and concentrated under reduced pressure. The crude residue was purified by silica column chromatography (0% to 40% MeOH/EtOAc) to afford ethyl (R)-12-(3-methoxypropoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalazine-7-carboxylate (255 mg, 98%). MS (m/z) 575.5 [M+H]+.

Synthesis of ethyl (R)-11-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl (R)-12-(3-methoxypropoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalazine-7-carboxylate (255 mg, 0.444 mmol), potassium cyclopropyltrifluoroborate (99 mg, 0.67 mmol), RuPhos (83 mg, 0.18 mmol) and Pd(OAc)$_2$ were suspended in PhMe (4.4 mL) and K$_3$PO$_4$ (2M in H$_2$O, 1.1 mL, 2.2 mmol) was added. The mixture was degassed by pulling vacuum and back filling with Ar 5×. After heating to reflux for 1.5 h, the reaction mixture was cooled to RT, diluted with EtOAc and washed with H$_2$O and brine. The organic layer was dried over MgSO$_4$, filtered and concentrated under reduced pressure. The crude residue was purified by silica column chromatography (0% to 40% MeOH/EtOAc) to afford ethyl (R)-11-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylate (204 mg, 99%). MS (m/z) 467.5 [M+H]+.

(R)-1-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid Ethyl (R)-11-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylate (204 mg, 0.437 mmol) was suspended in EtOH (4.4 mL) and treated with LiOH (2M in H$_2$O, 0.44 mL, 0.88 mmol) was added. The reaction was stirred at 60° C. for 2 h, then cooled to RT. TFA (0.1 mL) and DMF (3 mL) were added and the mixture was concentrated to a volume of 3.5 mL under reduced pressure. The crude solution was then purified by HPLC to afford the title compound. $^1$H NMR (400 MHz, Chloroform-d) δ 8.62 (s, 1H), 7.30 (s, 1H), 7.28 (s, 1H), 6.75 (s, 1H), 4.82 (d, 1H), 4.19 (ddt, 2H), 3.71-3.53 (m, 2H), 3.38 (d, 3H), 2.61-2.35 (m, 2H), 2.15 (h, 3H), 1.64 (td, 1H), 1.39 (d, 3H), 1.02 (dq, 2H), 0.79-0.68 (m, 2H), 0.65 (s, 3H). MS (m/z) 439.3 [M+H]+.

Example 29: (R)-11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylic acid

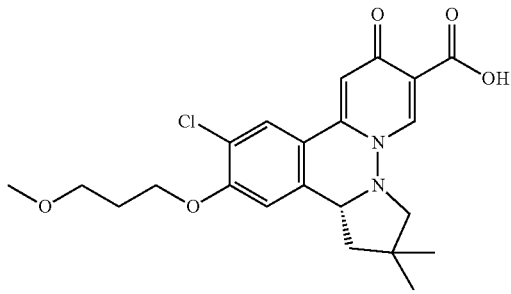

Synthesis of ethyl 11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylate Ethyl 11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylate was prepared ethyl 11-chloro-12-(3-methoxypropoxy)-8-oxo-2,3,8,13b-tetrahydro-1H-pyrido[2,1-a]pyrrolo[1,2-c]phthalazine-7-carboxylate in example 1 using tert-butyl 4,4-dimethyl-2-oxopyrrolidine-1-carboxylate in place of 1-(tert-butoxycarbonyl)-2-pyrrolidinone. $^1$H NMR (400 MHz, Chloroform-d) δ 8.31 (s, 1H), 7.73 (s, 1H), 6.87-6.77 (m, 2H), 4.69 (d, J=7.1 Hz, 1H), 4.35 (dd, J=7.1, 2.2 Hz, 2H), 4.23-4.08 (m, 2H), 3.58 (d, J=2.8 Hz, 2H), 3.34 (s, 3H), 3.01 (d, J=8.3 Hz, 1H), 2.74 (d, J=8.3 Hz, 1H), 2.36-2.19 (m, 2H), 2.1 (t, J=6.1 Hz, 2H), 1.36 (t, J=7.1 Hz, 3H), 1.26 (s, 3H), 0.89 (s, 3H). MS (m/z) 461.34 [M+H]+.

(R)-11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylic acid Ethyl 11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using IA 5 uM-4.6×150 mm columns with 30% isopropanol as the co-solvent. The faster eluting peak with a retention time of 3.77 min was taken up in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.66 (s, 1H), 7.81 (s, 1H), 7.04 (s, 1H), 6.86 (s, 1H), 4.76 (d, J=7.3 Hz, 1H), 4.22 (dt, J=6.4, 3.2 Hz, 2H), 3.61 (td, J=6.1, 3.4 Hz, 2H), 3.37 (s, 3H), 3.08 (d, J=8.3 Hz, 1H), 2.81 (d, J=8.2 Hz, 1H), 2.36 (d, J=7.5 Hz, 1H), 2.32-2.23 (m, 1H), 2.19-2.11 (m, 2H), 1.29 (s, 3H), 0.95 (s, 3H). MS (m/z) 433.357 [M+H]+.

Example 30: (S)-11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylic acid

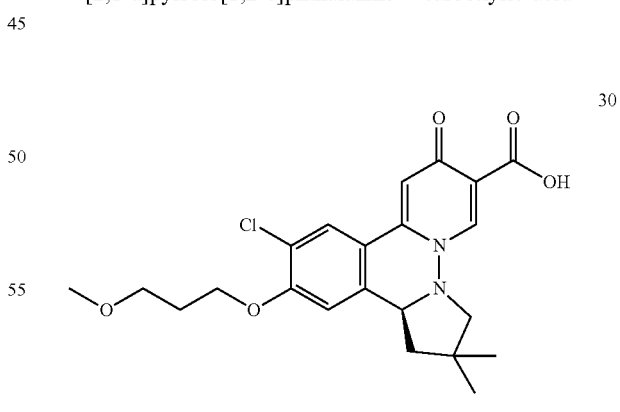

Ethyl 11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using IA 5 uM-4.6×150 mm columns with 30% isopropanol as the co-solvent. The slower eluting peak with a retention time of 4.99 min was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. $^1$H NMR (400 MHz, Chloroform-d) δ 8.66 (s, 1H), 7.81 (s, 1H), 7.04 (s, 1H), 6.86 (s, 1H), 4.76 (d, J=7.3 Hz, 1H), 4.22 (dt, J=6.4, 3.2 Hz, 2H), 3.61 (td, J=6.1, 3.4 Hz, 2H), 3.37 (s, 3H), 3.08 (d, J=8.3 Hz, 1H), 2.81 (d, J=8.2 Hz, 1H), 2.36 (d, J=7.5 Hz, 1H), 2.32-2.23 (m, 1H), 2.19-2.11 (m, 2H), 1.29 (s, 3H), 0.95 (s, 3H). MS (m/z) 433.357 [M+H]+.

Example 31: trans-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (racemate) and Example 32: cis-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (racemate)

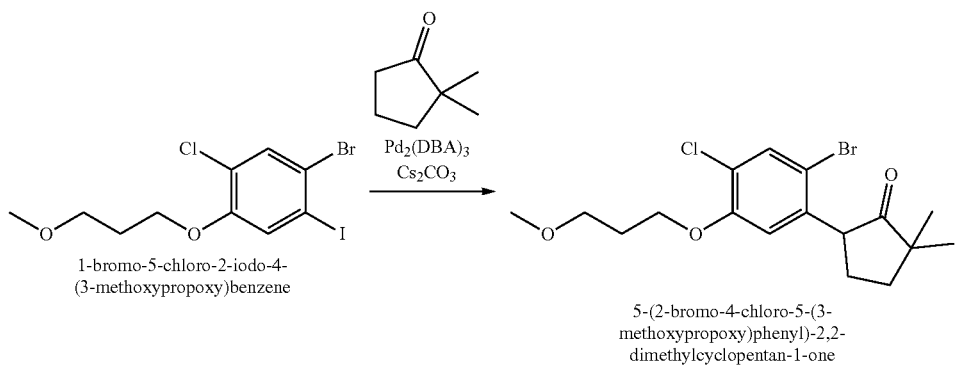

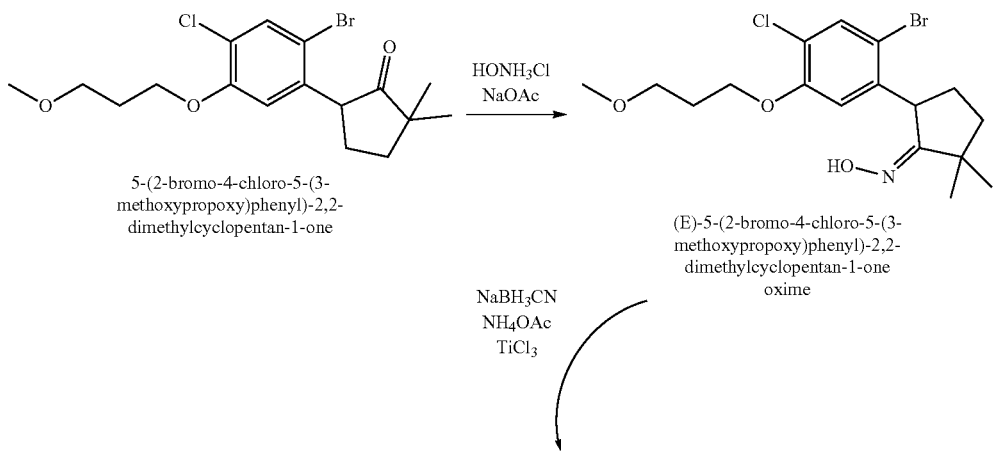

-continued

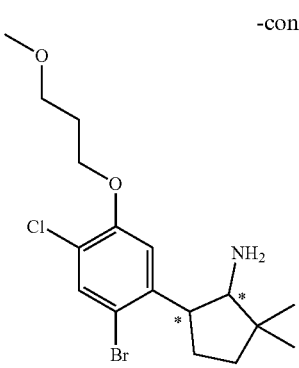
cis isomer
(cis)-5-(2-bromo-4-chloro-5-(3-methoxypropoxy)phenyl)-2,2-dimethylcyclopentan-1-amine

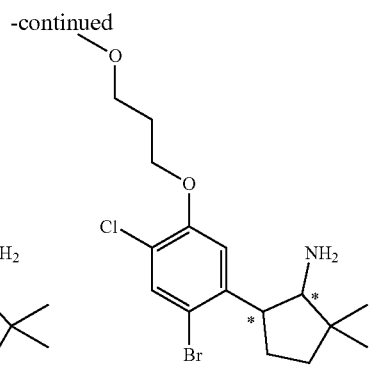
trans isomer
(trans)-5-(2-bromo-4-chloro-5-(3-methoxypropoxy)phenyl)-2,2-dimethylcyclopentan-1-amine

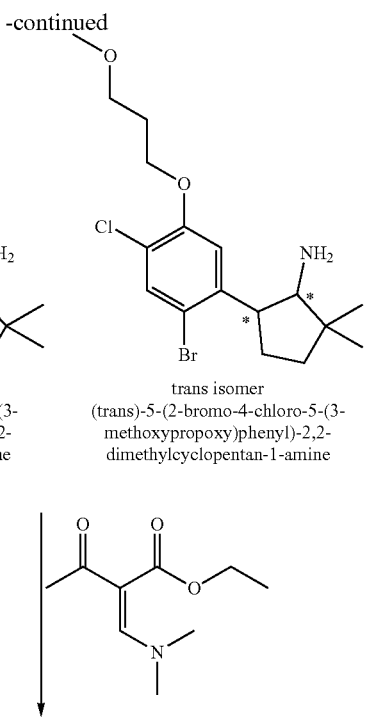

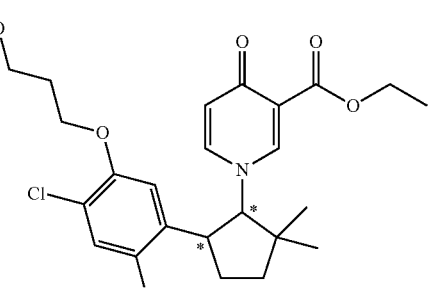
trans isomer
ethyl 1-((trans)-5-(2-bromo-4-chloro-5-(3-methoxypropoxy)phenyl)-2,2-dimethylcyclopentyl)-4-oxo-1,4-dihydropyridine-3-carboxylate

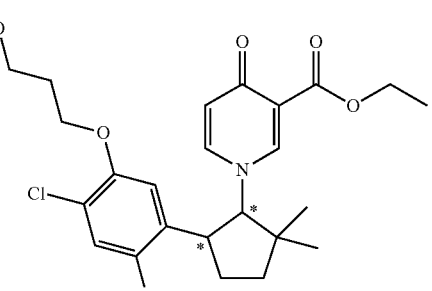
cis isomer
ethyl 1-((cis)-5-(2-bromo-4-chloro-5-(3-methoxypropoxy)phenyl)-2,2-dimethylcyclopentyl)-4-oxo-1,4-dihydropyridine-3-carboxylate

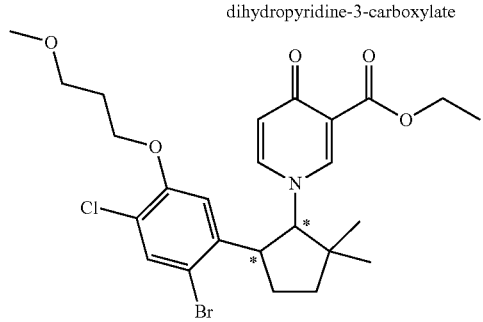
trans isomer
ethyl 1-((trans)-5-(2-bromo-4-chloro-5-(3-methoxypropoxy)phenyl)-2,2-dimethylcyclopentyl)-4-oxo-1,4-dihydropyridine-3-carboxylate

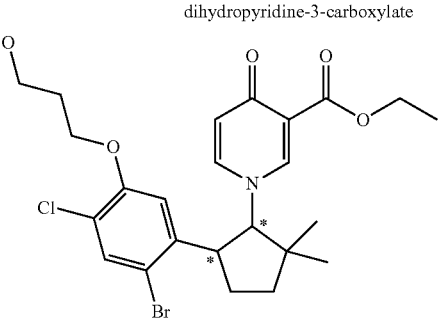
cis isomer
ethyl 1-((cis)-5-(2-bromo-4-chloro-5-(3-methoxypropoxy)phenyl)-2,2-dimethylcyclopentyl)-4-oxo-1,4-dihydropyridine-3-carboxylate Pd(OAc)$_2$
DPEPhos
K$_2$CO$_3$ Pd(OAc)$_2$
DPEPhos
K$_2$CO$_3$

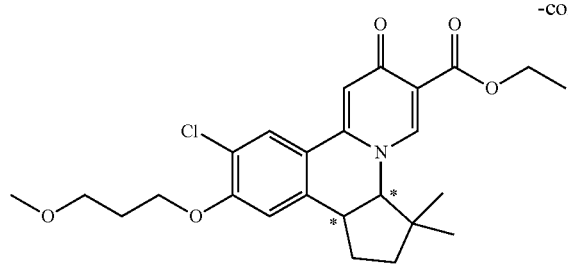

trans isomer
ethyl (trans)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylate

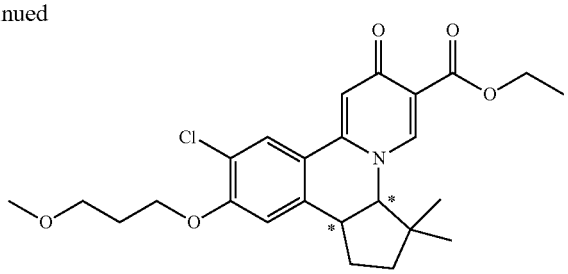

cis isomer
ethyl (cis)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylate Synthesis of 5-(2-bromo-4-chloro-5-(3-methoxypropoxy)phenyl)-2,2-dimethylcyclopentan-1-one Argon was bubbled through a mixture of 1-bromo-5-chloro-2-iodo-4-(3-methoxypropoxy)benzene (5.0 g, 12.33 mmol), $Cs_2CO_3$ (8.84 g, 27.13 mmol), $Pd_2(DBA)_3$ (0.28 g, 0.31 mmol), xantphos (0.43 g, 0.74 mmol), and 2,2-dimethylcyclopentan-1-one (1.38 g, 12.33 mmol) in dioxane (15 ml). The reaction was heated under inert atmosphere for 20 h. The mixture was cooled, diluted with ethyl acetate (150 ml) and washed with water (150 ml) followed by 0.5M NaCl (150 ml). The organic layer was dried with $Na_2SO_4$, filtered, and concentrated. Product was purified by silica chromatography using ethyl acetate in hexane. 2.5 g. $^1H$ NMR (400 MHz, Chloroform-d) δ 7.54 (s, 1H), 6.53 (s, 1H), 4.03 (td, J=6.2, 2.6 Hz, 2H), 3.88-3.79 (m, 1H), 3.62-3.49 (m, 2H), 3.34 (s, 3H), 2.54-2.41 (m, 1H), 2.05 (p, J=6.1 Hz, 2H), 1.99-1.78 (m, 3H), 1.19 (s, 3H), 1.13 (s, 3H).

Synthesis of 5-(2-bromo-4-chloro-5-(3-methoxypropoxy)phenyl)-2,2-dimethylcyclopentan-1-one oxime To a solution of 5-(2-bromo-4-chloro-5-(3-methoxypropoxy)phenyl)-2,2-dimethylcyclopentan-1-one in EtOH (4 ml) was added hydroxylamine hydrochloride (0.54 g, 7.7 mmol) and sodium acetate (0.63 g, 7.7 mmol). The mixture was heated at 80° C. for 30 minutes. The reaction vessel was sealed and the mixture was heated in a microwave reactor at 120° C. for 30 minutes. The reaction was incomplete. Additional hydroxylamine hydrochloride (2 eq.) and sodium acetate (2 eq.) was added and the mixture was heated at 120° C. for 30 minutes. After cooling the reaction vessel remained under pressure and the evolved gas was carefully released. The mixture was diluted with EtOAc (15 mL) and washed with water (2×15 mL). The organic layer was dried with $Na_2SO_4$, filtered, and concentrated. Product was purified by silica chromatography using EtOAc in hexane. 550 mg. $^1H$ NMR (400 MHz, Chloroform-d) δ 7.53 (s, 1H), 6.56 (s, 1H), 4.35 (dd, J=8.6, 6.4 Hz, 1H), 4.09-3.95 (m, 2H), 3.63-3.49 (m, 2H), 3.34 (s, 3H), 2.52-2.37 (m, 1H), 2.04 (p, J=6.1 Hz, 2H), 1.77-1.55 (m, 3H), 1.31 (s, 3H), 1.26 (s, 3H). MS (m/z) 406.1 [M+H]+.

cis-5-(2-Bromo-4-chloro-5-(3-methoxypropoxy)phenyl)-2,2-dimethylcyclopentan-1-amine and trans-5-(2-bromo-4-chloro-5-(3-methoxypropoxy)phenyl)-2,2-dimethylcyclopentan-1-amine To a solution of 5-(2-bromo-4-chloro-5-(3-methoxypropoxy)phenyl)-2,2-dimethylcyclopentan-1-one oxime (500 mg, 1.24 mmol) and ammonium acetate (405.36 mg, 4.94 mmol) in methanol (8 mL), portions of sodium cyanoborohydride (310.53 mg, 4.94 mmol) was added at 0° C. To the cooled solution was added dropwise titanium trichloride (12% in aq. HCl) (12%, 3175.58 mg, 2.47 mmol) maintaining an internal temperature below 10° C. The mixture was warmed to ambient temperature and sonicated for 30 mins. To the reaction was added ammonium acetate (405.36 mg, 4.94 mmol), sodium cyanoborohydride (310.53 mg, 4.94 mmol) and titanium trichloride (12% in aq. HCl) (12%, 1587.79 mg, 1.24 mmol). The mixture was sonicated for 1.5 h. The reaction mixture was partially concentrated, diluted with EtOAc (100 mL), washed with 0.2M HCl (2×100 mL), followed by 1M NaOH (100 mL), and brine. The organic layer was dried with $Na_2SO_4$, filtered, and concentrated. Product was purified by silica chromatography using ethanol in dichloromethane to give a partially purified product as a 3:2 mixture of diastereomers. 340 mg. MS (m/z) 392.4 [M+H]+.

cis-Ethyl 1-(5-(2-bromo-4-chloro-5-(3-methoxypropoxy)phenyl)-2,2-dimethylcyclopentyl)-4-oxo-1,4-dihydropyridine-3-carboxylate cis-ethyl 1-(5-(2-bromo-4-chloro-5-(3-methoxypropoxy)phenyl)-2,2-dimethylcyclopentyl)-4-oxo-1,4-dihydropyridine-3-carboxylate was prepared analogously to ethyl 11-(benzyloxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylate in Example 18. The products were purified by silica chromatography using ethanol in dichloromethane followed by purification by prep HPLC using acetonitrile in water with 0.1% TFA.

cis-Ethyl 1-(5-(2-bromo-4-chloro-5-(3-methoxypropoxy)phenyl)-2,2-dimethylcyclopentyl)-4-oxo-1,4-dihydropyridine-3-carboxylate $^1H$ NMR (400 MHz, Chloroform-d) δ 8.10 (d, J=2.4 Hz, 1H), 7.45 (s, 1H), 7.36 (d, J=7.7 Hz, 1H), 6.93 (d, J=7.5 Hz, 1H), 6.82 (s, 1H), 4.62 (d, J=7.8 Hz, 1H), 4.38-4.29 (m, 2H), 4.25-4.17 (m, 1H), 4.11-4.03 (m, 1H), 4.02-3.92 (m, 1H), 3.60-3.50 (m, 2H), 3.35 (s, 3H), 2.53-2.39 (m, 1H), 2.39-2.27 (m, 1H), 2.10-1.91 (m, 4H), 1.39 (s, 3H), 1.35 (t, J=7.1 Hz, 3H), 0.94 (s, 3H). MS (m/z) 542.2 [M+H]+.

trans-ethyl 1-(5-(2-bromo-4-chloro-5-(3-methoxypropoxy)phenyl)-2,2-dimethylcyclopentyl)-4-oxo-1,4-dihydropyridine-3-carboxylate $^1H$ NMR (400 MHz, Chloroform-d) δ 8.21 (d, J=2.5 Hz, 1H), 7.51 (s, 1H), 7.34 (d, J=7.9 Hz, 1H), 6.82 (s, 1H), 6.50

(d, J=7.7 Hz, 1H), 4.40-4.29 (m, 2H), 4.16-4.01 (m, 4H), 3.62-3.53 (m, 2H), 3.38 (s, 3H), 2.47-2.35 (m, 1H), 2.11-2.02 (m, 2H), 1.92-1.84 (m, 2H), 1.77-1.64 (m, 1H), 1.36 (t, J=7.1 Hz, 3H), 1.23 (s, 3H), 0.98 (s, 3H). MS (m/z) 542.2 [M+H]+.

cis-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

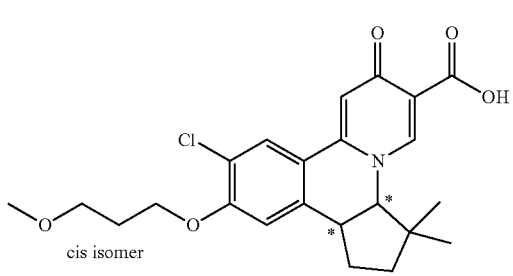

cis isomer cis-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid was prepared analogously to 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (Example 11) using cis-ethyl 1-(5-(2-bromo-4-chloro-5-(3-methoxypropoxy)phenyl)-2,2-dimethylcyclopentyl)-4-oxo-1,4-dihydropyridine-3-carboxylate. $^1$H NMR (400 MHz, Chloroform-d) δ 8.40 (s, 1H), 7.79 (s, 1H), 7.12 (s, 1H), 6.91 (d, J=1.1 Hz, 1H), 4.28-4.12 (m, 3H), 3.80 (t, J=7.6 Hz, 1H), 3.68-3.56 (m, 2H), 3.37 (s, 3H), 2.44-2.22 (m, 2H), 2.14 (p, J=6.2 Hz, 2H), 1.68 (ddd, J=13.3, 8.1, 5.3 Hz, 1H), 1.51 (dt, J=13.1, 8.0 Hz, 1H), 1.26 (s, 3H), 0.51 (s, 3H). MS (m/z) 432.3 [M+H]+.

trans-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

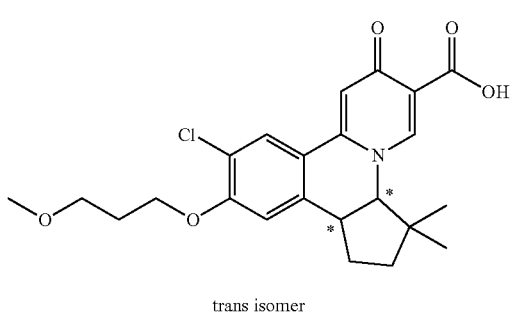

trans isomer trans-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid was prepared analogously to 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (Example 11) using trans-ethyl 1-(5-(2-bromo-4-chloro-5-(3-methoxypropoxy)phenyl)-2,2-dimethylcyclopentyl)-4-oxo-1,4-dihydropyridine-3-carboxylate. $^1$H NMR (400 MHz, Chloroform-d) δ 8.78 (d, J=0.7 Hz, 1H), 7.72 (s, 1H), 7.07 (s, 1H), 6.79 (d, J=1.1 Hz, 1H), 4.28-4.08 (m, 2H), 3.62-3.54 (m, 3H), 3.49-3.38 (m, 1H), 3.37 (s, 3H), 2.39-2.23 (m, 1H), 2.14 (p, J=6.1 Hz, 2H), 2.08-1.83 (m, 3H), 1.58 (s, 3H), 1.33 (s, 3H). MS (m/z) 432.3 [M+H]+.

Example 33: (3aS,12bR)-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

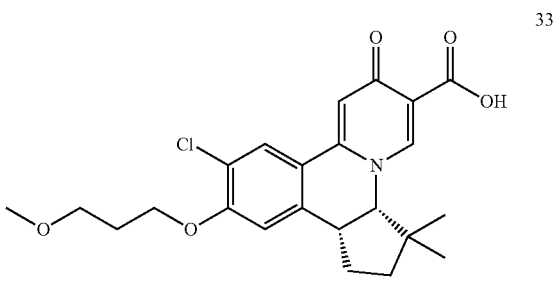 [SMILES: COCCCOc1cc2c(cc1Cl)-c1cc(=O)c(C(=O)O)cn1[C@H]1[C@@H]2CCC1(C)C]

cis-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (31) was separated into its enantiomers by chiral SFC chromatography using OD-H 4.6×100 mm columns with 30% isopropanol as the co-solvent. Compound 33 is the slower eluting peak retention time of 4.47 min. $^1$H NMR (400 MHz, Chloroform-d) δ 8.40 (s, 1H), 7.79 (s, 1H), 7.12 (s, 1H), 6.91 (d, J=1.1 Hz, 1H), 4.28-4.12 (m, 3H), 3.80 (t, J=7.6 Hz, 1H), 3.68-3.56 (m, 2H), 3.37 (s, 3H), 2.44-2.22 (m, 2H), 2.14 (p, J=6.2 Hz, 2H), 1.68 (ddd, J=13.3, 8.1, 5.3 Hz, 1H), 1.51 (dt, J=13.1, 8.0 Hz, 1H), 1.26 (s, 3H), 0.51 (s, 3H). MS (m/z) 432.3 [M+H]+.

Example 34: (3aR,12bS)-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

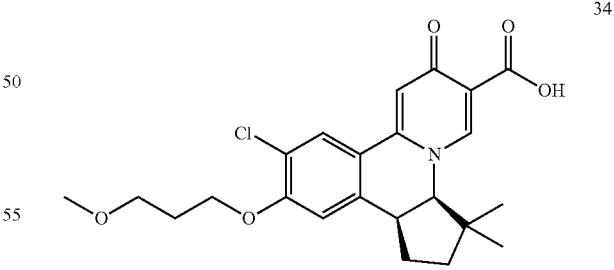

cis-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (31) was separated into its enantiomers by chiral SFC chromatography using OD-H 4.6×100 mm columns with 30% isopropanol as the co-solvent. Compound 34 is the faster eluting peak retention time of 3.52 min. $^1$H NMR (400 MHz, Chloroform-d) δ 8.40 (s, 1H), 7.79 (s, 1H), 7.12 (s, 1H), 6.91 (d, J=1.1 Hz, 1H), 4.28-4.12 (m, 3H), 3.80 (t, J=7.6 Hz, 1H), 3.68-3.56 (m, 2H), 3.37 (s, 3H), 2.44-2.22 (m, 2H), 2.14 (p, J=6.2 Hz, 2H), 1.68 (ddd, J=13.3, 8.1, 5.3 Hz, 1H), 1.51 (dt, J=13.1, 8.0 Hz, 1H), 1.26 (s, 3H), 0.51 (s, 3H). MS (m/z) 432.3 [M+H]+.

Example 35: ((3aS,12bS)-10-Chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

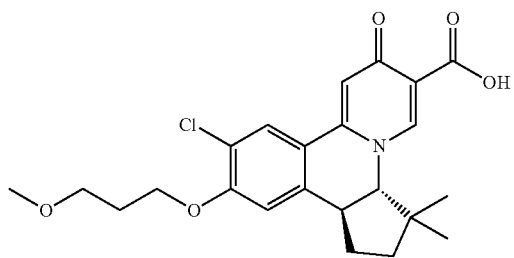

trans-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (32) was separated into its enantiomers by chiral SFC chromatography using AD-H 4.6×100 mm columns with 30% isopropanol as the co-solvent. Compound 35 is the slower eluting peak retention time of 4.72 min. $^1$H NMR (400 MHz, Chloroform-d) δ 8.78 (d, J=0.7 Hz, 1H), 7.72 (s, 1H), 7.07 (s, 1H), 6.79 (d, J=1.1 Hz, 1H), 4.28-4.08 (m, 2H), 3.62-3.54 (m, 3H), 3.49-3.38 (m, 1H), 3.37 (s, 3H), 2.39-2.23 (m, 1H), 2.14 (p, J=6.1 Hz, 2H), 2.08-1.83 (m, 3H), 1.58 (s, 3H), 1.33 (s, 3H). MS (m/z) 432.3 [M+H]+.

Example 36: ((3aR,12bR)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid

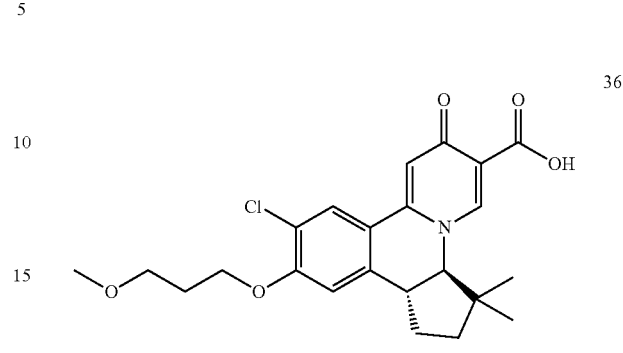

trans-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (32) was separated into its enantiomers by chiral SFC chromatography using AD-H 4.6×100 mm columns with 30% isopropanol as the co-solvent. Compound 36 is the faster eluting peak retention time of 4.06 min. $^1$H NMR (400 MHz, Chloroform-d) δ 8.78 (d, J=0.7 Hz, 1H), 7.72 (s, 1H), 7.07 (s, 1H), 6.79 (d, J=1.1 Hz, 1H), 4.28-4.08 (m, 2H), 3.62-3.54 (m, 3H), 3.49-3.38 (m, 1H), 3.37 (s, 3H), 2.39-2.23 (m, 1H), 2.14 (p, J=6.1 Hz, 2H), 2.08-1.83 (m, 3H), 1.58 (s, 3H), 1.33 (s, 3H). MS (m/z) 432.3 [M+H]+.

Example 37: ((R)-11-methoxy-3,3-dimethyl-8-oxo-12-((3-oxocyclobutyl)methoxy)-2,3,8,13b-tetrahydro-1H-pyrido[2,1-a]pyrrolo[1,2-c]phthalazine-7-carboxylic acid

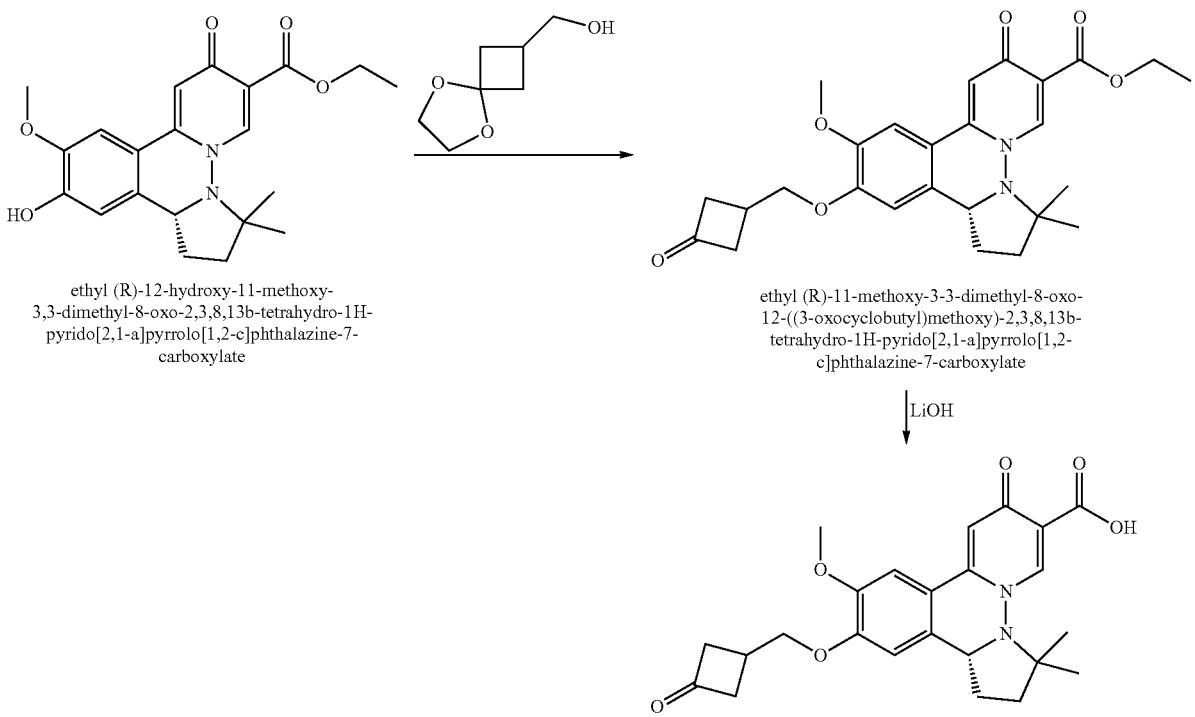

To a solution of ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (15 mg, 0.04 mmol) in THF (2 ml) was added triphenylphosphine (20 mg, 0.08 mmol), (5,8-dioxaspiro[3.4]octan-2-yl)methanol (5.6 mg, 0.04 mmol) followed by the dropwise addition of DIAD (12 µl, 0.6 mmol) over 10 min at 0° C. The mixture was stirred for 16 h at rt, concentrated under vacuum, and the resulting mixture was diluted with ethanol (0.5 ml) and treated with 2M LiOH (aq) (0.15 ml). After stirring for 2 h, the mixture was acidified with TFA. The product was purified by prep HPLC using acetonitrile in water with 0.1% TFA. $^1$H NMR (400 MHz, Chloroform-d) δ 8.59 (s, 1H), 7.32 (s, 1H), 7.23 (s, 1H), 6.79 (s, 1H), 4.80 (d, J=6.1 Hz, 1H), 4.22 (d, J=6.1 Hz, 2H), 3.94 (s, 3H), 3.38-3.18 (m, 2H), 3.19-2.81 (m, 2H), 2.67-2.19 (m, 2H), 1.91 (ddd, J=12.6, 7.8, 2.5 Hz, 1H), 1.63 (td, J=11.7, 7.5 Hz, 1H), 1.39 (s, 3H), 1.26 (t, J=5.4 Hz, 1H), 0.69 (s, 3H). MS (m/z) 439.5 [M+H]+.

Example 38: 13-chloro-12-(3-methoxypropoxy)-10,10-dimethyl-2-oxo-2,7,8,9,10,10a-hexahydrodipyrido[2,1-a:1',2'-c]phthalazine-3-carboxylic acid

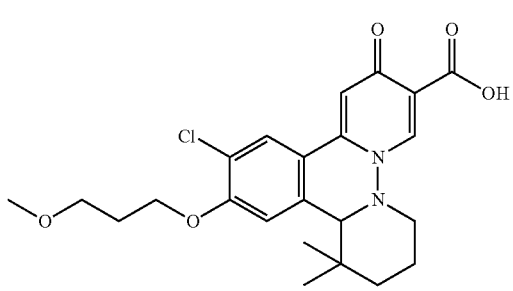

13-Chloro-12-(3-methoxypropoxy)-10,10-dimethyl-2-oxo-2,7,8,9,10,10a-hexahydrodipyrido[2,1-a:1',2'-c]phthalazine-3-carboxylic acid prepared similarly to example 11 using 3,3-dimethylpiperidine in place of 2,2-dimethylpiperidine. 1H NMR (400 MHz, Chloroform-d) δ 8.88 (s, 1H), 7.84 (s, 1H), 7.76-7.42 (m, 1H), 7.35 (s, 1H), 4.22 (t, 2H), 4.07 (s, 1H), 3.73-3.63 (m, 2H), 3.46-3.33 (m, 3H), 2.24-2.15 (m, 2H), 1.79 (d, 1H), 1.68-1.52 (m, 4H), 1.52-1.37 (m, 3H), 1.33-1.18 (m, 3H), 0.96-0.75 (m, 1H). MS (m/z) 447.2 [M+H]+.

Example 39: (R)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid

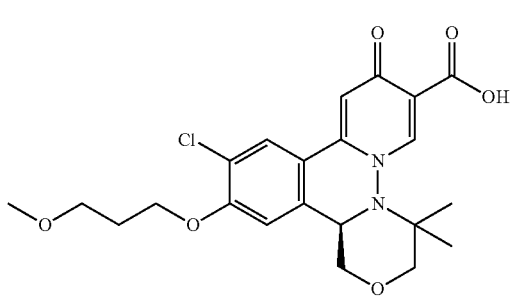

(R)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid was prepared similarly to example 13 using 2,2-dimethyltetrahydro-2H-pyran in place of 2,2-dimethylpiperidine was separated into its enantiomers by chiral SFC chromatography using OD-H 4.6×100 mm column with 30% methanol as the co-solvent. The faster eluting peak with a retention time of 4.7 min was taken up in in EtOH (1 mL) and 2M LiOH (0.3 mL) then stirred at room temperature until hydrolysis was complete. The mixture was acidified with TFA (0.5 mL) and water (0.5 mL), filtered and purified by HPLC. $^1$H NMR (400 MHz, Chloroform-d) δ 8.63 (s, 1H), 7.79 (s, 1H), 7.14 (s, 1H), 7.03 (s, 1H), 4.75 (d, 1H), 4.39 (s, 1H), 4.32-4.18 (m, 2H), 4.10 (dd, 1H), 3.65-3.57 (m, 3H), 3.57-3.46 (m, 1H), 3.38 (s, 3H), 2.16 (p, 2H), 1.11 (s, 3H), 0.54 (s, 3H). MS (m/z) 449.2 [M+H]+.

Example 40: (R)-13-bromo-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

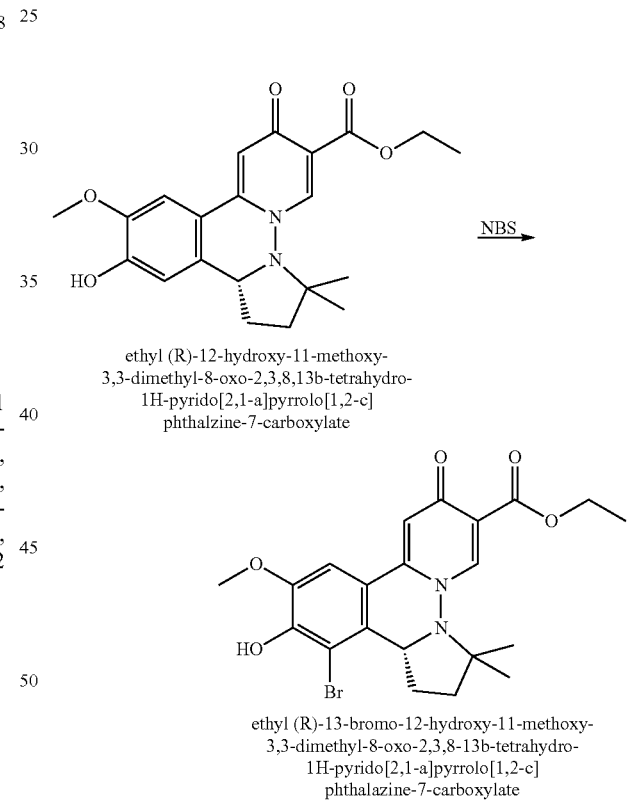

ethyl (R)-12-hydroxy-11-methoxy-3,3-dimethyl-8-oxo-2,3,8,13b-tetrahydro-1H-pyrido[2,1-a]pyrrolo[1,2-c]phthalzine-7-carboxylate ethyl (R)-13-bromo-12-hydroxy-11-methoxy-3,3-dimethyl-8-oxo-2,3,8-13b-tetrahydro-1H-pyrido[2,1-a]pyrrolo[1,2-c]phthalazine-7-carboxylate Synthesis of Ethyl (R)-13-bromo-12-hydroxy-11-methoxy-3,3-dimethyl-8-oxo-2,3,8,13b-tetrahydro-1H-pyrido[2,1-a]pyrrolo[1,2-c]phthalazine-7-carboxylate Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (48 mg, 0.12 mmol) was dissolved in a mixture of 0.4 mL acetic acid and 0.4 mL THF. Potassium acetate (61 mg, 0.62 mmol) was added and the reaction was cooled to 5° C. N-bromosuccinimide (22 mg, 0.12 mmol) was added in a single portion. After 3 minutes, LCMS analysis showed complete conversion. The crude mixture was diluted with 1M TFA and purified by preparative HPLC to provide ethyl (R)-13-bromo-12-hydroxy-11-methoxy-3,3-dimethyl-8-oxo-2,3,8,13b-tetrahydro-1H-pyrido[2,1-a]pyrrolo[1,2-c]phthalazine-7-carboxylate as a TFA salt after lyophilization. 1H NMR (400 MHz, DMSO-d6) δ 8.10 (s, 1H), 7.46 (s, 1H), 6.92 (s, 1H), 4.85 (dd, J=8.5, 4.5 Hz, 1H), 4.29-4.10 (m, 2H), 3.92 (s, 3H), 2.77 (dtd, J=12.5, 8.5, 3.5 Hz, 1H), 2.23 (dtd, J=13.7, 9.0, 4.7 Hz, 1H), 1.71 (dt, J=11.8, 9.0 Hz, 1H), 1.58 (ddd, J=12.1, 8.5, 3.6 Hz, 1H), 1.28-1.19 (m, 3H), 1.21 (s, 3H), 1.20 (s, 3H), 0.70 (s, 3H). MS (m/z) 463.2 [M+H]+.

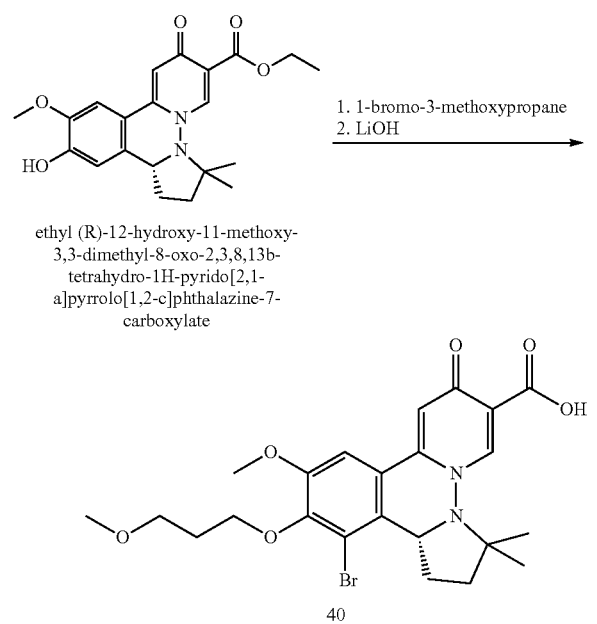

ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate 1. 1-bromo-3-methoxypropane
2. LiOH (R)-13-bromo-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid Ethyl (R)-13-bromo-12-hydroxy-11-methoxy-3,3-dimethyl-8-oxo-2,3,8,13b-tetrahydro-1H-pyrido[2,1-a]pyrrolo[1,2-c]phthalazine-7-carboxylate TFA salt (25 mg, 0.04 mmol) was combined in DMF (0.3 mL) with potassium carbonate (25 mg, 0.18 mmol) and 1-bromo-3-methoxypropane (16 µL, 0.15 mmol). The reaction mixture was stirred at 70° C. for 30 minutes after which time LCMS analysis showed complete conversion of the starting material. The reaction was cooled to room temperature. Aqueous lithium hydroxide (1 M, 0.07 mL, 0.07 mmol) was added and the mixture was stirred at for 25 minutes after which time LCMS analysis showed complete ester hydrolysis. The mixture was diluted with TFA and purified by preparative HPLC to provide (R)-13-bromo-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid as a TFA salt. ¹H NMR (400 MHz, Acetonitrile-d3) δ 8.42 (s, 1H), 7.48 (s, 1H), 7.20 (s, 1H), 4.99 (dd, J=8.6, 4.7 Hz, 1H), 4.22 (dt, J=9.3, 6.4 Hz, 1H), 4.08 (dt, J=9.4, 6.4 Hz, 1H), 3.97 (s, 3H), 3.58 (t, J=6.3 Hz, 2H), 3.32 (s, 3H), 2.99-2.86 (m, 1H), 2.40 (ddd, J=13.8, 9.1, 4.7 Hz, 1H), 2.02 (p, J=6.3 Hz, 2H), 1.90-1.77 (m, 1H), 1.68 (ddd, J=12.3, 8.6, 3.6 Hz, 1H), 1.30 (s, 3H), 0.76 (s, 3H). 19F NMR (376 MHz, Acetonitrile-d3) δ−77.29. MS (m/z) 507.3 [M+H]+.

Example 41: (R)-11-methoxy-3,3-dimethyl-8-oxo-12-(pyrimidin-2-yloxy)-2,3,8,13b-tetrahydro-1H-pyrido[2,1-a]pyrrolo[1,2-c]phthalazine-7-carboxylic acid Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (17 mg, 44 µmol) was combined with 2-chloropyrimidine (15 mg, 133 µmol) and potassium carbonate (24 mg, 0.18 mmol) in NMP (0.25 mL). The mixture was stirred at 70° C. for 18 hours, and then cooled to room temperature. Aqueous 1M lithium hydroxide (88 µL) and ethanol (0.2 mL) were added and the mixture was stirred at 40° C. for 20 minutes. The mixture was cooled to room temperature, diluted with TFA, and purified by preparative HPLC to provide (R)-11-methoxy-3,3-dimethyl-8-oxo-12-(pyrimidin-2-yloxy)-2,3,8,13b-tetrahydro-1H-pyrido[2,1-a]pyrrolo[1,2-c]phthalazine-7-carboxylic acid as a TFA salt. 1H NMR (400 MHz, Acetonitrile-d3) δ 8.56 (d, J=4.8 Hz, 2H), 8.48 (s, 1H), 7.57 (s, 1H), 7.37 (s, 1H), 7.32 (d, J=1.0 Hz, 1H), 7.18 (t, J=4.8 Hz, 1H), 4.89 (t, J=3.8 Hz, 1H), 2.48-2.39 (m, 2H), 1.93-1.85 (m, 1H), 1.65 (dt, J=12.7, 9.5 Hz, 1H), 1.38 (s, 3H), 0.71 (s, 3H). 19F NMR (376 MHz, Acetonitrile-d3) δ−77.31. MS (m/z) 436.3 [M+H]+.

Example 42: (R)-1-Methoxy-3,3-dimethyl-12-((1-methyl-1H-imidazol-5-yl)ethynyl)-8-oxo-2,3,8,13b-tetrahydro-1H-pyrido[2,1-a]pyrrolo[1,2-c]phthalazine-7-carboxylic acid

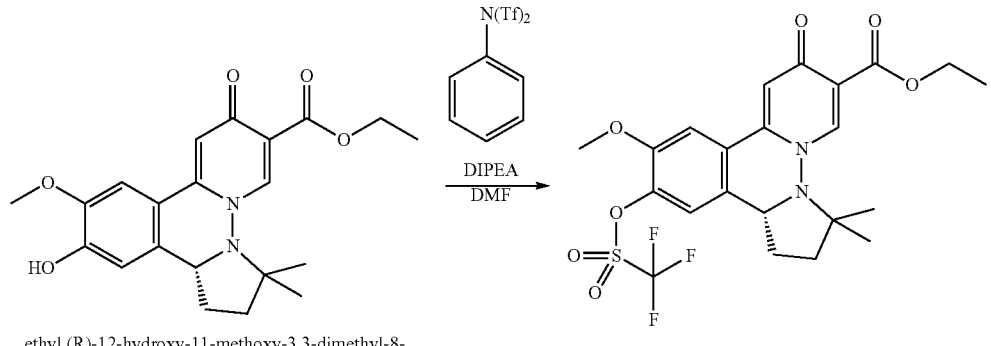

ethyl (R)-12-hydroxy-11-methoxy-3,3-dimethyl-8-oxo-2,3,8,13b-tetrahydro-1H-pyrido[2,1-a]pyrrolo[1,2-c]phthalzine-7-carboxylate ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate

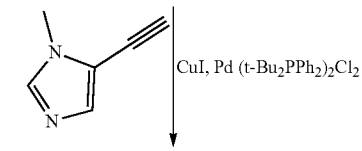

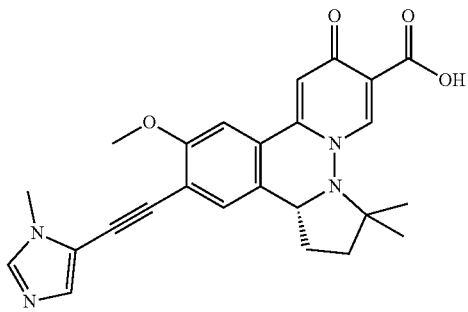

42

Synthesis of Ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (100 mg, 0.26 mmol) was combined with N-Phenyl-bis(trifluoromethanesulfonimide) (167 mg, 0.47 mmol) in DCM (2 mL) at room temperature. N,N-diisopropylethylamine (0.44 mL, 2.6 mmol) was added and the reaction was stirred at room temperature. After 20 minutes, LCMS analysis showed complete conversion. Aqueous NaHCO3 was added, the DCM layer was removed, dried over $Na_2SO_4$, filtered, and concentrated in vacuo. The mixture was purified by flash column chromatography (ethyl acetate/hexanes/ethanol) to provide ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate. $^1$H NMR (400 MHz, Chloroform-d) δ 8.31 (s, 1H), 7.35 (s, 1H), 7.16 (d, J=1.0 Hz, 1H), 6.98 (s, 1H), 4.76 (d, J=6.3 Hz, 1H), 4.38 (q, J=7.1 Hz, 2H), 3.97 (s, 3H), 2.45 (dddd, J=13.1, 10.7, 8.2, 6.5 Hz, 1H), 2.28 (ddt, J=13.3, 7.0, 2.2 Hz, 1H), 1.88 (ddd, J=12.7, 8.1, 2.6 Hz, 1H), 1.69 (s, 1H), 1.60 (ddd, J=12.7, 10.8, 7.7 Hz, 1H), 1.39 (t, J=7.1 Hz, 3H), 1.35 (s, 3H), 0.68 (s, 3H). MS (m/z) 517.2 [M+H]+.

(R)-11-Methoxy-3,3-dimethyl-12-((1-methyl-1H-imidazol-5-yl)ethynyl)-8-oxo-2,3,8,13b-tetrahydro-1H-pyrido[2,1-a]pyrrolo[1,2-c]phthalazine-7-carboxylic acid Ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (10 mg, 19 μmol) was combined with Copper(I) iodide (0.81 mg, 4 μmol) and Pd(tBu$_2$PPh)$_2$Cl$_2$ (2.06 mg, 3 μmol) in a vial equipped with a magnetic stir bar. 5-ethynyl-1-methyl-1H-imidazole (10 mg, 0.1 mmol) was added along with 1 mL MeCN/Et$_3$N (3:1). The mixture was placed under argon and stirred at 60° C. After 100 minutes, LCMS analysis showed complete conversion, the reaction was cooled to room temperature and quenched with 50 mg thiol-linked silica. The mixture was filtered, rinsing forward with MeCN/EtOH, and concentrated to dryness. The crude mixture was dissolved in ethanol (0.5 mL), aqueous 1M lithium hydroxide (0.1 ml), and the resulting mixture was stirred at 40° C. for 30 minutes after which time LCMS analysis showed complete conversion. The mixture was diluted with TFA and purified by preparative HPLC to provide (R)-11-methoxy-3,3-dimethyl-12-((1-methyl-1H-imidazol-5-yl)ethynyl)-8-oxo-2,3,8,13b-tetrahydro-1H-pyrido[2,1-a]pyrrolo[1,2-c]phthalazine-7-carboxylic acid as a TFA salt. 1H NMR (400 MHz, Acetonitrile-d3) δ 8.49 (s, 1H), 8.32 (s, 1H), 7.61 (d, J=1.0 Hz, 1H), 7.59 (d, J=1.3 Hz, 1H), 7.52 (s, 1H), 7.41 (s, 1H), 4.86 (d, J=5.9 Hz, 1H), 4.04 (s, 3H), 3.88 (s, 3H), 2.54-2.41 (m, 2H), 1.92-1.84 (m, 1H), 1.70-1.58 (m, 1H), 1.38 (s, 3H), 0.67 (s, 3H). 19F NMR (376 MHz, Acetonitrile-d3) δ−76.90. MS (m/z) 445.2 [M+H]+.

Example 43: (R)-11-Methoxy-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid

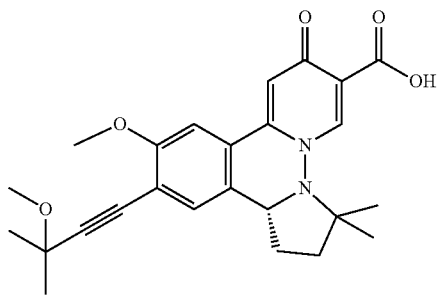

43

(R)-11-Methoxy-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid was prepared analogously to (R)-11-methoxy-3,3-dimethyl-12-((1-methyl-1H-imidazol-5-yl)ethynyl)-8-oxo-2,3,8,13b-tetrahydro-1H-pyrido[2,1-a]pyrrolo[1,2-c]phthalazine-7-carboxylic acid in example 43 using 3-methoxy-3-methylbut-1-yne in place of 5-ethynyl-1-methyl-1H-imidazole. $^1$H NMR (400 MHz, Acetonitrile-d3) δ 8.47 (s, 1H), 7.46 (s, 1H), 7.44 (s, 1H), 7.36 (s, 1H), 4.83 (d, J=6.0 Hz, 1H), 3.98 (s, 3H), 3.41 (s, 3H), 2.54-2.38 (m, 2H), 1.93-1.86 (m, 1H), 1.67-1.57 (m, 1H), 1.53 (s, 6H), 1.36 (s, 3H), 0.66 (s, 3H). 19F NMR (376 MHz, Acetonitrile-d3) δ−76.67. MS (m/z) 437.3 [M+H]+.

Example 44: (R)-12-(1-(Difluoromethyl)-1H-pyrazol-4-yl)-11-methoxy-3,3-dimethyl-8-oxo-2,3,8,13b-tetrahydro-1H-pyrido[2,1-a]pyrrolo[1,2-c]phthalazine-7-carboxylic acid

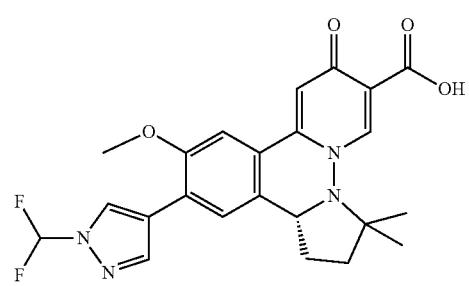

44

1-(difluoromethyl)-4-(4,4,5,5-tetramethyl-1,3,2-dioxaborolan-2-yl)-1H-pyrazole (24 mg, 0.097 mmol) was combined with potassium carbonate (19 mg, 0.14 mmol) in 0.4 mL dioxane and 0.4 mL water. The mixture was stirred under argon at 75° C. for 90 minutes. The reaction was then cooled to room temperature. Ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (10 mg, 19 μmol), Chloro(2-dicyclohexylphosphino-2',6'-di-i-propoxy-1,1'-biphenyl)(2-amino-1,1'-biphenyl-2-yl)palladium(II) (0.3 mg, 0.4 μmol), and Pd(tBu$_2$PPh)$_2$Cl$_2$ (1.4 mg, 0.2 μmol) were added. The mixture was placed under argon and heated at 80° C. for 35 minutes after which time LCMS analysis showed complete conversion. The reaction was cooled to room temperature and 1M aqueous lithium hydroxide (0.06 ml) was added. The reaction was stirred at 40° C. for 50 minutes after which time LCMS analysis showed complete conversion. The reaction was cooled to room temperature, diluted with TFA and purified by preparative HPLC to provide (R)-12-(1-(difluoromethyl)-1H-pyrazol-4-yl)-11-methoxy-3,3-dimethyl-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d3) δ 8.57 (s, 1H), 8.48 (s, 1H), 8.28 (s, 1H), 7.69 (d, J=1.0 Hz, 1H), 7.52 (s, 1H), 7.43 (t, J=59.9 Hz, 1H), 7.39 (s, 1H), 4.89 (d, J=6.3 Hz, 1H), 4.06 (s, 3H), 2.69-2.59 (m, 1H), 2.46 (dddd, J=13.1, 10.8, 8.1, 6.4 Hz, 1H), 1.91 (ddd, J=12.7, 8.2, 2.5 Hz, 1H), 1.64 (ddd, J=12.6, 10.9, 7.8 Hz, 1H), 1.38 (s, 3H), 0.67 (s, 3H). $^{19}$F NMR (376 MHz, Acetonitrile-d3) δ−77.32, −96.11 (d, J=60.0 Hz). MS (m/z) 457.3 [M+H]+.

Example 45: 10-Chloro-11-(3-methoxypropoxy)-2,2-dimethyl-7-oxo-1,2,7,12b-tetrahydroazeto[2,1-a]pyrido[1,2-c]phthalazine-6-carboxylic acid

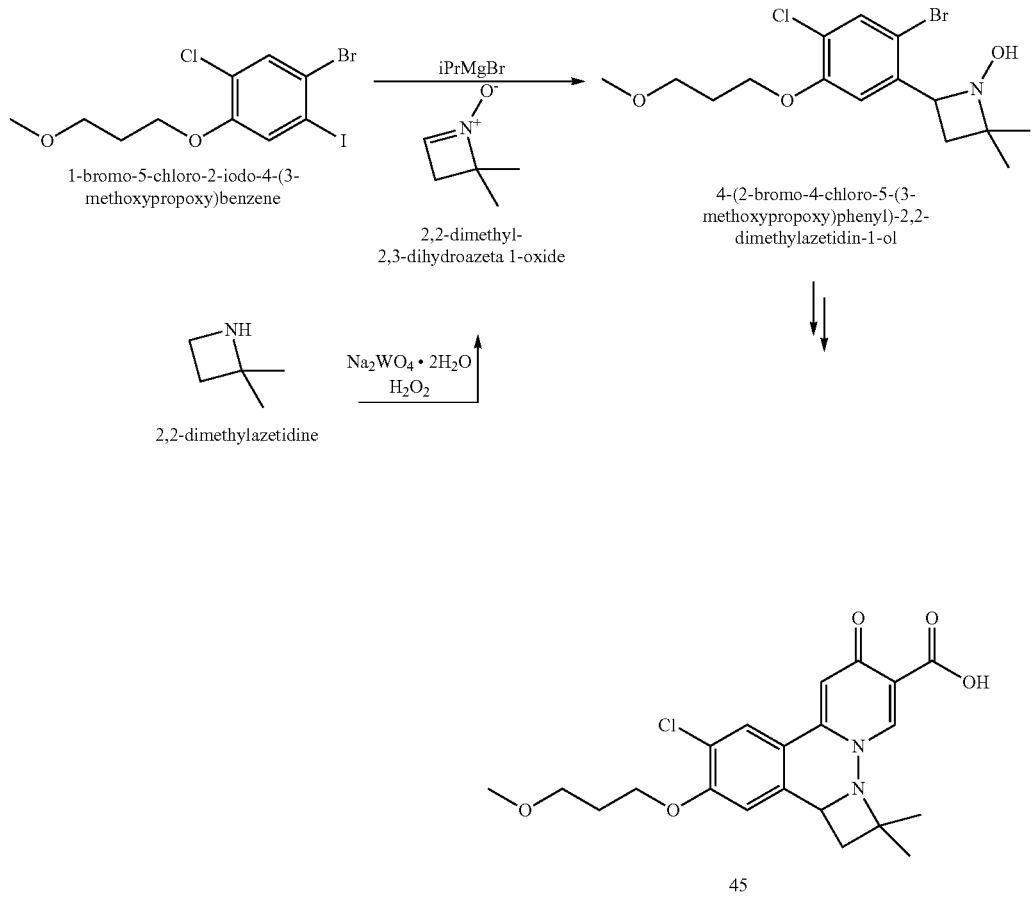

4-(2-bromo-4-chloro-5-(3-methoxypropoxy)phenyl)-2,2-dimethylazetidin-1-ol 2,2-dimethylazetidine (563 mg, 6.61 mmol) was combined with sodium tungstate dihydrate (619 mg, 1.98 mmol) in water (5 mL). The mixture was cooled to 0° C. and hydrogen peroxide (30 wt % in water, 1.5 mL, 15 mmol) was added dropwise over 10 minutes. The mixture was stirred while maintaining the temperature below 5° C. for 3 hours. The mixture was then extracted with $CH_2Cl_2$ (5×5 mL), the combined organic layers were dried over $Na_2SO_4$, filtered and concentrated in vacuo (100 mbar, bath set to 10° C.) to provide 2,2-dimethyl-2,3-dihydroazete 1-oxide: $^1H$ NMR (400 MHz, Chloroform-d) δ 6.61 (t, J=1.2 Hz, 1H), 2.43 (d, J=1.2 Hz, 2H), 1.48 (s, 6H); 13C NMR (101 MHz, Chloroform-d) δ 132.91, 80.37, 35.68, 22.47. Concurrently and in a separate round bottom flask, 1-bromo-5-chloro-2-iodo-4-(3-methoxypropoxy)benzene (3.30 g, 8.13 mmol) was dissolved in MeTHF (20 mL) at 0° C. under argon and a solution of isopropylmagnesium chloride lithium chloride (1.3 M in THF, 6.25 ml, 8.13 mmol) was added dropwise. The solution of Grignard reagent was stirred at 0° C. for 10 minutes, followed by addition of a solution of the 2,2-dimethyl-2,3-dihydroazete 1-oxide prepared above in 2-MeTHF (2 mL). After an additional 10 minutes at 0° C., the reaction was quenched with a mixture of aqueous $NH_4Cl$ and aqueous $NaHCO_3$. The mixture was diluted with EtOAc, the organics were removed, dried over sodium sulfate, filtered, concentrated, and purified by flash column chromatography (15%→35% EtOAc in hexanes) to provide 4-(2-bromo-4-chloro-5-(3-methoxypropoxy)phenyl)-2,2-dimethylazetidin-1-ol. $^1H$ NMR (400 MHz, Chloroform-d) δ 7.46 (s, 1H), 7.38 (s, 1H), 4.62 (t, J=9.1 Hz, 1H), 4.25-4.11 (m, 2H), 3.59 (td, J=6.1, 1.0 Hz, 2H), 3.37 (s, 3H), 2.46-2.33 (m, 1H), 2.08 (p, J=6.1 Hz, 2H), 1.42 (s, 3H), 1.28 (s, 3H). MS (m/z) 378.3 [M+H]+.

10-chloro-1-(3-methoxypropoxy)-2,2-dimethyl-7-oxo-1,2,7,12b-tetrahydroazeto[2,1-a]pyrido[1,2-c]phthalazine-6-carboxylic acid Prepared from 4-(2-bromo-4-chloro-5-(3-methoxypropoxy)phenyl)-2,2-dimethylazetidin-1-ol analogously to the conversion of 5-(2-bromo-4-chloro-5-(3-methoxypropoxy)phenyl)-2,2-dimethylpyrrolidin-1-ol to 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid. $^1H$ NMR (400 MHz, Acetonitrile-d3) δ 8.21 (s, 1H), 8.06 (s, 1H), 7.25 (s, 1H), 6.97 (d, J=1.0 Hz, 1H), 5.30 (dd, J=8.0, 2.9 Hz, 1H), 4.30-4.14 (m, 2H), 3.56 (t, J=6.3 Hz, 2H), 3.32 (s, 3H), 2.85 (dd, J=11.2, 8.0 Hz, 1H), 2.23 (dd, J=11.2, 2.9 Hz, 1H), 2.07 (p, J=6.4 Hz, 2H), 1.48 (s, 3H), 1.04 (s, 3H). 19F NMR (376 MHz, Acetonitrile-d3) δ −77.32. MS (m/z) 419.1 [M+H]+.

Example 46: (R)-10-chloro-11-(3-methoxy-propoxy)-2,2-dimethyl-7-oxo-1,2,7,12b-tetrahydroazeto[2,1-a]pyrido[1,2-c]phthalazine-6-carboxylic acid and (S)-10-chloro-1-(3-methoxypropoxy)-2,2-dimethyl-7-oxo-1,2,7,12b-tetrahydroazeto[2,1-a]pyrido[1,2-c]phthalazine-6-carboxylic acid

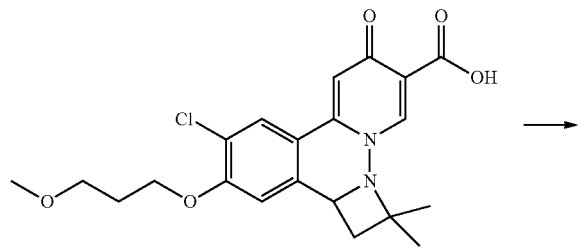

10-chloro-11-(methoxypropoxy)-2,2-dimethyl-7-oxo-1,2,7,12b-tetrahydroazeto[2,1-a]pyrido[1,2-c]phthalazine-6-carboxylic acid

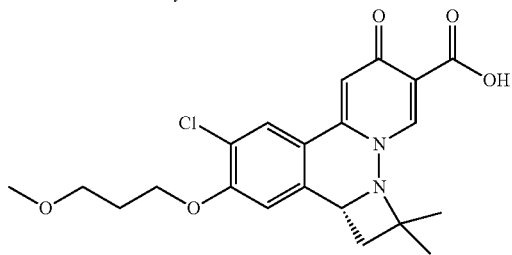

46

Racemic 10-chloro-11-(3-methoxypropoxy)-2,2-dimethyl-7-oxo-1,2,7,12b-tetrahydroazeto[2,1-a]pyrido[1,2-c]phthalazine-6-carboxylic acid was purified by SFC on an OD-H column with isopropanol as the co-solvent.

Example 47: (R)-11-chloro-12-(3-methoxy-propoxy)-1,1-dimethyl-8-oxo-2,3,8,13b-tetrahydro-1H-pyrido[2,1-a]pyrrolo[1,2-c]phthalazine-7-carboxylic acid

47

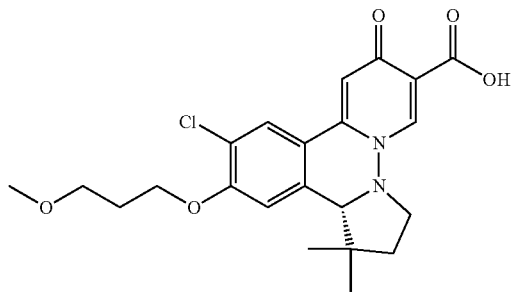

Synthesis of ethyl 11-chloro-12-(3-methoxy-propoxy)-1,1-dimethyl-8-oxo-2,3,8,13b-tetrahydro-1H-pyrido[2,1-a]pyrrolo[1,2-c]phthalazine-7-carboxylate Ethyl 11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylate was prepared similarly to example 1 using tert-butyl 3,3-dimethyl-2-oxopyrrolidine-1-carboxylate in place of 1-(tert-butoxycarbonyl)-2-pyrrolidinone. $^1$H NMR (400 MHz, Chloroform-d) δ 8.34 (s, 1H), 7.79 (s, 1H), 7.03 (d, J=1.0 Hz, 1H), 6.84 (s, 1H), 4.41-4.33 (m, 2H), 4.20 (s, 1H), 4.16 (t, J=6.1 Hz, 2H), 3.59 (td, J=6.1, 2.7 Hz, 2H), 3.47 (d, J=5.4 Hz, 1H), 3.35 (s, 3H), 3.20 (dd, J=5.9, 1.2 Hz, 1H), 2.15-2.08 (m, 2H), 1.86-1.77 (m, 1H), 1.68-1.59 (m, 1H), 1.49 (s, 3H), 1.41-1.33 (m, 6H). MS (m/z) 461.42 [M+H]+.

(R)-1-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylic acid ethyl 11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using IA 5 uM-4.6×150 mm columns with 30% isopropanol as the co-solvent. The slower eluting peak was taken up in in EtOH (1 mL) and 2M LiOH (0.3 ml) then stirred at room temperature until hydrolysis was complete. The mixture was acidified with TFA (0.5 mL) and water (0.5 mL), filtered and purified by HPLC. $^1$H NMR (400 MHz, Chloroform-d) δ 8.64 (s, 1H), 7.83 (s, 1H), 7.07 (s, 1H), 7.03 (s, 1H), 4.24-4.17 (m, 3H), 3.61 (td, J=6.0, 2.0 Hz, 2H), 3.54-3.45 (m, 1H), 3.40 (d, J=5.4 Hz, 1H), 3.36 (s, 3H), 2.18-2.10 (m, 2H), 1.97-1.90 (m, 1H), 1.82-1.77 (m, 1H), 1.52 (s, 3H), 1.31 (s, 3H). MS (m/z) 433.41 [M+H]+.

Example 48: (S)-11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylic acid

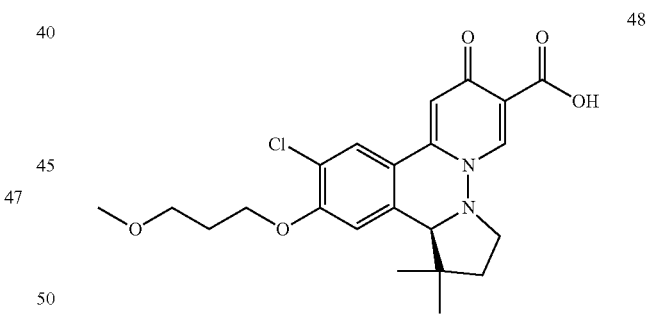

48

Ethyl 11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using IA 5 uM-4.6×150 mm columns with 30% isopropanol as the co-solvent. The faster eluting peak was taken up in in EtOH (1 ml) and 2M LiOH (0.3 ml) then stirred at room temperature until hydrolysis was complete. The mixture was acidified with TFA (0.5 mL) and water (0.5 mL), filtered and purified by HPLC. $^1$H NMR (400 MHz, Chloroform-d) δ8.63 (s, 1H), 7.82 (s, 1H), 7.07 (s, 1H), 7.02 (s, 1H), 4.23-4.17 (m, 3H), 3.61 (td, J=6.0, 2.0 Hz, 2H), 3.49 (d, J=6.2 Hz, 1H), 3.44-3.38 (m, 1H), 3.36 (s, 3H), 2.17-2.11 (m, 2H), 1.93 (d, J=4.8 Hz, 1H), 1.79 (d, J=6.3 Hz, 1H), 1.52 (s, 3H), 1.31 (s, 3H). MS (m/z) 433.314 [M+H]+.

Example 49: (R)-11-chloro-3,3-dimethyl-12-((3-methyloxetan-3-yl)methoxy)-8-oxo-2,3,8,13b-tetrahydro-1H-pyrido[2,1-a]pyrrolo[1,2-c]phthalazine-7-carboxylic acid

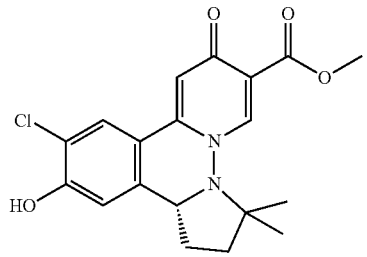

methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate

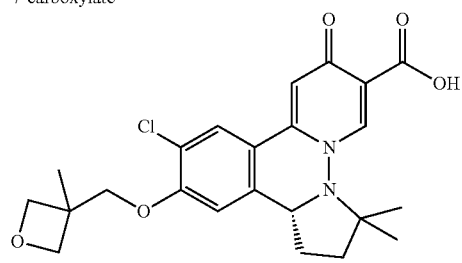

49

Methyl (R)-1-chloro-12-hydroxy-3,3-dimethyl-8-oxo-2,3,8,13b-tetrahydro-1H-pyrido[2,1-a]pyrrolo[1,2-c]phthalazine-7-carboxylate (10 mg, 0.027 mmol) was combined in DMF (0.5 mL) with cesium carbonate (7 mg, 0.05 mmol) and 3-(chloromethyl)-3-methyloxetane (10 mg, 0.08 mmol). The reaction mixture was stirred at 70° C. for 1 hour. The mixture was cooled to room temperature. Aqueous lithium hydroxide (1 M, 0.20 mL, 0.20 mmol) and ethanol (0.5 mL) were added and the mixture was overnight at rt. The mixture was then diluted with trifluoroacetic acid and purified by preparative HPLC to provide (R)-1-chloro-3,3-dimethyl-12-((3-methyloxetan-3-yl)methoxy)-8-oxo-2,3,8,13b-tetrahydro-1H-pyrido[2,1-a]pyrrolo[1,2-c]phthalazine-7-carboxylic acid. MS (m/z) 445.3 [M+H]+.

Example 50: (R)-12-((3,3-difluorocyclobutyl)methoxy)-11-methoxy-3,3-dimethyl-8-oxo-2,3,8,13b-tetrahydro-1H-pyrido[2,1-a]pyrrolo[1,2-c]phthalazine-7-carboxylic acid

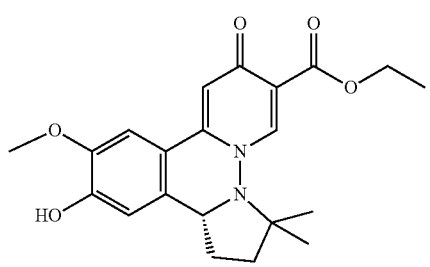

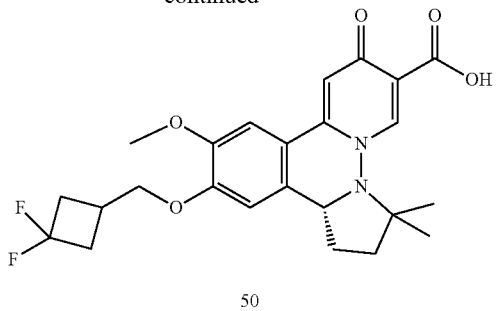

50

Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (59 mg, 150 μmol) was combined with 3-(bromomethyl)-1,1-difluorocyclobutane (85 mg, 460 μmol) and Potassium Carbonate (85 mg, 0.61 mmol) in DMF (0.4 mL). The mixture was stirred at 70° C. for 55 minutes, and then cooled to room temperature. Aqueous 1M lithium hydroxide (334 μL) was added and the mixture was stirred at 35° C. for 30 minutes. The mixture was cooled to room temperature, diluted with TFA, and purified by preparative HPLC to provide (R)-12-((3,3-difluorocyclobutyl)methoxy)-11-methoxy-3,3-dimethyl-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d3) δ 8.45 (s, 1H), 7.39 (s, 1H), 7.26 (s, 1H), 6.95 (d, J=0.9 Hz, 1H), 4.84 (d, J=6.2 Hz, 1H), 4.16 (qt, J=12.8, 6.5 Hz, 2H), 3.92 (s, 3H), 2.85-2.33 (m, 7H), 1.89 (ddd, J=12.6, 7.8, 2.7 Hz, 1H), 1.62 (ddd, J=12.4, 10.8, 7.8 Hz, 1H), 1.36 (s, 3H), 0.66 (s, 3H). 19F NMR (376 MHz, Acetonitrile-d3) δ−77.33, −84.17--85.00 (m), −93.89--94.83 (m). MS (m/z) 461.3 [M+H]+.

Example 51: (S)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid

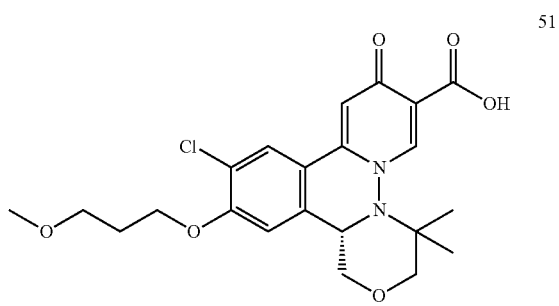 [SMILES: COCCCOc1cc2c(cc1Cl)-c1cc(=O)c(C(=O)O)cn1N1[C@@H]2COCC1(C)C]

51

(S)-12-Chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid was prepared similarly to example 12 using 2,2-dimethyltetrahydro-2H-pyran in place of 2,2-dimethylpiperidine was separated into its enantiomers by chiral SFC chromatography using OD-H 4.6×100 mm column with 30% methanol as the co-solvent. The slower eluting peak with a retention time of 5.3 min was taken up in in EtOH (1 ml) and 2M LiOH (0.3 ml) then stirred at room temperature until hydrolysis was complete. The mixture was acidified with TFA (0.5 mL) and water (0.5 mL), filtered and purified by HPLC. ¹H NMR (400 MHz, Chloroform-d) δ 8.63 (s, 1H), 7.79 (s, 1H), 7.14 (s, 1H), 7.03 (s, 1H), 4.75 (d, 1H), 4.39 (s, 1H), 4.32-4.18 (m, 2H), 4.10 (dd, 1H), 3.65-3.57 (m, 3H), 3.57-3.46 (m, 1H), 3.38 (s, 3H), 2.16 (p, 2H), 1.11 (s, 3H), 0.54 (s, 3H). MS (m/z) 449.2 [M+H]+.

Example 52: (R)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid and Example 53: (S)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid

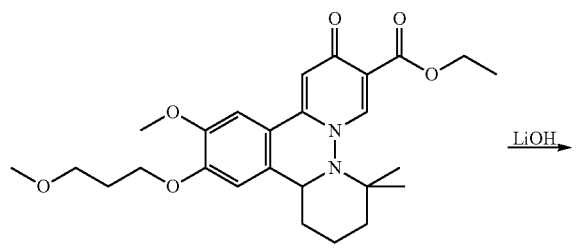

ethyl 13-methoxy-12-(3-methoxypropoxy)-7-7-dimethyl-2-oxo-2,7,8,9,10,10a-hexahydrodipyrido[2,1-a:1',2'-c]phthalazine-3-carboxylate LiOH

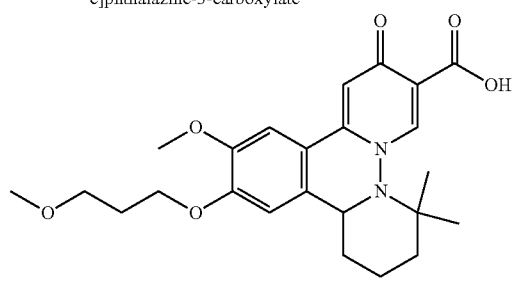

13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid Synthesis of 13-chloro-12-(3-methoxypropoxy)-7,7-dimethyl-2-oxo-2,7,8,9,10,10a-hexahydrodipyrido[2,1-a:1',2'-c]phthalazine-3-carboxylic acid Ethyl 13-methoxy-12-(3-methoxypropoxy)-7,7-dimethyl-2-oxo-2,7,8,9,10,10a-hexahydrodipyrido[2,1-a: 1',2'-c]phthalazine-3-carboxylate was prepared similarly to ethyl 13-chloro-12-(3-methoxypropoxy)-7,7-dimethyl-2-oxo-2,7,8,9,10,10a-hexahydrodipyrido[2,1-a: 1',2'-c]phthalazine-3-carboxylate in example 11 using 1-bromo-2-iodo-5-methoxy-4-(3-methoxypropoxy)benzene in place of 1-bromo-5-chloro-2-iodo-4-(3-methoxypropoxy)benzene. Instead of purifying the ester, it was hydrolyzed by adding 0.2 mL 2 M LiOH into the unworked up mixture, which was then filtered over celite, rinsing with DCM, concentrated, diluted with DMF and purified by HPLC. MS (m/z) 443.2 [M+H]+.

(R)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid

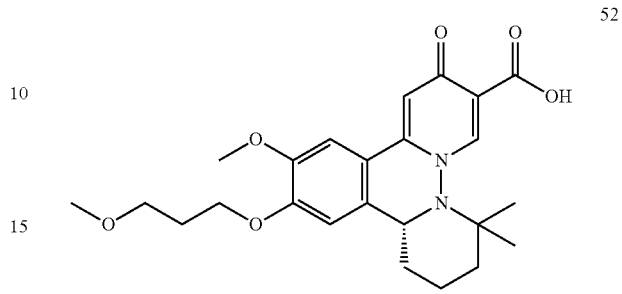

13-Methoxy-12-(3-methoxypropoxy)-7,7-dimethyl-2-oxo-2,7,8,9,10,10a-hexahydrodipyrido[2,1-a:1',2'-c]phthalazine-3-carboxylic acid was separated into its enantiomers by chiral SFC chromatography using OD-H 4.6×100 mm columns with 30% methanol as the co-solvent. (R)-13-methoxy-12-(3-methoxypropoxy)-7,7-dimethyl-2-oxo-2,7,8,9,10,10a-hexahydrodipyrido[2,1-a: 1',2'-c]phthalazine-3-carboxylic acid is the faster eluting peak with a retention time of 0.9 min. 1H NMR (400 MHz, Chloroform-d) δ 8.62 (s, 1H), 7.02 (s, 1H), 6.86 (s, 1H), 4.62-4.52 (m, 1H), 4.21 (t, 2H), 3.94 (s, 3H), 3.66-3.51 (m, 2H), 3.37 (s, 3H), 2.60-2.48 (m, 1H), 2.22-2.08 (m, 2H), 1.86-1.74 (m, 2H), 1.72-1.44 (m, 4H), 1.16 (s, 3H), 0.41 (s, 3H). MS (m/z) 443.2 [M+H]+.

Example 53: (S)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid

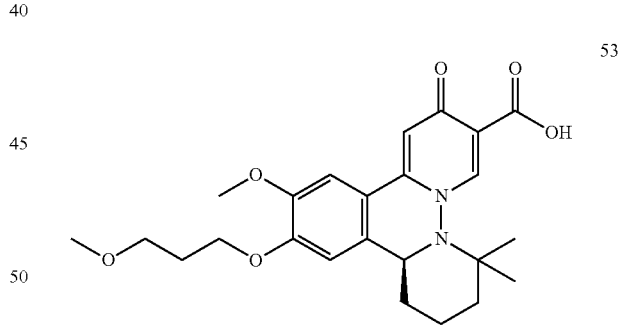

13-Methoxy-12-(3-methoxypropoxy)-7,7-dimethyl-2-oxo-2,7,8,9,10,10a-hexahydrodipyrido[2,1-a:1',2'-c]phthalazine-3-carboxylic acid was separated into its enantiomers by chiral SFC chromatography using OD-H 4.6×100 mm columns with 30% methanol as the co-solvent. (S)-13-methoxy-12-(3-methoxypropoxy)-7,7-dimethyl-2-oxo-2,7,8,9,10,10a-hexahydrodipyrido[2,1-a: 1',2'-c]phthalazine-3-carboxylic acid is the slower eluting peak with a retention time of 1.32 min. ¹H NMR (400 MHz, Chloroform-d) δ 8.62 (s, 1H), 7.02 (s, 1H), 6.86 (s, 1H), 4.62-4.52 (m, 1H), 4.21 (t, 2H), 3.94 (s, 3H), 3.66-3.51 (m, 2H), 3.37 (s, 3H), 2.60-2.48 (m, 1H), 2.22-2.08 (m, 2H), 1.86-1.74 (m, 2H), 1.72-1.44 (m, 4H), 1.16 (s, 3H), 0.41 (s, 3H). MS (m/z) 443.2 [M+H]+.

Example 54: (R)-11-chloro-12-((3,3-difluorocyclobutyl)methoxy)-3,3-dimethyl-8-oxo-2,3,8,13b-tetrahydro-1H-pyrido[2,1-a]pyrrolo[1,2-c]phthalazine-7-carboxylic acid

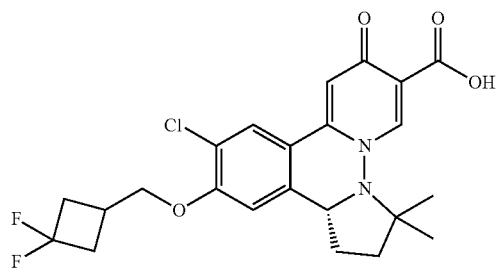

54

(R)-11-Chloro-12-((3,3-difluorocyclobutyl)methoxy)-3,3-dimethyl-8-oxo-2,3,8,13b-tetrahydro-1H-pyrido[2,1-a]pyrrolo[1,2-c]phthalazine-7-carboxylic acid was prepared similarly to example 55 using (3,3-difluorocyclobutyl)methanol in place of 3-(trifluoromethoxy)propan-1-ol. $^1$H NMR (400 MHz, Chloroform-d) δ 8.59 (s, 1H), 7.82 (s, 1H), 7.18 (s, 1H), 6.82 (s, 1H), 4.81 (d, 1H), 4.18-4.08 (m, 2H), 2.89-2.69 (m, 2H), 2.68-2.47 (m, 2H), 2.42-2.34 (m, 4H), 1.99-1.87 (m, 1H), 1.71-1.58 (m, 1H), 1.39 (s, 3H), 0.69 (s, 3H). MS (m/z) 465.2 [M+H]+.

Example 55: (R)-11-chloro-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid

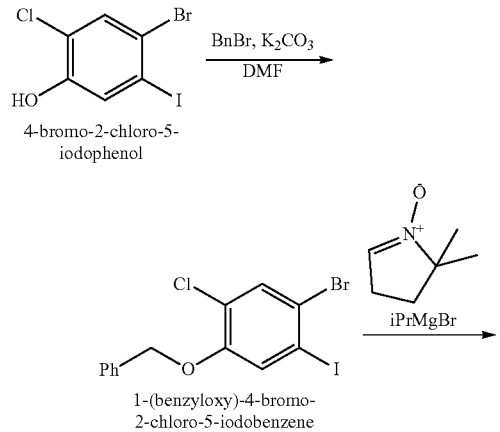

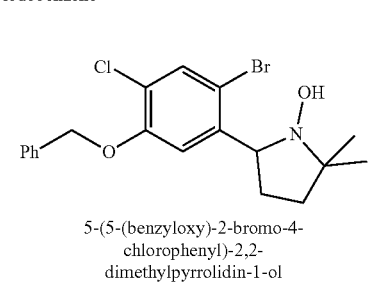

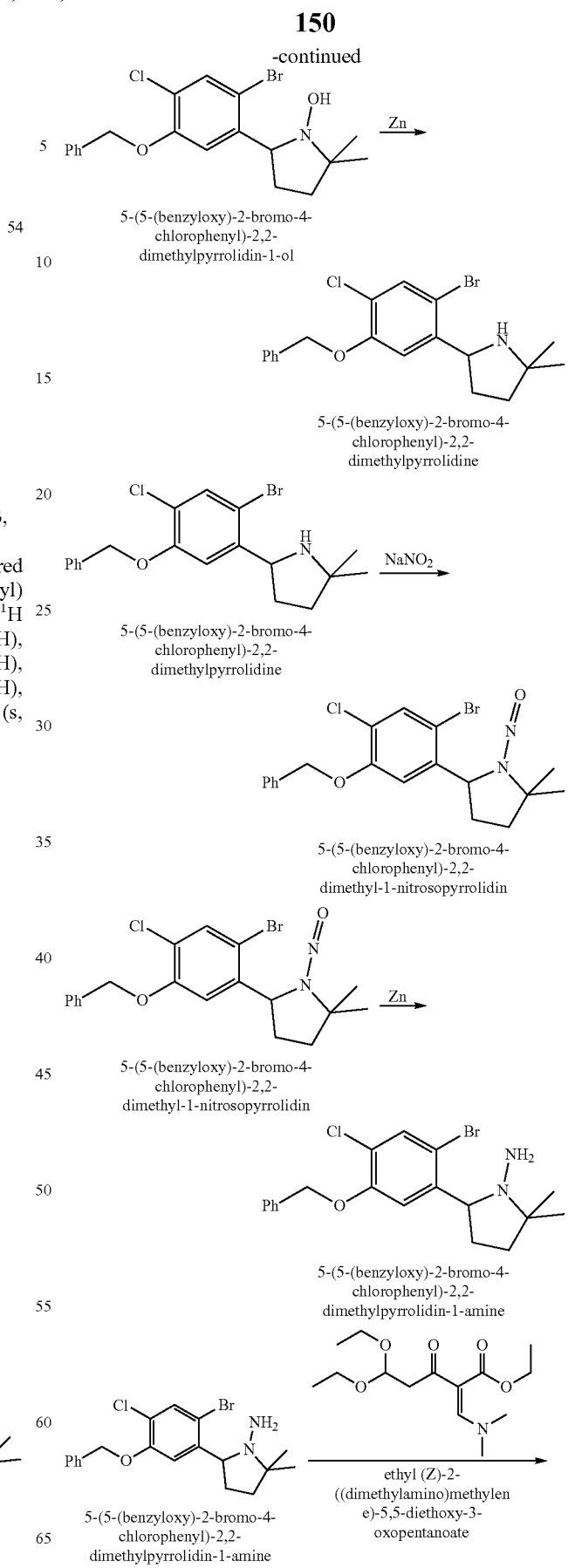

151

-continued

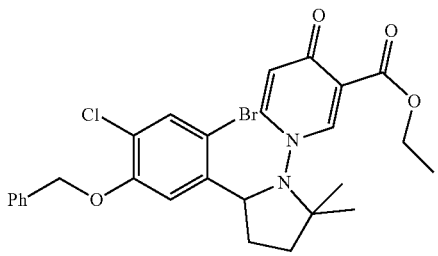

ethyl 1-(5-(5-(benzyloxy)-2-
bromo-4-chlorophenyl)-2,2-
dimethylpyrrolidin-1-yl)-4-oxo-1,4-
dihydropyridine-3-carboxylate

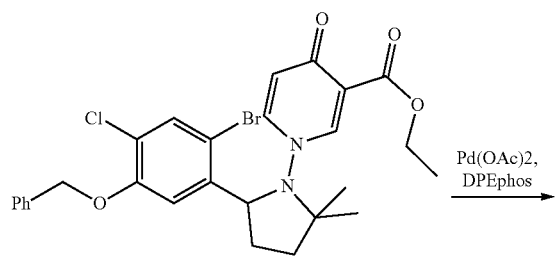

ethyl 1-(5-(5-(benzyloxy)-2-
bromo-4-chlorophenyl)-2,2-
dimethylpyrrolidin-1-yl)-4-oxo-1,4-
dihydropyridine-3-carboxylate Pd(OAc)2,
DPEphos

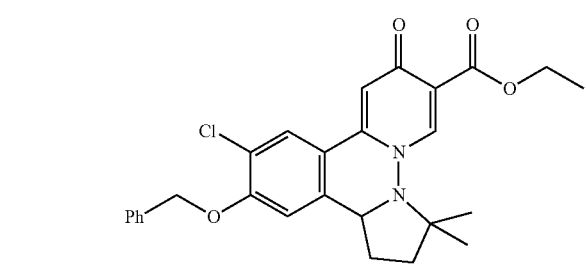

ethyl 12-(benzyloxy)-11-chloro-
3,3-dimethyl-8-oxo-2,3,8,13b-tetrahydro-
1H-pyrido[2,1-a]pyrrolo
[1,2-c]phthalazine-7-carboxylate

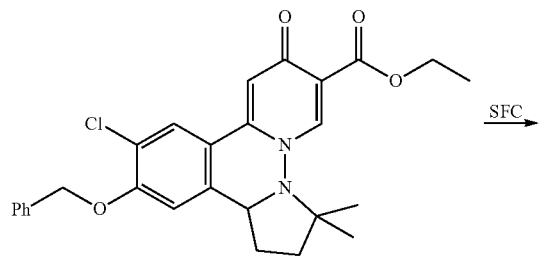

ethyl 12-(benzyloxy)-11-chloro-
3,3-dimethyl-8-oxo-2,3,8,13b-tetrahydro-
1H-pyrido[2,1-a]pyrrolo
[1,2-c]phthalazine-7-carboxylate

SFC

152

-continued

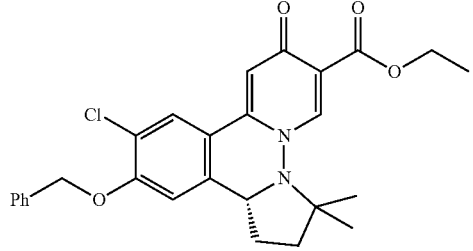

methyl (R)-12-(benzyloxy)-
11-chloro-3,3-dimethyl-8-oxo-2,3,8,13b-tetrahydro-
1H-pyrido[2,1-a]pyrrolo
[1,2-c]phthalazine-7-carboxylate Synthesis of
1-(benzyloxy)-4-bromo-2-chloro-5-iodobenzene To an RB add 4-bromo-2-chloro-5-iodophenol (10 g, 30 mmol), potassium carbonate (20.7 g, 150 mmol), and DMF (124 ml). Allow the mixture to stir for 10 minutes, then add benzyl bromide (4.2 ml, 36 mmol) and continue stirring overnight. Dilute the mixture with EtOAc, 5% LiCl solution, and brine. Wash the organic layer with 5% LiCl 2 times, dry organic layer over sodium sulfate, filter, and concentrate. The product was used crude in the next reaction. MS (m/z) 338.3 [M+H]+.

Synthesis of 5-(5-(benzyloxy)-2-bromo-4-chloro-
phenyl)-2,2-dimethylpyrrolidin-1-ol To a RB add 1-(benzyloxy)-4-bromo-2-chloro-5-iodobenzene (12.7 g, 30 mmol) and MeTHF (100 ml), cool the reaction to 0 C, then slowly add 1.3 M Isopropylmagnesium chloride lithium chloride complex solution (25.4 ml, 33 mmol) and stir for 10 minutes, then add 2,2-dimethyl-3,4-dihydro-2H-pyrrole 1-oxide (4.9 g, 44 mmol) and stir for 10 minutes. Reaction was checked by LC/MS and was done. Quench reaction with saturated NH4Cl and extract 2× with EtOAc, dry the organics over sodium sulfate, concentrate and purify by flash column chromatography. MS (m/z) 410.9 [M+H]+.

Synthesis of 5-(5-(benzyloxy)-2-bromo-4-chloro-
phenyl)-2,2-dimethylpyrrolidine

To a solution 5-(5-(benzyloxy)-2-bromo-4-chlorophenyl)-2,2-dimethylpyrrolidin-1-ol (7 g, 17 mmol) in TFA (102 ml) and water (41 ml) was added zinc powder (2.3 g, 35 mmol). The mixture was heated to 50 C until done about 30 minutes. The solution was concentrated under vacuum. The crude mixture was quenched with saturated sodium bicarbonate until fizzing stops. The product was extracted with DCM. The organic layer was washed with water, dried under Na2SO4, filtered, and concentrated. The product was used crude in the next reaction. MS (m/z) 394.8 [M+H]+.

Synthesis of 5-(5-(benzyloxy)-2-bromo-4-chloro-
phenyl)-2,2-dimethyl-1-nitrosopyrrolidine To a solution of 5-(5-(benzyloxy)-2-bromo-4-chlorophenyl)-2,2-dimethylpyrrolidine (6.7 g, 17 mmol) in THF (45 mL) was added an aqueous solution of NaNO2 (2.8 g, 41 mmol in 22.6 mL of water) followed by acetic acid (2.4 mL, 43 mmol). The mixture was stirred at 50 C until done (about 1 hour). The reaction mixture was then diluted with EtOAc, washed with brine, dried with Na₂SO₄, filtered, and concentrated. MS (m/z) 424.1 [M+H]+.

Synthesis of 5-(5-(benzyloxy)-2-bromo-4-chlorophenyl)-2,2-dimethylpyrrolidin-1-amine To a solution of 5-(5-(benzyloxy)-2-bromo-4-chlorophenyl)-2,2-dimethyl-1-nitrosopyrrolidine (6.8 g, 16 mmol) in TFA (97 ml) and water (39 ml) was added zinc powder (2.6 g, 40 mmol). The mixture was heated to 50 C until done about 30 minutes. The solution was concentrated under vacuum. The crude mixture was quenched with saturated sodium bicarbonate until fizzing stops. The product was extracted with DCM. The organic layer was washed with water, dried under Na₂SO₄, filtered, and concentrated. The product was used crude in the next reaction. MS (m/z) 410.0 [M+H]+.

Synthesis of ethyl 1-(5-(5-(benzyloxy)-2-bromo-4-chlorophenyl)-2,2-dimethylpyrrolidin-1-yl)-4-oxo-1,4-dihydropyridine-3-carboxylate To a solution of 5-(5-(benzyloxy)-2-bromo-4-chlorophenyl)-2,2-dimethylpyrrolidin-1-amine (6.6 g, 16 mmol) in EtOH (40 ml) was added ethyl (Z)-2-((dimethylamino)methylene)-5,5-diethoxy-3-oxopentanoate (6.9 g, 24 mmol). The mixture was heated to 60 C for 90 minutes after which water (2.5 ml) was added. The reaction was stirred overnight and checked for completion. The reaction was not complete so added TFA (0.3 ml). The crude mixture was diluted with brine and EtOAc, the aqueous layer was extracted 2× EtOAc. The organic layer was dried over Na₂SO₄, filtered, and concentrated. The product was purified by flash column chromatography. MS (m/z) 559.8 [M+H]+.

Synthesis of ethyl 12-(benzyloxy)-11-chloro-3,3-dimethyl-8-oxo-2,3,8,13b-tetrahydro-1H-pyrido[2,1-a]pyrrolo[1,2-c]phthalazine-7-carboxylate Ethyl 1-(5-(5-(benzyloxy)-2-bromo-4-chlorophenyl)-2,2-dimethylpyrrolidin-1-yl)-4-oxo-1,4-dihydropyridine-3-carboxylate (5.4 g, 10 mmol) was dissolved in DMA (80 mL) with potassium carbonate (3.3 g, 23 mmol) under argon. Pd(OAc)₂ (215 mg, 1 mmol), and (Oxydi-2,1-phenylene)bis(diphenylphosphine) (516 mg, 1 mmol) were added and the mixture was flushed with argon. The reaction was heated to 100° C. for 4 hours. Once cool dilute with EtOAc and brine, extract with EtOAc 2×, dry the organics over sodium sulfate, concentrate, and purify by flash column chromatography. MS (m/z) 479.8 [M+H]+.

Methyl (R)-12-(benzyloxy)-1-chloro-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-11-chloro-3,3-dimethyl-8-oxo-2,3,8,13b-tetrahydro-1H-pyrido[2,1-a]pyrrolo[1,2-c]phthalazine-7-carboxylate was separated into its enantiomers by chiral SFC using an IA column with 30% methanol as the co-solvent. The R isomer has a Retention time of 3.81 min. Under the chiral separation conditions and concentration most of the ethyl ester was exchanged to the methyl ester. ¹H NMR (400 MHz, Chloroform-d) δ 8.30 (s, 1H), 7.76 (s, 1H), 7.47-7.37 (m, 4H), 7.37-7.30 (m, 1H), 6.90 (s, 1H), 6.81 (s, 1H), 5.23 (s, 2H), 4.70 (d, 1H), 3.91 (s, 3H), 2.46-2.30 (m, 1H), 2.24-2.12 (m, 1H), 1.85-1.76 (m, 1H), 1.52-1.41 (m, 1H), 1.32 (s, 3H), 0.66 (s, 3H). MS (m/z) 465.4 [M+H]+.

Synthesis of methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate

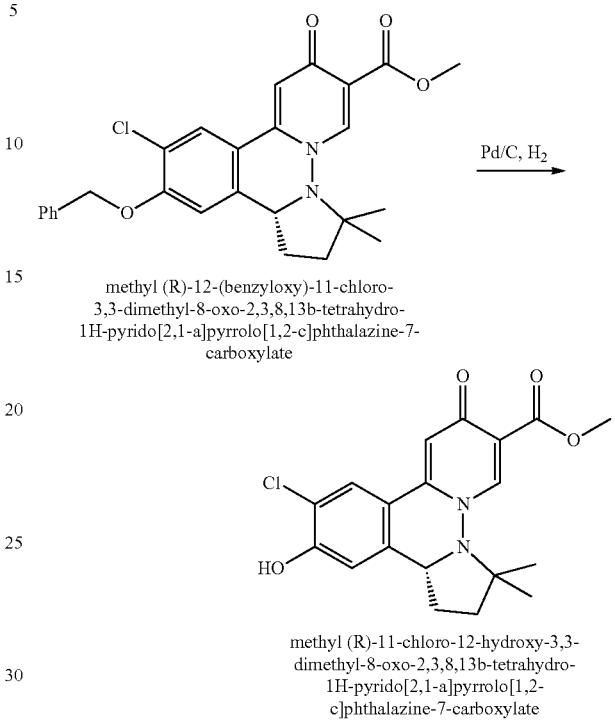

methyl (R)-12-(benzyloxy)-11-chloro-3,3-dimethyl-8-oxo-2,3,8,13b-tetrahydro-1H-pyrido[2,1-a]pyrrolo[1,2-c]phthalazine-7-carboxylate methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate Methyl (R)-12-(benzyloxy)-1-chloro-3,3-dimethyl-8-oxo-2,3,8,13b-tetrahydro-1H-pyrido[2,1-a]pyrrolo[1,2-c]phthalazine-7-carboxylate (795 mg, 1.7 mmol) was dissolved in ethanol (500 mL) and the solution was purged with argon. Palladium on carbon (10 wt %, wet, E101 NE/W, 109 mg) was added. The reaction was purged with argon, evacuated and refilled with hydrogen gas. The mixture was stirred vigorously under an atmosphere of hydrogen for 2 hours after which time LCMS analysis showed complete consumption of starting material. The reaction was purged with argon, diluted with ethyl acetate and filtered through celite. The solution was concentrated to methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate. MS (m/z) 375.2 [M+H]+.

Synthesis of (R)-11-chloro-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid

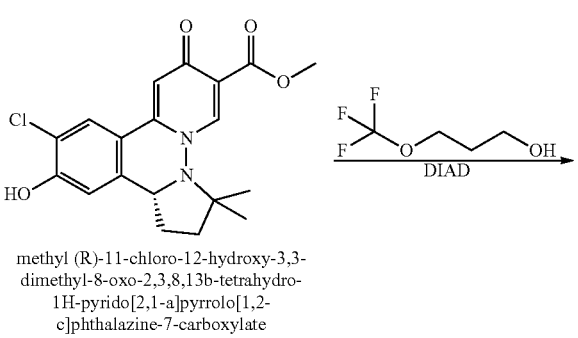

methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate -continued

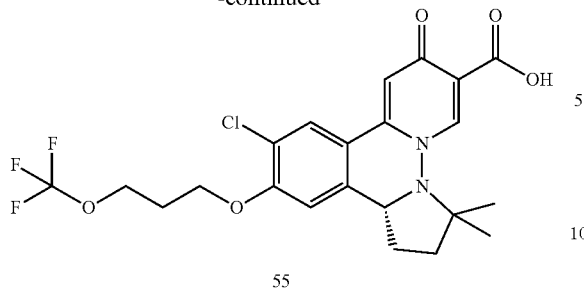

55

To a vial add to methyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate (10 mg, 0.03 mmol), 3-(trifluoromethoxy)propan-1-ol (7.7 mg, 0.05 mmol), THF (1 ml), Diisopropyl Azodicarboxylate (11 µl, 0.06 mmol), and Triphenylphosphine, polymer-supported (79%, 18 mg, 0.05 mmol), stir overnight, then add 0.2 ml 2 M LiOH to hydrolyze ester, dilute with 1 ml DMF, filter off solids and purify by HPLC. $^1$H NMR (400 MHz, Chloroform-d) δ 8.56 (s, 1H), 7.80 (s, 1H), 7.10 (s, 1H), 6.85 (s, 1H), 4.80 (d, 1H), 4.32-4.16 (m, 4H), 2.58-2.45 (m, 1H), 2.45-2.33 (m, 1H), 2.33-2.22 (m, 2H), 1.98-1.87 (m, 1H), 1.69-1.56 (m, 1H), 1.39 (s, 3H), 0.69 (s, 3H). MS (m/z) 487.2 [M+H]+.

Example 56: (R)-11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid

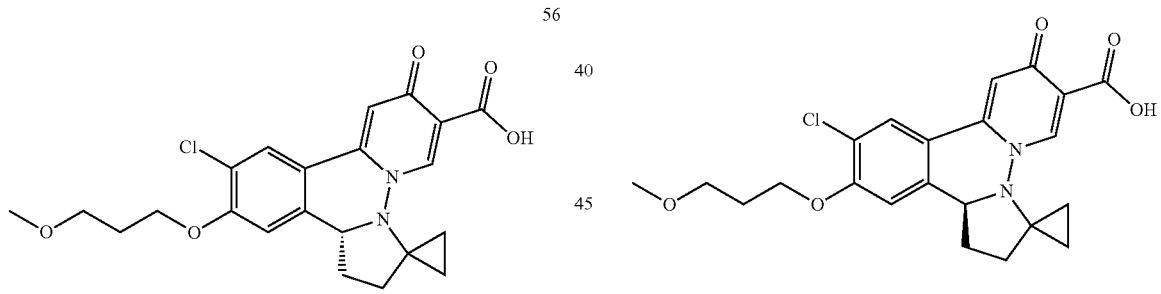

Synthesis of ethyl 11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylate ethyl 11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylate was prepared similarly to example 1 using tert-butyl 4-oxo-5-azaspiro[2.4]heptane-5-carboxylate in place of 1-(tert-butoxycarbonyl)-2-pyrrolidinone. $^1$H NMR (400 MHz, Chloroform-d) δ 8.10 (s, 1H), 7.73 (s, 1H), 6.88 (s, 1H), 6.80 (s, 1H), 4.75 (d, J=5.7 Hz, 1H), 4.33 (dd, J=7.1, 2.4 Hz, 2H), 4.25-4.13 (m, 2H), 3.60 (q, J=6.1 Hz, 2H), 3.35 (s, 3H), 2.56-2.41 (m, 2H), 2.12 (t, J=6.1 Hz, 3H), 1.73 (d, J=12.7 Hz, 1H), 1.35 (t, J=7.1 Hz, 3H), 0.59 (dt, J=10.7, 6.9 Hz, 2H), 0.23 (d, J=10.9 Hz, 1H), 0.10 (d, J=10.3 Hz, 1H). MS (m/z) 459.323 [M+H]+.

(R)-1-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylic acid ethyl 11-chloro-12-(3-methoxypropoxy)-1,1-dimethyl-8-oxo-2,3,8,13b-tetrahydro-1H-pyrido[2,1-a]pyrrolo[2-c]phthalazine-7-carboxylate was separated into its enantiomers by chiral SFC chromatography using IA 5 uM-4.6×150 mm columns with 30% isopropanol as the co-solvent. The slower eluting peak was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. 1H NMR (400 MHz, Chloroform-d) δ 8.39 (s, 1H), 7.79 (s, 1H), 7.01 (s, 1H), 6.92 (s, 1H), 4.81 (d, J=5.9 Hz, 1H), 4.27-4.19 (m, 2H), 3.62 (d, J=6.6 Hz, 2H), 3.37 (s, 3H), 2.64-2.49 (m, 2H), 2.15 (t, J=6.0 Hz, 3H), 1.76 (d, J=11.2 Hz, 1H), 0.65 (dd, J=17.2, 9.4 Hz, 2H), 0.13 (td, J=11.4, 11.0, 6.8 Hz, 2H). MS (m/z) 431.226 [M+H]+.

Example 57: (S)-11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid Ethyl 11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using IA 5 uM-4.6×150 mm columns with 30% isopropanol as the co-solvent. The faster eluting peak was taken up in in EtOH (1 ml) and 2M LiOH (0.3 ml) then stirred at room temperature until hydrolysis was complete. The mixture was acidified with TFA (0.5 ml) and water (0.5 ml), filtered and purified by HPLC. 1H NMR (400 MHz, Chloroform-d) δ 8.39 (s, 1H), 7.79 (s, 1H), 7.01 (s, 1H), 6.92 (s, 1H), 4.81 (d, J=5.9 Hz, 1H), 4.28-4.18 (m, 2H), 3.62 (d, J=6.5 Hz, 2H), 3.37 (s, 3H), 2.54 (dd, J=20.8, 7.9 Hz, 2H), 2.15 (t, J=6.1 Hz, 3H), 1.83-1.73 (m, 1H), 0.65 (dd, J=17.2, 9.4 Hz, 2H), 0.13 (td, J=11.1, 7.0 Hz, 2H). MS (m/z) 431.204 [M+H]+.

Example 58: (R)-11-methoxy-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid

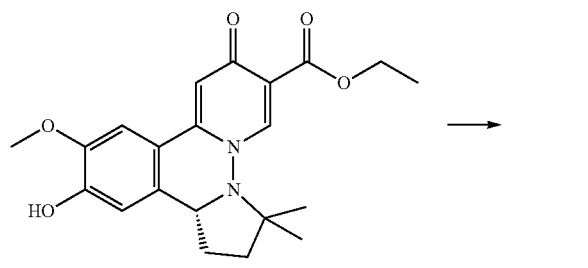

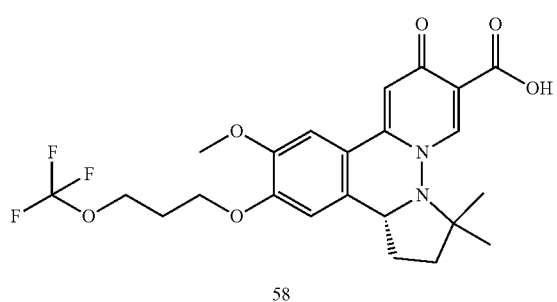

58

Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (26 mg, 68 µmol) was combined with 3-(trifluoromethoxy)propan-1-ol (18 mg, 130 µmol) and polymer-bound triphenylphosphine (100-200 mesh, 3 mmol/g 45 mg) in tetrahydrofuran (0.8 mL). Diisopropyl azodicarboxylate (28 µl, 0.14 mmol) was added and the mixture was stirred at room temperature for 4 hours. After this time additional reagents were added: 3-(trifluoromethoxy)propan-1-ol (10 mg, 72 µmol), polymer-bound triphenylphosphine (100-200 mesh, 3 mmol/g 10 mg), and diisopropyl azodicarboxylate (10 µl, 51 µmol). The mixture was stirred at room temperature for 1 hour. 1M LiOH (200 µl) was added and the mixture was stirred at 45° C. for 10 minutes. The mixture was cooled to room temperature, diluted with TFA, and purified by preparative HPLC to provide (R)-11-methoxy-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid as a TFA salt. 1H NMR (400 MHz, Acetonitrile-d3) δ 8.43 (s, 1H), 7.39 (s, 1H), 7.24 (s, 1H), 6.96 (s, 1H), 4.84 (d, J=6.2 Hz, 1H), 4.29-4.14 (m, 4H), 3.92 (s, 3H), 2.56-2.39 (m, 2H), 2.24-2.17 (m, 2H), 1.88 (ddd, J=12.5, 7.9, 2.7 Hz, 1H), 1.61 (td, J=12.2, 11.7, 7.8 Hz, 1H), 1.36 (s, 3H), 0.67 (s, 3H). 19F NMR (376 MHz, Acetonitrile-d3) δ −61.66, −77.20. MS (m/z) 483.2 [M+H]+.

Example 59: 11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid

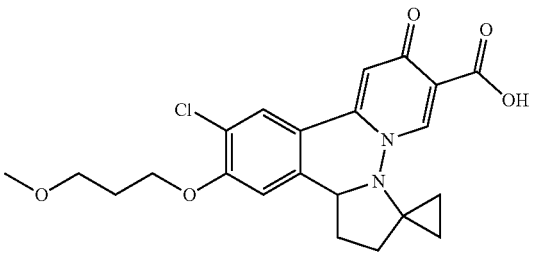

59

11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid Ethyl 11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylate (2.8 mg) was taken up in EtOH (1 ml), and 2M LiOH (0.3 ml) was added then stirred at room temperature until hydrolysis was complete. The mixture was acidified with 1N HCl to pH=2 and water (5 ml) was added, filtered to collect product. After washed with water and dried to provide 2.5 mg product. 1H NMR (400 MHz, Chloroform-d) δ 8.38 (s, 1H), 7.79 (s, 1H), 7.01 (s, 1H), 6.92 (s, 1H), 4.81 (d, J=5.9 Hz, 1H), 4.27-4.20 (m, 2H), 3.61 (dt, J=6.8, 5.7 Hz, 2H), 3.37 (s, 3H), 2.54 (dd, J=20.5, 7.8 Hz, 2H), 2.15 (t, J=6.0 Hz, 2H), 1.80-1.71 (m, 2H), 0.65 (ddd, J=11.0, 8.7, 7.1 Hz, 2H), 0.13 (dd, J=18.4, 11.0 Hz, 2H). MS (m/z) 431.2 [M+H]+.

Example 60: (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid

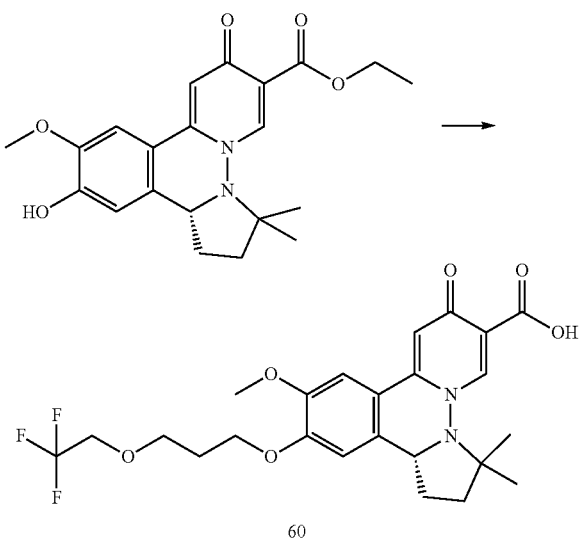 [SMILES: CCOC(=O)c1cn2c(cc1=O)-c1cc(OC)c(O)cc1[C@H]1CCC(C)(C)N12 ; COc1cc2c(cc1OCCCOCC(F)(F)F)[C@H]1CCC(C)(C)N1n1cc(C(=O)O)c(=O)cc1-2]

60

Ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (34 mg, 88 µmol) was combined with 1-bromo-3-(2,2,2-trifluoroethoxy)propane (49 mg, 221 µmol) and Potassium Carbonate (25 mg, 0.18 mmol) in DMF (0.4 mL). The mixture was stirred at 70° C. for 2.5 hours, and then cooled to room temperature. Aqueous 1M Lithium Hydroxide (334 µl) was added and the mixture was stirred at 30° C. for 30 minutes followed by stirring at 40° C. for 15 minutes. The mixture was cooled to room temperature, diluted with TFA, and purified by preparative HPLC to provide (R)-11-methoxy-3,3-dimethyl-8-oxo-12-(3-(2,2,2-trifluoroethoxy)propoxy)-2,3,8,13b-tetrahydro-1-H-pyrido[2,1-a]pyrrolo[1,2-c]phthalazine-7-carboxylic acid as a TFA salt. 1H NMR (400 MHz, Acetonitrile-d3) δ 8.43 (s, 1H), 7.39 (s, 1H), 7.23 (s, 1H), 6.95 (s, 1H), 4.84 (d, J=6.1 Hz, 1H), 4.29-4.10 (m, 2H), 3.96 (q, J=9.2 Hz, 2H), 3.92 (s, 3H), 3.81 (t, J=6.2 Hz, 2H), 2.55-2.37 (m, 2H), 2.10 (p, J=6.2 Hz, 2H), 1.88 (ddd, J=12.6, 7.8, 2.8 Hz, 1H), 1.61 (td, J=11.9, 11.5, 7.8 Hz, 1H), 1.36 (s, 3H), 0.67 (s, 3H). 19F NMR (376 MHz, Acetonitrile-d3) δ−75.58 (t, J=9.1 Hz), −77.29. MS (m/z) 497.2 [M+H]$^+$.

Example 61: (R)-1-methoxy-3,3-dimethyl-8-oxo-12-(3-phenoxypropoxy)-2,3,8,13b-tetrahydro-1H-pyrido[2,1-a]pyrrolo[1,2-c]phthalazine-7-carboxylic acid

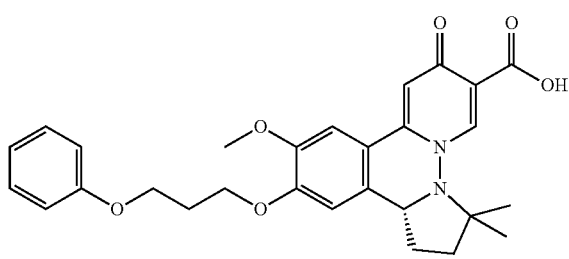

61

Prepared analogously to (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid in Example 60 using (3-bromopropoxy)benzene in place of 1-bromo-3-(2,2,2-trifluoroethoxy)propane. $^1$H NMR (400 MHz, Acetonitrile-d3) δ 8.44 (s, 1H), 7.38 (s, 1H), 7.35-7.27 (m, 2H), 7.25 (s, 1H), 6.99-6.88 (m, 4H), 4.81 (d, J=6.2 Hz, 1H), 4.41-4.24 (m, 2H), 4.18 (t, J=6.1 Hz, 2H), 3.91 (s, 3H), 2.57-2.32 (m, 2H), 2.27 (p, J=6.2 Hz, 2H), 1.87 (ddd, J=12.6, 7.9, 2.7 Hz, 1H), 1.60 (td, J=12.1, 11.6, 7.8 Hz, 1H), 1.35 (s, 3H), 0.66 (s, 3H). $^{19}$F NMR (376 MHz, Acetonitrile-d3) δ−77.33. MS (m/z) 491.2 [M+H]$^+$.

Example 62: (R)-12-(3-ethoxypropoxy)-11-methoxy-3,3-dimethyl-8-oxo-2,3,8,13b-tetrahydro-1H-pyrido[2,1-a]pyrrolo[1,2-c]phthalazine-7-carboxylic acid

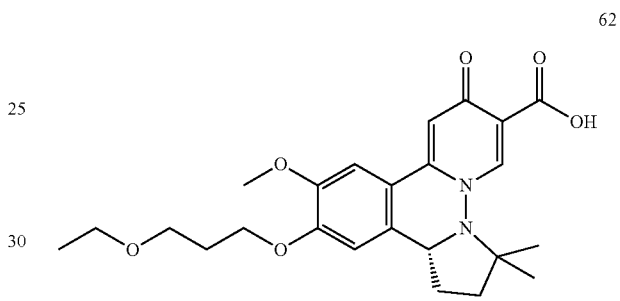

62

Prepared analogously to (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid in Example 60 using 1-bromo-3-ethoxypropane in place of 1-bromo-3-(2,2,2-trifluoroethoxy)propane. $^1$H NMR (400 MHz, Acetonitrile-d3) δ 8.43 (s, 1H), 7.38 (s, 1H), 7.23 (s, 1H), 6.95 (s, 1H), 4.84 (d, J=6.2 Hz, 1H), 4.26-4.10 (m, 2H), 3.92 (s, 3H), 3.58 (t, J=6.2 Hz, 2H), 3.49 (q, J=7.0 Hz, 2H), 2.58-2.36 (m, 2H), 2.04 (p, J=6.3 Hz, 2H), 1.92-1.83 (m, 1H), 1.62 (td, J=12.3, 11.7, 7.8 Hz, 1H), 1.36 (s, 3H), 1.16 (t, J=7.0 Hz, 3H), 0.67 (s, 3H). $^{19}$F NMR (376 MHz, Acetonitrile-d3) δ−77.33. MS (m/z) 443.2 [M+H]$^+$.

Example 63: (R)-11-Ethyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

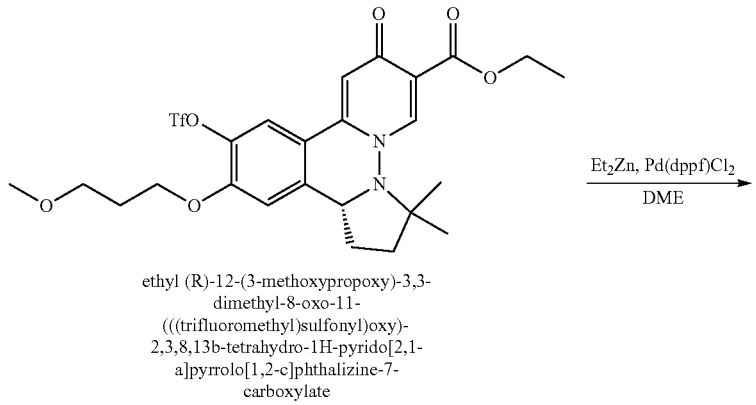

ethyl (R)-12-(3-methoxypropoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalizine-7-carboxylate $\xrightarrow{\text{Et}_2\text{Zn, Pd(dppf)Cl}_2}{\text{DME}}$

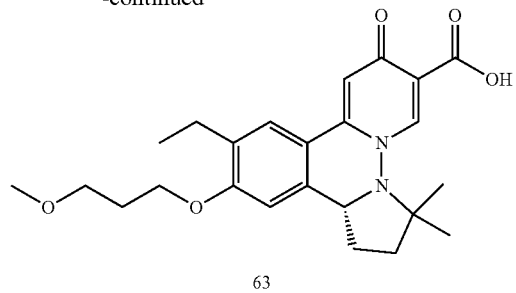

63

Synthesis of (R)-11-ethyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid Ethyl (R)-12-(3-methoxypropoxy)-3,3-dimethyl-8-oxo-11-(((trifluoromethyl)sulfonyl)oxy)-2,3,8,13b-tetrahydro-1H-pyrido[2,1-a]pyrrolo[1,2-c]phthalazine-7-carboxylate (175 mg, 0.305 mmol) and [1,1'-Bis(diphenylphosphino)ferrocene]palladium(II) dichloride (22 mg, 0.030 mmol) were suspended in DME and treated with diethyl zinc (1.1 M in PhMe, 1.4 mL, 1.5 mmol). The resulting solution was stirred at 85° C. o/n. Upon completion, the reaction mixture was cooled to RT and diluted with DCM. The organic suspension was washed with 10% HCl. The aqueous layer was then back extracted with DCM. The combined organics were dried over MgSO$_4$, filtered and concentrated under reduced pressure. The crude residue was purified by HPLC to provide the title compound. $^1$H NMR (400 MHz, Chloroform-d) δ 8.57 (s, 1H), 7.56 (s, 1H), 7.25 (s, 1H), 6.75 (s, 1H), 4.81 (d, J=5.8 Hz, 1H), 4.29-4.00 (m, 2H), 3.59 (q, J=5.6 Hz, 2H), 3.37 (s, 3H), 2.68 (p, J=7.2 Hz, 2H), 2.44 (p, J=10.5, 9.5 Hz, 2H), 2.11 (t, J=6.1 Hz, 2H), 1.89 (ddd, J=12.6, 7.5, 2.7 Hz, 1H), 1.64 (ddd, J=12.7, 10.9, 7.8 Hz, 1H), 1.41 (s, 3H), 1.24 (t, J=7.5 Hz, 3H), 0.66 (s, 3H). MS (m/z) 427.3 [M+H]$^+$.

Example 64: (R)-11-methoxy-12-(3-methoxy-3-methylbutoxy)-3,3-dimethyl-8-oxo-2,3,8,13b-tetrahydro-1H-pyrido[2,1-a]pyrrolo[1,2-c]phthalazine-7-carboxylic acid

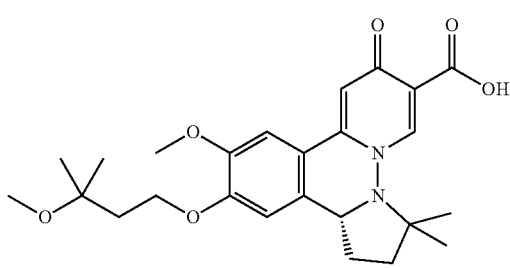

64

Prepared analogously to (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid in Example 60 using 1-bromo-3-methoxy-3-methylbutane in place of 1-bromo-3-(2,2,2-trifluoroethoxy)propane. $^1$H NMR (400 MHz, Acetonitrile-d3) δ 8.43 (s, 1H), 7.37 (s, 1H), 7.23 (s, 1H), 6.97 (s, 1H), 4.84 (d, J=6.3 Hz, 1H), 4.29-4.12 (m, 2H), 3.91 (s, 3H), 3.20 (s, 3H), 2.59-2.37 (m, 2H), 2.02 (t, J=7.3 Hz, 2H), 1.89 (ddd, J=12.6, 7.9, 2.7 Hz, 1H), 1.63 (td, J=11.4, 7.8 Hz, 1H), 1.36 (s, 3H), 1.24 (d, J=1.2 Hz, 6H), 0.67 (s, 3H). $^{19}$F NMR (376 MHz, Acetonitrile-d3) δ −77.31. MS (m/z) 457.3 [M+H]$^+$.

Example 65: (R)-12-(3-(tert-butoxy)propoxy)-11-methoxy-3,3-dimethyl-8-oxo-2,3,8,13b-tetrahydro-1H-pyrido[2,1-a]pyrrolo[1,2-c]phthalazine-7-carboxylic acid

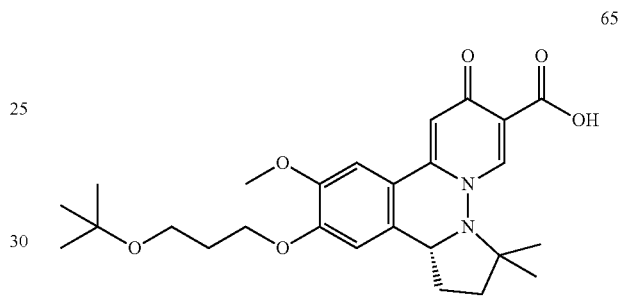

65

Prepared analogously to (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid in Example 60 using 1-bromo-3-(tert-butoxy)propane in place of 1-bromo-3-(2,2,2-trifluoroethoxy)propane. $^1$H NMR (400 MHz, Acetonitrile-d3) δ 8.44 (s, 1H), 7.38 (s, 1H), 7.25 (s, 1H), 6.96 (s, 1H), 4.84 (d, J=6.2 Hz, 1H), 4.28-4.10 (m, 2H), 3.92 (s, 3H), 3.53 (t, J=6.1 Hz, 2H), 2.58-2.36 (m, 2H), 2.01-1.97 (m, 2H), 1.89 (ddd, J=12.6, 7.8, 2.7 Hz, 1H), 1.62 (td, J=12.3, 11.7, 7.8 Hz, 1H), 1.36 (s, 3H), 1.17 (s, 9H), 0.67 (s, 3H). $^{19}$F NMR (376 MHz, Acetonitrile-d3) δ −77.34. MS (m/z) 471.3 [M+H]$^+$.

Example 66: (R)-11-cyclopropyl-3,3-dimethyl-12-(oxetan-3-ylmethoxy)-8-oxo-2,3,8,13b-tetrahydro-1H-pyrido[2,1-a]pyrrolo[1,2-c]phthalazine-7-carboxylic acid

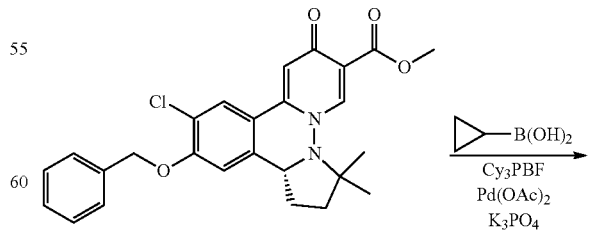

methyl (R)-12-(benzyloxy)-11-chloro-3,3-dimethyl-8-oxo-2,3,8,13b-tetrahydro-1H-pyrido[2,1-a]pyrrolo[1,2-c]phthalizine-7-carboxylate 163
-continued

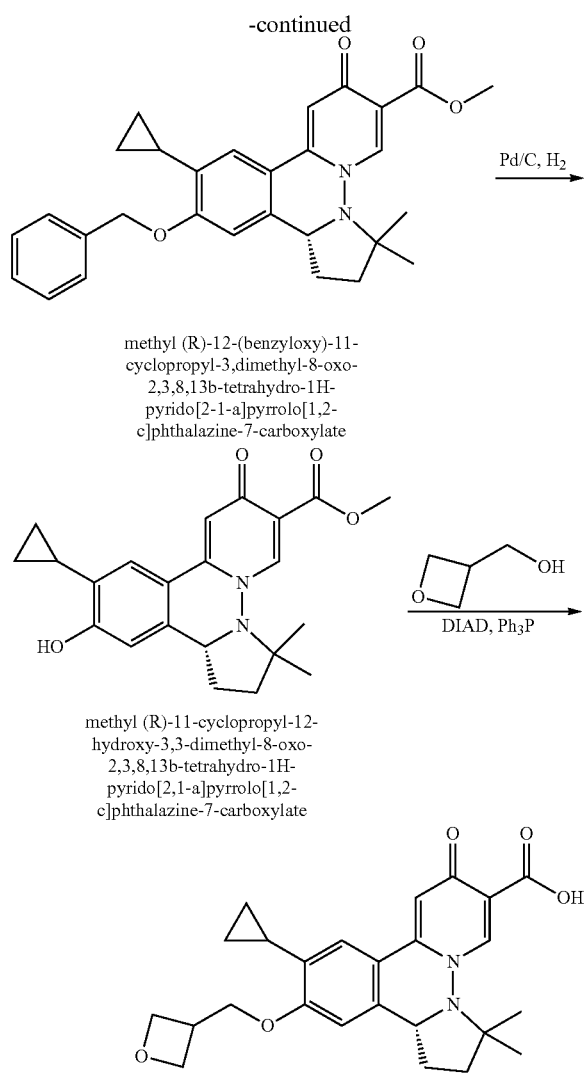

methyl (R)-12-(benzyloxy)-11-cyclopropyl-3,3-dimethyl-8-oxo-2,3,8,13b-tetrahydro-1H-pyrido[2-1-a]pyrrolo[1,2-c]phthalazine-7-carboxylate methyl (R)-11-cyclopropyl-12-hydroxy-3,3-dimethyl-8-oxo-2,3,8,13b-tetrahydro-1H-pyrido[2,1-a]pyrrolo[1,2-c]phthalazine-7-carboxylate

66

Synthesis of methyl (R)-12-(benzyloxy)-11-cyclopropyl-3,3-dimethyl-8-oxo-2,3,8,13b-12-tetrahydro-1H-pyrido[2,1-a]pyrrolo[1,2-c]phthalazine-7-carboxylate To a solution of methyl (R)-12-(benzyloxy)-11-chloro-3,3-dimethyl-8-oxo-2,3,8,13b-tetrahydro-1H-pyrido[2,1-a]pyrrolo[1,2-c]phthalazine-7-carboxylate (542 mg, 1.17 mmol) in toluene/water (4 ml/0.5 ml), was added cyclopropylboronic acid (500.7 mg, 5.83 mmol), tricyclohexylphosphonium tetrafluoroborate (244 mg), palladium (II) acetate (37 mg) and potassium phosphate tribasic (742 mg). The reaction mixture was degassed and filled with argon. After heating for 30 min at 135° C., the mixture was cooled to rt, diluted with EtOAc, and washed with brine. The organic layer was dried over MgSO₄, filtered and concentrated under reduced pressure. The crude residue was purified by silica column chromatography (0% to 20% MeOH/EtOAc) to provide 385 mg of methyl (R)-12-(benzyloxy)-11-cyclopropyl-3,3-dimethyl-8-oxo-2,3,8,13b-tetrahydro-1H-pyrido[2,1-a]pyrrolo[1,2-c]phthalazine-7-carboxylate. MS (m/z) 471.466 [M+H]⁺.

164

Synthesis of (R)-12-(3-methoxypropoxy)-3,3-dimethyl-11-(oxetan-3-yl)-8-oxo-2,3,8,13b-tetrahydro-1H-pyrido[2,1-a]pyrrolo[1,2-c]phthalazine-7-carboxylic acid (R)-12-(3-methoxypropoxy)-3,3-dimethyl-11-(oxetan-3-yl)-8-oxo-2,3,8,13b-tetrahydro-1H-pyrido[2,1-a]pyrrolo[1,2-c]phthalazine-7-carboxylic acid was prepared similarly to Example 55 by first debenzylation and then misunobu reaction using oxetan-3-yl-methanol. ¹H NMR (400 MHz, Chloroform-d) δ 8.53 (s, 1H), 7.05 (s, 1H), 6.74 (s, 1H), 4.93 (t, J=7.0 Hz, 2H), 4.79 (d, J=6.1 Hz, 1H), 4.65 (d, J=6.1 Hz, 2H), 4.33 (d, J=7.4 Hz, 1H), 4.27 (d, J=7.0 Hz, 1H), 3.58-3.47 (m, 1H), 2.54-2.37 (m, 2H), 2.20-2.10 (m, 1H), 1.94-1.85 (m, 1H), 1.67-1.56 (m, 3H), 1.37 (s, 3H), 1.01 (d, J=8.5 Hz, 2H), 0.66 (s, 3H). MS (m/z) 437.3 [M+H]⁺.

Example 67: (R)-13-fluoro-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

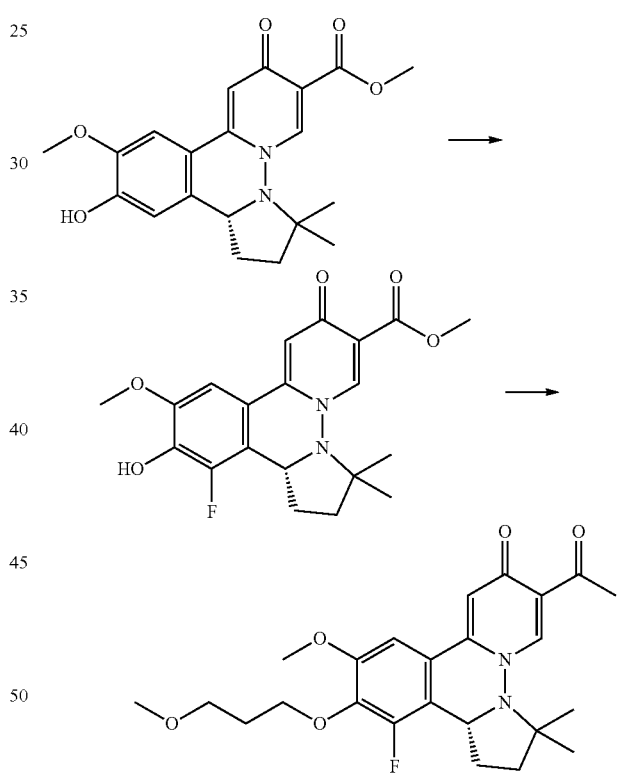

Synthesis of methyl (R)-13-fluoro-12-hydroxy-11-methoxy-3,3-dimethyl-8-oxo-2,3,8,13b-tetrahydro-1H-pyrido[2,1-a]pyrrolo[1,2-c]phthalazine-7-carboxylate Methyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate (30 mg, 81 μmol), N-fluorobenzenesulfonimide (38 mg, 0.12 mmol), and sodium bicarbonate (30 mg) were combined in 1,2-DCE (1 mL) and heated at 80° C. for 2 hours. The mixture was cooled to room temperature, filtered, and concentrated to dryness. The residue was redissolved in ACN/water and purified by preparative HPLC to provide methyl (R)-13-fluoro-12-hydroxy-11-methoxy-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Acetonitrile-d3) δ 8.30 (d, J=1.0 Hz, 1H), 7.70 (s, 1H), 6.97 (d, J=1.0 Hz, 1H), 4.73 (d, J=5.8 Hz, 1H), 3.93 (s, 3H), 3.83 (s, 3H), 2.45-2.28 (m, 2H), 1.87-1.76 (m, 1H), 1.57 (td, J=11.7, 7.9 Hz, 1H), 1.33 (s, 3H), 0.66 (s, 3H). MS (m/z) 389.2 [M+H]$^+$.

(R)-13-fluoro-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid Prepared analogously to (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid in Example 60 using 1-bromo-3-methoxypropane in place of 1-bromo-3-(2,2,2-trifluoroethoxy)propane and methyl (R)-13-fluoro-12-hydroxy-11-methoxy-3,3-dimethyl-8-oxo-2,3,8,13b-tetrahydro-1H-pyrido[2,1-a]pyrrolo[1,2-c]phthalazine-7-carboxylate in place of ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Acetonitrile-d3) δ 8.46 (d, J=1.0 Hz, 1H), 7.71 (s, 1H), 7.04 (s, 1H), 4.81 (d, J=6.1 Hz, 1H), 4.31-4.10 (m, 2H), 3.89 (s, 3H), 3.54 (td, J=6.2, 0.9 Hz, 2H), 3.32 (s, 3H), 2.57-2.35 (m, 2H), 2.06 (p, J=6.3 Hz, 2H), 1.93-1.82 (m, 1H), 1.66-1.52 (m, 1H), 1.36 (s, 3H), 0.65 (s, 3H). $^{19}$F NMR (376 MHz, Acetonitrile-d3) δ−77.08, −146.50. MS (m/z) 447.3 [M+H]$^+$.

Example 68: (R)-12-(imidazo[1,2-b]pyridazin-3-ylethynyl)-11-methoxy-3,3-dimethyl-8-oxo-2,3,8,13b-tetrahydro-1H-pyrido[2,1-a]pyrrolo[1,2-c]phthalazine-7-carboxylic acid

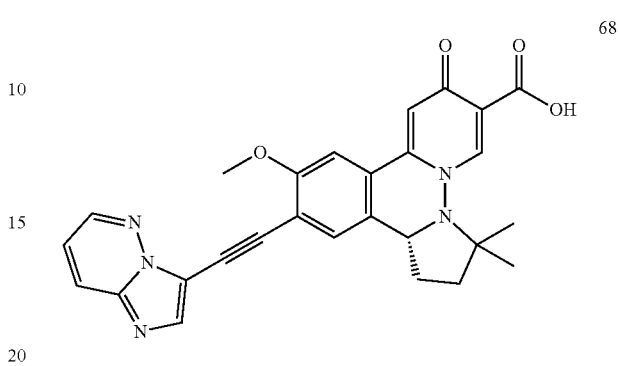

Prepared analogously to (R)-11-methoxy-3,3-dimethyl-12-((1-methyl-1H-imidazol-5-yl)ethynyl)-8-oxo-2,3,8,13-btetrahydro-1H-pyrido[2,1-a]pyrrolo[1,2-c]phthalazine-7-carboxylic acid in example 42 using 3-ethynylimidazo[1,2-b]pyridazine in place of 5-ethynyl-1-methyl-1H-imidazole. $^1$H NMR (400 MHz, Acetonitrile-d3) δ 8.69-8.59 (m, 1H), 8.49 (s, 1H), 8.17 (dd, J=9.3, 1.6 Hz, 1H), 8.12 (s, 1H), 7.63 (d, J=1.0 Hz, 1H), 7.52 (s, 1H), 7.43-7.35 (m, 2H), 4.88 (d, J=6.1 Hz, 1H), 4.05 (s, 3H), 2.59-2.38 (m, 1H), 1.94-1.87 (m, 2H), 1.67 (td, J=12.4, 11.7, 8.3 Hz, 1H), 1.38 (s, 3H), 0.69 (s, 3H). $^{19}$F NMR (376 MHz, Acetonitrile-d3) δ−77.27. MS (m/z) 482.1 [M+H]$^+$.

Example 69: (R)-12-(3-methoxypropoxy)-3,3-dimethyl-11-(methylsulfonyl)-8-oxo-2,3,8,13b-tetrahydro-1H-pyrido[2,1-a]pyrrolo[1,2-c]phthalazine-7-carboxylic acid

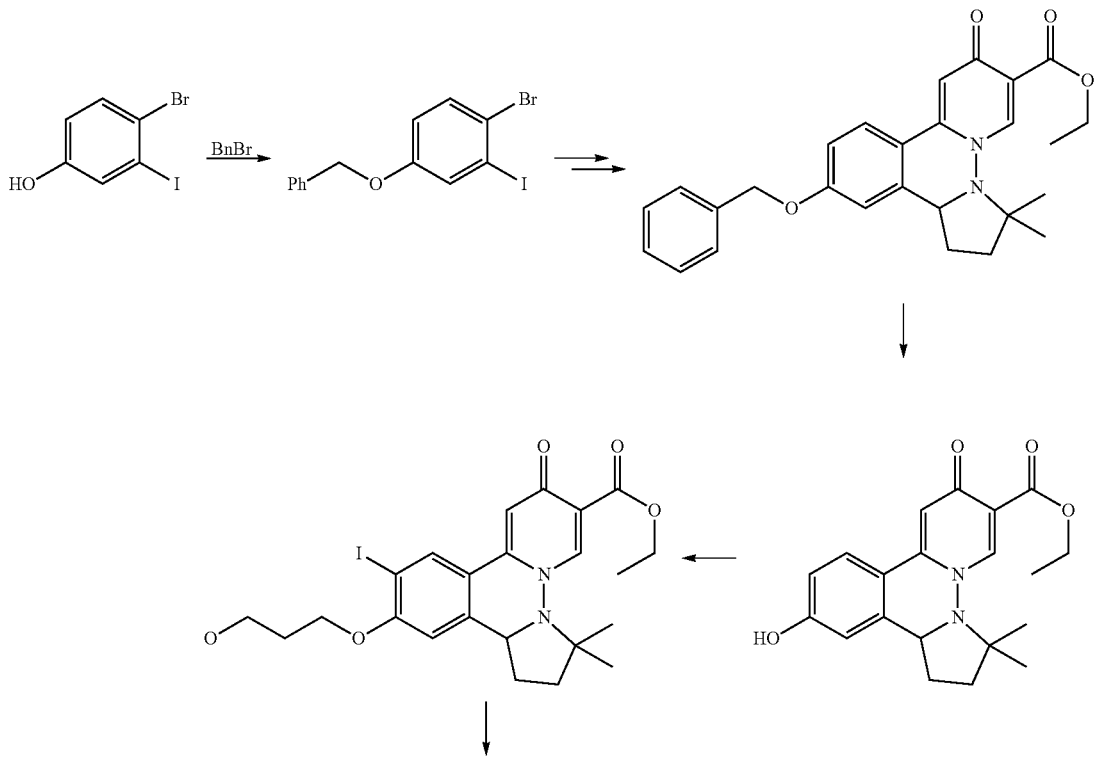

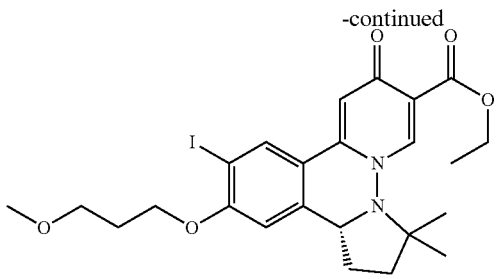

4-(benzyloxy)-1-bromo-2-iodobenzene 4-bromo-3-iodophenol (16.35 g, 54.7 mmol), benzyl bromide (8.45 ml, 71.1 mmol), and potassium carbonate, anhydrous (10.58 g, 76.58 mmol) were combined in DMF (100 ml) and stirred overnight at 50° C. The following day the reaction was warmed to 80° C. for 4 hours. The reaction was cooled to room temperature, diluted with water (100 mL) and extracted with EtOAc/Et$_2$O (100 mL). The combined organic layers were rinsed with aqueous sodium bicarbonate (50 mL), then brine (50 mL), dried over sodium sulfate, filtered, concentrated, and purified by flash column chromatography to provide 4-(benzyloxy)-1-bromo-2-iodobenzene. $^1$H NMR (400 MHz, Chloroform-d) δ 7.49 (d, J=3.0 Hz, 1H), 7.47 (d, J=8.8 Hz, 1H), 7.42-7.30 (m, 5H), 6.83 (dd, J=8.9, 2.9 Hz, 1H), 5.01 (s, 2H). MS (m/z) 390.9 [M+H]$^+$.

Ethyl 12-(benzyloxy)-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-3,3-dimethyl-8-oxo-2,3,8,13b-tetrahydro-1H-pyrido[2,1-a]pyrrolo[1,2-c]phthalazine-7-carboxylate was prepared similarly to ethyl 11-(benzyloxy)-12-(3-methoxypropoxy)-3,3-dimethyl-8-oxo-2,3,8,13btetrahydro-1H-pyrido[2,1-a]pyrrolo[1,2-c]phthalazine-7-carboxylate in example 18. $^1$H NMR (400 MHz, Acetonitrile-d3) δ 8.20 (s, 1H), 7.82 (d, J=8.7 Hz, 1H), 7.54-7.46 (m, 2H), 7.46-7.32 (m, 3H), 7.10-6.98 (m, 2H), 6.77 (s, 1H), 5.20 (dd, J=11.6, 2.0 Hz, 2H), 4.79 (d, J=5.9 Hz, 1H), 4.32-4.18 (m, 2H), 2.48-2.32 (m, 2H), 1.83 (ddd, J=12.6, 7.6, 3.3 Hz, 1H), 1.56 (ddd, J=12.6, 10.3, 8.2 Hz, 1H), 1.36-1.28 (m, 6H), 0.66 (s, 3H). MS (m/z) 445.5 [M+H]$^+$.

Ethyl 12-hydroxy-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-3,3-dimethyl-8-oxo-2,3,8,13b-tetrahydro-1H-pyrido[2,1-a]pyrrolo[1,2-c]phthalazine-7-carboxylate (3.5 g, 7.9 mmol) and palladium on carbon (10 wt %, wet) E101 NE/W (5%, 838 mg) were combined in EtOH (50 mL) under argon. The system was placed under vacuum and backfilled with hydrogen gas. The mixture was stirred vigorously for 30 minutes after which time LCMS analysis showed complete conversion. The mixture was diluted with EtOAc (50 mL) and filtered through celite. The supernatant was discarded. The wet cake, containing the desired product was rinsed with 3×100 mL hot DCM/EtOH. The resulting supernatant was concentrated in vacuo to provide ethyl 12-hydroxy-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Chloroform-d) δ 8.35 (s, 1H), 7.53 (d, J=8.8 Hz, 1H), 7.02 (dd, J=8.6, 2.3 Hz, 1H), 6.93 (d, J=2.7 Hz, 2H), 4.70 (d, J=5.9 Hz, 1H), 4.37 (qd, J=7.2, 1.8 Hz, 2H), 2.47-2.28 (m, 2H), 1.88-1.73 (m, 1H), 1.62 (td, J=11.3, 7.9 Hz, 1H), 1.37 (t, J=7.1 Hz, 3H), 1.33 (s, 3H), 0.66 (s, 3H). MS (m/z) 355.2 [M+H]$^+$.

Ethyl 11-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl 12-hydroxy-3,3-dimethyl-8-oxo-2,3,8,13b-tetrahydro-1H-pyrido[2,1-a]pyrrolo[1,2-c]phthalazine-7-carboxylate (2.44 g, 6.89 mmol) was suspended in EtOH (70 mL). 1M NaOH (7.57 ml) was added and the mixture was cooled to 0° C. N-iodosuccinimide (1.63 g, 7.23 mmol) in ethanol (20 mL) was added dropwise over 5 minutes. After 20 minutes, the reaction was quenched with aq Na$_2$S$_2$O$_3$ (10 mL). The mixture was stirred overnight, allowing to slowly warm to room temperature. The reaction was diluted with ethyl acetate (50 mL) and sat aq NH$_4$Cl (10 mL). The layers were separated, the organics were rinsed with brine (20 mL), and the combined aqueous layers were back extracted with ethyl acetate (50 mL). The combined organics were dried over magnesium sulfate, filtered, and concentrated in vacuo. The resulting crude solids were combined with 1-bromo-3-methoxypropane (1.7 g, 11 mmol) and potassium carbonate (1.9 g, 14 mmol) in DMF (11 mL). The mixture was stirred at 65° C. for 130 minutes. The mixture was cooled to rt, diluted with isopropyl acetate (50 mL) and water (30 mL). The layers were separated and the organic layer was rinsed with aq NaHCO$_3$ (20 mL), then brine (20 mL), then dried over sodium sulfate, filtered, and concentrated in vacuo. The reaction was purified by flash column chromatography to provide ethyl 11-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Chloroform-d) δ 8.28 (s, 1H), 8.15 (s, 1H), 6.94 (s, 1H), 6.68 (s, 1H), 4.71 (d, J=6.3 Hz, 1H), 4.38 (q, J=7.1 Hz, 2H), 4.22-4.07 (m, 2H), 3.75-3.57 (m, 2H), 3.38 (s, 3H), 2.51-2.27 (m, 2H), 2.13 (p, J=6.1 Hz, 2H), 1.85 (dd, J=12.1, 8.7 Hz, 1H), 1.70-1.55 (m, 1H), 1.39 (t, J=7.2 Hz, 3H), 1.34 (s, 3H), 0.70 (s, 3H). MS (m/z) 553.4 [M+H]$^+$.

Ethyl (R)-1-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl 11-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using OD-H 4.6×100 mm columns with 30% isopropanol as the co-solvent. The (R)-

Synthesis of (R)-12-(3-methoxypropoxy)-3,3-dimethyl-11-(methylsulfonyl)-8-oxo-2,3,8,13b-tetrahydro-1H-pyrido[2,1-a]pyrrolo[1,2-c]phthalazine-7-carboxylic acid

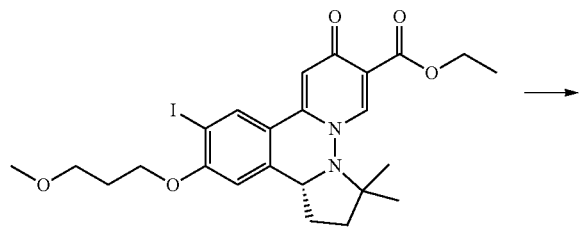

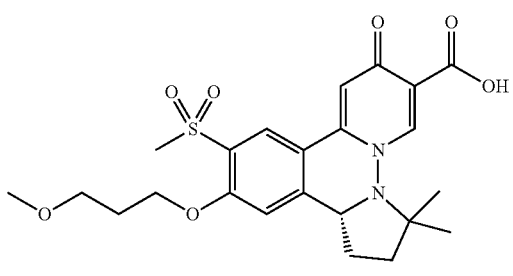

69

Ethyl (R)-11-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate (39 mg, 71 μmol) was combined with 1,4-diazabicyclo[2.2.2]octane bis(sulfur dioxide) adduct (10 mg, 42 μmol), palladium (II) acetate (0.95 mg, 4.24 μmol), and butyldi-1-adamantylphosphine (2.33 mg, 6.5 μmol) in isopropanol (0.5 mL) and triethylamine (30 μL, 212 μmol) under argon. The mixture was warmed to 80° C. and stirred for 2.5 hours. The mixture was cooled to 40° C. and iodomethane (13 μl, 0.21 mmol) was added. After 30 minutes, 1M LiOH (0.2 mL) was added and the mixture was stirred at 40° C. After an additional 10 minutes, the mixture was diluted with aq TFA (1M) and purified by preparative HPLC to provide (R)-12-(3-methoxypropoxy)-3,3-dimethyl-11-(methylsulfonyl)-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d3) δ 8.45 (s, 1H), 8.37 (s, 1H), 7.21 (s, 2H), 4.92 (d, J=6.3 Hz, 1H), 4.47-4.29 (m, 2H), 3.60 (t, J=6.0 Hz, 2H), 3.32 (s, 3H), 3.24 (s, 3H), 2.59-2.49 (m, 1H), 2.12 (p, J=6.1 Hz, 2H), 1.94-1.86 (m, 1H), 1.69-1.59 (m, 1H), 1.37 (s, 3H), 0.67 (s, 3H). $^{19}$F NMR (376 MHz, Acetonitrile-d3) δ−77.11. MS (m/z) 377.3 [M+H]$^+$.

Example 70: (R)-12-(3-hydroxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid

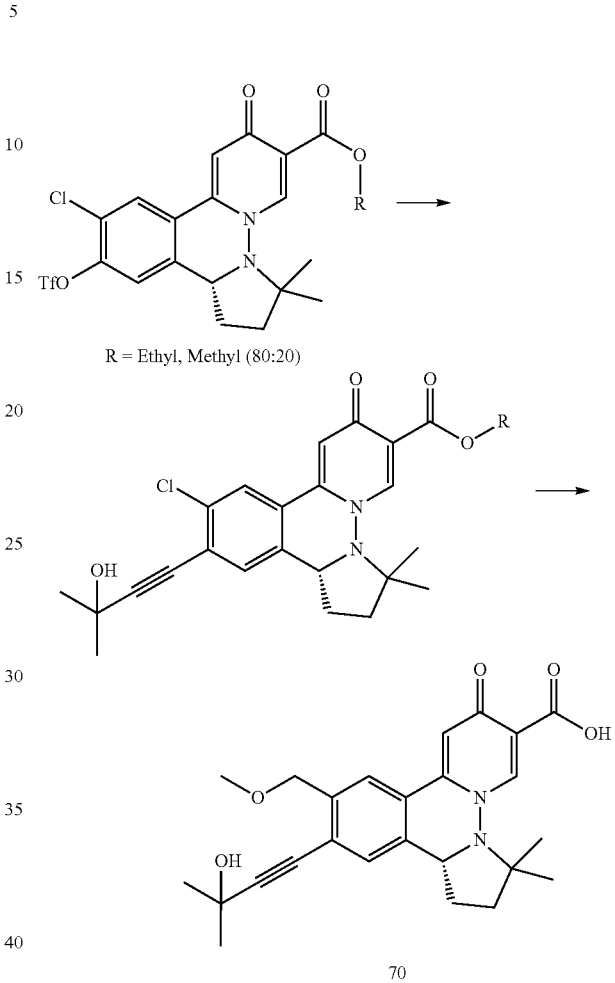

70

An 80:20 mixture of ethyl (R)-11-chloro-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate and methyl (R)-11-chloro-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (129 mg, −0.25 mmol) was combined with Pd(tBu$_2$PPh)$_2$Cl$_2$ (14 mg, 0.020 mmol), CuI (7.0 mg, 0.037 mmol), and 2-methylbut-3-yn-2-ol (72 μl, 0.74 mmol) in acetonitrile/triethylamine (3:1, 1 mL) under argon. The mixture was stirred at 60° C. for 30 minutes after which time LCMS analysis showed complete conversion. The crude mixture was concentrated to dryness, redissolved in DMF/MeCN, diluted with aq TFA (1M) and purified by preparative HPLC to provide ethyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate: MS (m/z) 455.3 [M+H]$^+$; and methyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate: MS (m/z) 441.4 [M+H]$^+$. Ethyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate (53 mg, 0.093 mmol) was combined with trifluoro(methoxymethyl)-borane, potassium salt (40 mg, 0.26 mmol), Ruphos Pd G2 (5.1 mg, 0.007 mmol), and potassium carbonate (52 mg, 0.37 mmol) in dioxane:water (5:1, 1 mL) under argon in a sealed vial. The mixture was stirred at 110° C. for 2.5 hours, after which time it was cooled to 50° C. and 1M lithium hydroxide (0.19 ml) was added. The mixture was stirred for 90 minutes, then cooled to room temperature, diluted with TFA and acetonitrile, and purified by preparative HPLC to provide (R)-12-(3-hydroxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d3) δ 8.47 (s, 1H), 8.01 (s, 1H), 7.50 (d, J=1.1 Hz, 1H), 7.29 (s, 1H), 4.88 (d, J=5.9 Hz, 1H), 4.62 (t, J=0.8 Hz, 2H), 3.47 (s, 3H), 2.60-2.43 (m, 2H), 1.94-1.86 (m, 1H), 1.67-1.60 (m, 1H), 1.58 (s, 6H), 1.37 (s, 3H), 0.63 (s, 3H). $^{19}$F NMR (376 MHz, Acetonitrile-d3) δ −77.28. MS (m/z) 437.2 [M+H]$^+$.

Example 71: (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid

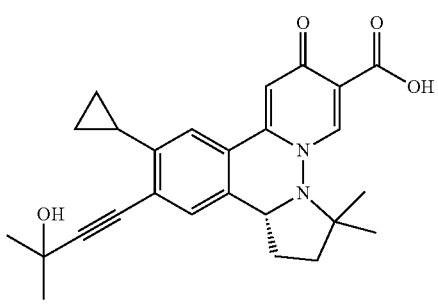

A mixture of ethyl (R)-11-chloro-12-(3-hydroxy-3-methylbut-1-yn-11-yl)-3,3-dimethyl-8-oxo-2,3,8,13b-tetrahydro-1H-pyrido[2,1-a]pyrrolo[1,2-c]phthalazine-7-carboxylate (28 mg, 0.062 mmol) and methyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate (25 mg, 0.057 mmol) was combined with cyclopropylboronic acid MIDA ester (51 mg, 0.26 mmol), Ruphos Pd G2 (5.1 mg, 0.007 mmol), and potassium carbonate (52 mg, 0.37 mmol) in dioxane:water (5:1, 1 mL) under argon in a sealed vial. The mixture was stirred at 110° C. for 1 hour. The mixture was cooled to 50° C. and 1M lithium hydroxide (0.09 ml) was added. After 2 hours, the mixture was cooled to room temperature, diluted with TFA and acetonitrile, and purified by preparative HPLC to provide (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d3) δ 8.45 (s, 1H), 7.45 (d, J=1.0 Hz, 1H), 7.38 (s, 1H), 7.33 (s, 1H), 4.84 (d, J=6.0 Hz, 1H), 2.53-2.34 (m, 3H), 1.89 (ddd, J=12.7, 7.7, 3.1 Hz, 1H), 1.67-1.59 (m, 1H), 1.59 (s, 6H), 1.36 (s, 3H), 1.17-1.04 (m, 2H), 0.95-0.84 (m, 2H), 0.61 (s, 3H). $^{19}$F NMR (376 MHz, Acetonitrile-d3) δ −77.32. MS (m/z) 433.2 [M+H]$^+$.

Example 72: (R)-11-cyclopropyl-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid

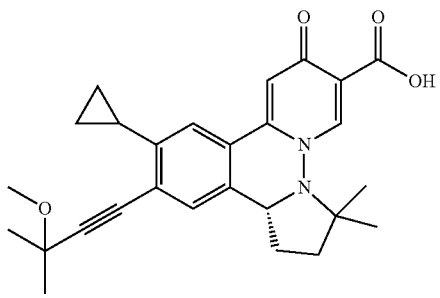

Prepared similarly to (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 71, using 3-methoxy-3-methylbut-1-yne in place of 2-methylbut-3-yn-2-ol. $^1$H NMR (400 MHz, Methanol-d4) δ 8.60 (s, 1H), 7.54-7.48 (m, 2H), 7.41 (s, 1H), 4.87 (d, J=6.2 Hz, 1H), 3.44 (s, 3H), 2.57-2.43 (m, 2H), 1.93 (ddd, J=12.8, 7.8, 2.6 Hz, 1H), 1.64 (td, J=12.1, 11.6, 7.9 Hz, 1H), 1.57 (s, 6H), 1.39 (s, 3H), 1.14-1.06 (m, 2H), 0.89 (dt, J=5.6, 3.5 Hz, 2H), 0.63 (s, 3H). MS (m/z) 447.3 [M+H]$^+$ Example 73: (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

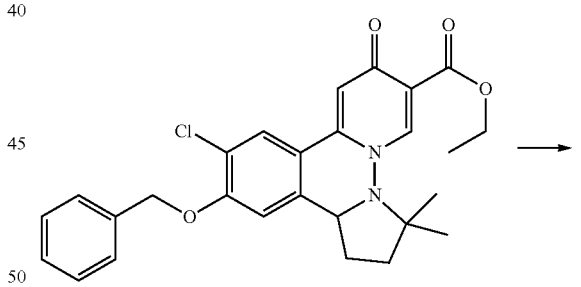

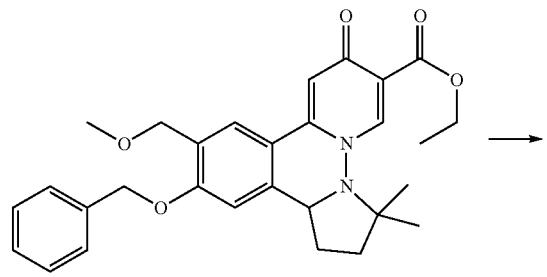

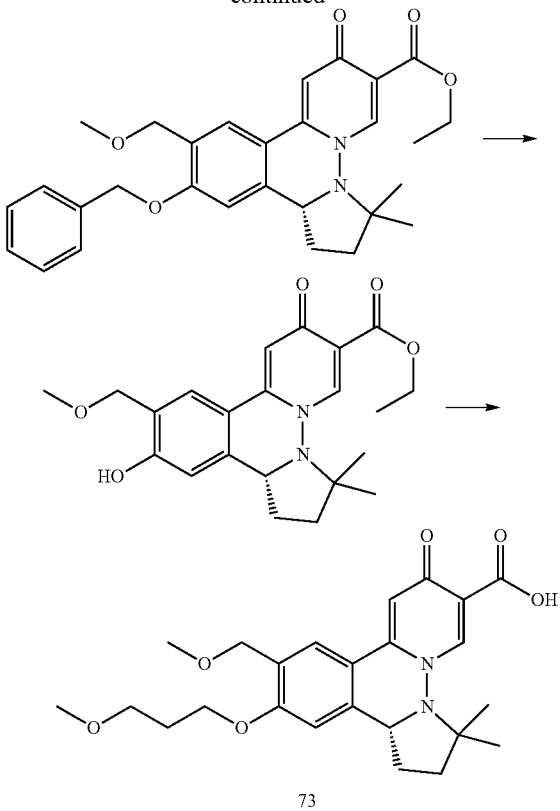

Synthesis of ethyl 12-(benzyloxy)-11-(methoxymethyl)-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-11-chloro-3,3-dimethyl-8-oxo-2,3,8,13b-tetrahydro-1H-pyrido[2,1-a]pyrrolo[1,2-c]phthalazine-7-carboxylate (737 mg, 1.54 mmol) was combined with trifluoro(methoxymethyl)-borane, potassium salt (701 mg, 4.62 mmol), Pd RuPhos G3 (154 mg, 0.185 mmol), RuPhos (129 mg, 0.28 mmol), and cesium carbonate (2.51 g, 7.69 mmol) in toluene:water (3:1, 10 mL) under argon in a sealed vial. The mixture was heated at 110° C. for 90 minutes with vigorous stirring, then cooled to room temperature, the aqueous layer was removed, and the organics were concentrated in vacuo and purified by flash column chromatography (hexanes/ethyl acetate/ethanol/triethylamine) to provide ethyl 12-(benzyloxy)-11-(methoxymethyl)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Chloroform-d) δ 8.27 (s, 1H), 7.84 (s, 1H), 7.45-7.30 (m, 5H), 7.00 (s, 1H), 6.75 (s, 1H), 5.24-5.08 (m, 2H), 4.77-4.68 (m, 1H), 4.60-4.47 (m, 2H), 4.38 (q, J=7.1 Hz, 2H), 3.51 (s, 0H), 3.50-3.44 (m, 3H), 2.47-2.32 (m, 1H), 2.25 (t, J=10.3 Hz, 1H), 1.79 (dd, J=11.7, 8.9 Hz, 1H), 1.54-1.45 (m, 1H), 1.39 (t, J=7.1 Hz, 3H), 1.32 (s, 3H), 0.67 (s, 3H). MS (m/z) 489.5 [M+H]$^+$.

Synthesis of ethyl (R)-12-(benzyloxy)-11-(methoxymethyl)-3,3-dimethyl-8-oxo-2,3,8,13b-tetrahydro-1H-pyrido[2,1-a]pyrrolo[1,2-c]phthalazine-7-carboxylate Ethyl 12-(benzyloxy)-11-(methoxymethyl)-3,3-dimethyl-8-oxo-2,3,8,13b-tetrahydro-1H-pyrido[2,1-a]pyrrolo[1,2-c]phthalazine-7-carboxylate was separated into its enantiomers by chiral SFC chromatography using AD-H 4.6×100 mm columns with 30% isopropanol as the co-solvent. The (R)-enantiomer is the faster eluting peak with a retention time of 5.18 min. MS (m/z) 489.5 [M+H]$^+$.

Synthesis of ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate Ethyl (R)-12-(benzyloxy)-11-(methoxymethyl)-3,3-dimethyl-8-oxo-2,3,8,13b-tetrahydro-1H-pyrido[2,1-a]pyrrolo[1,2-c]phthalazine-7-carboxylate (288 mg, 589 µmol) was combined with palladium on carbon (10 wt %, wet) E101 NE/W (5%, 63 mg) in ethanol (10 mL) under argon. The system was placed under vacuum and backfilled with hydrogen gas. The mixture was stirred vigorously for 55 minutes. The mixture was diluted with DCM (50 mL) and filtered through celite. The supernatant was concentrated to provide ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate. MS (m/z) 399.3 [M+H]$^+$.

Synthesis of (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid Ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate (82 mg, 210 µmol) was combined with potassium carbonate (71 mg, 0.52 mmol) and 1-bromo-3-methoxypropane (63 mg, 0.41 mmol) in DMF (0.8 mL) and stirred at 85° C. for 30 minutes, after which time LCMS analysis showed complete conversion. The mixture was cooled to room temperature and filtered, rinsing forward with acetonitrile (3×0.3 mL). 1M lithium hydroxide (0.4 mL) was added and the mixture was stirred at room temperature overnight. The reaction was diluted with 1M TFA purified by preparative HPLC to provide (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid as a TFA salt. $^1$H NMR (400 MHz, Acetonitrile-d$_3$) δ 8.45 (s, 1H), 7.90 (s, 1H), 7.21 (s, 1H), 6.98 (s, 1H), 4.87 (d, J=6.3 Hz, 1H), 4.56-4.42 (m, 2H), 4.20 (ddt, J=27.5, 9.6, 6.2 Hz, 2H), 3.56 (t, J=6.2 Hz, 2H), 3.43 (s, 3H), 3.32 (s, 3H), 2.63-2.39 (m, 2H), 2.05 (p, J=6.2 Hz, 2H), 1.90 (ddd, J=12.7, 8.0, 2.9 Hz, 1H), 1.62 (ddd, J=12.7, 10.6, 7.9 Hz, 1H), 1.36 (s, 3H), 0.64 (s, 3H). $^{19}$F NMR (376 MHz, Acetonitrile-d$_3$) δ −77.30. MS (m/z) 443.5 [M+H]$^+$.

Example 74: (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid

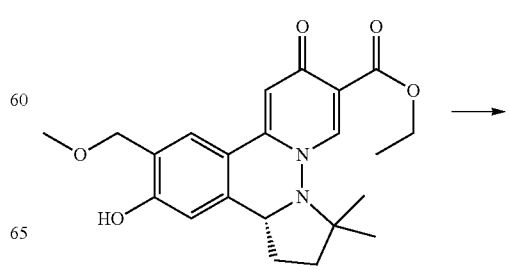

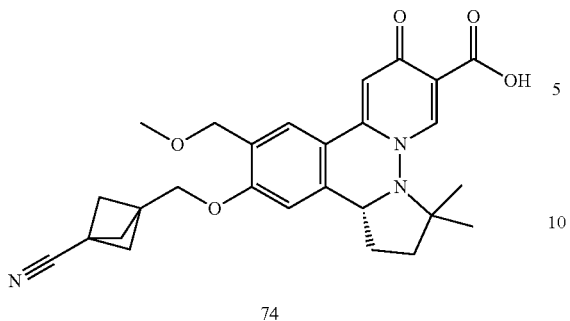

74

Prepared similarly to (R)-11-methoxy-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid in example 58, except using ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate in place of ethyl (R)-12-hydroxy-11-methoxy-3,3-dimethyl-8-oxo-2,3,8,13b-tetrahydro-1Hpyrido[2,1-a]pyrrolo[1,2-c]phthalazine-7-carboxylate and 3-(hydroxymethyl)bicyclo[1.1.1]pentane-1-carbonitrile in place of 3-(trifluoromethoxy)propan-1-ol. $^1$H NMR (400 MHz, Acetonitrile-d3) δ 8.45 (s, 1H), 7.91 (s, 1H), 7.22 (s, 1H), 6.90 (s, 1H), 4.86 (d, J=6.2 Hz, 1H), 4.60-4.41 (m, 2H), 4.21 (d, J=11.1 Hz, 1H), 4.11 (d, J=11.1 Hz, 1H), 3.43 (s, 3H), 2.57-2.39 (m, 1H), 2.33 (s, 6H), 1.90 (ddd, J=12.7, 7.8, 3.0 Hz, 1H), 1.68-1.52 (m, 1H), 1.36 (s, 3H), 0.63 (s, 3H). 19F NMR (376 MHz, Acetonitrile-d3) δ −77.33. MS (m/z) 476.2 [M+H]$^+$.

Example 75: (R)-12-(benzyloxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid

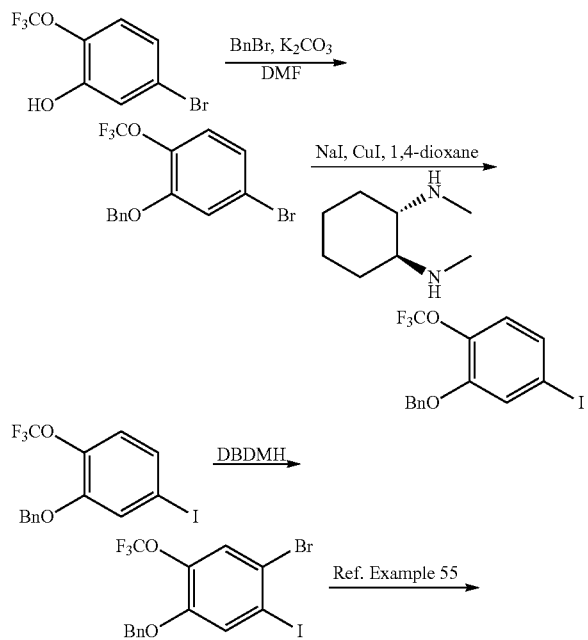

75

Synthesis of 2-(benzyloxy)-4-bromo-1-(trifluoromethoxy)benzene

To an RB add 5-bromo-2-(trifluoromethoxy)phenol (20 g, 77.8 mmol), potassium carbonate (12.91 g, 93.4 mmol), and DMF (80 ml). Allow the mixture to stir for 10 minutes, then add benzyl bromide (9.7 ml, 81.7 mmol) and continue stirring overnight. Dilute the mixture with EtOAc, 5% LiCl solution, and brine. Wash the organic layer with 5% LiCl two times, dry organic layer over sodium sulfate, filter, and concentrate. The residue was purified by silica gel chromatography to afford the title compound. $^1$H NMR (400 MHz, DMSO-d6) δ 7.54 (d, J=2.2 Hz, 1H), 7.45-7.36 (m, 4H), 7.35-7.26 (m, 2H), 7.20 (dd, J=8.6, 2.2 Hz, 1H), 5.23 (s, 2H).

Synthesis of 2-(benzyloxy)-4-iodo-1-(trifluoromethoxy)benzene

A RB was charged with CuI (646 mg, 3.39 mmol), 2-(benzyloxy)-4-bromo-1-(trifluoromethoxy)benzene (11.78, 33.94 mmol) and NaI (10.17 g, 67.87 mmol), briefly evacuated and backfilled with argon. trans-N,N'-dimethyl-1,2-cyclohexanediamine (1.07 mL, 3.39 mmol), and 1,4-dioxane (30 mL) were added under argon. The reaction mixture was stirred at 110° C. for 22-24 h. The resulting suspension was allowed to reach room temperature, diluted with 30% aq ammonia (5 mL), poured into water (20 mL), and extracted with ethyl acetate. The combined organic phases were dried over MgSO$_4$, concentrated, and the residue was purified by flash chromatography on silica gel to provide the desired product. $^1$H NMR (400 MHz, DMSO-d6) δ 7.64 (d, J=2.0 Hz, 1H), 7.48-7.25 (m, 6H), 7.13 (dq, J=8.4, 1.2 Hz, 1H), 5.21 (s, 2H).

Synthesis of 1-(benzyloxy)-4-bromo-5-iodo-2-(trifluoromethoxy)benzene 2-(Benzyloxy)-4-iodo-1-(trifluoromethoxy)benzene (27.90 g, 70.79 mmol) was dissolved in 300 mL of methylene chloride, to it was added DBDMH (12.14 g, 42.47 mmol) and TMSOTf (7.7 mL, 42 mmol). The reaction mixture was allowed to stir at ambient temperature overnight. The reaction mixture was diluted with methylene chloride; wash with saturated NaHCO3 and brine. The organic phase was dried over MgSO$_4$, concentrated, and the residue was purified by flash chromatography on silica gel to provide the desired product. $^1$H NMR (400 MHz, DMSO-d6) δ 7.84 (s, 1H), 7.74 (q, J=1.1 Hz, 1H), 7.45-7.29 (m, 5H), 5.22 (s, 2H).

Synthesis of (R)-12-(benzyloxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid The title compound was prepared according to the method presented for the synthesis of Example 55 utilizing 1-(benzyloxy)-4-bromo-5-iodo-2-(trifluoromethoxy)benzene: MS (m/z): 501.19 [M+H]+. $^1$H NMR (400 MHz, Chloroform-d) δ 8.60 (s, 1H), 7.69 (d, J=1.4 Hz, 1H), 7.51-7.33 (m, 4H), 7.26 (d, J=6.9 Hz, 2H), 6.93 (s, 1H), 5.43-5.16 (m, 2H), 4.78 (d, J=6.4 Hz, 1H), 2.47 (d, J=4.3 Hz, 1H), 2.36-2.13 (m, 1H), 1.88 (ddd, J=12.6, 8.1, 2.5 Hz, 1H), 1.50 (td, J=11.7, 7.5 Hz, 1H), 1.38 (s, 3H), 0.64 (s, 3H).

Example 76: (R)-11-chloro-12-(1-(difluoromethyl)-1H-pyrazol-4-yl)-3,3-dimethyl-8-oxo-2,3,8,13b-tetrahydro-1H-pyrido[2,1-a]pyrrolo[1,2-c]phthalazine-7-carboxylic acid

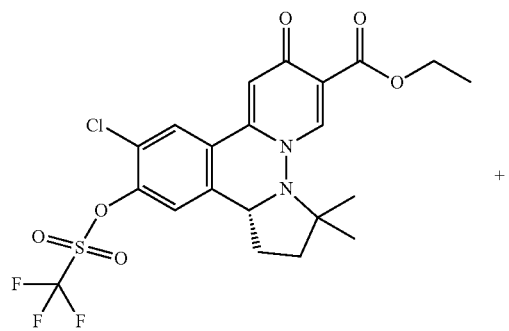

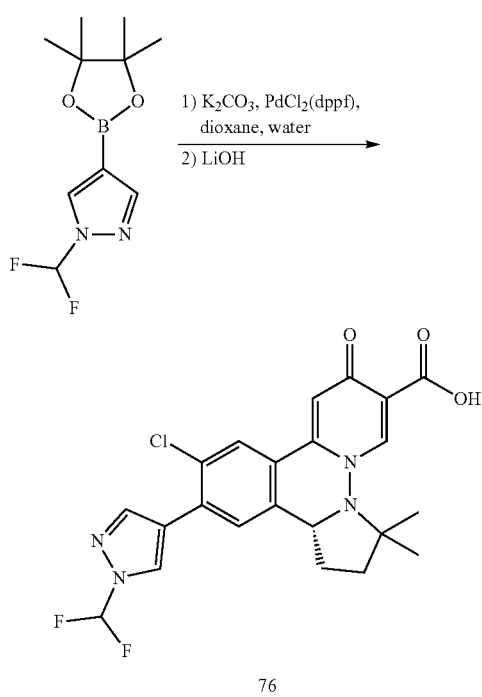

Ethyl (R)-11-chloro-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (30 mg, 0.058 mmol), 1-(difluoromethyl)-4-(4,4,5,5-tetramethyl-1,3,2-dioxaborolan-2-yl)-1H-pyrazole (28 mg, 0.11 mmol), [1,1'-bis(diphenylphosphino)ferrocene]dichloropalladium(II) (2.4 mg, 0.003 mmol), and potassium carbonate (24 mg, 0.17 mmol) were charged in a microwave tube and placed under argon. 1,4-dioxane (1.2 mL) and water (0.2 mL) were added, and the reaction mixture was heated to 120° C. in a microwave reactor (Biotage® Initiator+) for 10 minutes. The reaction mixture was cooled to ambient temperature and to it was added 0.1 ml 2 N LiOH, and the reaction was stirred until complete. The reaction mixture was partitioned between EtOAc and 0.1 N HCl. the aqueous layer was removed. The organic layer was concentrated under vacuum, and the resulting residue was purified by RP-HPLC to provide the title compound. MS (m/z) 461.12 [M+H]+). $^1$H NMR (400 MHz, Chloroform-d) δ 8.67 (s, 1H), 8.32 (s, 1H), 8.04 (s, 1H), 7.94 (s, 1H), 7.47 (d, J=1.1 Hz, 1H), 7.41 (s, 1H), 7.45-7.09 (m, 1H), 4.87 (d, J=6.2 Hz, 1H), 2.67-2.35 (m, 2H), 2.06-1.90 (m, 1H), 1.68 (td, J=11.6, 7.7 Hz, 1H), 1.42 (s, 3H), 0.71 (s, 3H).

Example 77: (R)-12-(3-methoxypropoxy)-3,3-dimethyl-11-(oxetan-3-yl)-8-oxo-2,3,8,13b-tetrahydro-1H-pyrido[2,1-a]pyrrolo[1,2-c]phthalazine-7-carboxylic acid

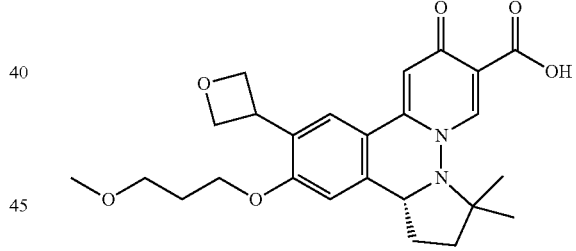

(R)-12-(3-methoxypropoxy)-3,3-dimethyl-11-(oxetan-3-yl)-8-oxo-2,3,8,13b-tetrahydro-1H-pyrido[2,1-a]pyrrolo[1,2-c]phthalazine-7-carboxylic acid was prepared similarly to example 28 using ethyl (R)-11-iodo-12-(3-methoxypropoxy)-3,3-dimethyl-8-oxo-2,3,8,13b-tetrahydro-1H-pyrido[2,1-a]pyrrolo[1,2-c]phthalazine-7-carboxylate and trifluoro(oxetan-3-yl)-14-borane, potassium salt in place of ethyl (R)-12-(3-methoxypropoxy)-3,3-dimethyl-8-oxo-11-((((trifluoromethyl)sulfonyl)oxy)-2,3,8,13b-tetrahydro-1H-pyrido[2,1-a]pyrrolo[1,2-c]phthalazine-7-carboxylate and cyclopropyltrifluoro-14-borane, potassium salt. $^1$H NMR (400 MHz, Chloroform-d) δ 9.83 (s, 1H), 8.55 (s, 1H), 7.57 (s, 1H), 7.15 (s, 1H), 6.76 (s, 1H), 4.24-4.08 (m, 2H), 3.57 (dd, J=5.4, 1.3 Hz, 2H), 3.37 (s, 3H), 2.99 (d, J=6.2 Hz, 2H), 2.80 (dd, J=7.1, 1.3 Hz, 2H), 2.54-2.34 (m, 3H), 2.19-2.02 (m, 3H), 1.89 (ddd, J=12.4, 7.8, 2.6 Hz, 1H), 1.71-1.55 (m, 1H), 1.37 (s, 3H), 0.66 (s, 3H). MS (m/z) 455.583 [M+H]+.

Example 78: (R)-11-methoxy-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid

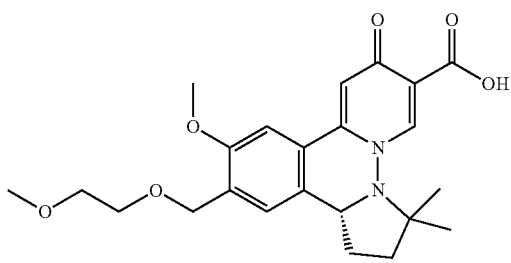

(R)-11-methoxy-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid was prepared similarly to example 44 using trifluoro((2-methoxyethoxy)methyl)-14-borane, potassium salt in place of 1-(difluoromethyl)-4-(4,4,5,5-tetramethyl-1,3,2-dioxaborolan-2-yl)-1H-pyrazole. $^1$H NMR (400 MHz, Chloroform-d) δ 8.58 (s, 1H), 7.49 (s, 1H), 7.19 (s, 1H), 7.14 (s, 1H), 4.80 (d, J=6.0 Hz, 1H), 4.65 (s, 2H), 3.90 (s, 3H), 3.75-3.71 (m, 2H), 3.65-3.61 (m, 2H), 3.43 (s, 3H), 2.54-2.37 (m, 2H), 1.89-1.83 (m, 1H), 1.65-1.55 (m, 1H), 1.37 (s, 3H), 0.65 (s, 3H). MS (m/z) 429.639 [M+H]$^+$.

Example 79: (R)-12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid

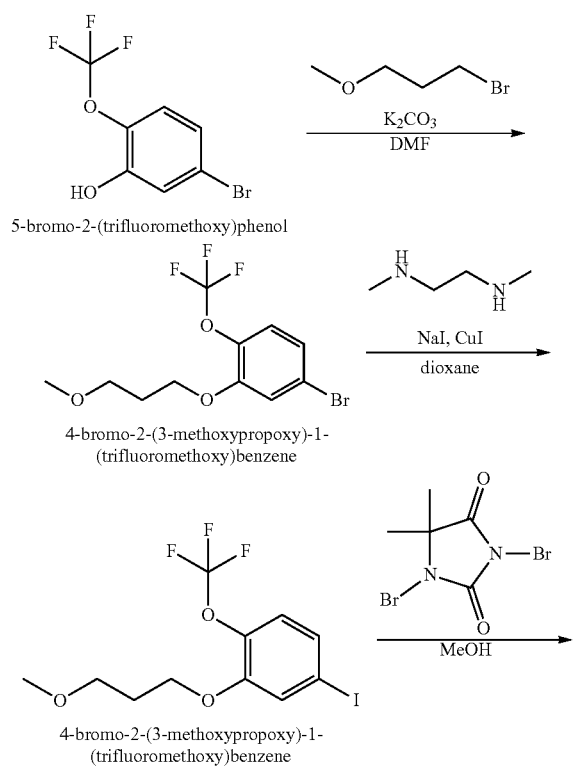

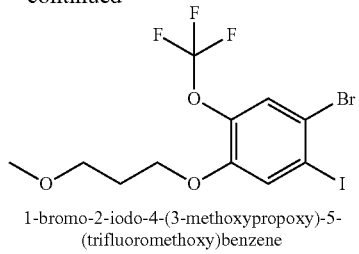

1-bromo-2-iodo-4-(3-methoxypropoxy)-5-(trifluoromethoxy)benzene

Synthesis of 4-Bromo-2-(3-methoxypropoxy)-1-(trifluoromethoxy)

4-Bromo-2-(3-methoxypropoxy)-1-(trifluoromethoxy) benzene was prepared similarly to 1-bromo-5-chloro-2-iodo-4-(3-methoxypropoxy)benzene using 5-bromo-2-(trifluoromethoxy)phenol in place of of 4-bromo-2-chloro-5-iodophenol.

Synthesis of 4-iodo-2-(3-methoxypropoxy)-1-(trifluoromethoxy)benzene

4-Bromo-2-(3-methoxypropoxy)-1-(trifluoromethoxy) benzene (6.01 g, 18.3 mmol), NaI (5.47 g, 36.5 mmol), CuI (348 mg, 1.83 mmol) and N,N'-dimethylethylenediamine (0.39 mL, 3.7 mmol) were combined in 18 mL dioxane. The reaction mixture was degassed by pulling vacuum and back-filling the reaction vessel with Ar 5×. After degassing, the stirred mixture was heated to 110° C. overnight. Upon completion, the mixture was cooled to RT, diluted with EtOAc, filtered over celite and concentrated under reduced pressure. The resulting residue was dissolved in EtOAc and washed successively with 5% ammonia, water and brine. The organics were dried over MgSO$_4$, filtered and concentrated to provide the title compound (6.59 g, 96%), which was carried on without further purification.

Synthesis of 1-bromo-2-iodo-4-(3-methoxypropoxy)-5-(trifluoromethoxy)benzene

4-Iodo-2-(3-methoxypropoxy)-1-(trifluoromethoxy)benzene (6.07 g, 16.1 mmol) was suspended in 32 mL MeOH and treated with DBDMH (11.07 g, 38.73 mmol). After stirring 3 days at RT, the reaction mixture was diluted with EtOAc, washed with saturated aqueous NaHCO$_3$ and brine, dried over MgSO$_4$, filtered and concentrated under reduced pressure. The crude residue wash purified by silica column chromatography (0% to 10% EtOAc/hex) to afford the title compound (6.37 g, 87%).

Synthesis of ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate Ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate was prepared similarly to ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate, using 1-bromo-2-iodo-4-(3-methoxypropoxy)-5-(trifluoromethoxy)benzene in place of 1-bromo-5-chloro-2-iodo-4-(3-methoxypropoxy)benzene.

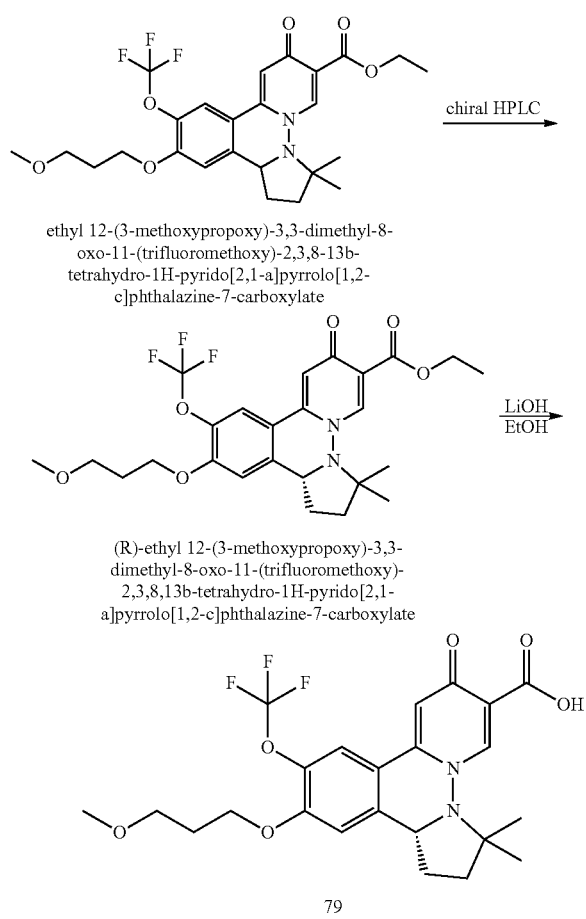

ethyl 12-(3-methoxypropoxy)-3,3-dimethyl-8-oxo-11-(trifluoromethoxy)-2,3,8-13b-tetrahydro-1H-pyrido[2,1-a]pyrrolo[1,2-c]phthalazine-7-carboxylate (R)-ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate

79

Purification of (R)-ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate Ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate was separated into its constituent enantiomers by reverse phase chiral HPLC using a Chirlapak AD-H column (SFC with 20% IPA). The R-enantiomer was assigned as the faster-eluting peak.

Synthesis of (R)-12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid (R)-12-(3-Methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid was prepared similarly to Example 4, using (R)-ethyl 12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate in place of ethyl 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Chloroform-d) δ 8.59 (s, 1H), 7.65 (d, J=1.3 Hz, 1H), 7.14 (s, 1H), 6.96 (s, 1H), 4.87 (d, J=6.2 Hz, 1H), 4.34-4.10 (m, 2H), 3.70-3.47 (m, 2H), 3.36 (s, 3H), 2.53 (dq, J=13.9, 7.9, 6.7 Hz, 1H), 2.12 (p, J=6.0 Hz, 2H), 1.94 (ddd, J=12.8, 8.0, 2.5 Hz, 1H), 1.65 (ddd, J=12.6, 10.7, 7.6 Hz, 1H), 1.39 (s, 3H), 0.69 (s, 3H). MS (m/z) 483.5 [M+H]$^+$.

Example 80: (R)-11-chloro-3,3-bis(methoxymethyl)-12-(3-methoxypropoxy)-8-oxo-2,3,8,13b-tetrahydro-1H-pyrido[2,1-a]pyrrolo[1,2-c]phthalazine-7-carboxylic acid

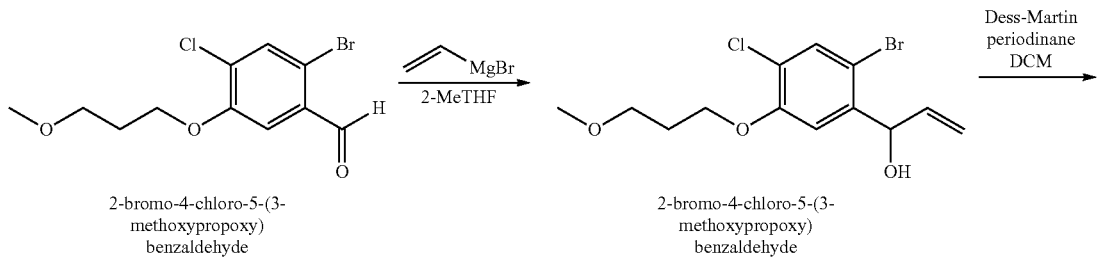

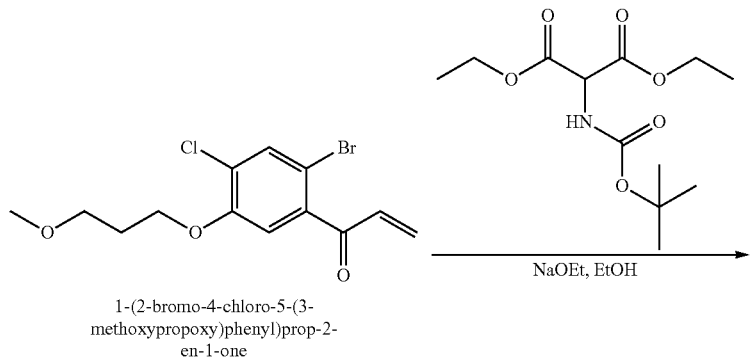

-continued

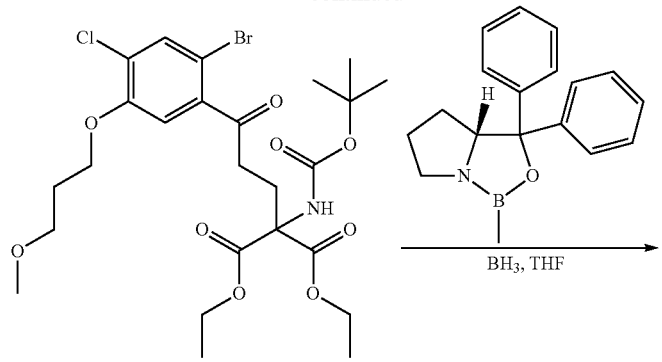

diethyl 2-(3-(2-bromo-4-chloro-5-(3-methoxypropoxy)phenyl)-3-oxopropyl)-2-((tert-butoxycarbonyl)amino)malonate

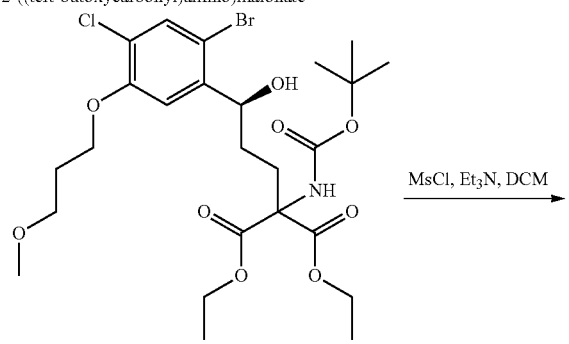

diethyl (S)-2-(3-(2-bromo-4-chloro-5-(3-methoxypropoxy)phenyl)-3-hydroxypropyl)-2-((tert-butoxycarbonyl)amino)malonate

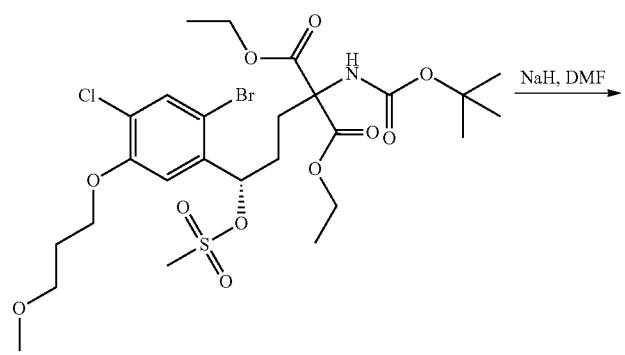

diethyl (S)-2-(3-2-bromo-4-chloro-5-(3-methoxypropoxy)phenyl)-3-((methylsulfonyl)oxy)propyl)-2-((tert-butoxycarbonyl)amino)malonate

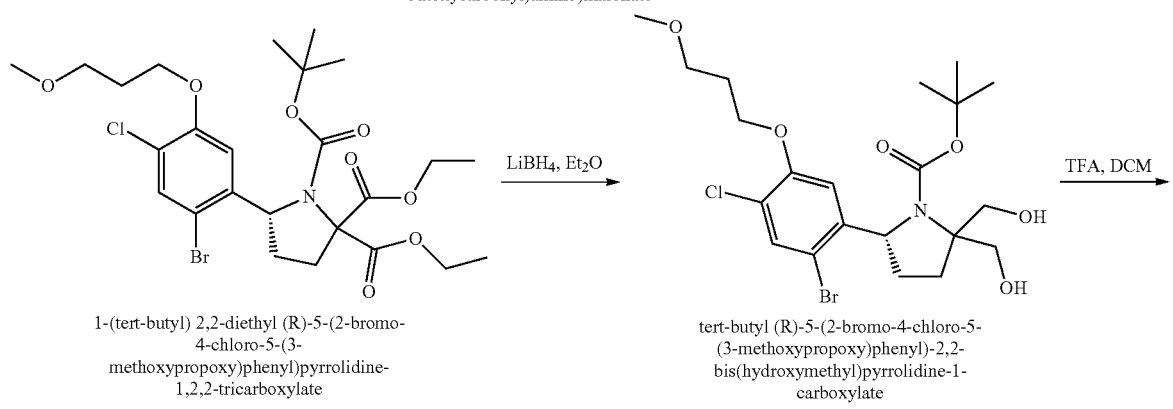

1-(tert-butyl) 2,2-diethyl (R)-5-(2-bromo-4-chloro-5-(3-methoxypropoxy)phenyl)pyrrolidine-1,2,2-tricarboxylate tert-butyl (R)-5-(2-bromo-4-chloro-5-(3-methoxypropoxy)phenyl)-2,2-bis(hydroxymethyl)pyrrolidine-1-carboxylate

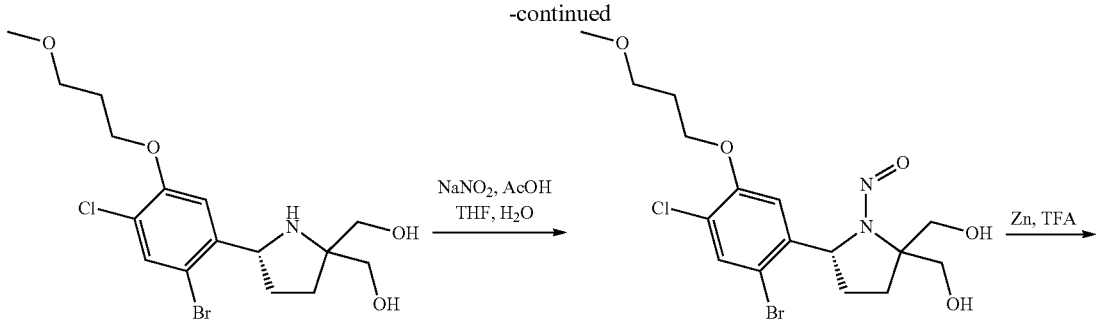
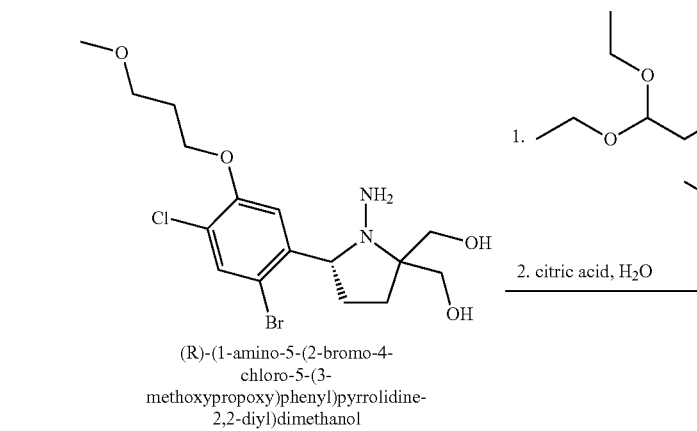
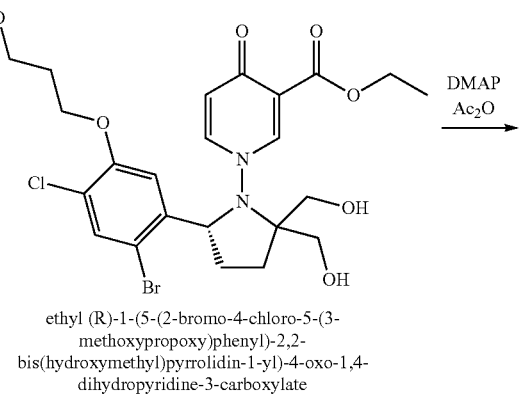
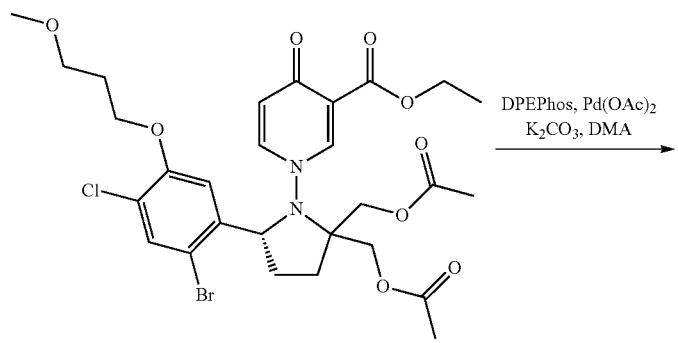

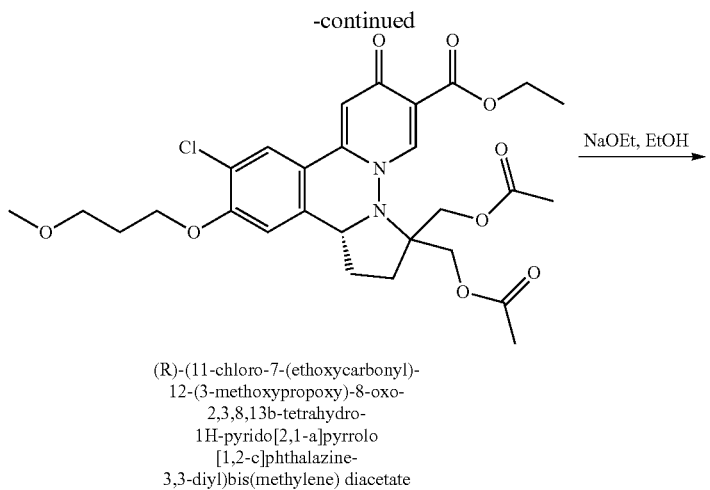

(R)-(11-chloro-7-(ethoxycarbonyl)-
12-(3-methoxypropoxy)-8-oxo-
2,3,8,13b-tetrahydro-
1H-pyrido[2,1-a]pyrrolo
[1,2-c]phthalazine-
3,3-diyl)bis(methylene) diacetate

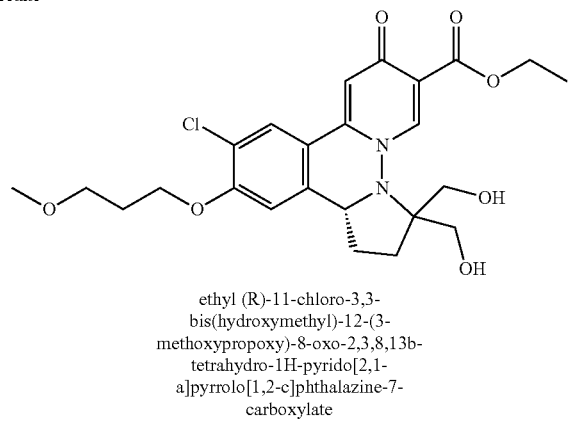

ethyl (R)-11-chloro-3,3-
bis(hydroxymethyl)-12-(3-
methoxypropoxy)-8-oxo-2,3,8,13b-
tetrahydro-1H-pyrido[2,1-
a]pyrrolo[1,2-c]phthalazine-7-
carboxylate Synthesis of 1-(2-bromo-4-chloro-5-(3-methoxypropoxy)phenyl)prop-2-en-1-ol To a solution of 2-bromo-4-chloro-5-(3-methoxypropoxy) benzaldehyde (1 g, 3.25 mmol) in 2-methyltetrahydrofuran (12 ml) was added dropwise over 20 minutes at −20° C. vinylmagnesium bromide (1M in tetrahydrofuran) (3.3 ml). The mixture was warmed to room temperature and stirred for 1 hour. The reaction was quenched with sat NH₄Cl (aq, 20 ml) and extracted with ethyl acetate (8 ml). The organic layer was washed with brine (20 ml). The organic layer was dried with anhydrous sodium sulfate, filtered, and concentrated. The crude product was taken to next step without further purification (1.09 g). ¹H NMR (400 MHz, Chloroform-d) δ 7.51 (s, 1H), 7.14 (s, 1H), 5.97 (ddd, J=17.1, 10.4, 5.4 Hz, 1H), 5.52 (d, J=5.5 Hz, 1H), 5.39 (dt, J=17.1, 1.4 Hz, 1H), 5.23 (dt, J=10.4, 1.3 Hz, 1H), 4.21-4.04 (m, 3H), 3.58 (t, J=6.1 Hz, 3H), 3.35 (s, 3H), 2.09 (q, J=6.1 Hz, 3H).

Synthesis of 1-(2-bromo-4-chloro-5-(3-methoxypropoxy)phenyl)prop-2-en-1-one

To a solution of 1-(2-bromo-4-chloro-5-(3-methoxypropoxy)phenyl)prop-2-en-1-ol (1.09 g, 3.25 mmol) in dichloromethane (20 ml) was added portionwise at 0° C. Dess-Martin periodinane (1.65 g, 3.9 mmol). The mixture was warmed to room temperature and stirred for 1 hour. The reaction mixture was washed with water (20 ml), followed by 1M NaHCO₃ (aq, 20 ml), and water (20 ml). The organic layer was dried with anhydrous sodium sulfate, filtered, and concentrated. Product was purified by silica chromatography using ethyl acetate in hexane (350 mg). ¹H NMR (400 MHz, Chloroform-d) δ 7.59 (s, 1H), 6.92 (s, 1H), 6.74 (dd, J=17.5, 10.5 Hz, 1H), 6.16 (dd, J=17.5, 1.0 Hz, 1H), 6.08 (dd, J=10.5, 1.0 Hz, 1H), 4.11 (t, J=6.2 Hz, 2H), 3.57 (t, J=6.0 Hz, 2H), 3.34 (s, 3H), 2.22-1.89 (m, 2H).

Synthesis of Diethyl 2-(3-(2-bromo-4-chloro-5-(3-methoxypropoxy)phenyl)-3-oxopropyl)-2-((tert-butoxycarbonyl)amino)malonate To a solution of 1-(2-bromo-4-chloro-5-(3-methoxypropoxy)phenyl)prop-2-en-1-one (3.8 g, 11.39 mmol) in ethanol (10 ml) was added diethyl 2-((tert-butoxycarbonyl)amino)malonate (2.9 ml, 11.39 mmol) followed by sodium ethoxide (0.08 g, 1.14 mmol). After stirring at room temperature for 1 hour, the mixture was concentrated, diluted with ethyl acetate (50 ml) and washed with water. The organic layer was dried with anhydrous sodium sulfate, filtered, and concentrated. Product was purified by silica chromatography using ethyl acetate in hexanes (5.4 g). ¹H NMR (400 MHz, Chloroform-d) δ 7.55 (s, 1H), 6.94 (s, 1H), 5.92 (s, 1H), 4.35-4.16 (m, 4H), 4.12 (t, J=6.1 Hz, 2H), 3.57 (t, J=6.1 Hz, 2H), 3.35 (s, 3H), 3.04-2.82 (m, 2H), 2.76-2.65 (m, 2H), 2.08 (p, J=6.1 Hz, 2H), 1.42 (s, 9H), 1.26 (t, J=7.1 Hz, 6H).

Synthesis of diethyl (S)-2-(3-(2-bromo-4-chloro-5-(3-methoxypropoxy)phenyl)-3-hydroxypropyl)-2-((tert-butoxycarbonyl)amino)malonate To a solution of borane dimethylsulfide complex in tetrahydrofuran (2M) (4.4 ml) and (R)-(+)-2-Methyl-CBSoxazaborolidine (0.16 g, 0.58 mmol) in tetrahydrofuran (20 ml) was added dropwise at 0° C. diethyl 2-(3-(2-bromo-4-chloro-5-(3-methoxypropoxy)phenyl)-3-oxopropyl)-2-((tert-butoxycarbonyl)amino)malonate (5.4 g, 8.87 mmol) in tetrahydrofuran (10 ml) over 1.5 h. After the addition was complete, mixture was stirred for 1 hour. The reaction was quenched with ethanol (40 ml) and the mixture was stirred for 30 minutes. The resulting solution was concentrated under vacuum and the product was purified by silica chromatography using ethyl acetate in hexanes (4.8 g). Enantiomeric ratio was determined to be 85:15 from NMR analysis of the Mosher amide of 1-(tert-butyl) 2,2-diethyl (R)-5-(2-bromo-4-chloro-5-(3-methoxypropoxy)phenyl)pyrrolidine-1,2,2-tricarboxylate in a subsequent step. $^1$H NMR (400 MHz, Chloroform-d) δ 7.47 (s, 1H), 7.15 (s, 1H), 5.90 (s, 1H), 4.95 (dd, J=8.4, 3.5 Hz, 1H), 4.22 (q, J=8.0, 6.1 Hz, 5H), 4.12 (t, J=6.2 Hz, 2H), 3.58 (t, J=6.1 Hz, 2H), 3.35 (s, 3H), 2.61-2.35 (m, 2H), 2.08 (p, J=6.2 Hz, 2H), 1.70-1.52 (m, 3H), 1.41 (s, 9H), 1.24 (t, J=7.1 Hz, 6H).

Synthesis diethyl (S)-2-(3-(2-bromo-4-chloro-5-(3-methoxypropoxy)phenyl)-3-((methylsulfonyl)oxy)propyl)-2-((tert-butoxycarbonyl)amino)malonate To a solution of diethyl (S)-2-(3-(2-bromo-4-chloro-5-(3-methoxypropoxy)phenyl)-3-hydroxypropyl)-2-((tert-butoxycarbonyl)amino)malonate (4 g, 6.6 mmol) and triethylamine (1.19 ml, 8.57 mmol) in dichloromethane (24 ml) was added dropwise methanesulfonyl chloride (0.56 ml, 7.25 mmol) at 0° C. The mixture was warmed to room temperature and stirred for 30 minutes. The resulting solution was washed with 0.1M HCl (aq, 40 ml). The organic layer was washed with dichloromethane (20 ml). The aqueous layers were back extracted with dichloromethane (20 ml). The organic layers were combined, dried with anhydrous sodium sulfate, filtered, and concentrated. Product was purified by silica chromatography using ethyl acetate in hexanes (3.6 g). $^1$H NMR (400 MHz, Chloroform-d) δ 7.52 (s, 1H), 7.02 (s, 1H), 5.89 (s, 1H), 5.79 (t, J=6.3 Hz, 1H), 4.32-4.15 (m, 2H), 4.11 (t, J=6.2 Hz, 2H), 3.58 (t, J=6.1 Hz, 2H), 3.35 (s, 3H), 2.92 (s, 3H), 2.54-2.29 (m, 2H), 2.08 (p, J=6.1 Hz, 2H), 1.89-1.69 (m, 3H), 1.40 (s, 9H), 1.26-1.21 (m, 6H).

Synthesis of 1-(tert-butyl) 2,2-diethyl (R)-5-(2-bromo-4-chloro-5-(3-methoxypropoxy)phenyl)pyrrolidine-1,2,2-tricarboxylate To a solution of diethyl (S)-2-(3-(2-bromo-4-chloro-5-(3-methoxypropoxy)phenyl)-3-((methylsulfonyl)oxy)propyl)-2-((tert-butoxycarbonyl)amino)malonate (3.6 g, 5.26 mmol) in dimethylformamide (12 ml) was added portionwise sodium hydride (0.15 g, 6.31 mmol). The reaction was stirred at 20° C. for 2 h and allowed to sit for 18 hours at 4° C. To the reaction was added acetic acid (0.32 g, 5.26 mmol) and the mixture was concentrated under vacuum. The product was extracted with ethyl acetate (50 ml) and washed twice with 5% LiCl (aq, 50 ml). The organic layer was dried with anhydrous sodium sulfate, filtered, and concentrated. The crude product was taken to next step without further purification (3.1 g). MS (m/z) δ16.0 [M+H]$^+$.

Synthesis of tert-butyl (R)-5-(2-bromo-4-chloro-5-(3-methoxypropoxy)phenyl)-2,2-bis(hydroxymethyl)pyrrolidine-1-carboxylate To a solution of 1-(tert-butyl) 2,2-diethyl (R)-5-(2-bromo-4-chloro-5-(3-methoxypropoxy)phenyl)pyrrolidine-1,2,2-tricarboxylate (2.9 g, 4.89 mmol) in diethyl ether (30 ml) was added 2M lithium borohydride in tetrahydrofuran (13.5 ml). The reaction was stirred at 20° C. for 4 h. To the reaction was added water (10 ml) and the mixture was stirred for 10 minutes. The product was extracted with ethyl acetate (50 ml) and washed twice with brine (50 ml). The organic layer was dried with anhydrous sodium sulfate, filtered, and concentrated. The crude product was taken to next step without further purification (3.1 g). MS (m/z) 509.7 [M+H]$^+$.

Synthesis of (R)-(5-(2-bromo-4-chloro-5-(3-methoxypropoxy)phenyl)pyrrolidine-2,2-diyl)dimethanol A solution of tert-butyl (R)-5-(2-bromo-4-chloro-5-(3-methoxypropoxy)phenyl)-2,2-bis(hydroxymethyl)pyrrolidine-1-carboxylate (2.49 g, 4.89 mmol) in dichloromethane (20 ml) and trifluoroacetic acid (20 ml) was stirred for 1 hour. The mixture was concentrated, diluted with isopropyl acetate (50 ml) and concentrated. The crude product was dissolved in isopropyl acetate (40 ml) and basified with 1.0M NaOH (40 ml). The organic layer was dried with anhydrous sodium sulfate, filtered, and concentrated. The crude product was taken to next step without further purification (1.9 g). MS (m/z) 410.2 [M+H]$^+$.

Synthesis of ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate Ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate was prepared analogously to Example 1 using (R)-(5-(2-bromo-4-chloro-5-(3-methoxypropoxy)phenyl)pyrrolidine-2,2-diyl)dimethanol in place of 2-(2-bromo-4-chloro-5-(3-methoxypropoxy)phenyl)pyrrolidine (1.2 g). $^1$H NMR (400 MHz, Chloroform-d) δ 7.51 (s, 1H), 6.89 (s, 1H), 5.40 (dd, J=8.9, 6.0 Hz, 1H), 4.36 (d, J=11.5 Hz, 1H), 4.16-3.99 (m, 5H), 3.52 (td, J=5.8, 1.7 Hz, 2H), 3.35 (s, 3H), 2.69-2.58 (m, 1H), 2.26-2.17 (m, 1H), 2.08-1.93 (m, 3H), 1.90-1.78 (m, 1H). MS (m/z) 438.9 [M+H]$^+$.

Synthesis of ethyl (R)-1-(5-(2-bromo-4-chloro-5-(3-methoxypropoxy)phenyl)-2,2-bis(hydroxymethyl)pyrrolidin-1-yl)-4-oxo-1,4-dihydropyridine-3-carboxylate A solution of ethyl (R)-11-hydroxy-12-(3-methoxypropoxy)-3,3-dimethyl-8-oxo-2,3,8,13b-tetrahydro-1H-pyrido[2,1-a]pyrrolo[1,2-c]phthalazine-7-carboxylate (1.17 g, 2.77 mmol) and ethyl (Z)-2-((dimethylamino)methylene)-5,5-diethoxy-3-oxopentanoate (0.87 g, 3.04 mmol) in ethanol (5 ml) was heated at 60° C. for 1 hour. A solution of citric acid (0.8 g, 4.15 mmol) in water (2.0 ml) and added and the reaction was stirred for 1 hour at 60° C. The mixture was concentrated, and the product was extracted with ethyl acetate (50 ml) and washed with water (50 ml), followed by 1M K$_2$HPO$_4$ (aq, 50 ml), and water (50 ml). The organic layer was dried with anhydrous sodium sulfate, filtered, and concentrated. Product was purified by silica chromatography using ethanol in dichloromethane (1.05 g). $^1$H NMR (400 MHz, Chloroform-d) δ 8.42 (s, 1H), 7.92 (s, 1H), 7.44 (s, 1H), 7.19 (s, 1H), 6.27 (s, 1H), 5.24 (t, J=7.8 Hz, 1H), 4.29 (q, J=7.1 Hz, 2H), 4.16 (s, 0H), 4.14-4.04 (m, 1H), 3.75-3.65

(m, 4H), 3.59 (q, J=5.9 Hz, 2H), 3.38 (s, 3H), 2.43 (s, 1H), 2.26-2.13 (m, 1H), 2.12-1.95 (m, 3H), 1.75-1.63 (m, 1H), 1.33 (t, J=7.1 Hz, 3H). MS (m/z) 575.30 [M+H]+.

Synthesis of (R)-(5-(2-bromo-4-chloro-5-(3-methoxypropoxy)phenyl)-1-(3-(ethoxycarbonyl)-4-oxopyridin-1(4H)-yl)pyrrolidine-2,2-diyl)bis(methylene) diacetate A solution of ethyl (R)-1-(5-(2-bromo-4-chloro-5-(3-methoxypropoxy)phenyl)-2,2-bis(hydroxymethyl)pyrrolidin-1-yl)-4-oxo-1,4-dihydropyridine-3-carboxylate (1.05 g, 1.83 mmol) and 4-dimethylaminopyridine (11.2 mg, 0.09 mmol) in acetic anhydride (10 ml) was heated at 60° C. for 1 hour. The mixture was concentrated, diluted with ethyl acetate (40 ml) and washed with water (2×40 ml). The aqueous layers were combined, back-extracted with ethyl acetate (40 ml), and organic layer was washed with water (40 ml). The organic layers were combined, dried with anhydrous sodium sulfate, filtered, and concentrated. Product was purified by silica chromatography using ethanol in dichloromethane (1.1 g). MS (m/z) δ59.3 [M+H]+.

Synthesis of (R)-(11-chloro-7-(ethoxycarbonyl)-12-(3-methoxypropoxy)-8-oxo-2,3,8,13b-tetrahydro-1H-pyrido[2,1-a]pyrrolo[1,2-c]phthalazine-3,3-diyl)bis(methylene) diacetate (11-chloro-7-(ethoxycarbonyl)-12-(3-methoxypropoxy)-8-oxo-2,3,8,13b-tetrahydro-1H-pyrido[2,1-a]pyrrolo[1,2-c]phthalazine-3,3-diyl)bis(methylene) diacetate was prepared analogously to Example 1 using (5-(2-bromo-4-chloro-5-(3-methoxypropoxy)phenyl)-1-(3-(ethoxycarbonyl)-4-oxopyridin-1 (4H)-yl)pyrrolidine-2,2-diyl)bis(methylene) diacetate in place of ethyl 1-(2-(2-bromo-4-chloro-5-(3-methoxypropoxy)phenyl)pyrrolidin-1-yl)-4-oxo-1,4-dihydropyridine-3-carboxylate (215 mg, 0.42 mmol). The crude product was taken to next step without further purification (1.1 g). MS (m/z) 577.5 [M+H]+.

Synthesis ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate To a solution of (R)-(11-chloro-7-(ethoxycarbonyl)-12-(3-methoxypropoxy)-8-oxo-2,3,8,13b-tetrahydro-1H-pyrido[2,1-a]pyrrolo[1,2-c]phthalazine-3,3-diyl)bis(methylene) diacetate (964.72 mg, 1.67 mmol) in ethanol (5 ml) was added sodium ethoxide (50.16 mg, 0.84 mmol). After stirring for 20 minutes, acetic acid (60 ul) was added and the mixture was concentrated under vacuum. Product was purified by silica chromatography using ethanol in dichloromethane (430 mg). 1H NMR (400 MHz, DMSO-d6) δ 8.44 (s, 1H), 8.06 (s, 1H), 7.16 (s, 1H), 6.83 (s, 1H), 4.94 (t, J=5.5 Hz, 1H), 4.76 (d, J=5.8 Hz, 1H), 4.41 (t, J=4.7 Hz, 1H), 4.29-4.10 (m, 3H), 3.54-3.41 (m, 4H), 3.24 (s, 3H), 2.94 (qd, J=11.2, 4.7 Hz, 2H), 2.62-2.52 (m, 1H), 2.23-2.09 (m, 1H), 1.97 (p, J=6.3 Hz, 2H), 1.69 (dd, J=12.9, 7.2 Hz, 1H), 1.32-1.19 (m, 4H). MS (m/z) 493.4 [M+H]+.

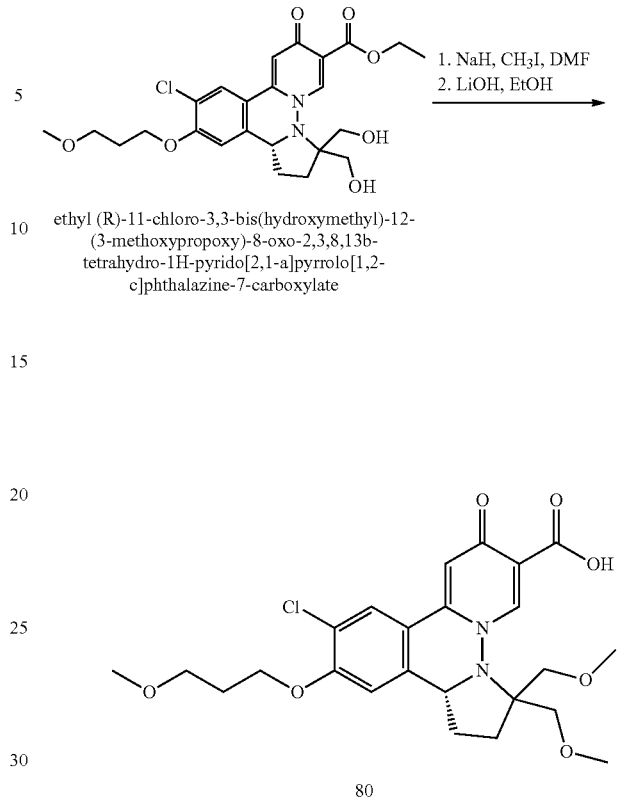

ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate

80

Synthesis of (R)-11-chloro-3,3-bis(methoxymethyl)-12-(3-methoxypropoxy)-8-oxo-2,3,8,13b-tetrahydro-1H-pyrido[2,1-a]pyrrolo[1,2-c]phthalazine-7-carboxylic acid To a solution of ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate (10 mg, 20.29 μmol) in dimethylformamide (200 μl) was added sodium hydride (2.3 mg, 101.4 μmol). After stirring for 1 min, iodomethane (6.31 μl, 101.43 μmol) was added the reaction was stirred for 1 hour. Additional sodium hydride (2.33 mg, 101.43 μmol) was added. After stirring for 20 minutes, the mixture was diluted with ethanol (0.5 ml) and 2M LiOH (aq, 300 ul). After stirring at room temperature for 30 minutes, the mixture was acidified with concentrated HCl (~50 ul) and concentrated under vacuum. The product was purified by preparative HPLC using acetonitrile in water with 0.1% trifluoroacetic acid (4.2 mg). 1H NMR (400 MHz, Chloroform-d) δ8.76 (s, 1H), 7.80 (s, 1H), 7.12 (s, 1H), 6.85 (d, J=1.0 Hz, 1H), 4.81 (t, J=3.4 Hz, 1H), 4.29-4.09 (m, 2H), 3.70-3.57 (m, 2H), 3.47-3.40 (m, 4H), 3.38 (s, 3H), 2.99 (d, J=10.5 Hz, 1H), 2.88 (d, J=10.6 Hz, 1H), 2.85 (s, 3H), 2.48-2.38 (m, 2H), 2.15 (p, J=6.1 Hz, 2H), 1.97-1.89 (m, 1H), 1.53-1.40 (m, 1H). MS (m/z) 493.4 [M+H]+.

Example 81: (R)-11-chloro-12-(3-methoxypropoxy)-2',2'-dimethyl-8-oxo-1,2,8,13b-tetrahydrospiro[pyrido[2,1-a]pyrrolo[1,2-c]phthalazine-3,5'-[1,3]dioxane]-7-carboxylic acid

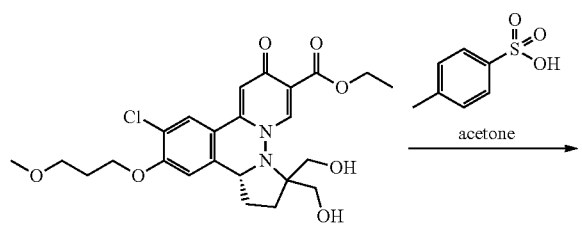

ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate

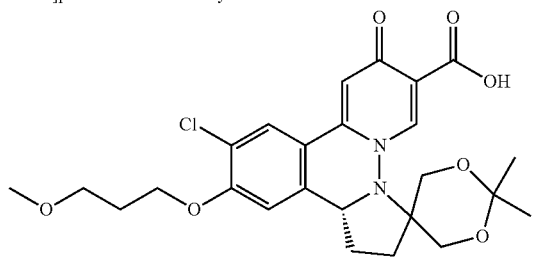

81

To a solution of ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate (10 mg, 20.3 mol) in acetone (0.4 ml) was added p-toluenesulfonic acid monohydrate (1.0 mg, 5.1 μmol) followed by 3 Å activated molecular sieves. The reaction was stirred 18 hours at 60° C. The mixture was filtered through celite and concentrated. The resulting crude mixture was diluted with ethanol (0.5 ml) and 2M LiOH (aq, 0.1 ml). After stirring at room temperature for 1 hour, the mixture was acidified with concentrated HCl and the product was purified by preparative HPLC using acetonitrile in water with 0.1% trifluoroacetic acid (6.4 mg). During purification ~15% of the starting diol was formed as a bi-product. $^1$H NMR (400 MHz, Chloroform-d) δ 9.05 (s, 1H), 7.85 (s, 1H), 7.23 (s, 1H), 6.88 (s, 1H), 4.83 (d, J=5.3 Hz, 1H), 4.30-4.15 (m, 2H), 4.09 (dd, J=12.1, 2.2 Hz, 1H), 3.86 (d, J=12.0 Hz, 1H), 3.71-3.57 (m, 2H), 3.49 (d, J=13.2 Hz, 1H), 3.39 (s, 4H), 3.21 (dd, J=13.1, 2.2 Hz, 1H), 2.57-2.34 (m, 2H), 2.20-2.12 (m, 2H), 1.85-1.72 (m, 1H), 1.46-1.33 (m, 1H), 1.30 (s, 3H), 1.14 (s, 3H). MS (m/z) 505.4 [M+H]$^+$.

Example 82: (R)-11'-chloro-12'-(3-methoxypropoxy)-8'-oxo-1',2',8',13b'-tetrahydrospiro[oxetane-3,3'-pyrido[2,1-a]pyrrolo[1,2-c]phthalazine]-7'-carboxylic acid

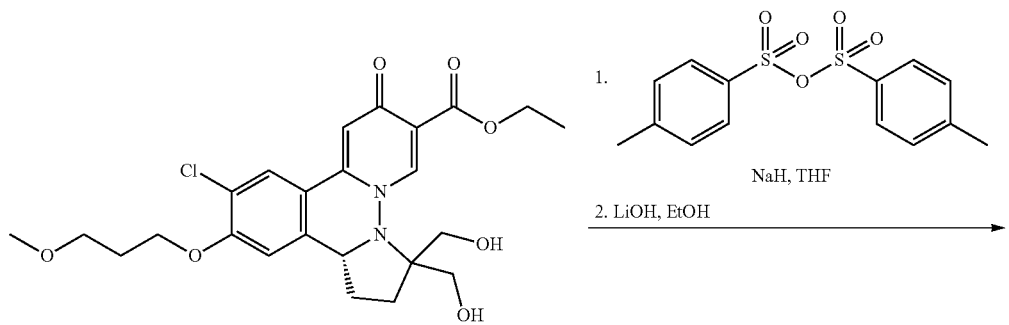

ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate

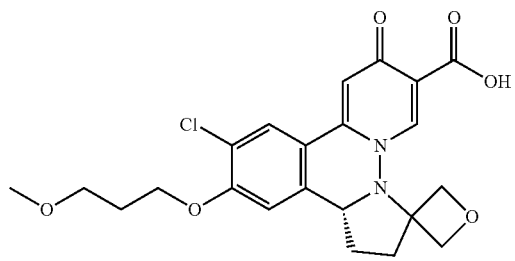

82

To a stirred solution of ethyl (R)-11-chloro-3,3-bis(hydroxymethyl)-12-(3-methoxypropoxy)-8-oxo-2,3,8,13b-tetrahydro-1H-pyrido[2,1-a]pyrrolo[1,2-c]phthalazine-7-carboxylate (10 mg, 0.02 mmol) in tetrahydrofuran (0.3 ml) was added sodium hydride (60% dispersion in mineral oil) (4.1 mg, 0.1 mmol). After stirring at room temperature for 5 minutes, the reaction was heated to 60° C. and a solution of p-toluenesulfonic anhydride (7.9 mg, 0.02 mmol) in tetrahydrofuran (0.3 ml) was added dropwise. After stirring for 30 minutes, the mixture was partially concentrated and diluted with ethanol (0.5 ml) and 2M LiOH (aq, 0.1 ml). After stirring at room temperature for 1 hour, the mixture was acidified with concentrated HCl and the product was purified by preparative HPLC using acetonitrile in water with 0.1% trifluoroacetic acid (3.1 mg). $^1$H NMR (400 MHz, Chloroform-d) δ 8.72 (s, 1H), 7.81 (s, 1H), 7.14 (s, 1H), 6.86 (s, 1H), 4.87 (d, J=7.4 Hz, 1H), 4.74 (t, J=3.6 Hz, 1H), 4.59 (d, J=7.4 Hz, 1H), 4.30-4.14 (m, 2H), 4.13 (d, J=7.4 Hz, 1H), 3.80 (d, J=7.4 Hz, 1H), 3.69-3.52 (m, 2H), 3.38 (s, 3H), 2.54 (dt, J=12.3, 5.6 Hz, 1H), 2.49-2.37 (m, 2H), 2.24 (dt, J=13.1, 9.1 Hz, 1H), 2.15 (p, J=6.0 Hz, 2H). MS (m/z) 447.4 [M+H]$^+$.

Example 83: (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid

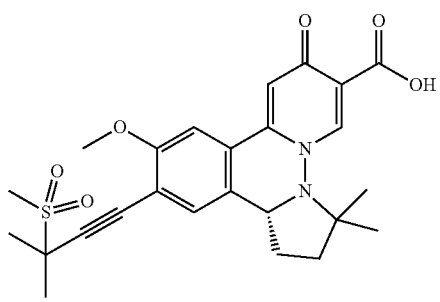

83

Pd(tBu$_2$PPh)$_2$Cl$_2$ (10.31 mg, 0.015 mmol) and CuI (4.056 mg, 0.021 mmol) were added into a round bottom flask (5 ml) containing ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (50 mg, 0.097 mmol) and 3-methyl-3-(methylsulfonyl)but-1-yne (70 mg, 0.484 mmol) in MeCN (0.6 ml) and Et3N (0.3 ml), after degassing the reaction mixture, it was stirred at 60° C. for 1 h. Sample of reaction mixture was taken for LC-MS and it showed the reaction was complete. The reaction mixture was cooled to rt, and quenched with thiol-linked silica, after stirring or 5 min, solid was filtered and was rinsed forward with 1:1 EtOH:MeCN. Filtrate was concentrate to dryness. The crude material was dissolved in EtOH (0.5 ml) and LiOH (0.5 ml, 1N) was added. The mixture was stirred for 30 min and then TFA was added to quench reaction. The solvent was stripped off, and the crude material was purified by HPLC. $^1$H NMR (400 MHz, Chloroform-d) δ 8.62 (s, 1H), 7.48-7.34 (m, 2H), 7.26 (s, 2H), 7.24 (s, 1H), 4.77 (d, J=5.5 Hz, 1H), 3.96 (s, 3H), 3.15 (s, 3H), 2.52-2.28 (m, 2H), 1.92 (ddd, J=12.6, 7.4, 3.1 Hz, 1H), 1.77 (s, 6H), 1.74-1.55 (m, 1H), 1.39 (s, 3H), 0.66 (s, 3H). MS (m/z) 485.11 (M+H$^+$).

Example 84: (R)-12-(3-(cyclopropylsulfonyl)-3-methylbut-1-yn-1-yl)-11-methoxy-3,3-dimethyl-8-oxo-2,3,8,13b-tetrahydro-1H-pyrido[2,1-a]pyrrolo[1,2-c]phthalazine-7-carboxylic acid

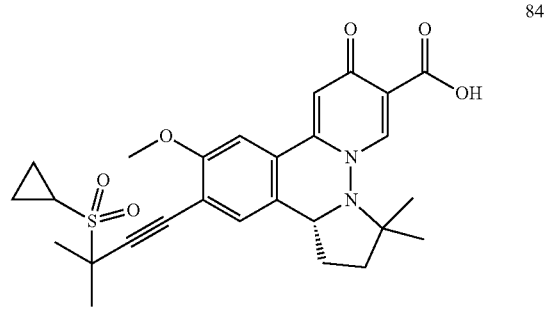 [SMILES: COc1cc2c(cc1C#CC(C)(C)S(=O)(=O)C1CC1)[C@H]1CCC(C)(C)N1n1cc(C(=O)O)c(=O)cc1-2]

84

Prepared similarly to (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid in Example 83 using ((2-methylbut-3-yn-2-yl)sulfonyl)cyclopropane in place of 3-methyl-3-(methylsulfonyl)but-1-yne. $^1$H NMR (400 MHz, Chloroform-d) δ 8.63 (s, 1H), 7.53 (s, 1H), 7.44-7.34 (m, 1H), 7.26 (s, 3H), 4.78 (d, J=5.3 Hz, 1H), 3.95 (s, 3H), 3.00-2.64 (m, 1H), 2.61-2.35 (m, 2H), 1.92 (ddd, J=12.5, 7.3, 3.3 Hz, 1H), 1.79 (s, 6H), 1.75-1.58 (m, 3H), 1.47-1.30 (m, 5H), 1.14 (ddd, J=7.6, 4.6, 2.6 Hz, 2H), 0.66 (s, 3H). MS (m/z) 511.5 (M+H$^+$).

Example 85: (R)-11'-chloro-12'-(3-methoxy-3-methylbut-1-yn-1-yl)-8'-oxo-1',2',8',13b'-tetrahydrospiro[cyclopropane-1,3'-pyrido[2,1-a]pyrrolo[1,2-c]phthalazine]-7'-carboxylic acid

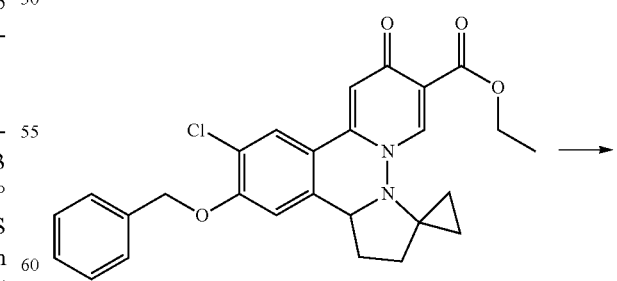

ethyl 12'-(benzyloxy)-11'-chloro-8'-oxo-1',2',8',13b'-tetrahydrospiro]cyclopropane-1,3'-pyrido[2,1-a]pyrrolo[1,2-c]phthalazine]-7'-carboxylate -continued

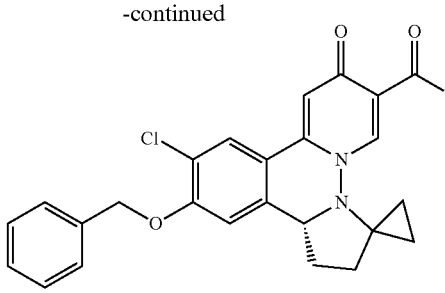

methyl (R)-12'-(benzyloxy)-11'-chloro-8'-oxo-1',2',8',13b'-tetrahydrospiro]cyclopropane-1,3'-pyrido[2,1-a]pyrrolo[2,1-c]phthalazine]-7'-carboxylate

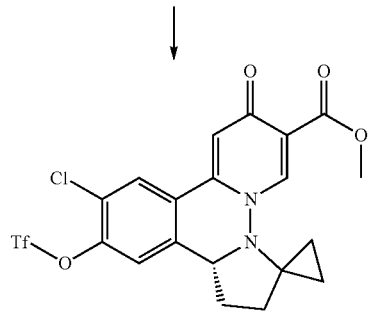

methyl (R)-11'-chloro-8'-oxo-12'-(((trifluoromethyl)sulfonyl)oxy)-1',2',8',13b'-tetrahydrospiro]cyclopropane-1,3'-pyrido[2,1-a]pyrrolo[1,2-c]phthalazine]-7'-carboxylate Synthesis of methyl (R)-12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate Ethyl 12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate was prepared similarly to ethyl 11-chloro-12-(3-methoxypropoxy)-8-oxo-2,3,8,13b-tetrahydro-1H-pyrido[2,1-a]pyrrolo[1,2-c]phthalazine-7-carboxylate in Example 1, but using tert-butyl 5-oxo-4-azaspiro[2.4]heptane-4-carboxylate in place of tert-butyl 2-oxopyrrolidine-1-carboxylate and 1-(benzyloxy)-4-bromo-2-chloro-5-iodobenzene in place of 1-bromo-5-chloro-2-iodo-4-(3-methoxypropoxy)benzene. Ethyl 12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate was separated into its enantiomers by chiral SFC chromatography using AD-H 5×250 mm columns with 40% methanol as the co-solvent. The (R)-enantiomer was found to be the faster eluting enantiomer. During separation and concentration of the solvent the ethyl ester was converted to the methyl ester. $^1$H NMR (400 MHz, Chloroform-d) δ 8.14 (s, 1H), 7.76 (s, 1H), 7.48-7.37 (m, 4H), 7.37-7.31 (m, 1H), 6.87 (s, 1H), 6.85 (s, 1H), 5.25 (d, J=2.1 Hz, 2H), 4.72 (d, J=5.9 Hz, 1H), 3.88 (s, 3H), 2.46 (s, 1H), 2.32 (d, J=9.3 Hz, 1H), 2.01 (dd, J=12.4, 9.6 Hz, 1H), 1.63-1.51 (m, 1H), 0.89-0.82 (m, 1H), 0.59 (dd, J=8.8, 5.4 Hz, 1H), 0.20 (d, J=10.7 Hz, 1H), 0.07 (d, J=10.2 Hz, 1H). MS (m/z) 463.7 [M+H]$^+$.

Synthesis of methyl (R)-11'-chloro-8'-oxo-12'-(((trifluoromethyl)sulfonyl)oxy)-1',2',8',13b'-tetrahydrospiro[cyclopropane-1,3'-pyrido[2,1-a]pyrrolo[1,2-c]phthalazine]-7'-carboxylate Prepared from methyl (R)-12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate in a manner similar to the preparation of (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate in Example 42. MS (m/z) 505.6 [M+H]$^+$.

Synthesis of (R)-11'-chloro-12'-(3-methoxy-3-methylbut-1-yn-1-yl)-8'-oxo-1',2',8',13b'-tetrahydrospiro[cyclopropane-1,3'-pyrido[2,1-a]pyrrolo[1,2-c]phthalazine]-7'-carboxylic acid

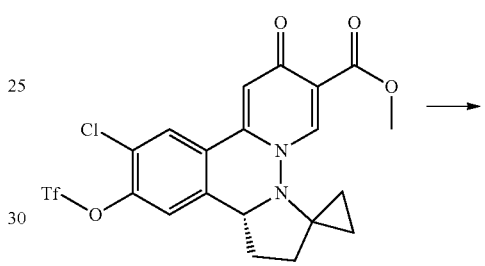

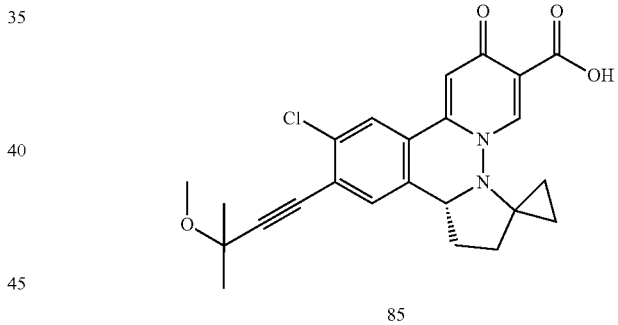

85

Prepared similarly to (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid in Example 83 using 3-methoxy-3-methylbut-1-yne to replace 3-methyl-3-(methylsulfonyl)but-1-yne and methyl (R)-11'-chloro-8'-oxo-12'-(((trifluoromethyl)sulfonyl)oxy)-1',2',8',13b'-tetrahydrospiro[cyclopropane-1,3'-pyrido[2,1-a]pyrrolo[1,2-c]phthalazine]-7'-carboxylate to replace ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate. $^1$H NMR (400 MHz, Chloroform-d) δ 8.44 (s, 1H), 7.84 (s, 1H), 7.51 (d, J=1.1 Hz, 1H), 7.26 (s, 2H), 7.16 (s, 1H), 5.04-4.59 (m, 1H), 3.47 (s, 3H), 3.36 (s, 2H), 2.57 (td, J=9.3, 8.8, 5.2 Hz, 2H), 2.15 (ddd, J=12.2, 8.5, 3.3 Hz, 1H), 1.77 (dt, J=12.9, 9.5 Hz, 1H), 1.59 (s, 6H), 1.46 (s, 4H), 0.66 (ddd, J=21.8, 10.9, 6.9 Hz, 2H), 0.11 (ddd, J=23.8, 10.9, 6.8 Hz, 2H). MS (m/z) 439.78 (M+H$^+$).

Example 86: (R)-11'-chloro-12'-(1-(oxetan-3-yl)-1H-pyrazol-4-yl)-8'-oxo-1',2',8',13b'-tetrahydrospiro[cyclopropane-1,3'-pyrido[2,1-a]pyrrolo[1,2-c]phthalazine]-7'-carboxylic acid

Example 87: (R)-11'-(methoxymethyl)-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid

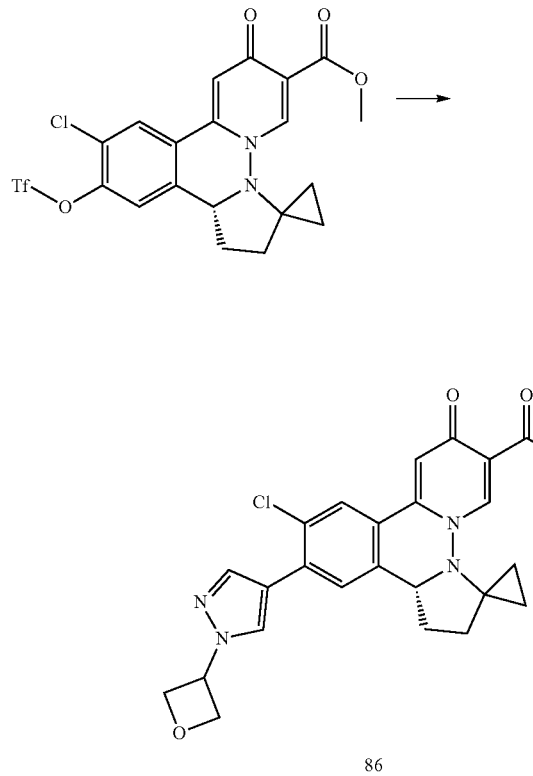

86

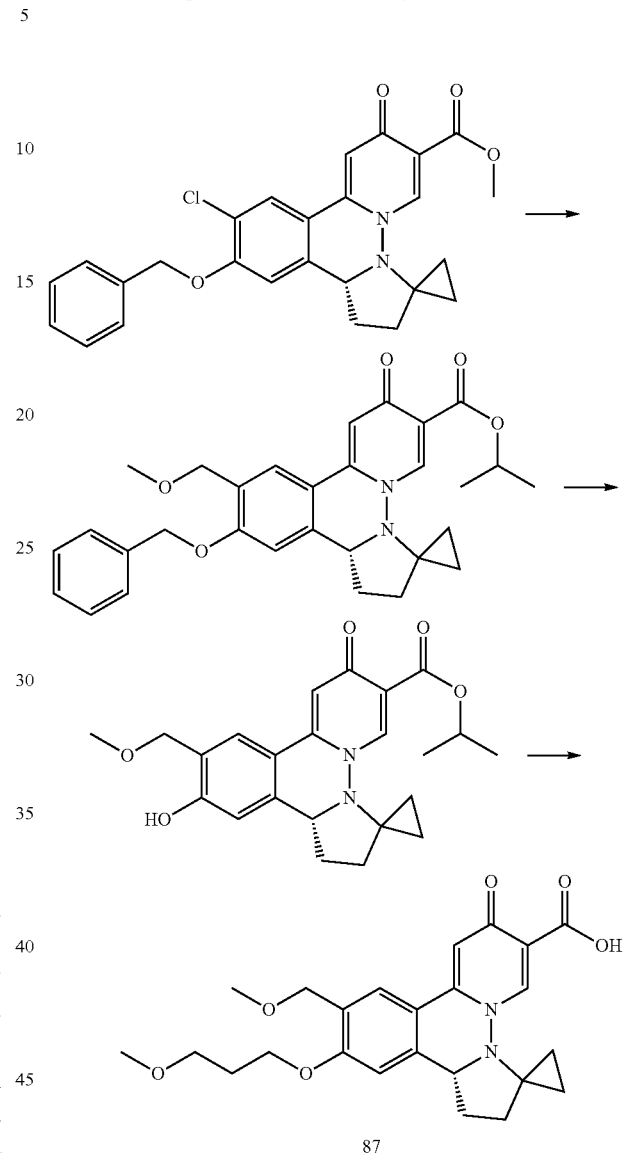

87

Methyl (R)-11'-chloro-8'-oxo-12'-((((trifluoromethyl)sulfonyl)oxy)-1',2',8',13b'-tetrahydrospiro[cyclopropane-1,3'-pyrido[2,1-a]pyrrolo[1,2-c]phthalazine]-7'-carboxylate (17 mg, 0.034 mmol) was combined with 1-(3-Oxetanyl)-1H-pyrazole-4-boronic acid pinacol ester (25 mg, 0.10 mmol), Dichloro 1,1-bis(diphenylphosphino)ferrocene palladium (II) dichloromethane (1.4 mg, 1.6 µmol), and potassium carbonate (14 mg, 0.10 mmol) in dioxane (1.7 mL) and water (0.3 mL) in a microwave vial. The mixture was heated under microwave irradiation at 120° C. for 10 minutes, then cooled to room temperature and 2N LiOH (0.1 mL) was added. After LCMS analysis indicated complete conversion, the mixture was diluted with TFA and water and extracted with ethyl acetate×2. The combined organic layers were concentrated, redissolved in DMF and purified by HPLC to provide (R)-11'-chloro-12'-(1-(oxetan-3-yl)-1H-pyrazol-4-yl)-8'-oxo-1',2',8',13b'-tetrahydrospiro[cyclopropane-1,3'-pyrido[2,1-a]pyrrolo[1,2-c]phthalazine]-7'-carboxylic acid. $^1$H NMR (400 MHz, Chloroform-d) δ 8.47 (s, 1H), 8.18 (s, 1H), 7.99 (s, 1H), 7.90 (s, 1H), 7.52 (s, 1H), 7.23 (s, 1H), 5.55 (t, J=6.8 Hz, 1H), 5.32-5.00 (m, 4H), 4.87 (d, J=5.4 Hz, 1H), 2.59 (d, J=10.0 Hz, 2H), 2.16 (s, 1H), 1.78 (d, J=10.8 Hz, 1H), 0.76-0.52 (m, 2H), 0.28--0.13 (m, 2H). MS (m/z) 465.60 (M+H$^+$).

Synthesis of Isopropyl (R)-12'-(benzyloxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylate Methyl (R)-12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate (234 mg, 0.51 mmol) was dissolved in isopropanol (10 mL) with 2 drops of acetic acid. The mixture was stirred at reflux for 2.5 hours, then cooled to room temperature to provide isopropyl (R)-12'-(benzyloxy)-11'-chloro-8'-oxo-1',2',8',13b'-tetrahydrospiro[cyclopropane-1,3'-pyrido[2,1-a]pyrrolo[1,2-c]phthalazine]-7'-carboxylate. MS (m/z) 491.3 [M+H]+. The crude ester was combined with trifluoro(methoxymethyl)-borane, potassium salt (230 mg, 1.52 mmol), Pd RuPhos G4 (52 mg, 0.061 mmol), RuPhos (42 mg, 0.091 mmol), and cesium carbonate (823 mg, 2.53 mmol) in toluene:water (3:1, 5 mL) under argon in a sealed vial. The mixture was heated at 110° C. for 45 minutes with vigorous stirring, then cooled to room temperature, the aqueous layer was removed, and the organics were concentrated in vacuo and purified by flash column chromatography (hexanes/ethyl acetate/ethanol/triethylamine) to provide isopropyl (R)-12'-(benzyloxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylate. MS (m/z) 501.4 [M+H]+.

Synthesis of (R)-11'-(methoxymethyl)-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid isopropyl (R)-12'-(benzyloxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylate (180 mg, 360 μmol)) was combined with Palladium on carbon (10 wt %, wet) E101 NE/W (5%, 38 mg) in ethanol (5 mL) under argon. The system was placed under vacuum and backfilled with hydrogen gas. The mixture was stirred vigorously for 45 minutes after which time LCMS analysis showed complete conversion. The mixture was diluted with DCM (50 mL) and filtered through celite. The supernatant was concentrated to provide crude isopropyl (R)-12'-hydroxy-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylate. The crude solids were combined with potassium carbonate (149 mg, 1.08 mmol) and 1-bromo-3-methoxypropane (166 mg, 1.08 mmol) in DMF (2 mL) and stirred at 80° C. for 75 minutes after which time LCMS analysis showed complete conversion. 1M lithium hydroxide (0.3 mL) was added and the mixture was stirred at 60° C. for 30 minutes. The mixture was cooled to rt, the aqueous layer was removed and the organic layer was diluted with 1M TFA and MeCN and purified by preparative HPLC to provide (R)-11'-(methoxymethyl)-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid as a TFA salt. $^1$H NMR (400 MHz, Acetonitrile-d3) δ 8.28 (s, 1H), 7.92 (s, 1H), 7.14 (s, 1H), 7.05 (s, 1H), 4.92 (d, J=6.0 Hz, 1H), 4.51 (ddt, J=4.5, 0.7 Hz, 2H), 4.33-4.11 (m, 2H), 3.57 (td, J=6.2, 0.7 Hz, 2H), 3.45 (s, 3H), 3.33 (s, 3H), 2.73-2.61 (m, 1H), 2.56-2.43 (m, 1H), 2.14-2.02 (m, 3H), 1.77 (dt, J=12.9, 9.6 Hz, 1H), 0.67 (dt, J=10.3, 6.5 Hz, 1H), 0.57 (dt, J=11.0, 6.8 Hz, 1H), 0.19-0.06 (m, 2H). $^{19}$F NMR (376 MHz, Acetonitrile-d3) δ−77.29. MS (m/z) 441.3 [M+H]$^+$.

Example 88: (R)-12-(3-(((1-(Difluoromethyl)cyclopropyl)carbamoyl)oxy)propoxy)-11-(methoxymethyl)-3,3-dimethyl-8-oxo-2,3,8,13b-tetrahydro-H-pyrido[2,1-a]pyrrolo[1,2-c]phthalazine-7-carboxylic acid

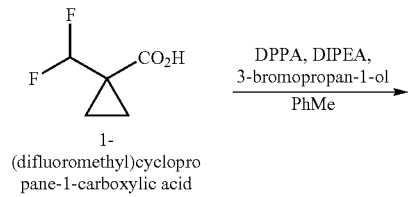

1-(difluoromethyl)cyclopropane-1-carboxylic acid

DPPA, DIPEA,
3-bromopropan-1-ol
PhMe

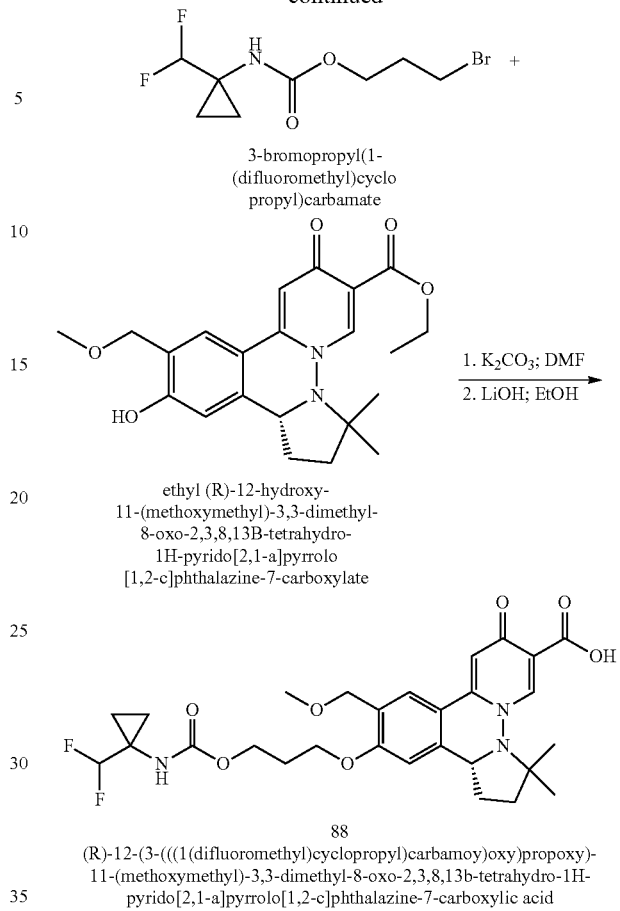

3-bromopropyl(1-(difluoromethyl)cyclopropyl)carbamate ethyl (R)-12-hydroxy-11-(methoxymethyl)-3,3-dimethyl-8-oxo-2,3,8,13B-tetrahydro-1H-pyrido[2,1-a]pyrrolo[1,2-c]phthalazine-7-carboxylate 1. K$_2$CO$_3$; DMF
2. LiOH; EtOH 88
(R)-12-(3-(((1(difluoromethyl)cyclopropyl)carbamoy)oxy)propoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid Synthesis of 3-bromopropyl (1-(difluoromethyl)cyclopropyl)carbamate 1-(Difluoromethyl)cyclopropane-1-carboxylic acid (2.00 g, 14.7 mmol) was suspended in PhMe (8 mL). DIPEA (3.33 mL, 19.1 mmol) and DPPA (3.33 mL, 15.4 mmol) were added and the reaction mixture was stirred at reflux for 1.5 h. After cooling to RT, 3-bromopropan-1-ol (0.53 mL, 5.9 mmol) and DCM (8 mL) were added. The reaction mixture was stirred o/n at RT. Upon completion, the reaction mixture was concentrated under reduced pressure. The crude residue was purified by silica column chromatography (0% to 30% EtOAc/hex) to provide 3-bromopropyl (1-(difluoromethyl)cyclopropyl)carbamate (1.60 g, 87%).

Synthesis of (R)-12-(3-(((1-(difluoromethyl)cyclopropyl)carbamoyl)oxy)propoxy)-1-(methoxymethyl)-3,3-dimethyl-8-oxo-2,3,8,13b-tetrahydro-H-pyrido[2,1-a]pyrrolo[1,2-c]phthalazine-7-carboxylic acid The title compound was prepared similarly to (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (Example 73), substituting 3-bromopropyl (1-(difluoromethyl)cyclopropyl)carbamate for 1-bromo-3-methoxypropane. $^1$H NMR (400 MHz, Chloroform-d) δ 8.57 (s, 1H), 7.85 (s, 1H), 7.29 (s, 1H), 6.78 (s, 1H), 5.84 (t, J=57.7 Hz, 1H), 5.57 (s, 1H), 4.83 (d, J=5.9 Hz, 1H), 4.49 (s, 2H), 4.28 (t, J=5.9 Hz, 2H), 4.14 (dd, J=11.1, 5.0 Hz, 2H), 3.49 (s, 3H), 2.27-2.07 (m, 2H), 1.90 (ddd, J=12.8, 7.5, 2.6 Hz, 1H), 1.62 (td, J=11.6, 7.7 Hz, 1H), 1.37 (s, 3H), 1.11 (q, J=5.6 Hz, 2H), 0.95 (p, J=2.7 Hz, 2H), 0.64 (s, 3H). MS (m/z) 562.6 [M+H]+.

Example 89: (R)-3,3-dimethyl-12-(3-methyl-3-(methylsulfonyl)but-1-yn-1-yl)-8-oxo-11-(trifluoromethoxy)-2,3,8,13b-tetrahydro-1H-pyrido[2,1-a]pyrrolo[1,2-c]phthalazine-7-carboxylic acid

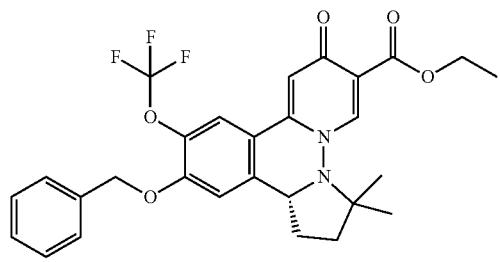

ethyl (R)-12-(benzyloxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate

→

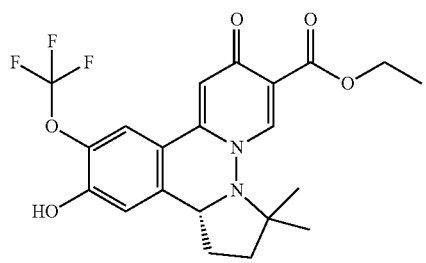

ethyl (R)-12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate

→

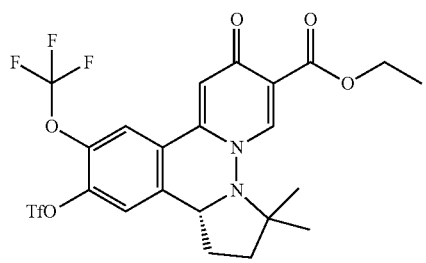

ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate

→

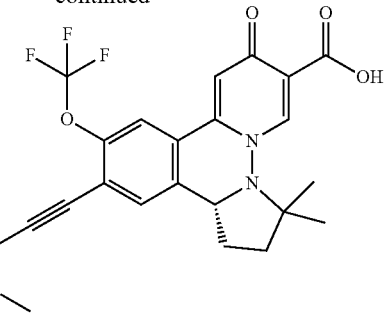

89

Synthesis of ethyl (R)-12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate (JZ-B)

The title compound was prepared similarly to ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate in example 14 using ethyl (R)-12-(benzyloxy)-3,3-dimethyl-8-oxo-11-(trifluoromethoxy)-2,3,8,13b-tetrahydro-1H-pyrido[2,1-a]pyrrolo[1,2-c]phthalazine-7-carboxylate in place of ethyl (R)-12-(benzyloxy)-11-methoxy-3,3-dimethyl-8-oxo-2,3,8,13b-tetrahydro-1H-pyrido[2,1-a]pyrrolo[1,2-c]phthalazine-7-carboxylate: MS (m/z) 439.15 [M+H]+.

Synthesis of ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate The title compound was prepared similarly to ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate in example 42 using ethyl (R)-12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate in place of ethyl (R)-12-hydroxy-11-methoxy-3,3-dimethyl-8-oxo-2,3,8,13b-tetrahydro-1H-pyrido[2,1-a]pyrrolo[1,2-c]phthalazine-7-carboxylate: MS (m/z) 571.15 [M+H]+.

Synthesis of (R)-3,3-dimethyl-12-(3-methyl-3-(methylsulfonyl)but-1-yn-1-yl)-8-oxo-11-(trifluoromethoxy)-2,3,8,13b-tetrahydro-1H-pyrido[2,1-a]pyrrolo[1,2-c]phthalazine-7-carboxylic acid (89)

The title compound was prepared similarly to (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid in example 83 using ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate in place of ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate: $^1$H NMR (400 MHz, Chloroform-d) δ 8.66 (s, 1H), 7.72 (d, J=1.5 Hz, 1H), 7.55 (d, J=1.0 Hz, 1H), 7.44 (s, 1H), 4.83 (d, J=6.2 Hz, 1H), 3.09 (s, 3H), 2.70-2.34 (m, 2H), 1.98 (ddd, J=12.8, 8.0, 2.7 Hz, 1H), 1.78 (s, 6H), 1.67 (ddd, J=13.0, 10.9, 7.8 Hz, 1H), 1.41 (s, 3H), 0.67 (s, 3H). MS (m/z): 539.11 [M+H]+.

Example 90: (R)-12-(3-methoxy-3-methylbut-1-yn-1-yl)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid

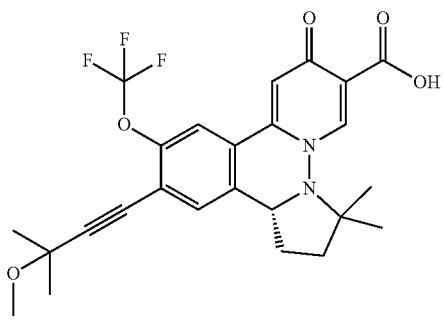

90

The title compound was prepared similarly to (R)-1-Methoxy-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 43 using ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate in place of ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate: MS (m/z): 491.49 [M+H]+. 1H NMR (400 MHz, Chloroform-d) δ 8.60 (s, 1H), 7.66 (d, J=1.4 Hz, 1H), 7.49 (d, J=1.1 Hz, 1H), 7.21 (s, 1H), 4.81 (d, J=6.2 Hz, 1H), 3.44 (s, 3H), 2.62-2.32 (m, 2H), 1.95 (ddd, J=12.8, 8.0, 2.8 Hz, 1H), 1.66 (ddd, J=12.7, 10.7, 7.8 Hz, 1H), 1.57 (s, 6H), 1.40 (s, 3H), 0.68 (s, 3H).

Example 91: (R)-3,3-dimethyl-8-oxo-12-(2-(3-oxo-[1,2,4]triazolo[4,3-a]pyridin-2(3H)-yl)ethoxy)-11-(trifluoromethoxy)-2,3,8,13b-tetrahydro-H-pyrido[2,1-a]pyrrolo[1,2-c]phthalazine-7-carboxylic acid

91

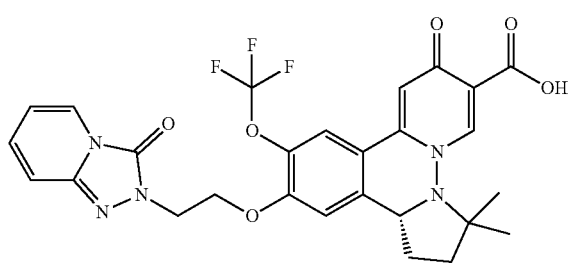

The title compound was prepared similarly to (R)-12-(3-(((1-(Difluoromethyl)cyclopropyl)carbamoyl)oxy)propoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 88 using (R)-ethyl 12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate and 2-(2-bromoethyl)-[1,2,4]triazolo[4,3-a]pyridin-3(2H)-one in place of (R)-ethyl 12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate and 3-bromopropyl (1-(difluoromethyl)cyclopropyl)carbamate: MS (m/z): 572.20 [M+H]+. 1H NMR (400 MHz, Chloroform-d) δ 8.58 (s, 1H), 7.79 (dt, J=7.1, 1.3 Hz, 1H), 7.62 (d, J=1.3 Hz, 1H), 7.22-7.03 (m, 3H), 6.98 (s, 1H), 6.56 (ddd, J=7.2, 6.1, 1.3 Hz, 1H), 4.78 (d, J=6.3 Hz, 1H), 4.64-4.39 (m, 4H), 2.65-2.34 (m, 2H), 1.92 (ddd, J=11.0, 8.0, 2.7 Hz, 1H), 1.62 (td, J=11.5, 7.6 Hz, 1H), 1.38 (s, 3H), 0.67 (d, J=8.1 Hz, 3H).

Example 92: (R)-12-((3-cyanobicyclo[1.1.1]pentan-1-yl)methoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid

92

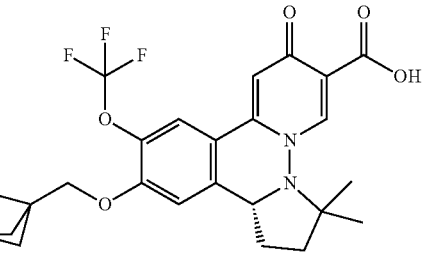

The title compound was prepared similarly to (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 74 using ethyl (R)-12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate in place of (R)-ethyl 12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate: MS (m/z): 516.28 [M+H]+). 1H NMR (400 MHz, Chloroform-d) δ 8.61 (s, 1H), 7.69 (d, J=1.3 Hz, 1H), 7.29 (s, 1H), 6.83 (s, 1H), 4.82 (d, J=6.4 Hz, 1H), 4.19-4.02 (m, 2H), 2.54 (dd, J=11.3, 6.3 Hz, 1H), 2.36 (s, 7H), 1.95 (ddd, J=11.2, 8.0, 2.6 Hz, 1H), 1.69-1.55 (m, 1H), 1.40 (d, J=2.0 Hz, 3H), 0.68 (s, 3H).

Example 93: (R)-3,3-dimethyl-12-(1-(oxetan-3-yl)-1H-pyrazol-4-yl)-8-oxo-11-(trifluoromethoxy)-2,3,8,13b-tetrahydro-1H-pyrido[2,1-a]pyrrolo[1,2-c]phthalazine-7-carboxylic acid

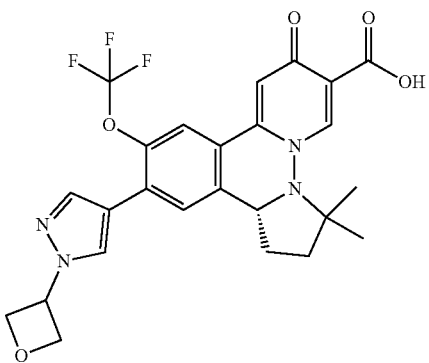

93

The title compound was prepared similarly to (R)-11-chloro-12-(1-(difluoromethyl)-1H-pyrazol-4-yl)-3,3-dimethyl-8-oxo-2,3,8,13b-tetrahydro-1H-pyrido[2,1-a]pyrrolo[1,2-c]phthalazine-7-carboxylic acid in example 76 using (R)-ethyl 3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate and 1-(oxetan-3-yl)-4-(4,4,5,5-tetramethyl-1,3,2-dioxaborolan-2-yl)-1H-pyrazole in place of ethyl (R)-11-chloro-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate and 1-(difluoromethyl)-4-(4,4,5,5-tetramethyl-1,3,2-dioxaborolan-2-yl)-1H-pyrazole: MS (m/z): 517.16 [M+H]$^+$. $^1$H NMR (400 MHz, Chloroform-d) δ 8.63 (s, 1H), 8.07 (d, J=0.8 Hz, 1H), 8.02 (s, 1H), 7.74 (d, J=1.5 Hz, 1H), 7.58 (d, J=1.1 Hz, 1H), 7.32 (s, 1H), 5.62-5.48 (m, 1H), 5.23-5.03 (m, 4H), 4.88 (t, J=6.6 Hz, 1H), 2.55 (dd, J=16.5, 9.3 Hz, 2H), 1.97 (ddd, J=11.3, 7.9, 2.9 Hz, 1H), 1.69 (td, J=11.2, 7.7 Hz, 1H), 1.42 (s, 3H), 0.71 (s, 3H).

Example 94: (R)-11-(methoxymethyl)-12-(3-(oxetan-3-yloxy)propoxy)-8-oxo-2,3,8,13b-tetrahydro-1H-pyrido[2,1-a]pyrrolo[1,2-c]phthalazine-7-carboxylic acid

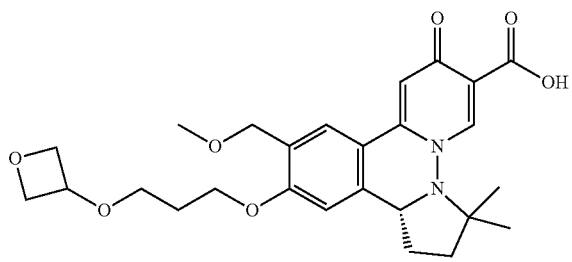 [SMILES: CC1(C)CC[C@@H]2c3cc(OCCCOC4COC4)c(Cl)cc3-c3cc(=O)c(C(=O)O)cn3N21]

94

Prepared analogously to (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 74 using 3-(oxetan-3-yloxy)propan-1-ol in place of 3-(hydroxymethyl)bicyclo[1.1.1]pentane-1-carbonitrile. This compound was free based prior to lyophilization. $^1$H NMR (400 MHz, Acetonitrile-d3) δ 8.40 (s, 1H), 7.87 (s, 1H), 7.13 (s, 1H), 6.97 (s, 1H), 4.86 (d, J=6.3 Hz, 1H), 4.72 (td, J=6.2, 0.9 Hz, 2H), 4.60-4.52 (m, 1H), 4.51-4.41 (m, 4H), 4.22 (ddt, J=27.9, 9.7, 6.1 Hz, 2H), 3.56 (t, J=6.2 Hz, 2H), 3.41 (s, 3H), 2.62-2.36 (m, 2H), 2.05 (p, J=6.2 Hz, 2H), 1.89 (ddd, J=12.7, 8.0, 2.9 Hz, 1H), 1.61 (ddd, J=12.7, 10.6, 7.9 Hz, 1H), 1.35 (s, 3H), 0.63 (s, 3H). MS (m/z) 485.6 [M+H]$^+$.

Example 95: (R)-11-(methoxymethyl)-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid

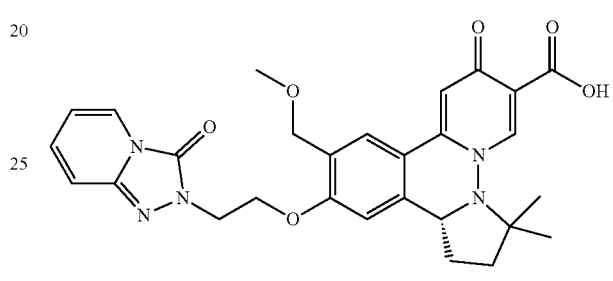

95

Prepared analogously to (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid in example 73 using 2-(2-bromoethyl)-[1,2,4]triazolo[4,3-a]pyridin-3(2H)-one in place of 1-bromo-3-methoxypropane. $^1$H NMR (400 MHz, Acetonitrile-d3) δ 8.44 (s, 1H), 7.85 (s, 1H), 7.70 (dt, J=7.1, 1.2 Hz, 1H), 7.18 (s, 1H), 7.15 (ddd, J=9.5, 6.2, 1.3 Hz, 1H), 7.09 (dt, J=9.5, 1.2 Hz, 1H), 6.97 (s, 1H), 6.54 (ddd, J=7.2, 6.2, 1.2 Hz, 1H), 4.83 (d, J=6.4 Hz, 1H), 4.61-4.44 (m, 2H), 4.44-4.26 (m, 4H), 3.30 (s, 3H), 2.60-2.38 (m, 2H), 1.88 (ddd, J=12.7, 8.0, 2.9 Hz, 1H), 1.59 (ddd, J=12.7, 10.5, 7.9 Hz, 1H), 1.35 (s, 3H), 0.60 (s, 3H). $^{19}$F NMR (376 MHz, Acetonitrile-d3) δ−77.34. MS (m/z) 532.5 [M+H]$^+$.

Example 96: (R)-11-cyclopropyl-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid

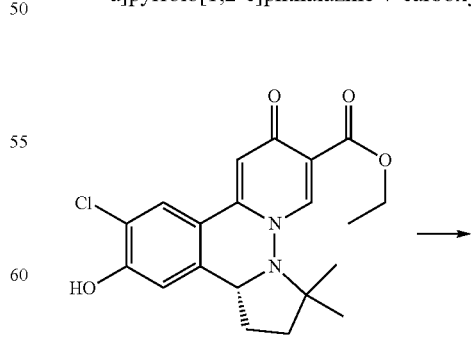

ethyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate

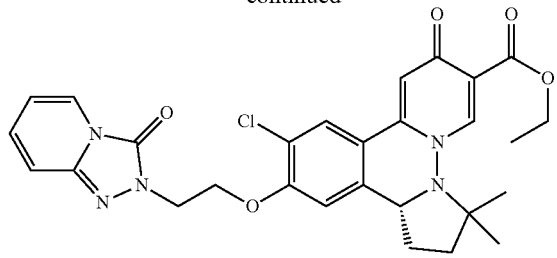

ethyl (R)-11-chloro-3,3-dimethyl-8-oxo-12-(2-
(3-oxo-[1,2,4]triazolo[4,3-a]pyridin-2(3H)-
yl)ethoxy)2,3,8,13b-tetrahydro-1H-
pyrido[2,1-a]pyrrolo[1,2-c]phthalazine]-7-
carboxylate

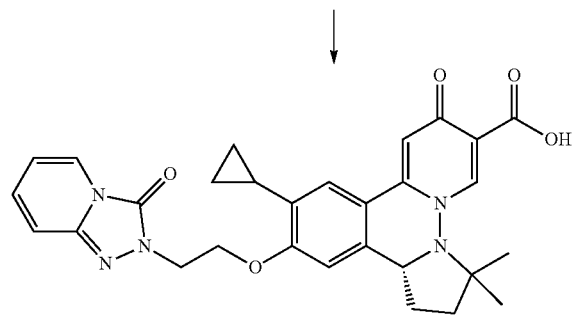

96
(R)-11-cyclopropyl-3,3-dimethyl-8-oxo-
12-(2-(3-oxo-[1,2,4]triazolo[4,3-a]
pyridin-2(3H)-yl)ethoxy)2,3,8,13b-
tetrahydro-1H-pyrido[2,1-a]pyrrolo[2,1-c]
phthalazine]-7-carboxylic acid Ethyl (R)-11-chloro-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylate Prepared analogously to (R)-11-(methoxymethyl)-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid in example 95 using ethyl (R)-1-chloro-12-hydroxy-3,3-dimethyl-8-oxo-2,3,8,13b-tetrahydro-1H-pyrido[2,1-a]pyrrolo[1,2-c]phthalazine-7-carboxylate in place of ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate. MS (m/z) 550.3 [M+H]+.

(R)-11-cyclopropyl-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid Prepared analogously to (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 71 using ethyl (R)-1-chloro-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylate in place of ethyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Acetonitrile-d3) δ 8.41 (s, 1H), 7.70 (dt, J=7.1, 1.2 Hz, 1H), 7.29 (s, 1H), 7.18 (s, 1H), 7.17-7.12 (m, 1H), 7.09 (dt, J=9.5, 1.2 Hz, 1H), 6.92 (s, 1H), 6.55 (ddd, J=7.2, 6.2, 1.1 Hz, 1H), 4.80 (d, J=6.3 Hz, 1H), 4.53 (qt, J=10.4, 5.2 Hz, 2H), 4.38 (t, J=5.2 Hz, 2H), 2.47-2.33 (m, 2H), 2.11-2.02 (m, 1H), 1.86 (ddd, J=12.7, 8.0, 2.7 Hz, 1H), 1.58 (td, J=11.4, 7.8 Hz, 1H), 1.34 (s, 3H), 0.91-0.79 (m, 2H), 0.70-0.64 (m, 2H), 0.60 (s, 3H). $^{19}$F NMR (376 MHz, Acetonitrile-d3) δ−77.33. MS (m/z) 528.4 [M+H]+.

Example 97: (R)-12-(3-methoxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid

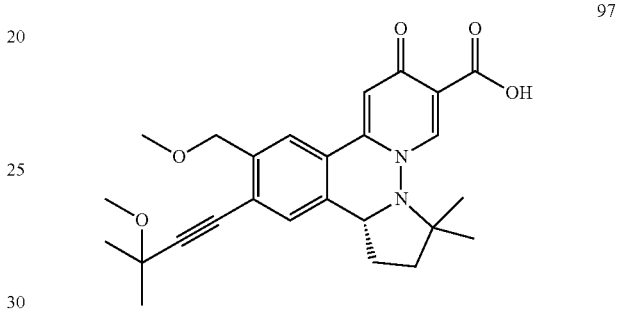

97

Prepared analogously to (R)-12-(3-hydroxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 70 using 3-methoxy-3-methylbut-1-yne in place of 2-methylbut-3-yn-2-ol. $^1$H NMR (400 MHz, Acetonitrile-d3) δ 8.47 (s, 1H), 8.01 (s, 1H), 7.54 (s, 1H), 7.30 (s, 1H), 4.88 (d, J=6.1 Hz, 1H), 4.68-4.57 (m, 2H), 3.46 (s, 3H), 3.42 (s, 3H), 2.57-2.43 (m, 2H), 1.94-1.87 (m, 1H), 1.68-1.58 (m, 1H), 1.56 (s, 6H), 1.37 (s, 3H), 0.63 (s, 3H). $^{19}$F NMR (376 MHz, Acetonitrile-d3) δ−77.33. MS (m/z) 451.5 [M+H]+.

Example 98: (R)-11-chloro-3,3-dimethyl-12-(3-(oxetan-3-yloxy)propoxy)-8-oxo-2,3,8,13b-tetrahydro-1H-pyrido[2,1-a]pyrrolo[1,2-c]phthalazine-7-carboxylic acid

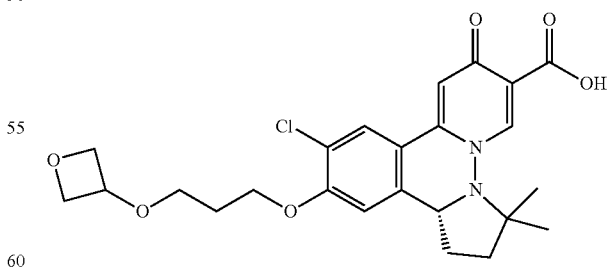

Prepared analogously to (R)-11-(methoxymethyl)-3,3-dimethyl-12-(3-(oxetan-3-yloxy)propoxy)-8-oxo-2,3,8,13b-tetrahydro-1H-pyrido[2,1-a]pyrrolo[1,2-c]phthalazine-7-carboxylic acid using ethyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate in place of ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Acetonitrile-d3) δ 8.43 (s, 1H), 8.03 (s, 1H), 7.18 (s, 1H), 7.09 (s, 1H), 4.86 (d, J=6.4 Hz, 1H), 4.72 (t, J=6.4 Hz, 2H), 4.57 (p, J=5.4 Hz, 1H), 4.51-4.42 (m, 2H), 4.30 (ddt, J=27.2, 9.7, 6.2 Hz, 2H), 3.58 (t, J=6.1 Hz, 2H), 2.63-2.39 (m, 2H), 2.08 (p, J=6.3 Hz, 2H), 1.93-1.84 (m, 1H), 1.65 (td, J=12.6, 11.8, 7.9 Hz, 1H), 1.36 (s, 3H), 0.67 (s, 3H). MS (m/z) 475.2 [M+H]$^+$.

Example 99: (R)-12-((3-cyanobicyclo[1.1.1]pentan-1-yl)methoxy)-11-cyclopropyl-3,3-dimethyl-8-oxo-2,3,8,13b-tetrahydro-1H-pyrido[2,1-a]pyrrolo[1,2-c]phthalazine-7-carboxylic acid

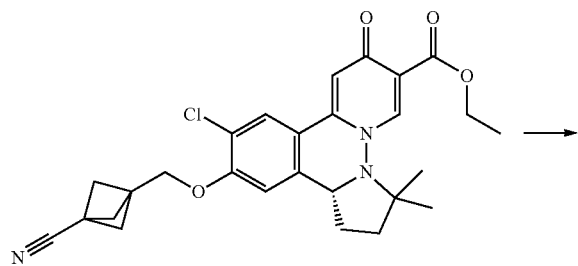

ethyl (R)-11-chloro-12-((3-cyanobicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylate

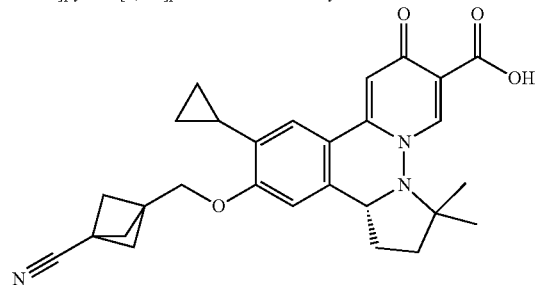

99
(R)-12-((3-cyanobicyclo[1.1.1]pentan-1-yl)methoxy)-11-cyclopropyl-3,3-dimethyl-8-oxo-2,3,8,13b-tetrahydro-1H-pyrido[2,1-a]pyrrolo[1,2-c]phthalazine-7-carboxylic acid Ethyl (R)-11-chloro-12-((3-cyanobicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylate was prepared analogously to (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 74, using ethyl (R)-11-chloro-12-hydroxy-3,3-dimethyl-8-oxo-2,3,8,13b-tetrahydro-1H-pyrido[2,1-a]pyrrolo[1,2-c]phthalazine-7-carboxylate in place of ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate and omitting the lithium hydroxide hydrolysis step. (R)-12-((3-cyanobicyclo[1.1.1]pentan-1-yl)methoxy)-11-cyclopropyl-3,3-dimethyl-8-oxo-2,3,8,13b-tetrahydro-1H-pyrido[2,1-a]pyrrolo[1,2-c]phthalazine-7-carboxylic acid was prepared from ethyl (R)-11-chloro-12-((3-cyanobicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylate analogously to the preparation of (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 71. $^1$H NMR (400 MHz, Acetonitrile-d3) δ 8.43 (s, 1H), 7.38 (s, 1H), 7.24 (s, 1H), 6.84 (d, J=0.9 Hz, 1H), 4.82 (d, J=6.2 Hz, 1H), 4.21 (d, J=11.0 Hz, 1H), 4.11 (d, J=11.0 Hz, 1H), 2.57-2.37 (m, 2H), 2.35 (s, 6H), 2.18 (tt, J=8.6, 5.4 Hz, 1H), 1.88 (ddd, J=12.6, 7.8, 2.8 Hz, 1H), 1.59 (ddd, J=12.5, 10.7, 7.9 Hz, 1H), 1.35 (s, 3H), 1.05-0.91 (m, 2H), 0.88-0.74 (m, 2H), 0.61 (s, 3H). $^{19}$F NMR (376 MHz, Acetonitrile-d3) δ−77.32. MS (m/z) 472.5 [M+H]$^+$.

Example 100: (R)-12-((3-cyanobicyclo[1.1.1]pentan-1-yl)methoxy)-11-ethyl-3,3-dimethyl-8-oxo-2,3,8,13b-tetrahydro-1H-pyrido[2,1-a]pyrrolo[1,2-c]phthalazine-7-carboxylic acid

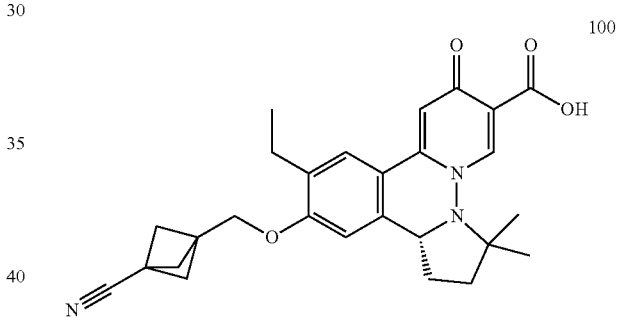

100

Ethyl (R)-11-chloro-12-((3-cyanobicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylate (62 mg, 126 μmol) was combined with Pd RuPhos G4 (8.5 mg, 10 μmol) and RuPhos (5.8 mg, 13 μmol) in N-methylpyrrolidine (1 mL) under argon. Diethylzinc (0.57 mL, 1.1 M solution in toluene) was added and the mixture was stirred at 80° C. for 5 minutes after which time LCMS analysis showed complete conversion to the desired product. The mixture was cooled to room temperature, concentrated to remove toluene, diluted with aqueous TFA, and purified by purified by HPLC to provide the title compound. $^1$H NMR (400 MHz, Acetonitrile-d3) δ 8.44 (s, 1H), 7.76 (s, 1H), 7.23 (s, 1H), 6.84 (s, 1H), 4.84 (d, J=6.2 Hz, 1H), 4.19 (d, J=11.0 Hz, 1H), 4.08 (d, J=11.0 Hz, 1H), 2.70 (qd, J=7.2, 5.0 Hz, 2H), 2.55-2.37 (m, 2H), 2.34 (s, 6H), 1.89 (ddd, J=12.6, 7.8, 2.8 Hz, 1H), 1.67-1.49 (m, 1H), 1.36 (s, 3H), 1.23 (t, J=7.5 Hz, 3H), 0.64 (s, 3H). $^{19}$F NMR (376 MHz, Acetonitrile-d3) δ−77.33. MS (m/z) 460.6 [M+H]+.

Example 101: (S)-12-cyclopropyl-13-(3-methoxy-propoxy)-4,4-dimethyl-9-oxo-3,4,9,14b-tetrahydro-1H-[1,4]oxazino[3,4-a]pyrido[1,2-c]phthalazine-8-carboxylic acid

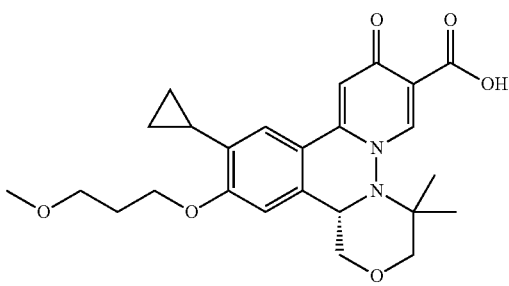

Prepared analogously to (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 71, using ethyl (S)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylate (example 51) in place of ethyl (R)-11-chloro-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylate. $^1$H NMR (400 MHz, Acetonitrile-d3) δ 8.52 (s, 1H), 7.35 (s, 1H), 7.23 (s, 1H), 7.03 (s, 1H), 4.85 (dt, J=12.7, 1.3 Hz, 1H), 4.50 (d, J=2.9 Hz, 1H), 4.26-4.14 (m, 2H), 4.02 (dd, J=12.8, 3.2 Hz, 1H), 3.65-3.46 (m, 4H), 3.33 (s, 3H), 2.22 (tt, J=8.5, 5.3 Hz, 1H), 2.09 (p, J=6.2 Hz, 2H), 1.06 (s, 3H), 1.02-0.93 (m, 2H), 0.90-0.73 (m, 2H), 0.45 (s, 3H). $^{19}$F NMR (376 MHz, Acetonitrile-d3) δ −77.31. MS (m/z) 455.5 [M+H]$^+$.

Example 102: (S)-12-(methoxymethyl)-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid

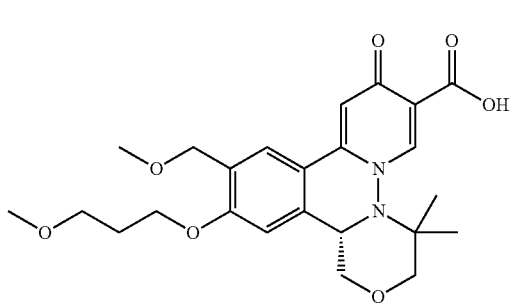

Prepared analogously to (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid in example 73, using ethyl (S)-13-hydroxy-12-(methoxymethyl)-4,4-dimethyl-9-oxo-3,4,9,14b-tetrahydro-1H-[1,4]oxazino[3,4-a]pyrido[1,2-c]phthalazine-8-carboxylate (example 51) in place of ethyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate. $^1$H NMR (Chloroform-d) δ: 8.60 (s, 1H), 7.84 (s, 1H), 7.20 (s, 1H), 6.93 (s, 1H), 4.76 (d, 1H), 4.56-4.48 (m, 2H), 4.45-4.37 (m, 1H), 4.28-4.20 (m, 1H), 4.20-4.13 (m, 1H), 4.12-3.97 (m, 1H), 3.66-3.53 (m, 4H), 3.51 (s, 3H), 3.37 (s, 3H), 2.16-2.06 (m, 2H), 1.09 (s, 3H), 0.51 (s, 3H). MS (m/z) 459.2 [M+H]$^+$. A procedure for the preparation of 3,3-dimethyl-3,6-dihydro-2H-1,4-oxazine 4-oxide used in the preparation of ethyl (S)-13-hydroxy-12-(methoxymethyl)-4,4-dimethyl-9-oxo-3,4,9,14b-tetrahydro-1H-[1,4]oxazino[3,4-a]pyrido[1,2-c]phthalazine-8-carboxylate is given below.

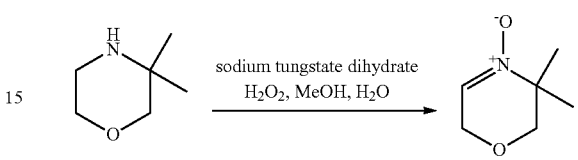

Synthesis of
3,3-dimethyl-3,6-dihydro-2H-1,4-oxazine 4-oxide

To a solution of 3,3-dimethylmorpholine (10 g, 89 mmol) in MeOH (100 ml), was slowly added sodium tungstate dihydrate (2.8 g, 8.9 mmol, dissolved in 5 ml water). The mixture was cooled to 0° C. stirred for 10 minutes, then 30% Hydrogen peroxide (23 ml, 224 mmol) was added and the mixture was stirred for 1 hour then warmed to RT and stirred another hour. The reaction was quenched with Na$_2$SO$_3$ dissolved in water. The resulting mixture was decanted into a round bottom, rinsing with MeOH and concentrated to remove most of the solvent. Sodium chloride was added to the mixture which was then extracted 3× with chloroform. The combined organics were dried over sodium sulfate, concentrated and purified by flash column chromatography. $^1$H NMR (Chloroform-d) δ: 6.94 (t, 1H), 4.33 (d, 2H), 3.65 (s, 2H), 1.37 (s, 7H). MS (m/z) 130.1 [M+H]+.

Example 103: (R)-11-(difluoromethoxy)-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid

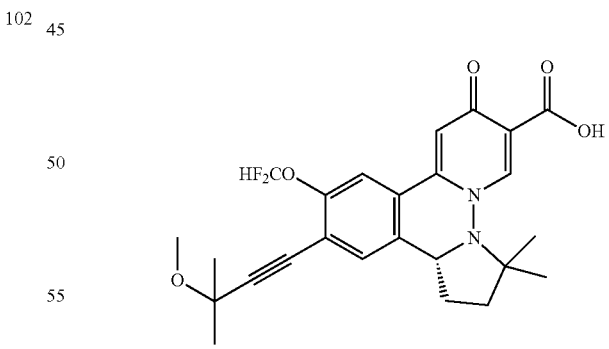

Prepared similarly to (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid (example 84) using ethyl (R)-11-(difluoromethoxy)-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate to replace ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1, 2-c]phthalazine-7-carboxylate. ¹H NMR (400 MHz, Chloroform-d) δ 8.60 (s, 1H), 7.59 (s, 1H), 7.47 (d, J=1.1 Hz, 1H), 7.25 (d, J=0.9 Hz, 2H), 6.64 (t, J=72.8 Hz, 1H), 4.80 (d, J=6.0 Hz, 1H), 3.40 (d, J=32.0 Hz, 6H), 2.65-2.36 (m, 2H), 1.93 (d, J=2.8 Hz, 0H), 1.66 (ddd, J=12.5, 10.7, 7.7 Hz, 1H), 1.57 (s, 6H), 1.46 (s, 6H), 1.39 (s, 3H), 0.67 (s, 3H). MS=473.6 (M+H⁺)

Example 104: (R)-12-((3-cyanobicyclo[1.1.1]pentan-1-yl)methoxy)-11-(difluoromethoxy)-3,3-dimethyl-8-oxo-2,3,8,13b-tetrahydro-1H-pyrido[2,1-a]pyrrolo[1,2-c]phthalazine-7-carboxylic acid

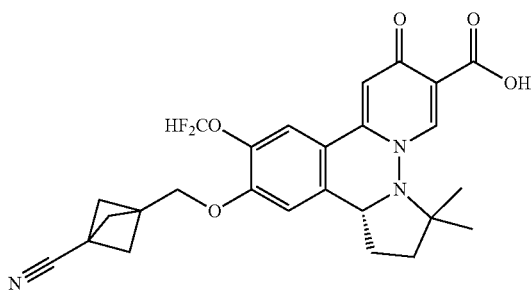

Prepared similarly to (R)-12-((3-cyanobicyclo[1.1.1]pentan-1-yl)methoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid (example 92) using ethyl (R)-12-hydroxy-3,3-dimethyl-8-oxo-11-(difluoromethoxy)-2,3,8,13b-tetrahydro-1H-pyrido[2,1-a]pyrrolo[1,2-c]phthalazine-7-carboxylate in place of ethyl (R)-12-hydroxy-3,3-dimethyl-8-oxo-11-(trifluoromethoxy)-2,3,8,13b-tetrahydro-1H-pyrido[2,1-a]pyrrolo[1,2-c]phthalazine-7-carboxylate. ¹H NMR (400 MHz, Chloroform-d) δ 8.60 (s, 1H), 7.62 (s, 1H), 6.80 (s, 1H), 6.57 (s, 1H), 4.81 (d, J=6.0 Hz, 1H), 4.10 (m, 2H), 3.70 (s, 1H), 2.53 (m, 1H), 2.36 (s, 6H), 2.15 (s, 1H) 1.94 (m, 1H), 1.62 (m, 1H), 1.39 (s, 3H), 1.26 (m, 1H), 0.67 (s, 3H). MS=498.7 (M+H⁺)

Example 105: (R)-11-(difluoromethoxy)-12-((3-(methoxymethyl)bicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylic acid

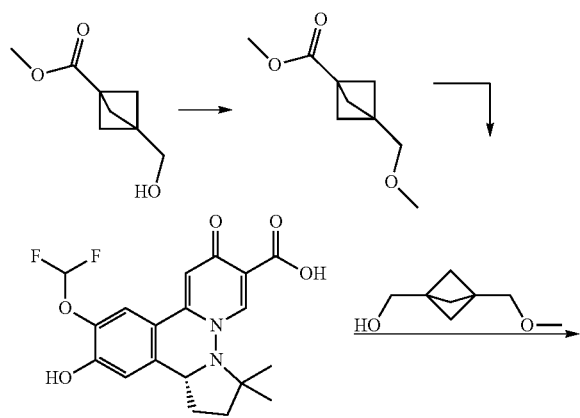

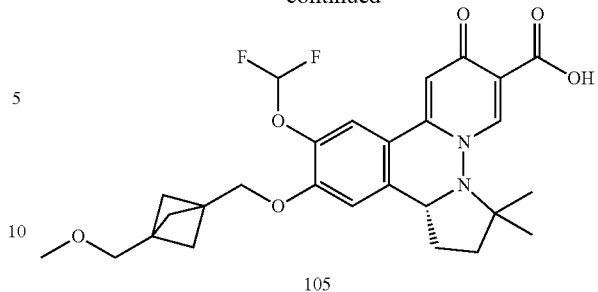

Methyl 3-(methoxymethyl)bicyclo[1.1.1]pentane-1-carboxylate: At 0° C., to methyl 3-(hydroxymethyl)bicyclo[1.1.1]pentane-1-carboxylate (0.6 g, 0.32 mmol) was added NaH (60%, 0.2 g, 4.99 mmol), then the mixture was stirred at 0° C. for 30 min, then Iodomethane (0.71 ml, 7.68 mmol) was added, the mixture was stirred at rt for 2 h, TLC (20% EA/Hex) showed SM was still left. NaH (60%, 0.31 g, 7.68 mmol) was added at 0° C., after 30 min, Iodomethane (0.71 ml, 7.68 mmol) was added again. Then the mixture was stirred at rt for overnight. TLC showed reaction was complete. Et2O/H2O was added and two phases separated. Organic phase was dried with MgSO4 and solvent was removed in vacuo. Crude material was used for next step.

(3-(methoxymethyl)bicyclo[1.1.1]pentan-1-yl)methanol

At 0° C., to methyl 3-(methoxymethyl)bicyclo[1.1.1]pentane-1-carboxylate (0.33 g, 0 mol) (crude) in THF (5 ml) was added 1M lithium aluminum hydride (2.13 ml) in THF dropwise, then stirred at rt overnight. TLC showed complete conversion. Then the reaction was diluted with Et₂O and washed with H₂O. The organic phase was dried with MgSO₄ and solvent was removed under vacuo. The crude material was used directly to next step.

(R)-11-(difluoromethoxy)-12-((3-(methoxymethyl)bicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylic acid To dry ethyl 11-(difluoromethoxy)-12-hydroxy-3,3-dimethyl-8-oxo-2,3,8,13b-tetrahydro-1H-pyrido[2,1-a]pyrrolo[1,2-c]phthalazine-7-carboxylate (50 mg, 0.12 mmol) was added THF (2 ml) and (Tributylphosphoranylidene)acetonitrile (86.11 mg, 0.36 mmol). The mixture was heated to 80° C. with vented needle. 30 min later reaction was cooled to rt, the (3-(methoxymethyl)bicyclo[1.1.1]pentan-1-yl)methanol (42.28 mg, 0.3 mmol) was added. it was heated at 90 C for 1 h. then TLC showed complete conversion. the reaction mixture was cooled to room temp. 1M LiOH (0.59 ml) was added to crude reaction. After 2 h, hydrolysis was complete. Solvent was stripped off, and the residue was purified by HPLC. ¹H NMR (400 MHz, Chloroform-d) δ 8.59 (s, 1H), 7.59 (s, 1H), 7.21 (s, 1H), 6.87-6.83 (m, 1H), 6.62 (t, J=74.1 Hz, 1H), 4.80 (d, J=6.3 Hz, 1H), 4.13 (q, J=10.4 Hz, 2H), 3.44 (s, 2H), 3.38 (d, J=4.1 Hz, 4H), 2.51 (dddd, J=13.9, 10.7, 8.1, 6.7 Hz, 1H), 2.43-2.31 (m, 1H), 1.93 (ddd, J=12.7, 7.9, 2.5 Hz, 1H), 1.82 (s, 6H), 1.73 (s, 1H), 1.63 (ddd, J=12.6, 10.9, 7.6 Hz, 1H), 1.39 (s, 3H), 0.68 (s, 3H). MS=517.8 (M+H⁺)

217

Example 106: (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylic acid

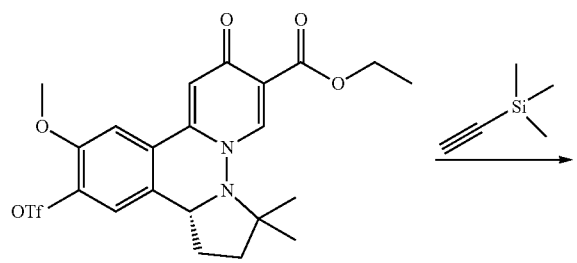

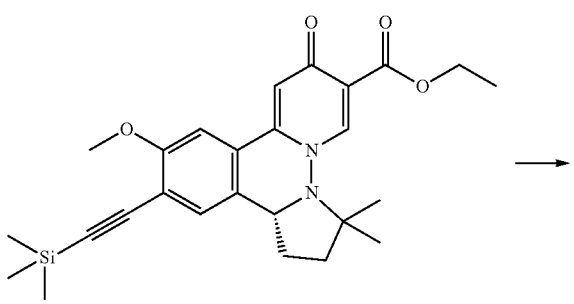

218

-continued

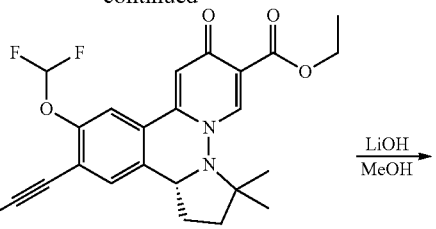

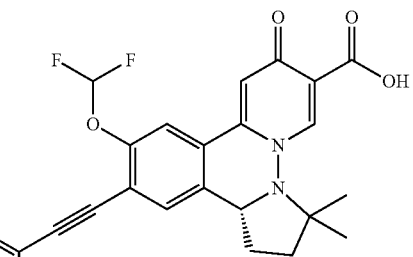

106

Ethyl (R)-11-methoxy-3,3-dimethyl-8-oxo-12-((trimethylsilyl)ethynyl)-2,3,8,13b-tetrahydro-1H-pyrido[2,1-a]pyrrolo[1,2-c]phthalazine-7-carboxylate Copper(i) iodide (0.01 g, 0 mol) and Pd(tBu2PPh)2Cl2 (0.02 g, 0 mol) were charged in a vial containing ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (0.1 g, 0 mol) and ethynyltrimethylsilane (0.1 g, 0 mol), then MeCN/Et3N (3:1) (12 ml) was added. After degassing, the mixture was stirred at 60° C. for 2 h. LCMS showed complete conversion. The mixture was cooled to rt, and quenched with thiol-linked silica, stirred for 5 min, after filtration to remove silica gel, the solvent was removed under vacuo. The residue was purified by SGC from 1-100% Hex/EA to provide the title compound.

Ethyl (R)-11-(difluoromethoxy)-12-ethynyl-3,3-dimethyl-8-oxo-2,3,8,13b-tetrahydro-1H-pyrido[2,1-a]pyrrolo[1,2-c]phthalazine-7-carboxylate A solution of ethyl (R)-11-(difluoromethoxy)-3,3-dimethyl-8-oxo-12-((trimethylsilyl)ethynyl)-2,3,8,13b-tetrahydro-1H-pyrido[2,1-a]pyrrolo[1,2-c]phthalazine-7-carboxylate (100 mg, 199.75 μmol) and Potassium Carbonate (82.82 mg, 0.6 mmol) in EtOH (8 ml) was stirred at rt for 1 h. LCMS shows desired reaction complete. The solid was filtered off, and solvent was stripped off. the crude was used directly without further purification.

Ethyl (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylate Pd(tBu₂PPh)₂Cl₂ (9.94 mg, 0.014 mmol) and CuI (2.67 mg, 0.0014 mmol) were added into a round bottom flask

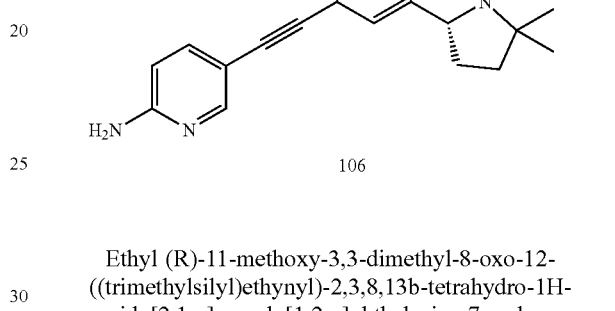

containing ethyl (R)-11-(difluoromethoxy)-12-ethynyl-3,3-dimethyl-8-oxo-2,3,8,13b-tetrahydro-1H-pyrido[2,1-a]pyrrolo[1,2-c]phthalazine-7-carboxylate (60 mg, 0.14 mmol) and 5-bromopyridin-2-amine (24.2 mg, 0.14 mmol) in DMF (1 ml) and Et3N (0.2 ml), after degassing the reaction mixture, it was stirred at 60° C. for 1 h. The reaction mixture was cooled to rt, and extracted with ethyl acetate (50 ml), washed with brine and dried with Mg$_2$SO$_4$. After removed solvent, the residue was taken up in DCM and purified by column to provide 12.7 mg of ethyl (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylate. MS (m/z) 521.622 (M+H$^+$).

(R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylic acid Into the solution of ethyl (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylate (12.5 mg, 0.024 mmol) in MeOH (2 ml), was added LiOH (2.5N, 0.2 ml) at rt., after 30 minutes, the reaction was quenched with addition of TFA (0.2 ml). The solvent was stripped off, and the crude material was purified by HPLC. To provide 12 mg of (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylic acid as TFA salt. $^1$H NMR (400 MHz, Methanol-d4) δ 8.63 (s, 1H), 8.13 (s, 1H), 7.89 (s, 1H), 7.76 (s, 1H), 7.42 (s, 1H), 7.12 (s, 1H), 6.90 (s, 1H), 2.56 (s, 3H), 1.96 (s, 1H), 1.68 (s, 1H), 1.41 (s, 3H), 0.69 (s, 3H). MS (m/z) 493.516 (M+H$^+$).

Example 107: (R)-12'-((3-cyanobicyclo[1.1.1]pentan-1-yl)methoxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylic acid

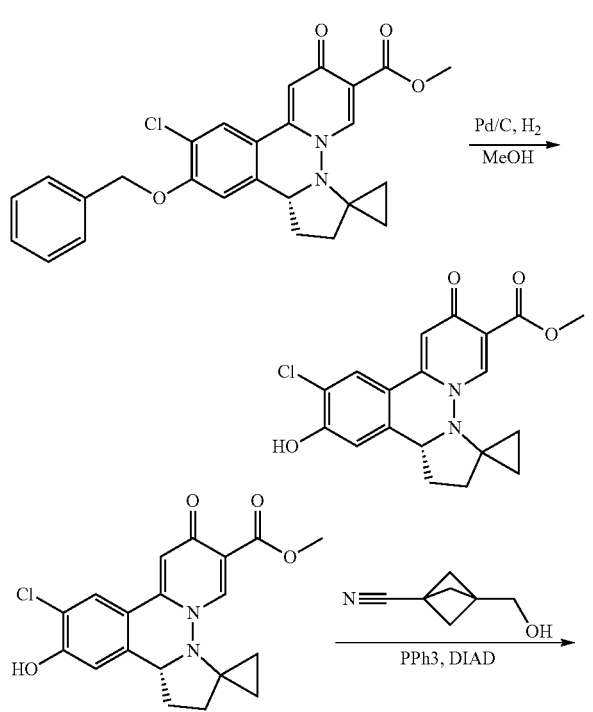

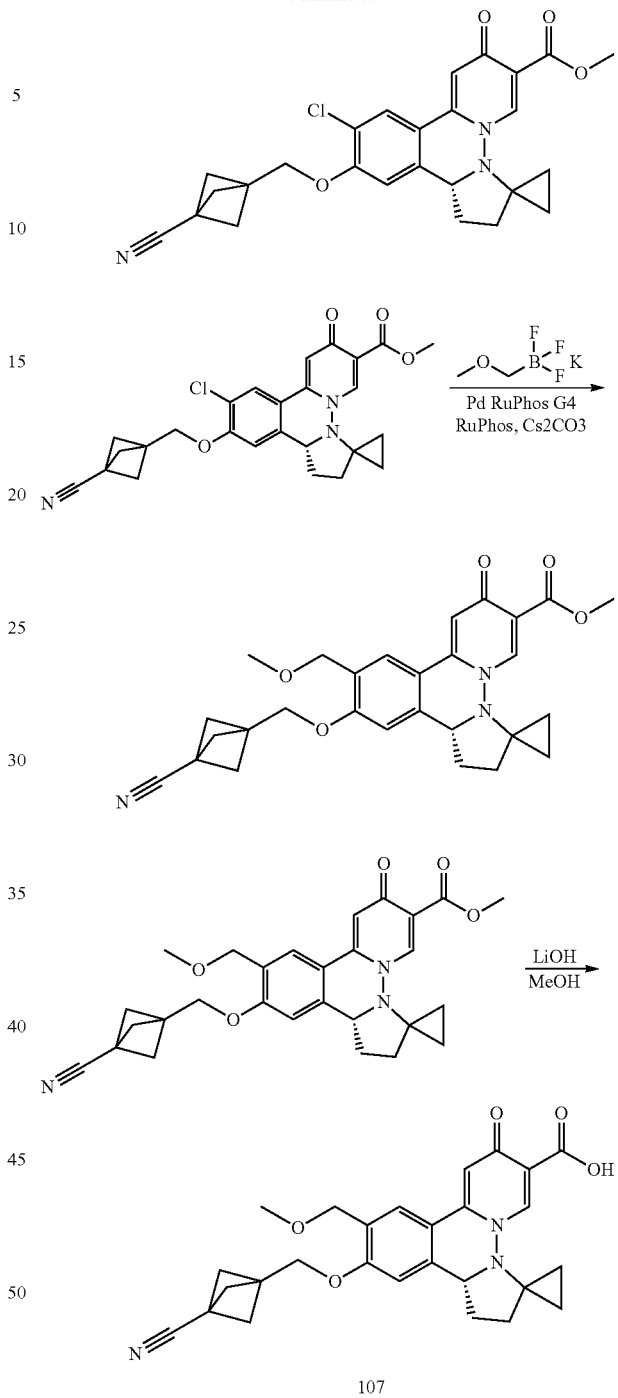

(R)-12'-((3-cyanobicyclo[1.1.1]pentan-1-yl)methoxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylic acid was prepared similarly to compound 74 following the same reaction sequences in example 73 and example 75. $^1$H NMR (400 MHz, Chloroform-d) δ 8.42 (s, 1H), 7.89 (s, 1H), 7.25 (s, 1H), 6.71 (s, 1H), 4.83 (d, J=6.0 Hz, 1H), 4.50 (d, J=3.0 Hz, 2H), 4.11-4.03 (m, 2H), 3.54 (s, 3H), 2.61-2.54 (m, 2H), 2.36 (s, 6H), 2.14-2.08 (m, 2H), 1.75-1.68 (m, 1H), 0.63 (dd, J=17.5, 8.1 Hz, 2H), 0.09 (dd, J=11.8, 4.8 Hz, 2H). MS (m/z) 474.491 [M+H]$^+$.

Example 108: (R)-11-(difluoromethoxy)-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid

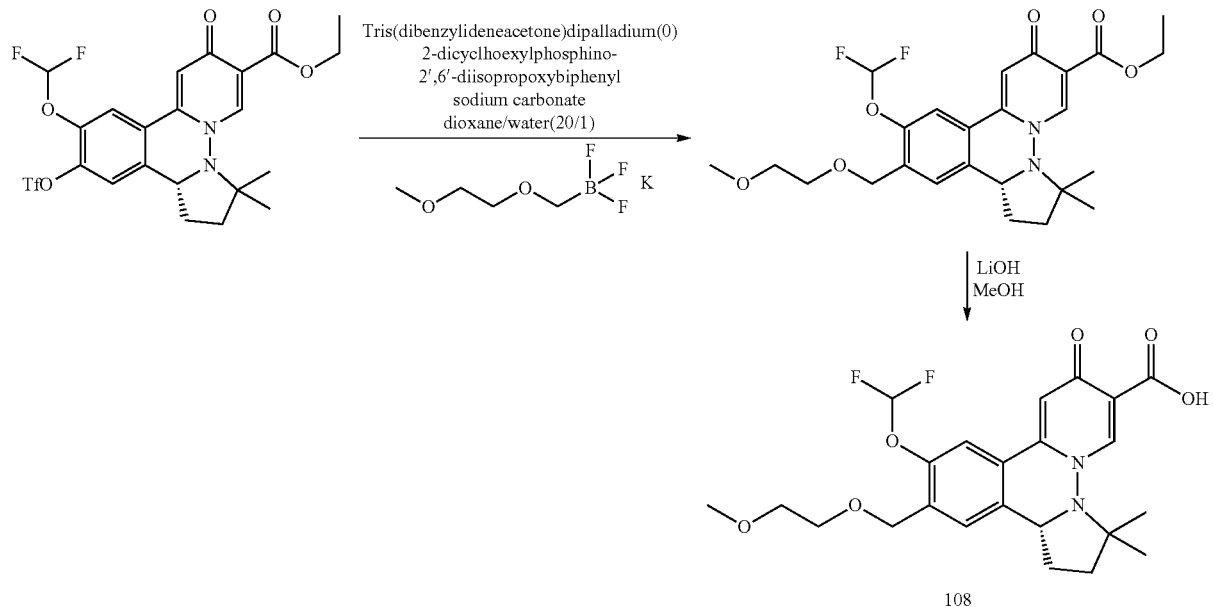

108

Ethyl (R)-11-(difluoromethoxy)-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate (135 mg, 0.244 mmol) was combined with trifluoro((2-methoxyethoxy)methyl)-14-borane, potassium salt (71.9 mg, 0.367 mmol), Tris(dibenzylideneacetone)dipalladium(0)(11.2 mg, 0.012 mmol), 2-dicyclohexylphosphino-2',6'-diisopropoxybiphenyl (13.1 mg, 0.029 mmol) and sodium carbonate (38.9 mg, 0.39 mmol), in dioxane/water (20/1) (2 ml) under argon in a sealed vial. The mixture was heated at 110° C. for 2 h with vigorous stirring, then cooled to room temperature, extracted with ethyl acetate and the organics were concentrated in vacuo and purified by flash column chromatography to provide 24 mg of ethyl (R)-11-(difluoromethoxy)-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylate. MS (m/z) 493.74 [M+H]$^+$. Into the solution of ethyl (R)-11-(difluoromethoxy)-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylate (24 mg, 0.049 mmol) in MeOH (2 ml) was added LiOH (2.5N, 0.2 ml) at rt., after 30 min., the reaction was quenched with addition of TFA (0.2 ml). The solvent was stripped off, and the crude material was purified by HPLC. To provide 10 mg of (R)-11-(difluoromethoxy)-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid. $^1$H NMR (400 MHz, Chloroform-d) δ 8.61 (s, 1H), 7.61 (s, 1H), 7.53 (s, 1H), 7.27 (s, 1H), 6.71 (d, J=72.8 Hz, 1H), 4.83 (s, 1H), 4.68 (s, 2H), 3.74 (d, J=5.1 Hz, 2H), 3.64 (d, J=4.8 Hz, 2H), 3.42 (s, 3H), 2.50 (d, J=5.3 Hz, 2H), 1.94-1.87 (m, 1H), 1.68-1.58 (m, 1H), 1.39 (s, 3H), 0.66 (s, 3H). $^{19}$F NMR (376 MHz, Chloroform-d) δ −76.31, −81.75 (d, J=71.7 Hz). MS (m/z) 465.7 [M+H]$^+$.

Example 109: (R)-11-(methoxymethyl)-12-((1-(methoxymethyl)cyclopropyl)methoxy)-3,3-dimethyl-8-oxo-2,3,8,13b-tetrahydro-1H-pyrido[2,1-a]pyrrolo[1,2-c]phthalazine-7-carboxylic acid

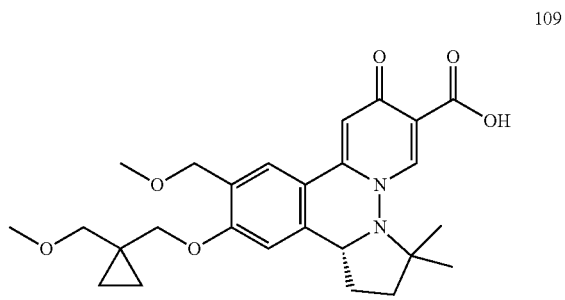 [SMILES: COCc1cc2c(cc1OCC1(COC)CC1)[C@H]1CCC(C)(C)N1n1cc(C(=O)O)c(=O)cc1-2]

109

Prepared analogously to (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid in example 74 using (1-(methoxymethyl)cyclopropyl) methanol in place of 3-(hydroxymethyl)bicyclo[1.1.1]pentane-1-carbonitrile. $^1$H NMR (400 MHz, Chloroform-d) δ 8.53 (s, 1H), 7.84 (s, 1H), 7.15 (s, 1H), 6.74 (s, 1H), 4.97 (q, J=6.1 Hz, 2H), 4.79 (d, J=6.2 Hz, 1H), 4.52 (d, J=1.4 Hz, 1H), 4.05-3.91 (m, 2H), 3.51 (s, 2H), 3.44-3.32 (m, 4H), 3.29 (s, 2H), 3.24 (s, 1H), 2.54-2.30 (m, 2H), 1.87 (ddd, J=10.8, 7.7, 2.6 Hz, 1H), 1.67-1.59 (m, 1H), 1.37 (s, 3H), 1.25 (dd, J=8.5, 6.3 Hz, 6H), 1.12 (d, J=6.8 Hz, 1H), 0.72-0.61 (m, 5H), 0.50 (s, 2H). MS (m/z) 469.4 [M+H]$^+$.

Example 110: (R)-11'-(methoxymethyl)-12'-(3-methoxypropoxy)-8'-oxo-1',2',8',13b'-tetrahydrospiro[cyclobutane-1,3'-pyrido[2,1-a]pyrrolo[1,2-c]phthalazine]-7'-carboxylic acid

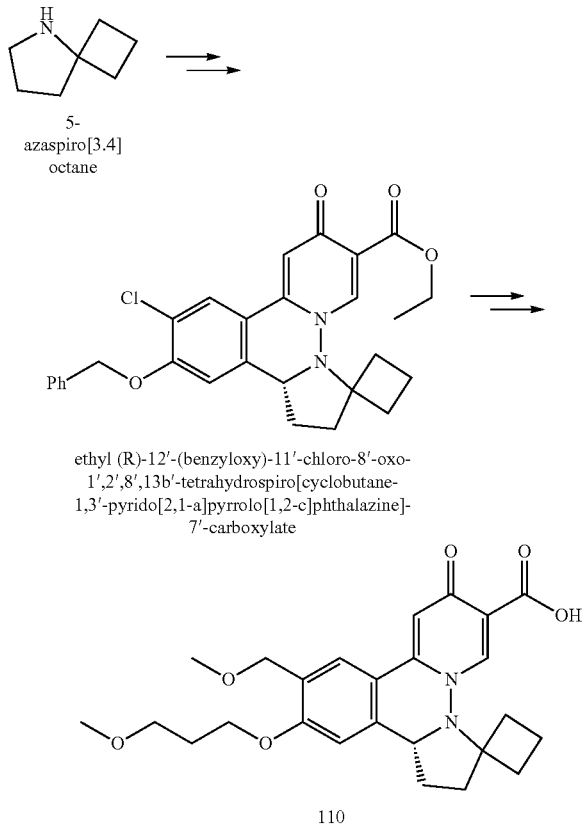

5-azaspiro[3.4]octane ethyl (R)-12'-(benzyloxy)-11'-chloro-8'-oxo-1',2',8',13b'-tetrahydrospiro[cyclobutane-1,3'-pyrido[2,1-a]pyrrolo[1,2-c]phthalazine]-7'-carboxylate

110

5-azaspiro[3.4]octane was converted to 5-azaspiro[3.4]oct-5-ene 5-oxide in a method analogous to the preparation of 2,2-dimethyl-2,3,4,5-tetrahydropyridine 1-oxide (example 11). The 5-azaspiro[3.4]oct-5-ene 5-oxide was converted to ethyl (R)-12'-(benzyloxy)-11'-chloro-8'-oxo-1',2',8',13b'-tetrahydrospiro[cyclobutane-1,3'-pyrido[2,1-a]pyrrolo[1,2-c]phthalazine]-7'-carboxylate using a sequence analogous to that used for the preparation of methyl (R)-12-(benzyloxy)-11-chloro-3,3-dimethyl-8-oxo-2,3,8,13b-tetrahydro-1H-pyrido[2,1-a]pyrrolo[1,2-c]phthalazine-7-carboxylate. The ethyl (R)-12'-(benzyloxy)-11'-chloro-8'-oxo-1',2',8',13b'-tetrahydrospiro[cyclobutane-1,3'-pyrido[2,1-a]pyrrolo[1,2-c]phthalazine]-7'-carboxylate was converted to R)-11'-(methoxymethyl)-12'-(3-methoxypropoxy)-8'-oxo-1',2',8',13b'-tetrahydrospiro[cyclobutane-1,3'-pyrido[2,1-a]pyrrolo[1,2-c]phthalazine]-7'-carboxylic acid using a sequence analogous to that used for the preparation of (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid in example 73. $^1$H NMR (400 MHz, Acetonitrile-d3) δ 8.46 (s, 1H), 7.89 (s, 1H), 7.19 (s, 1H), 6.97 (s, 1H), 4.80 (d, J=6.7 Hz, 1H), 4.57-4.41 (m, 2H), 4.20 (ddt, J=29.9, 9.5, 6.2 Hz, 2H), 3.56 (td, J=6.2, 1.1 Hz, 2H), 3.42 (s, 3H), 3.32 (s, 3H), 2.60-2.51 (m, 1H), 2.48-2.35 (m, 1H), 2.25-2.00 (m, 6H), 1.59-1.37 (m, 3H), 0.96-0.85 (m, 1H). $^{19}$F NMR (376 MHz, Acetonitrile-d3) δ−77.3. MS (m/z) 455.4 [M+H]$^+$.

Example 111: Synthesis of (R)-12-(3-hydroxypropoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid

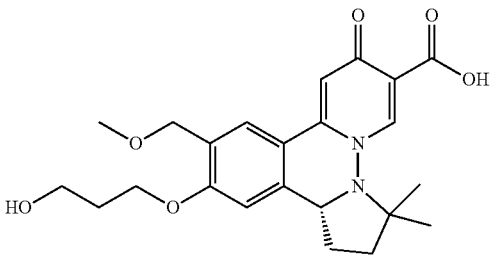

111

Prepared analogously to (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid in example 73 using 3-bromopropan-1-ol in place of 1-bromo-3-methoxypropane. $^1$H NMR (400 MHz, Acetonitrile-d3) δ 8.43 (s, 1H), 7.90 (s, 1H), 7.18 (s, 1H), 7.04-6.97 (m, 1H), 4.88 (d, J=6.4 Hz, 1H), 4.56-4.43 (m, 2H), 4.24 (ddt, J=28.3, 9.6, 6.1 Hz, 2H), 3.73 (t, J=6.1 Hz, 2H), 3.42 (s, 3H), 2.66-2.39 (m, 2H), 2.00 (p, J=6.1 Hz, 2H), 1.90 (ddd, J=12.7, 8.0, 2.9 Hz, 1H), 1.62 (ddd, J=12.7, 10.6, 7.8 Hz, 1H), 1.36 (s, 3H), 0.65 (s, 3H). $^{19}$F NMR (376 MHz, Acetonitrile-d3) δ−77.3. MS (m/z) 429.5 [M+H]$^+$.

Example 112: Synthesis of (R)-11-(difluoromethoxy)-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid

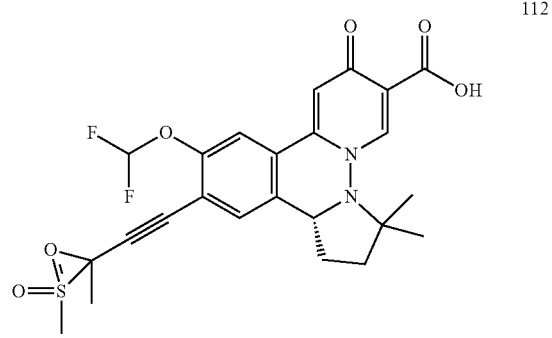

112

The compound of this example was prepared analogous to (R)-11-Methoxy-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid in example 43 using ethyl (R)-11-(difluoromethoxy)-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate in place of ethyl (R)-11-methoxy-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate, and 3-methyl-3-(methylsulfonyl)but-1-yne in place of 3-methoxy-3-methylbut-1-yne. MS (m/z): 521.53 [M+H]$^+$. $^1$H NMR (400 MHz, Chloroform-d) δ 8.63 (s, 1H), 7.60 (s, 1H), 7.50 (d, J=1.1 Hz, 1H), 7.40 (s, 1H), 7.25 (s, 1H), 6.68 (t, J=72.5 Hz, 1H), 4.81 (d, J=6.1 Hz, 1H), 3.11 (s, 3H), 2.70-2.36 (m, 2H), 2.10-1.54 (m, 9H), 1.40 (s, 3H), 0.67 (s, 3H).

Example 113: Synthesis of (R)-11-(hydroxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid

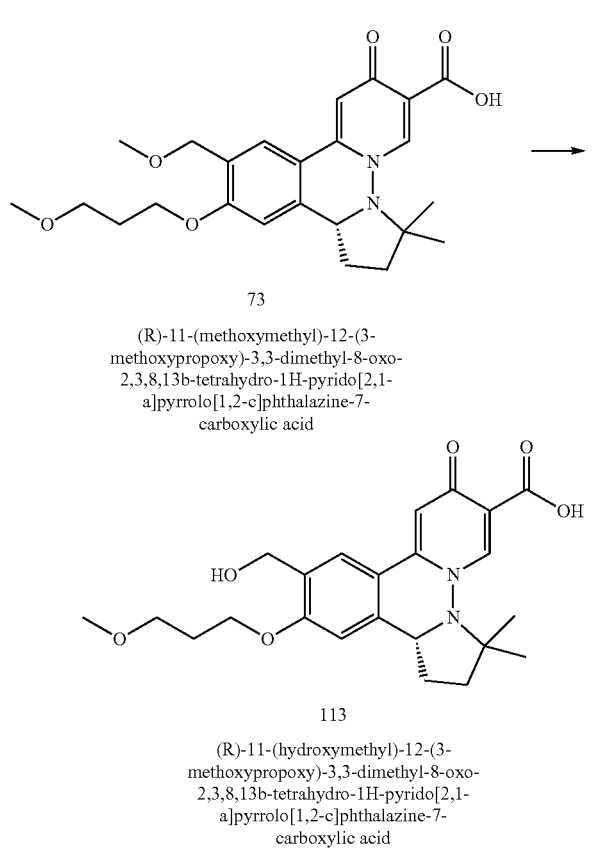

73
(R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid 113
(R)-11-(hydroxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid To a solution of (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (example 73, 0.012 g, 0.027 mmol) in 0.40 mL 1:1 DMF:H₂O was added 0.2 mL concentrated sulfuric acid (0.368 mg; 0.003 mmol). The solution was heated to 90° C. for 2 hours. After 2 hours, the reaction was diluted with dichloromethane and water. Saturated NaHCO₃ solution (aq.) was added until the aqueous layer pH was <3. The layers were separated and the dichloromethane layer was concentrated under reduced pressure. The crude residue was purified by preparative HPLC to afford (R)-11-(hydroxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid (113) as trifluoroacetic acid salt (0.003 g; 0.00553 mmol; 20.4%). $^1$H NMR (400 MHz, Acetonitrile-d3) δ 8.43 (s, 1H), 7.92 (s, 1H), 7.17 (s, 1H), 6.96 (s, 1H), 4.87 (d, J=6.5 Hz, 1H), 4.64 (s, 2H), 4.21 (ddt, J=27.6, 9.6, 6.1 Hz, 2H), 3.67-3.48 (m, 8H), 3.32 (s, 3H), 2.60-2.38 (m, 1H), 2.06 (p, J=6.1 Hz, 2H), 1.90 (ddd, J=12.6, 8.0, 2.8 Hz, 1H), 1.62 (ddd, J=12.7, 10.6, 7.9 Hz, 1H), 1.33 (d, J=29.8 Hz, 4H), 0.66 (s, 3H). $^{19}$F NMR (376 MHz, Acetonitrile-d3) δ−76.30. MS (m/z) 429.5 [M+H]+.

Example 114: (S)-12'-(methoxymethyl)-13'-(3-methoxypropoxy)-9'-oxo-9',14b'-dihydro-1'H,3'H-spiro[cyclobutane-1,4'-[1,4]oxazino[3,4-a]pyrido[1,2-c]phthalazine]-8'-carboxylic acid

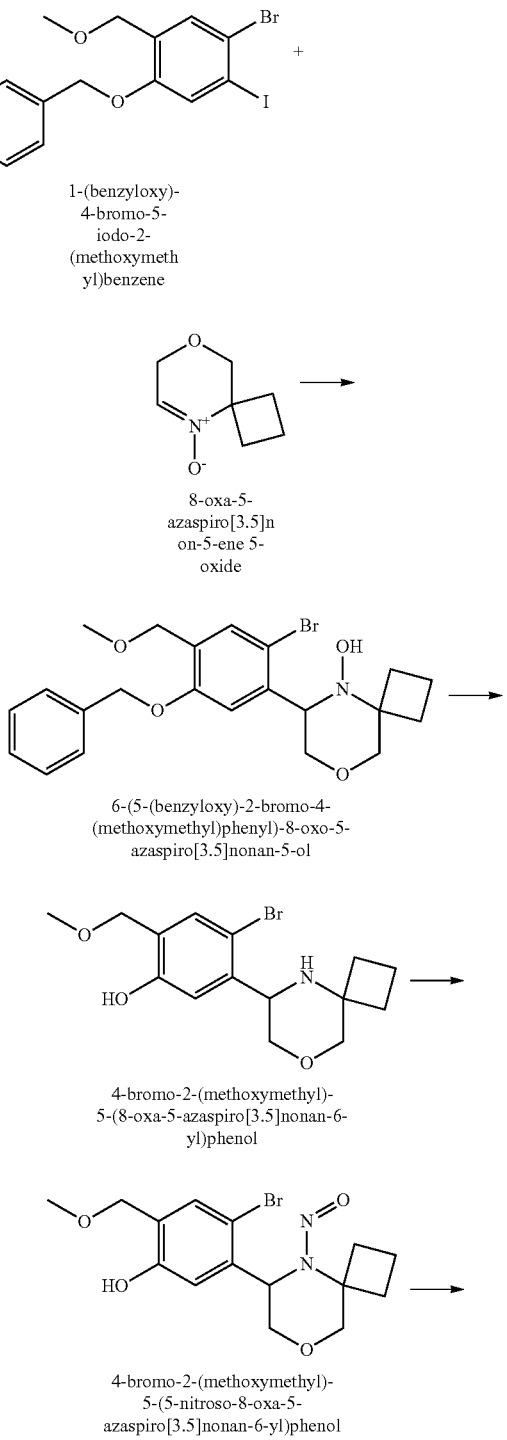

1-(benzyloxy)-4-bromo-5-iodo-2-(methoxymethyl)benzene 8-oxa-5-azaspiro[3.5]non-5-ene 5-oxide 6-(5-(benzyloxy)-2-bromo-4-(methoxymethyl)phenyl)-8-oxo-5-azaspiro[3.5]nonan-5-ol 4-bromo-2-(methoxymethyl)-5-(8-oxa-5-azaspiro[3.5]nonan-6-yl)phenol 4-bromo-2-(methoxymethyl)-5-(5-nitroso-8-oxa-5-azaspiro[3.5]nonan-6-yl)phenol

227

-continued

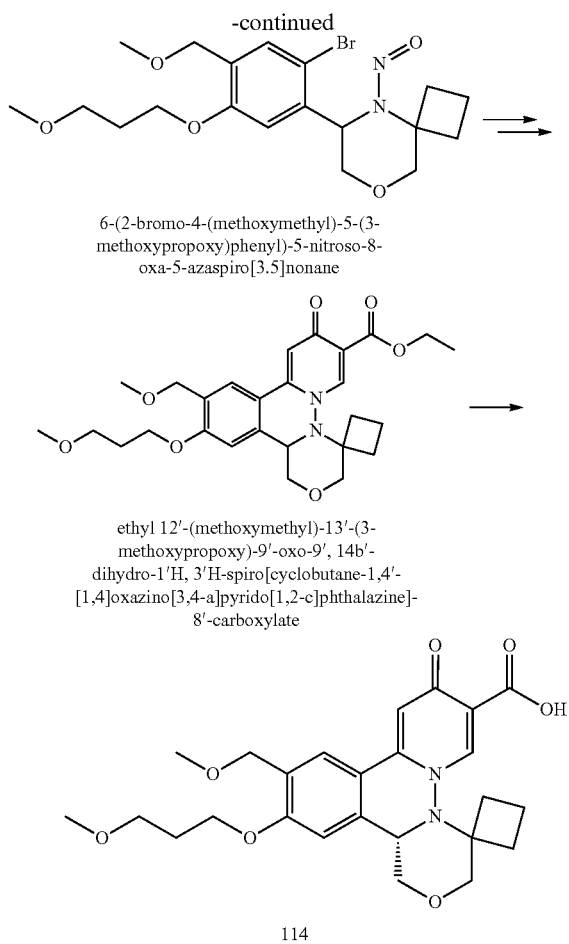

6-(2-bromo-4-(methoxymethyl)-5-(3-methoxypropoxy)phenyl)-5-nitroso-8-oxa-5-azaspiro[3.5]nonane ethyl 12'-(methoxymethyl)-13'-(3-methoxypropoxy)-9'-oxo-9', 14b'-dihydro-1'H, 3'H-spiro[cyclobutane-1,4'-[1,4]oxazino[3,4-a]pyrido[1,2-c]phthalazine]-8'-carboxylate

114

(S)-12'-(methoxymethyl)-13'-(3-methoxypropoxy)-9'-oxo-9', 14b'-dihydro-1'H, 3'H-spiro[cyclobutane-1,4'-[1,4]oxazino[3,4-a]pyrido[1,2-c]phthalazine]-8'-carboxylic acid Synthesis of 6-(5-(benzyloxy)-2-bromo-4-(methoxymethyl)phenyl)-8-oxa-5-azaspiro[3.5]nonan-5-ol 8-oxa-5-azaspiro[3.5]non-5-ene 5-oxide was prepared analogously to 3,3-dimethyl-3,6-dihydro-2H-1,4-oxazine 4-oxide (example 102) and reacted with the Grignard reagent formed from 1-(benzyloxy)-4-bromo-5-iodo-2-(methoxymethyl)benzene similarly to the procedure in example 55 to produce 6-(5-(benzyloxy)-2-bromo-4-(methoxymethyl)phenyl)-8-oxa-5-azaspiro[3.5]nonan-5-ol. MS (m/z) 439.0 [M+H]+.

Synthesis of 4-bromo-2-(methoxymethyl)-5-(8-oxa-5-azaspiro[3.5]nonan-6-yl)phenol 4-bromo-2-(methoxymethyl)-5-(8-oxa-5-azaspiro[3.5]nonan-6-yl)phenol was prepared similarly to example 55 using 6-(5-(benzyloxy)-2-bromo-4-(methoxymethyl)phenyl)-8-oxa-5-azaspiro[3.5]nonan-5-ol in place of 5-(5-(benzyloxy)-2-bromo-4-chlorophenyl)-2,2-dimethylpyrrolidin-1-ol. MS (m/z) 342.4 [M+H]+.

228

Synthesis of 4-bromo-2-(methoxymethyl)-5-(5-nitroso-8-oxa-5-azaspiro[3.5]nonan-6-yl)phenol 4-bromo-2-(methoxymethyl)-5-(5-nitroso-8-oxa-5-azaspiro[3.5]nonan-6-yl)phenol was prepared similarly to example 55 using 4-bromo-2-(methoxymethyl)-5-(8-oxa-5-azaspiro[3.5]nonan-6-yl)phenol in place of 5-(5-(benzyloxy)-2-bromo-4-chlorophenyl)-2,2-dimethylpyrrolidine. MS (m/z) 371.3 [M+H]+.

Synthesis of (S)-12'-(methoxymethyl)-13'-(3-methoxypropoxy)-9'-oxo-9',14b'-dihydro-1'H,3'H-spiro[cyclobutane-1,4'-[1,4]oxazino[3,4-a]pyrido[1,2-c]phthalazine]-8'-carboxylic acid (114)

6-(2-bromo-4-(methoxymethyl)-5-(3-methoxypropoxy)phenyl)-5-nitroso-8-oxa-5-azaspiro[3.5]nonane was prepared similarly to example 1 using 4-bromo-2-(methoxymethyl)-5-(5-nitroso-8-oxa-5-azaspiro[3.5]nonan-6-yl)phenol in place of 4-bromo-2-chloro-5-iodophenol. MS (m/z) 411.6 [M-NO]+. This material was carried forward using a sequence analogous to that in example 55. Ethyl 12'-(methoxymethyl)-13'-(3-methoxypropoxy)-9'-oxo-9',14b'-dihydro-1'H,3'H-spiro[cyclobutane-1,4'-[1,4]oxazino[3,4-a]pyrido[1,2-c]phthalazine]-8'-carboxylate (MS (m/z) 499.5 [M+H]+) was separated into its enantiomers by chiral SFC using a CHIRALPAK IA column with 30% methanol as the co-solvent. Under the chiral separation conditions and concentration most of the ethyl ester was exchanged to the methyl ester. The desired S isomer eluted first and was hydrolyzed using aqueous lithium hydroxide and purified by preparative HPLC to provide (S)-12'-(methoxymethyl)-13'-(3-methoxypropoxy)-9'-oxo-9',14b'-dihydro-1'H,3'H-spiro[cyclobutane-1,4'-[1,4]oxazino[3,4-a]pyrido[1,2-c]phthalazine]-8'-carboxylic acid as a TFA salt. $^1$H NMR (400 MHz, Chloroform-d) δ 8.55 (s, 1H), 7.84 (s, 1H), 7.28 (s, 1H), 6.91 (s, 1H), 4.71 (d, 1H), 4.57-4.47 (m, 2H), 4.35 (s, 1H), 4.29-4.09 (m, 3H), 4.09-3.95 (m, 1H), 3.68-3.61 (m, 1H), 3.58 (t, 2H), 3.51 (s, 3H), 3.37 (s, 3H), 2.14-2.04 (m, 2H), 2.04-1.91 (m, 1H), 1.68-1.57 (m, 1H), 1.51-1.31 (m, 3H), 1.31-1.15 (m, 1H). MS (m/z) 471.3 [M+H]+.

Example 115: Synthesis of (R)-12-((S)-3-(tert-butoxycarbonyl)pyrrolidin-1-yl)-3,3-dimethyl-8-oxo-11-(trifluoromethoxy)-2,3,8,13b-tetrahydro-H-pyrido[2,1-a]pyrrolo[1,2-c]phthalazine-7-carboxylic acid (115)

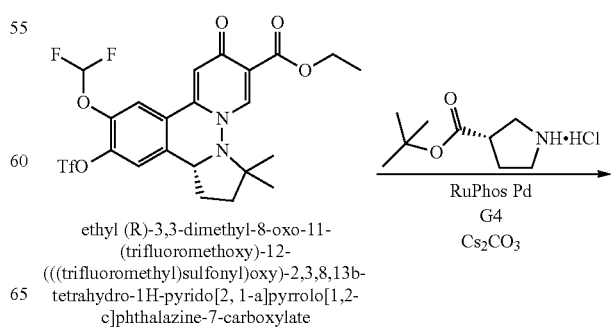

ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate RuPhos Pd G4
Cs$_2$CO$_3$

229

-continued

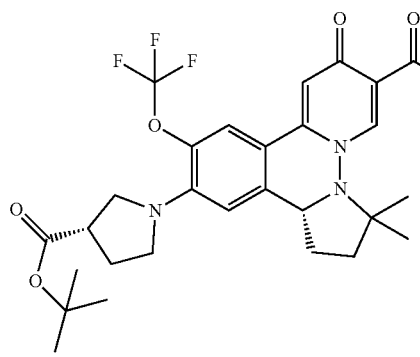

115
(R)-12-((S)-3-(tert-butoxycarbonyl)pyrrolidin-
1-yl)-3,3-dimethyl-8-oxo-11-
(trifluoromethoxy)-2,3,8,13b-tetrahdyro-1H-
pyrido[2,1-a]pyrrolo[1,2-c]phthalazine-7-
carboxylic acid A reaction mixture of ethyl (R)-3,3-dimethyl-8-oxo-11-(trifluoromethoxy)-12-(((trifluoromethyl)sulfonyl)oxy)-2,3,8,13b-tetrahydro-1H-pyrido[2,1-a]pyrrolo[1,2-c]phthalazine-7-carboxylate (50 mg, 0.088 mmol), tert-butyl (S)-pyrrolidine-3-carboxylate hydrochloride (36 mg, 0.18 mmol), cesium carbonate (57 mg, 0.17 mmol) and RuPhos Pd G4 (7 mg, 0.0088 mmol) in 1 mL of toluene was degassed and purged with nitrogen. The resulting mixture was heated to 130° C. for overnight. After cooling to room temperature, added 0.1 mL of 2N LiOH and 1 mL of ethanol, stirred at room temperature until hydrolysis was complete. The reaction was quenched with TFA and then partitioned between water and ethyl acetate. The organic layer was separated, washed with brine, dried over Na$_2$SO$_4$ and concentrated to dryness. The residue was purified by RP-HPLC to afford the title compound. MS (m/z): 564.50 [M+H]$^+$. $^1$H NMR (400 MHz, Chloroform-d) δ 8.55 (s, 1H), 7.54 (d, J=1.5 Hz, 1H), 7.11 (s, 1H), 6.51 (s, 1H), 4.73 (d, J=6.3 Hz, 1H), 3.89-3.50 (m, 4H), 3.11 (p, J=7.2 Hz, 1H), 2.57-2.31 (m, 2H), 2.33-2.07 (m, 2H), 1.90 (ddd, J=11.2, 8.1, 2.7 Hz, 1H), 1.76-1.60 (m, 1H), 1.47 (s, 9H), 1.38 (s, 3H), 0.69 (s, 3H).

Example 116: Synthesis of (R)-12-(2-carboxyethoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid (116)

230

-continued

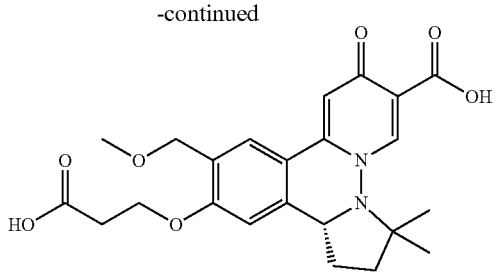

116
(R)-12-(2-carboxyethoxy)-11-(methoxymethyl)-
3,3-dimethyl-8-oxo-2,3,8,13b-tetrahdyro-1H-
pyrido[2,1-a]pyrrolo[1,2-c]phthalazine-7-
carboxylic acid To a solution of methyl (R)-12-hydroxy-11-(methoxymethyl)-3,3-dimethyl-8-oxo-2,3,8,13-tetrahydro-1H-pyrido[2,1-a]pyrrolo[1,2-c]phthalazine-7-carboxylate (50 mg, 0.13 mmol) in 0.7 mL dry DMF at 0° C. was added sodium hydride (60%, 16 mg, 0.39 mmol). The reaction mixture was stirred at 0° C. for 30 min under nitrogen. A solution of 3-Bromopropionic acid (30 mg, 0.2 mmol) in 0.3 mL of DMF was added and the mixture was stirred at room temperature for 30 min, then heated it at 70° C. for 3 h. The reaction was cooled to 0° C., and sodium hydride (16 mg, 0.39 mmol) was added. The resulting mixture was heated at 70° C. overnight. The reaction was quenched by saturated NH$_4$Cl and partitioned between EtOAc and 1 N HCl. The organic layer was dried over Na$_2$SO$_4$, filtered, and concentrated under reduced pressure. The product was dissolved in 1 mL of methanol and added 0.1 mL of 1 N LiOH, stirred at room temperature for 20 min. It was purified by RP-HPLC to afford the title compound. MS (m/z): 443.23 [M+H]$^+$. 1H NMR (400 MHz, Chloroform-d) δ 8.49 (s, 1H), 7.79 (s, 1H), 7.10 (s, 1H), 6.76 (s, 1H), 4.76 (d, J=6.3 Hz, 1H), 4.42 (s, 2H), 4.36-4.10 (m, 2H), 3.42 (s, 3H), 2.80 (t, J=6.3 Hz, 2H), 2.40 (dd, J=17.0, 9.8 Hz, 2H), 1.84 (t, J=9.7 Hz, 1H), 1.65-1.48 (m, 1H), 1.32 (s, 3H), 0.60 (s, 3H).

Example 117: Synthesis of (R)-11-(methoxymethyl)-12-((R)-3-(methoxymethyl)pyrrolidin-1-yl)-3,3-dimethyl-8-oxo-2,3,8,13b-tetrahydro-1H-pyrido[2,1-a]pyrrolo[1,2-c]phthalazine-7-carboxylic acid (117)

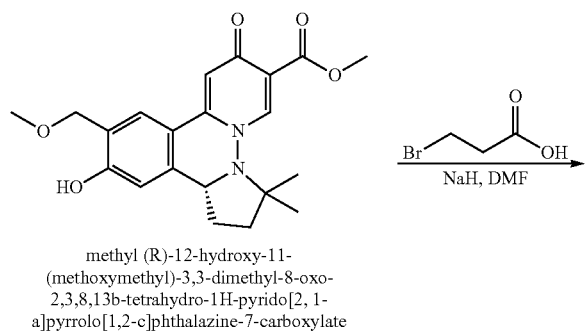

methyl (R)-12-hydroxy-11-
(methoxymethyl)-3,3-dimethyl-8-oxo-
2,3,8,13b-tetrahydro-1H-pyrido[2,1-
a]pyrrolo[1,2-c]phthalazine-7-carboxylate

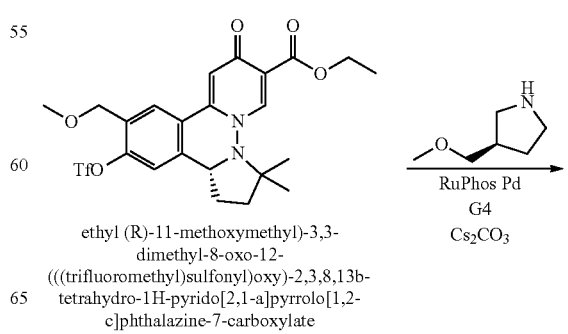

ethyl (R)-11-methoxymethyl)-3,3-
dimethyl-8-oxo-12-
(((trifluoromethyl)sulfonyl)oxy)-2,3,8,13b-
tetrahydro-1H-pyrido[2,1-a]pyrrolo[1,2-
c]phthalazine-7-carboxylate

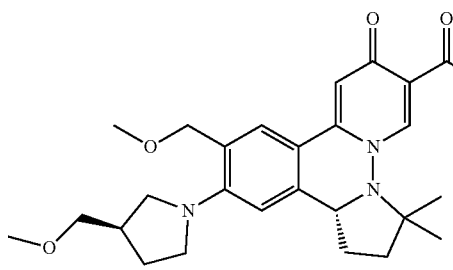

117
(R)-11-(methoxymethyl)-12-((r)-3-
(methoxymethyl)pyrrolidin-1-yl)-
3,3-dimethyl-8-oxo-2,3,8,13b-tetrahdyro-1H-
pyrido[2,1-a]pyrrolo[1,2-c]phthalazine-7-
carboxylic acid

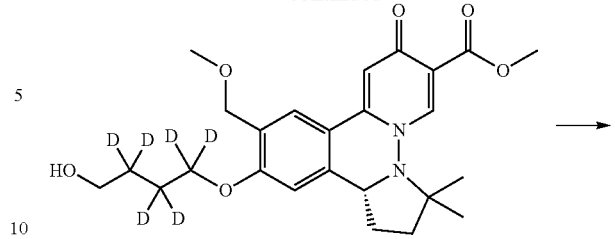

methyl (R)-12-(3-hydroxypropoxy-
1,1,2,2,3,3-d$_6$)-11(methyoxymethyl)-
3,3-dimethyl-8-oxo-2,3,8,13b-
tetrahydro-1H-pyrido[2,1-
a]pyrrolo[1,2-c]phthalazine-7-
carboxylate Compound 117 was prepared similarly to (R)-12-((S)-3-(tert-butoxycarbonyl)pyrrolidin-1-yl)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid (115) using ethyl (R)-11-(methoxymethyl)-3,3-dimethyl-8-oxo-12-(((trifluoromethyl)sulfonyl)oxy)-2,3,8,13b-tetrahydro-1H-pyrido[2,1-a]pyrrolo[1,2-c]phthalazine-7-carboxylate and (R)-3-(methoxymethyl)pyrrolidine hydrochloride: MS (m/z): 468.43 [M+H]+. $^1$H NMR (400 MHz, Chloroform-d) δ 8.53 (s, 1H), 7.66 (s, 1H), 7.16 (s, 1H), 6.49 (s, 1H), 4.73 (d, J=5.9 Hz, 1H), 4.61-4.40 (m, 2H), 3.70-3.50 (m, 3H), 3.48-3.32 (m, 9H), 2.63 (p, J=6.9 Hz, 1H), 2.43 (dd, J=18.0, 7.2 Hz, 2H), 2.12 (dq, J=12.3, 6.7 Hz, 1H), 1.98-1.75 (m, 2H), 1.71-1.57 (m, 1H), 1.37 (s, 3H), 0.68 (s, 3H).

Example 118: Synthesis of (R)-11-(methoxymethyl)-12-(3-methoxypropoxy-1,1,2,2,3,3-d6)-3,3-dimethyl-8-oxo-2,3,8,13b-tetrahydro-1H-pyrido[2,1-a]pyrrolo[1,2-c]phthalazine-7-carboxylic acid (118)

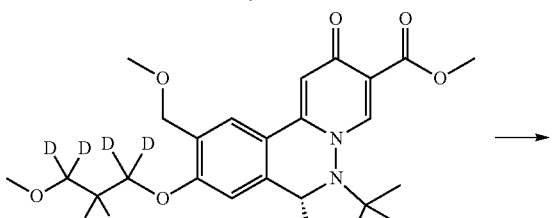

methyl (R)-11-(methoxymethyl)-12
(3-methoxypropoxy-1,1,2,2,3,3-d$_6$)-
3,3-dimethyl-8-oxo-2,3,8,13b-
tetrahydro-1H-pyrido[2,1-
a]pyrrolo[1,2-c]phthalazine-7-
carboxylate

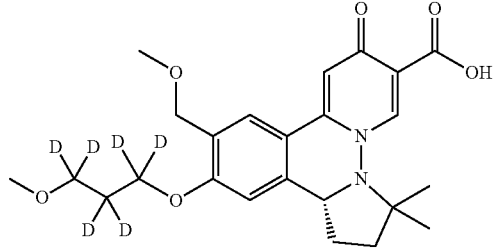

118
(R)-11-(methoxymethyl)-12-3-
methoxypropoxy-1,1,2,2,3,3-d$_6$)-
3,3-dimethyl-8-oxo-2,3,8,13b-
tetrahydro-1H-pyrido[2,1-
a]pyrrolo[1,2-c]phthalazine-7-
carboxyic acid

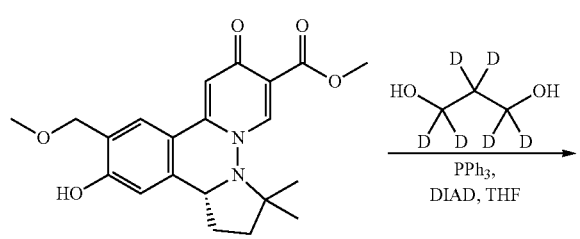

methyl (R)-12-hydroxy-11-
(methoxymethyl)-3,3-dimethyl-
8-oxo-2,3,8,13b-tetrahydro-
1H-pyrido[2,1-a]pyrrolo
[1,2-c]phthalazine-7-carboxylate PPh$_3$,
DIAD, THF Synthesis of methyl (R)-12-(3-hydroxypropoxy-1,1,2,2,3,3-d6)-11-(methoxymethyl)-3,3-dimethyl-8-oxo-2,3,8,13b-tetrahydro-1H-pyrido[2,1-a]pyrrolo[1,2-c]phthalazine-7-carboxylate To a mixture of methyl (R)-12-hydroxy-11-(methoxymethyl)-3,3-dimethyl-8-oxo-2,3,8,13b-tetrahydro-1H-pyrido[2,1-a]pyrrolo[1,2-c]phthalazine-7-carboxylate (300 mg, 0.78 mmol), propane-d6-1,3-diol (256 mg, 3 mmol), and Triphenylphosphine (614 mg, 2.3 mmol) in THF (6 ml) was added diisopropyl azodicarboxylate (0.38 mL, 2 mmol). The reaction was allowed to stir at room temperature for 30 minutes. The product was purified by silica gel chromatography to afford the title compound. MS (m/z) 449.30 [M+H]+.

Synthesis of methyl (R)-11-(methoxymethyl)-12-(3-methoxypropoxy-1,1,2,2,3,3-d6)-3,3-dimethyl-8-oxo-2,3,8,13b-tetrahydro-1H-pyrido[2,1-a]pyrrolo[1,2-c]phthalazine-7-carboxylate To a solution of methyl (R)-12-(3-hydroxypropoxy-1,1,2,2,3,3-d6)-11-(methoxymethyl)-3,3-dimethyl-8-oxo-2,3,8,13b-tetrahydro-1H-pyrido[2,1-a]pyrrolo[1,2-c]phthalazine-7-carboxylate (300 mg, 0.7 mmol) in 5 mL dry DMF at 0° C. was added sodium hydride (60%, 107 mg, 2.7 mmol). The mixture was stirred at 0° C. for 30 min under $N_2$. A solution of iodomethane (0.13 mL, 2 mmol) in 1 mL of DMF was added and the mixture was stirred at room temperature for 40 min. The reaction was quenched by saturated $NH_4Cl$ and partitioned between EtOAc and 1 N HCl. The organic layer was dried over $Na_2SO_4$, filtered, and concentrated under reduced pressure to afford the title compound. MS (m/z): 463.32 $[M+H]^+$.

Synthesis of (R)-11-(methoxymethyl)-12-(3-methoxypropoxy-1,1,2,2,3,3-d6)-3,3-dimethyl-8-oxo-2,3,8,13b-tetrahydro-1H-pyrido[2,1-a]pyrrolo[1,2-c]phthalazine-7-carboxylic acid (118)

Methyl (R)-11-(methoxymethyl)-12-(3-methoxypropoxy-1,1,2,2,3,3-d6)-3,3-dimethyl-8-oxo-2,3,8,13b-tetrahydro-1H-pyrido[2,1-a]pyrrolo[1,2-c]phthalazine-7-carboxylate (1.74 g, 3.76 mmol) was dissolved in 36 mL of THF/MeOH/water (3:2:1), to it was added lithium hydroxide monohydrate (316 mg, 7.5 mmol). The reaction mixture was stirred at room temperature for overnight. The resulting product was partitioned between 1N HCl and EtOAc. The organic was separated and concentrated to dryness. The residue was purified on RP-HPLC to afford the title compound. $^1$H NMR (400 MHz, Chloroform-d) δ 8.56 (s, 1H), 7.85 (s, 1H), 7.26 (d, J=0.9 Hz, 1H), 6.77 (d, J=1.0 Hz, 1H), 4.81 (d, J=6.2 Hz, 1H), 4.65-4.28 (m, 2H), 3.51 (s, 3H), 3.37 (s, 3H), 2.72-2.33 (m, 2H), 1.89 (ddd, J=12.6, 7.8, 2.6 Hz, 1H), 1.62 (td, J=11.7, 7.7 Hz, 1H), 1.38 (s, 3H), 0.66 (s, 3H). MS (m/z): 449.36 [M+H]+.

Biological Example 1

NTCP-HepG2 Antiviral Assay for Secreted HBsAg

HepG2 cells stably expressing sodium-taurocholate cotransporting polypeptide (NTCP-HepG2) were grown in Dulbecco's Modified Eagle Medium (DMEM) without sodium pyruvate (Thermo Fisher Scientific, Waltham, Mass.) supplemented with 10% fetal bovine serum, 2 mM L-glutamine, 1% penicillin/streptomycin, and 0.25 mg/mL G-418. NTCP-HepG2 cells were infected with 4000 genome equivalent per cell of genotype D (AD38-derived) HBV in DMEM without sodium pyruvate (Thermo Fisher Scientific, Waltham, Mass.) supplemented with 2% fetal bovine serum, 2 mM L-glutamine, 1% penicillin/streptomycin, 2.5% DMSO, and 4% PEG 8000 (Promega, Madison, Wis.). After 24-hour incubation, cells were washed three times with OptiMEM (Thermo Fisher Scientific, Waltham, Mass.) and fed with fresh DMEM without sodium pyruvate (Thermo Fisher Scientific, Waltham, Mass.) supplemented with 2% fetal bovine serum, 2 mM L-glutamine, 1% penicillin/streptomycin, and 2.5% DMSO. At 4 days after infection, infected NTCP-HepG2 cells were seeded on 384-well plates pre-coated with collagen at a density of 20000 cells per well containing serially diluted compounds of the present disclosure or DMSO (0.5%) in a final volume of 80 μl of DMEM without sodium pyruvate (Thermo Fisher Scientific, Waltham, Mass.) supplemented with 2% fetal bovine serum, 2 mM L-glutamine, 1% penicillin/streptomycin, and 1% DMSO. After an incubation time of 5 days, cell culture supernatant was collected and measured for HBsAg.

Secreted HBsAg in the supernatant were measured using a multiplex chemiluminescent MSD assay (Meso Scale Discovery, Rockville, Md.) using capture and detection antibody pairs specific for HBsAg. The $EC_{50}$ values were calculated from the fit of the dose-response curves to a four-parameter equation. All $EC_{50}$ values represent geometric mean values of a minimum of four determinations. $EC_{50}$ values for certain compounds of the present disclosure are reported in Table 1 below.

Biological Example 2: MT-4 Cytotoxicity Assay

The MT-4 cell line (HTLV-1 transformed, human T lymphoblastoid cells) was obtained from the NIH AIDS Reagent program (Bethesda, Md.). MT-4 cells were maintained in RPMI-1640 media (Thermo Fisher Scientific, Waltham, Mass.) supplemented with 10% fetal bovine serum, 100 Units/mL penicillin, and 100 μg/mL streptomycin. For the MT-4 cytotoxicity assay, 0.4 μL of serially diluted solutions of certain compounds disclosed herein were added to 40 μL of cell maintenance media in 384-well black, solid bottom plate using a Biomek FX workstation (Beckman Coulter, Brea, Calif.). Two thousand cells in 35 μL were added to each well using a Biotek uFlow Workstation (Biotek, Winooski, Vt.). Each assay plate contained 10 μM puromycin (final concentration) and 0.5% DMSO in RPMI-1640 media as positive and negative controls, respectively. Assay plates were incubated for five days at 37° C. in an incubator set at 5% $CO_2$ and 90% humidity. After five days, 22 μL of Cell Titer Glo reagent (Promega, Madison, Wis.) was added to the assay plates with a Biotek uFlow Workstation. Plates were subsequently placed on an Envision Plate Reader (Perkin Elmer, Waltham, Mass.) for five minutes before the luminescence signal was read. $CC_{50}$ values were defined as the compound concentration that caused a 50% decrease in luminescence signal, and were calculated by non-linear regression using Pipeline Pilot software by applying a four parameter fit equation (Accelrys, San Diego, Calif.) and are reported in the following Table 1.

TABLE 1

| Compound No. | Structure | Name | NTCP HBsAg EC$_{50}$ (nM) | MT-4 CC$_{50}$ (μM) |
|---|---|---|---|---|
| 1 | 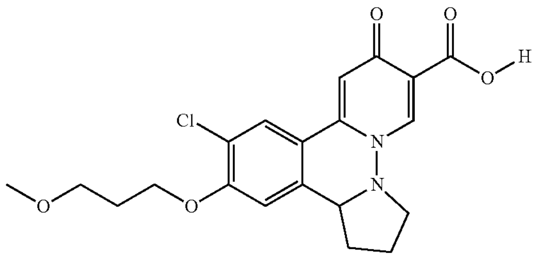 [SMILES: COCCCOc1cc2c(cc1Cl)-c1cc(=O)c(C(=O)O)cn1N1CCCC21] | 11-chloro-12-(3-methoxypropoxy)-8-oxo-2,3,8,13b-tetrahydro-1H-pyrido[2,1-a]pyrrolo[1,2-c]phthalazine-7-carboxylic acid | 90 | 8.0 |
| 2 | 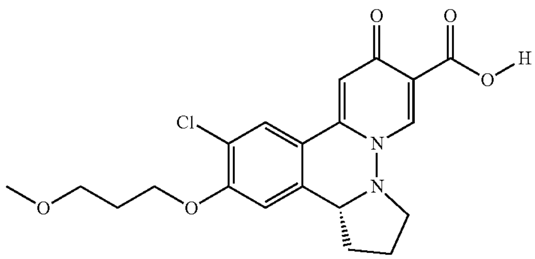 [SMILES: COCCCOc1cc2c(cc1Cl)-c1cc(=O)c(C(=O)O)cn1N1CCC[C@H]21] | (R)-11-chloro-12-(3-methoxypropoxy)-8-oxo-2,3,8,13b-tetrahydro-1H-pyrido[2,1-a]pyrrolo[1,2-c]phthalazine-7-carboxylic acid | 110 | 3.9 |
| 3 | 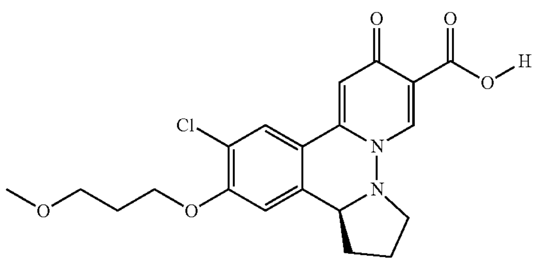 [SMILES: COCCCOc1cc2c(cc1Cl)-c1cc(=O)c(C(=O)O)cn1N1CCC[C@@H]21] | (S)-11-chloro-12-(3-methoxypropoxy)-8-oxo-2,3,8,13b-tetrahydro-1H-pyrido[2,1-a]pyrrolo[1,2-c]phthalazine-7-carboxylic acid | >1000 | 9.1 |
| 4 | 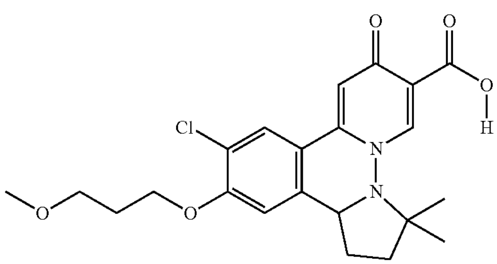 [SMILES: COCCCOc1cc2c(cc1Cl)-c1cc(=O)c(C(=O)O)cn1N1C2CCC1(C)C] | 11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 3.9 | >10 |
| 5 | 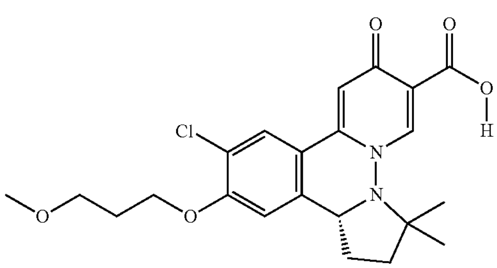 [SMILES: COCCCOc1cc2c(cc1Cl)-c1cc(=O)c(C(=O)O)cn1N1[C@@H]2CCC1(C)C] | (R)-11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 1.7 | >10 |

TABLE 1-continued

| Compound No. | Structure | Name | NTCP HBsAg EC$_{50}$ (nM) | MT-4 CC$_{50}$ (μM) |
|---|---|---|---|---|
| 6 | 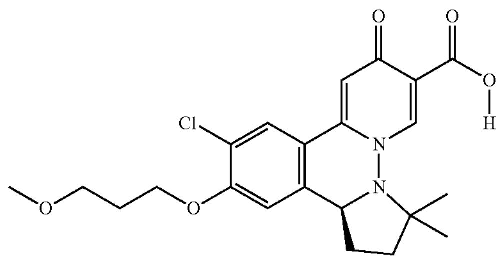 [SMILES: COCCCOc1cc2c(cc1Cl)-c1cc(=O)c(C(=O)O)cn1N1[C@H]2CCC1(C)C] | (S)-11-chloro-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 300 | >10 |
| 7 | 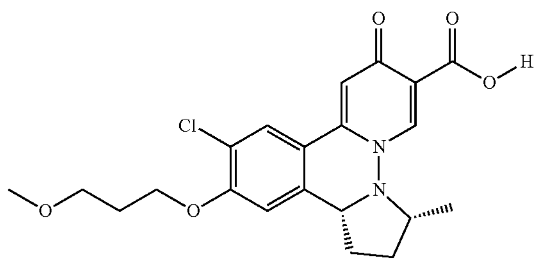 [SMILES: COCCCOc1cc2c(cc1Cl)-c1cc(=O)c(C(=O)O)cn1N1[C@H](C)CC[C@H]21] | (3R,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid | 32 | >10 |
| 8 | 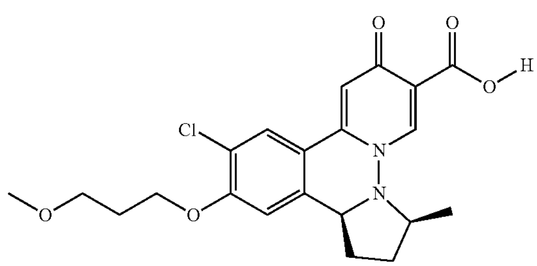 [SMILES: COCCCOc1cc2c(cc1Cl)-c1cc(=O)c(C(=O)O)cn1N1[C@@H](C)CC[C@@H]21] | (3S,13bS)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid | 200 | >10 |
| 9 | 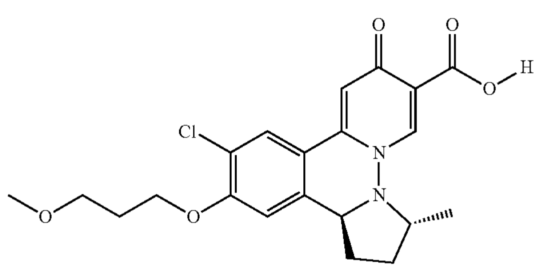 [SMILES: COCCCOc1cc2c(cc1Cl)-c1cc(=O)c(C(=O)O)cn1N1[C@H](C)CC[C@@H]21] | (3R,13bS)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid | 45 | >10 |
| 10 | 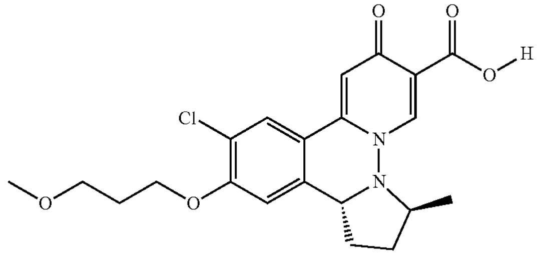 [SMILES: COCCCOc1cc2c(cc1Cl)-c1cc(=O)c(C(=O)O)cn1N1[C@@H]2CC[C@@H]1C] | (3S,13bR)-11-chloro-12-(3-methoxypropoxy)-3-methyl-8-oxo-2,3,8,13b-tetrahydro-1H-pyrido[2,1-a]pyrrolo[1,2-c]phthalazine-7-carboxylic acid | 5.7 | >10 |

TABLE 1-continued

| Compound No. | Structure | Name | NTCP HBsAg EC$_{50}$ (nM) | MT-4 CC$_{50}$ (μM) |
|---|---|---|---|---|
| 11 | 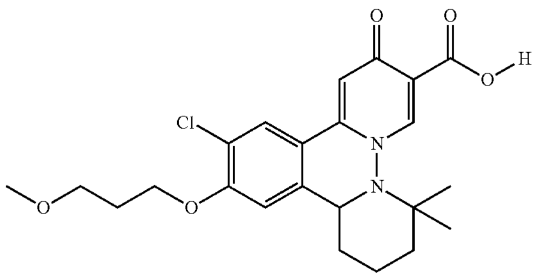 [SMILES: COCCCOc1cc2c(cc1Cl)-c1cc(=O)c(C(=O)O)cn1N1C2CCCC1(C)C] | 13-chloro-12-(3-methoxypropoxy)-7,7-dimethyl-2-oxo-2,7,8,9,10,10a-hexahydrodipyrido[2,1-a:1',2'-c]phthalazine-3-carboxylic acid | 4.3 | >10 |
| 12 | 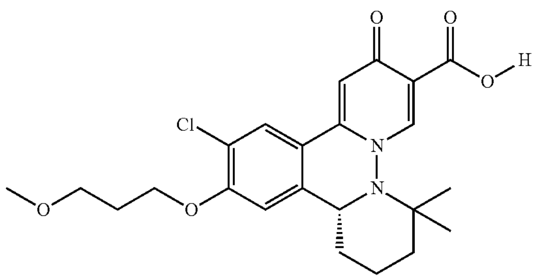 [SMILES: COCCCOc1cc2c(cc1Cl)-c1cc(=O)c(C(=O)O)cn1N1[C@@H]2CCCC1(C)C] | (R)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid | 2.5 | 8.8 |
| 13 | 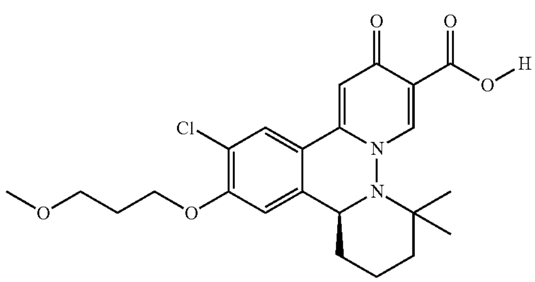 [SMILES: COCCCOc1cc2c(cc1Cl)-c1cc(=O)c(C(=O)O)cn1N1[C@H]2CCCC1(C)C] | (S)-13-chloro-12-(3-methoxypropoxy)-7,7-dimethyl-2-oxo-2,7,8,9,10,10a-hexahydrodipyrido[2,1-a:1',2'-c]phthalazine-3-carboxylic acid | 34 | >10 |
| 14 | 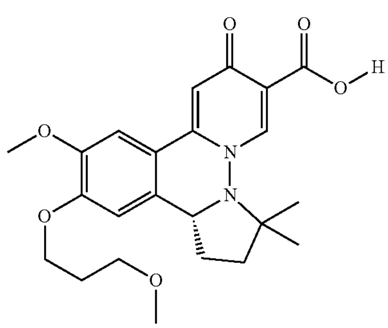 [SMILES: COCCCOc1cc2c(cc1OC)-c1cc(=O)c(C(=O)O)cn1N1[C@@H]2CCC1(C)C] | (R)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 2.1 | >10 |
| 15 | 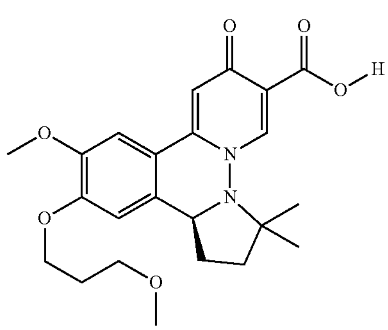 [SMILES: COCCCOc1cc2c(cc1OC)-c1cc(=O)c(C(=O)O)cn1N1[C@H]2CCC1(C)C] | (S)-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 350 | >10 |

TABLE 1-continued

| Compound No. | Structure | Name | NTCP HBsAg EC$_{50}$ (nM) | MT-4 CC$_{50}$ (μM) |
|---|---|---|---|---|
| 16 | 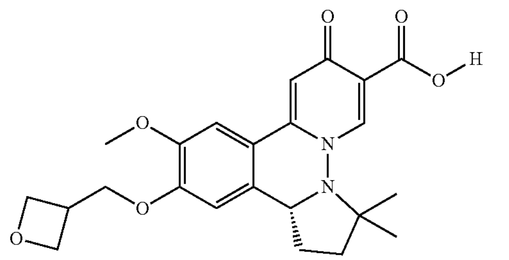 [SMILES: COc1cc2c(cc1OCC1COC1)[C@H]1CCC(C)(C)N1n1cc(C(=O)O)c(=O)cc1-2] | (R)-11-methoxy-3,3-dimethyl-12-(oxetan-3-ylmethoxy)-8-oxo-2,3,8,13b-tetrahydro-1H-pyrido[2,1-a]pyrrolo[1,2-c]phthalazine-7-carboxylic acid | 7.8 | >10 |
| 17 | 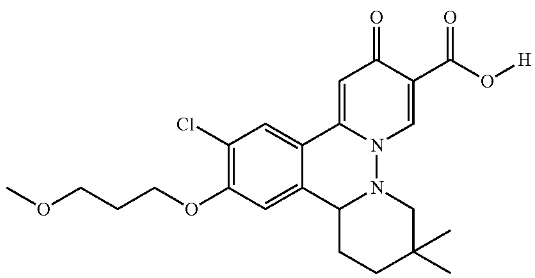 [SMILES: COCCCOc1cc2c(cc1Cl)-c1cc(=O)c(C(=O)O)cn1N1CC(C)(C)CCC21] | 13-chloro-12-(3-methoxypropoxy)-8,8-dimethyl-2-oxo-2,7,8,9,10,10a-hexahydrodipyrido[2,1-a:1',2'-c]phthalazine-3-carboxylic acid | 110 | >10 |
| 18 | 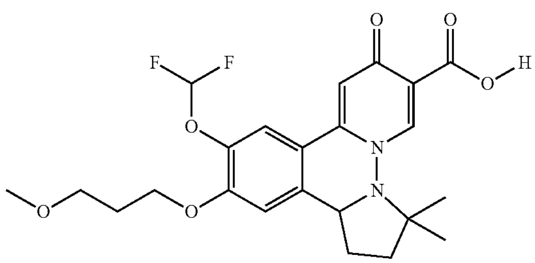 [SMILES: COCCCOc1cc2c(cc1OC(F)F)-c1cc(=O)c(C(=O)O)cn1N1C2CCC1(C)C] | 11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 4.0 | >10 |
| 19 | 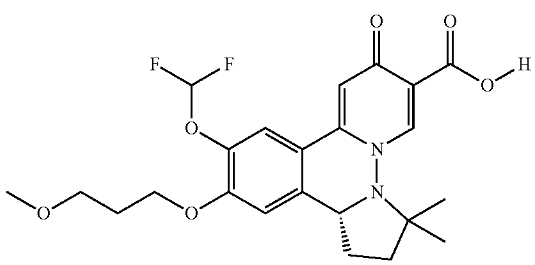 [SMILES: COCCCOc1cc2c(cc1OC(F)F)-c1cc(=O)c(C(=O)O)cn1N1[C@@H]2CCC1(C)C] | (R)-11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 1.2 | >10 |
| 20 | 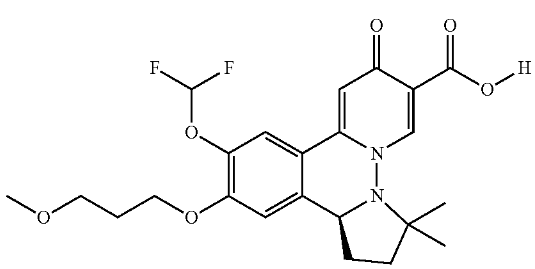 [SMILES: COCCCOc1cc2c(cc1OC(F)F)-c1cc(=O)c(C(=O)O)cn1N1[C@H]2CCC1(C)C] | (S)-11-(difluoromethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 43 | >10 |

TABLE 1-continued

| Compound No. | Structure | Name | NTCP HBsAg EC$_{50}$ (nM) | MT-4 CC$_{50}$ (μM) |
|---|---|---|---|---|
| 21 | 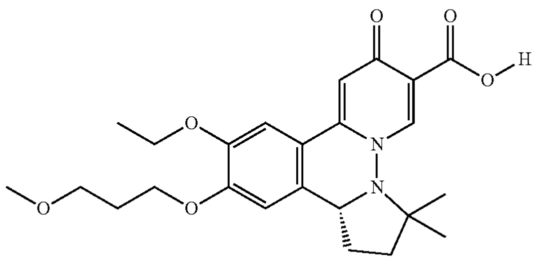 [SMILES: CCOc1cc2c(cc1OCCCOC)[C@H]1CCC(C)(C)N1n1cc(C(=O)O)c(=O)cc1-2] | (R)-11-ethoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 7.5 | >10 |
| 22 | 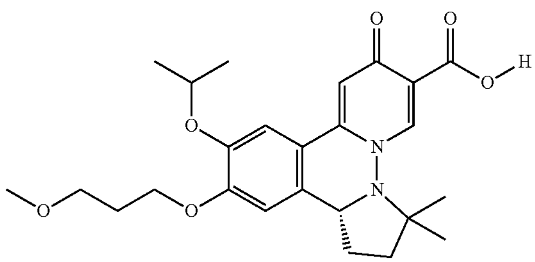 [SMILES: COCCCOc1cc2c(cc1OC(C)C)-c1cc(=O)c(C(=O)O)cn1N1[C@@H]2CCC1(C)C] | (R)-11-isopropoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 12 | >10 |
| 23 | 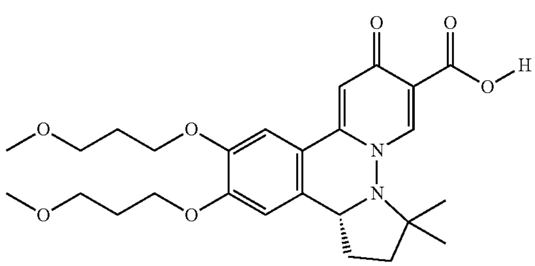 [SMILES: COCCCOc1cc2c(cc1OCCCOC)[C@H]1CCC(C)(C)N1n1cc(C(=O)O)c(=O)cc1-2] | (R)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid | 53 | >10 |
| 24 | 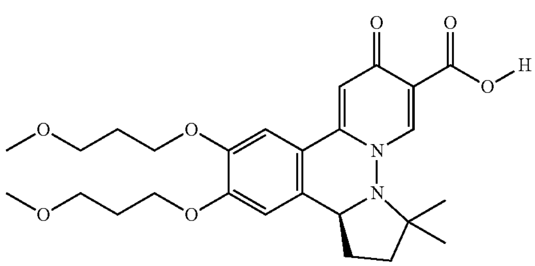 [SMILES: COCCCOc1cc2c(cc1OCCCOC)[C@@H]1CCC(C)(C)N1n1cc(C(=O)O)c(=O)cc1-2] | (S)-11,12-bis(3-methoxypropoxy)-3,3-dimethyl-8-oxo-2,3,8,13b-tetrahydro-1H-pyrido[2,1-a]pyrrolo[1,2-c]phthalazine-7-carboxylic acid | >1000 | >10 |
| 25 | 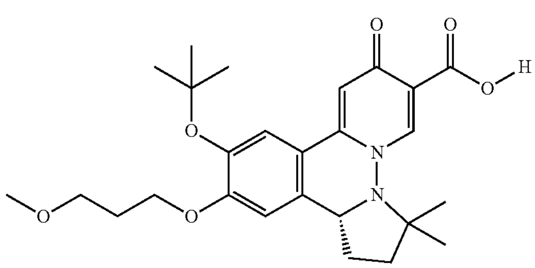 [SMILES: COCCCOc1cc2c(cc1OC(C)(C)C)-c1cc(=O)c(C(=O)O)cn1N1[C@@H]2CCC1(C)C] | (R)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 160 | >10 |

TABLE 1-continued

| Compound No. | Structure | Name | NTCP HBsAg EC$_{50}$ (nM) | MT-4 CC$_{50}$ (μM) |
|---|---|---|---|---|
| 26 | 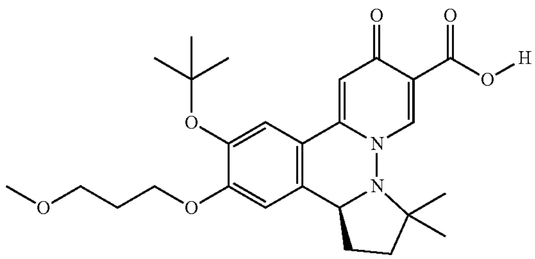 [SMILES: COCCCOc1cc2c(cc1OC(C)(C)C)-c1cc(=O)c(C(=O)O)cn1N1[C@H]2CCC1(C)C] | (S)-11-(tert-butoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | >1000 | >10 |
| 27 | 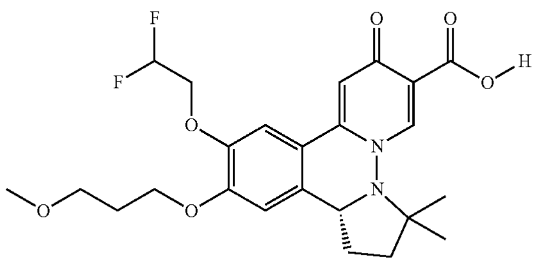 [SMILES: COCCCOc1cc2c(cc1OCC(F)F)-c1cc(=O)c(C(=O)O)cn1N1[C@@H]2CCC1(C)C] | (R)-11-(2,2-difluoroethoxy)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 3.7 | >10 |
| 28 | 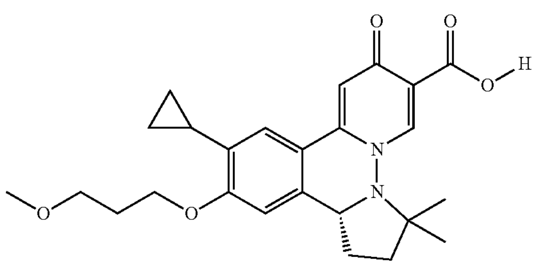 [SMILES: COCCCOc1cc2c(cc1C1CC1)-c1cc(=O)c(C(=O)O)cn1N1[C@@H]2CCC1(C)C] | (R)-11-cyclopropyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 0.78 | 8.7 |
| 29 | 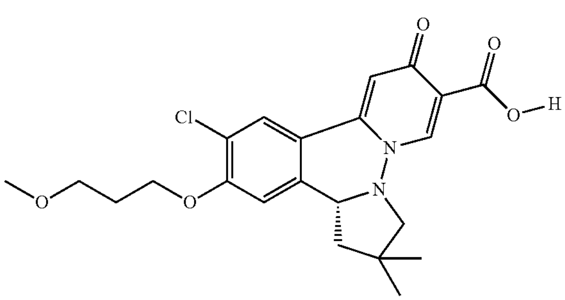 [SMILES: COCCCOc1cc2c(cc1Cl)-c1cc(=O)c(C(=O)O)cn1N1CC(C)(C)C[C@H]21] | (R)-11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylic acid | 14 | >10 |
| 30 | 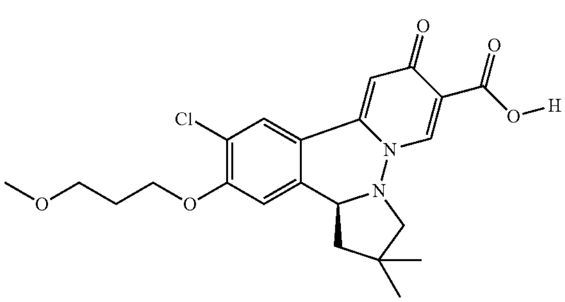 [SMILES: COCCCOc1cc2c(cc1Cl)-c1cc(=O)c(C(=O)O)cn1N1CC(C)(C)C[C@@H]21] | (S)-11-chloro-12-(3-methoxypropoxy)-2,2-dimethyl-8-oxo-2,3,8,13b-tetrahydro-1H-pyrido[2,1-a]pyrrolo[1,2-c]phthalazine-7-carboxylic acid | 10 | >10 |

TABLE 1-continued

| Compound No. | Structure | Name | NTCP HBsAg EC$_{50}$ (nM) | MT-4 CC$_{50}$ (μM) |
| --- | --- | --- | --- | --- |
| 31 | 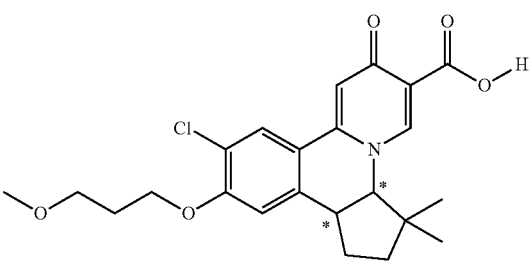<br>*cis isomer | trans-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (racemate) | 6.4 | >10 |
| 32 | 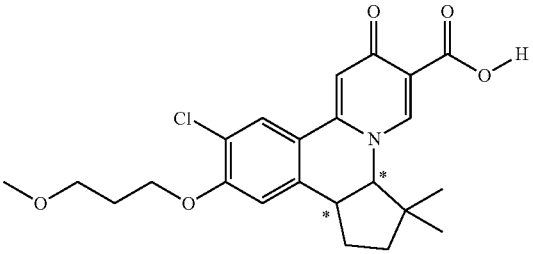<br>*trans isomer | cis-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid (racemate) | 120 | 6.0 |
| 33 | 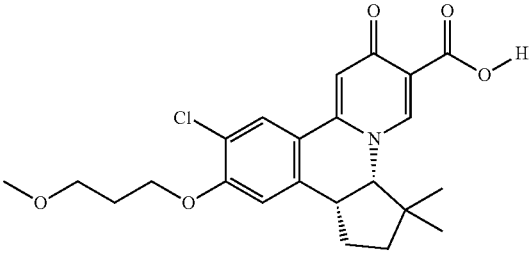 [SMILES: COCCCOc1cc2c(cc1Cl)-c1cc(=O)c(C(=O)O)cn1[C@H]1[C@@H]2CCC1(C)C] | (3aS,12bR)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid | 1.8 | 7.9 |
| 34 | 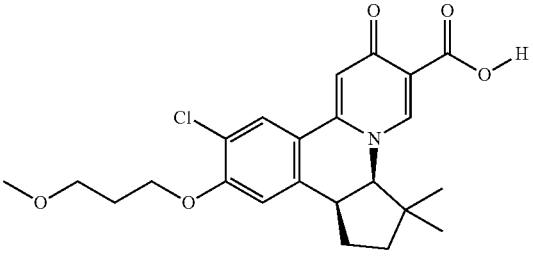 [SMILES: COCCCOc1cc2c(cc1Cl)-c1cc(=O)c(C(=O)O)cn1[C@@H]1[C@H]2CCC1(C)C] | (3aR,12bS)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid | 220 | >10 |
| 35 | 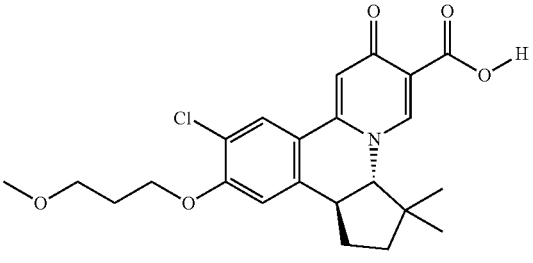 [SMILES: COCCCOc1cc2c(cc1Cl)-c1cc(=O)c(C(=O)O)cn1[C@H]1[C@H]2CCC1(C)C] | (3aS,12bS)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid | 49 | >10 |

TABLE 1-continued

| Compound No. | Structure | Name | NTCP HBsAg EC$_{50}$ (nM) | MT-4 CC$_{50}$ (μM) |
|---|---|---|---|---|
| 36 | 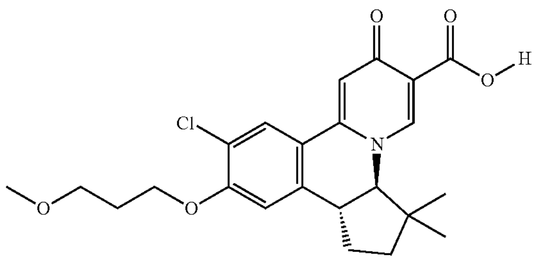 [SMILES: COCCCOc1cc2c(cc1Cl)-c1cc(=O)c(C(=O)O)cn1[C@@H]1[C@@H]2CCC1(C)C] | (3aR,12bR)-10-chloro-11-(3-methoxypropoxy)-3,3-dimethyl-7-oxo-1,2,3,3a,7,12b-hexahydrocyclopenta[c]pyrido[2,1-a]isoquinoline-6-carboxylic acid | 170 | >10 |
| 37 | 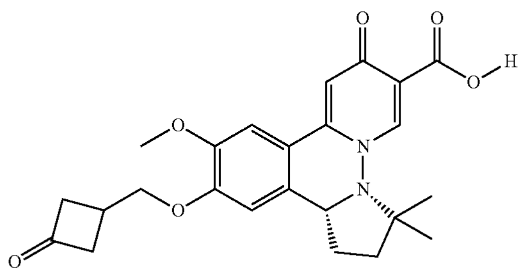 | (R)-11-methoxy-3,3-dimethyl-8-oxo-12-((3-oxocyclobutyl)methoxy)-2,3,8,13b-tetrahydro-1H-pyrido[2,1-a]pyrrolo[1,2-c]phthalazine-7-carboxylic acid | 4.0 | >10 |
| 38 | 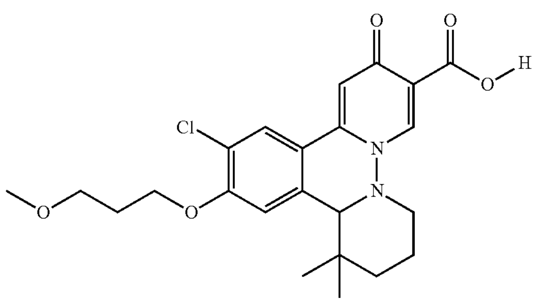 [SMILES: COCCCOc1cc2c(cc1Cl)-c1cc(=O)c(C(=O)O)cn1N1CCCC(C)(C)C21] | 13-chloro-12-(3-methoxypropoxy)-10,10-dimethyl-2-oxo-2,7,8,9,10,10a-hexahydrodipyrido[2,1-a:1',2'-c]phthalazine-3-carboxylic acid | 27 | 9.9 |
| 39 | 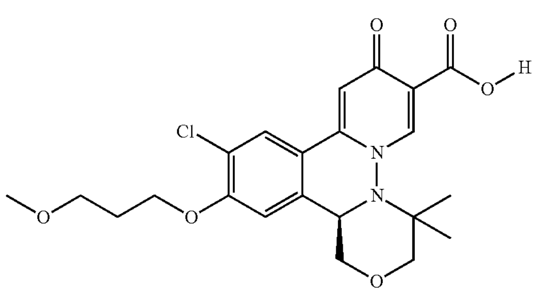 [SMILES: COCCCOc1cc2c(cc1Cl)-c1cc(=O)c(C(=O)O)cn1N1[C@H]2COCC1(C)C] | (R)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid | 680 | >10 |
| 40 | 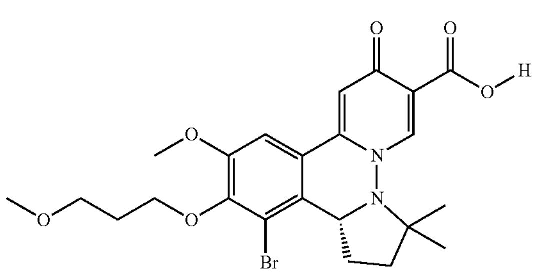 [SMILES: COCCCOc1c(OC)cc2c(c1Br)[C@H]1CCC(C)(C)N1n1cc(C(=O)O)c(=O)cc1-2] | (R)-13-bromo-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 360 | 8.8 |

TABLE 1-continued

| Compound No. | Structure | Name | NTCP HBsAg EC$_{50}$ (nM) | MT-4 CC$_{50}$ (μM) |
|---|---|---|---|---|
| 41 | 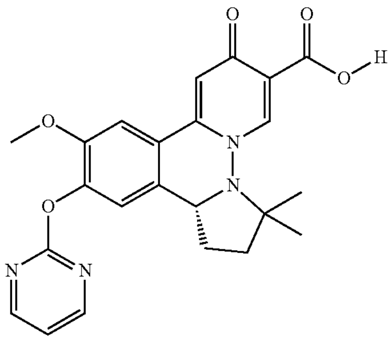 [SMILES: COc1cc2c(cc1Oc1ncccn1)[C@H]1CCC(C)(C)N1n1cc(C(=O)O)c(=O)cc1-2] | (R)-11-methoxy-3,3-dimethyl-8-oxo-12-(pyrimidin-2-yloxy)-2,3,8,13b-tetrahydro-1H-pyrido[2,1-a]pyrrolo[1,2-c]phthalazine-7-carboxylic acid | 120 | >10 |
| 42 | 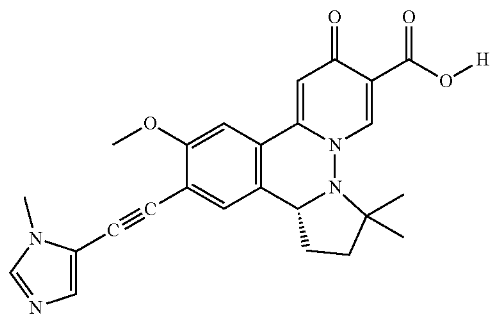 [SMILES: COc1cc2c(cc1C#Cc1cncn1C)[C@H]1CCC(C)(C)N1n1cc(C(=O)O)c(=O)cc1-2] | (R)-11-methoxy-3,3-dimethyl-12-((1-methyl-1H-imidazol-5-yl)ethynyl)-8-oxo-2,3,8,13b-tetrahydro-1H-pyrido[2,1-a]pyrrolo[1,2-c]phthalazine-7-carboxylic acid | 4.8 | >10 |
| 43 | 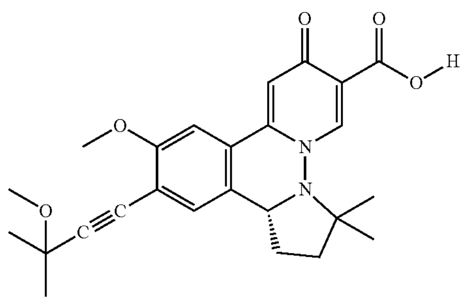 [SMILES: COc1cc2c(cc1C#CC(C)(C)OC)[C@H]1CCC(C)(C)N1n1cc(C(=O)O)c(=O)cc1-2] | (R)-11-methoxy-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid | 7.6 | >10 |
| 44 | 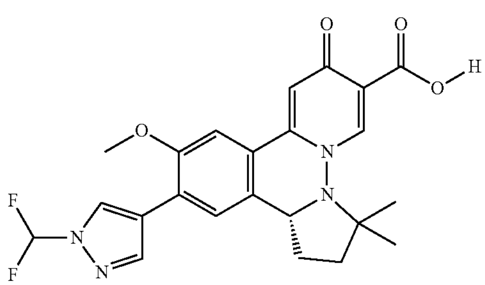 [SMILES: COc1cc2c(cc1-c1cnn(C(F)F)c1)[C@H]1CCC(C)(C)N1n1cc(C(=O)O)c(=O)cc1-2] | (R)-12-(1-(difluoromethyl)-1H-pyrazol-4-yl)-11-methoxy-3,3-dimethyl-8-oxo-2,3,8,13b-tetrahydro-1H-pyrido[2,1-a]pyrrolo[1,2-c]phthalazine-7-carboxylic acid | 5.5 | 3.0 |
| 45 | 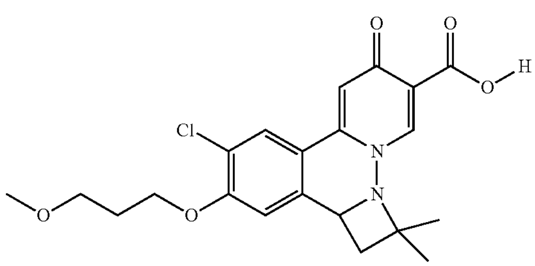 [SMILES: COCCCOc1cc2c(cc1Cl)-c1cc(=O)c(C(=O)O)cn1N1C2CC1(C)C] | 10-chloro-11-(3-methoxypropoxy)-2,2-dimethyl-7-oxo-1,2,7,12b-tetrahydroazeto[2,1-a]pyrido[1,2-c]phthalazine-6-carboxylic acid | nd | nd |

TABLE 1-continued

| Compound No. | Structure | Name | NTCP HBsAg EC$_{50}$ (nM) | MT-4 CC$_{50}$ (μM) |
|---|---|---|---|---|
| 46 | 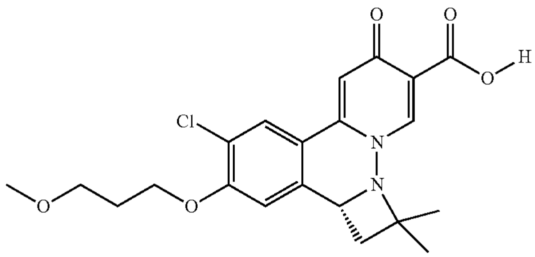 [SMILES: COCCCOc1cc2c(cc1Cl)-c1cc(=O)c(C(=O)O)cn1N1[C@@H]2CC1(C)C] | (R)-10-chloro-11-(3-methoxypropoxy)-2,2-dimethyl-7-oxo-1,2,7,12b-tetrahydroazeto[2,1-a]pyrido[1,2-c]phthalazine-6-carboxylic acid | 7.8 | >10 |
| 47 | 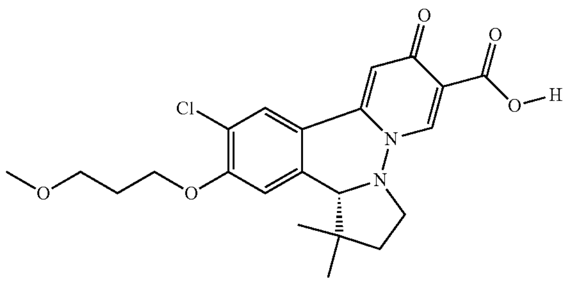 [SMILES: COCCCOc1cc2c(cc1Cl)-c1cc(=O)c(C(=O)O)cn1N1CCC(C)(C)[C@H]21] | (R)-11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylic acid | 16 | 1.7 |
| 48 | 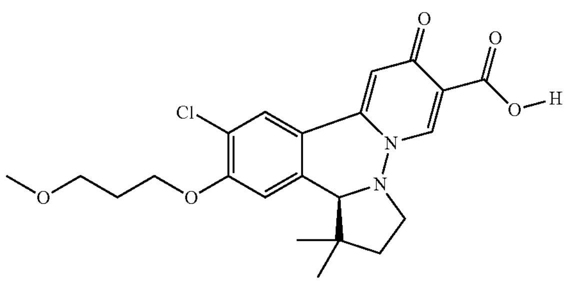 [SMILES: COCCCOc1cc2c(cc1Cl)-c1cc(=O)c(C(=O)O)cn1N1CCC(C)(C)[C@@H]21] | (S)-11-chloro-12-(3-methoxypropoxy)-1,1-dimethyl-8-oxo-2,3,8,13b-tetrahydro-1H-pyrido[2,1-a]pyrrolo[1,2-c]phthalazine-7-carboxylic acid | >1000 | 2.2 |
| 49 | 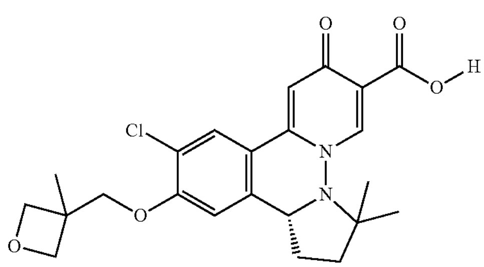 [SMILES: CC1(COc2cc3c(cc2Cl)-c2cc(=O)c(C(=O)O)cn2N2[C@@H]3CCC2(C)C)COC1] | (R)-11-chloro-3,3-dimethyl-12-((3-methyloxetan-3-yl)methoxy)-8-oxo-2,3,8,13b-tetrahydro-1H-pyrido[2,1-a]pyrrolo[1,2-c]phthalazine-7-carboxylic acid | 3.8 | >10 |
| 50 | 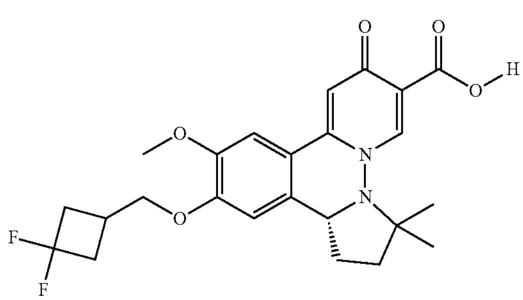 [SMILES: COc1cc2c(cc1OCC1CC(F)(F)C1)[C@H]1CCC(C)(C)N1n1cc(C(=O)O)c(=O)cc1-2] | (R)-12-((3,3-difluorocyclobutyl)methoxy)-11-methoxy-3,3-dimethyl-8-oxo-2,3,8,13b-tetrahydro-1H-pyrido[2,1-a]pyrrolo[1,2-c]phthalazine-7-carboxylic acid | 1.0 | >10 |

TABLE 1-continued

| Compound No. | Structure | Name | NTCP HBsAg EC$_{50}$ (nM) | MT-4 CC$_{50}$ (μM) |
| --- | --- | --- | --- | --- |
| 51 | 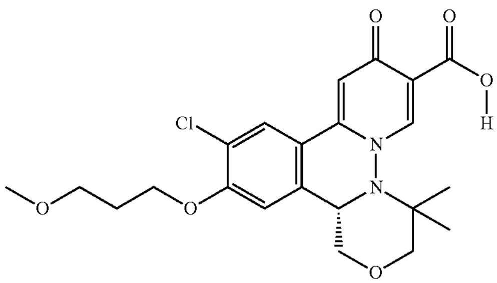 [SMILES: COCCCOc1cc2c(cc1Cl)-c1cc(=O)c(C(=O)O)cn1N1[C@@H]2COCC1(C)C] | (S)-12-chloro-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid | 2.9 | >10 |
| 52 | 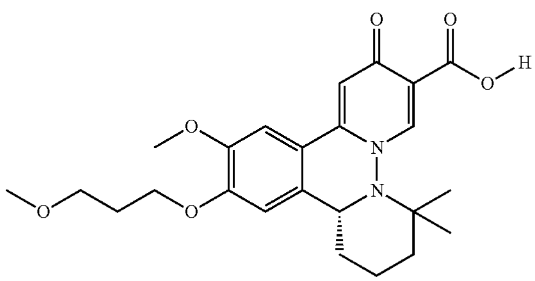 [SMILES: COCCCOc1cc2c(cc1OC)-c1cc(=O)c(C(=O)O)cn1N1[C@@H]2CCCC1(C)C] | (R)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid | 0.91 | >10 |
| 53 | 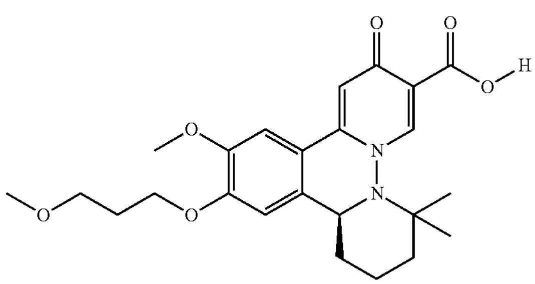 [SMILES: COCCCOc1cc2c(cc1OC)-c1cc(=O)c(C(=O)O)cn1N1[C@H]2CCCC1(C)C] | (S)-13-methoxy-12-(3-methoxypropoxy)-7,7-dimethyl-2-oxo-2,7,8,9,10,10a-hexahydrodipyrido[2,1-a:1',2'-c]phthalazine-3-carboxylic acid | 9.1 | 9.7 |
| 54 | 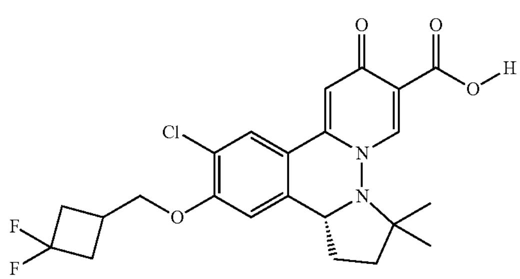 [SMILES: CC1(C)CC[C@@H]2c3cc(OCC4CC(F)(F)C4)c(Cl)cc3-c3cc(=O)c(C(=O)O)cn3N21] | (R)-11-chloro-12-((3,3-difluorocyclobutyl)methoxy)-3,3-dimethyl-8-oxo-2,3,8,13b-tetrahydro-1H-pyrido[2,1-a]pyrrolo[1,2-c]phthalazine-7-carboxylic acid | 0.75 | 5.3 |
| 55 | 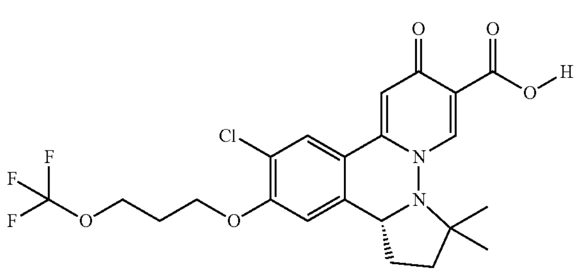 [SMILES: CC1(C)CC[C@@H]2c3cc(OCCCOC(F)(F)F)c(Cl)cc3-c3cc(=O)c(C(=O)O)cn3N21] | (R)-11-chloro-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid | 3.7 | 6.8 |

TABLE 1-continued

| Compound No. | Structure | Name | NTCP HBsAg EC$_{50}$ (nM) | MT-4 CC$_{50}$ (μM) |
|---|---|---|---|---|
| 56 | 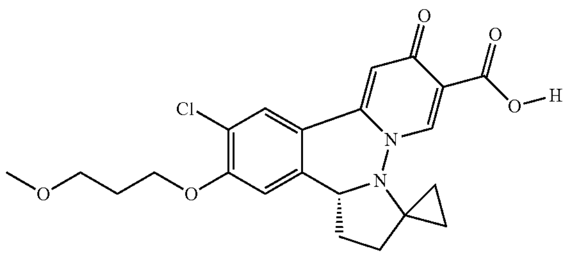 [SMILES: COCCCOc1cc2c(cc1Cl)-c1cc(=O)c(C(=O)O)cn1N1[C@@H]2CCC12CC2] | (R)-11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid | 1.5 | >10 |
| 57 | 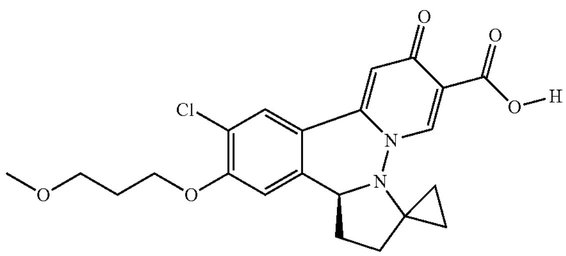 [SMILES: COCCCOc1cc2c(cc1Cl)-c1cc(=O)c(C(=O)O)cn1N1[C@H]2CCC12CC2] | (S)-11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid | >1000 | >10 |
| 58 | 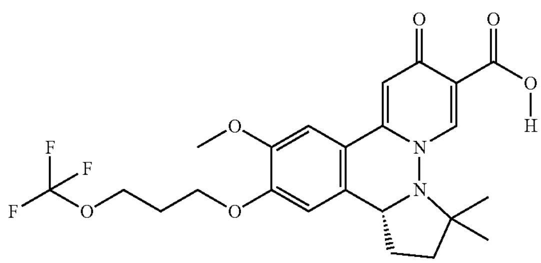 [SMILES: COc1cc2c(cc1OCCCOC(F)(F)F)[C@H]1CCC(C)(C)N1n1cc(C(=O)O)c(=O)cc1-2] | (R)-11-methoxy-3,3-dimethyl-8-oxo-12-(3-(trifluoromethoxy)propoxy)-2,3,8,13b-tetrahydro-1H-pyrido[2,1-a]pyrrolo[1,2-c]phthalazine-7-carboxylic acid | 4.8 | 9.3 |
| 59 | 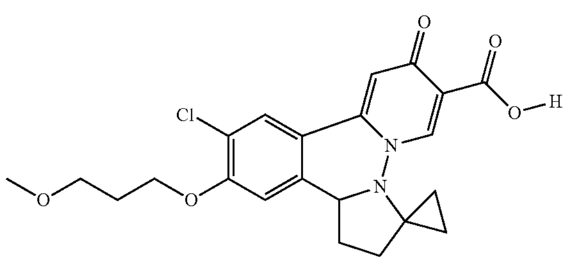 [SMILES: COCCCOc1cc2c(cc1Cl)-c1cc(=O)c(C(=O)O)cn1N1C2CCC12CC2] | 11'-chloro-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid | 6.0 | >10 |
| 60 | 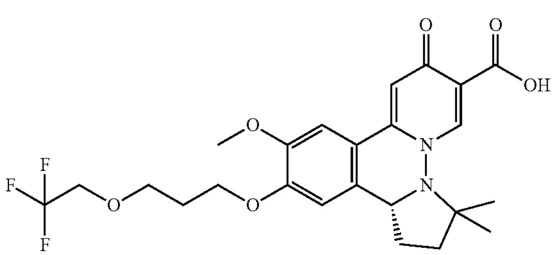 [SMILES: COc1cc2c(cc1OCCCOCC(F)(F)F)[C@H]1CCC(C)(C)N1n1cc(C(=O)O)c(=O)cc1-2] | (R)-11-methoxy-3,3-dimethyl-8-oxo-12-(3-(2,2,2-trifluoroethoxy)propoxy)-2,3,8,13b-tetrahydro-1H-pyrido[2,1-a]pyrrolo[1,2-c]phthalazine-7-carboxylic acid | 1.2 | >10 |
| 61 | 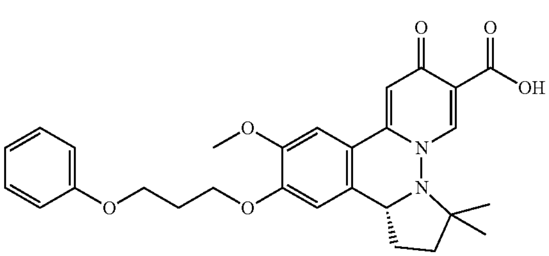 [SMILES: COc1cc2c(cc1OCCCOc1ccccc1)[C@H]1CCC(C)(C)N1n1cc(C(=O)O)c(=O)cc1-2] | (R)-11-methoxy-3,3-dimethyl-8-oxo-12-(3-phenoxypropoxy)-2,3,8,13b-tetrahydro-1H-pyrido[2,1-a]pyrrolo[1,2-c]phthalazine-7-carboxylic acid | 0.94 | 6.0 |

TABLE 1-continued

| Compound No. | Structure | Name | NTCP HBsAg EC$_{50}$ (nM) | MT-4 CC$_{50}$ (μM) |
|---|---|---|---|---|
| 62 | 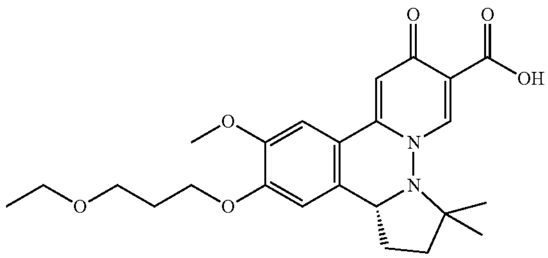 [SMILES: CCOCCCOc1cc2c(cc1OC)-c1cc(=O)c(C(=O)O)cn1N1[C@@H]2CCC1(C)C] | (R)-12-(3-ethoxypropoxy)-11-methoxy-3,3-dimethyl-8-oxo-2,3,8,13b-tetrahydro-1H-pyrido[2,1-a]pyrrolo[1,2-c]phthalazine-7-carboxylic acid | 0.67 | >10 |
| 63 | 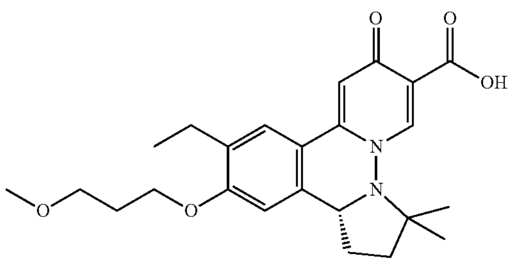 [SMILES: CCc1cc2c(cc1OCCCOC)[C@H]1CCC(C)(C)N1n1cc(C(=O)O)c(=O)cc1-2] | (R)-11-ethyl-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 0.34 | >10 |
| 64 | 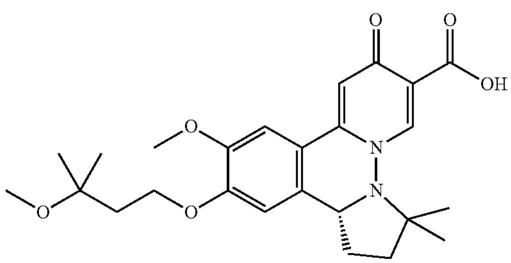 [SMILES: COc1cc2c(cc1OCCC(C)(C)OC)[C@H]1CCC(C)(C)N1n1cc(C(=O)O)c(=O)cc1-2] | (R)-11-methoxy-12-(3-methoxy-3-methylbutoxy)-3,3-dimethyl-8-oxo-2,3,8,13b-tetrahydro-1H-pyrido[2,1-a]pyrrolo[1,2-c]phthalazine-7-carboxylic acid | 0.84 | >10 |
| 65 | 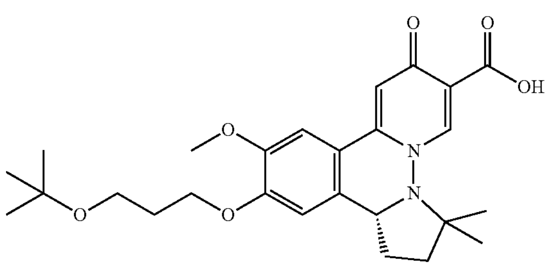 [SMILES: COc1cc2c(cc1OCCCOC(C)(C)C)[C@H]1CCC(C)(C)N1n1cc(C(=O)O)c(=O)cc1-2] | (R)-12-(3-(tert-butoxy)propoxy)-11-methoxy-3,3-dimethyl-8-oxo-2,3,8,13b-tetrahydro-1H-pyrido[2,1-a]pyrrolo[1,2-c]phthalazine-7-carboxylic acid | 0.41 | >10 |
| 66 | 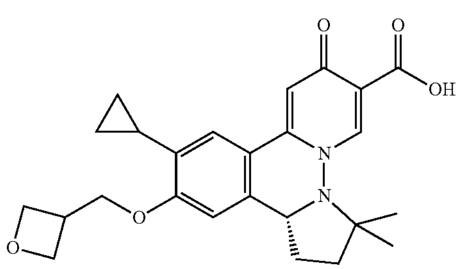 [SMILES: CC1(C)CC[C@@H]2c3cc(OCC4COC4)c(C4CC4)cc3-c3cc(=O)c(C(=O)O)cn3N21] | (R)-11-cyclopropyl-3,3-dimethyl-12-(oxetan-3-ylmethoxy)-8-oxo-2,3,8,13b-tetrahydro-1H-pyrido[2,1-a]pyrrolo[1,2-c]phthalazine-7-carboxylic acid | 0.97 | >10 |

TABLE 1-continued

| Compound No. | Structure | Name | NTCP HBsAg EC$_{50}$ (nM) | MT-4 CC$_{50}$ (μM) |
|---|---|---|---|---|
| 67 | 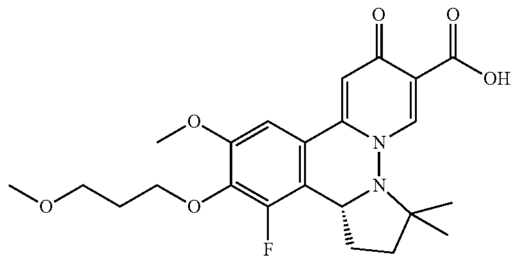 [SMILES: COCCCOc1c(OC)cc2c(c1F)[C@H]1CCC(C)(C)N1n1cc(C(=O)O)c(=O)cc1-2] | (R)-13-fluoro-11-methoxy-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 5.3 | >10 |
| 68 | 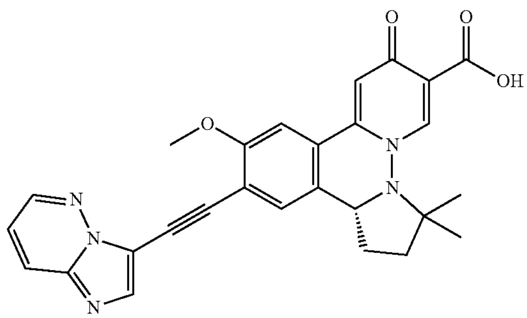 [SMILES: COc1cc2c(cc1C#Cc1cnc3cccnn13)[C@H]1CCC(C)(C)N1n1cc(C(=O)O)c(=O)cc1-2] | (R)-12-(imidazo[1,2-b]pyridazin-3-ylethynyl)-11-methoxy-3,3-dimethyl-8-oxo-2,3,8,13b-tetrahydro-1H-pyrido[2,1-a]pyrrolo[1,2-c]phthalazine-7-carboxylic acid | 2.9 | >10 |
| 69 | 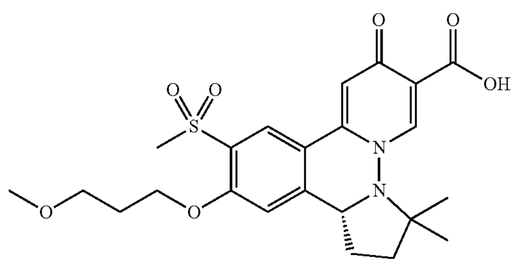 [SMILES: COCCCOc1cc2c(cc1S(C)(=O)=O)-c1cc(=O)c(C(=O)O)cn1N1[C@@H]2CCC1(C)C] | (R)-12-(3-methoxypropoxy)-3,3-dimethyl-11-(methylsulfonyl)-8-oxo-2,3,8,13b-tetrahydro-1H-pyrido[2,1-a]pyrrolo[1,2-c]phthalazine-7-carboxylic acid | 52 | >10 |
| 70 | 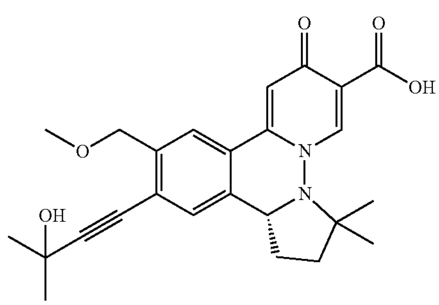 [SMILES: COCc1cc2c(cc1C#CC(C)(C)O)[C@H]1CCC(C)(C)N1n1cc(C(=O)O)c(=O)cc1-2] | (R)-12-(3-hydroxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid | 21.1 | >10 |
| 71 | 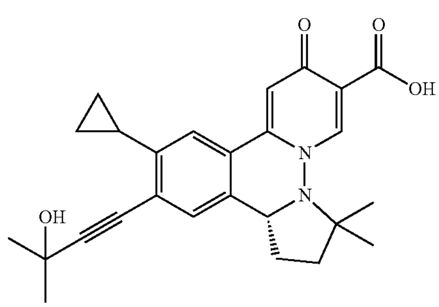 [SMILES: CC(C)(O)C#Cc1cc2c(cc1C1CC1)-c1cc(=O)c(C(=O)O)cn1N1[C@@H]2CCC1(C)C] | (R)-11-cyclopropyl-12-(3-hydroxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid | 2.5 | >10 |

TABLE 1-continued

| Compound No. | Structure | Name | NTCP HBsAg EC$_{50}$ (nM) | MT-4 CC$_{50}$ (μM) |
|---|---|---|---|---|
| 72 | 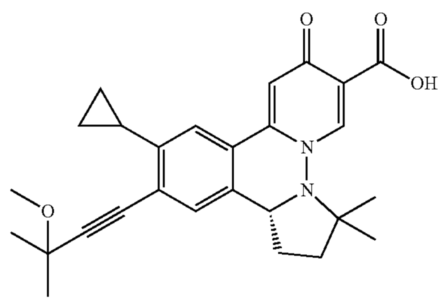 [SMILES: COC(C)(C)C#Cc1cc2c(cc1C1CC1)-c1cc(=O)c(C(=O)O)cn1N1[C@@H]2CCC1(C)C] | (R)-11-cyclopropyl-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid | 0.95 | 6.4 |
| 73 | 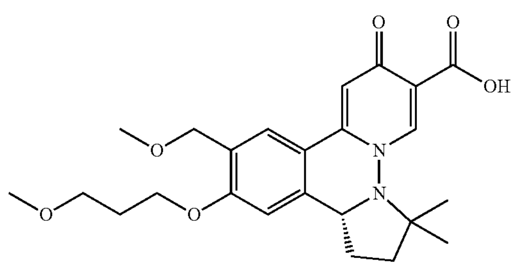 [SMILES: COCCCOc1cc2c(cc1COC)-c1cc(=O)c(C(=O)O)cn1N1[C@@H]2CCC1(C)C] | (R)-11-(methoxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 1.9 | >10 |
| 74 | 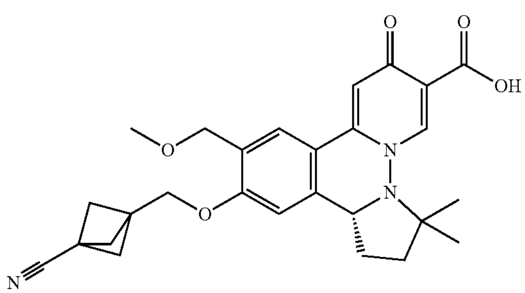 [SMILES: COCc1cc2c(cc1OCC13CC(C#N)(C1)C3)[C@H]1CCC(C)(C)N1n1cc(C(=O)O)c(=O)cc1-2] | (R)-12-((3-cyanobicyclo[1.1.1]pentan-1-yl)methoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid | 3.8 | >10 |
| 75 | 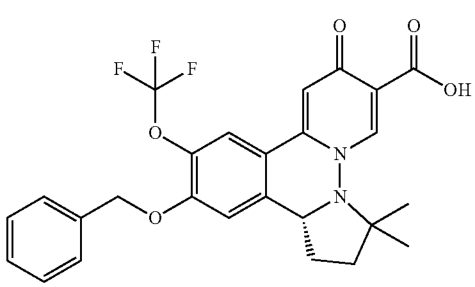 [SMILES: CC1(C)CC[C@@H]2c3cc(OCc4ccccc4)c(OC(F)(F)F)cc3-c3cc(=O)c(C(=O)O)cn3N21] | (R)-12-(benzyloxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid | 6.1 | 5.0 |
| 76 | 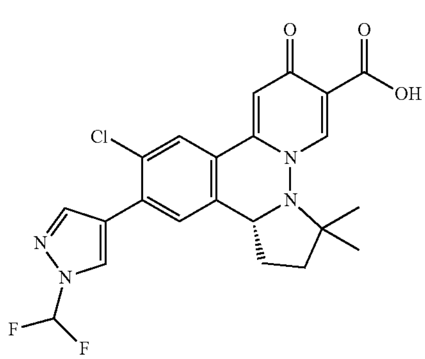 [SMILES: CC1(C)CC[C@@H]2c3cc(-c4cnn(C(F)F)c4)c(Cl)cc3-c3cc(=O)c(C(=O)O)cn3N21] | (R)-11-chloro-12-(1-(difluoromethyl)-1H-pyrazol-4-yl)-3,3-dimethyl-8-oxo-2,3,8,13b-tetrahydro-1H-pyrido[2,1-a]pyrrolo[1,2-c]phthalazine-7-carboxylic acid | 6.3 | 4.4 |

TABLE 1-continued

| Compound No. | Name | NTCP HBsAg EC$_{50}$ (nM) | MT-4 CC$_{50}$ (μM) |
|---|---|---|---|
| 77 | (R)-12-(3-methoxypropoxy)-3,3-dimethyl-11-(oxetan-3-yl)-8-oxo-2,3,8,13b-tetrahydro-1H-pyrido[2,1-a]pyrrolo[1,2-c]phthalazine-7-carboxylic acid | 12.5 | >10 |
| 78 | (R)-11-methoxy-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid | 70 | >10 |
| 79 | (R)-12-(3-methoxypropoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid | 1.1 | >10 |
| 80 | (R)-11-chloro-3,3-bis(methoxymethyl)-12-(3-methoxypropoxy)-8-oxo-2,3,8,13b-tetrahydro-1H-pyrido[2,1-a]pyrrolo[1,2-c]phthalazine-7-carboxylic acid | 45 | >10 |
| 81 | (R)-11-chloro-12-(3-methoxypropoxy)-2',2'-dimethyl-8-oxo-1,2,8,13b-tetrahydrospiro[pyrido[2,1-a]pyrrolo[1,2-c]phthalazine-3,5'-[1,3]dioxane]-7-carboxylic acid | 386 | >10 |

TABLE 1-continued

| Compound No. | Structure | Name | NTCP HBsAg EC$_{50}$ (nM) | MT-4 CC$_{50}$ (μM) |
|---|---|---|---|---|
| 82 | 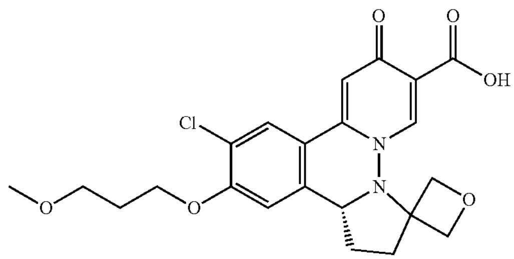 [SMILES: COCCCOc1cc2c(cc1Cl)-c1cc(=O)c(C(=O)O)cn1N1[C@@H]2CCC12COC2] | (R)-11'-chloro-12'-(3-methoxypropoxy)-8'-oxo-1',2',8',13b'-tetrahydrospiro[oxetane-3,3'-pyrido[2,1-a]pyrrolo[1,2-c]phthalazine]-7'-carboxylic acid | 72 | >10 |
| 83 | 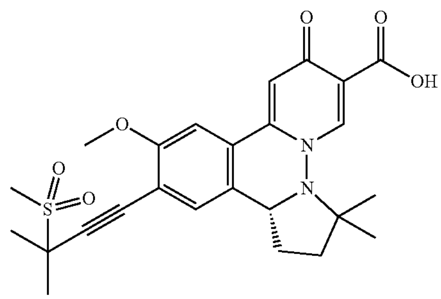 [SMILES: COc1cc2c(cc1C#CC(C)(C)S(C)(=O)=O)[C@H]1CCC(C)(C)N1n1cc(C(=O)O)c(=O)cc1-2] | (R)-11-methoxy-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid | 9.6 | >10 |
| 84 | 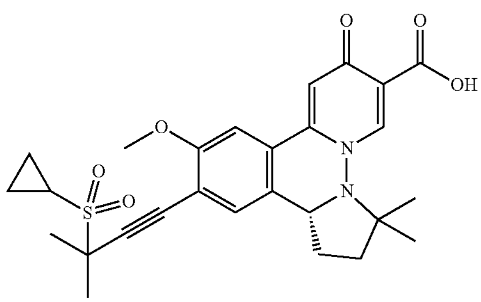 [SMILES: COc1cc2c(cc1C#CC(C)(C)S(=O)(=O)C1CC1)[C@H]1CCC(C)(C)N1n1cc(C(=O)O)c(=O)cc1-2] | (R)-12-(3-(cyclopropylsulfonyl)-3-methylbut-1-yn-1-yl)-11-methoxy-3,3-dimethyl-8-oxo-2,3,8,13b-tetrahydro-1H-pyrido[2,1-a]pyrrolo[1,2-c]phthalazine-7-carboxylic acid | 11.2 | >10 |
| 85 | 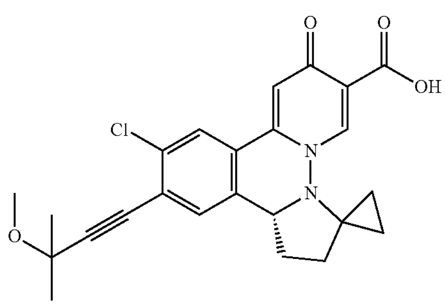 [SMILES: COC(C)(C)C#Cc1cc2c(cc1Cl)-c1cc(=O)c(C(=O)O)cn1N1[C@@H]2CCC12CC2] | (R)-11'-chloro-12'-(3-methoxy-3-methylbut-1-yn-1-yl)-8'-oxo-1',2',8',13b'-tetrahydrospiro[cyclopropane-1,3'-pyrido[2,1-a]pyrrolo[1,2-c]phthalazine]-7'-carboxylic acid | 4.1 | >10 |
| 86 | 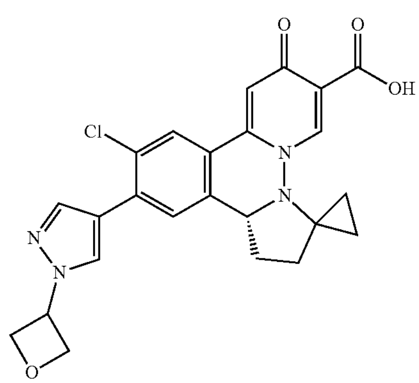 [SMILES: O=C(O)c1cn2c(cc1=O)-c1cc(Cl)c(-c3cnn(C4COC4)c3)cc1[C@H]1CCC3(CC3)N12] | (R)-11'-chloro-12'-(1-(oxetan-3-yl)-1H-pyrazol-4-yl)-8'-oxo-1',2',8',13b'-tetrahydrospiro[cyclopropane-1,3'-pyrido[2,1-a]pyrrolo[1,2-c]phthalazine]-7'-carboxylic acid | 24.8 | >10 |

TABLE 1-continued

| Compound No. | Structure | Name | NTCP HBsAg EC$_{50}$ (nM) | MT-4 CC$_{50}$ (μM) |
|---|---|---|---|---|
| 87 | 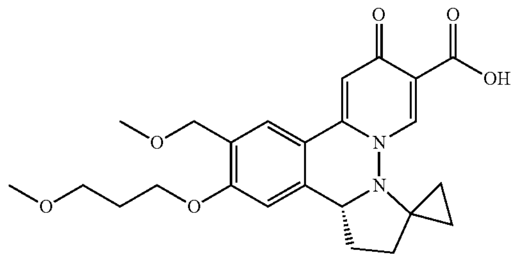 [SMILES: COCCCOc1cc2c(cc1COC)-c1cc(=O)c(C(=O)O)cn1N1[C@@H]2CCC12CC2] | (R)-11'-(methoxymethyl)-12'-(3-methoxypropoxy)-8'-oxo-1',2',8',13b'-tetrahydrospiro[cyclopropane-1,3'-pyrido[2,1-a]pyrrolo[1,2-c]phthalazine]-7'-carboxylic acid | 4.2 | >10 |
| 88 | 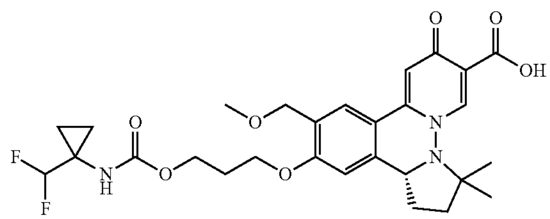 [SMILES: COCc1cc2c(cc1OCCCOC(=O)NC1(C(F)F)CC1)[C@H]1CCC(C)(C)N1n1cc(C(=O)O)c(=O)cc1-2] | (R)-12-(3-(((1-(difluoromethyl)cyclopropyl)carbamoyl)oxy)propoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid | 5.4 | >10 |
| 89 | 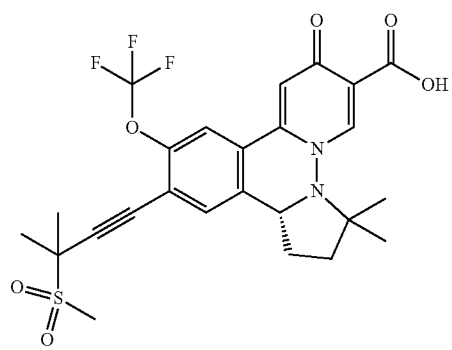 [SMILES: CC1(C)CC[C@@H]2c3cc(C#CC(C)(C)S(C)(=O)=O)c(OC(F)(F)F)cc3-c3cc(=O)c(C(=O)O)cn3N21] | (R)-3,3-dimethyl-12-(3-methyl-3-(methylsulfonyl)but-1-yn-1-yl)-8-oxo-11-(trifluoromethoxy)-2,3,8,13b-tetrahydro-1H-pyrido[2,1-a]pyrrolo[1,2-c]phthalazine-7-carboxylic acid | 13.7 | >10 |
| 90 | 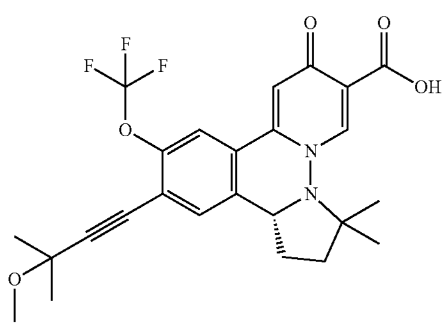 [SMILES: COC(C)(C)C#Cc1cc2c(cc1OC(F)(F)F)-c1cc(=O)c(C(=O)O)cn1N1[C@@H]2CCC1(C)C] | (R)-12-(3-methoxy-3-methylbut-1-yn-1-yl)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid | 5.0 | >10 |
| 91 | 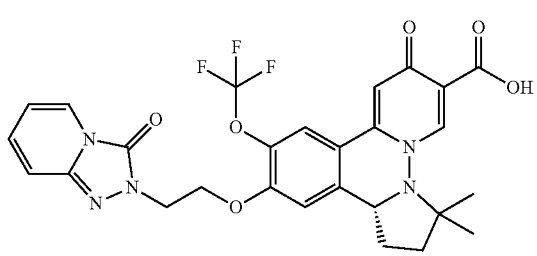 [SMILES: CC1(C)CC[C@@H]2c3cc(OCCn4nc5ccccn5c4=O)c(OC(F)(F)F)cc3-c3cc(=O)c(C(=O)O)cn3N21] | (R)-3,3-dimethyl-8-oxo-12-(2-(3-oxo-[1,2,4]triazolo[4,3-a]pyridin-2(3H)-yl)ethoxy)-11-(trifluoromethoxy)-2,3,8,13b-tetrahydro-1H-pyrido[2,1-a]pyrrolo[1,2-c]phthalazine-7-carboxylic acid | 3.0 | >10 |

TABLE 1-continued

| Compound No. | Structure | Name | NTCP HBsAg EC$_{50}$ (nM) | MT-4 CC$_{50}$ (μM) |
|---|---|---|---|---|
| 92 | 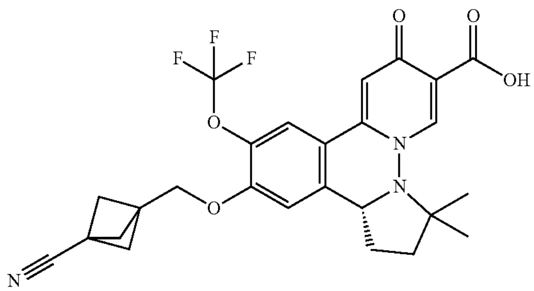 [SMILES: CC1(C)CC[C@@H]2c3cc(OCC45CC(C#N)(C4)C5)c(OC(F)(F)F)cc3-c3cc(=O)c(C(=O)O)cn3N21] | (R)-12-((3-cyanobicyclo[1.1.1]pentan-1-yl)methoxy)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid | 3.0 | 8.1 |
| 93 | 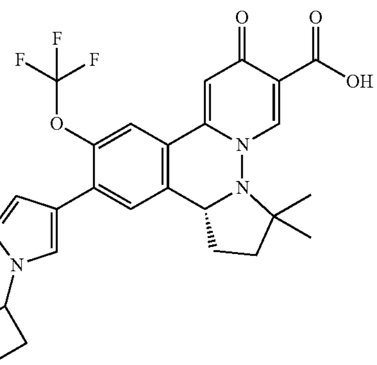 | (R)-3,3-dimethyl-12-(1-(oxetan-3-yl)-1H-pyrazol-4-yl)-8-oxo-11-(trifluoromethoxy)-2,3,8,13b-tetrahydro-1H-pyrido[2,1-a]pyrrolo[1,2-c]phthalazine-7-carboxylic acid | 4.4 | >10 |
| 94 | 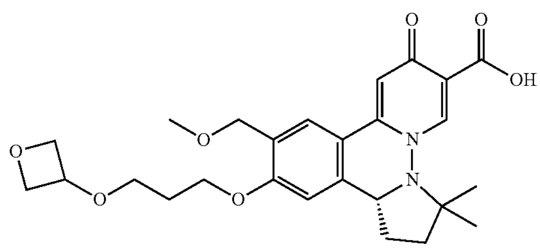 [SMILES: COCc1cc2c(cc1OCCCOC1COC1)[C@H]1CCC(C)(C)N1n1cc(C(=O)O)c(=O)cc1-2] | (R)-11-(methoxymethyl)-3,3-dimethyl-12-(3-(oxetan-3-yloxy)propoxy)-8-oxo-2,3,8,13b-tetrahydro-1H-pyrido[2,1-a]pyrrolo[1,2-c]phthalazine-7-carboxylic acid | 6.0 | >10 |
| 95 | 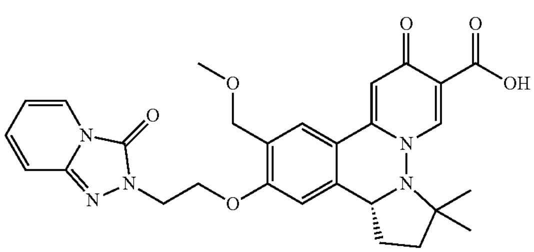 [SMILES: COCc1cc2c(cc1OCCn1nc3ccccn3c1=O)[C@H]1CCC(C)(C)N1n1cc(C(=O)O)c(=O)cc1-2] | (R)-11-(methoxymethyl)-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid | 4.6 | >10 |
| 96 | 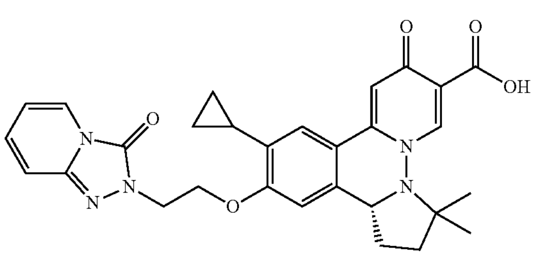 [SMILES: CC1(C)CC[C@@H]2c3cc(OCCn4nc5ccccn5c4=O)c(C4CC4)cc3-c3cc(=O)c(C(=O)O)cn3N21] | (R)-11-cyclopropyl-3,3-dimethyl-8-oxo-12-(2-(3-oxo-[1,2,4]triazolo[4,3-a]pyridin-2(3H)-yl)ethoxy)-2,3,8,13b-tetrahydro-1H-pyrido[2,1-a]pyrrolo[1,2-c]phthalazine-7-carboxylic acid | 0.17 | >10 |

TABLE 1-continued

| Compound No. | Structure | Name | NTCP HBsAg EC$_{50}$ (nM) | MT-4 CC$_{50}$ (μM) |
|---|---|---|---|---|
| 97 | 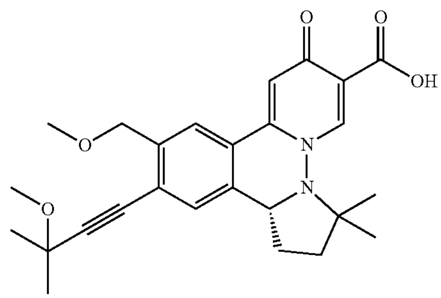 [SMILES: COCc1cc2c(cc1C#CC(C)(C)OC)[C@H]1CCC(C)(C)N1n1cc(C(=O)O)c(=O)cc1-2] | (R)-12-(3-methoxy-3-methylbut-1-yn-1-yl)-11-(methoxymethyl)-3,3-dimethyl-8-oxo-2,3,8,13b-tetrahydro-1H-pyrido[2,1-a]pyrrolo[1,2-c]phthalazine-7-carboxylic acid | 8.6 | >10 |
| 98 | 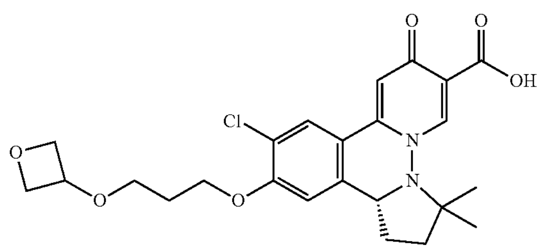 [SMILES: CC1(C)CC[C@@H]2c3cc(OCCCOC4COC4)c(Cl)cc3-c3cc(=O)c(C(=O)O)cn3N21] | (R)-11-chloro-3,3-dimethyl-12-(3-(oxetan-3-yloxy)propoxy)-8-oxo-2,3,8,13b-tetrahydro-1H-pyrido[2,1-a]pyrrolo[1,2-c]phthalazine-7-carboxylic acid | 2.2 | >10 |
| 99 | 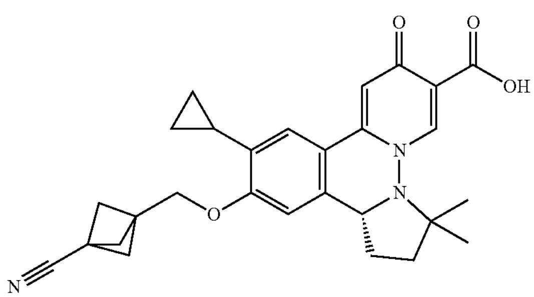 [SMILES: CC1(C)CC[C@@H]2c3cc(OCC45CC(C#N)(C4)C5)c(C4CC4)cc3-c3cc(=O)c(C(=O)O)cn3N21] | (R)-12-((3-cyanobicyclo[1.1.1]pentan-1-yl)methoxy)-11-cyclopropyl-3,3-dimethyl-8-oxo-2,3,8,13b-tetrahydro-1H-pyrido[2,1-a]pyrrolo[1,2-c]phthalazine-7-carboxylic acid | 0.66 | 3.6 |
| 100 | 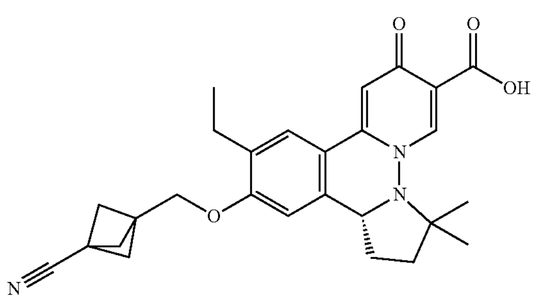 [SMILES: CCc1cc2c(cc1OCC13CC(C#N)(C1)C3)[C@H]1CCC(C)(C)N1n1cc(C(=O)O)c(=O)cc1-2] | (R)-12-((3-cyanobicyclo[1.1.1]pentan-1-yl)methoxy)-11-ethyl-3,3-dimethyl-8-oxo-2,3,8,13b-tetrahydro-1H-pyrido[2,1-a]pyrrolo[1,2-c]phthalazine-7-carboxylic acid | 0.48 | 3.9 |
| 101 | 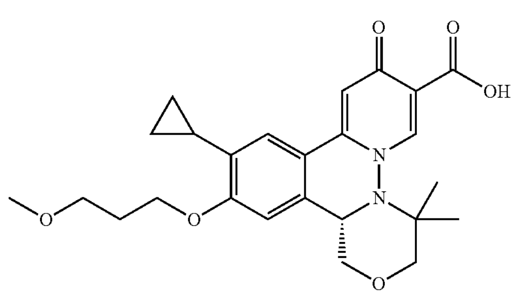 [SMILES: COCCCOc1cc2c(cc1C1CC1)-c1cc(=O)c(C(=O)O)cn1N1[C@@H]2COCC1(C)C] | (S)-12-cyclopropyl-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid | 0.70 | 8.2 |

TABLE 1-continued

| Compound No. | Structure | Name | NTCP HBsAg EC$_{50}$ (nM) | MT-4 CC$_{50}$ (μM) |
|---|---|---|---|---|
| 102 | 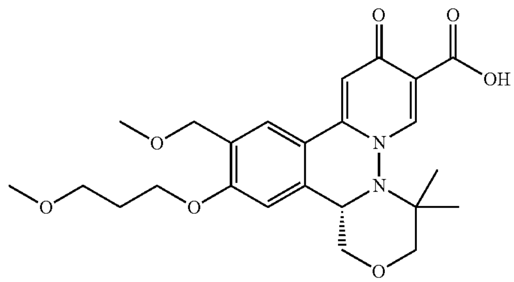 [SMILES: COCCCOc1cc2c(cc1COC)-c1cc(=O)c(C(=O)O)cn1N1[C@@H]2COCC1(C)C] | (S)-12-(methoxymethyl)-13-(3-methoxypropoxy)-4,4-dimethyl-9-oxo-3,4,9,14b-tetrahydro-1H-[1,4]oxazino[3,4-a]pyrido[1,2-c]phthalazine-8-carboxylic acid | 11.5 | >10 |
| 103 | 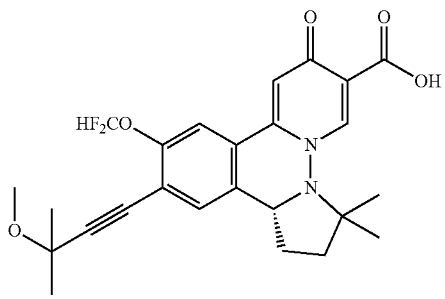 | (R)-11-(difluoromethoxy)-12-(3-methoxy-3-methylbut-1-yn-1-yl)-3,3-dimethyl-8-oxo-2,3,8,13b-tetrahydro-1H-pyrido[2,1-a]pyrrolo[1,2-c]phthalazine-7-carboxylic acid | 0.82 | >10 |
| 104 | 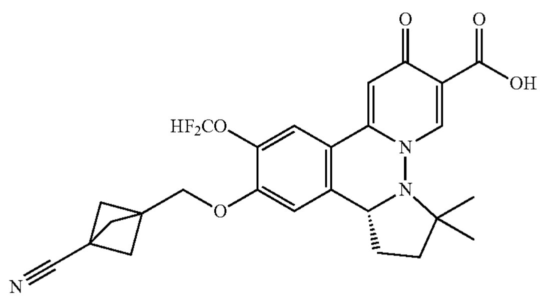 | (R)-12-((3-cyanobicyclo[1.1.1]pentan-1-yl)methoxy)-11-(difluoromethoxy)-3,3-dimethyl-8-oxo-2,3,8,13b-tetrahydro-1H-pyrido[2,1-a]pyrrolo[1,2-c]phthalazine-7-carboxylic acid | 2.7 | >10 |
| 105 | 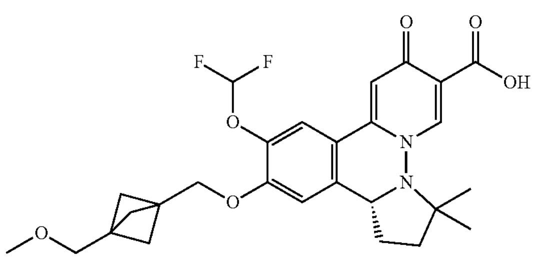 [SMILES: COCC12CC(COc3cc4c(cc3OC(F)F)-c3cc(=O)c(C(=O)O)cn3N3[C@@H]4CCC3(C)C)(C1)C2] | (R)-11-(difluoromethoxy)-12-((3-(methoxymethyl)bicyclo[1.1.1]pentan-1-yl)methoxy)-3,3-dimethyl-8-oxo-2,3,8,13b-tetrahydro-1H-pyrido[2,1-a]pyrrolo[1,2-c]phthalazine-7-carboxylic acid | 1.4 | >10 |
| 106 | 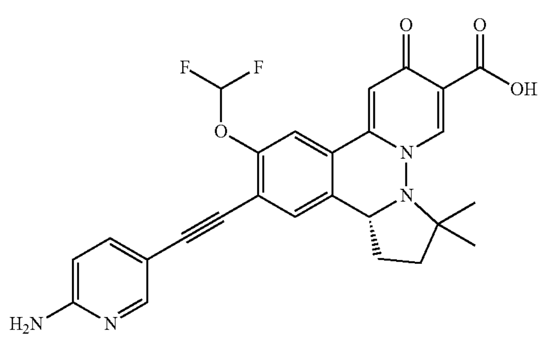 [SMILES: CC1(C)CC[C@@H]2c3cc(C#Cc4ccc(N)nc4)c(OC(F)F)cc3-c3cc(=O)c(C(=O)O)cn3N21] | (R)-12-((6-aminopyridin-3-yl)ethynyl)-11-(difluoromethoxy)-3,3-dimethyl-8-oxo-2,3,8,13b-tetrahydro-1H-pyrido[2,1-a]pyrrolo[1,2-c]phthalazine-7-carboxylic acid | 0.37 | 7.5 |

TABLE 1-continued

| Compound No. | Structure | Name | NTCP HBsAg EC$_{50}$ (nM) | MT-4 CC$_{50}$ (μM) |
|---|---|---|---|---|
| 107 | 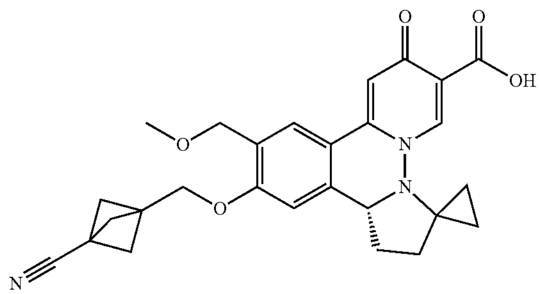 [SMILES: COCc1cc2c(cc1OCC13CC(C#N)(C1)C3)[C@H]1CCC3(CC3)N1n1cc(C(=O)O)c(=O)cc1-2] | (R)-12'-((3-cyanobicyclo[1.1.1]pentan-1-yl)methoxy)-11'-(methoxymethyl)-8'-oxo-1',2',8',13b'-tetrahydrospiro[cyclopropane-1,3'-pyrido[2,1-a]pyrrolo[1,2-c]phthalazine]-7'-carboxylic acid | 5.9 | 7.8 |
| 108 | 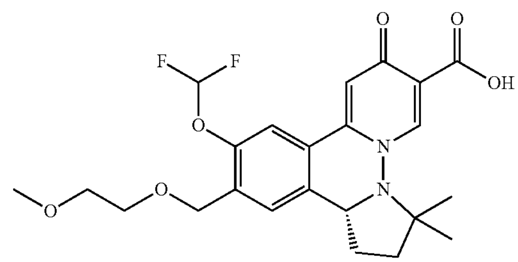 [SMILES: COCCOCc1cc2c(cc1OC(F)F)-c1cc(=O)c(C(=O)O)cn1N1[C@@H]2CCC1(C)C] | (R)-11-(difluoromethoxy)-12-((2-methoxyethoxy)methyl)-3,3-dimethyl-8-oxo-2,3,8,13b-tetrahydro-1H-pyrido[2,1-a]pyrrolo[1,2-c]phthalazine-7-carboxylic acid | 16.8 | >10 |
| 109 | 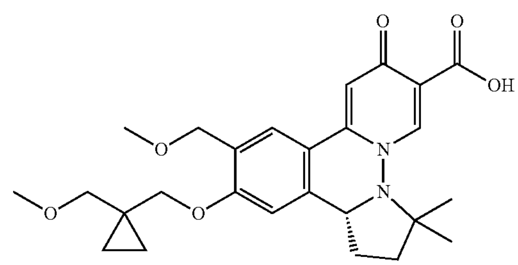 [SMILES: COCc1cc2c(cc1OCC1(COC)CC1)[C@H]1CCC(C)(C)N1n1cc(C(=O)O)c(=O)cc1-2] | (R)-11-(methoxymethyl)-12-((1-(methoxymethyl)cyclopropyl)methoxy)-3,3-dimethyl-8-oxo-2,3,8,13b-tetrahydro-1H-pyrido[2,1-a]pyrrolo[1,2-c]phthalazine-7-carboxylic acid | 13.2 | >10 |
| 110 | 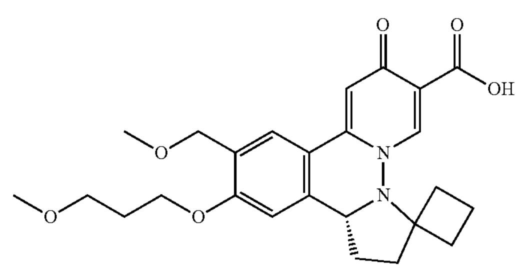 [SMILES: COCCCOc1cc2c(cc1COC)-c1cc(=O)c(C(=O)O)cn1N1[C@@H]2CCC12CCC2] | (R)-11'-(methoxymethyl)-12'-(3-methoxypropoxy)-8'-oxo-1',2',8',13b'-tetrahydrospiro[cyclobutane-1,3'-pyrido[2,1-a]pyrrolo[1,2-c]phthalazine]-7'-carboxylic acid | 3.9 | >10 |
| 111 | 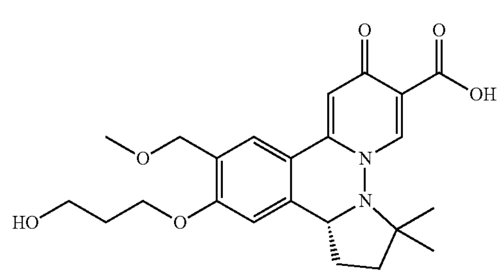 [SMILES: COCc1cc2c(cc1OCCCO)[C@H]1CCC(C)(C)N1n1cc(C(=O)O)c(=O)cc1-2] | (R)-12-(3-hydroxypropoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid | 32.2 | >10 |

TABLE 1-continued

| Compound No. | Structure | Name | NTCP HBsAg EC$_{50}$ (nM) | MT-4 CC$_{50}$ (μM) |
|---|---|---|---|---|
| 112 | 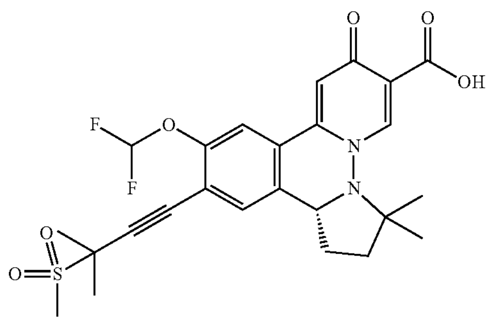 [SMILES: CC1(C)CC[C@@H]2c3cc(C#CC(C)(C)S(C)(=O)=O)c(OC(F)F)cc3-c3cc(=O)c(C(=O)O)cn3N21] | (R)-11-(difluoromethoxy)-3,3-dimethyl-12-(3-methyl-3-(methylsulfonyl)but-1-yn-1-yl)-8-oxo-2,3,8,13b-tetrahydro-1H-pyrido[2,1-a]pyrrolo[1,2-c]phthalazine-7-carboxylic acid | 2.7 | >10 |
| 113 | 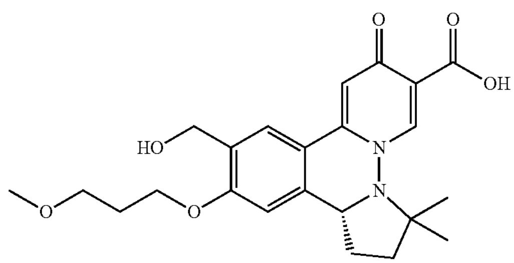 [SMILES: COCCCOc1cc2c(cc1CO)-c1cc(=O)c(C(=O)O)cn1N1[C@@H]2CCC1(C)C] | (R)-11-(hydroxymethyl)-12-(3-methoxypropoxy)-3,3-dimethyl-8-oxo-2,3,8,13b-tetrahydro-1H-pyrido[2,1-a]pyrrolo[1,2-c]phthalazine-7-carboxylic acid | 22.7 | >10 |
| 114 | 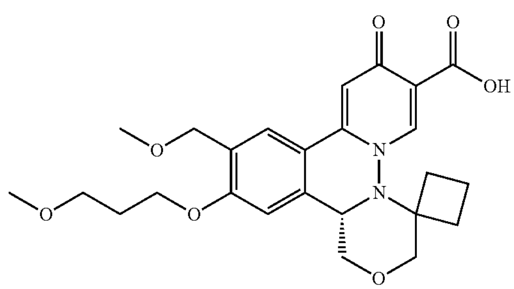 [SMILES: COCCCOc1cc2c(cc1COC)-c1cc(=O)c(C(=O)O)cn1N1[C@@H]2COCC12CCC2] | (S)-12'-(methoxymethyl)-13'-(3-methoxypropoxy)-9'-oxo-9',14b'-dihydro-1'H,3'H-spiro[cyclobutane-1,4'-[1,4]oxazino[3,4-a]pyrido[1,2-c]phthalazine]-8'-carboxylic acid | 67.6 | >10 |
| 115 | 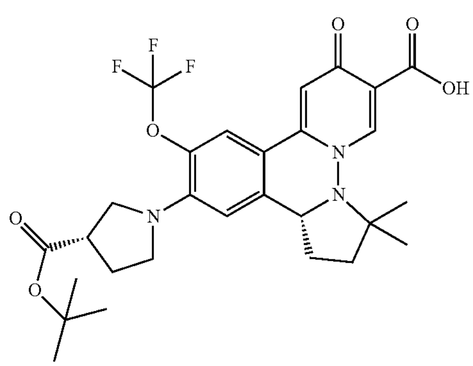 [SMILES: CC(C)(C)OC(=O)[C@H]1CCN(c2cc3c(cc2OC(F)(F)F)-c2cc(=O)c(C(=O)O)cn2N2[C@@H]3CCC2(C)C)C1] | (R)-12-((S)-3-(tert-butoxycarbonyl)pyrrolidin-1-yl)-3,3-dimethyl-8-oxo-11-(trifluoromethoxy)-2,3,8,13b-tetrahydro-1H-pyrido[2,1-a]pyrrolo[1,2-c]phthalazine-7-carboxylic acid | 2.9 | 8.3 |
| 116 | 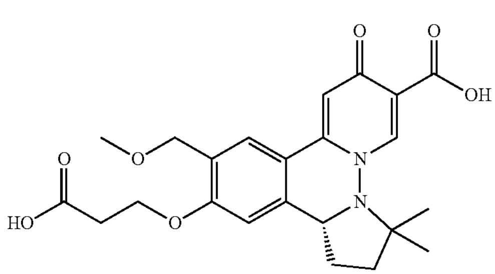 [SMILES: COCc1cc2c(cc1OCCC(=O)O)[C@H]1CCC(C)(C)N1n1cc(C(=O)O)c(=O)cc1-2] | (R)-12-(2-carboxyethoxy)-11-(methoxymethyl)-3,3-dimethyl-8-oxo-2,3,8,13b-tetrahydro-1H-pyrido[2,1-a]pyrrolo[1,2-c]phthalazine-7-carboxylic acid | nd | nd |

TABLE 1-continued

| Compound No. | Structure | Name | NTCP HBsAg $EC_{50}$ (nM) | MT-4 $CC_{50}$ (μM) |
|---|---|---|---|---|
| 117 | 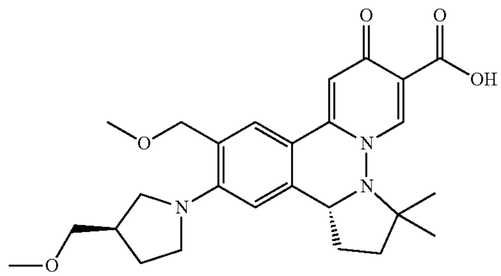 [SMILES: COCc1cc2c(cc1N1CC[C@@H](COC)C1)[C@H]1CCC(C)(C)N1n1cc(C(=O)O)c(=O)cc1-2] | (R)-11-(methoxymethyl)-12-((R)-3-(methoxymethyl)pyrrolidin-1-yl)-3,3-dimethyl-8-oxo-2,3,8,13b-tetrahydro-1H-pyrido[2,1-a]pyrrolo[1,2-c]phthalazine-7-carboxylic acid | 5.3 | 9.7 |
| 118 | | R)-11-(methoxymethyl)-12-(3-methoxypropoxy-1,1,2,2,3,3-d6)-3,3-dimethyl-8-oxo-2,3,8,13b-tetrahydro-1H-pyrido[2,1-a]pyrrolo[1,2-c]phthalazine-7-carboxylic acid | 4.1 | >10 | nd indicates no data
The compounds demonstrated inhibition of production and/or secretion of HBsAg.

Biological Example 3: In Vitro Metabolic Stability

Pooled hepatic microsomes were diluted in 0.1 mM potassium phosphate buffer to 1.0 mg/mL final protein concentration. Alamethicin was added to the microsomal fraction to permeabilize the membrane to allow access of the UDP-glucronic acid (UDPGA) co-substrate to the active site of the UDP glucuronosyl transferase (UGT) enzymes. The final concentration was 25 μg/mL (ratio 25 μg alamethicin/mg microsomal protein) and the microsomes were then placed on ice for 15 min prior to the start of the reaction. Test compound was added to a final concentration of 1 μM. Positive control compounds known to be metabolized by oxidative and UGT enzymes were used. The metabolic reaction was warmed to 37° C. and initiated by the addition of a cofactor mix that consisted of 1.55 mM NADP, 3.3 mM glucose-6-phosphate, 0.4 U/mL glucose-6-phosphate dehydrogenase, 5 mM UDP-glucuronic acid and 3.3 mM $MgCl_2$, all dissolved in 0.1 M potassium phosphate buffer, pH 7.4. At 2, 12, 25, 45, and 65 min, 25 μL aliquots of the reaction mixture were transferred to plates containing 225 μl of quenching solution (acetonitrile containing 300 nM labetalol IS and 0.1% formic acid). After quenching, the plates are centrifuged at 3000×g for 30 minutes to precipitate proteins, and 10 μL aliquots of the supernatant are analyzed by HPLC coupled to a high-resolution mass spectrometer.

For hepatocyte stability incubations, cells were obtained from BioreclamationIVT (Baltimore, Md.), thawed according to the manufacturer's directions, and resuspended to a final concentration of $1 \times 10^6$ cells/mL in Krebs-Henseleit buffer prewarmed to 37° C. The total cell count and the proportion of viable cells were determined by Trypan Blue dye exclusion using a hemocytometer. The final concentration of test compounds and positive controls was 2 μM. Incubations were carried out in duplicate wells of a 24-well plate out with gentle shaking at 37° C. under a humid atmosphere of 95% air/5% $CO_2$ (v/v). Aliquots (50 μL) were removed after 0, 1, 3, and 6 hours and added to 100 μL quenching solution. Samples were then processed and analyzed in a manner similar to the microsomal stability samples.

Quantification of test compounds and positive controls were performed using analyte/internal standard peak area ratios (PAR) measured on a Q-Exactive mass spectrometer (Thermo Scientific, San Jose, Calif.) coupled to an Aria Transcend LX-4 multiplex UHPLC system (Thermo Scientific, San Jose, Calif.). A Hypersil Gold C18 UHPLC column (1.9 m particle size, 50×2.1 mm) was used with mobile phases A and B consisting of 0.1% formic acid in water and 0.1% formic acid in acetonitrile, respectively. Elution was achieved by a series of linear gradients with increasing proportions of mobile phase B. The mass spectrometer was configured with a heated electrospray source and operated in positive ion mode. Analytes and the MS internal standard peak areas were obtained from full scan high resolution spectra (100-1400 m/z, resolution 70,000) using the exact masses of the compounds (+5 ppm). Half-lives of compounds in the incubations were calculated from extracted data using GMSU/QuickCalc (Gubbs, Inc.) and data are summarized in the following Table 2.

TABLE 2

Stability in dog, rat, cynomolgus monkey and human hepatocytes

| | hepatocyte stability $T_{1/2}$ (h) | | | |
|---|---|---|---|---|
| | Rat | Dog | Cyno | Human |
| Example 33 | 1.6 | 5.7 | 5.6 | 21.6 |
| Example 5 | >39.5 | >39.5 | 20.8 | >39.5 |

These data suggest that compounds of disclosed herein, e.g. Formula (I), (Ia), (II) and (IIa), having an additional ring nitrogen (Example 5) in place of carbon (Example 33) have improved in vitro metabolic stability. This suggests that compounds disclosed herein, e.g. Formula (I), (Ia), (II) and (IIa) may be administered at lower doses and/or less frequently with reduced likelihood of toxic intermediates to treat or prevent an HBV infection.

Biological Example 4: Toxicology Study

Human iPSC Neurite Outgrowth Assay

Figure 2:
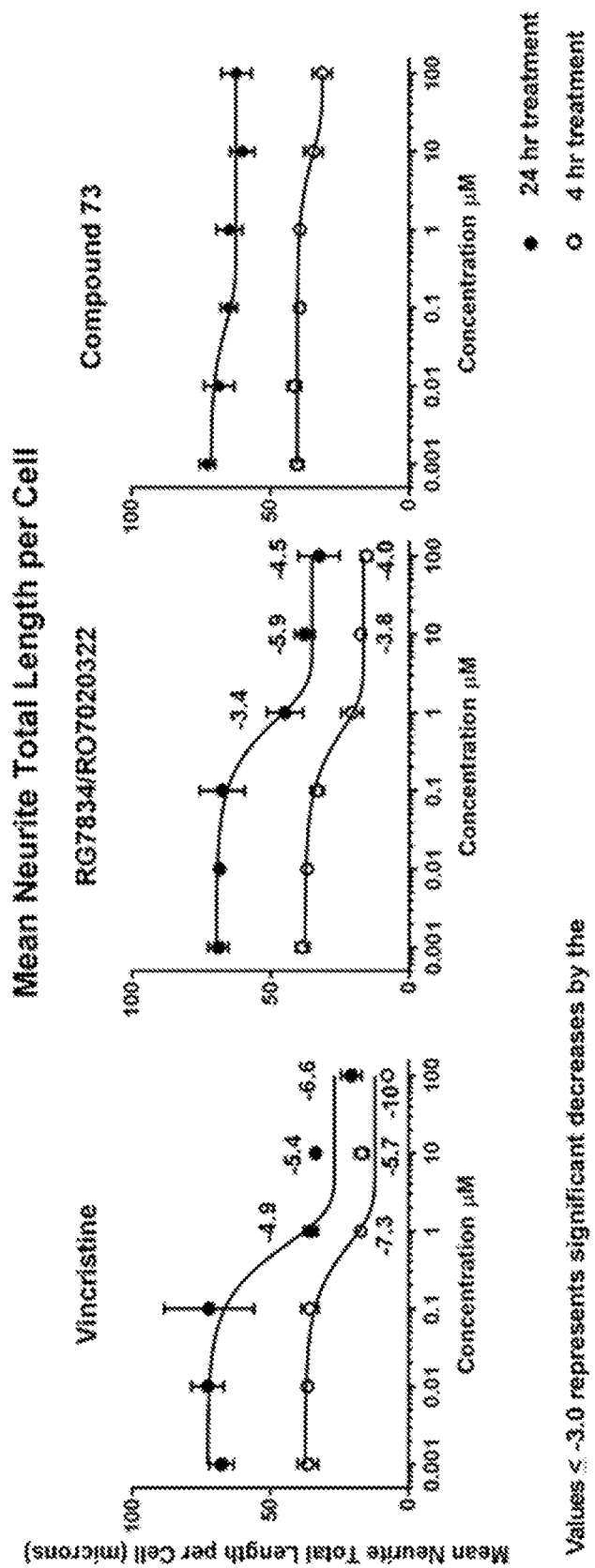
FIG. 2 is a series of graphs plotting mean neurite total length per cell as a function of concentration of compound, where the compound is Vincristine, RG783/R07020332, and compound 73.

Human induced pluripotent stem cell (iPSC) derived iCell GABAergic Neurons (Cellular Dynamics Inc.) were seeded at a density of 67,500 cells per square centimeter into 384 well plates. The neurons were plated for 1 hour in attachment media before exchange for serum-free growth media (Cellular Dynamics Inc.). The serum-free growth media was exchanged for fresh media and the plated neurons were treated with test compounds and control compounds at 6 concentrations (1 nM-100 µM) at 4 and 24 hour timepoints in triplicate wells. Optimum neuron cell attachment to the plates was obtained at the 24 hour timepoint. Vincristine was utilized as the positive control for toxic inhibition of neurite outgrowth and 0.1% DMSO treatment was used for control treatment of neurons. Celltracker and DRAQ7 stains were applied prior to fixation of cells to assess nuclear and cell viability. Cells were then fixed for 20 minutes in 4% formaldehyde in PBS containing Hoechst dye and then fixative was replaced with PBS twice. High content imaging was performed with 9 fields of 20× magnification on a CX7 HCS system with an algorithm to enable quantification of neurite lengths and neurite branch points in all treatment groups. The results of the counts and measurements were then analyzed by the strictly standardized mean difference (SSMD) method of analysis to measure effect size for any decreases in mean neurite total length per cell (microns) or changes in mean branch point counts per cell (PhenoVista Biosciences, San Diego). The results are shown in FIGS. 1 and 2. FIG. 1 depicting plots of mean branch point counts per cell as a function of concentration for Vincristine, RG783/R07020322, and Compound 73 (free base, purified without addition of TFA). FIG. 2 shows plots of mean neurite total length per cell as a function of concentration for Vincristine, RG783/R07020322, and Compound 73. Vincristine has the following structure:

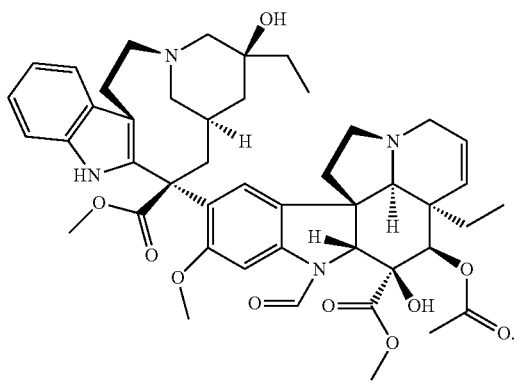

Compound RG783/R07020322 has the following structure:

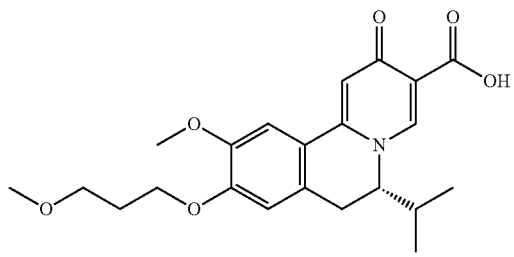 [SMILES: COCCCOc1cc2c(cc1OC)-c1cc(=O)c(C(=O)O)cn1[C@H](C(C)C)C2]

No significant changes of effect were observed for neuron counts or neuron viability at any of the tested concentrations for RG7834/R07020322, Vincristine and Compound 73 when compared to 0.1% DMSO control treated iCell neurons by the SSMD analysis. No significant effects were observed for neurite outgrowth lengths or branch point counts for Compound 73 at any concentration in either the 4 or 24 hour treatments when compared to 0.1% DMSO control treated neurons by the SSMD analysis as shown in FIG. 1, FIG. 2, Table 3, and Table 4.

In contrast, for Vincristine and RG7834/R07020322, significant decreases in neurite total length and branch point counts were observed at 4 and 24 hour timepoints when compared to 0.1% DMSO treated neurons. Significant decreases in mean neurite total length per cell occurred at 1, 10 and 100 µM for Vincristine and RG7834/R07020322 with a dose response in FIG. 2 and Table 3. In the 4 hour treatments, significant decreases in neurite total length at 10 and 100 µM RG7834/R07020322 and from 1-10 µM for the Vincristine treatment was observed. Significant decreases in branch point counts for both Vincristine and RG7834/R07020322 at 1, 10 and 100 µM in the 24 hour treatments were also observed but were not seen in neurons treated with Compound 73 (FIG. 1, Table 4).

These data suggest that Compound 73 has improved acute neurotoxicity liabilities as shown in an assay of human-derived iPSC neurons over that of RG7834/R07020322 and the neurotoxic chemotherapeutic drug Vincristine. The lack of effect by the SSMD analysis on neurite morphology at any concentration for Compound 73 is in contrast to observations of neurite changes for RG7834/R07020322 and Vincristine at concentrations up to 100 µM for 24 hours. The results distinguish Compound 73 from more potently neurotoxic compounds.

TABLE 3

Strictly Standardized Mean Difference (SSMD) Values of Neurite Total Lengths.

| | Decreased Neurite Length SSMD Values | | | | | |
|---|---|---|---|---|---|---|
| | 0.001 µM | 0.01 µM | 0.1 µM | 1 µM | 10 µM | 100 µM |
| 0.1% DMSO 24 hr 4 hr Compound 73 | | | Control | | | |
| 24 hr | NS | NS | NS | NS | NS | NS |
| 4 hr | NS | NS | NS | NS | NS | NS |
| RG7834/ R07020322 | | | | | | |
| 24 hr | NS | NS | NS | -3.4 | -5.9 | -4.5 |
| 4 hr | NS | NS | NS | NS | -3.8 | -4.0 |

TABLE 3-continued

Strictly Standardized Mean Difference (SSMD) Values of Neurite Total Lengths.

| | Decreased Neurite Length SSMD Values | | | | | |
|---|---|---|---|---|---|---|
| | 0.001 µM | 0.01 µM | 0.1 µM | 1 µM | 10 µM | 100 µM |
| Vincristine | | | | | | |
| 24 hr | NS | NS | NS | −4.9 | −5.4 | −6.6 |
| 4 hr | NS | NS | NS | −7.3 | −5.7 | −10 |

NS = no significant effect and >−3 SSMD Value.
Values of ≤−3 values are significant for decreased length

TABLE 4

Strictly Standardized Mean Difference (SSMD) Values of Neurite Branch Point Counts

| | Branch Point Count SSMD Values | | | | | |
|---|---|---|---|---|---|---|
| | 0.001 µM | 0.01 µM | 0.1 µM | 1 µM | 10 µM | 100 µM |
| 0.1% DMSO | Control | | | | | |
| 24 hr | | | | | | |
| 4 hr | | | | | | |
| Compound 73 | | | | | | |
| 24 hr | NS | NS | NS | NS | NS | NS |
| 4 hr | NS | NS | NS | NS | NS | NS |
| RG7834/ RO7020322 | | | | | | |
| 24 hr | NS | NS | NS | −3.3 | −3.4 | −5.0 |
| 4 hr | NS | NS | NS | NS | NS | −5.2 |
| Vincristine | | | | | | |
| 24 hr | NS | NS | NS | −3.1 | −3.6 | −6.0 |
| 4 hr | NS | NS | NS | NS | −3.0 | −3.5 |

NS = no significant effect and >−3 SSMD Values.
Values of ≤−3 considered significant for decreased branching

The invention claimed is:

1. A compound of Formula (I):

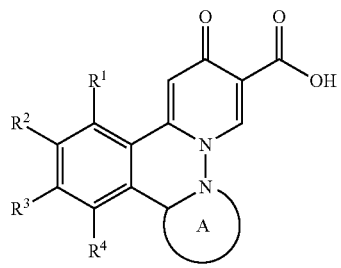

wherein:

A is a 4-7 membered cycloalkyl or heterocyclyl ring substituted with 0-8 $R^5$ groups;

$R^1$ is H or halogen;

$R^2$ is selected from the group consisting of halogen, $R^{2a}O$—, $C_{1-6}$ alkyl, $C_{3-10}$ cycloalkyl, 3-7 membered heterocyclyl, —$NR^aR^b$, —$S(O)_{0-2}R^a$, or —CN, wherein each $C_{1-6}$alkyl, $C_{3-10}$ cycloalkyl or 3-7 membered heterocyclyl is optionally substituted with 1-5 $R^{20}$ groups;

$R^{2a}$ is selected from the group consisting of H, $C_{3-6}$ cycloalkyl or $C_{1-6}$ alkyl, wherein each $C_{3-6}$ cycloalkyl or $C_{1-6}$ alkyl is optionally substituted with 1-5 $R^{20}$ groups;

$R^3$ is selected from the group consisting of $R^{3a}O$—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —$NR^aR^b$, and —$S(O)_{0-2}R^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;

$R^{3a}$ is selected from the group consisting of H, $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxy$C_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

$R^4$ is H or halogen;

each $R^5$ is independently selected from the group consisting of $C_{1-6}$ alkyl, $C_{1-6}$ alkoxy, $C_{2-6}$ alkenyl, $C_{2-6}$ alkynyl, —$NR^aR^b$, halogen, —$C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$OR^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein any two $R^5$ groups on the same carbon atom can optionally form a =O; and any two $R^5$ groups can optionally join together to form a $C_{3-6}$ cycloalkyl or 3-6 membered heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen; or a pharmaceutically acceptable salt thereof.

2. The compound of claim 1, wherein $R^2$ is selected from the group consisting of chloro, methoxy, ethoxy, methoxymethyl, —OCH(CH$_3$)$_2$, OC(CH$_3$)$_3$, cyclopropyl, —OCF$_3$, —OCHF$_2$ and

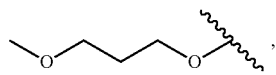 [SMILES: *OCCCOC], or a pharmaceutically acceptable salt thereof.

3. The compound of claim 1, wherein $R^2$ is methoxymethyl, or a pharmaceutically acceptable salt thereof.

4. The compound of claim 1, wherein $R^3$ is $C_{1-6}$ alkoxyC$_{1-6}$alkyl, or a pharmaceutically acceptable salt thereof.

5. The compound of claim 1, wherein $R^3$ is

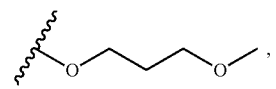 [SMILES: *OCCCOC], or a pharmaceutically acceptable salt thereof.

6. The compound of claim 1, wherein $R^1$ and $R^4$ are both H, or a pharmaceutically acceptable salt thereof.

7. The compound of claim 1, wherein $R^1$ and $R^4$ are both H and $R^2$ is cyclopropyl or methoxymethyl, or a pharmaceutically acceptable salt thereof.

8. The compound of claim 1, having Formula (Ic):

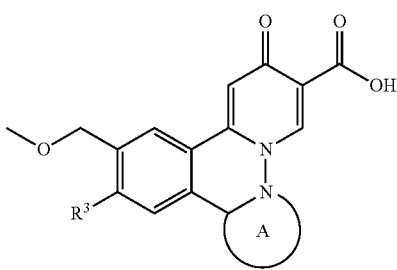

wherein:
A is a 4-7 membered cycloalkyl or heterocyclyl ring substituted with 0-8 $R^5$ groups;
$R^1$ is H or halogen;
$R^3$ is selected from the group consisting of $R^{3a}$O—, $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, $C_{3-10}$ cycloalkyl, —NR$^a$R$^b$, and —S(O)$_{0-2}$R$^a$, wherein each $C_{1-6}$ alkyl, 5-10 membered heteroaryl, 3-12 membered heterocyclyl, $C_{2-6}$ alkenyl, $C_{2-6}$ alkynyl, $C_{6-10}$ aryl, or $C_{3-10}$ cycloalkyl is optionally substituted with 1-5 $R^{20}$ groups;
$R^{3a}$ is selected from the group consisting of H, $C_{1-6}$ alkyl, $C_{1-6}$ alkoxyC$_{1-6}$alkyl, 5-10 membered heteroaryl, 3-12 membered heterocyclyl, $C_{6-10}$ aryl and $C_{3-10}$ cycloalkyl, wherein each $C_{1-6}$ alkyl, $C_{1-6}$ alkoxyC$_{1-6}$alkyl, 5-10 membered heteroaryl, 3-12 membered heterocyclyl, $C_{6-10}$ aryl and $C_{3-10}$ cycloalkyl is optionally substituted with 1-5 $R^{20}$ groups;

$R^4$ is H or halogen;
each $R^5$ is independently selected from the group consisting of $C_{1-6}$ alkyl, $C_{1-6}$ alkoxy, $C_{2-6}$ alkenyl, $C_{2-6}$ alkynyl, —NR$^a$R$^b$, halogen, —C(O)R$^a$, —C(O)OR$^a$, —C(O)NR$^a$R$^b$, —OC(O)NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —OR$^a$, $C_{6-10}$ aryl, $C_{3-10}$ cycloalkyl, 5-10 membered heteroaryl and 3-12 membered heterocyclyl, wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;
wherein any two $R^5$ groups on the same carbon atom can optionally form a =O; and any two $R^5$ groups can optionally join together to form a $C_{3-6}$ cycloalkyl or 3-6 membered heterocyclyl ring optionally substituted with 1-3 $R^{21}$ groups;
each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;
each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —OR$^a$, —C(O)R$^a$, —C(O)OR$^a$, —C(O)NR$^a$R$^b$, —OC(O)NR$^a$R$^b$, —NR$^a$R$^b$, —NR$^a$C(O)R$^b$, —NR$^a$C(O)OR$^b$, —S(O)$_{0-2}$R$^a$, —S(O)$_2$NR$^a$R$^b$, —NR$^a$S(O)$_2$R$^b$, —N$_3$, —CN, or —NO$_2$; and
each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen; or a pharmaceutically acceptable salt thereof.

9. The compound of claim 1, wherein at least two $R^5$ groups are methyl bound at the same carbon atom, or a pharmaceutically acceptable salt thereof.

10. The compound of claim 1, wherein A is:

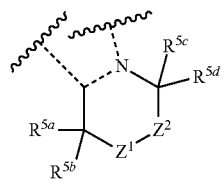

wherein:
$Z^1$ is a bond, O, NR$^a$ or CR$^{5e}$R$^{5f}$;
$Z^2$ is a bond, O, NR$^a$ or CR$^{5g}$R$^{5h}$;

provided only one of $Z^1$ and $Z^2$ is O or $NR^a$;

each of $R^{5a}$, $R^{5b}$, $R^{5c}$, $R^{5d}$, $R^{5e}$, $R^{5f}R^{5g}$ and $R^{5h}$ are independently selected from the group consisting of H, $C_{1-6}$ alkyl, $C_{1-6}$ alkoxy, $C_{2-6}$ alkenyl, $C_{2-6}$ alkynyl, —$NR^aR^b$, halogen, $C(O)R^a$, —$C(O)OR^a$, —$C(O)NR^aR^b$, —$OC(O)NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, —$NO_2$, —$OR^a$, $C_{6-10}$ aryl, $C_{3-10}$ cycloalkyl, 5-10 membered heteroaryl and 3-12 membered heterocyclyl wherein each $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-10 membered heteroaryl and 3-12 membered heterocyclyl is optionally substituted with 1-5 $R^{20}$ groups;

wherein up to two of $R^{5a}$ and $R^{5b}$, $R^{5c}$ and $R^{5d}$, $R^{5e}$ and $R^{5f}$, or $R^{5g}$ and $R^{5h}$ can form a =O;

wherein any two of $R^{5a}$, $R^{5b}$, $R^{5c}$, $R^{5d}$, $R^{5e}$, $R^{5f}R^{5g}$ and $R^{5h}$ can join together to form a cycloalkyl or heterocyclyl ring optionally substituted with 1-3 $R^{21}$ groups;

each $R^a$ and $R^b$ is independently selected from the group consisting H; or $C_{1-6}$ alkyl, $C_{3-10}$ cycloalkyl, 3-12 membered heterocyclyl, $C_{6-10}$ aryl, 5-10 membered heteroaryl, each of which is optionally substituted with from one to five $R^{21}$ groups; or $R^a$ and $R^b$ together with the atoms to which they are attached form a 3-12 membered heterocyclyl optionally substituted with one to five $R^{21}$ groups;

each $R^{20}$ is independently selected from the group consisting $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl, halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$, or two $R^{20}$ groups appended to the same group can join together to form a fused, spiro or bridged $C_{3-10}$ cylcloalkyl or 3-12 membered heterocyclyl ring, wherein each $C_{1-6}$ alkyl, $C_{3-10}$ cycloalkyl, $C_{1-6}$ alkoxy, 3-12 membered heterocyclyl, $C_{6-10}$ aryl, 5-10 membered heteroaryl is optionally substituted with from one to five halogen, oxo, —$OR^a$, —$C(O)R^a$, —$C(O)OR^a$, —$C(O)NR^aR^b$, —$OC(O)NR^aR^b$, —$NR^aR^b$, —$NR^aC(O)R^b$, —$NR^aC(O)OR^b$, —$S(O)_{0-2}R^a$, —$S(O)_2NR^aR^b$, —$NR^aS(O)_2R^b$, —$N_3$, —CN, or —$NO_2$; and each $R^{21}$ is independently selected from the group consisting $C_{1-6}$ alkyl, $C_{1-6}$haloalkyl, $C_{3-10}$ cycloalkyl, $C_{1-6}$ alkoxy, 3-12 membered heterocyclyl, $C_{6-10}$ aryl, 5-10 membered heteroaryl, hydroxyl, amino, $C_{1-6}$ alkylamino, —CN or halogen;

or a pharmaceutically acceptable salt thereof.

11. The compound of claim 1 selected from:

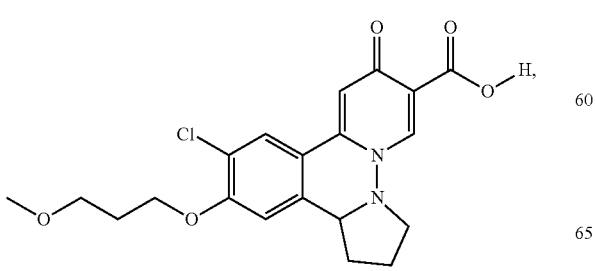

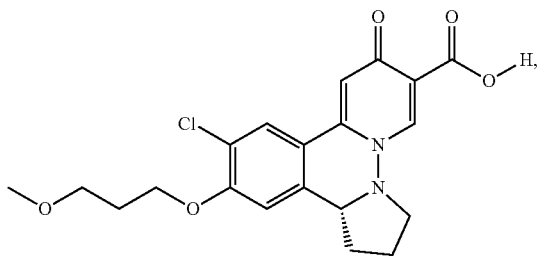

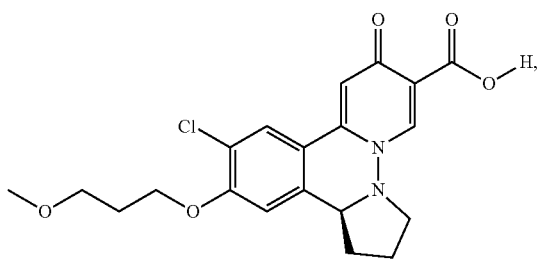

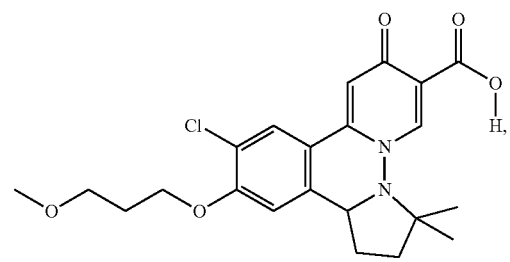

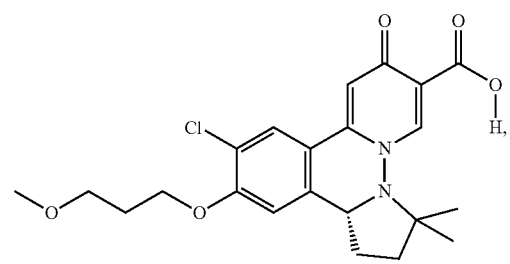

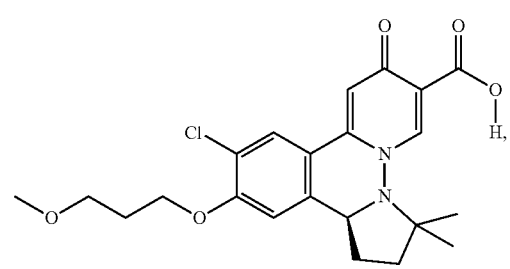

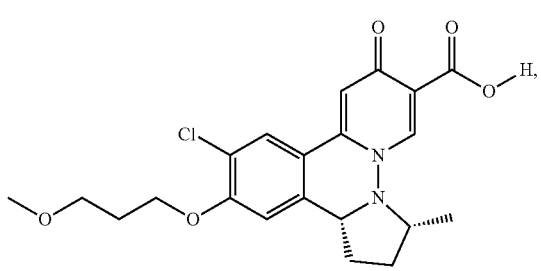

291
-continued
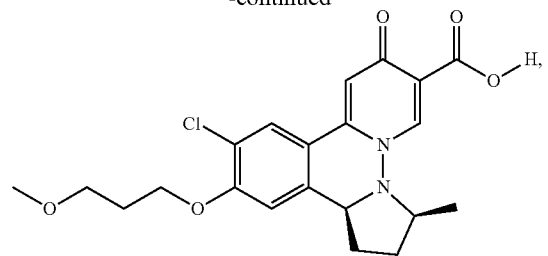
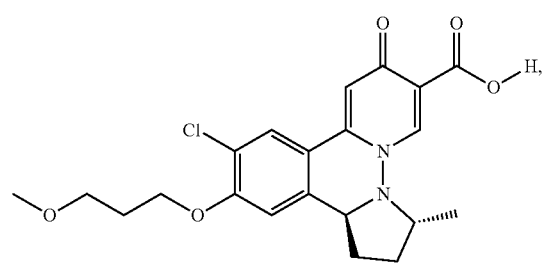
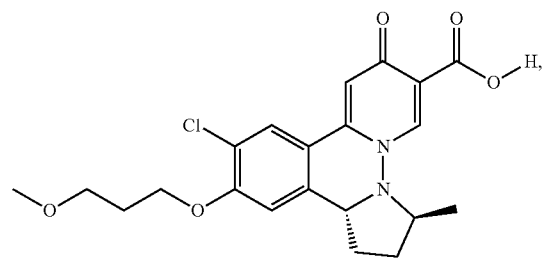
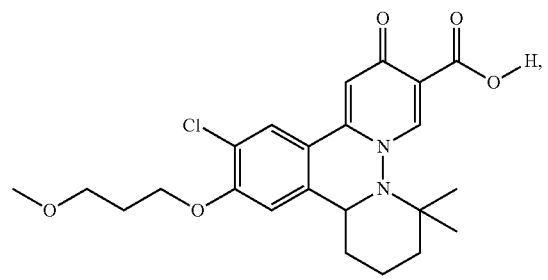
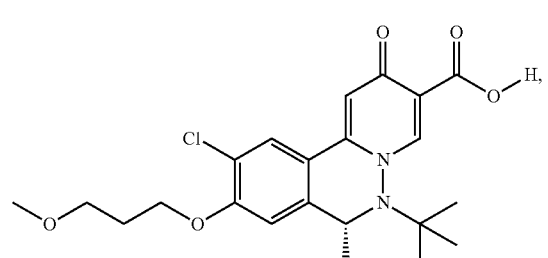
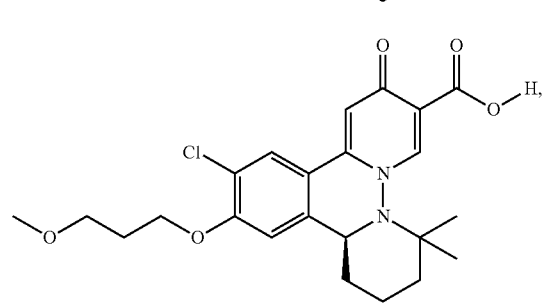
292
-continued
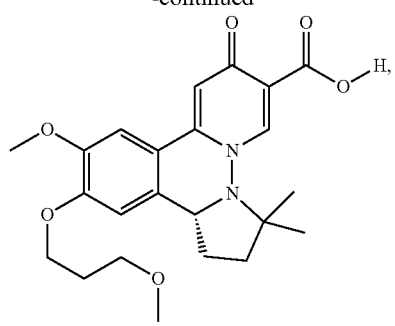
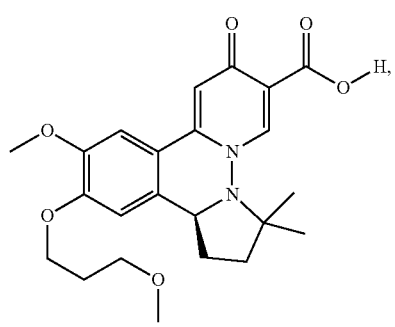
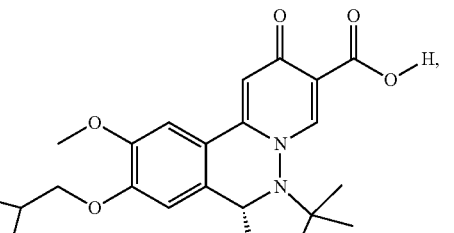
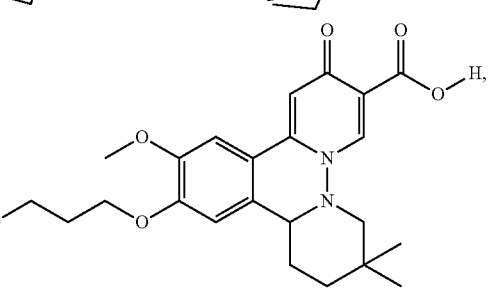
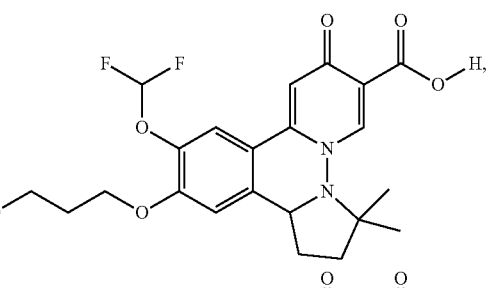
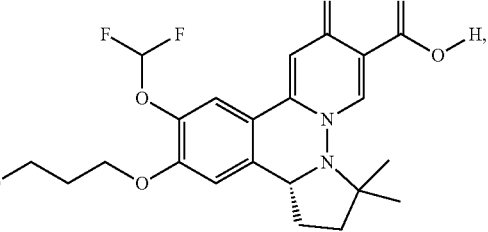

293
-continued
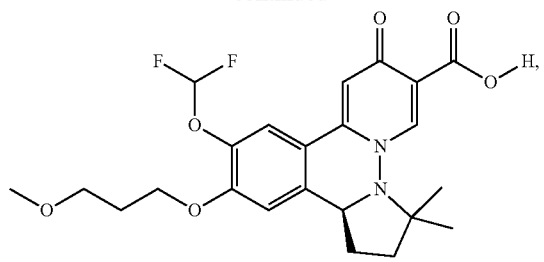
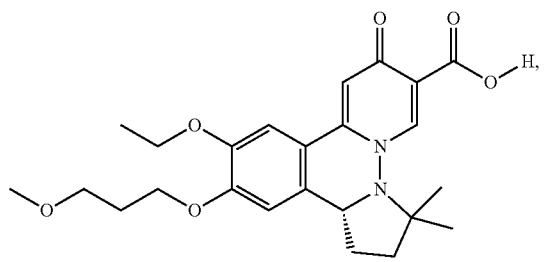
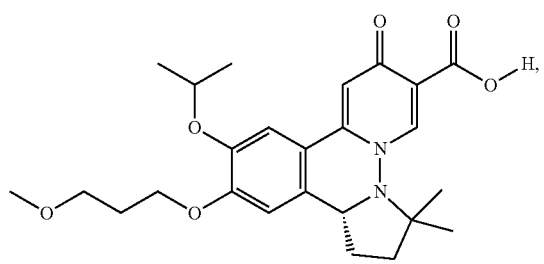
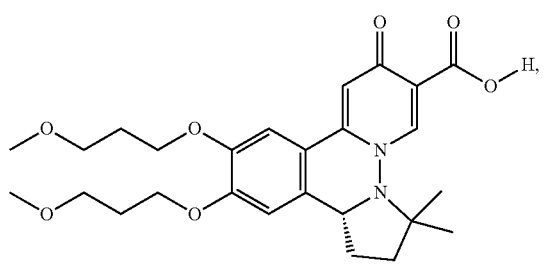
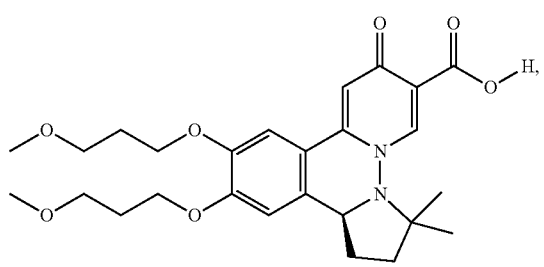
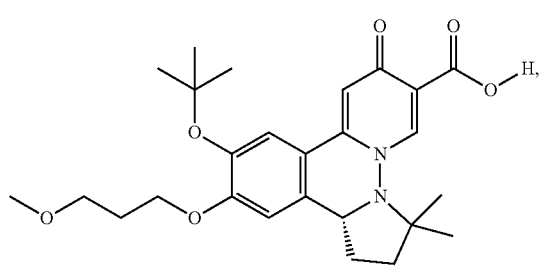
294
-continued
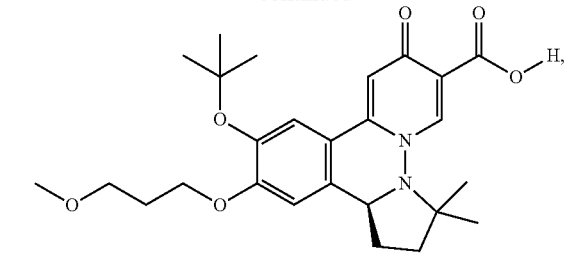
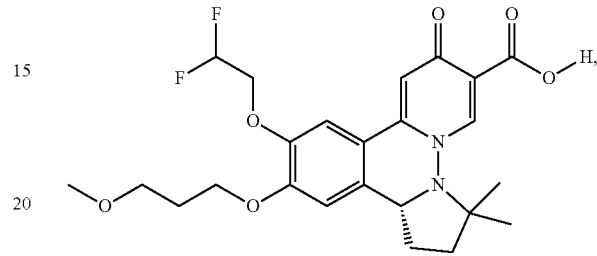
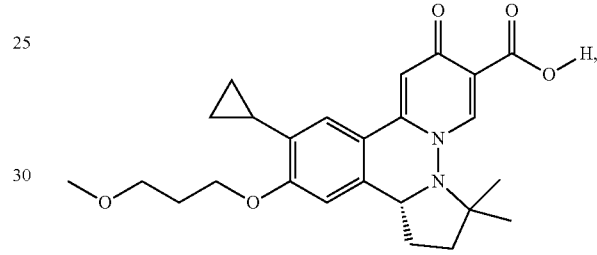
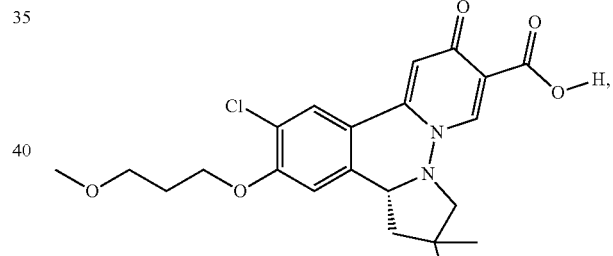
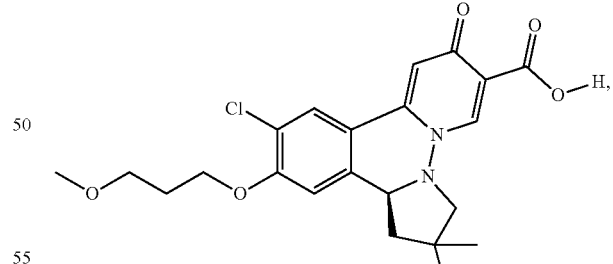
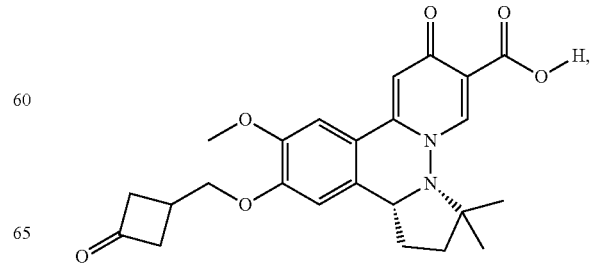

295
-continued
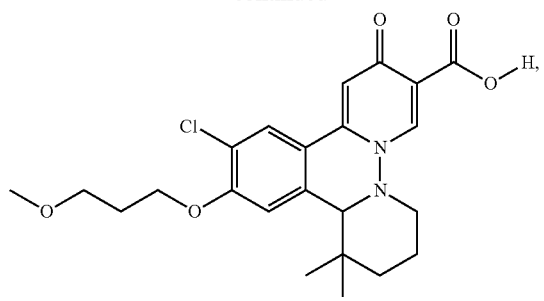
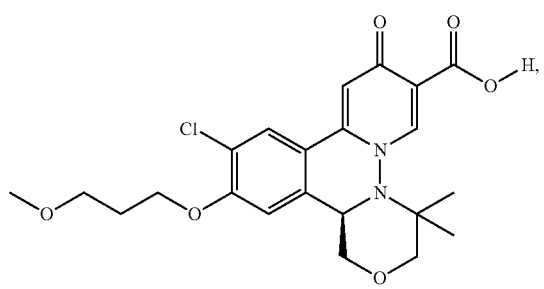
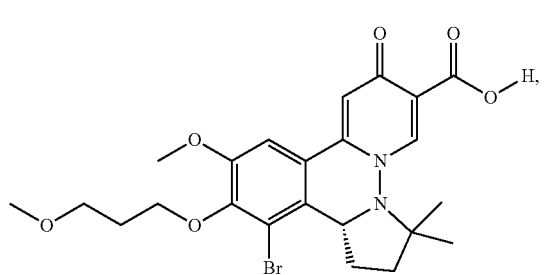
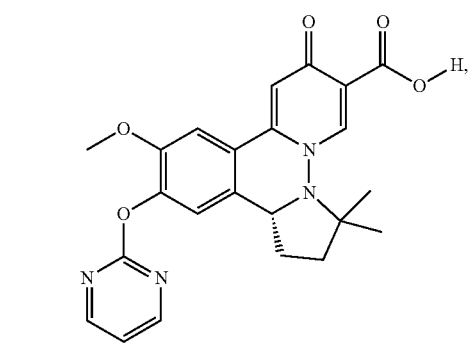
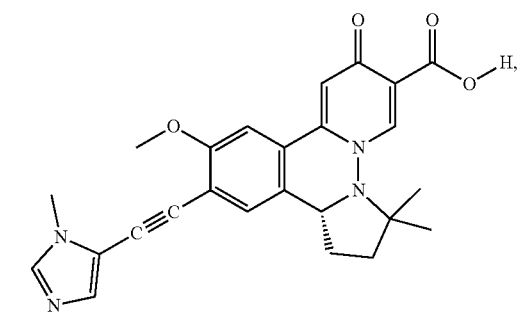
296
-continued
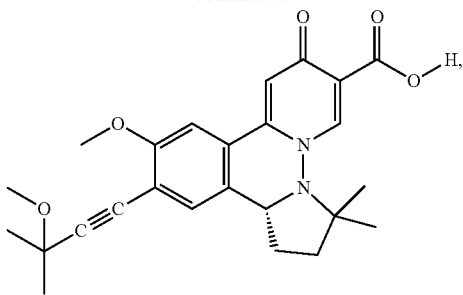
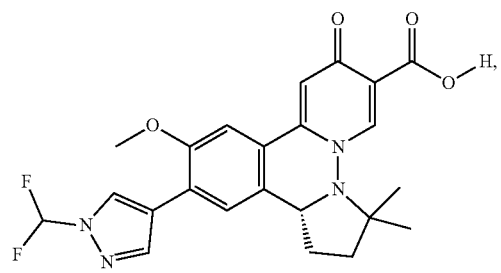
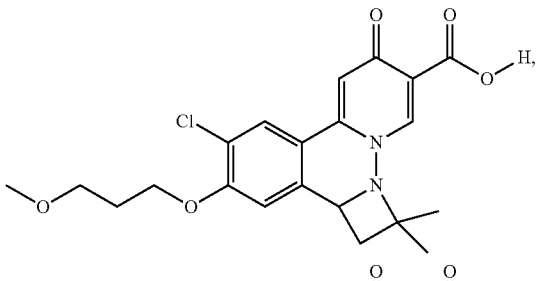
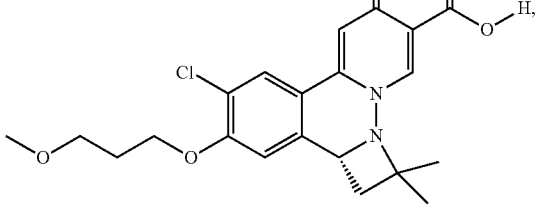
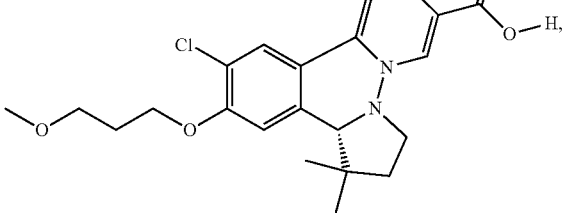
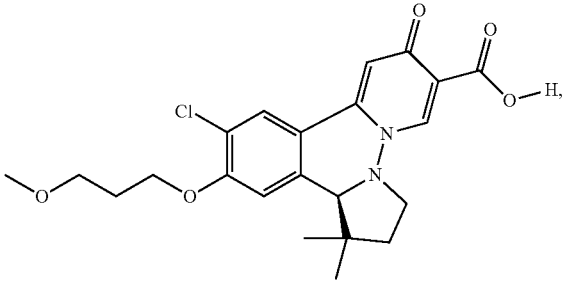

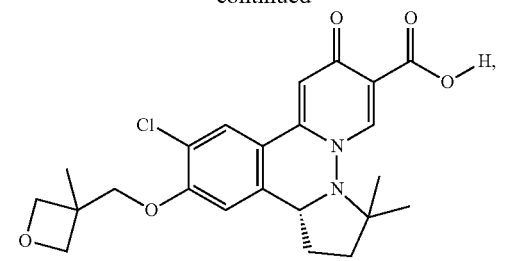
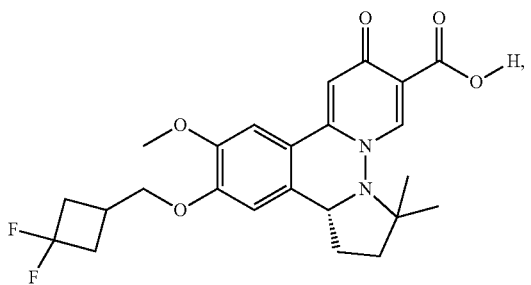
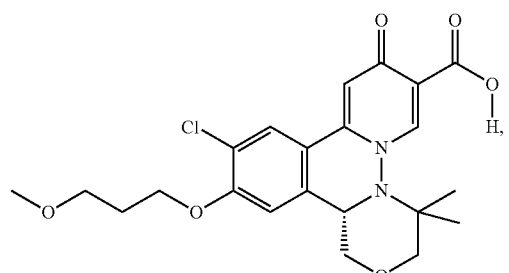
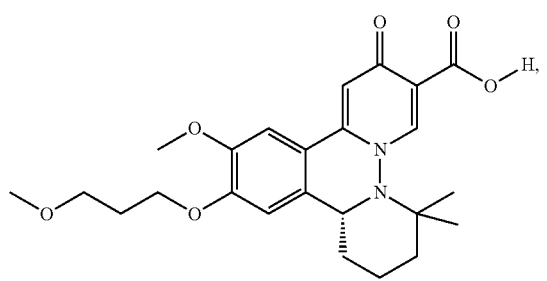
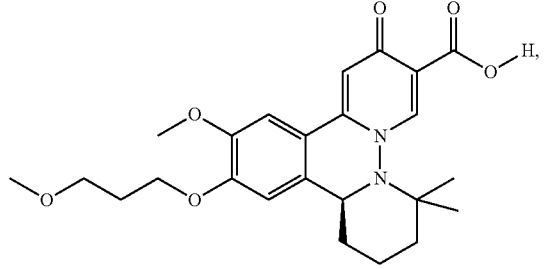
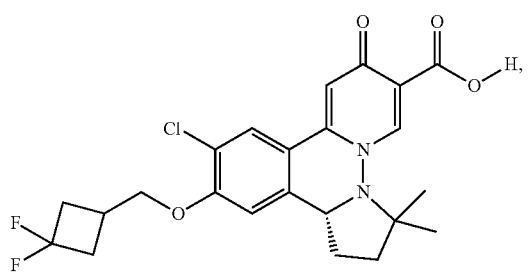
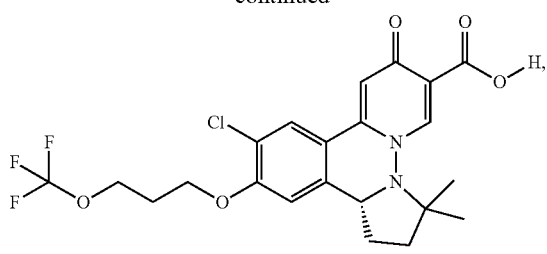
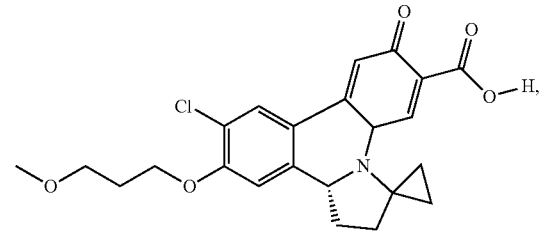
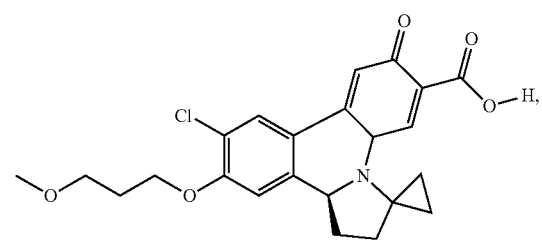
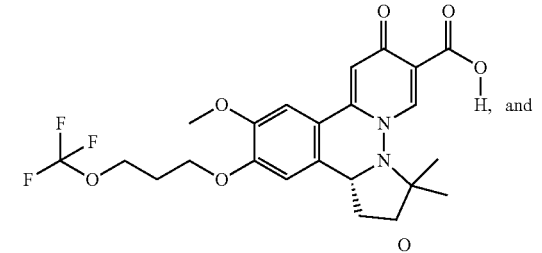
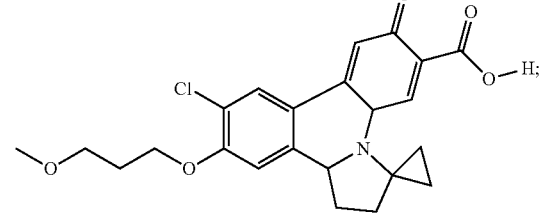
or a pharmaceutically acceptable salt thereof.
12. The compound of claim 1 selected from:
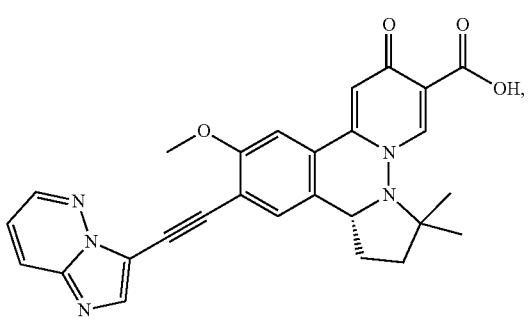

-continued
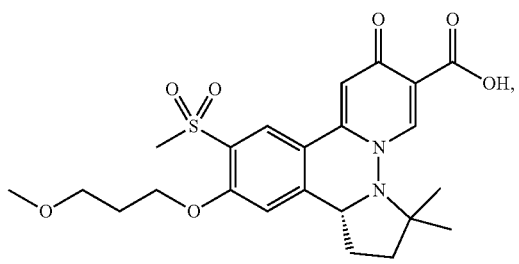
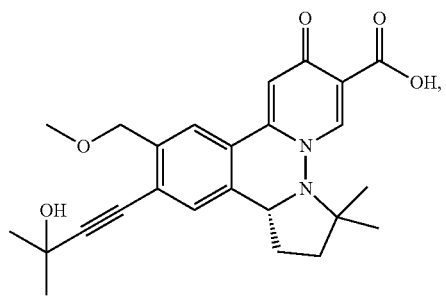
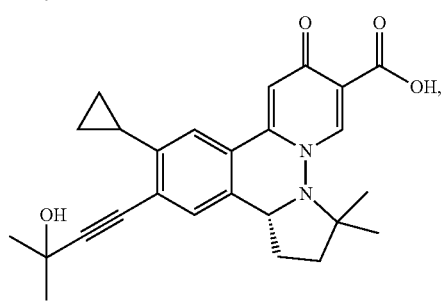
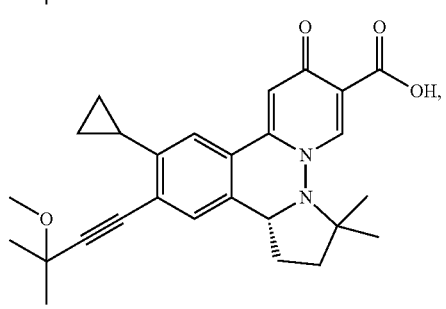
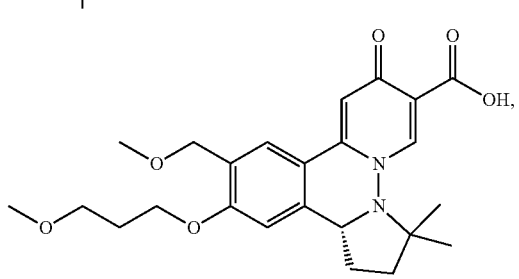
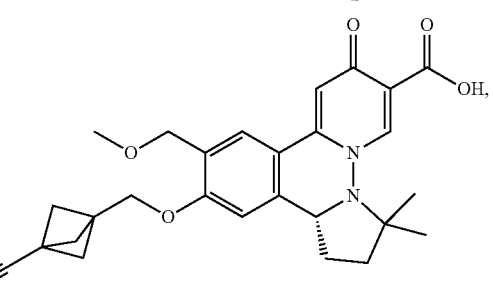
-continued
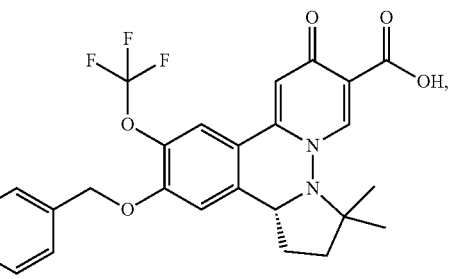
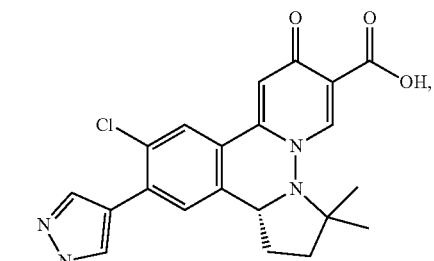
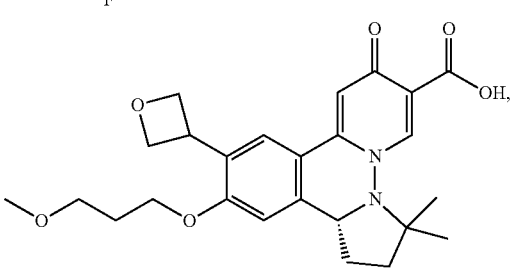
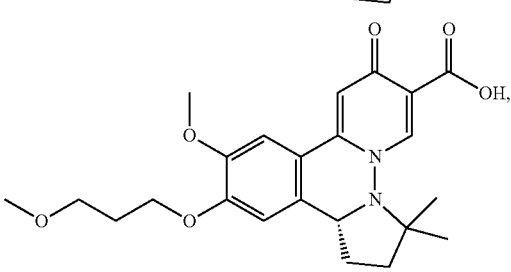
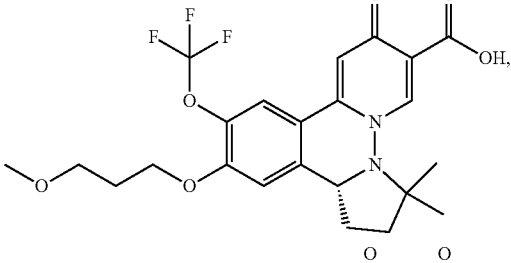
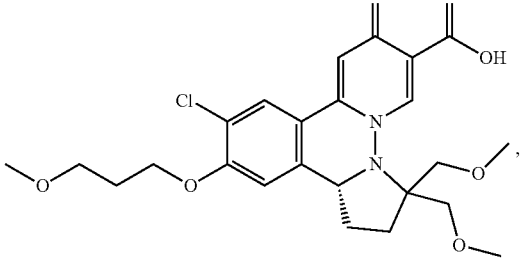

301
-continued
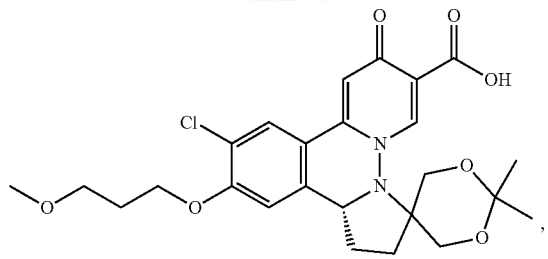
,
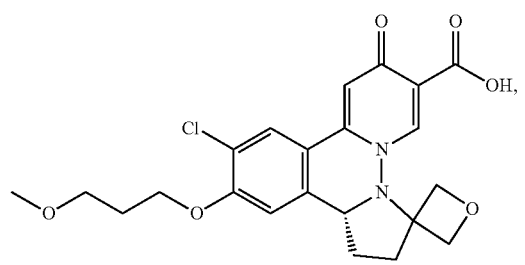
,
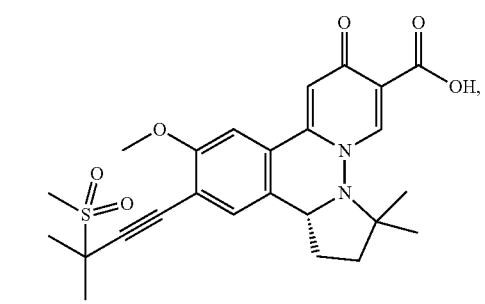
,
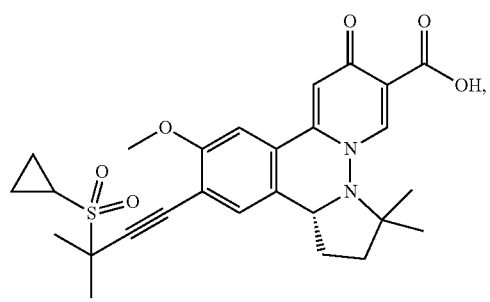
,
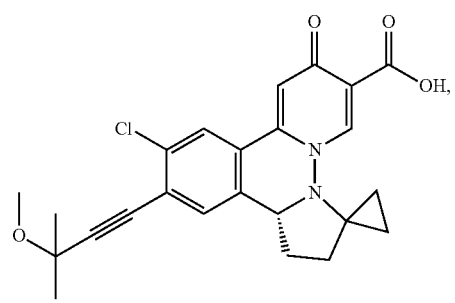
,
302
-continued
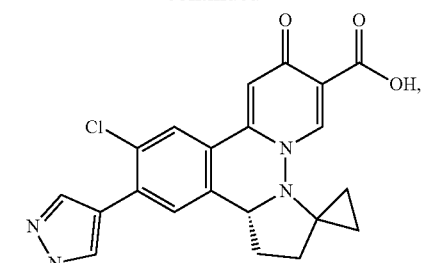
,
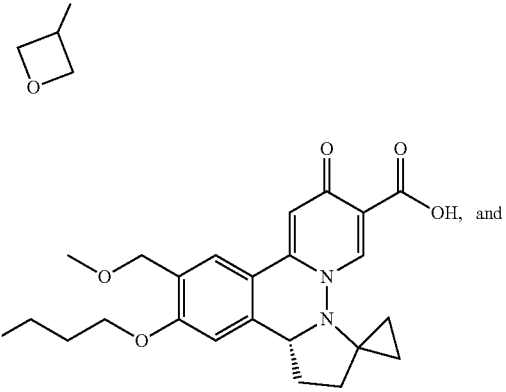
,
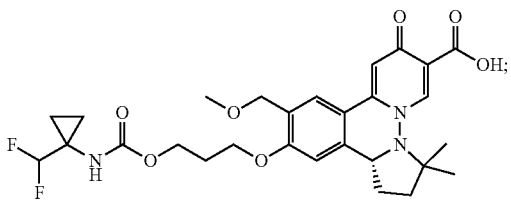 [SMILES: COCc1cc2c(cc1OCCCOC(=O)NC1(C(F)F)CC1)[C@H]1CCC(C)(C)N1n1cc(C(=O)O)c(=O)cc1-2]
;
or a pharmaceutically acceptable salt thereof.
13. The compound of claim 1 selected from:
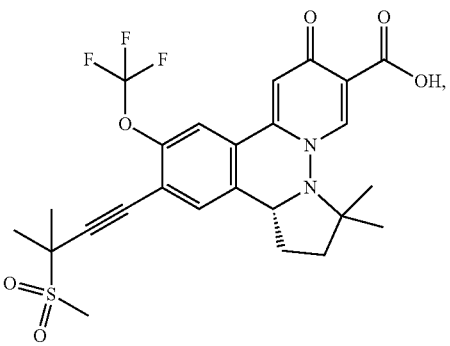
,
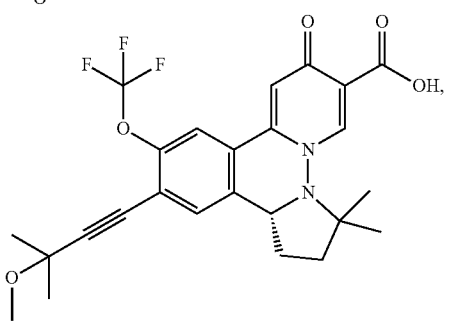
, 303
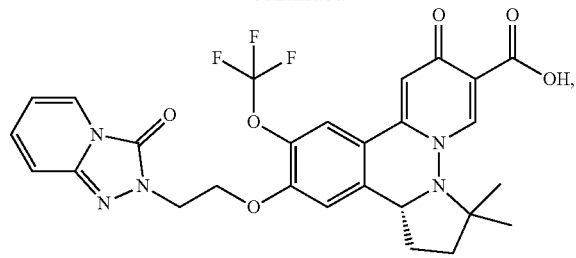
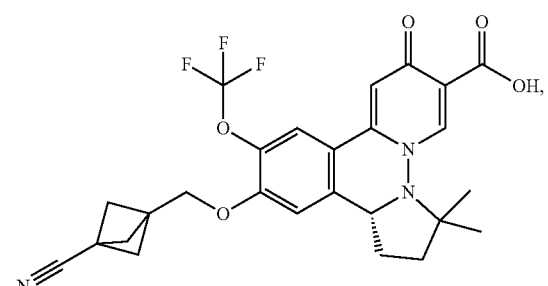
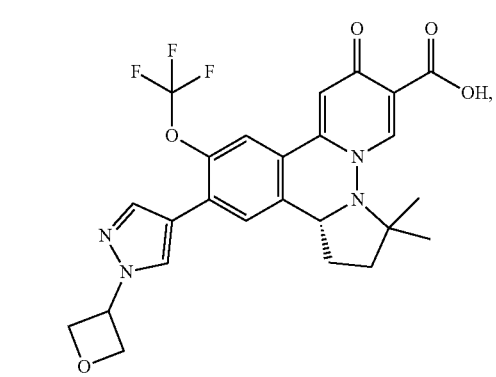
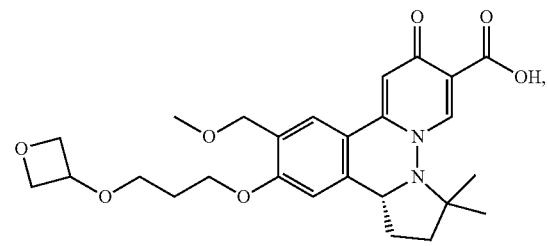
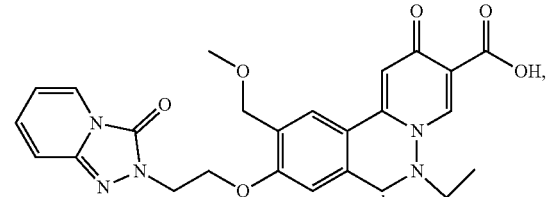
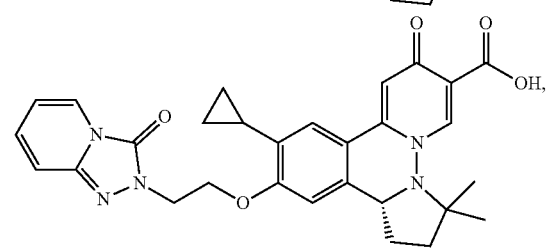
304
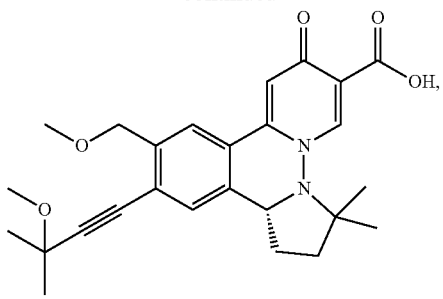
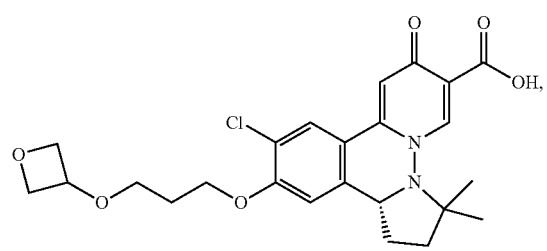
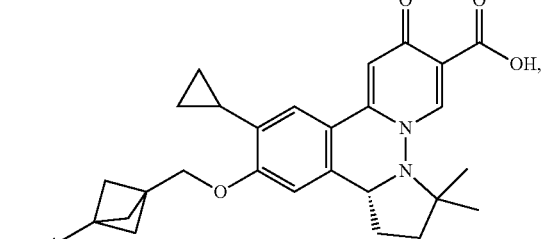
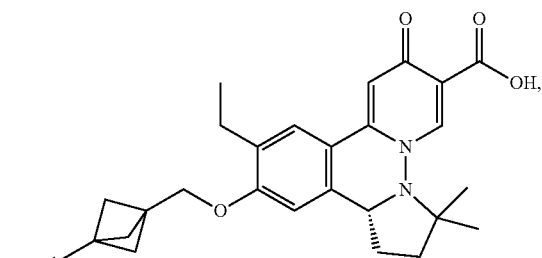
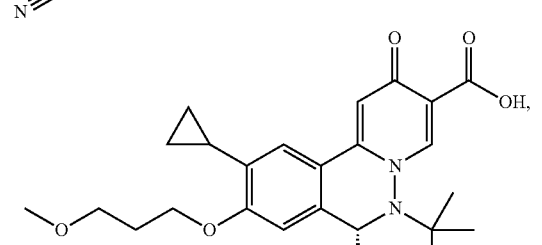
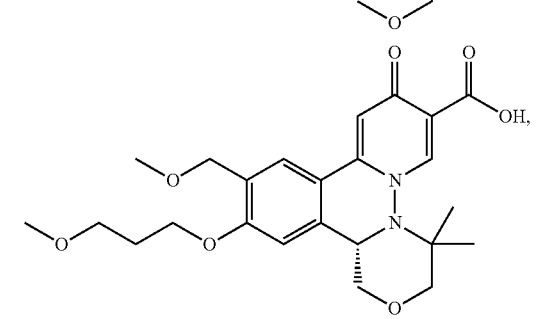

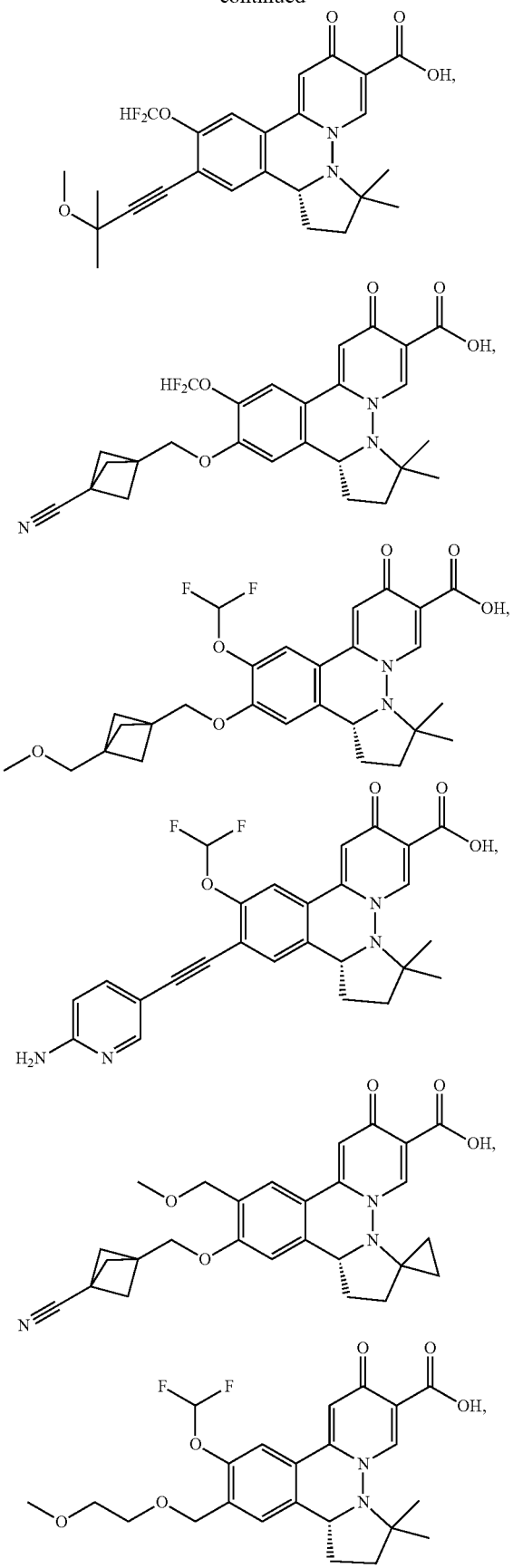
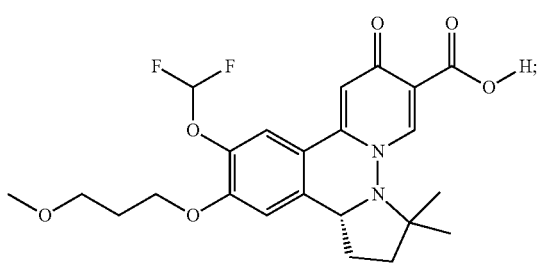
or a pharmaceutically acceptable salt thereof.
14. The compound of claim 1 having the formula:
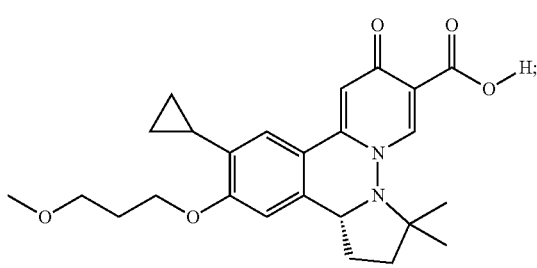
or a pharmaceutically acceptable salt thereof.
15. The compound of claim 1 having the formula:
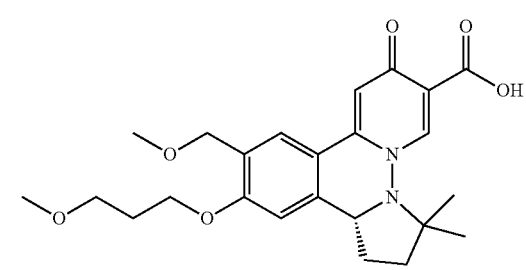 [SMILES: COCCCOc1cc2c(cc1COC)-c1cc(=O)c(C(=O)O)cn1N1[C@@H]2CCC1(C)C]
or a pharmaceutically acceptable salt thereof.
16. The compound of claim 1 having the formula:
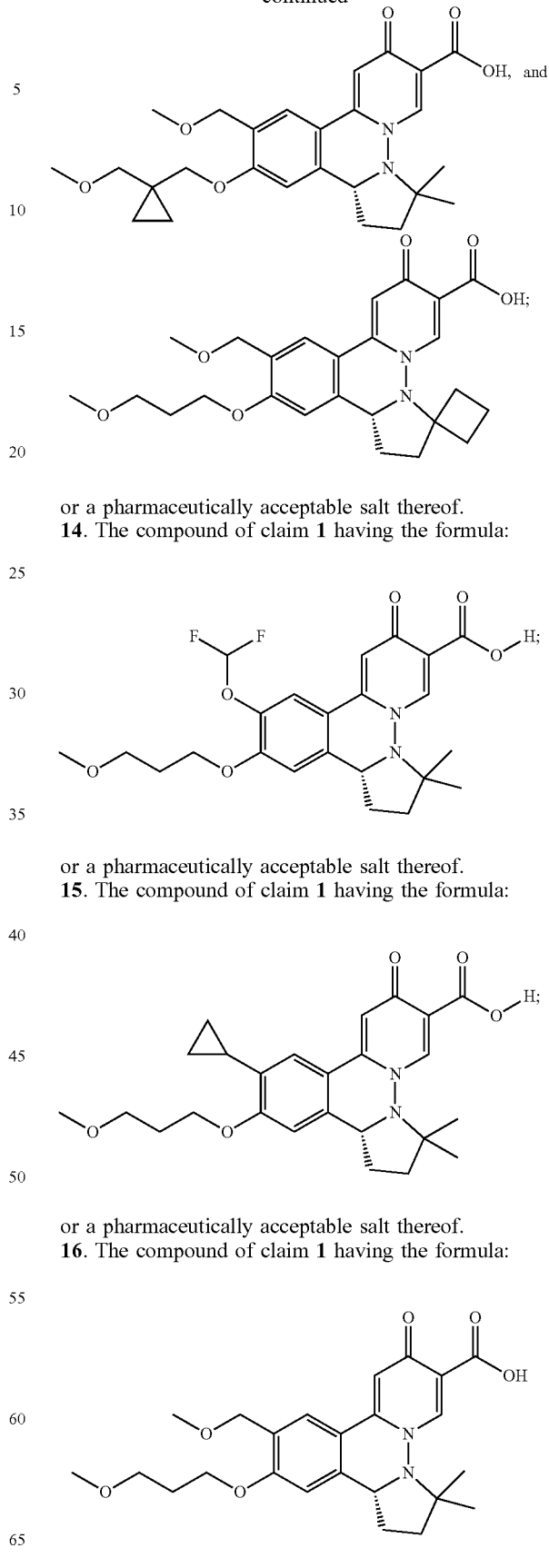
or a pharmaceutically acceptable salt thereof.

17. The compound of claim 1 having the formula:

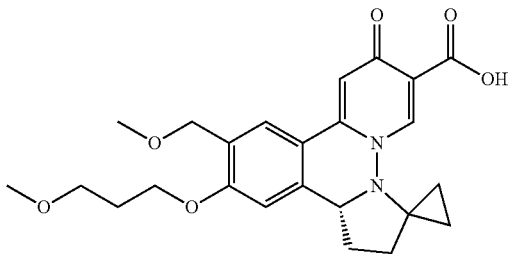 [SMILES: COCCCOc1cc2c(cc1COC)-c1cc(=O)c(C(=O)O)cn1N1[C@@H]2CCC12CC2]

or a pharmaceutically acceptable salt thereof.

18. A pharmaceutical composition comprising a compound or pharmaceutically acceptable salt of claim 1, and a pharmaceutically acceptable excipient.

19. A method of treating or preventing an HBV infection comprising administering to an individual in need thereof a therapeutically effective amount of a compound or pharmaceutically acceptable salt of claim 1 to the individual.

20. The compound of claim 1 selected from:

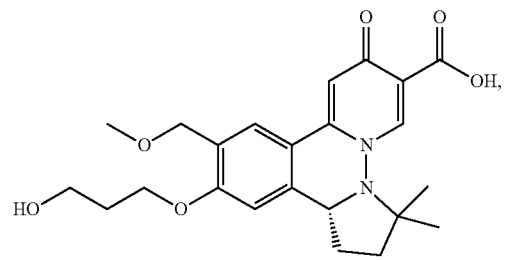

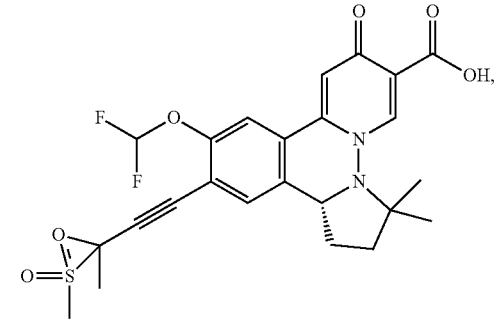

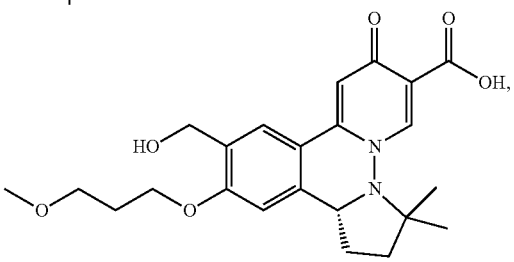

-continued

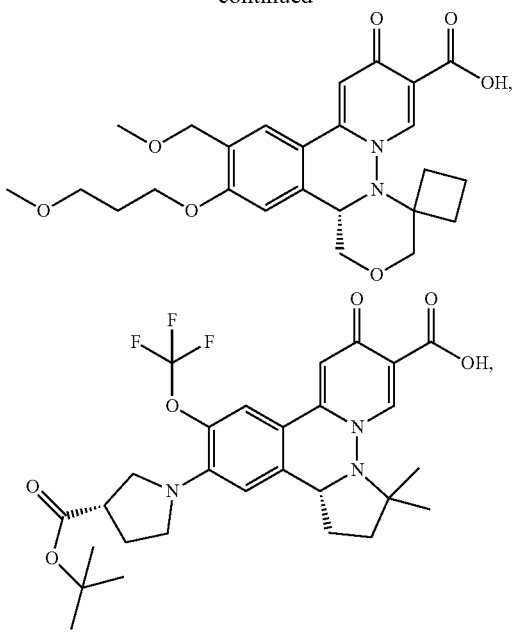

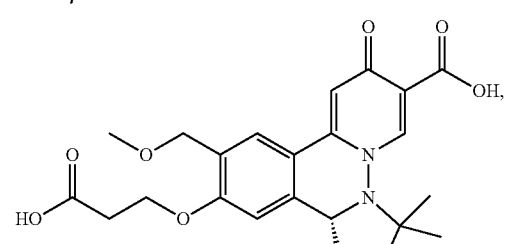

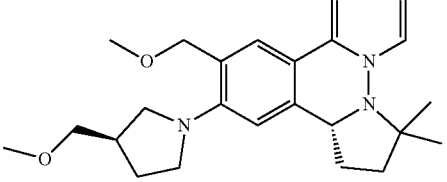

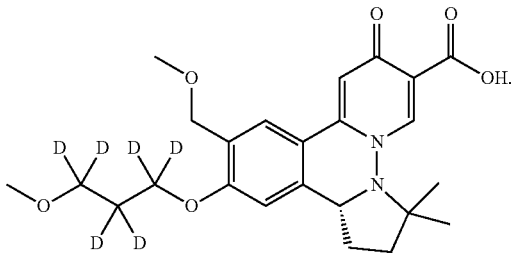

* * * * *